(12) United States Patent
Crowe, Jr. et al.

(10) Patent No.: US 12,410,241 B2
(45) Date of Patent: Sep. 9, 2025

(54) HUMAN MONOCLONAL ANTIBODIES TO ENTEROVIRUS D68

(71) Applicant: VANDERBILT UNIVERSITY, Nashville, TN (US)

(72) Inventors: James E. Crowe, Jr., Nashville, TN (US); Matthew R. Vogt, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 862 days.

(21) Appl. No.: 17/630,053

(22) PCT Filed: Jul. 24, 2020

(86) PCT No.: PCT/US2020/043415
§ 371 (c)(1),
(2) Date: Jan. 25, 2022

(87) PCT Pub. No.: WO2021/021605
PCT Pub. Date: Feb. 4, 2021

(65) Prior Publication Data
US 2022/0289828 A1    Sep. 15, 2022

Related U.S. Application Data

(60) Provisional application No. 63/047,330, filed on Jul. 2, 2020, provisional application No. 62/899,503, filed on Sep. 12, 2019, provisional application No. 62/878,955, filed on Jul. 26, 2019.

(51) Int. Cl.
| | | |
|---|---|---|
| C07K 16/10 | (2006.01) | |
| A61K 39/00 | (2006.01) | |
| A61K 39/42 | (2006.01) | |
| A61P 31/14 | (2006.01) | |
| G01N 33/569 | (2006.01) | |

(52) U.S. Cl.
CPC .......... *C07K 16/1009* (2013.01); *A61K 39/42* (2013.01); *A61P 31/14* (2018.01); *C07K 16/10* (2013.01); *G01N 33/56983* (2013.01); *A61K 2039/505* (2013.01); *A61K 2039/55* (2013.01); *C07K 2317/21* (2013.01); *C07K 2317/34* (2013.01); *G01N 2333/085* (2013.01); *G01N 2469/10* (2013.01)

(58) Field of Classification Search
None
See application file for complete search history.

(56) References Cited

PUBLICATIONS

Office Communication issued in corresponding European Patent Application No. 20754112.9, dated Aug. 31, 2023.
Vogt, Matthew R., et al. "Human antibodies neutralize enterovirus D68 and protect against infection and paralytic disease." *Science immunology* 5.49 (2020): eaba4902.
(Continued)

*Primary Examiner* — Thomas J. Visone
*Assistant Examiner* — Katherine A. Willard
(74) *Attorney, Agent, or Firm* — pH IP Law

(57) ABSTRACT

The present disclosure is directed to human and engineered antibodies and fragments thereof binding to enterovirus D68 (EV-D68), engineered cells producing the same, and of using the antibodies and fragments thereof in methods for both diagnosing and treating EV-D68 infections. Also disclosed are vaccine formulations comprising one of more of the antibody and fragments thereof, as well as vectors encoding the same.

26 Claims, 91 Drawing Sheets
Specification includes a Sequence Listing.

(56) References Cited

PUBLICATIONS

Zheng, Huiwen, et al. "Single B cells reveal the antibody responses of rhesus macaques immunized with an inactivated enterovirus D68 vaccine." *Archives of Virology* 165 (2020): 1777-1789.
Howard et al., "Molecular Epidemiology of Rhinovirus Detections in Young Children", *Open Forum Infect Dis.*, 3(1):ofw001, 2016.
Imamura et al., "Antigenic and Receptor Binding Properties of Enterovirus 68", *J Virol.*, 88(5):2374-84, 2014.
Invitation to Correct Defects in the International Application and to Pay fees issued in PCT/US2020/043415, mailed Aug. 5, 2020.
Invitation to Pay Additional Fees issued in PCT/US2020/043415, mailed Oct. 22, 2020.
Karrron et al., Respiratory Syncytial Virus Vaccines. In: Plotkin SA, MD, Orenstein WA, MD, DSc (HON), Offit PA, MD, Edwards KM, MD, eds. Plotkin's Vaccines. 7 ed. Philadelphia, PA: Elsevier, Inc., 1373-1383, 2018.
Liu et al., "Sialic acid-dependent cell entry of human enterovirus D68", *Nat Commun.*, 6(1):1-7, 2015.
Liu et al., "Structure and inhibition of EV-D68, a virus that causes respiratory illness in children", *Science*, 347(6217):71-4, 2015a.
Miao et al., "Monoclonal Antibodies to VP1 Recognize a Broad Range of Enteroviruses", *J Clin Microbiol.*, 47(10):3108-3113, 2009.
Mishra et al., "Antibodies to Enteroviruses in Cerebrospinal Fluid of Patients with Acute Flaccid Myelitis", *MBio*, 10(4):e01903-19, 2019.
Patel et al., "Enterovirus D-68 Infection, Prophylaxis, and Vaccination in a Novel Permissive Animal Model, the Cotton Rat (*Sigmodon hispidus*)", *PLoS One* 11, 11(11):e0166336 2016.

PCT International Search Report and Written Opinion issued in International Application No. PCT/US2020/043415, dated Dec. 14, 2020.
Schubert et al., "Pan-viral serology implicates enteroviruses in acute flaccid myelitis", *Nat Med*, 25(11):1748-1752, 2019.
Strebel et al., Measles Vaccines. In: Plotkin SA, MD, Orenstein WA, MD, DSc (HON), Offit PA, MD, Edwards KM, MD, eds. Plotkin's Vaccines. 7 ed. Philadelphia, PA: Elsevier, Inc., 860-920, 2018.
Sutter et al., Poliovirus Vaccine-Live. In: Plotkin SA, MD, Orenstein WA, MD, DSc (HON), Offit PA, MD, Edwards KM, MD, eds. Plotkin's Vaccines. 7 ed. Philadelphia, PA: Elsevier, Inc., :1268-1335, 2018.
Vidor et al., Poliovirus Vaccine-Inactivated. In: Plotkin SA, MD, Orenstein WA, MD, DSc (HON), Offit PA, MD, Edwards KM, MD, eds. Plotkin's Vaccines. 7 ed. Philadelphia, PA: Elsevier, Inc., 1233-1267, 2018.
Zhang et al., "Neutralization of enterovirus D68 isolated from the 2014 US outbreak by commercial intravenous immune globulin products", *J Clin Virol.*, 69:172-75, 2015.
Zhang et al., Viral strategies for triggering and manipulating mitophagy, Autophagy, 14(10):1665-1673, 2018.
Zhang et al., "Enterovirus D68 virus-like particles expressed in *Pichia pastoris* potently induce neutralizing antibody responses and confer protection against lethal viral infection in mice ", *Emerg Microbes Infect.*,7:3, 2018a.
Zheng et al., "A novel Neutralizing Antibody Specific to the DE Loop of VP1 can Inhibit EV-D68 Infection in Mice", *The Journal of Immunology*, 201(9):22-1767, 2018.
Zheng et al., "Atomic structures of enterovirus D68 in complex with two monoclonal antibodies define distinct mechanisms of viral neutralizations", *Nature Microbiology*, 4(1):124-133, 2018.

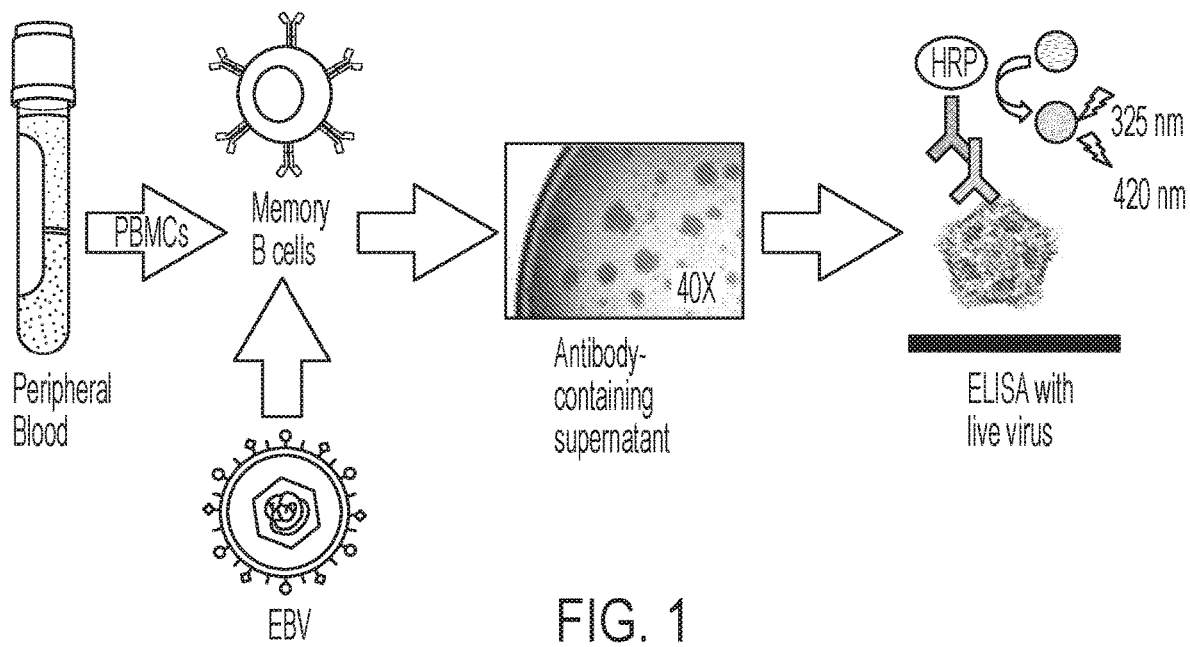
FIG. 1
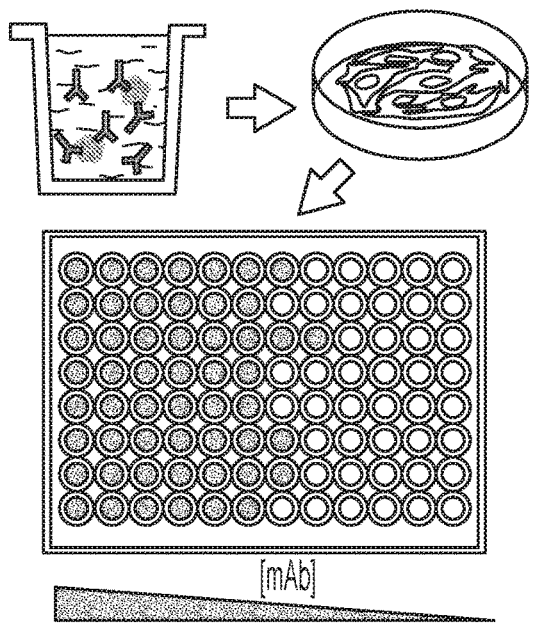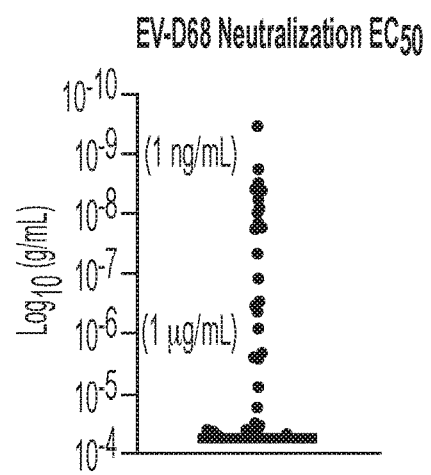
FIG. 2

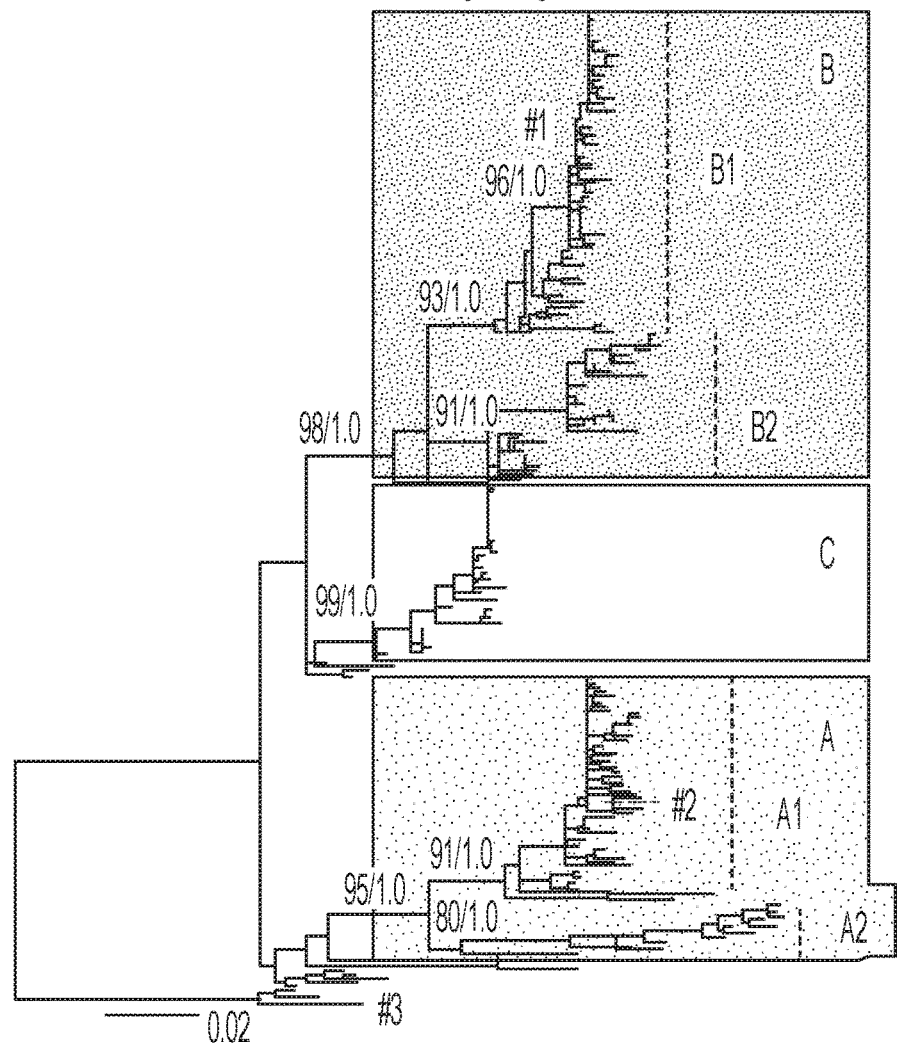
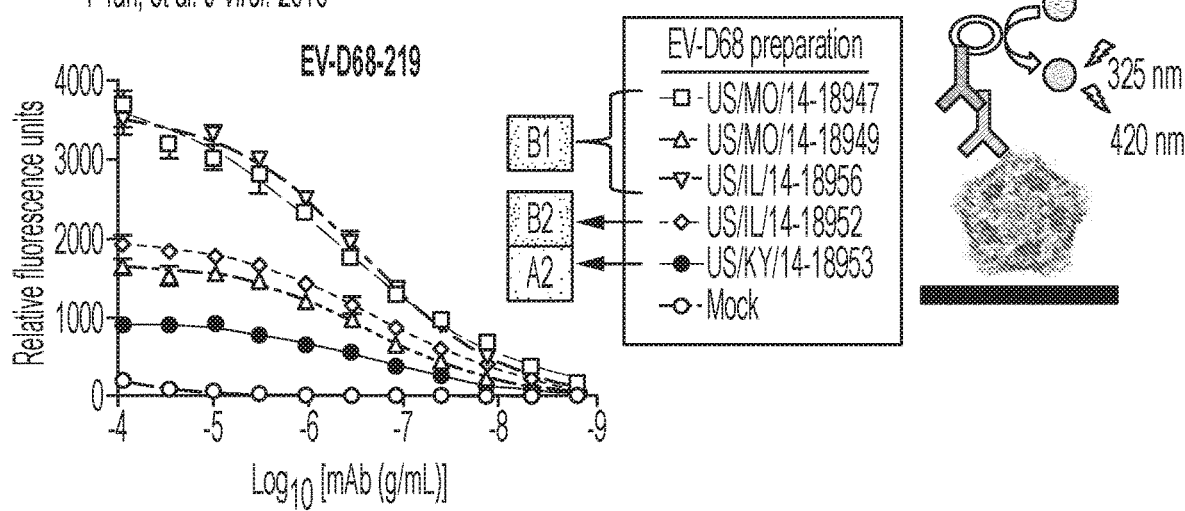
FIG. 3

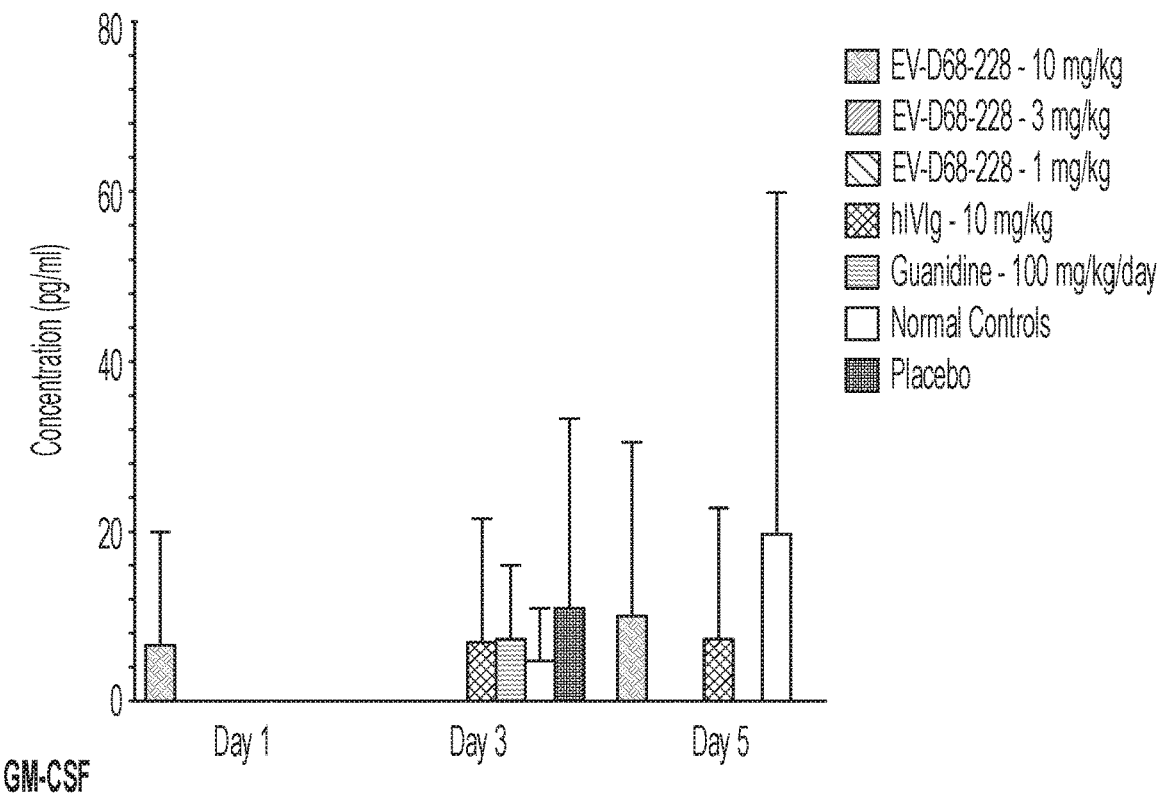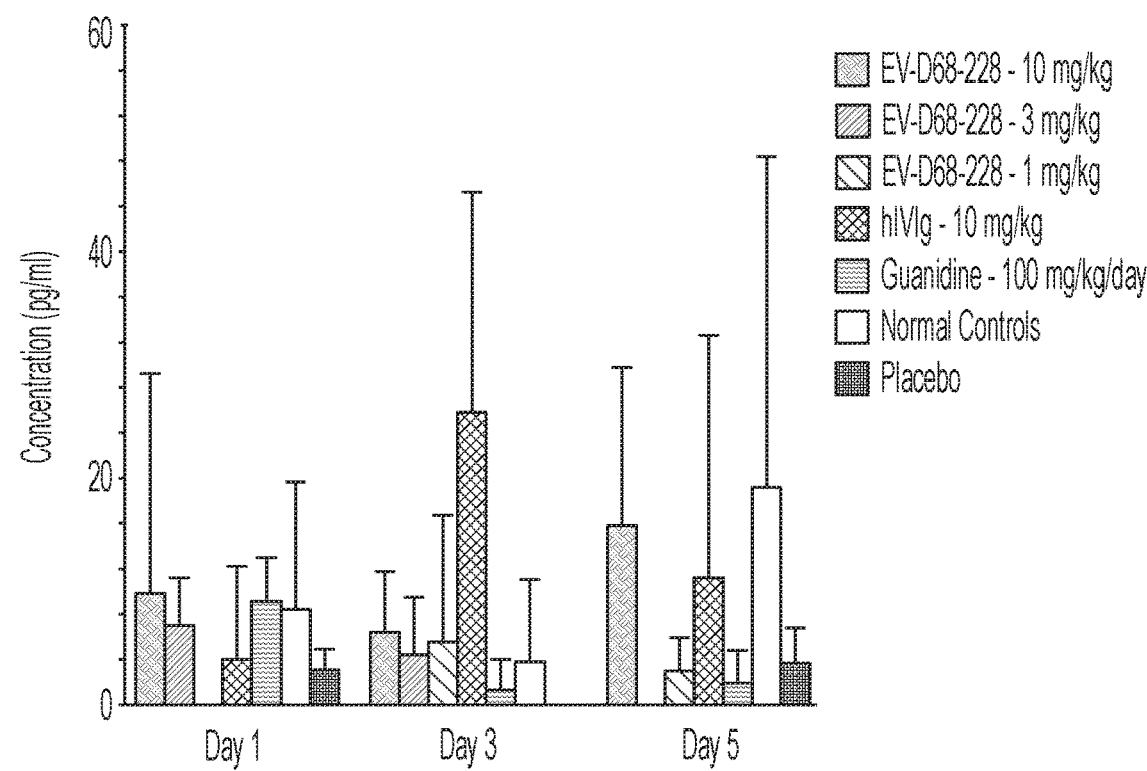
FIG. 14

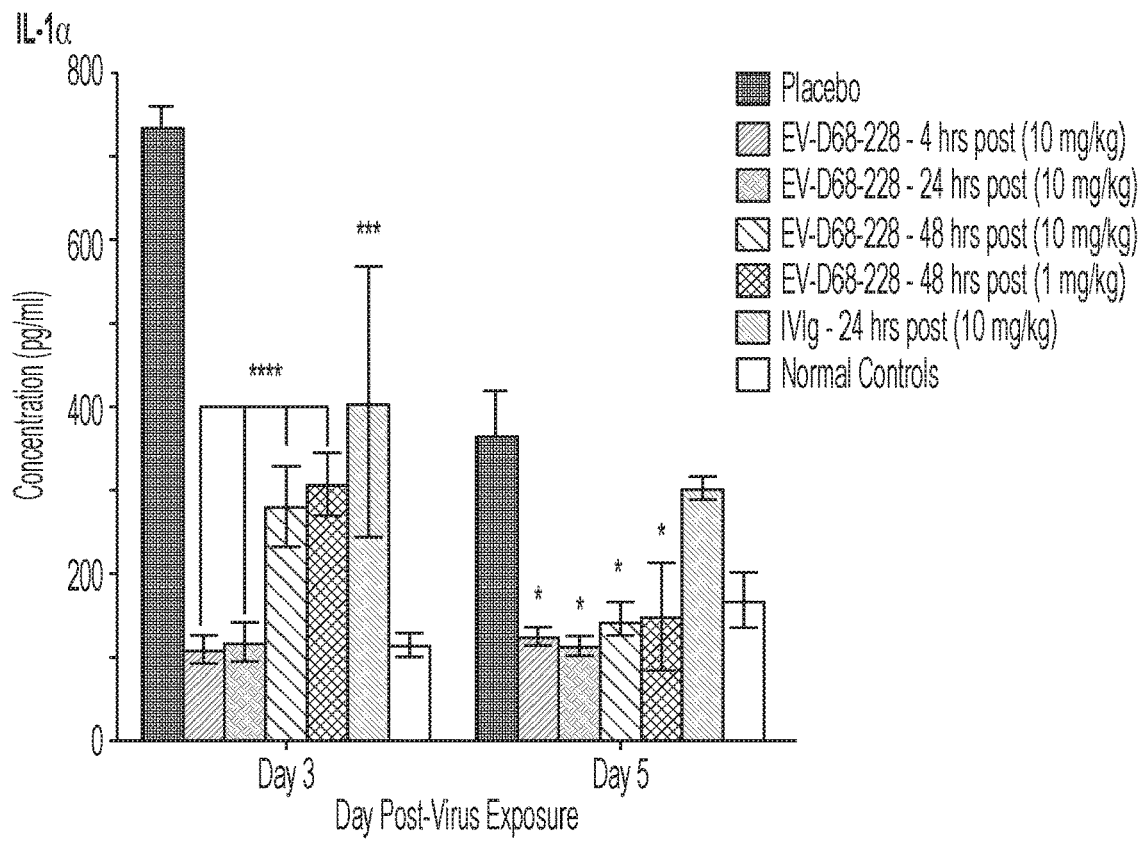
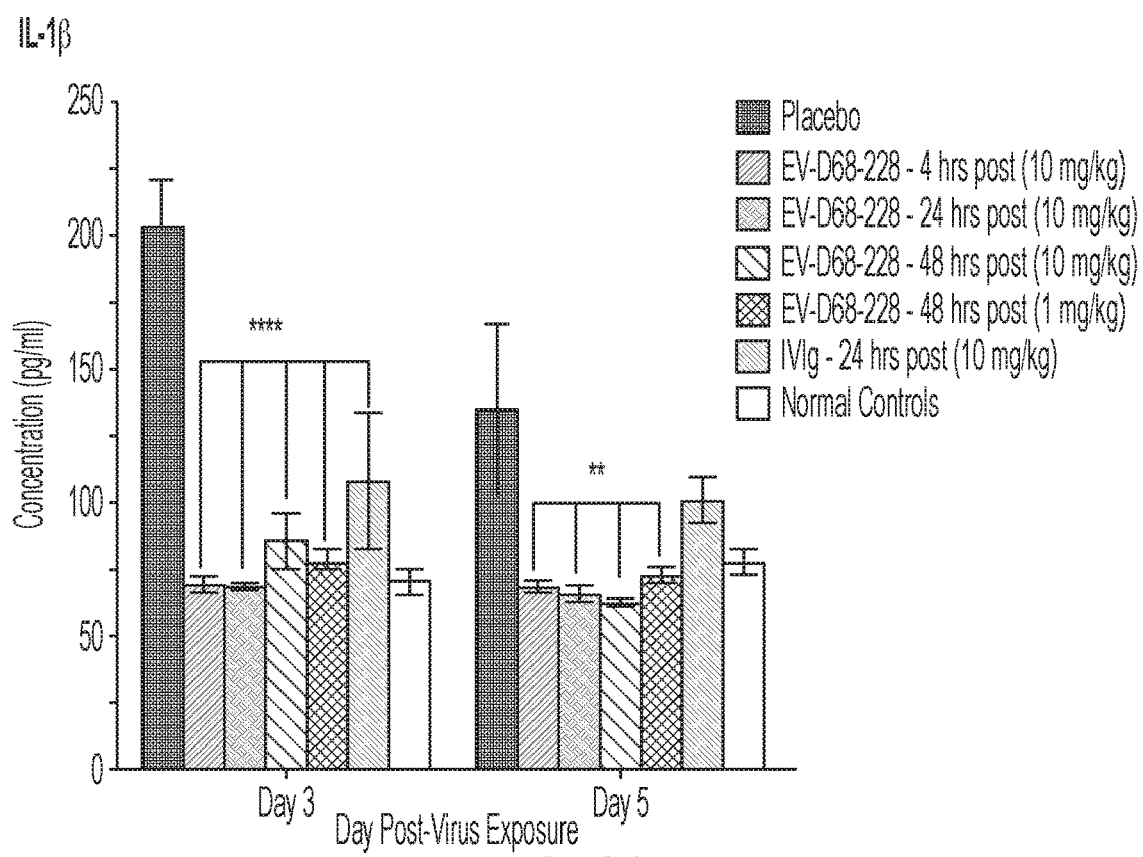
FIG. 21

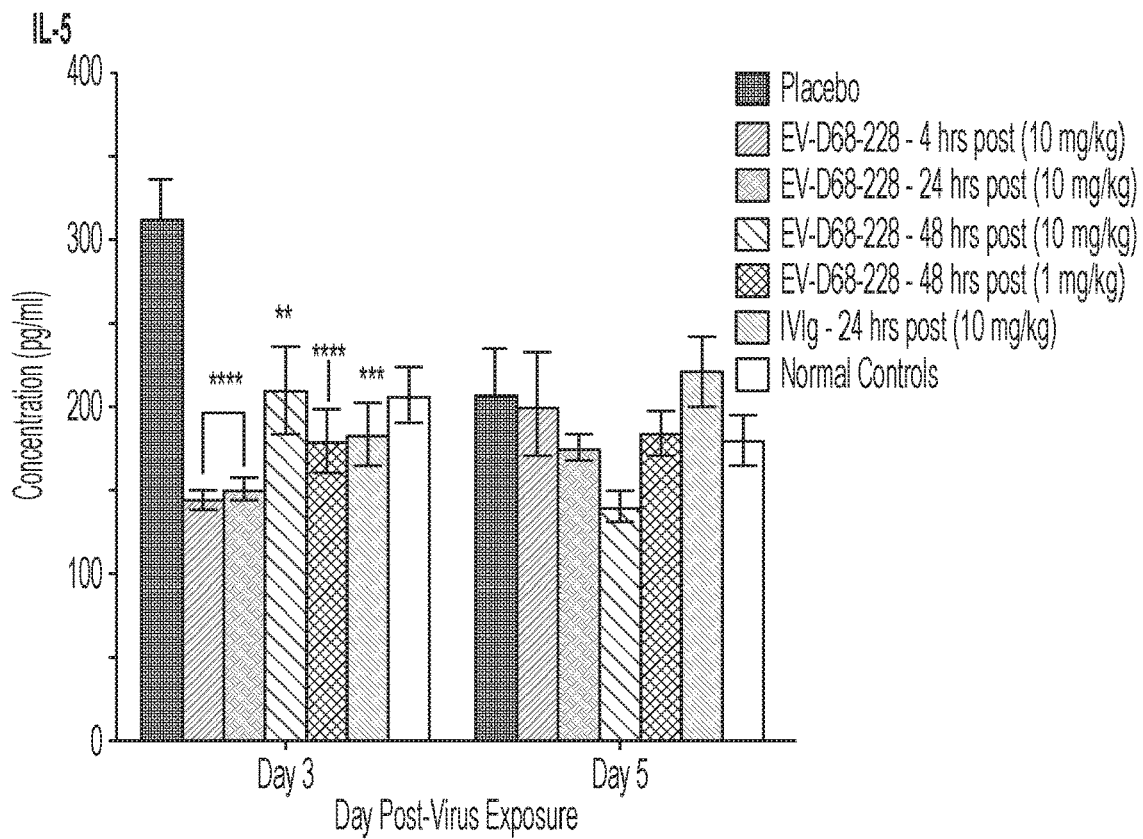
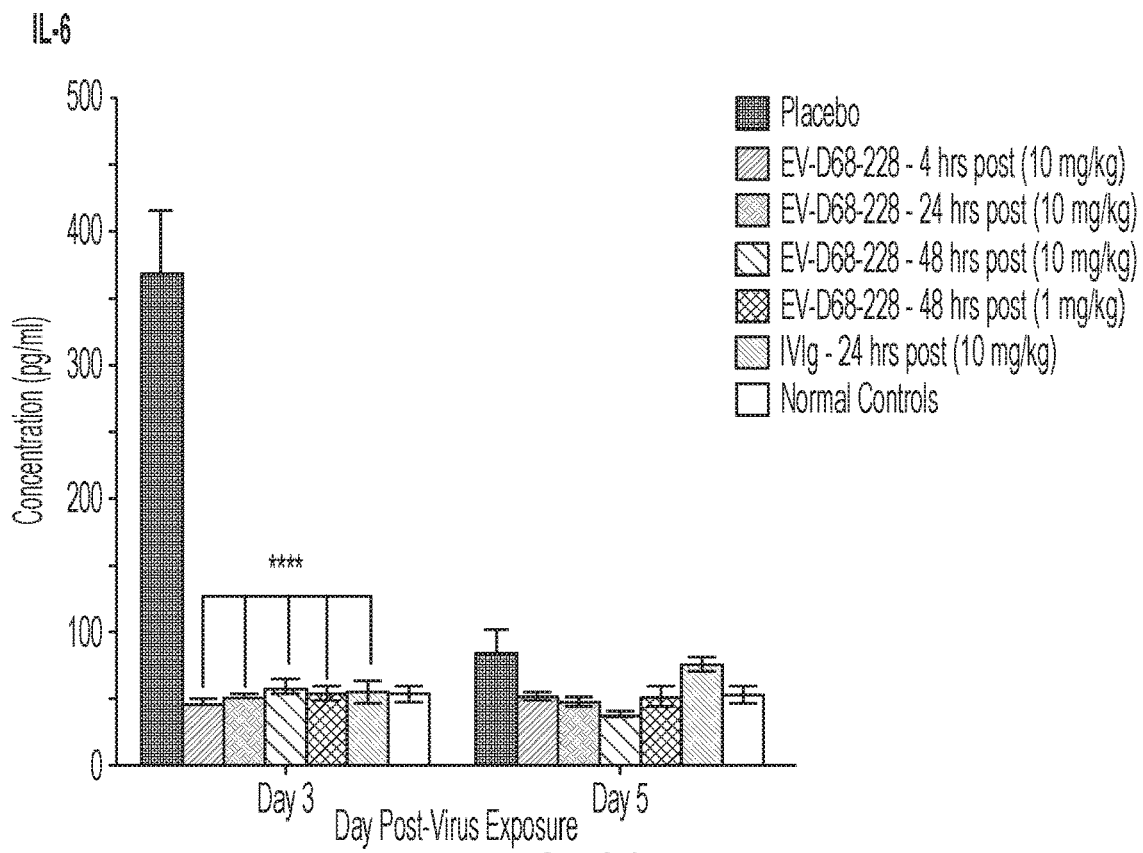
FIG. 22

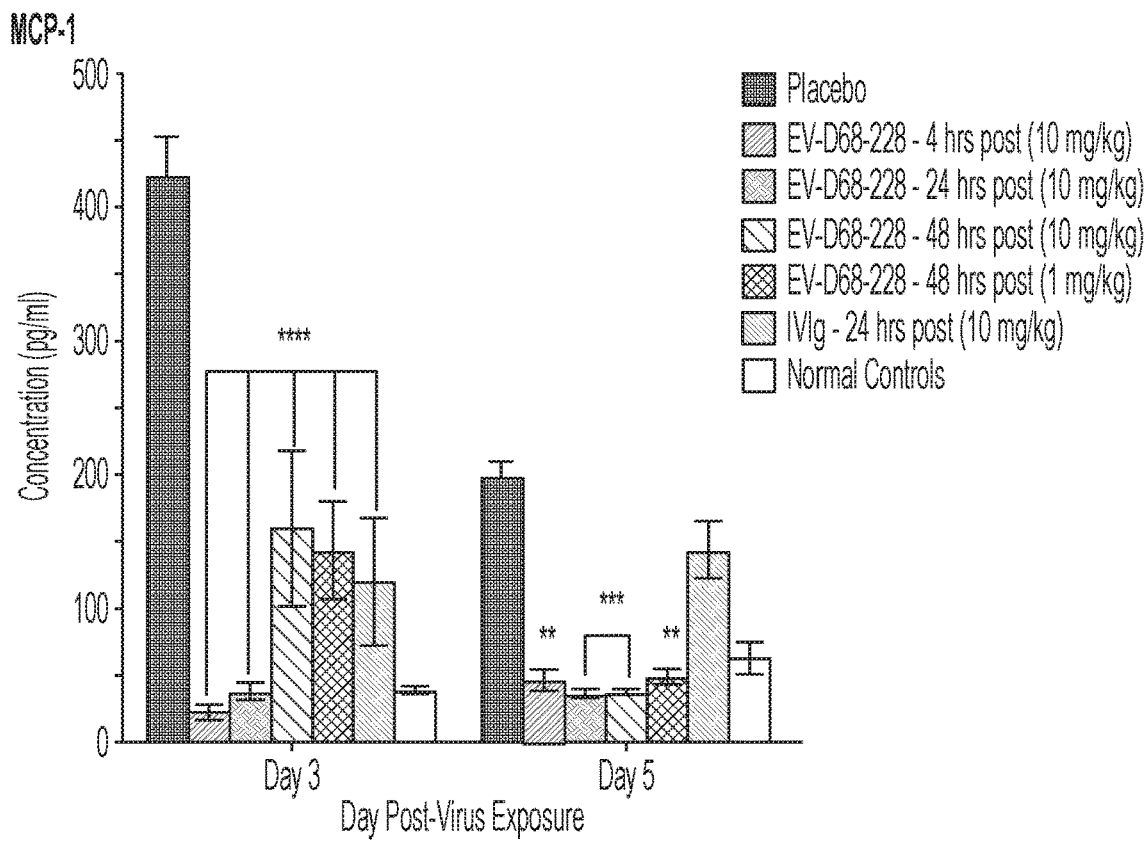
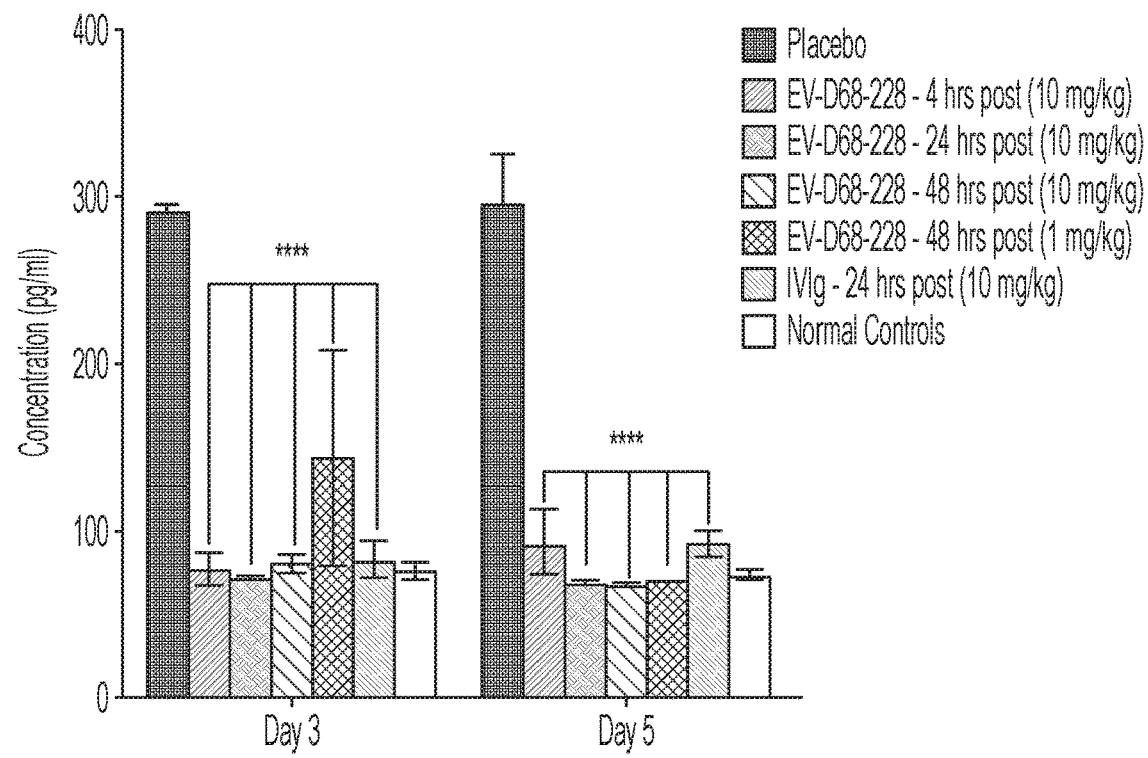
FIG. 23

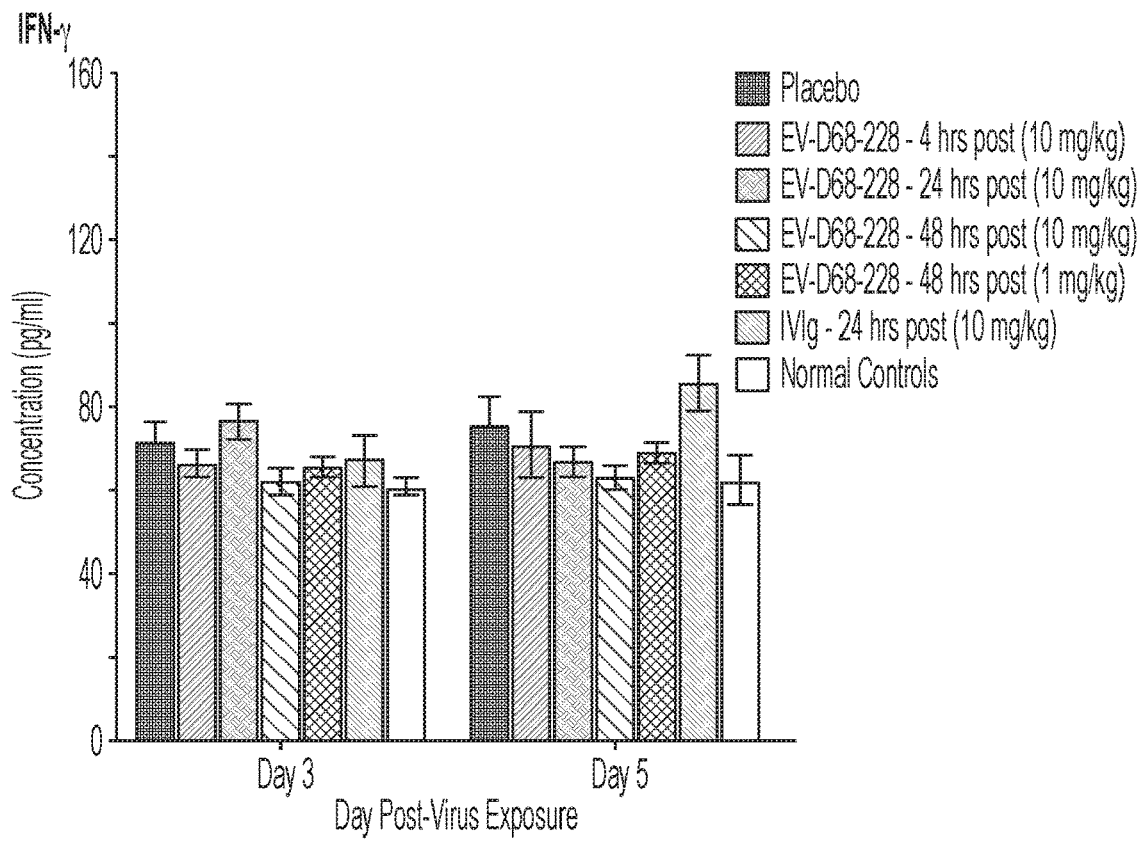
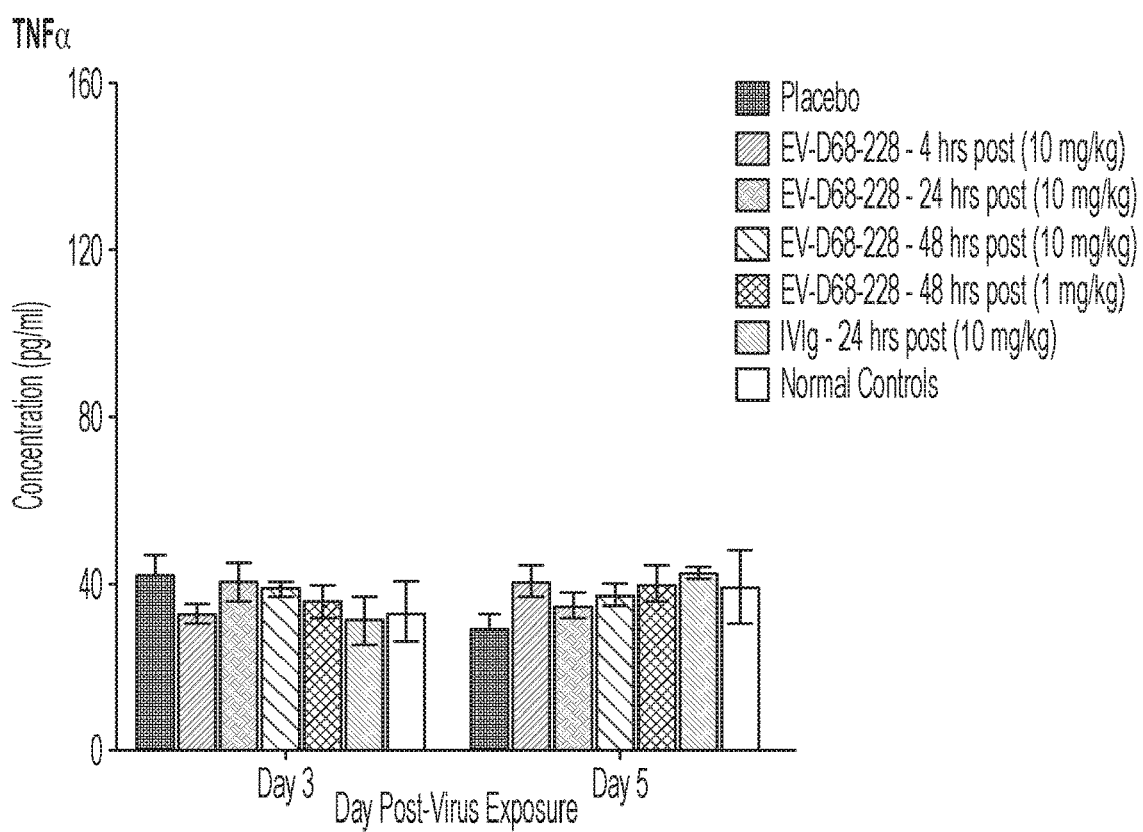
FIG. 26

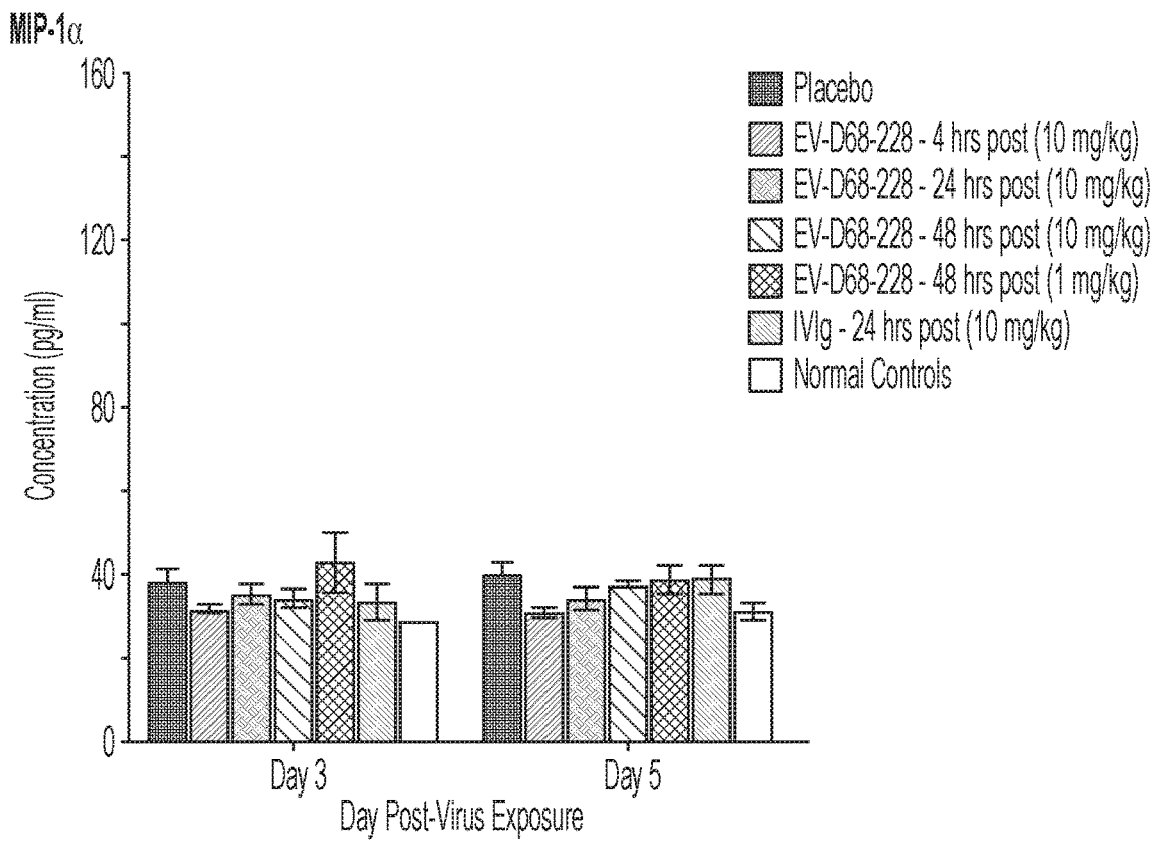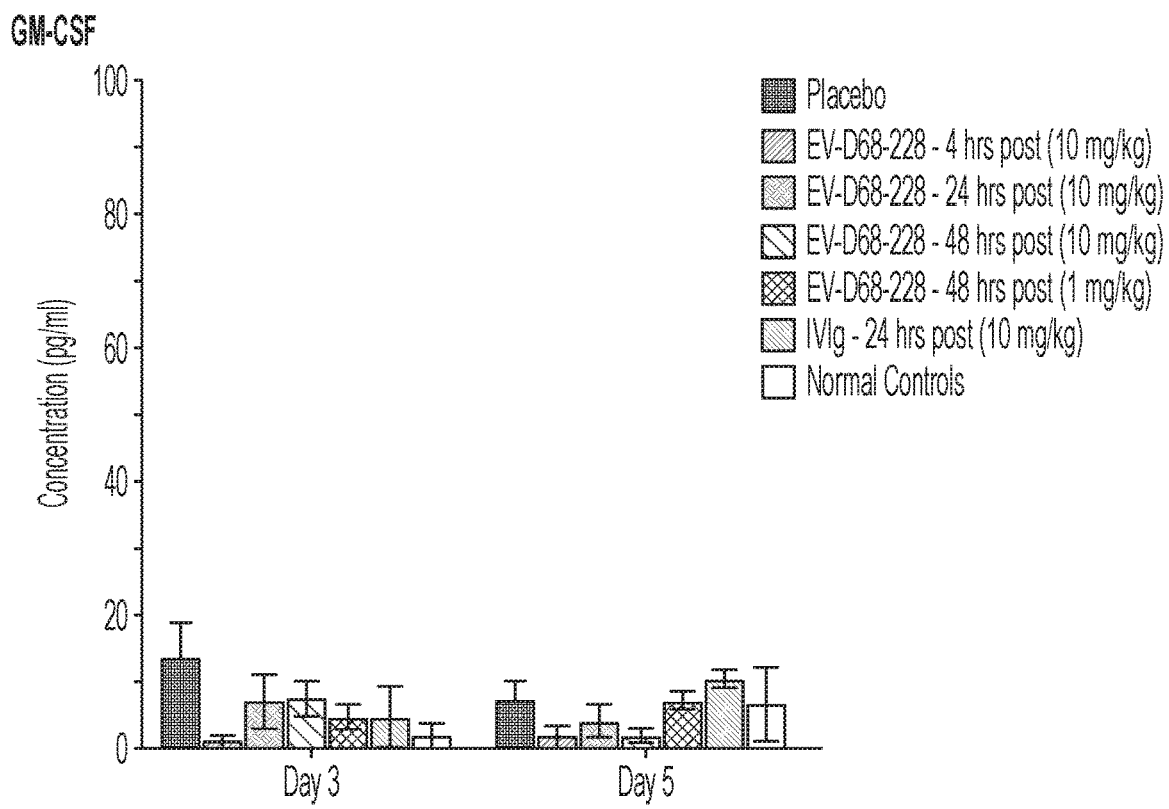
FIG. 27

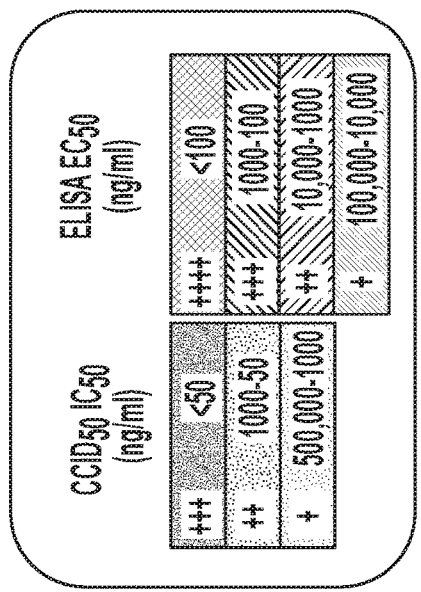
FIG. 33A-C

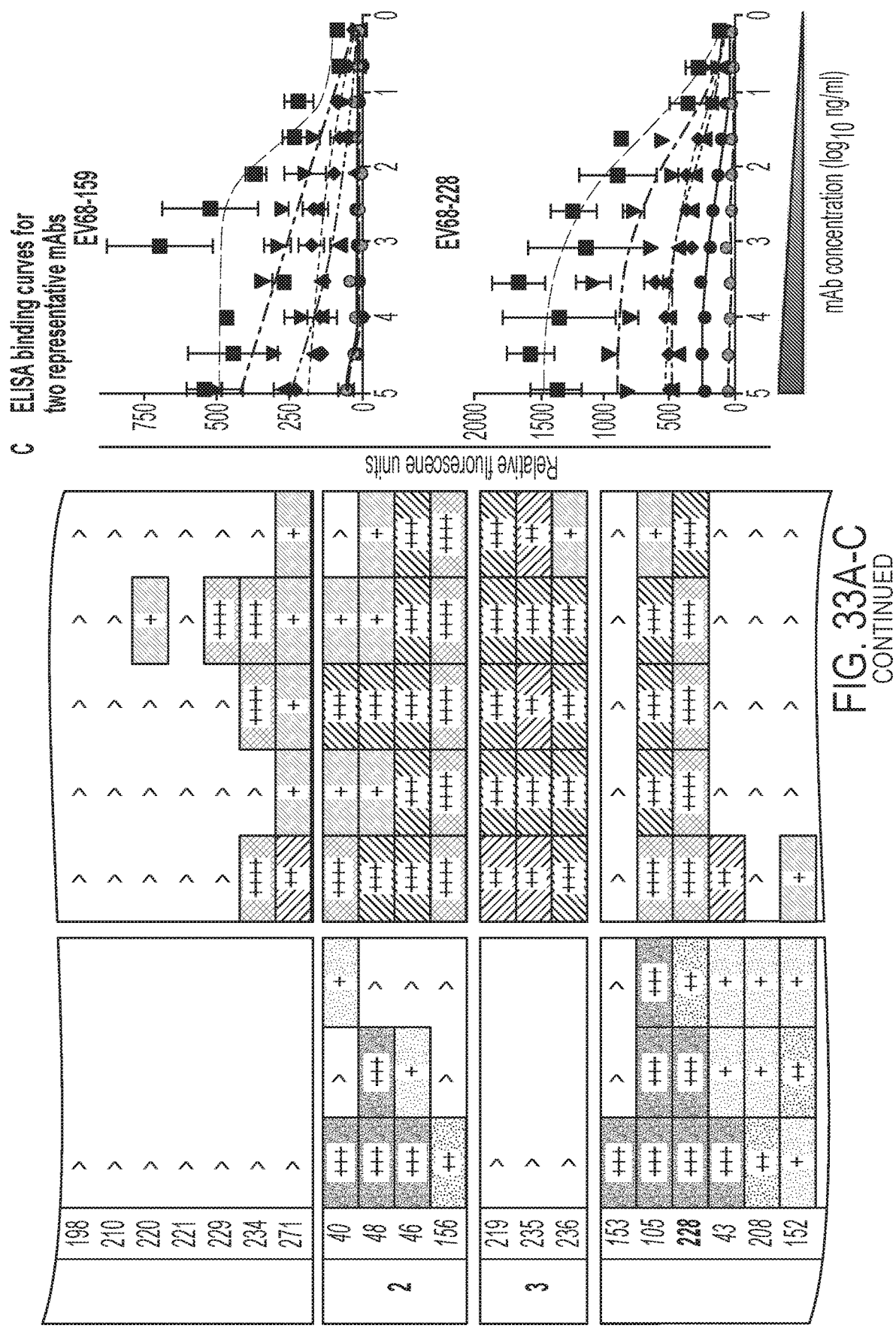
FIG. 33A-C CONTINUED

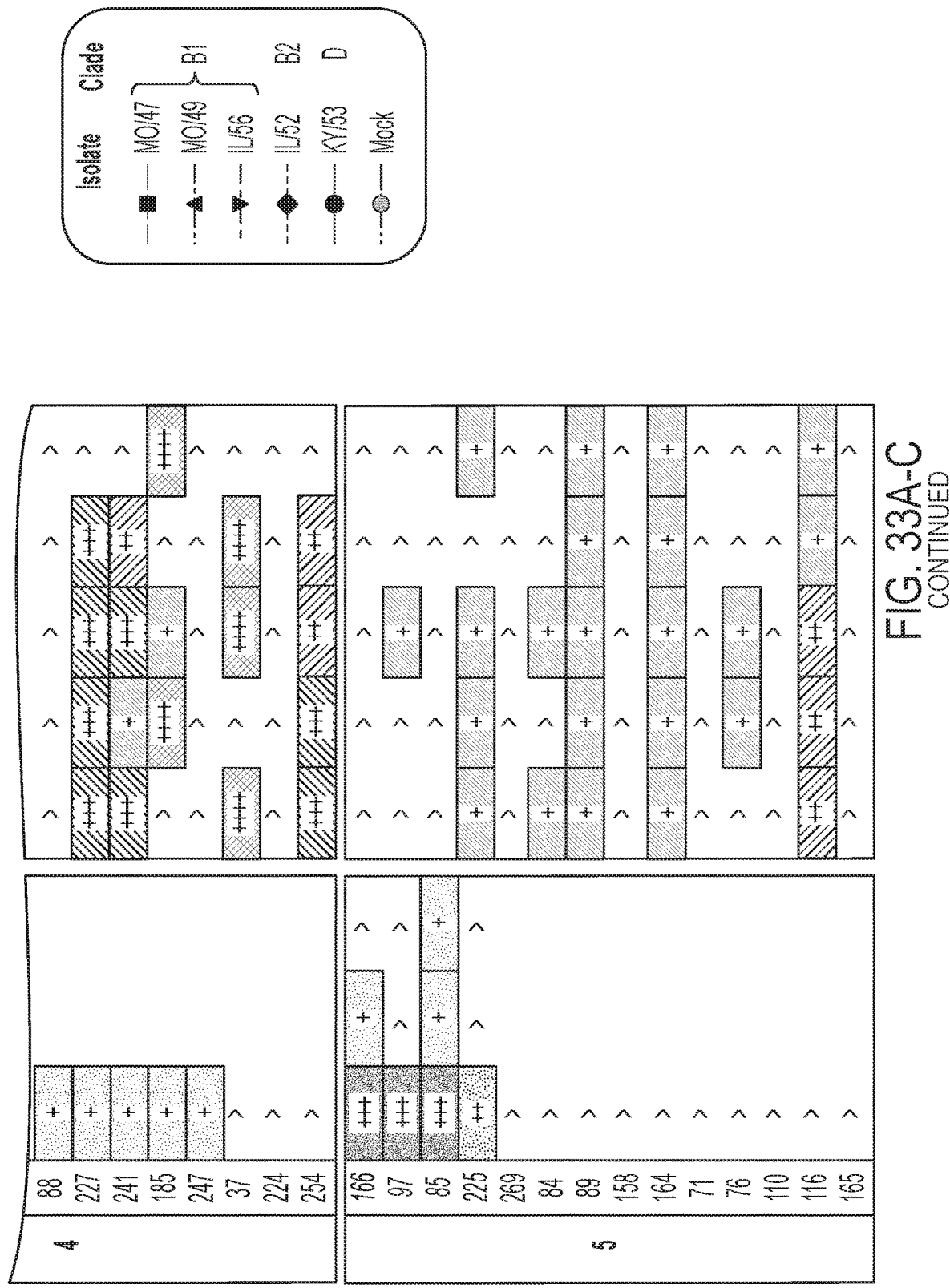
FIG. 33A-C CONTINUED

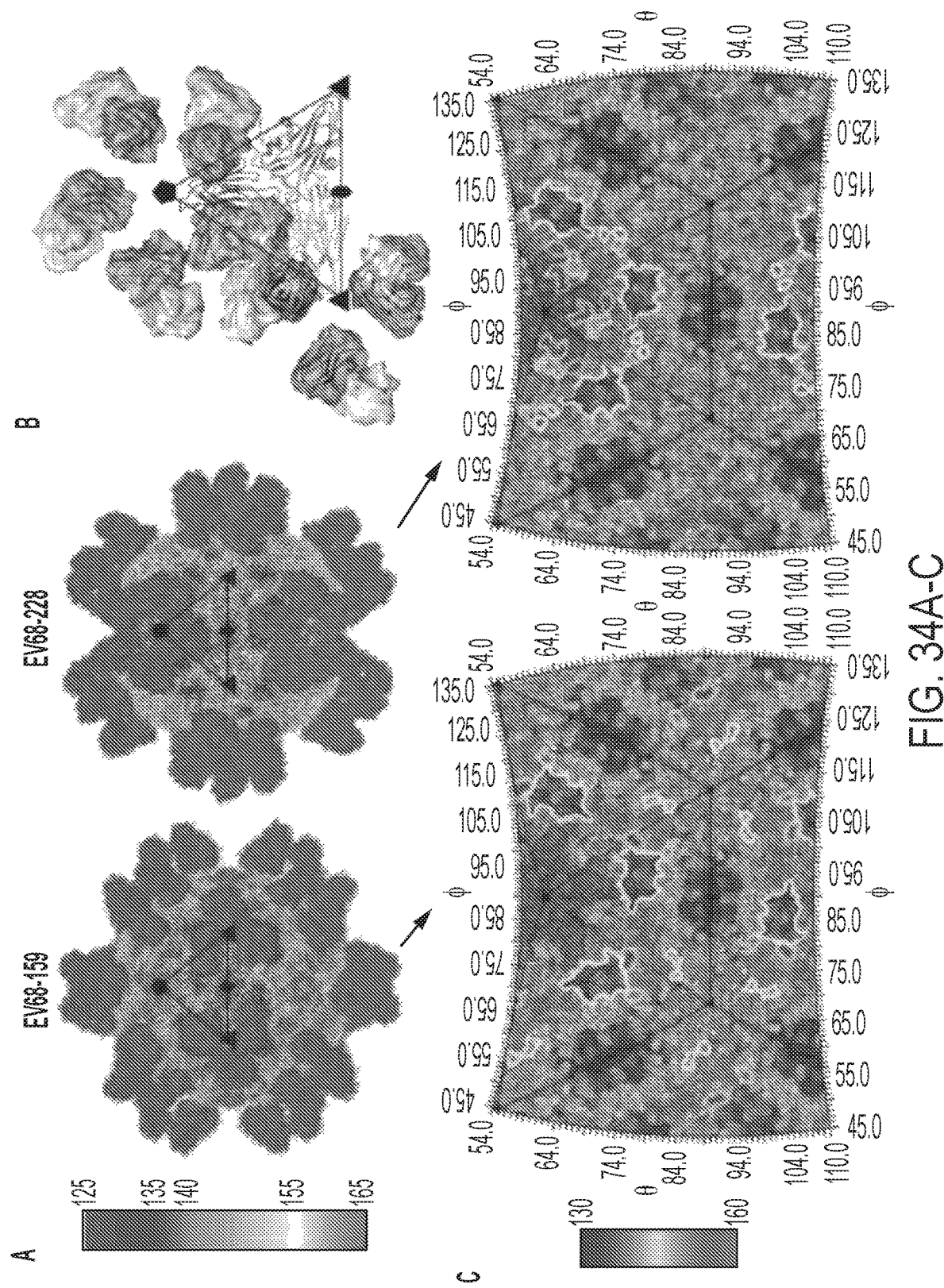
FIG. 34A-C

| Competition group | mAb | Neutralization IC50 | | | Binding EC50 | | | | | Subject | IgG subtype | Light chain | WB |
|---|---|---|---|---|---|---|---|---|---|---|---|---|---|
| | | B1 IL56 | D KY153 | N/A Fermon | B1 MO/47 | B1 MO/49 | B1 IL56 | B1 IL52 | D KY153 | | | | |
| | | | | | Clade and isolate tested | | | | | | | | |
| | 159 | 0.32 | | | 21 | > | | 28 | > | 6 | 1 | L | |
| | 150 | 16 | 28,000 | 38,000 | 12 | 56 | 180 | 15 | > | 1 | 1 | K | |
| | 95 | 100 | > | 2,800 | 4,700 | 2,700 | 36 | | | 5 | 3 | L | |
| | 266 | 250 | 70 | > | 57 | 14 | 4,800 | 4,700 | 3,200 | 5 | 1 | L | |
| | 41 | 2,400 | > | > | 73 | 390 | > | 4,200 | 30 | 5 | 3 | L | |
| | 98 | 2,400 | > | > | 13,000 | 68,000 | 59 | 49 | > | 5 | 3 | L | |
| 1 | 231 | 6,700 | > | > | | | 52,000 | | | 5 | 1 | K | |
| | 178 | 16,000 | > | > | | | | | | 3 | 3 | K | |
| | 162 | 27,000 | > | > | 52 | 2,300 | 94 | 48 | > | 10 | 1 | K | |
| | 161 | > | > | > | 1,700 | > | 50,000 | 2,000 | > | 8 | 3 | K | |
| | 242 | > | > | > | 160 | 150 | 26,000 | 820 | > | 3 | 3 | K | |
| | 72 | > | > | > | 23 | 16 | 290 | 48 | > | 1 | 3 | L | |
| | 74 | > | > | > | > | > | 13 | 48 | > | 1 | 1 | L | |
| | 75 | > | > | > | 100 | 180 | 140 | > | 140 | 1 | 1 | L | |
| | 79 | > | > | > | > | > | > | 190 | > | 1 | 1 | L | |
| | 114 | > | > | > | 7,500 | 45,000 | 16,000 | 96,000 | 380 | 1 | 1 | L | |
| | 160 | > | > | > | 1,400 | 18,000 | 2,500 | 50,000 | > | 7 | 3 | L | |
| | 181 | > | > | > | > | > | > | > | > | 1 | 3 | K | |
| | 183 | > | > | > | | | | | | 1 | 1 | L | |

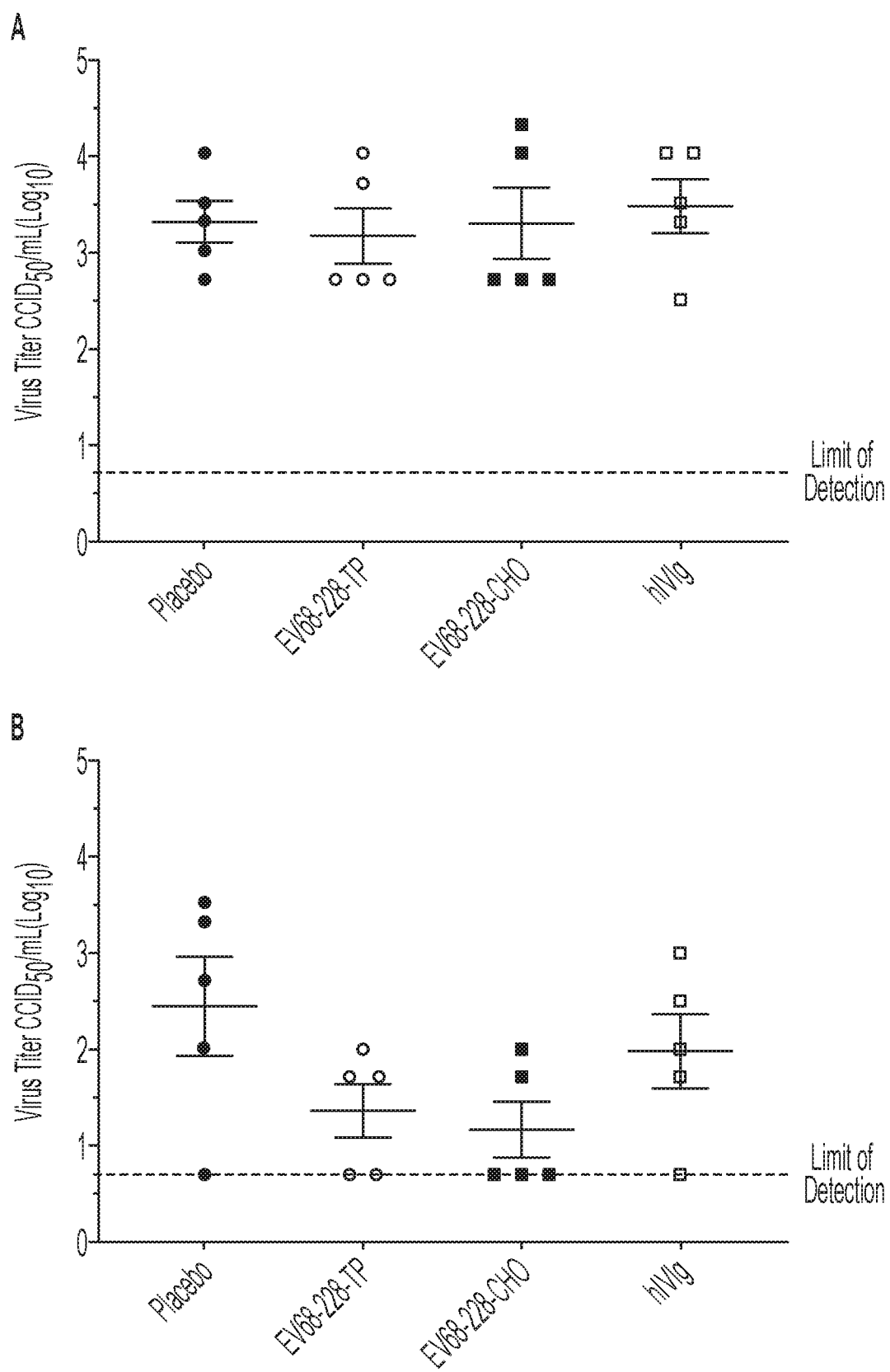
FIG. 79A-B

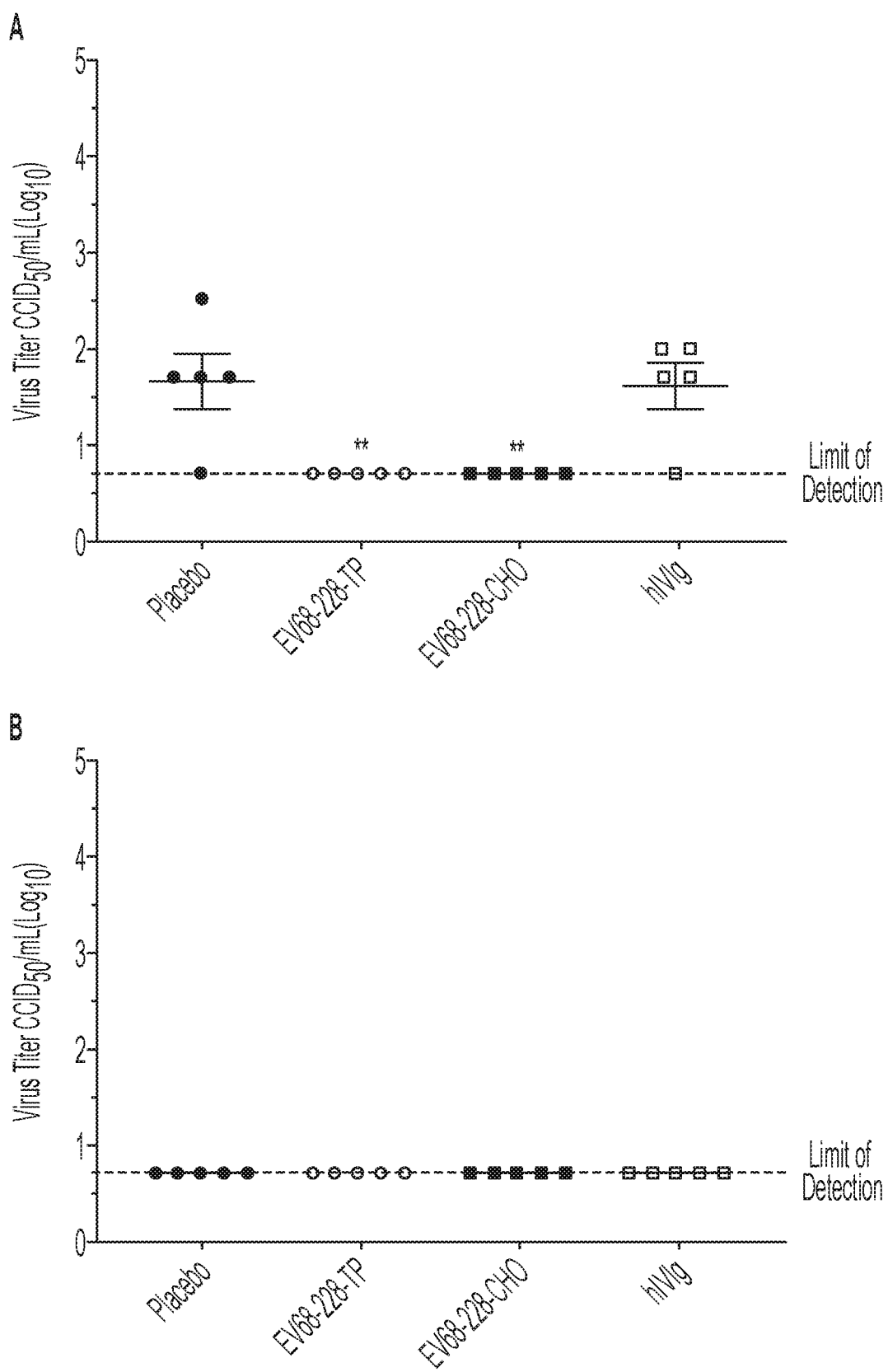
FIG. 80A-B

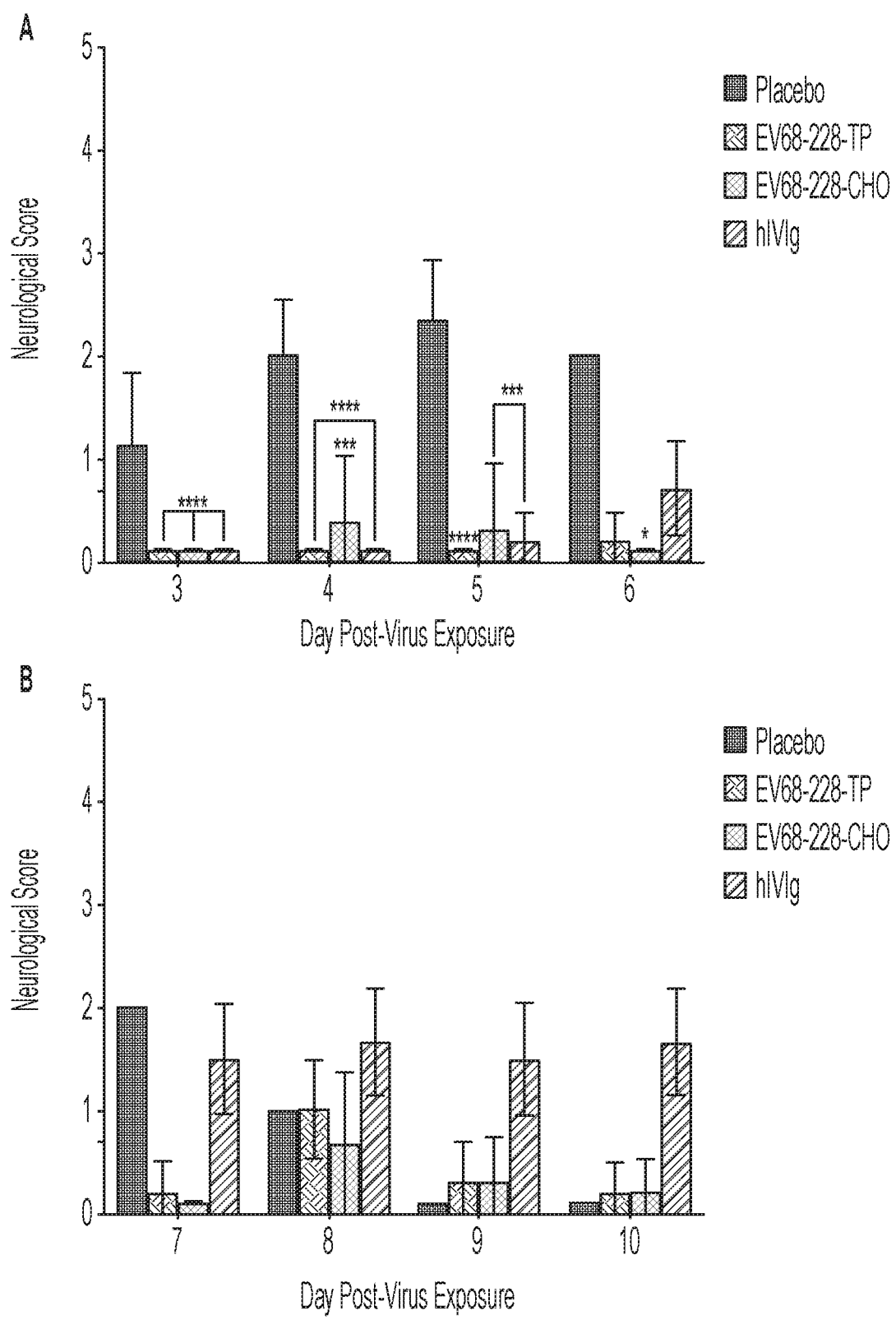
FIG. 81A-B ved Jul. 24, 2020, which claims benefit of
HUMAN MONOCLONAL ANTIBODIES TO ENTEROVIRUS D68

PRIORITY CLAIM

This application is a national phase application under 35 U.S.C. § 371 of International Application No. PCT/US2020/043415, filed Jul. 24, 2020, which claims benefit of priority to U.S. Provisional Application Ser. Nos. 62/878,955, 62/899,503 and 63/047,330, filed Jul. 26, 2019, Sep. 12, 2019 and Jul. 2, 2020, respectively, the entire contents of each application being incorporated by reference herein.

REFERENCE TO A SEQUENCE LISTING

The instant application contains a Sequence Listing which has been submitted electronically in ASCII format and is hereby incorporated by reference in its entirety. Said ASCII copy, created on Mar. 27, 2025, is named VBLTP0294US_ST25.txt and is 288,928 bytes in size.

BACKGROUND

1. Field of the Disclosure

The present disclosure relates generally to the fields of medicine, infectious disease, and immunology. More particular, the disclosure relates to human antibodies binding to enterovirus D68 and methods of using such antibodies to diagnose and treat enterovirus D68 infections.

2. Background

Enterovirus-D68 (EV-D68) is a positive-sense, single-stranded RNA virus of the Enterovirus genus of the Picornaviridae family. Other common human pathogens within this genus include poliovirus, echovirus, coxsackievirus, rhinovirus, and other numbered enteroviruses such as enterovirus-A71 (Zell et al., 2017). While structurally and genetically similar, these viruses cause a wide variety of childhood diseases including neonatal sepsis, myocarditis, poliomyelitis, meningitis, respiratory tract infections, and hand, foot, and mouth disease. Much like the rhinoviruses, EV-D68 is primarily a respiratory pathogen that is acid-labile and replicates best at 33° C. (Oberste et al., 2004). These similarities are such that a strain of EV-D68 was even initially reported as rhinovirus 87 (Blomqvist et al., 2002).

From its initial identification in a California child with pneumonia in 1962 (Schieble et al., 1967) through the turn of the century, EV-D68 was detected only rarely (Khetsuriani et al., 2006). Since then, EV-D68 has been recognized increasingly as a pathogen of emerging importance due to its worldwide detection in outbreaks of primarily respiratory illness in children (Xiang and Wang, 2016). The largest ever known outbreak occurred in 2014 in the United States with 1,152 confirmed cases spanning all states except for Alaska (Oermann et al., 2015). This number likely grossly underestimates the actual number of cases of EV-D68 in 2014 because mild upper respiratory tract infection would not likely result in the specialized testing needed to detect this virus. Children with asthma experienced especially severe infections (Biggs et al., 2017), although a study of one institution found that EV-D68 was no more severe than non-EV-D68 enterovirus/rhinovirus infections in children with asthma (Overdahl et al., 2016). Over half of the hospitalized patients were admitted to intensive care units, with 80% receiving supplemental oxygen, 23% requiring non-invasive ventilation, 8% requiring intubation and mechanical ventilation, and 1% died (Midgley et al., 2015).

Concurrent with the 2014 outbreak, a small cluster of pediatric patients with acute onset flaccid paralysis and cranial nerve dysfunction was noted in Colorado (Messacar et al., 2015). This syndrome has been designated acute flaccid myelitis (AFM), defined as a poliomyelitis-like illness with typically asymmetric, flaccid limb weakness and myelitis of primarily gray matter seen on spinal cord imaging (Div. of Viral Diseases, CDC, 2018). Since the 2014 outbreak, many more cases and clusters of AFM have been associated with EV-D68. To date, 74 AFM cases with positive EV-D68 testing from any patient source have been identified across 6 continents (Messacar et al., 2018). While the Centers for Disease Control and Prevention (CDC) does not officially recognize EV-D68 as a proven cause of AFM (Nat'l Center for Immun Resp. Disease), many experts find the preponderance of evidence compelling enough to consider the relationship between the two to be causal (Messacar et al. 2018). Because of continued worldwide outbreaks, the World Health Organization Research and Development Blueprint now lists EV-D68 as a major public health risk (Ann. Rev. of Diseases, 2018).

As EV-D68 has emerged only recently as a priority pathogen, most initial studies focused on defining the epidemiology of the virus rather than characterizing the immune response. Therefore, the study of humoral immunity to EV-D68 is nascent. The role of serum antibodies in protection from other viruses of the Enterovirus genus is varied. For example, three doses of inactivated poliovirus vaccine approaches 100% induction of serum neutralizing antibodies and is 80-96% effective at preventing paralytic poliomyelitis; however, vaccination does not fully prevent enteric or nasopharyngeal poliovirus shedding (Vidor et al., 2018) due to its inability to induce nasal or duodenal IgA (Sutter et al., 2018). Studies of rhinovirus infection show that humoral immunity to specific serotypes of virus fails to protect reliably against homotypic virus reinfection within months (Howard et al., 2016). These differences in extent of protection associated with antibody responses likely are due to the differing sites of pathology for these viruses: secondary neuronal spread after initial enteral infection for polioviruses versus localized respiratory tract infection for rhinoviruses. EV-D68 infection can cause disease in the respiratory tract and is associated with disease in the central nervous system, so the role of antibodies in protection and disease pathogenesis is likely to be complex. A better understanding this role would aid in the development of vaccines and therapies for EV-D68 infections.

SUMMARY

Thus, in accordance with the present disclosure, there is provided a method of detecting enterovirus D68 (EV-D68) infection in a subject comprising (a) contacting a sample from said subject with an antibody or antibody fragment having clone-paired heavy and light chain CDR sequences from Tables 3 and 4, respectively; and (b) detecting EV-D68 in said sample by binding of said antibody or antibody fragment to a EV-D68 antigen in said sample. The sample may be a body fluid, such as blood, sputum, tears, saliva, mucous or serum, semen, cervical or vaginal secretions, amniotic fluid, placental tissues, urine, exudate, transudate, tissue scrapings, respiratory droplets or aerosol, feces, etc. Detection may comprise, for example, ELISA, RIA, lateral flow assay, Western blot, and the like. The method may further comprise performing steps (a) and (b) a second time and determining a change in EV-D68 antigen levels as compared to the first assay.

The antibody or antibody fragment may be encoded by clone-paired variable sequences as set forth in Table 1, by light and heavy chain variable sequences having 70%, 80%, or 90% identity to clone-paired variable sequences as set forth in Table 1, or by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment.

In another aspect, the present disclosure provides a method of treating a subject infected with enterovirus D68 (EV-D68) or reducing the likelihood of infection of a subject at risk of contracting EV-D68, comprising delivering to said subject an antibody or antibody fragment having clone-paired heavy and light chain CDR sequences from Tables 3 and 4, respectively. The antibody or antibody fragment may be encoded by clone-paired variable sequences as set forth in Table 1, by light and heavy chain variable sequences having 70%, 80%, or 90% identity to clone-paired variable sequences as set forth in Table 1, or by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be any isotype, including without limitation IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE, DHS or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody.

The antibody or antibody fragment may be administered prior to infection or after infection, e.g., such as at or less than about 7 days, about 5 days, about 3 days, about 2 days, or about 1 day following infection. Treating may treat lung infection and/or neurologic infection, or wherein treating reduces lung infection and/or neurologic infection. Delivering may comprise antibody or antibody fragment administration systemically, by aerosol delivery, etc., or genetic delivery with an RNA or DNA sequence or vector encoding the antibody or antibody fragment. The method may further comprise treating said subject with a second therapy, such as an anti-viral therapy or an anti-inflammatory therapy.

In yet another aspect, there is provided a monoclonal antibody, wherein the antibody or antibody fragment is characterized by clone-paired heavy and light chain CDR sequences from Tables 3 and 4, respectively. The antibody or antibody fragment may be encoded by clone-paired variable sequences as set forth in Table 1, by light and heavy chain variable sequences having 70%, 80%, or 90% identity to clone-paired variable sequences as set forth in Table 1, or by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be any isotype, including without limitation IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE, DHS or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment may further comprise a cell penetrating peptide and/or is an intrabody.

A hybridoma or engineered cell encoding an antibody or antibody fragment wherein the antibody or antibody fragment is characterized by clone-paired heavy and light chain CDR sequences from Tables 3 and 4, respectively. The hybridoma or engineered cell may encode an antibody or antibody fragment encoded by clone-paired variable sequences as set forth in Table 1, by light and heavy chain variable sequences having 70%, 80%, or 90% identity to clone-paired variable sequences as set forth in Table 1, or by light and heavy chain variable sequences having 95% identity to clone-paired sequences as set forth in Table 1. The hybridoma or engineered cell may contain an antibody or antibody fragment comprising light and heavy chain variable sequences according to clone-paired sequences from Table 2, comprising light and heavy chain variable sequences having 70%, 80% or 90% identity to clone-paired sequences from Table 2, or comprising light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE, DHS or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment further comprises a cell penetrating peptide and/or is an intrabody.

Also provided is a vaccine formulation comprising one or more antibodies or antibody fragments characterized by clone-paired heavy and light chain CDR sequences from Tables 3 and 4, respectively. The antibody or antibody fragment may be encoded by clone-paired variable sequences as set forth in Table 1, by light and heavy chain variable sequences having 70%, 80%, or 90% identity to clone-paired variable sequences as set forth in Table 1, or by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE, DHS or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment further comprises a cell penetrating peptide and/or is an intrabody.

Still another embodiment comprises a vaccine formulation comprising one or more expression vectors encoding an antibody or antibody fragment characterized by clone-paired heavy and light chain CDR sequences from Tables 3 and 4, respectively. The antibody or antibody fragment may be encoded by clone-paired variable sequences as set forth in Table 1, by light and heavy chain variable sequences having 70%, 80%, or 90% identity to clone-paired variable sequences as set forth in Table 1, or by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE, DHS or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The expression vector(s) is/are Sindbis virus or VEE vector(s). The vaccine formulation may be formulated for delivery by needle injection, jet injection, or electroporation. The vaccine formulation may further comprise one or more expression vectors encoding for a second antibody or antibody fragment, such as a distinct antibody or antibody fragment characterized by clone-paired heavy and light chain CDR sequences from Tables 3 and 4, respectively. The antibody or antibody fragment is encoded by clone-paired variable sequences as set forth in Table 1, by light and heavy chain variable sequences having 70%, 80%, or 90% identity to clone-paired variable sequences as set forth in Table 1, or by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2.

Still a further embodiment comprises a method of protecting the health of a placenta and/or fetus of a pregnant subject infected with or at risk of infection with enterovirus D68, comprising delivering to said subject an antibody or antibody fragment having clone-paired heavy and light chain CDR sequences from Tables 3 and 4, respectively. The antibody or antibody fragment may be encoded by clone-paired variable sequences as set forth in Table 1, by light and heavy chain variable sequences having 70%, 80%, or 90% identity to clone-paired variable sequences as set forth in Table 1, or by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE, DHS or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment further comprises a cell penetrating peptide and/or is an intrabody.

The antibody or antibody fragment may be administered prior to infection or after infection, e.g., such as at or less than about 7 days, about 5 days, about 3 days, about 2 days, or about 1 day following infection. The subject may be a pregnant female, a sexually active female, or a female undergoing fertility treatments. Delivering may comprise antibody or antibody fragment administration, or genetic delivery with an RNA or DNA sequence or vector encoding the antibody or antibody fragment. The antibody or antibody fragment may increase the size of the placenta as compared to an untreated control. The antibody or antibody fragment may reduce viral load and/or pathology of the fetus as compared to an untreated control.

In still yet another embodiment, there is provided a method of determining the antigenic integrity, correct conformation and/or correct sequence of an enterovirus D68 antigen comprising (a) contacting a sample comprising said antigen with a first antibody or antibody fragment having clone-paired heavy and light chain CDR sequences from Tables 3 and 4, respectively; and (b) determining antigenic integrity, correct conformation and/or correct sequence of said antigen by detectable binding of said first antibody or antibody fragment to said antigen. The sample may comprise recombinantly produced antigen or may comprise a vaccine formulation or vaccine production batch. Detection may comprise ELISA, RIA, western blot, a biosensor using surface plasmon resonance or biolayer interferometry, or flow cytometric staining.

The first antibody or antibody fragment is encoded by clone-paired variable sequences as set forth in Table 1, by light and heavy chain variable sequences having 70%, 80%, or 90% identity to clone-paired variable sequences as set forth in Table 1, or by light and heavy chain variable sequences having 95% identity to clone-paired sequences as set forth in Table 1. The first antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The first antibody fragment may be a recombinant scFv (single chain fragment variable) antibody, Fab fragment, $F(ab')_2$ fragment, or Fv fragment. The method may further comprise performing steps (a) and (b) a second time to determine the antigenic stability of the antigen over time.

The method may further comprise (c) contacting a sample comprising said antigen with a second antibody or antibody fragment having clone-paired heavy and light chain CDR sequences from Tables 3 and 4, respectively; and (d) determining antigenic integrity of said antigen by detectable binding of said second antibody or antibody fragment to said antigen. The second antibody or antibody fragment is encoded by clone-paired variable sequences as set forth in Table 1, by light and heavy chain variable sequences having 70%, 80%, or 90% identity to clone-paired variable sequences as set forth in Table 1, or by light and heavy chain variable sequences having 95% identity to clone-paired sequences as set forth in Table 1. The second antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The second antibody fragment may be a recombinant scFv (single chain fragment variable) antibody, Fab fragment, $F(ab')_2$ fragment, or Fv fragment. The method may comprise performing steps (c) and (d) a second time to determine the antigenic stability of the antigen over time.

Also provided is a human monoclonal antibody or antibody fragment, or hybridoma or engineered cell producing the same, wherein said antibody binds to EV-D68 across at least two viral clades.

An additional embodiment comprises a human monoclonal antibody or antibody fragment, or hybridoma or engineered cell producing the same, wherein said antibody binds to EV-D68 VP1, VP2 and VP3. The antibody may bind to EV-D68 VP1 DE loop, and/or to EV-D68 VP2 EE loop, and/or to EV-D68 VP3 N-terminal loop.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 1. Antibody isolation. Sixty-four human monoclonal antibodies were isolated and screened using an indirect ELISA in which live virus isolates from the 2014 EV-D68 outbreak are directly coated onto an ELISA plate. Any hits are then fused with myeloma cells to make a hybridoma, which will theoretically continue dividing forever. After purifying antibodies, a number of in vitro characterization steps are performed to define their phenotypes.

FIG. 2. Antibody neutralization in vitro. In vitro neutralization is performed using the cell culture 50% infectious dose, or $CCID_{50}$ assay. Some antibodies are quite potent, some still very potent, and others weak, with about ⅓ of the mAbs showing some detectable neutralizing activity FIG. 3. Cross-reactive binding among clades. To compare across all mAbs, a heat map was generated using the half maximal effective concentration, or $EC_{50}$, from ELISAs. Some bind very well to all clades, while some have notable dropout, typically with the distant A2 clade.

FIG. 23. Expt. NIA-1849. Lung concentrations of MCP-1 and RANTES from EV-D68-infected AG129 mice treated post-infection with EV-D68-228. Treatment with EV-D68-228 within 48 hours post-infection significantly reduced concentrations of MCP-1 and RANTES on days 3 and 5 post-infection compared to placebo-treated mice. Treatment with IVIg 24 hours post-infection significantly reduced lung concentrations of MCP-1 at day 3 post-infection and reduced concentrations of RANTES at days 3 and 5 post-infection. (P<0.01, *P<0.001, ****P<0.0001 compared to placebo-treated mice). Designation of samples in graph corresponds left-to-right with vertical legend top-to-bottom.

FIG. 26. Expt. NIA-1869. Lung concentrations of IFNγ and TNFα from EV-D68-infected AG129 mice treated post-infection with EV-D68-228. No significant changes in concentrations of IFNγ or TNFα were observed after infection with EV-D68. Designation of samples in graph corresponds left-to-right with vertical legend top-to-bottom.

FIG. 27. Expt. NIA-1869. Lung concentrations of MIP-1α and GM-CSF from EV-D68-infected AG129 mice treated post-infection with EV-D68-228. No significant changes in concentrations of MIP-1α or GM-CSF were observed after infection with EV-D68. Designation of samples in graph corresponds left-to-right with vertical legend top-to-bottom.

(FIGS. 37A-B) Mice were inoculated with virus 24 hours after indicated dose of antibody, then viral titers were measured at indicated time points. (FIGS. 37C-D) Mice were inoculated with virus followed by 10 mg/kg (except where indicated) of antibody 4, 24, or 48 hours later, then viral titers were measured.

(FIGS. 39A-C) Mice were inoculated with virus 24 hours after indicated dose of antibody, then (FIG. 39A) viral titers were measured (n=3 per time point), (FIG. 39B) survival was monitored, and (FIG. 39C) neurologic scores (n=6 per time point) were recorded at indicated time points. Higher scores indicate more severe motor impairment. (FIGS. 39D-F) Mice were inoculated with virus followed by a 10 mg/kg dose of antibody, then (FIG. 39D) viral titers were measured (n=3 per time point), (FIG. 39E) survival was monitored, and (FIG. 39F) neurologic scores (n=6 per time point, except n=9 for 120 hr post) were recorded. Colored vertical arrows indicate time of treatment.

(FIG. 48C) post-infection. No lung virus titers were detected in mice treated with 10 mg/kg of EV68-228-TP or EV68-228-CHO at days 1, 3, or 5 post-infection. Treatment with 10 mg/kg of hIVIg only significantly reduced lung virus titers on day 5 post-infection. (P<0.01, **P<0.0001 compared to placebo-treated mice.)

228-TP or EV68-228-CHO. Treatment with 10 mg/kg of EV68-228-TP or EV68-228-CHO significantly reduced lung concentrations of MIP-1α on day 3 post-infection and reduced concentrations of RANTES on days 3 and 5 post-infection. No significant changes in concentrations of TNFα or GM-CSF were observed after infection with EV-D68. (****P<0.0001 compared to placebo-treated mice). Designation of samples in graph corresponds left-to-right with vertical legend top-to-bottom.

Figure 60:
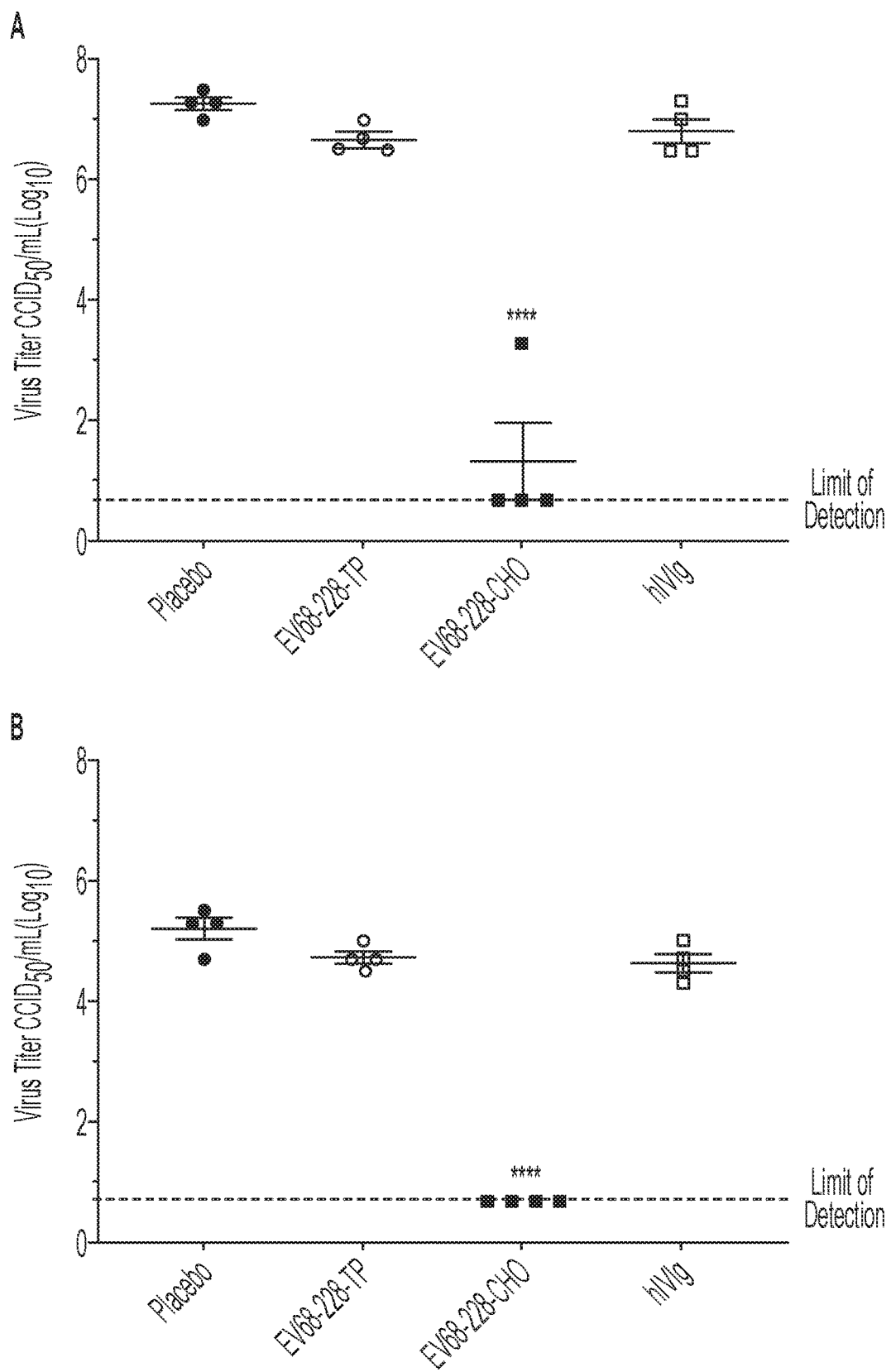

FIGS. 60A-B. Expt. NIA-1930. Lung virus titers of EV-D68-infected AG129 mice treated 48 hours post-infection with EV68-228-TP or EV68-228-CHO. Lung virus titers are shown on day 3 (FIG. 60A) and day 5 (FIG. 60B) post-infection. Only EV68-228-CHO significantly reduced lung virus titers on days 3 or 5 post-infection. (****P<0.0001 compared to placebo-treated mice).

Figure 61:
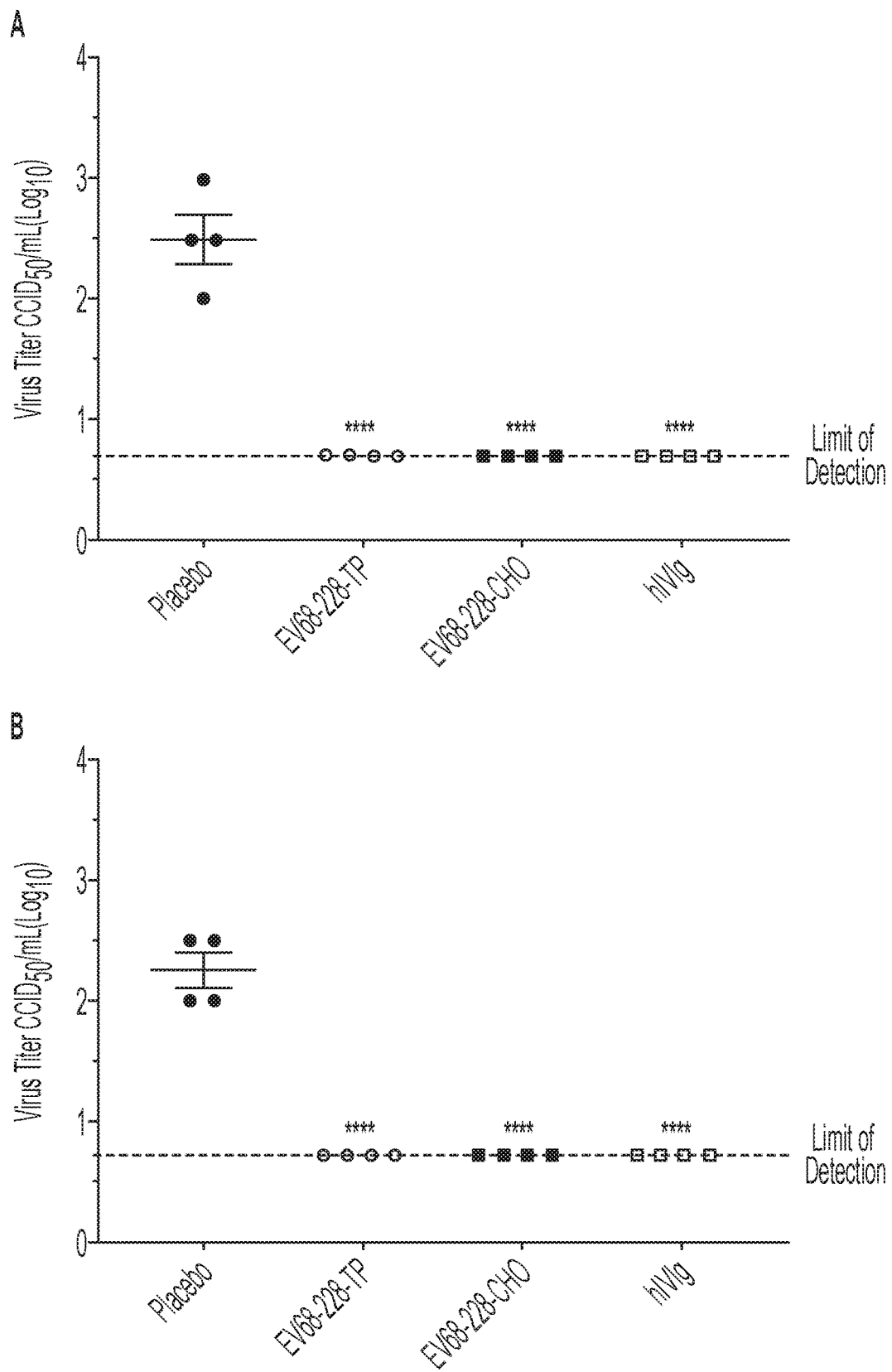

FIGS. 61A-B. Expt. NIA-1930. Blood virus titers of EV-D68-infected AG129 mice treated 48 hours post-infection with EV68-228-TP or EV68-228-CHO. Blood virus titers are shown at day 3 (FIG. 61A) and day 5 (FIG. 61B) post-infection. No virus was detected in the blood of mice treated with 10 mg/kg of EV68-228-TP or EV68-228-CHO on days 3 or 5 post-infection. Treatment with 10 mg/kg of hIVIg significantly reduced blood virus titers at days 3 and 5 post-infection. (****P<0.0001 compared to placebo-treated mice).

Figure 62:
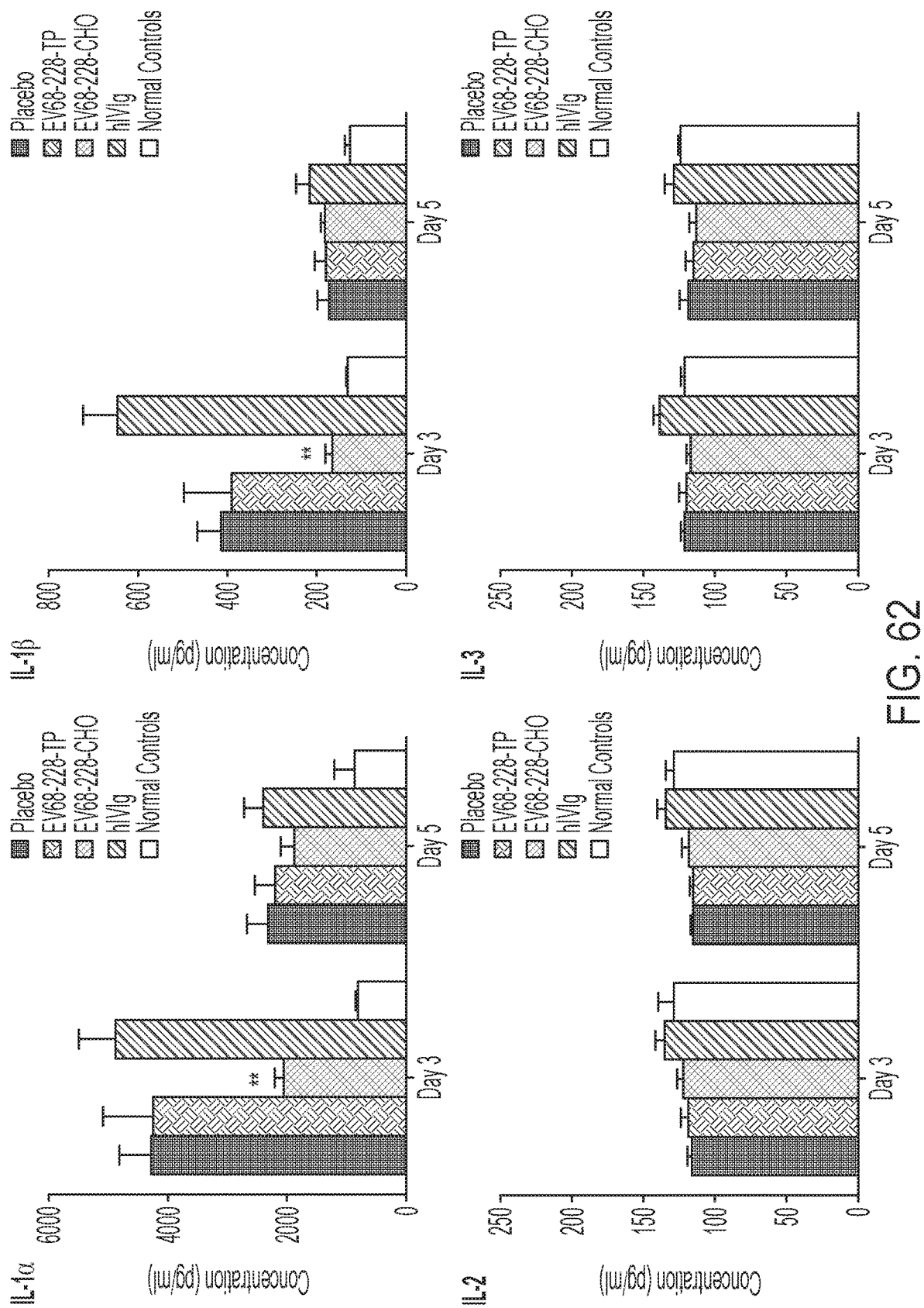

FIG. 62. Expt. NIA-1930. Lung concentrations of IL-1α, IL-1β, IL-2, and IL-3 from EV-D68-infected AG129 mice treated 48 hours post-infection with EV68-228-TP or EV68-228-CHO. Only treatment with 10 mg/kg of EV68-228-CHO significantly reduced concentrations of IL-1α and IL-1β on day 3 post-infection. No significant changes were observed in concentrations of IL-2 or IL-3 following infection. (**P<0.01 compared to placebo-treated mice). Designation of samples in graph corresponds left-to-right with vertical legend top-to-bottom.

Figure 63:
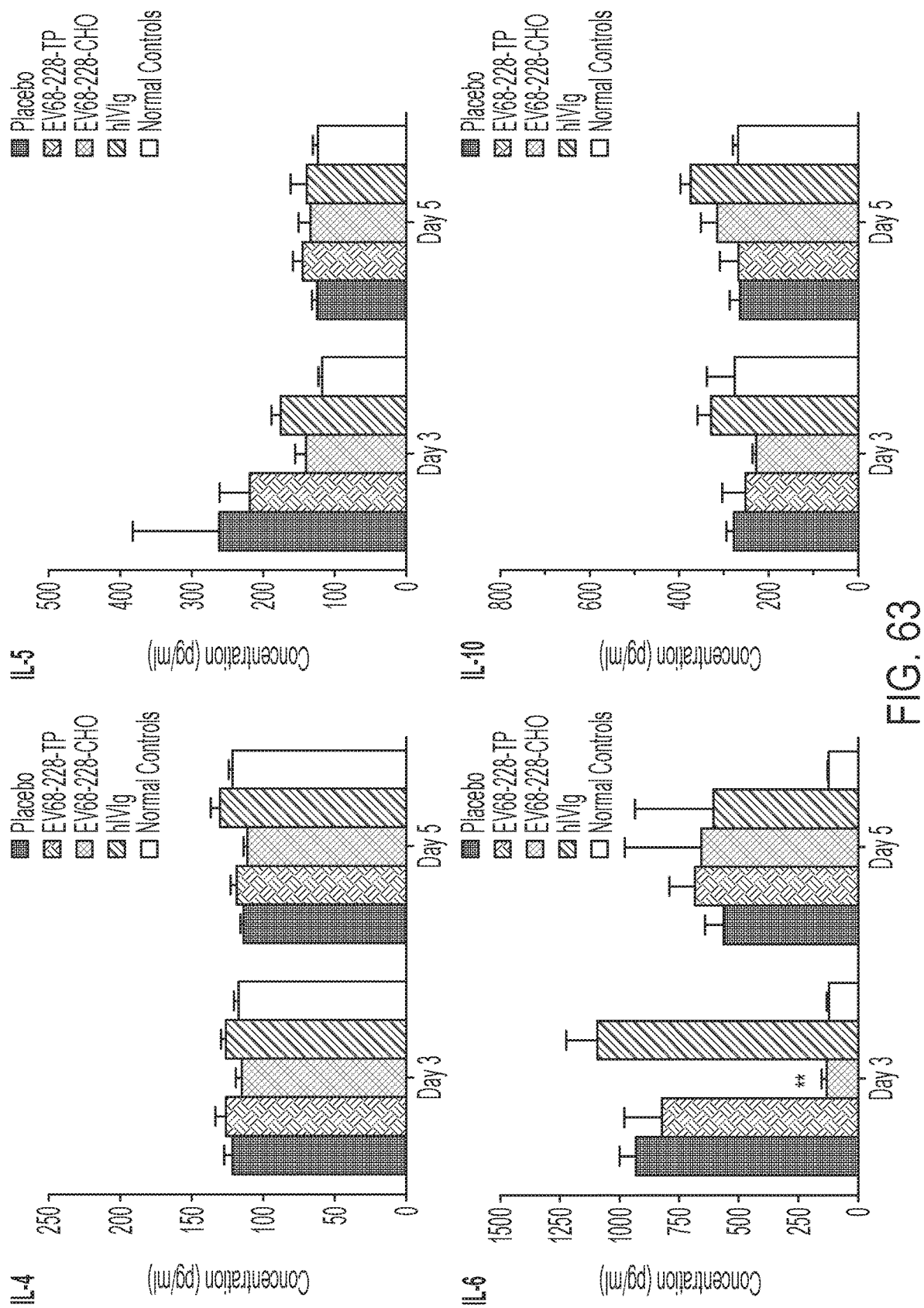

FIG. 63. Expt. NIA-1930. Lung concentrations of IL-4, IL-5, IL-6, and IL-10 from EV-D68-infected AG129 mice treated 48 hours post-infection with EV68-228-TP or EV68-228-CHO. Treatment with 10 mg/kg of EV68-228-TP or EV68-228-CHO significantly reduced concentrations of IL-6 on day 3 post-infection. No significant changes were observed in concentrations of IL-4, IL-5, or IL-10 following infection. (**P<0.01 compared to placebo-treated mice). Designation of samples in graph corresponds left-to-right with vertical legend top-to-bottom.

Figure 64:
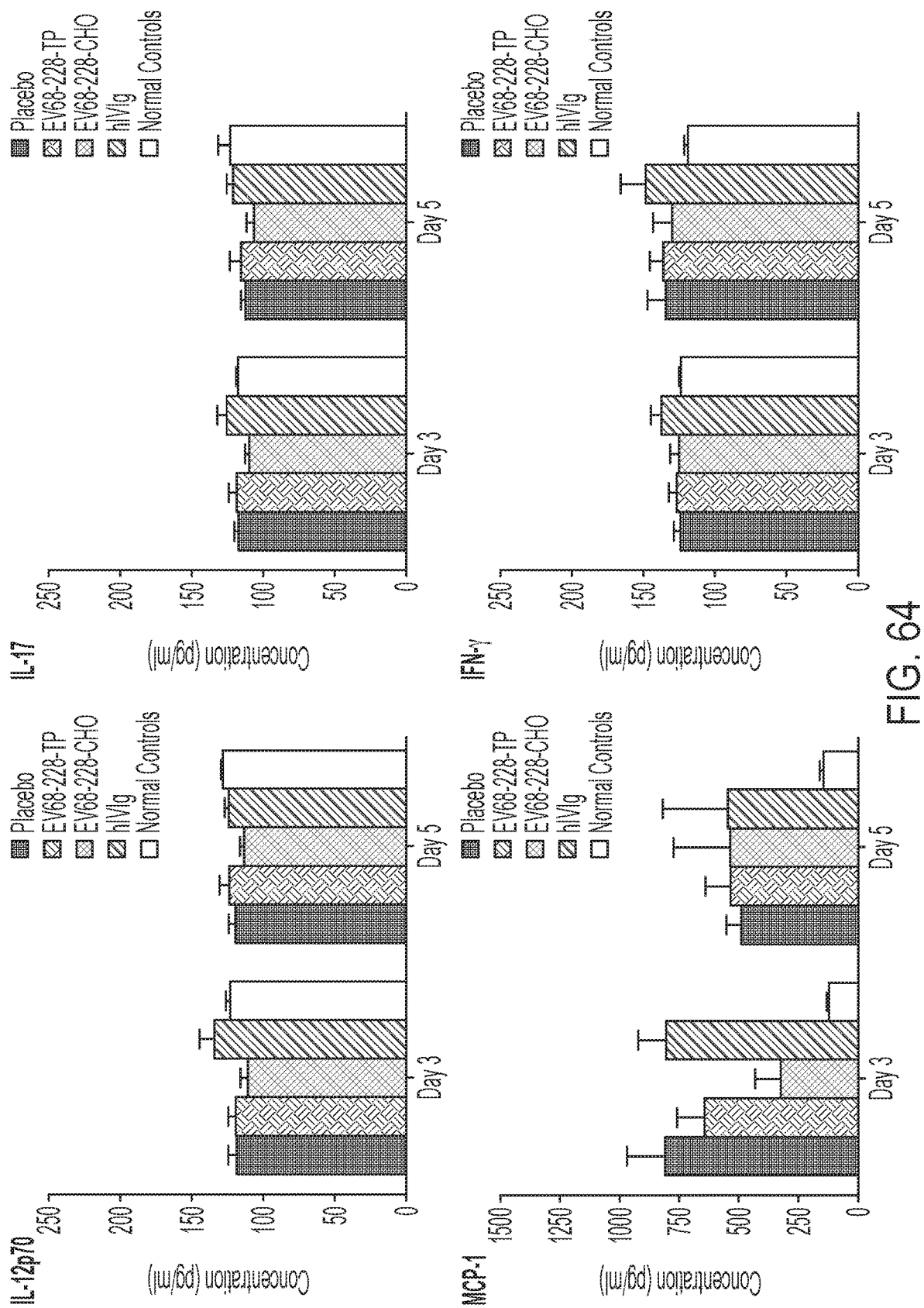

FIG. 64. Expt. NIA-1930. Lung concentrations of IL-12p70, IL-17, MCP-1, and IFN-γ from EV-D68-infected AG129 mice treated 48 hours post-infection with EV68-228-TP or EV68-228-CHO. No significant changes were observed in concentrations of IL-12p70, IL-17, MCP-1, or IFN-γ following infection. Designation of samples in graph corresponds left-to-right with vertical legend top-to-bottom.

Figure 65:
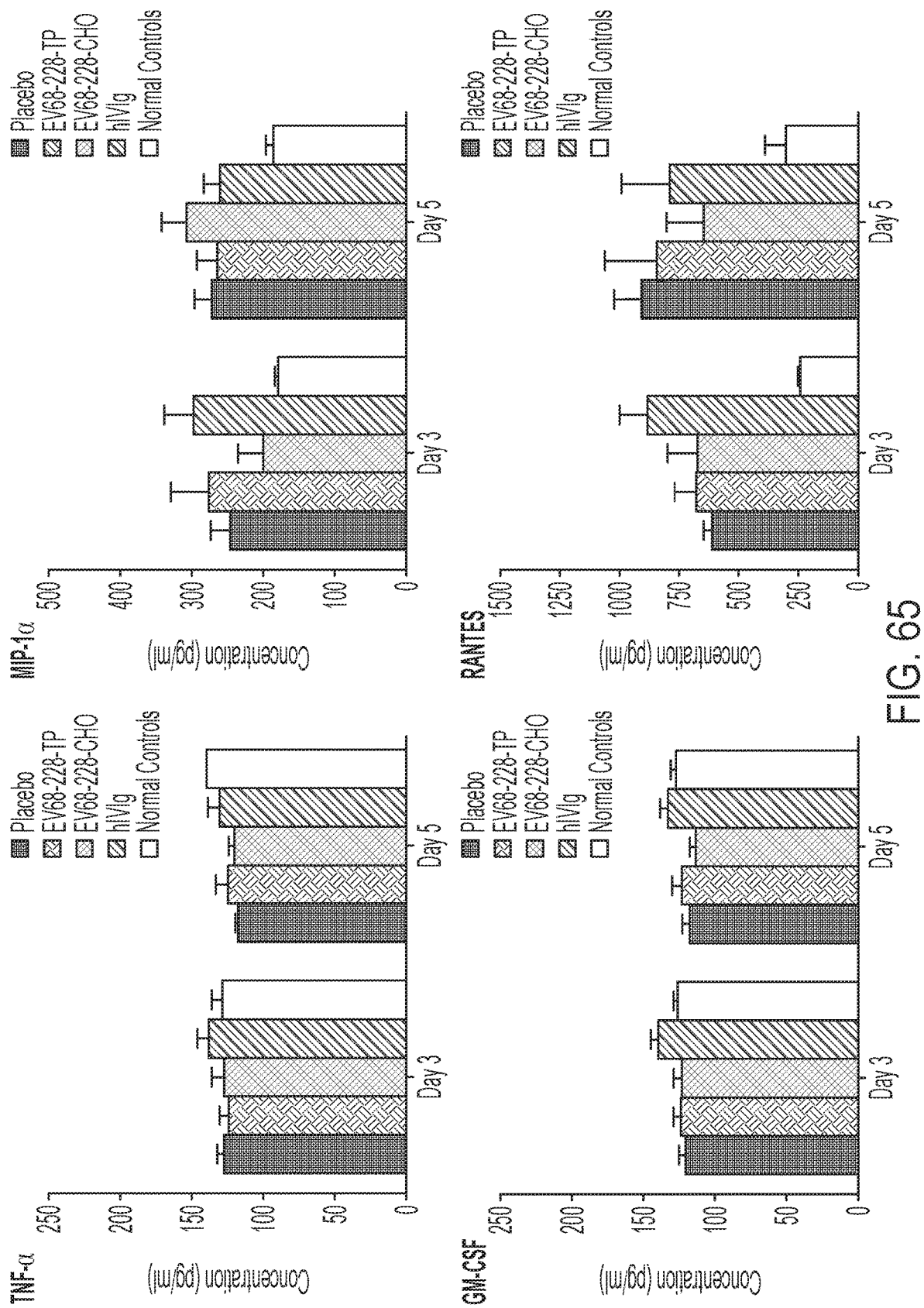

FIG. 65. Expt. NIA-1930. Lung concentrations of TNFα, MIP-1α, GM-CSF, and RANTES from EV-D68-infected AG129 mice treated 48 hours post-infection with EV68-228-TP or EV68-228-CHO. No significant changes in concentrations of TNFα, MIP-1α, GM-CSF, or RANTES were observed after infection with EV-D68. Designation of samples in graph corresponds left-to-right with vertical legend top-to-bottom.

Figure 66:
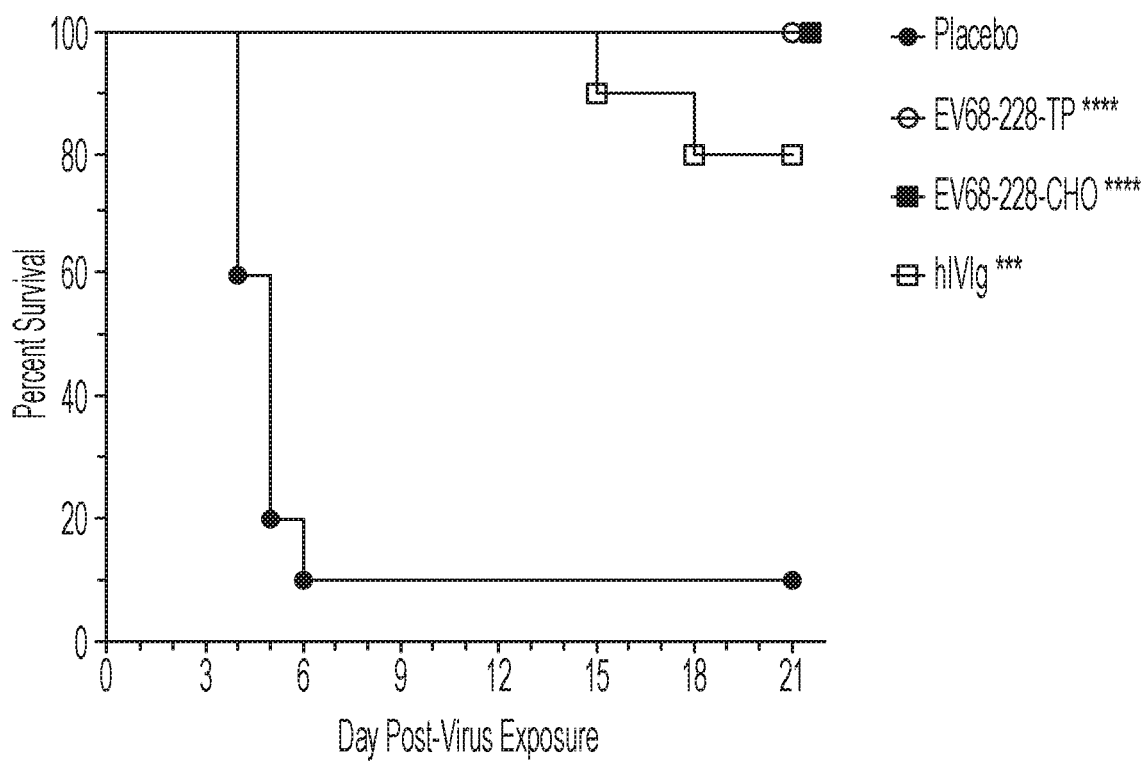

FIG. 66. Expt. NIA-1931. Survival of 10-day-old AG129 mice infected with EV-D68 and treated 24 hours pre-infection with EV68-228-TP or EV68-228-CHO. (n=10 mice/group). Treatment with a dose of 10 mg/kg of EV68-228-TP or completely protected mice from mortality. All ten mice treated with 10 mg/kg of EV68-228-CHO were protected from mortality. A dose of 10 mg/kg of IVIg protected eight of ten mice from mortality. Nine of the ten of the placebo-treated mice succumbed to the infection (*P<0.001, **P<0.0001 compared to placebo-treated mice).

Figure 67:
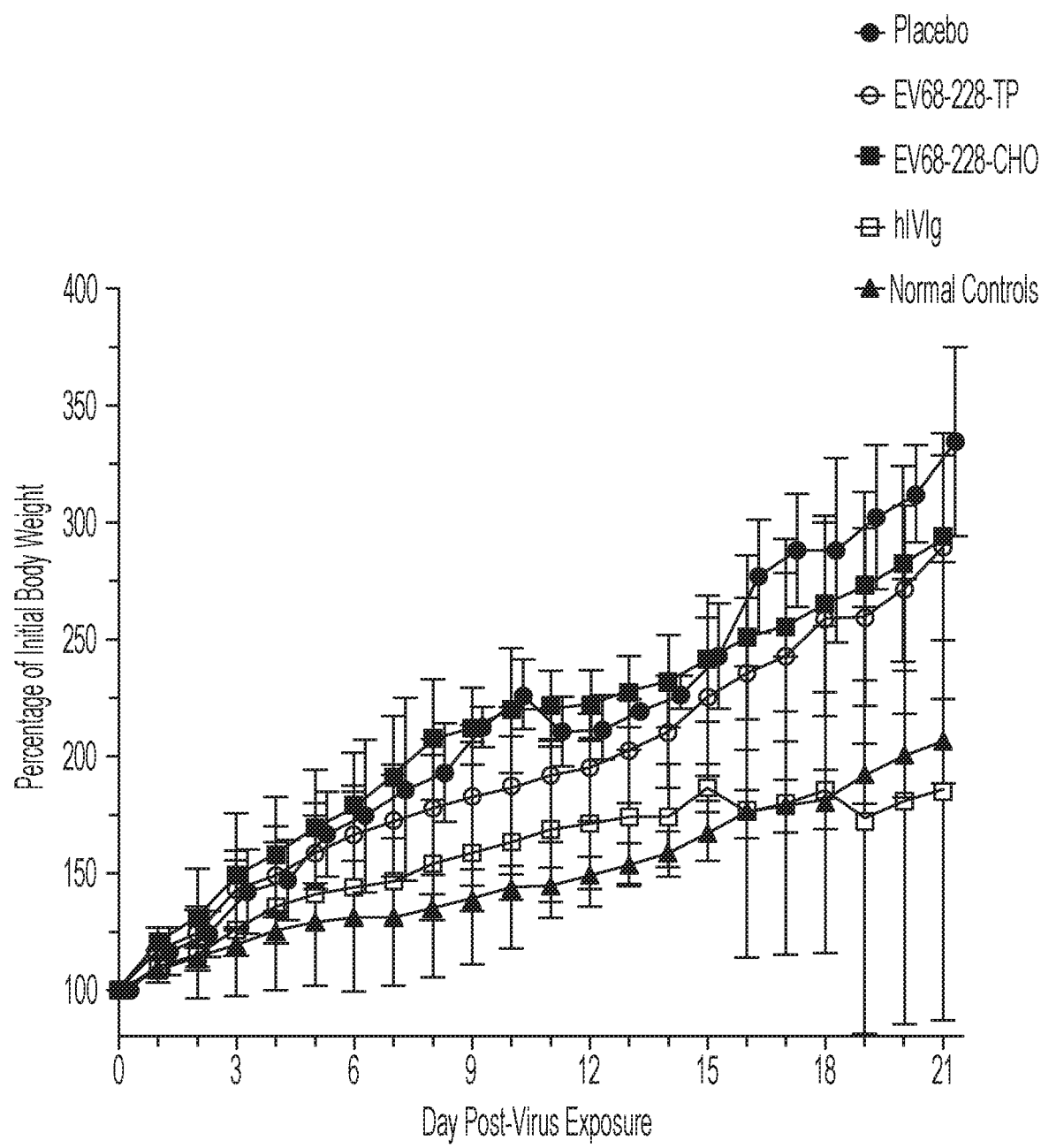

FIG. 67. Expt. NIA-1931. Percentages of initial body weight of EV-D68-infected 10-day-old AG129 mice treated 24 hours pre-infection with EV68-228-TP or EV68-228-CHO. No significant differences in weight loss were observed in mice treated 24 hours pre-infection with 10 mg/kg doses EV68-228-TP or EV68-228-CHO compared to placebo-treated mice. Treatment with a 10 mg/kg dose of hIVIg did not protect mice from weight loss.

Figure 68:
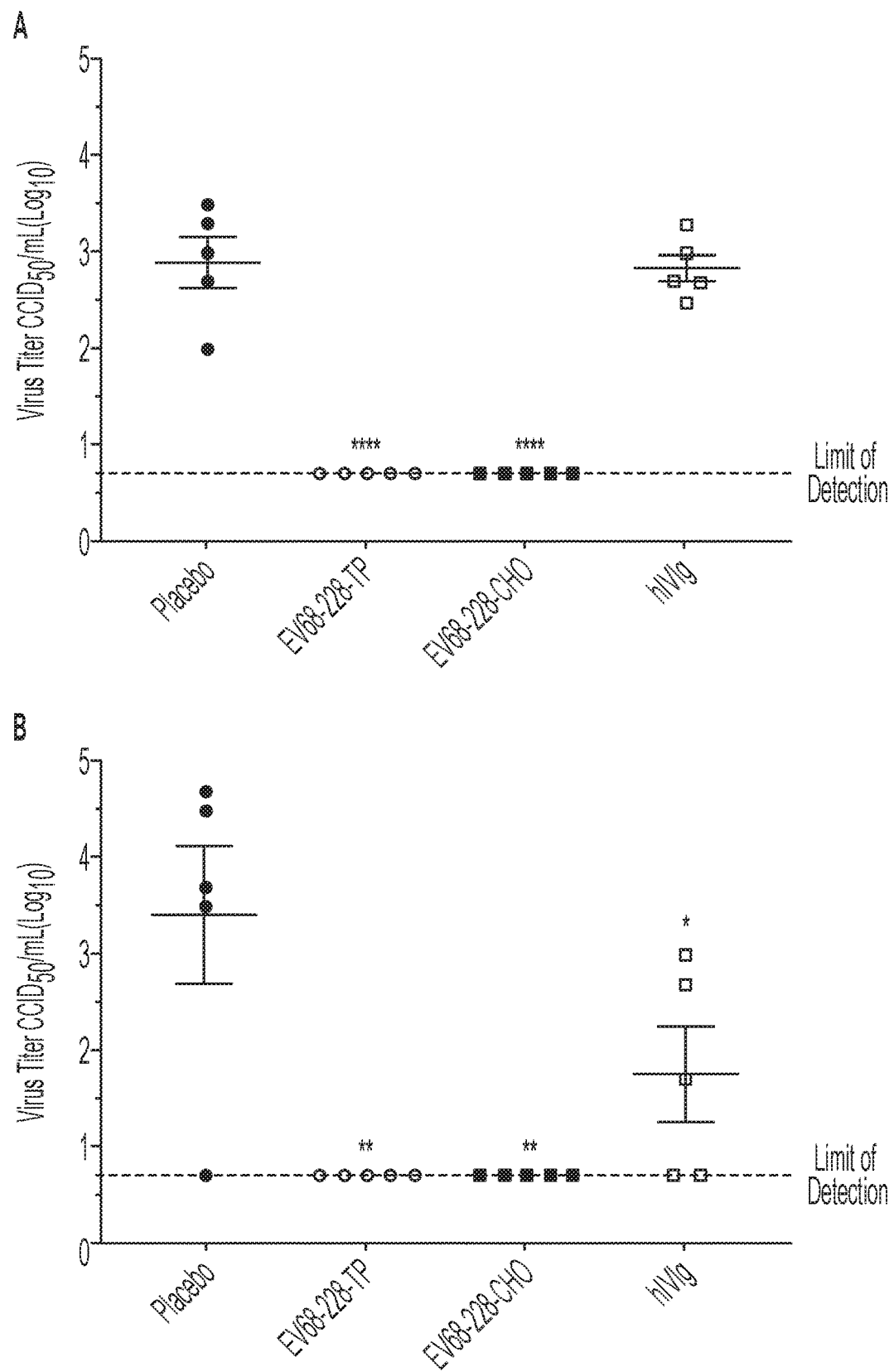

FIGS. 68A-B. Expt. NIA-1931. Blood virus titers on days 1 and 3 post-infection of 10-day-old AG129 mice infected with EV-D68 and treated 24 hours pre-infection with EV68-228-TP or EV68-228-CHO. Blood virus titers are shown on day 1 (FIG. 68A) and day 3 (FIG. 68B) post-infection. Treatment 24 hours pre-infection with 10 mg/kg of EV68-228-TP significantly reduced virus titers on days 1 and 3 post-infection. Treatment 24 hours pre-infection with 10 mg/kg of EV68-228-CHO significantly reduced virus titers on days 1 and 3 post-infection. Treatment 24 hours pre-infection with a dose of 10 mg/kg of IVIg significantly reduced blood virus titers on day 3 post-infection. (*P<0.05, P<0.01, **P<0.0001 compared to placebo-treated mice).

Figure 69:
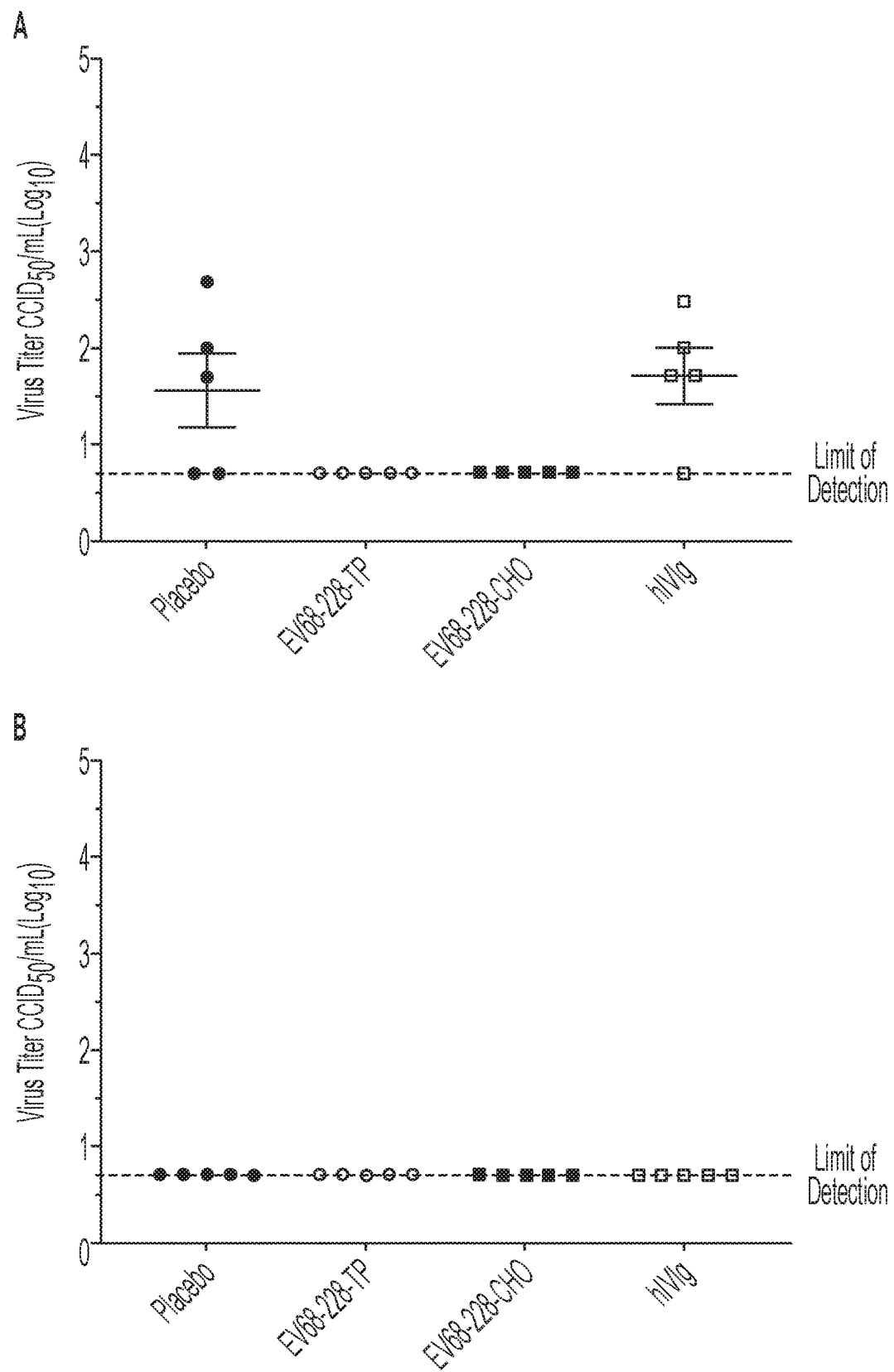

FIGS. 69A-B. Expt. NIA-1931. Blood virus titers on days 5 and 7 post-infection of 10-day-old AG129 mice infected with EV-D68 and treated 24 hours pre-infection with EV68-228-TP or EV68-228-CHO. Blood virus titers are shown on day 5 (FIG. 69A) and day 7 (FIG. 69B) post-infection. Treatment 24 hours pre-infection with 10 mg/kg of EV68-228-TP or EV68-228-CHO reduced virus titers on day 5 post-infection. No virus was detected at day 7 post-infection.

Figure 70:
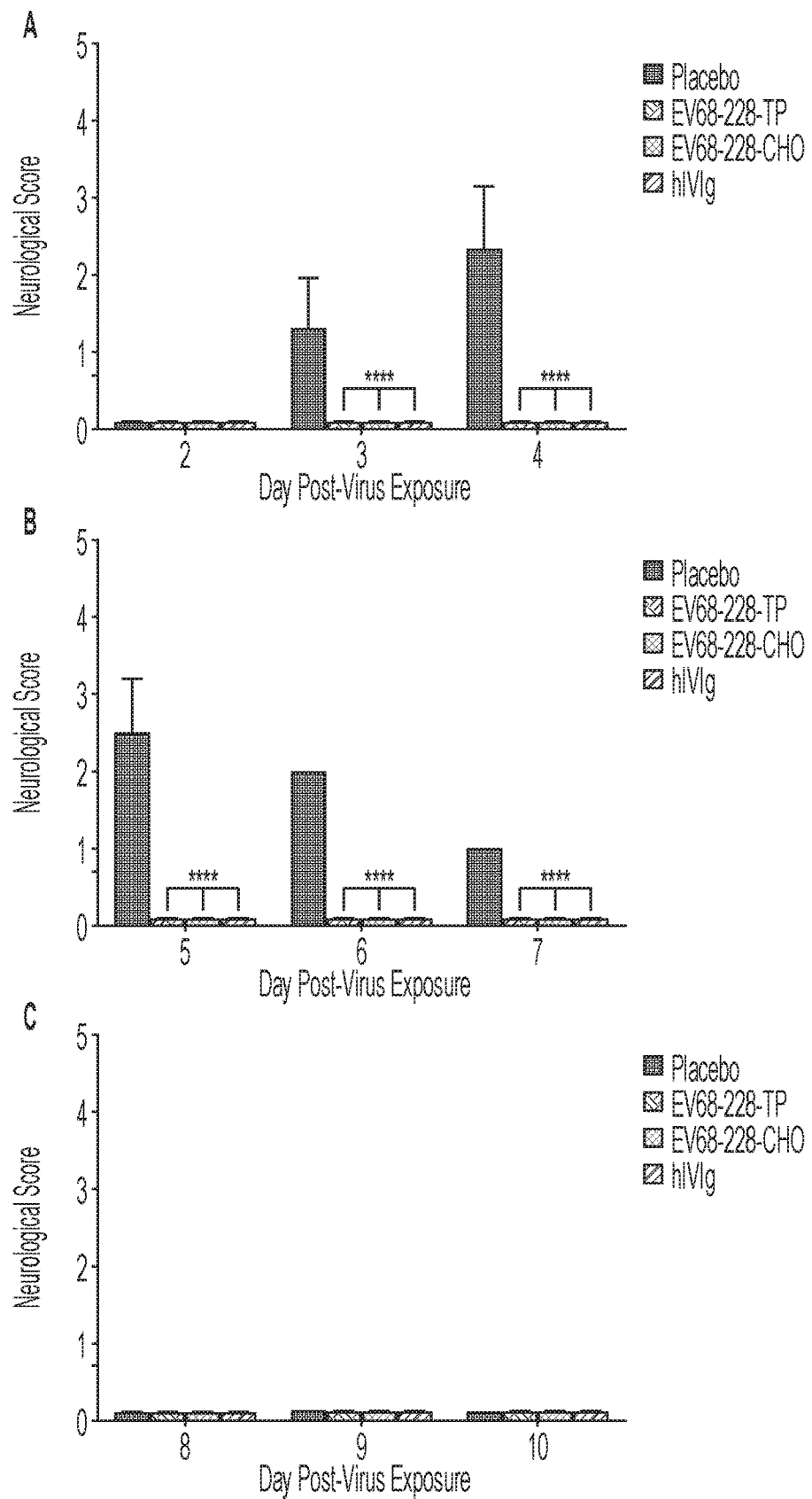

FIGS. 70A-C. Expt. NIA-1931. Neurological scores of 10-day-old AG129 mice infected with EV-D68 and treated 24 hours pre-infection with EV68-228-TP or EV68-228-CHO on days 2-10 post-infection. Neurological scores are shown for days 2-4 (FIG. 70A), days 5-7 (FIG. 70B), and days 8-10 (FIG. 70C) post-infection. Treatment 24 hours pre-infection with 10 mg/kg of EV68-228-TP or EV68-228-CHO completely prevented clinical signs of paralysis as measured by neurological scores. No neurological scores were observed in mice treated with a dose of 10 mg/kg of IVIg 24 hours pre-infection. (****P<0.0001 compared to placebo-treated mice).

Figure 71:
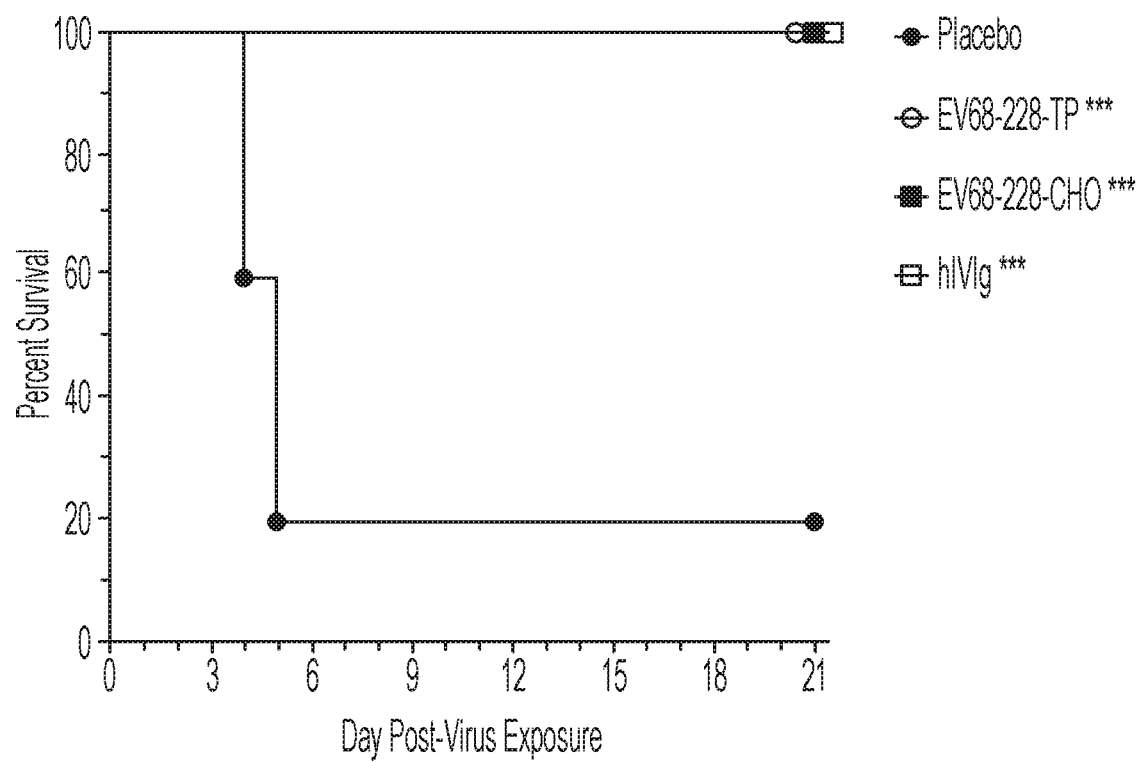

FIG. 71. Expt. NIA-1931. Survival of 10-day-old AG129 mice infected with EV-D68 and treated 24 hours post-infection with EV68-228-TP or EV68-228-CHO. (n=10 mice/group). Treatment with a dose of 10 mg/kg of EV68-228-TP or completely protected mice from mortality. All ten mice treated with 10 mg/kg of EV68-228-CHO were protected from mortality. A dose of 10 mg/kg of IVIg protected ten of ten mice from mortality. Eight of the ten of the placebo-treated mice succumbed to the infection (***P<0.001 compared to placebo-treated mice).

Figure 72:
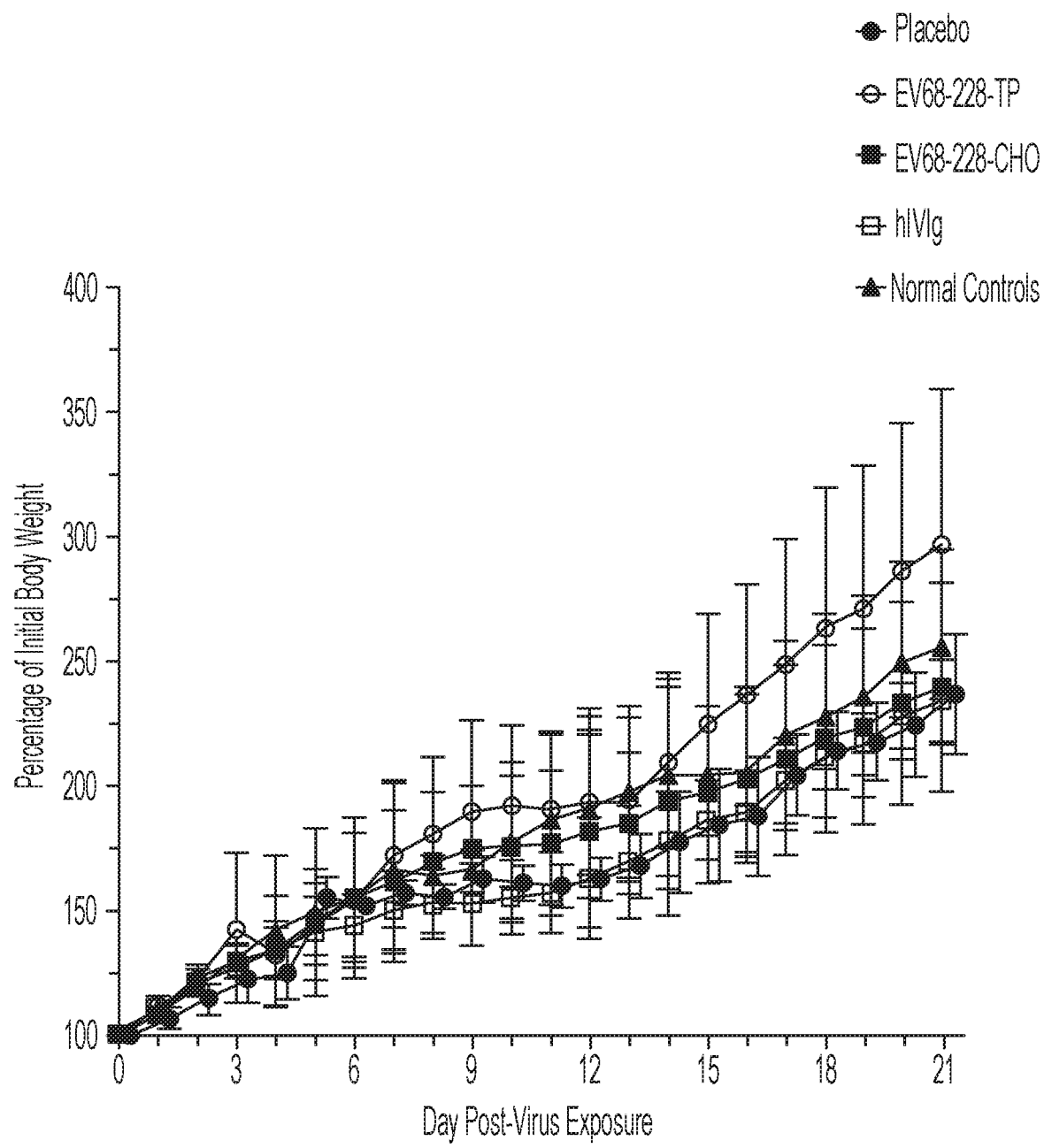

FIG. 72. Expt. NIA-1931. Percentages of initial body weight of EV-D68-infected 10-day-old AG129 mice treated 24 hours post-infection with EV68-228-TP or EV68-228-CHO. No significant differences in weight loss were observed in mice treated 24 hours post-infection with 10 mg/kg doses EV68-228-TP or EV68-228-CHO compared to placebo-treated mice. Treatment with a 10 mg/kg dose of hIVIg did not protect mice from weight loss.

Figure 73:
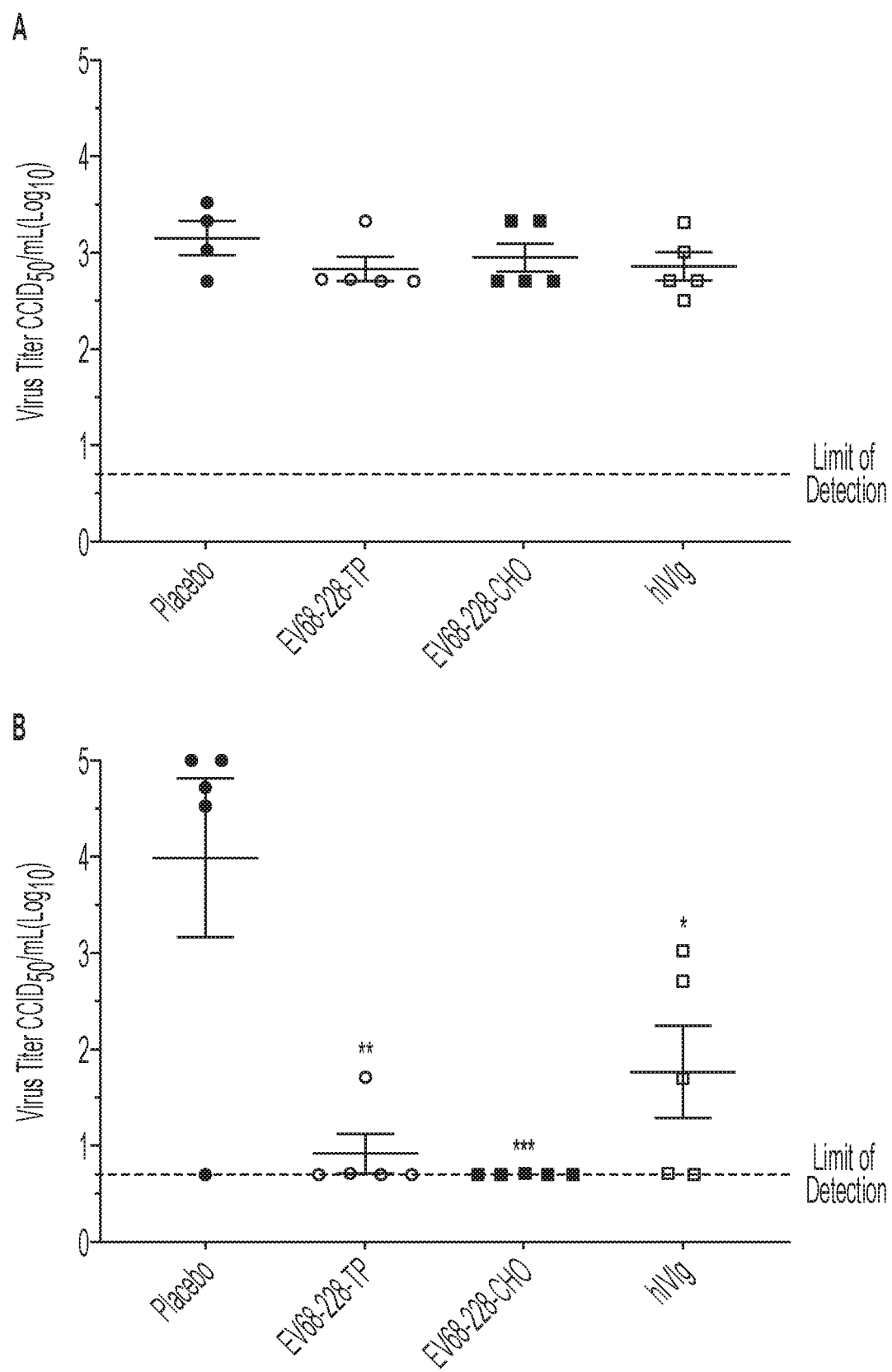

FIGS. 73A-B. Expt. NIA-1931. Blood virus titers on days 1 and 3 post-infection of 10-day-old AG129 mice infected with EV-D68 and treated 24 hours post-infection with EV68-228-TP or EV68-228-CHO. Blood virus titers are shown on day 1 (FIG. 73A) and day 3 (FIG. 73B) post-infection. Treatment 24 hours post-infection with 10 mg/kg of EV68-228-TP significantly reduced virus titers on day 3 post-infection. Treatment 24 hours post-infection with 10 mg/kg of EV68-228-CHO significantly reduced virus titers on day 3 post-infection. Treatment 24 hours post-infection with a dose of 10 mg/kg of IVIg significantly reduced blood virus titers on day 3 post-infection. (*$P<0.05$, $P<0.01$, **$P<0.0001$ compared to placebo-treated mice).

Figure 74:
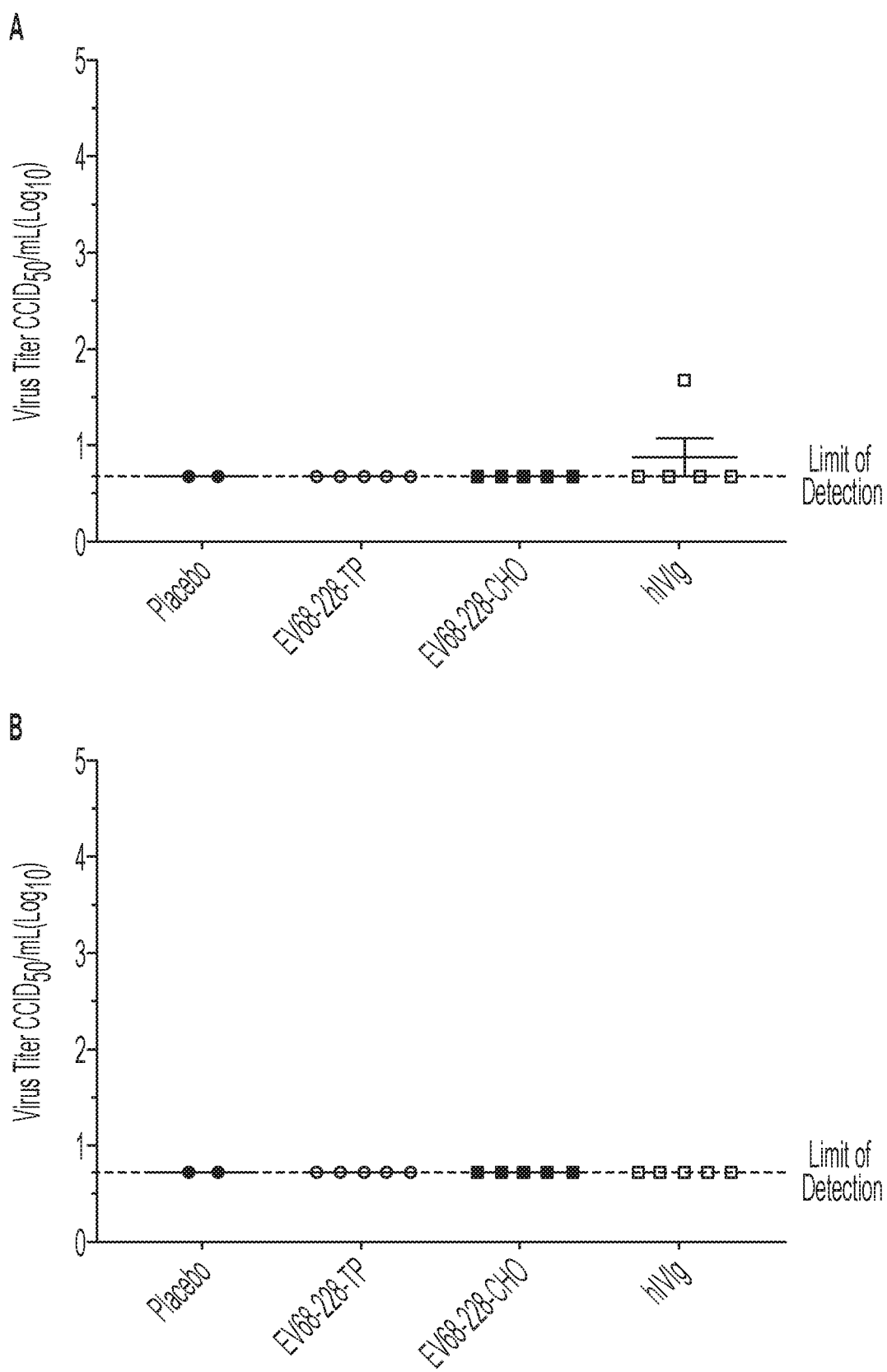

FIGS. 74A-B. Expt. NIA-1931. Blood virus titers on days 5 and 7 post-infection of 10-day-old AG129 mice infected with EV-D68 and treated 24 hours post-infection with EV68-228-TP or EV68-228-CHO. Blood virus titers are shown on day 5 (FIG. 74A) and day 7 (FIG. 74B) post-infection. No virus was detected after treatment 24 hours post-infection with 10 mg/kg of EV68-228-TP or EV68-228-CHO on day 5 post-infection. No virus was detected in any mice at day 7 post-infection.

Figure 75:
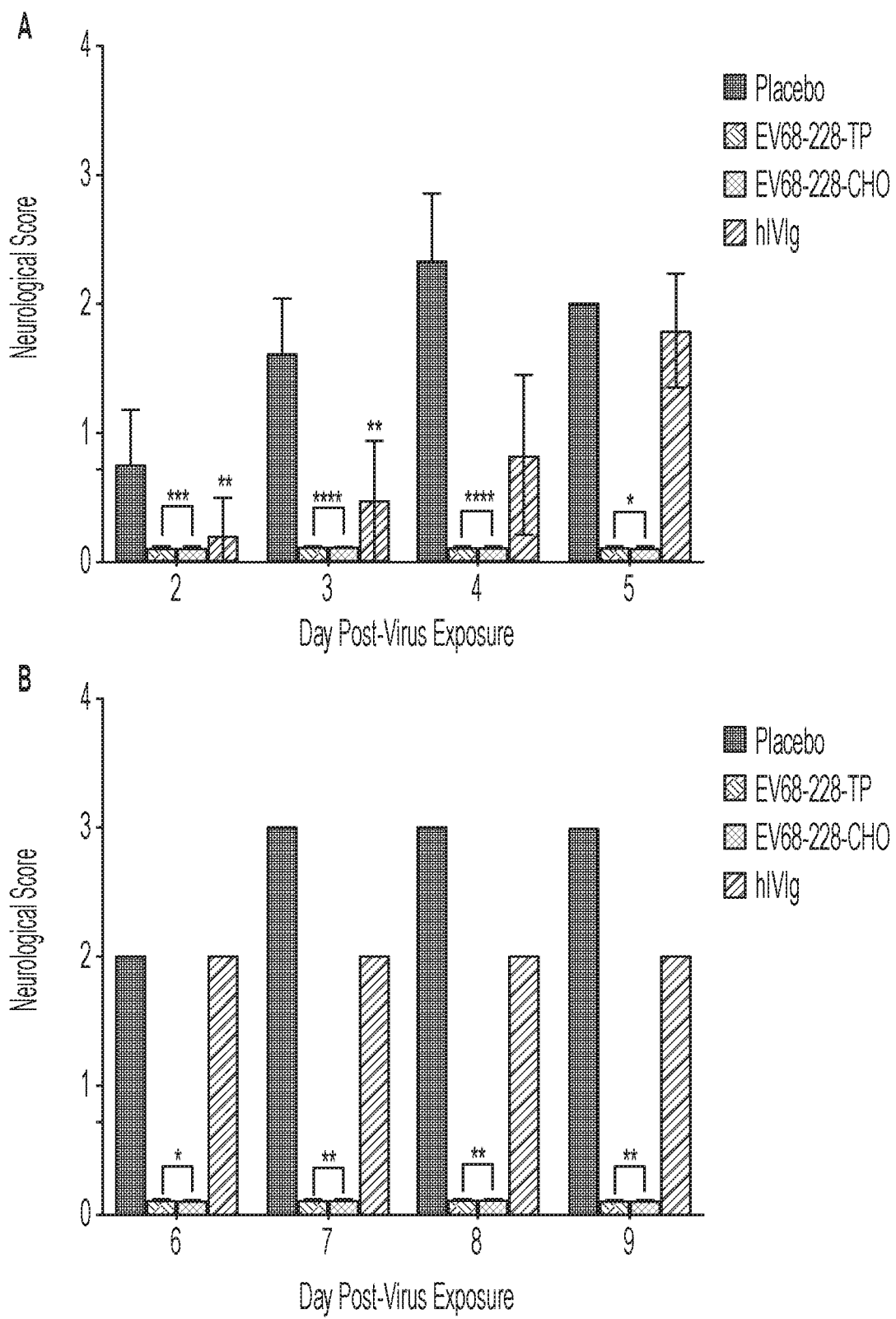

FIGS. 75A-B. Expt. NIA-1931. Neurological scores of 10-day-old AG129 mice infected with EV-D68 and treated 24 hours post-infection with EV68-228-TP or EV68-228-CHO on days 2-9 post-infection. Neurological scores are shown for days 2-5 (FIG. 75A) and days 6-9 (FIG. 75B) post-infection. Treatment 24 hours post-infection with 10 mg/kg of EV68-228-TP or EV68-228-CHO significantly reduced signs of paralysis as measured by neurological scores on days 2-9 post-infection. Treatment with hIVIg at a dose of 10 mg/kg 24 hours after infection only reduced neurological scores on days 2 and 3 post-infection. (*$P<0.05$, $P<0.01$, *$P<0.001$, ****$P<0.0001$ compared to placebo-treated mice). Designation of samples in graph corresponds left-to-right with vertical legend top-to-bottom.

Figure 76:
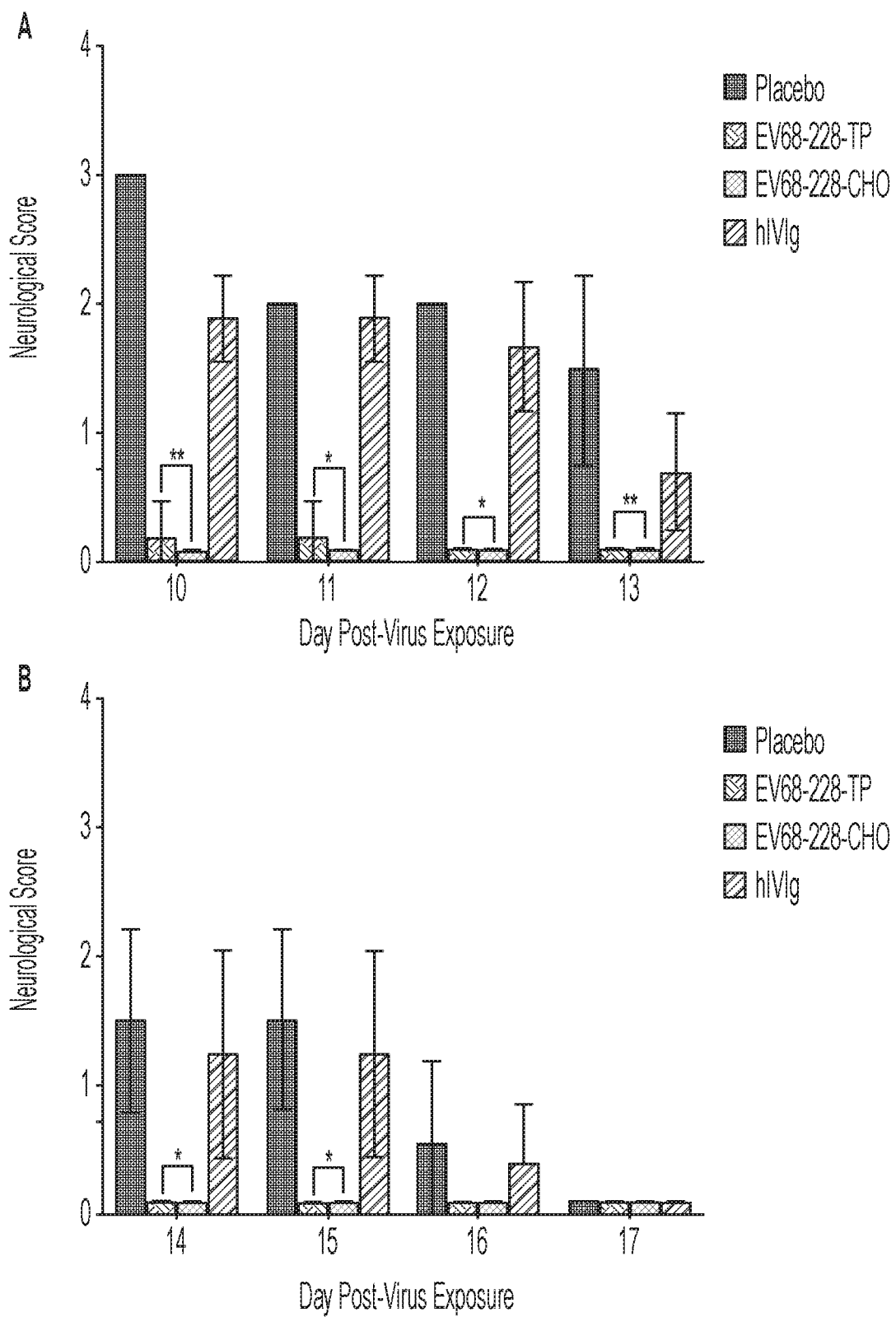

FIGS. 76A-B. Expt. NIA-1931. Neurological scores of 10-day-old AG129 mice infected with EV-D68 and treated 24 hours post-infection with EV68-228-TP or EV68-228-CHO on days 10-17 post-infection. Neurological scores are shown for days 10-13 (FIG. 76A) and days 14-17 (FIG. 76B) post-infection. Treatment 24 hours post-infection with 10 mg/kg of EV68-228-TP or EV68-228-CHO significantly reduced signs of paralysis as measured by neurological scores on days 10-16 post-infection. Treatment with hIVIg at a dose of 10 mg/kg 24 hours after infection did not significantly reduce neurological scores. (*$P<0.05$, **$P<0.01$ compared to placebo-treated mice). Designation of samples in graph corresponds left-to-right with vertical legend top-to-bottom.

Figure 77:
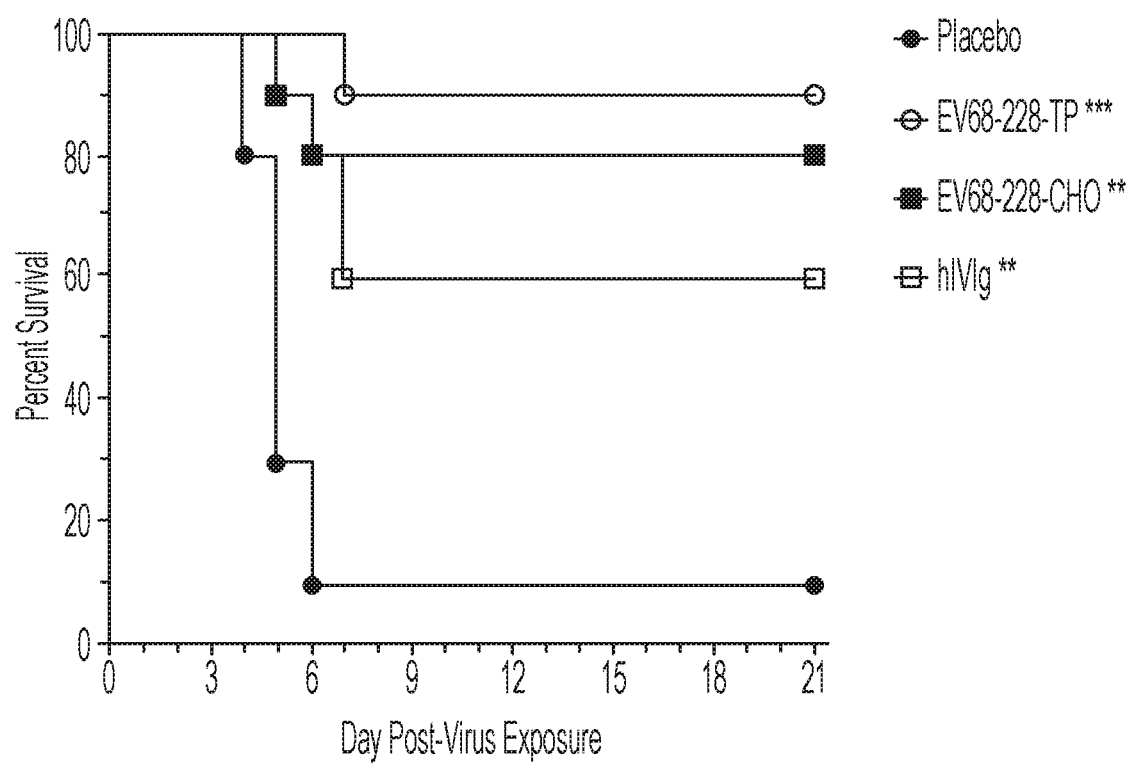

FIG. 77. Expt. NIA-1931. Survival of 10-day-old AG129 mice infected with EV-D68 and treated 48 hours post-infection with EV68-228-TP or EV68-228-CHO. (n=10 mice/group). Treatment with a dose of 10 mg/kg of EV68-228-TP protected nine of ten mice from mortality. Eight of ten mice treated with 10 mg/kg of EV68-228-CHO were protected from mortality. A dose of 10 mg/kg of IVIg protected six of ten mice from mortality. Nine of the ten of the placebo-treated mice succumbed to the infection ($P<0.01$, *$P<0.001$ compared to placebo-treated mice).

Figure 78:
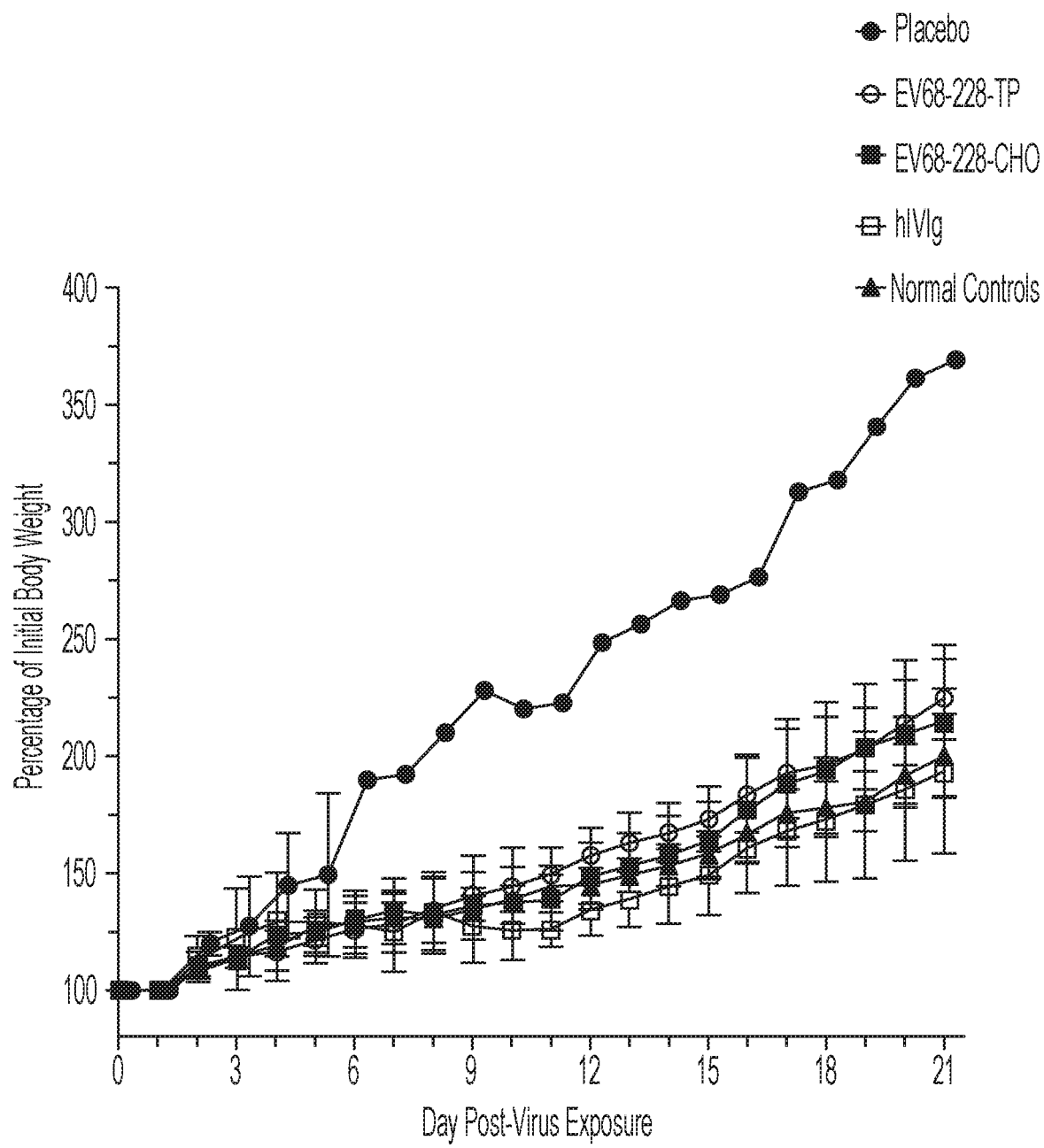

FIG. 78. Expt. NIA-1931. Percentages of initial body weight of EV-D68-infected 10-day-old AG129 mice treated 48 hours post-infection with EV68-228-TP or EV68-228-CHO. No significant differences in weight loss were observed in mice treated 24 hours post-infection with 10 mg/kg doses EV68-228-TP or EV68-228-CHO compared to placebo-treated mice. Treatment with a 10 mg/kg dose of hIVIg did not protect mice from weight loss.

FIGS. 79A-B. Expt. NIA-1931. Blood virus titers on days 1 and 3 post-infection of 10-day-old AG129 mice infected with EV-D68 and treated 48 hours post-infection with EV68-228-TP or EV68-228-CHO. Blood virus titers are shown on day 1 (FIG. 79A) and day 3 (FIG. 79B) post-infection. Treatment 48 hours post-infection with 10 mg/kg of EV68-228-TP or EV68-228-CHO did not significantly reduce blood virus titers. Treatment 48 hours post-infection with a dose of 10 mg/kg of IVIg did not significantly reduce blood virus titers.

FIGS. 80A-B. Expt. NIA-1931. Blood virus titers on days 5 and 7 post-infection of 10-day-old AG129 mice infected with EV-D68 and treated 48 hours post-infection with EV68-228-TP or EV68-228-CHO. Blood virus titers are shown on day 5 (FIG. 80A) and day 7 (FIG. 80B) post-infection. No virus was detected after treatment 24 hours post-infection with 10 mg/kg of EV68-228-TP or EV68-228-CHO on day 5 post-infection. No virus was detected in any mice at day 7 post-infection.

FIGS. 81A-B. Expt. NIA-1931. Neurological scores of 10-day-old AG129 mice infected with EV-D68 and treated 48 hours post-infection with EV68-228-TP or EV68-228-CHO on days 3-10 post-infection. Neurological scores are shown for days 3-6 (FIG. 81A) and days 7-10 (FIG. 81B) post-infection. Treatment 48 hours post-infection with 10 mg/kg of EV68-228-TP significantly reduced neurological scores on days 3-5 post-infection. A single administration of a 10 mg/kg dose of EV68-228-CHO 48 hours after infection significantly reduced signs of paralysis as measured by neurological scores on days 3-6 post-infection. Treatment with hIVIg at a dose of 10 mg/kg 48 hours after infection did not significantly reduce neurological scores post-infection. (*$P<0.05$, *$P<0.001$, **$P<0.0001$ compared to placebo-treated mice). Designation of samples in graph corresponds left-to-right with vertical legend top-to-bottom.

DESCRIPTION OF ILLUSTRATIVE EMBODIMENTS

As discussed above, enterovirus D68 (EV-D68) can cause outbreaks of respiratory illness across the world, mostly in children. Clusters of acute flaccid myelitis, a poliomyelitis-like neuromuscular weakness syndrome, often occur concurrently with EV-D68 respiratory outbreaks. Seroepidemiologic studies have found that the serum of nearly everyone older than 2 to 5 years contains anti-EV-D68 neutralizing antibodies, suggesting that EV-D68 is a ubiquitous pathogen of childhood. However, knowledge of the viral epitopes against which the humoral immune response is directed is only inferred from previous studies of related viruses. Here, the inventors have generated 64 human monoclonal antibodies against EV-D68, some of which are potently neutralizing. These are believed to be the first human mAbs against this pathogen and the inventors propose their use in detecting, treating and preventing EV-D68 infections. These and other aspects of the disclosure are described in detail below.

I. ENTEROVIRUS D68

Enterovirus 68 (EV68, EV-D68, HEV68) is a member of the Picornaviridae family, an enterovirus. First isolated in California in 1962 and once considered rare, it has been on a worldwide upswing in the 21st century. It is suspected of causing a polio-like disorder called acute flaccid myelitis.

EV68 is one of the more than one hundred types of enteroviruses, a group of ssRNA viruses containing the polioviruses, coxsackieviruses, and echoviruses, and it is unenveloped. Unlike all other enteroviruses, EV68 displays acid lability and a lower optimum growth temperature, both characteristic features of the human rhinoviruses. It was previously called human rhinovirus 87 by some researchers. Children less than 5 years old and children with asthma appear to be most at risk for the illness, although illness in adults with asthma and immunosuppression have also been reported.

Since its discovery, EV68 had been described mostly sporadically in isolated cases. Six clusters (equal to or more than 10 cases) or outbreaks between 2005 and 2011 have been reported from the Philippines, Japan, the Netherlands, and the states of Georgia, Pennsylvania and Arizona in the United States. EV68 was found in 2 of 5 children during a 2012/13 cluster of polio-like disease in California. In August 2014, the virus caused clusters of respiratory disease in the United States. By mid-October 691 people in 46 states and the District of Columbia had come down with a respiratory illness caused by EV-D68 and five children died. In 2016, 29 cases were reported in Europe (5 in France and Scotland. 3 each in Sweden, Norway and Spain).

Since the year 2000, the original virus strains diversified and evolved a genetically distinct outbreak strain, clade B1. It is Clade B1, but not older strains, which has been associated with AFM and is neuropathic in animal models. Cases have been described to occur late in the enterovirus season (roughly the period of time between the spring equinox and autumn equinox), which is typically during August and September in the Northern Hemisphere.

EV68 almost exclusively causes respiratory illness, which varies from mild to severe, but can cause a range of symptoms, from none at all, to subtle flu-like symptoms, to debilitating respiratory illness and a suspected rare involvement in a syndrome with polio-like symptoms. Like all enteroviruses, it can cause variable rashes, abdominal pain and soft stools. Initial symptoms are similar to those for the common cold, including a runny nose, sore throat, cough, and fever. As the disease progresses, more serious symptoms may occur, including difficulty breathing as in pneumonia, reduced alertness, a reduction in urine production, and dehydration, and may lead to respiratory failure.

The degree of severity of symptoms experienced seems to depend on the demographic population in question. Experts estimate that the majority of the population has, in fact, been exposed to the enterovirus, but that no symptoms are exhibited in healthy adults. In contrast, EV-D68 is disproportionately debilitating in very young children, as well as the very weak. While several hundred people (472), mostly youth, have been exposed to the disease, less than a hundred of those patients have been diagnosed with severe symptoms (such as paralysis).

The virus has been suspected as one cause of acute flaccid myelitis a rare muscle weakness, usually due to polio, since two California children who tested positive for the virus had paralysis of one or more limbs reaching peak severity within 48 hours of onset. Recovery of motor function was poor at 6-month follow-up. As of October 2014, the CDC was investigating 10 cases of paralysis and/or cranial dysfunction in Colorado and other reports around the country, coinciding with the increase in enterovirus D68 activity. As of October 2014, it was believed that the actual number of cases might be 100 or more. As of 2018 the link of EV-D68 and the paralysis is strong, meeting six Bradford Hill criteria fully and two partially. The CDC issued a statement on Oct. 17, 2018 claiming "Right now, we know that poliovirus is not the cause of these AFM cases. CDC has tested every stool specimen from the AFM patients, none of the specimens have tested positive for the poliovirus." In 2014, a real-time PCR test to speed up detection was developed by CDC.

There is no specific treatment and no vaccine, so the illness has to run its course; treatment is directed against symptoms (symptomatic treatment). Most people recover completely; however, some need to be hospitalized, and some have died as a result of the virus. Five EV68 paralysis cases were unsuccessfully treated with steroids, intravenous immunoglobulin and/or plasma exchange. The treatment had no apparent benefit as no recovery of motor function was seen. A 2015 study suggested the antiviral drug pleconaril may be useful for the treatment of EV-D68.

Since the virus is spread through saliva and phlegm as well as stool, washing hands is important. Sick people can attempt to decrease spreading the virus by basic sanitary measures, such as covering the nose and mouth when sneezing or coughing. Other measures including cleaning surfaces and toys. For hospitalized patients with EV-D68 infection, the CDC recommends transmission-based precautions, i.e., standard precautions, contact precautions, as is recommended for all enteroviruses, and to consider droplet precautions. According to the CDC in 2003, surfaces in healthcare settings should be cleaned with a hospital-grade disinfectant with an EPA label claim for any of several non-enveloped viruses (e.g., norovirus, poliovirus, rhinovirus).

A. Viral Epitopes

Measurements of serum antibody virus neutralization capacity reflect the activity of an entire polyclonal antibody repertoire. However, to fully understand the humoral response to a virus it is necessary to define the specific viral epitopes to which individual antibodies bind and determine whether antibody binding to specific epitopes protects against disease. Historically, four neutralizing immunoepitopes (Nim) for viruses of the Enterovirus genus were identified through studies of murine monoclonal antibodies raised against rhinovirus-B14 (Rossmann et al., 1985). Studies of EV-D68 specific monoclonal antibody epitopes have not been performed to date. Determination of the crystal structure of EV-D68, however, suggested the likely location of the four Nims on the EV-D68 virion by observations of structural homology with rhinoviruses (Liu et al., 2015a). Studies comparing the amino acid sequences of the surface proteins of recent human isolates of EV-D68 from the U.S. (Zhang et al., 2015) or Japan (Imamura et al., 2014) to that of the Fermon reference virus strain suggest that mutations in the Nims and nearby flanking residues have occurred, especially in the BC and DE loops of capsid protein VP1 that are disordered in the crystal structure (Liu et al., 2015a). It is possible that these VP1 polymorphisms contribute to increased pathogenicity of the virus by eluding pre-existing humoral immunity. Murine monoclonal antibodies are available commercially (sources include GeneTex, ThermoFisher, and Sigma), but aside from listing the specific viral surface protein that was used as an immunogen, information is not available on the epitopes for these antibodies. Notably, some of these commercial antibodies were generated from immunogens of other Enterovirus genus viruses, suggesting the ability of heterotypic antibodies to bind to EV-D68. Further supporting this possibility, two murine mAbs cross-reacted to 40 different enterovirus species, although curiously EV-D68 was the only virus tested that they did not react to (Miao et al., 2009). Heterotypic molecular recognition of EV-D68 by antibodies induced by other types of enteroviruses might contribute to the observed universal EV-D68 seroprevalence early in life. Understanding the fine specificity of human antibody epitopes on EV-D68 and the type specificity or breadth of such antibodies will require studies with cloned human monoclonal antibodies induced by natural infection.

Figure 41:
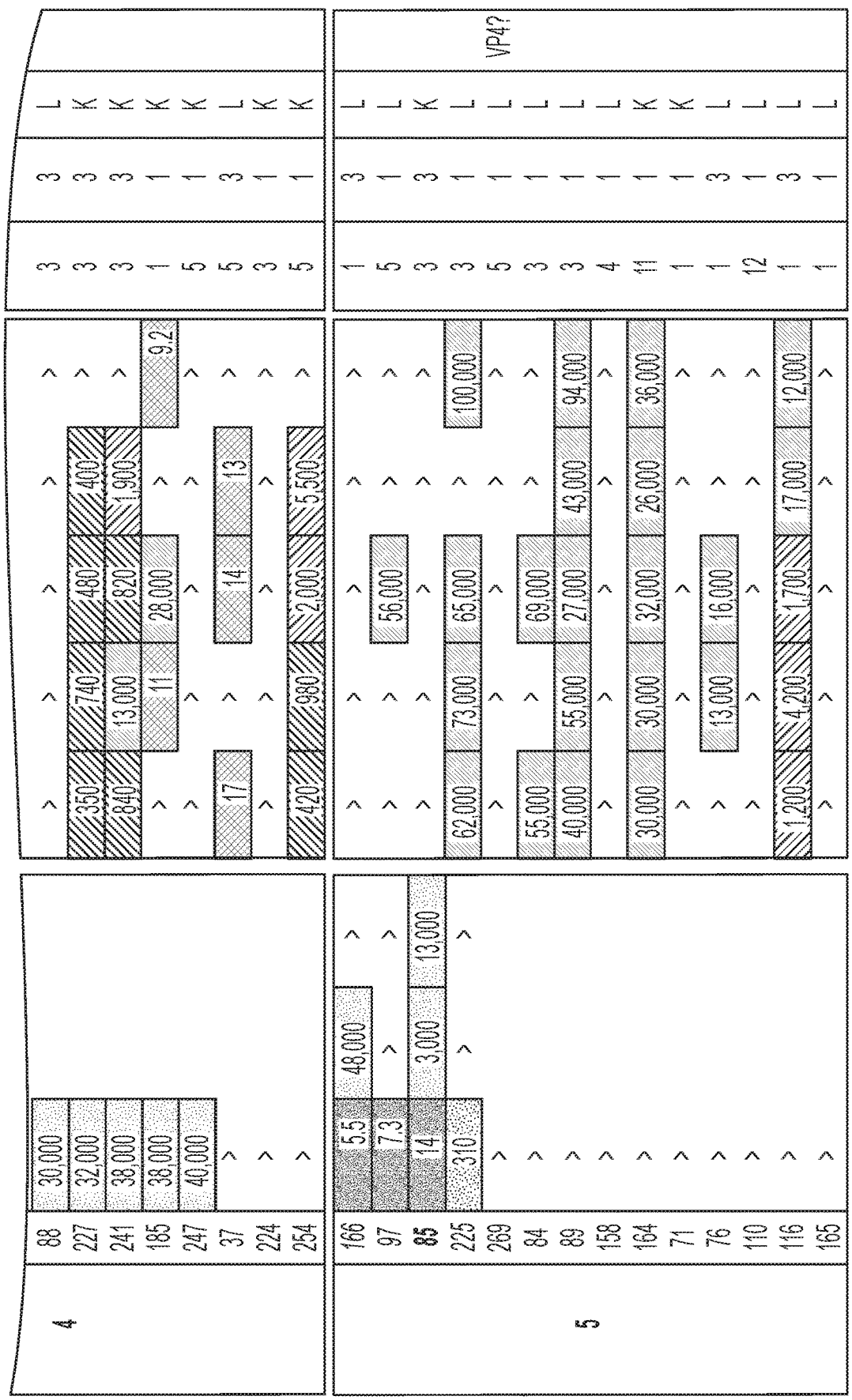
FIG. 41. Detailed characteristics of human mAbs. MAbs were ranked within competition-binding group by $IC_{50}$ value in a $CCID_{50}$ neutralization assay using a B1 clade isolate. The inventors also tested neutralization of a D clade and Fermon (Fer.) isolate for the 21 most potently neutralizing mAbs. ">" denotes neutralization was not detected when tested at concentrations up to 50 µg/mL. Blank cells indicate not tested. Clone numbers listed with red or blue font are potently neutralizing mAbs, with blue clone names indicating the two mAbs studied in detail in later figures. Final $IC_{50}$ values for each mAb are the average of the logarithm of the $EC_{50}$ values from three separate experiments performed in duplicate. Binding strength to live virus isolates are denoted based on $EC_{50}$ values generated using indirect ELISA with purified mAb dilutions to fit sigmoidal dose response curves. ">" indicates the predicted $EC_{50}$ value exceeds the maximum concentration tested of 100 µg/mL, suggesting poor or no binding. Final $EC_{50}$ values for each mAb are the average of the logarithm of the $EC_{50}$ values from three separate experiments performed in duplicate. IgG subtypes were determined phenotypically. Light chain types are kappa (κ) or lambda (L) and were determined genetically. WB indicates western blot reactivity, and all mAbs were tested, with blank rows indicating no reactivity.

During the 2014 EV-D68 outbreak in the U.S., nearly all viral isolates were of the newly emergent B1 clade, with fewer detections of virus from the closely related B2 or distantly related D clades (Tan et al., 2016). All but one of the subjects for this study were infected with B1 clade isolates (Table E). Since 2014, B3 clade viruses have dominated, and B1 clade viruses are no longer circulating (Dyrdak et al., 2019); in 2018 all EV-D68 isolates sequenced by the U.S. Centers for Disease Control and Prevention were from the B3 clade (Kujawski et al., 2019). The inventors first measured the in vitro neutralization capability of each mAb in a 50% cell culture infectious dose ($CCID_{50}$) assay using a B1 clade EV-D68 isolate (FIG. 33A). Twenty-eight mAbs demonstrated neutralization with a half maximal inhibitory concentration ($IC_{50}$) below 50 µg/mL, with mAb EV68-159 exhibiting the strongest neutralization at an $IC_{50}$ value of 0.32 ng/mL (FIG. 41). The inventors further tested the 21 most potently neutralizing mAbs against a D clade isolate and found that 11 mAbs neutralized that virus, with 7 of those exhibiting at least a ten-fold decrease in potency by $IC_{50}$ value for the heterologous virus. The Fermon strain is an isolate from 1962 and is so distantly related to modern EV-D68 isolates that it does not fit into the clade classification scheme (Tan et al., 2016). Nine mAbs neutralized the Fermon laboratory reference strain, but less potently than they inhibited the contemporary B1 clade virus.

Figure 42:
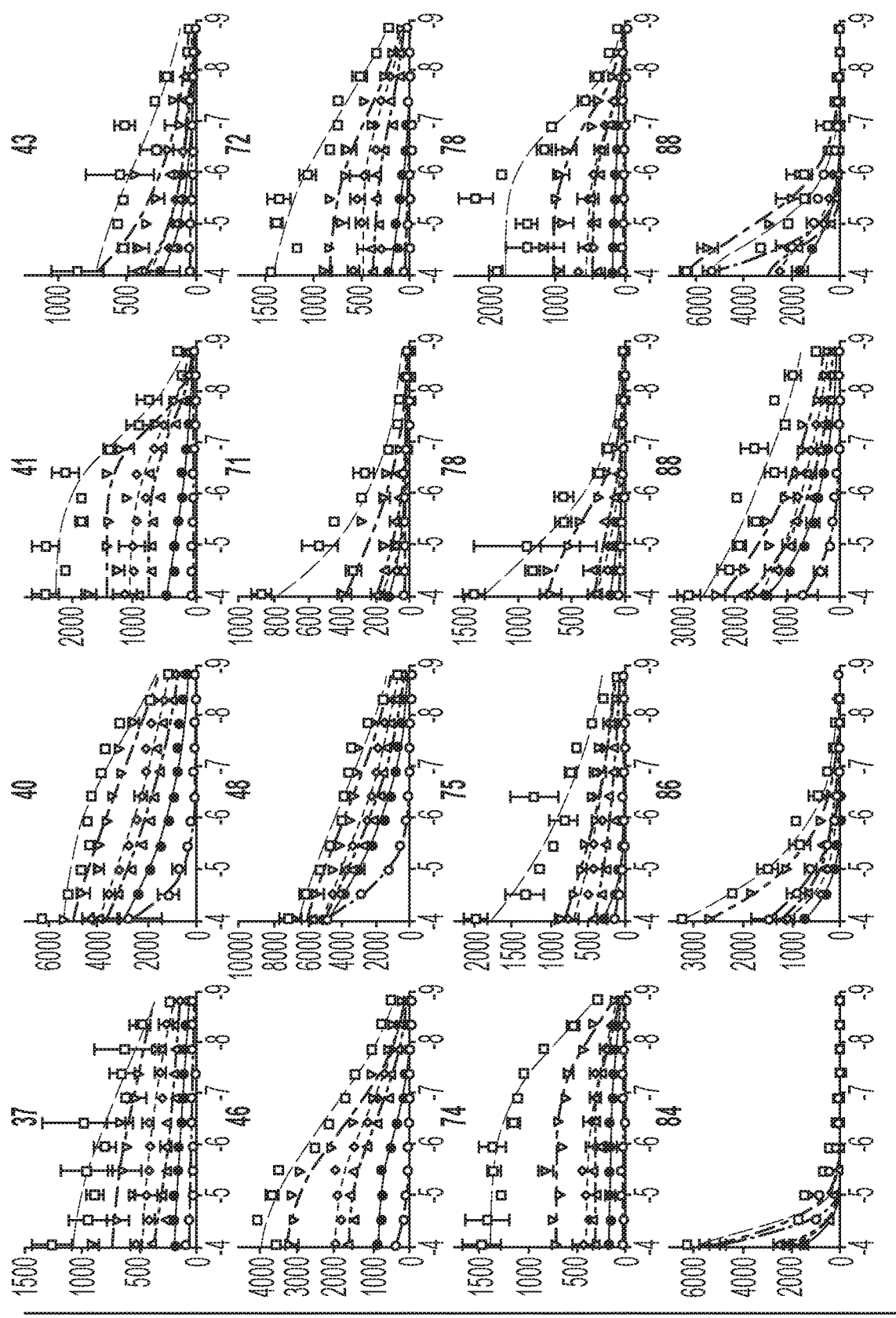
FIG. 42. Indirect ELISA data for all mAbs. Binding strength to live virus isolates is denoted by $EC_{50}$ values generated by using indirect ELISA with purified mAb dilutions to fit sigmoidal dose response curves. Shown are representative data from one of three experiments, with error bars indicating the standard deviation of duplicate technical replicates. Final $EC_{50}$ values for each mAb are the average of the logarithm of the $EC_{50}$ values from all three experiments. The mock preparation of virus was from an RD cell monolayer that was not inoculated with virus but was prepared in the same manner as virus-infected cells.
Figure 42:
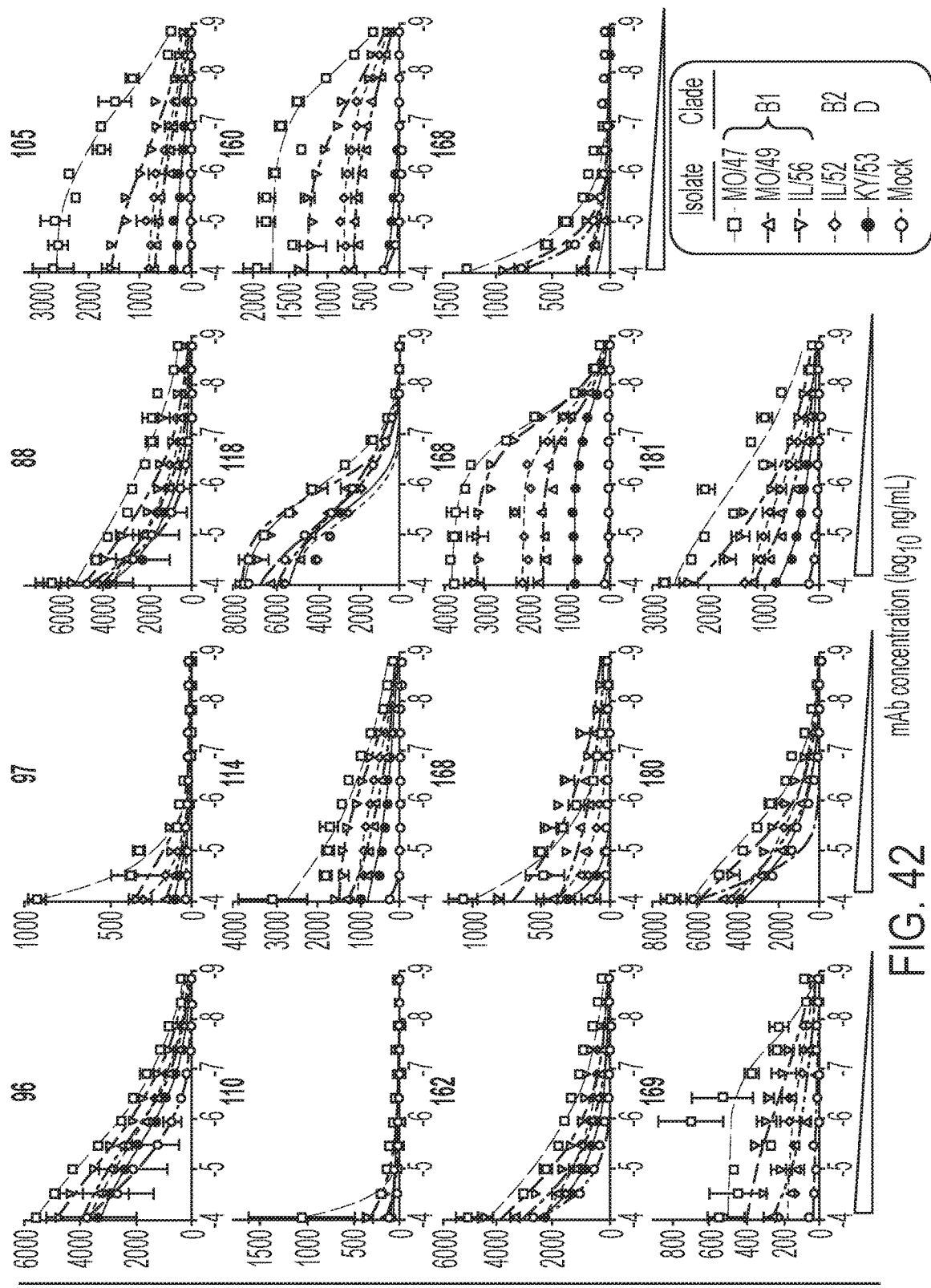
Figure 42:
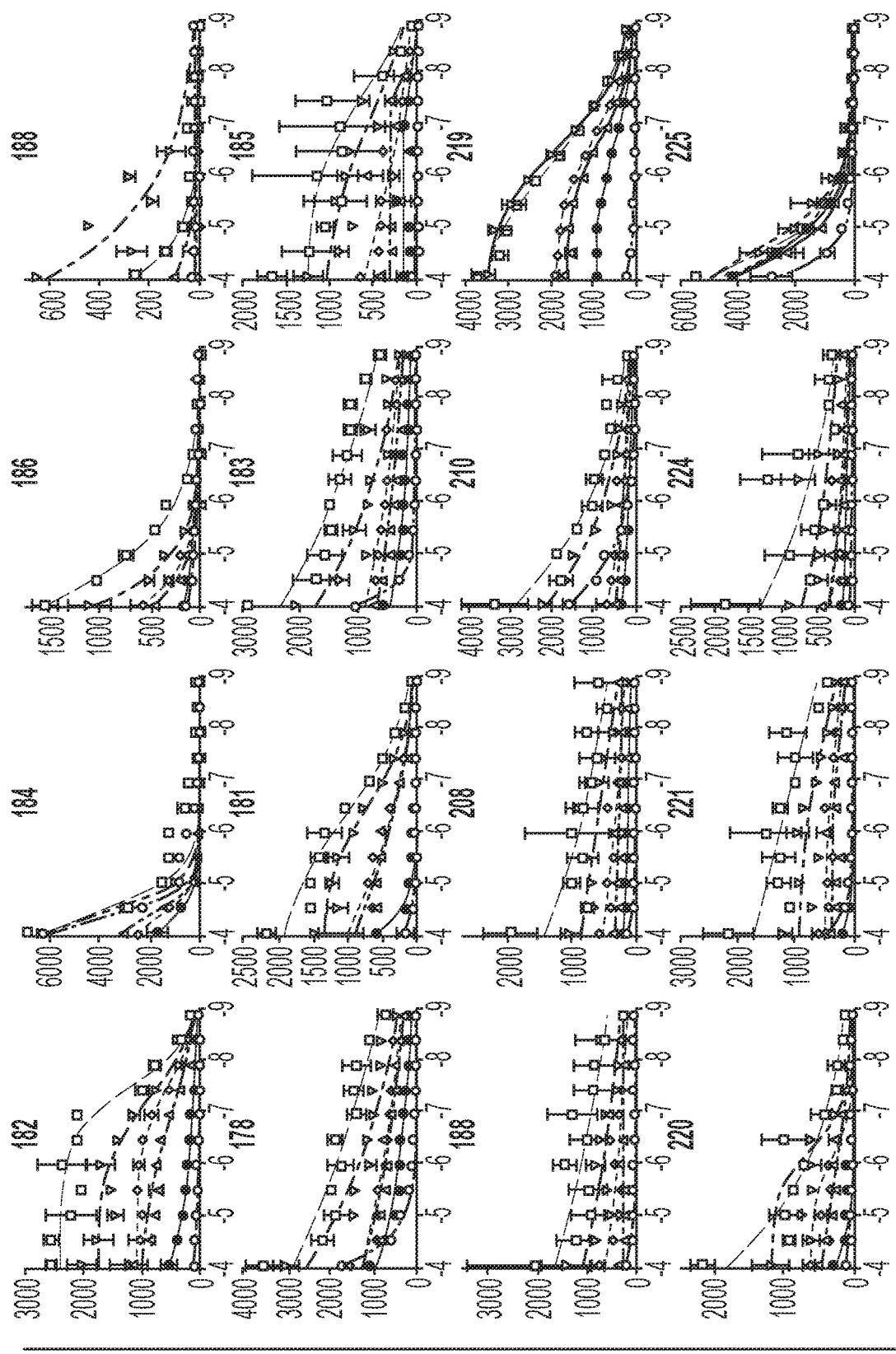
Figure 42:
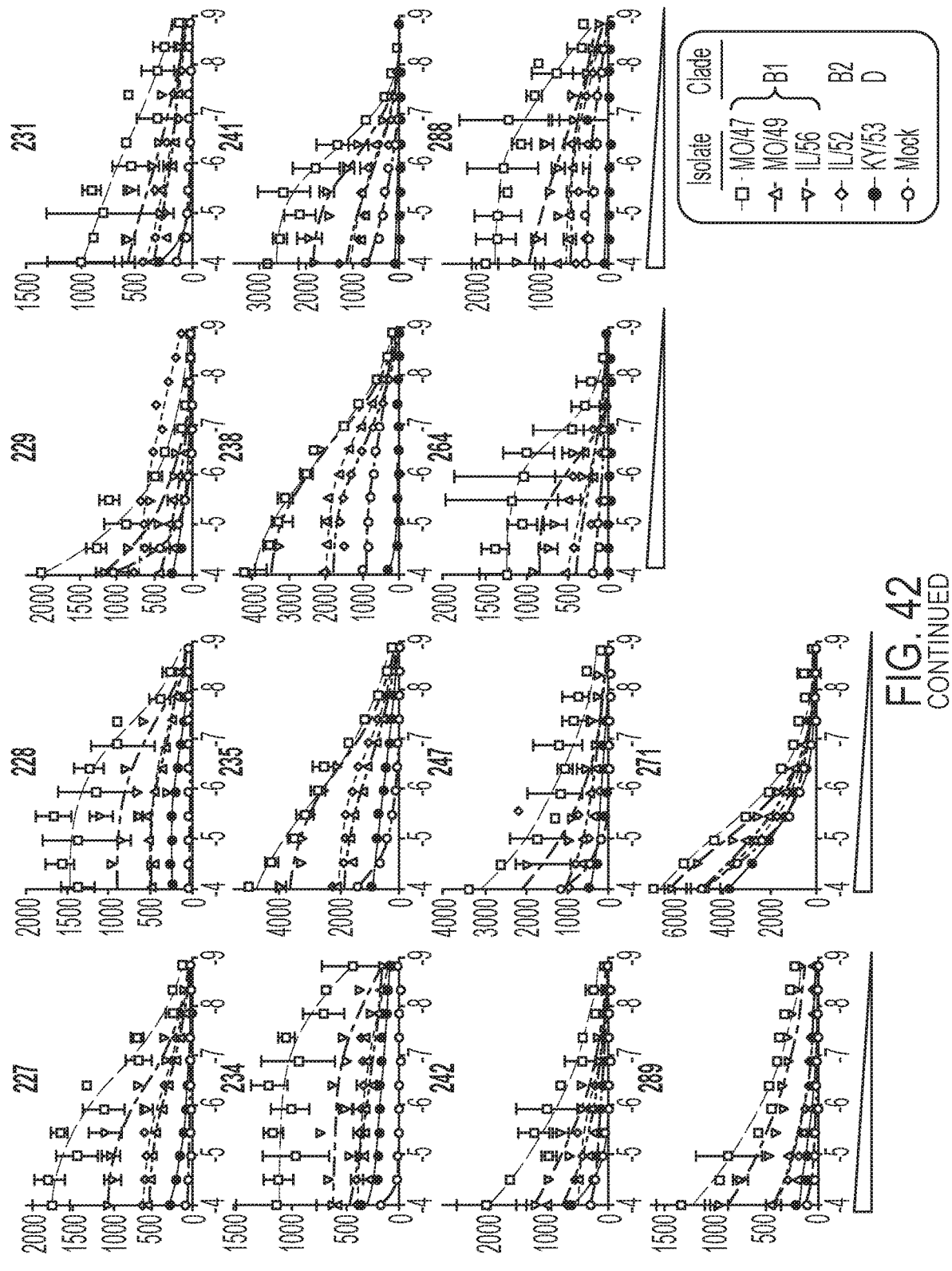

Recognizing that neutralization assays may underestimate cross-reactivity, the inventors used the same indirect ELISA approach described above to generate half-maximal effective concentrations ($EC_{50}$) of purified mAb for binding to representative EV-D68 isolates from the B1, B2, or D clades (FIGS. 33B-C, and FIG. 42). Of the mAbs with $EC_{50}$ values for binding of ≤1 µg/mL to B1 clade isolates, all bound to a B2 clade isolate, whereas about half also bound to a D clade isolate (FIG. 33B and FIG. 41). An additional class of mAbs was observed that bound weakly in general but cross-reacted to viruses from all clades tested.

Figure 43:
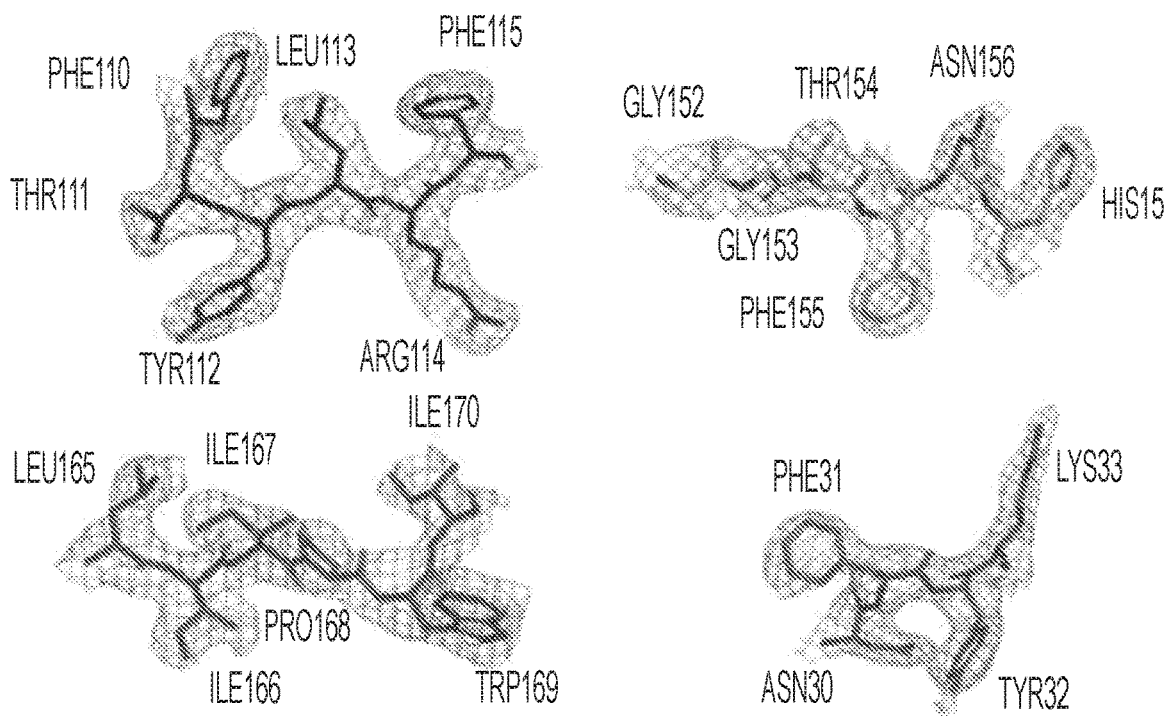
FIG. 43. Representative densities from the EV-D68: Fab EV68-228 electron density map. Viral proteins are colored in blue (VP1), green (VP2), red (VP3) and magenta (VP4).
Figure 44:
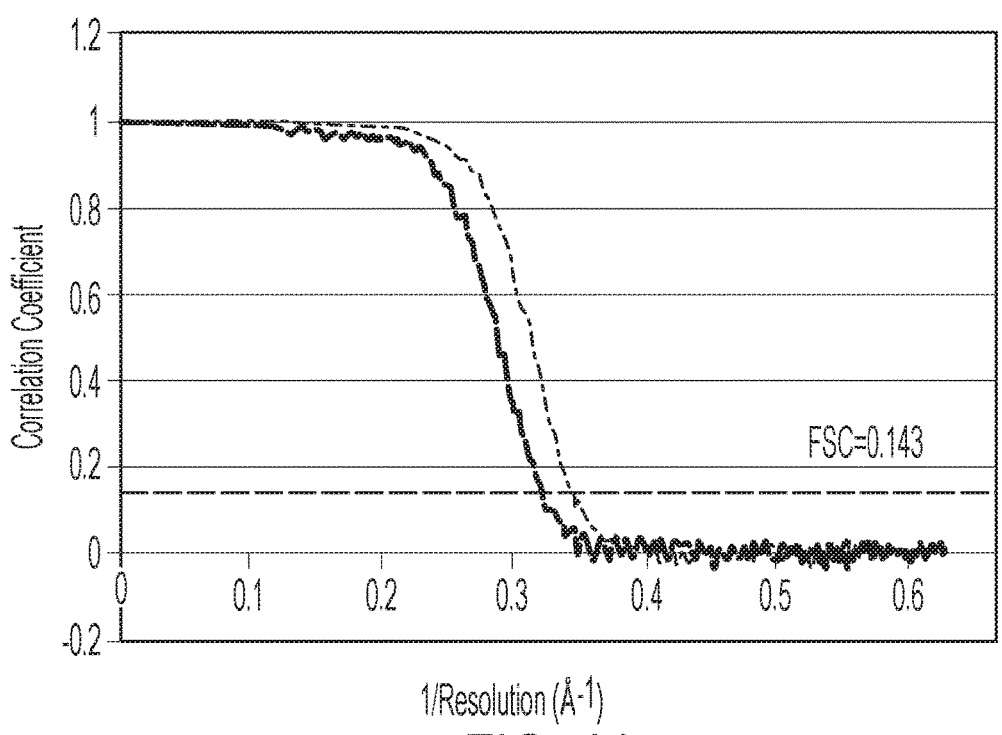
FIG. 44. Estimates of immune complex map resolutions. Map resolutions are estimated based on the gold-standard Fourier shell correlation (FSC) cutoff of 0.143. The final resolutions for EV68-159 (red curve) or EV68-228 (blue curve) complexes are 2.9 Å or 3.1 Å, respectively.
Figure 45:
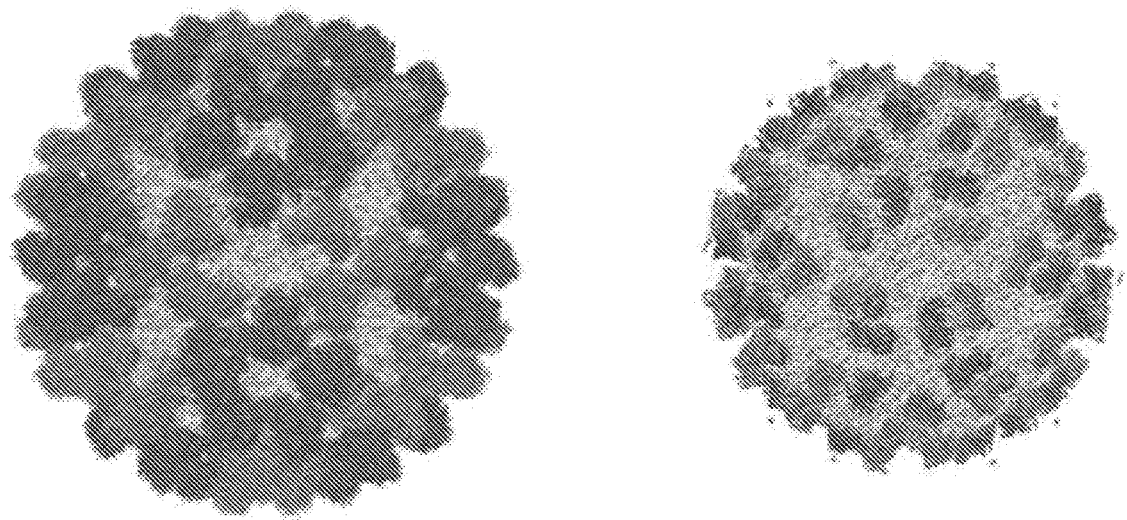
FIG. 45. Comparison of The Fab binding sites. EV68-159 and EV68-228 are colored in gold and blue, respectively, and the viral surface is colored in cyan. The left panel shows both variable domains and constant domains, whereas the right panel shows only the variable domains, demonstrating that the footprints of the two Fabs do not overlap.

To date, structural studies of antibody-EV-D68 interactions have been limited to murine mAbs (Zheng et al., 2019). The inventors selected two potently neutralizing human mAbs, the clade-specific mAb EV68-159 and the highly cross-reactive mAb EV68-228, to make immune complexes with antigen binding fragments (Fabs) and a B1 clade EV-D68 isolate for cryo-electron microscopy (cryo-EM) studies. The final density maps attained a resolution of 2.9 Å (EV68-159) or 3.1 Å (EV68-228) (FIG. 34A, FIG. 43, FIG. 44, and Table G). The structures revealed two distinct binding sites: EV68-159 attached around the three-fold axes of symmetry, whereas EV68-228 bound around the five-fold axes between depressions that form the canyon regions (FIGS. 34A-C, FIG. 45). Thus, for each Fab, a total of 60 copies bound to the virus particle. The Fab variable domains, which interacted with the viral surface, displayed strong densities similar to the viral capsid proteins, and an atomic model of each Fab was built together with the four viral capsid proteins. In contrast, the Fab constant domains, which are located further from the viral surface, displayed weaker densities and were excluded from atomic model building. The backbone of the polypeptide chains and the majority of amino acid side chains are well-ordered in the density maps, demonstrating the critical features of the binding interface between virus particle and Fab molecule.

B. Animal Models of Neurologic Disease

Measuring neutralization of viruses by antibodies in vitro is typically the most rapid and reproducible method to characterize the antiviral function of antibodies. However, this mode of testing does not measure effector functions mediated by the Fc portion of antibodies that operate only in vivo, such as complement activation or engagement with cell-surface Fc receptors. Consequently, the magnitude of in vitro neutralization capacity may not correlate perfectly with the levels of inhibition of viral replication or protection against disease observed in vivo (reviewed in (Lu et al., 2018)). Many of the Fc-mediated effector functions of antibodies require Fc receptor bearing cells of the innate or adaptive immune systems to mediate full protective effects. Small animal models of infection are needed for assessment of efficacy of humoral immunity in preclinical studies.

Investigators in Colorado (Hixon et al., 2017a; 2017b), Utah (Morrey et al., 2018), and China (Zhang et al., 2018) have reported murine models of EV-D68 since early 2017. In all three reported models, mice of no greater than 10 days old are inoculated with virus. Across these models, EV-D68 has been shown capable of causing flaccid limb paralysis and death when administered by intraperitoneal (Hixon et al., 2017a; 2017b; Morrey et al., 2018; Zhang et al., 2018), intramuscular (Hixon et al. 2017a; 2017b), or intracerebral routes (Hixon et al., 2017b). Notably, intranasal inoculation led to paralysis in only two of 73 outbred NIH Swiss Webster mice tested, with virus detected in the spinal cord (Hixon et al., 2017b), whereas intranasal inoculation of AG129 mice, which lack interferon type-I and -II receptors, caused paralysis in two of four mice with virus detected in muscle but not spinal cord (Morrey et al., 2018). However, all studies in which humoral immunity was evaluated in mice used non-physiologic routes of virus inoculation.

Viral antigen has been visualized in tissues by immunostaining in skeletal muscle (Morrey et al., 2018; Zhang et al., 2018) and spinal cord (Hixon et al., 2017b; Morrey et al., 2018). Involvement of both muscle and spinal cord suggests that EV-D68 may induce paralysis by two mechanisms: 1) direct pathologic effect on skeletal muscles and 2) loss of central motor neurons. Motor neurons in the spinal cord were infected, which is analogous to the pathogenesis of poliomyelitis. This pattern of murine neuron involvement in immunostaining studies also correlates with findings of gray matter change on spinal cord imaging in patients with AFM (Hixon et al., 2017b; Morrey et al., 2018). More sensitive real-time quantitative RT-PCR tests detected EV-D68 RNA chiefly in muscle and spinal cord, but also in brain, heart, lung, intestine, liver, spleen, kidney, and blood (Zhang et al., 2018). However, other than in spinal cord and muscle, the amounts of RNA detected were of questionable significance and may well reflect viral genome copies present in blood within these tissues rather than true tropism for these tissues.

Studies in these models of paralysis and lethality facilitated preliminary studies of the ability of antibodies to protect from neurologic disease. Heat-inactivated serum from immune mice passively transferred to naïve mice prevented neurologic disease, even when EV-D68 was inoculated directly by the intracerebral route (Hixon et al., 2017b). Also, therapeutic administration of human IVIG reduced motor impairment even up to 6 days after infection of mice (Hixon et al., 2017a), consistent with findings of high titers of EV-D68 specific antibodies in IVIG (Zhang et al., 2015). This observation provides hope that vaccines or human monoclonal antibodies could mediate a therapeutic effect after an individual patient is identified to have features of AFM temporally associated with EV-D68. Further, targeted vaccination or immunoprophylaxis of populations such as infants and toddlers with waning maternal humoral immunity during a known outbreak of EV-D68 could prevent cases of AFM.

C. Animal Models of Respiratory Disease

The major limitations of current murine studies of EV-D68 infection are the use of non-physiologic routes of inoculation to induce paralysis and death and the lack of respiratory disease, which is the chief manifestation of EV-D68 infection in humans. For both cotton rats (*Sigmodon hispidus*) (Patel et al., 2016) and ferrets (*Mustela putorius furo*) (Zheng et al., 2017a) a single study of each has demonstrated that intranasal inoculation with EV-D68 results in replication of virus in the nose and lungs and induces increases in pro-inflammatory innate immune molecule transcripts in the lungs. Clinical symptoms consistent with upper respiratory tract infection (cough, nasal discharge, and dry nose) also developed in ~25% of inoculated ferrets. Neither study assessed for the presence of EV-D68 in muscle or central nervous system tissues nor noted apparent limb weakness or paralysis. Vaccination of cotton rats indicated that some levels of pre-existing humoral immunity did not protect fully against respiratory infection and may in fact be harmful (Patel et al., 2016), in findings that are described further below.

The theoretical advantage of cotton rats and ferrets as models for human respiratory viral infections is that their respiratory epithelia may more closely mimic that of humans, especially in terms of sialylation of glycans on epithelial surfaces, which are heavily α2,6-linked in humans but not in mice (Gagneux et al., 2003). EV-D68 bound preferentially to α2,6-linked sialic acids over α2,3-linked sialic acids in an in vitro glycan array (Imamura et al., 2014) Staining of the respiratory tract with fluorescently labeled lectins indicated that cotton rats have only α2,6-linked sialic acids in their lower respiratory tracts with a mix of α2,6- and α2,3-linked sialic acids in the upper airways (Blanco et al., 2018). Using similar lectin-based methods, ferrets were shown to have α2,6-linked sialic acids on epithelial glycans of the upper respiratory tract (Leigh et al., 1995), with a mix of α2,6- and α2,3-linked sialic acids in the lower airways (Zheng et al., 2017a). However, more recent and sophisticated glycomic analyses of human (Walther et al., 2013), mouse (Bern et al., 2013), and ferret (Jia et al., 2014) respiratory tissues indicated that a more complex array of glycan modifications than simply density of α2,6-linked sialylation likely determines the tropism of respiratory viruses for different animal species. Nonetheless, the success of initial studies in rats and ferrets at mimicking human EV-D68 respiratory disease are encouraging for their further development as models of human pathogenesis.

D. Vaccines

Experimental vaccine candidates for EV-D68 have not yet entered clinical development, however initial studies inoculating mice with either virus-like particle (VLP) vaccines made in yeast (Zhang et al., 2018a) or insect cells (Dai et al., 2018) or beta-propiolactone-inactivated EV-D68 (Zhang et al., 2018) have shown promise. The VLP vaccines induced antibody responses that protected mice from subsequent lethal intraperitoneal challenge. With each of these vaccine candidates, passive transfer of vaccine immune serum to naïve mice was sufficient for protection from lethal intraperitoneal challenge. A possible drawback of VLP based vaccines is the uncertainty of whether these synthetic constructs fully recapitulate all conformationally sensitive structures on the surface of the particles. Many potent human virus neutralizing antibodies for other viruses recognize complex quaternary antigenic sites with strict conformational constraints (Crowe, J E, 2017). The integrity of human antibody epitopes on VLPs cannot be assessed currently since these epitopes are unknown. Further tempering the promise of these murine vaccine studies are findings in cotton rats inoculated intramuscularly with either live or UV-inactivated EV-D68 and subsequently challenged intranasally with a homologous live virus, in which enhanced inflammation was seen in the lung compared to infection of naïve animals (Patel et al., 2016). Specifically, UV-inactivated virus vaccination did not limit viral replication in the lung or nose and skewed the resultant cytokine signature toward a Th2 phenotype, rather than a balanced Th1 and Th2 phenotype seen with immunity from live virus vaccination Enhanced inflammation and disease have been noted with inactivated virus vaccine candidates for respiratory syncytial virus (Karron, R, 2018) and measles (Strebel et al., 2018). Further careful study of the immune correlates of protection or enhancement caused by EV-D68 vaccine candidates is necessary given these mixed findings.

II. MONOCLONAL ANTIBODIES AND PRODUCTION THEREOF

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In particular embodiments, the antibody is purified: (1) to greater than 95% by weight of antibody as determined by the Lowry method, and most particularly more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 basic heterotetramer units along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable region ($V_H$) followed by three constant domains ($C_H$) for each of the alpha and gamma chains and four $C_H$ domains for mu and isotypes. Each L chain has at the N-terminus, a variable region ($V_L$) followed by a constant domain ($C_L$) at its other end. The $V_L$ is aligned with the $V_H$ and the $C_L$ is aligned with the first constant domain of the heavy chain ($C_{H1}$). Particular amino acid residues are believed to form an interface between the light chain and heavy chain variable regions. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa and lambda based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha, delta, epsilon, gamma and mu, respectively. They gamma and alpha classes are further divided into subclasses on the basis of relatively minor differences in $C_H$ sequence and function, humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC), antibody-dependent cellular phagocytosis (ADCP), antibody-dependent neutrophil phagocytosis (ADNP), and antibody-dependent complement deposition (ADCD).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. et al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_{sub}H$ when numbered in accordance with AHo; Honneger, A. and Plunkthun, A. J. Mol. Biol. 309:657-670 (2001)).

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present disclosure may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567) after single cell sorting of an antigen specific B cell, an antigen specific plasmablast responding to an infection or immunization, or capture of linked heavy and light chains from single cells in a bulk sorted antigen specific collection. The "monoclonal antibodies" may also be isolated from phage antibody libraries using the techniques described in Clackson et al., Nature, 352:624-628 (1991) and Marks et al., J. Mol. Biol., 222: 581-597 (1991), for example.

A. General Methods

It will be understood that monoclonal antibodies binding to EV-D68 will have several applications. These include the production of diagnostic kits for use in detecting and diagnosing EV-D68 infection, as well as for treating the same. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection or vaccination with a licensed or experimental vaccine. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants in animals include complete Freund's adjuvant (a non-specific stimulator of the immune response containing killed *Mycobacterium tuberculosis*), incomplete Freund's adjuvants and aluminum hydroxide adjuvant and in humans include alum, CpG, MFP59 and combinations of immunostimulatory molecules ("Adjuvant Systems", such as AS01 or AS03). Additional experimental forms of inoculation to induce EV-D68-specific B cells is possible, including nanoparticle vaccines, or gene-encoded antigens delivered as DNA or RNA genes in a physical delivery system (such as lipid nanoparticle or on a gold biolistic bead), and delivered with needle, gene gun, transcutaneous electroporation device. The antigen gene also can be carried as encoded by a replication competent or defective viral vector such as adenovirus, adeno-associated virus, poxvirus, herpesvirus, or alphavirus replicon, or alternatively a virus like particle.

In the case of human antibodies against natural pathogens, a suitable approach is to identify subjects that have been exposed to the pathogens, such as those who have been diagnosed as having contracted the disease, or those who have been vaccinated to generate protective immunity against the pathogen or to test the safety or efficacy of an experimental vaccine. Circulating anti-pathogen antibodies can be detected, and antibody encoding or producing B cells from the antibody-positive subject may then be obtained.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens, lymph nodes, tonsils or adenoids, bone marrow aspirates or biopsies, tissue biopsies from mucosal organs like lung or GI tract, or from circulating blood. The antibody-producing B lymphocytes from the immunized animal or immune human are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984). HMMA2.5 cells or MFP-2 cells are particularly useful examples of such cells.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. In some cases, transformation of human B cells with Epstein Barr virus (EBV) as an initial step increases the size of the B cells, enhancing fusion with the relatively large-sized myeloma cells. Transformation efficiency by EBV is enhanced by using CpG and a Chk2 inhibitor drug in the transforming medium. Alternatively, human B cells can be activated by co-culture with transfected cell lines expressing CD40 Ligand (CD154) in medium containing additional soluble factors, such as IL-21 and human B cell Activating Factor (BAFF), a Type II member of the TNF superfamily Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986) and there are processes for better efficiency (Yu et al., 2008). Fusion procedures usually produce viable hybrids at low frequencies, about $1\times10^{-6}$ to $1\times10^{-8}$, but with optimized procedures one can achieve fusion efficiencies close to 1 in 200 (Yu et al., 2008). However, relatively low efficiency of fusion does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture medium. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the medium is supplemented with hypoxanthine and thymidine as a source of nucleotides (HAT medium). Where azaserine is used, the medium is supplemented with hypoxanthine. Ouabain is added if the B cell source is an EBV-transformed human B cell line, in order to eliminate EBV-transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonal antibodies. Single B cells labelled with the antigen of interest can be sorted physically using paramagnetic bead selection or flow cytometric sorting, then RNA can be isolated from the single cells and antibody genes amplified by RT-PCR. Alternatively, antigen-specific bulk sorted populations of cells can be segregated into microvesicles and the matched heavy and light chain variable genes recovered from single cells using physical linkage of heavy and light chain amplicons, or common barcoding of heavy and light chain genes from a vesicle. Matched heavy and light chain genes form single cells also can be obtained from populations of antigen specific B cells by treating cells with cell-penetrating nanoparticles bearing RT-PCR primers and barcodes for marking transcripts with one barcode per cell. The antibody variable genes also can be isolated by RNA extraction of a hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity. Those of skill in the art, by assessing the binding specificity/affinity of a given antibody using techniques well known to those of skill in the art, can determine whether such antibodies fall within the scope of the instant claims. For example, the epitope to which a given antibody bind may consist of a single contiguous sequence of 3 or more (e.g., 3, 4, 5, 6, 7, 8, 9, 10, 11, U, 13, 14, 15, 16, 17, 18, 19, 20) amino acids located within the antigen molecule (e.g., a linear epitope in a domain). Alternatively, the epitope may consist of a plurality of non-contiguous amino acids (or amino acid sequences) located within the antigen molecule (e.g., a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Cross-blocking can be measured in various binding assays such as ELISA, biolayer interferometry, or surface plasmon resonance. Other methods include alanine scanning mutational analysis, peptide blot analysis (Reineke (2004) Methods Mol. Biol. 248: 443-63), peptide cleavage analysis, high-resolution electron microscopy techniques using single particle reconstruction, cryoEM, or tomography, crystallographic studies and NMR analysis. In addition, methods such as epitope excision, epitope extraction and chemical modification of antigens can be employed (Tomer (2000) Prot. Sci. 9: 487496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267: 252-259; Engen and Smith (2001) Anal. Chem. 73: 256A-265A. When the antibody neutralizes EV-D68, antibody escape mutant variant organisms can be isolated by propagating EV-D68 in vitro or in animal models in the presence of high concentrations of the antibody. Sequence analysis of the EV-D68 gene encoding the antigen targeted by the antibody reveals the mutation(s) conferring antibody escape, indicating residues in the epitope or that affect the structure of the epitope allosterically.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the disclosure into groups of antibodies binding different epitopes.

The present disclosure includes antibodies that may bind to the same epitope, or a portion of the epitope. Likewise, the present disclosure also includes antibodies that compete for binding to a target or a fragment thereof with any of the specific exemplary antibodies described herein. One can easily determine whether an antibody binds to the same epitope as, or competes for binding with, a reference antibody by using routine methods known in the art. For example, to determine if a test antibody binds to the same epitope as a reference, the reference antibody is allowed to bind to target under saturating conditions. Next, the ability of a test antibody to bind to the target molecule is assessed. If the test antibody is able to bind to the target molecule following saturation binding with the reference antibody, it can be concluded that the test antibody binds to a different epitope than the reference antibody. On the other hand, if the test antibody is not able to bind to the target molecule following saturation binding with the reference antibody, then the test antibody may bind to the same epitope as the epitope bound by the reference antibody.

To determine if an antibody competes for binding with a reference anti-EV-D68 antibody, the above-described binding methodology is performed in two orientations: In a first orientation, the reference antibody is allowed to bind to the EV-D68 antigen under saturating conditions followed by assessment of binding of the test antibody to the EV-D68 antigen. In a second orientation, the test antibody is allowed to bind to the EV-D68 antigen molecule under saturating conditions followed by assessment of binding of the reference antibody to the EV-D68 antigen. If, in both orientations, only the first (saturating) antibody is capable of binding to EV-D68, then it is concluded that the test antibody and the reference antibody compete for binding to EV-D68. As will be appreciated by a person of ordinary skill in the art, an antibody that competes for binding with a reference antibody may not necessarily bind to the identical epitope as the reference antibody but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art. Structural studies with EM or crystallography also can demonstrate whether or not two antibodies that compete for binding recognize the same epitope.

In another aspect, there are provided monoclonal antibodies having clone-paired CDRs from the heavy and light chains as illustrated in Tables 3 and 4, respectively. Such antibodies may be produced by the clones discussed below in the Examples section using methods described herein.

In another aspect, the antibodies may be defined by their variable sequence, which include additional "framework" regions. These are provided in Tables 1 and 2 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below). Each of the foregoing applies to the nucleic acid sequences set forth as Table 1 and the amino acid sequences of Table 2.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogeny pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor 11:105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One particular example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example with the parameters described herein, to determine percent sequence identity for the polynucleotides and polypeptides of the disclosure. Software for performing BLAST analyses is publicly available through the National Center for Biotechnology Information. The rearranged nature of an antibody sequence and the variable length of each gene requires multiple rounds of BLAST searches for a single antibody sequence. Also, manual assembly of different genes is difficult and error-prone. The sequence analysis tool IgBLAST (world-wide-web at ncbi.nlm.nih.gov/igblast/) identifies matches to the germline V, D and J genes, details at rearrangement junctions, the delineation of Ig V domain framework regions and complementarity determining regions. IgBLAST can analyze nucleotide or protein sequences and can process sequences in batches and allows searches against the germline gene databases and other sequence databases simultaneously to minimize the chance of missing possibly the best matching germline V gene.

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) Proc. Natl. Acad. Sci. USA 89:10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

Yet another way of defining an antibody is as a "derivative" of any of the below-described antibodies and their antigen-binding fragments. The term "derivative" refers to an antibody or antigen-binding fragment thereof that immunospecifically binds to an antigen but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, as variants having altered CH1, hinge, CH2, CH3 or CH4 regions, so as to form, for example antibodies, etc., having variant Fc regions that exhibit enhanced or impaired effector or binding characteristics. The term "derivative" additionally encompasses non-amino acid modifications, for example, amino acids that may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment, the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al. (2002) "*Lack Of Fucose On Human IgG N-Linked Oligosaccharide Improves Binding To Human Fcgamma Rill And Antibody-Dependent Cellular Toxicity,*" J. Biol. Chem. 277(30): 26733-26740; Davies J. et al. (2001) "*Expression Of GnTIII In A Recombinant Anti-CD20 CHO Production Cell Line: Expression Of Antibodies With Altered Glycoforms Leads To An Increase In ADCC Through Higher Affinity For FC Gamma RIII,*" Biotechnology & Bioengineering 74(4): 288-294). Methods of altering carbohydrate contents are known to those skilled in the art, see, e.g., Wallick, S. C. et al. (1988) "*Glycosylation Of A VH Residue Of A Monoclonal Antibody Against Alpha* (1 - - - 6) *Dextran Increases Its Affinity For Antigen,*" J. Exp. Med. 168(3): 1099-1109; Tao, M. H. et al. (1989) "*Studies Of Aglycosylated Chimeric Mouse-Human IgG. Role Of Carbohydrate In The Structure And Effector Functions Mediated By The Human IgG Constant Region,*" J. Immunol. 143(8): 2595-2601; Routledge, E. G. et al. (1995) "*The Effect Of Aglycosylation On The Immunogenicity Of A Humanized Therapeutic CD*3 *Monoclonal Antibody,*" Transplantation 60(8):847-53; Elliott, S. et al. (2003) "*Enhancement Of Therapeutic Protein In Vivo Activities Through Glycoengineering,*" Nature Biotechnol. 21:414-21; Shields, R. L. et al. (2002) "*Lack Of Fucose On Human IgG N-Linked Oligosaccharide Improves Binding To Human Fcgamma RIII And Antibody-Dependent Cellular Toxicity,*" J. Biol. Chem. 277(30): 26733-26740).

A derivative antibody or antibody fragment can be generated with an engineered sequence or glycosylation state to confer preferred levels of activity in antibody dependent cellular cytotoxicity (ADCC), antibody-dependent cellular phagocytosis (ADCP), antibody-dependent neutrophil phagocytosis (ADNP), or antibody-dependent complement deposition (ADCD) functions as measured by bead-based or cell-based assays or in vivo studies in animal models.

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

C. Engineering of Antibody Sequences

In various embodiments, one may choose to engineer sequences of the identified antibodies for a variety of reasons, such as improved expression, improved cross-reactivity or diminished off-target binding. Modified antibodies may be made by any technique known to those of skill in the art, including expression through standard molecular biological techniques, or the chemical synthesis of polypeptides. Methods for recombinant expression are addressed elsewhere in this document. The following is a general discussion of relevant goals techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full-length IgG antibodies can be generated by subcloning heavy and light chain Fv DNAs from the cloning vector into an IgG plasmid vector, transfected into 293 (e.g., Freestyle) cells or CHO cells, and antibodies can be collected and purified from the 293 or CHO cell supernatant. Other appropriate host cells systems include bacteria, such as *E. coli*, insect cells (S2, Sf9, Sf29, High Five), plant cells (e.g., tobacco, with or without engineering for human-like glycans), algae, or in a variety of non-human transgenic contexts, such as mice, rats, goats or cows.

Expression of nucleic acids encoding antibodies, both for the purpose of subsequent antibody purification, and for immunization of a host, is also contemplated. Antibody coding sequences can be RNA, such as native RNA or modified RNA. Modified RNA contemplates certain chemical modifications that confer increased stability and low immunogenicity to mRNAs, thereby facilitating expression of therapeutically important proteins. For instance, N1-methyl-pseudouridine (N1m$\Psi$) outperforms several other nucleoside modifications and their combinations in terms of translation capacity. In addition to turning off the immune/eIF2$\alpha$ phosphorylation-dependent inhibition of translation, incorporated N1m$\Psi$ nucleotides dramatically alter the dynamics of the translation process by increasing ribosome pausing and density on the mRNA. Increased ribosome loading of modified mRNAs renders them more permissive for initiation by favoring either ribosome recycling on the same mRNA or de novo ribosome recruitment. Such modifications could be used to enhance antibody expression in vivo following inoculation with RNA. The RNA, whether native or modified, may be delivered as naked RNA or in a delivery vehicle, such as a lipid nanoparticle.

Alternatively, DNA encoding the antibody may be employed for the same purposes. The DNA is included in an expression cassette comprising a promoter active in the host cell for which it is designed. The expression cassette is advantageously included in a replicable vector, such as a conventional plasmid or minivector. Vectors include viral vectors, such as poxviruses, adenoviruses, herpesviruses, adeno-associated viruses, and lentiviruses are contemplated. Replicons encoding antibody genes such as alphavirus replicons based on VEE virus or Sindbis virus are also contemplated. Delivery of such vectors can be performed by needle through intramuscular, subcutaneous, or intradermal routes, or by transcutaneous electroporation when in vivo expression is desired.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), F(ab')$_2$) that are produced, for example, by the proteolytic cleavage of the mAbs, or single-chain immunoglobulins producible, for example, via recombinant means. F(ab') antibody derivatives are monovalent, while F(ab')$_2$ antibody derivatives are bivalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to IgG$_1$ can increase antibody dependent cell cytotoxicity, switching to class A can improve tissue distribution, and switching to class M can improve valency.

Alternatively or additionally, it may be useful to combine amino acid modifications with one or more further amino acid modifications that alter C1q binding and/or the complement dependent cytotoxicity (CDC) function of the Fc region of an IL-23p19 binding molecule. The binding polypeptide of particular interest may be one that binds to C1q and displays complement dependent cytotoxicity. Polypeptides with pre-existing C1q binding activity, optionally further having the ability to mediate CDC may be modified such that one or both of these activities are enhanced Amino acid modifications that alter C1q and/or modify its complement dependent cytotoxicity function are described, for example, in WO/0042072, which is hereby incorporated by reference.

One can design an Fc region of an antibody with altered effector function, e.g., by modifying C1q binding and/or FcγR binding and thereby changing CDC activity and/or ADCC activity. "Effector functions" are responsible for activating or diminishing a biological activity (e.g., in a subject). Examples of effector functions include, but are not limited to: C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of an antibody with improved C1q binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

FcRn binding. Fc mutations can also be introduced and engineered to alter their interaction with the neonatal Fc receptor (FcRn) and improve their pharmacokinetic properties. A collection of human Fc variants with improved binding to the FcRn have been described (Shields et al., (2001). High resolution mapping of the binding site on human IgG1 for FcγRI, FcγRII, FcγRIII, and FcRn and design of IgG1 variants with improved binding to the FcγR, (J. Biol. Chem. 276:6591-6604). A number of methods are known that can result in increased half-life (Kuo and Aveson, (2011)), including amino acid modifications may be generated through techniques including alanine scanning mutagenesis, random mutagenesis and screening to assess the binding to the neonatal Fc receptor (FcRn) and/or the in vivo behavior. Computational strategies followed by mutagenesis may also be used to select one of amino acid mutations to mutate.

The present disclosure therefore provides a variant of an antigen binding protein with optimized binding to FcRn. In a particular embodiment, the said variant of an antigen binding protein comprises at least one amino acid modification in the Fc region of said antigen binding protein, wherein said modification is selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 384, 385, 386, 387, 389, 390, 392, 393, 394, 395, 396, 397, 398, 399, 400, 401, 403, 404, 408, 411, 412, 414, 415, 416, 418, 419, 420, 421, 422, 424, 426, 428, 433, 434, 438, 439, 440, 443, 444, 445, 446 and 447 of the Fc region as compared to said parent polypeptide, wherein the numbering of the amino acids in the Fc region is that of the EU index in Kabat. In a further aspect of the disclosure the modifications are M252Y/S254T/T256E.

Additionally, various publications describe methods for obtaining physiologically active molecules whose half-lives are modified, see for example Kontermann (2009) either by introducing an FcRn-binding polypeptide into the molecules or by fusing the molecules with antibodies whose FcRn-binding affinities are preserved but affinities for other Fc receptors have been greatly reduced or fusing with FcRn binding domains of antibodies.

Derivatized antibodies may be used to alter the half-lives (e.g., serum half-lives) of parental antibodies in a mammal, particularly a human Such alterations may result in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies of the present disclosure or fragments thereof in a mammal, preferably a human, results in a higher serum titer of said antibodies or antibody fragments in the mammal, and thus reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor.

Beltramello et al. (2010) previously reported the modification of neutralizing mAbs, due to their tendency to enhance dengue virus infection, by generating in which leucine residues at positions 1.3 and 1.2 of CH2 domain (according to the IMGT unique numbering for C-domain) were substituted with alanine residues. This modification, also known as "LALA" mutation, abolishes antibody binding to FcγRI, FcγRII and FcγRIIIa, as described by Hessell et al. (2007). The variant and unmodified recombinant mAbs were compared for their capacity to neutralize and enhance infection by the four dengue virus serotypes. LALA variants retained the same neutralizing activity as unmodified mAb but were completely devoid of enhancing activity. LALA mutations of this nature are therefore contemplated in the context of the presently disclosed antibodies.

Altered Glycosylation. A particular embodiment of the present disclosure is an isolated monoclonal antibody, or antigen binding fragment thereof, containing a substantially homogeneous glycan without sialic acid, galactose, or fucose. The monoclonal antibody comprises a heavy chain variable region and a light chain variable region, both of which may be attached to heavy chain or light chain constant regions respectively. The aforementioned substantially homogeneous glycan may be covalently attached to the heavy chain constant region.

Another embodiment of the present disclosure comprises a mAb with a novel Fc glycosylation pattern. The isolated monoclonal antibody, or antigen binding fragment thereof, is present in a substantially homogenous composition represented by the GNGN or G1/G2 glycoform. Fc glycosylation plays a significant role in anti-viral and anti-cancer properties of therapeutic mAbs. The disclosure is in line with a recent study that shows increased anti-lentivirus cell-mediated viral inhibition of a fucose free anti-HIV mAb in vitro. This embodiment of the present disclosure with homogenous glycans lacking a core fucose, showed increased protection against specific viruses by a factor greater than two-fold. Elimination of core fucose dramatically improves the ADCC activity of mAbs mediated by natural killer (NK) cells but appears to have the opposite effect on the ADCC activity of polymorphonuclear cells (PMNs).

The isolated monoclonal antibody, or antigen binding fragment thereof, comprising a substantially homogenous composition represented by the GNGN or G1/G2 glycoform exhibits increased binding affinity for Fc gamma RI and Fc gamma RIII compared to the same antibody without the substantially homogeneous GNGN glycoform and with G0, G1F, G2F, GNF, GNGNF or GNGNFX containing glycoforms. In one embodiment of the present disclosure, the antibody dissociates from Fc gamma RI with a Kd of $1 \times 10^{-8}$ M or less and from Fc gamma RIII with a Kd of $1 \times 10^{-7}$ M or less.

Glycosylation of an Fc region is typically either N-linked or O-linked. N-linked refers to the attachment of the carbohydrate moiety to the side chain of an asparagine residue. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation site(s) that are not present in the polypeptide. Addition of glycosylation sites to the Fc region of an antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the antibody is expressed in cells that express beta (1,4)-N-acetylglucosaminyltransferase III (GnT III), such that GnT III adds GlcNAc to the IL-23p19 antibody. Methods for producing antibodies in such a fashion are provided in WO/9954342, WO/03011878, patent publication 20030003097A1, and Umana et al., Nature Biotechnology, 17:176-180, February 1999. Cell lines can be altered to enhance or reduce or eliminate certain post-translational modifications, such as glycosylation, using genome editing technology such as Clustered Regularly Interspaced Short Palindromic Repeats (CRISPR). For example, CRISPR technology can be used to eliminate genes encoding glycosylating enzymes in 293 or CHO cells used to express recombinant monoclonal antibodies.

Elimination of monoclonal antibody protein sequence liabilities. It is possible to engineer the antibody variable gene sequences obtained from human B cells to enhance their manufacturability and safety. Potential protein sequence liabilities can be identified by searching for sequence motifs associated with sites containing:

1) Unpaired Cys residues,
2) N-linked glycosylation,
3) Asn deamidation,
4) Asp isomerization,
5) SYE truncation,
6) Met oxidation,
7) Trp oxidation,
8) N-terminal glutamate,
9) Integrin binding,
10) CD11c/CD18 binding, or
11) Fragmentation Such motifs can be eliminated by altering the synthetic gene for the cDNA encoding recombinant antibodies.

Protein engineering efforts in the field of development of therapeutic antibodies clearly reveal that certain sequences or residues are associated with solubility differences (Fernandez-Escamilla et al., *Nature Biotech.*, 22 (10), 1302-1306, 2004; Chennamsetty et al., *PNAS*, 106 (29), 11937-11942, 2009; Voynov et al., *Biocon. Chem.*, 21(2), 385-392, 2010) Evidence from solubility-altering mutations in the literature indicate that some hydrophilic residues such as aspartic acid, glutamic acid, and serine contribute significantly more favorably to protein solubility than other hydrophilic residues, such as asparagine, glutamine, threonine, lysine, and arginine.

Stability. Antibodies can be engineered for enhanced biophysical properties. One can use elevated temperature to unfold antibodies to determine relative stability, using average apparent melting temperatures. Differential Scanning Calorimetry (DSC) measures the heat capacity, $C_p$, of a molecule (the heat required to warm it, per degree) as a function of temperature. One can use DSC to study the thermal stability of antibodies. DSC data for mAbs is particularly interesting because it sometimes resolves the unfolding of individual domains within the mAb structure, producing up to three peaks in the thermogram (from unfolding of the Fab, $C_H2$, and $C_H3$ domains). Typically unfolding of the Fab domain produces the strongest peak. The DSC profiles and relative stability of the Fc portion show characteristic differences for the human $IgG_1$, $IgG_2$, $IgG_3$, and $IgG_4$ subclasses (Garber and Demarest, *Biochem. Biophys. Res. Commun.* 355, 751-757, 2007). One also can determine average apparent melting temperature using circular dichroism (CD), performed with a CD spectrometer. Far-UV CD spectra will be measured for antibodies in the range of 200 to 260 nm at increments of 0.5 nm. The final spectra can be determined as averages of 20 accumulations. Residue ellipticity values can be calculated after background subtraction. Thermal unfolding of antibodies (0.1 mg/mL) can be monitored at 235 nm from 25-95° C. and a heating rate of 1° C./min One can use dynamic light scattering (DLS) to assess for propensity for aggregation. DLS is used to characterize size of various particles including proteins. If the system is not disperse in size, the mean effective diameter of the particles can be determined. This measurement depends on the size of the particle core, the size of surface structures, and particle concentration. Since DLS essentially measures fluctuations in scattered light intensity due to particles, the diffusion coefficient of the particles can be determined. DLS software in commercial DLA instruments displays the particle population at different diameters. Stability studies can be done conveniently using DLS. DLS measurements of a sample can show whether the particles aggregate over time or with temperature variation by determining whether the hydrodynamic radius of the particle increases. If particles aggregate, one can see a larger population of particles with a larger radius. Stability depending on temperature can be analyzed by controlling the temperature in situ. Capillary electrophoresis (CE) techniques include proven methodologies for determining features of antibody stability. One can use an iCE approach to resolve antibody protein charge variants due to deamidation, C-terminal lysines, sialylation, oxidation, glycosylation, and any other change to the protein that can result in a change in pI of the protein. Each of the expressed antibody proteins can be evaluated by high throughput, free solution isoelectric focusing (IEF) in a capillary column (cIEF), using a Protein Simple Maurice instrument. Whole-column UV absorption detection can be performed every 30 seconds for real time monitoring of molecules focusing at the isoelectric points (pIs). This approach combines the high resolution of traditional gel IEF with the advantages of quantitation and automation found in column-based separations while eliminating the need for a mobilization step. The technique yields reproducible, quantitative analysis of identity, purity, and heterogeneity profiles for the expressed antibodies. The results identify charge heterogeneity and molecular sizing on the antibodies, with both absorbance and native fluorescence detection modes and with sensitivity of detection down to 0.7 µg/mL.

Solubility. One can determine the intrinsic solubility score of antibody sequences. The intrinsic solubility scores can be calculated using CamSol Intrinsic (Sormanni et al., *J Mol Biol* 427, 478-490, 2015). The amino acid sequences for residues 95-102 (Kabat numbering) in HCDR3 of each antibody fragment such as a scFv can be evaluated via the online program to calculate the solubility scores. One also can determine solubility using laboratory techniques. Various techniques exist, including addition of lyophilized protein to a solution until the solution becomes saturated and the solubility limit is reached, or concentration by ultrafiltration in a microconcentrator with a suitable molecular weight cut-off. The most straightforward method is induction of amorphous precipitation, which measures protein solubility using a method involving protein precipitation using ammonium sulfate (Trevino et al., *J Mol Biol*, 366: 449-460, 2007). Ammonium sulfate precipitation gives quick and accurate information on relative solubility values. Ammonium sulfate precipitation produces precipitated solutions with well-defined aqueous and solid phases and requires relatively small amounts of protein. Solubility measurements performed using induction of amorphous precipitation by ammonium sulfate also can be done easily at different pH values. Protein solubility is highly pH dependent, and pH is considered the most important extrinsic factor that affects solubility.

Autoreactivity. Generally, it is thought that autoreactive clones should be eliminated during ontogeny by negative selection, however it has become clear that many human naturally occurring antibodies with autoreactive properties persist in adult mature repertoires, and the autoreactivity may enhance the antiviral function of many antibodies to pathogens. It has been noted that HCDR3 loops in antibodies during early B cell development are often rich in positive charge and exhibit autoreactive patterns (Wardemann et al., *Science* 301, 1374-1377, 2003). One can test a given antibody for autoreactivity by assessing the level of binding to human origin cells in microscopy (using adherent HeLa or HEp-2 epithelial cells) and flow cytometric cell surface staining (using suspension Jurkat T cells and 293S human embryonic kidney cells). Autoreactivity also can be surveyed using assessment of binding to tissues in tissue arrays.

Preferred residues ("Human Likeness"). B cell repertoire deep sequencing of human B cells from blood donors is being performed on a wide scale in many recent studies. Sequence information about a significant portion of the human antibody repertoire facilitates statistical assessment of antibody sequence features common in healthy humans. With knowledge about the antibody sequence features in a human recombined antibody variable gene reference database, the position specific degree of "Human Likeness" (HL) of an antibody sequence can be estimated. HL has been shown to be useful for the development of antibodies in clinical use, like therapeutic antibodies or antibodies as vaccines. The goal is to increase the human likeness of antibodies to reduce potential adverse effects and anti-antibody immune responses that will lead to significantly decreased efficacy of the antibody drug or can induce serious health implications. One can assess antibody characteristics of the combined antibody repertoire of three healthy human blood donors of about 400 million sequences in total and created a novel "relative Human Likeness" (rHL) score that focuses on the hypervariable region of the antibody. The rHL score allows one to easily distinguish between human (positive score) and non-human sequences (negative score). Antibodies can be engineered to eliminate residues that are not common in human repertoires.

D. Single Chain Antibodies

A single chain variable fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma or B cell. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alanine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Multispecific Antibodies

In certain embodiments, antibodies of the present disclosure are bispecific or multispecific. Bispecific antibodies are antibodies that have binding specificities for at least two different epitopes. Exemplary bispecific antibodies may bind to two different epitopes of a single antigen. Other such antibodies may combine a first antigen binding site with a binding site for a second antigen. Alternatively, an antipathogen arm may be combined with an arm that binds to a triggering molecule on a leukocyte, such as a T-cell receptor molecule (e.g., CD3), or Fc receptors for IgG (FcγR), such as FcγRI (CD64), FcγRII (CD32) and Fc gamma RIII (CD16), so as to focus and localize cellular defense mechanisms to the infected cell. Bispecific antibodies may also be used to localize cytotoxic agents to infected cells. These antibodies possess a pathogen-binding arm and an arm that binds the cytotoxic agent (e.g., saporin, anti-interferon-α, vinca alkaloid, ricin A chain, methotrexate or radioactive isotope hapten). Bispecific antibodies can be prepared as full-length antibodies or antibody fragments (e.g., F(ab')$_2$ bispecific antibodies). WO 96/16673 describes a bispecific anti-ErbB2/anti-Fc gamma RIII antibody and U.S. Pat. No. 5,837,234 discloses a bispecific anti-ErbB2/anti-Fc gamma RI antibody. A bispecific anti-ErbB2/Fc alpha antibody is shown in WO98/02463. U.S. Pat. No. 5,821,337 teaches a bispecific anti-ErbB2/anti-CD3 antibody.

Methods for making bispecific antibodies are known in the art. Traditional production of full-length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable regions with the desired binding specificities (antibody-antigen combining sites) are fused to immunoglobulin constant domain sequences. Preferably, the fusion is with an Ig heavy chain constant domain, comprising at least part of the hinge, $C_{H2}$, and $C_{H3}$ regions. It is preferred to have the first heavy-chain constant region ($C_{H1}$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

In a particular embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_{H3}$ domain In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Techniques exist that facilitate the direct recovery of Fab'-SH fragments from *E. coli*, which can be chemically coupled to form bispecific antibodies. Shalaby et al., J. Exp. Med., 175: 217-225 (1992) describe the production of a humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described (Merchant et al., *Nat. Biotechnol,* 16, 677-681 (1998) doi:10.1038/nbt0798-677pmid: 9661204). For example, bispecific antibodies have been produced using leucine zippers (Kostelny et al., J. Immunol., 148(5):1547-1553, 1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a $V_H$ connected to a $V_L$ by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

In a particular embodiment, a bispecific or multispecific antibody may be formed as a DOCK-AND-LOCK™ (DNL™) complex (see, e.g., U.S. Pat. Nos. 7,521,056; 7,527,787; 7,534,866; 7,550,143 and 7,666,400, the Examples section of each of which is incorporated herein by reference.) Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., FEBS Letters. 2005; 579: 3264; Wong and Scott, Nat. Rev. Mol. Cell Biol. 2004; 5: 959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Antibodies with more than two valencies are contemplated. For example, trispecific antibodies can be prepared (Tutt et al., J. Immunol. 147: 60, 1991; Xu et al., *Science,* 358(6359):85-90, 2017). A multivalent antibody may be internalized (and/or catabolized) faster than a bivalent antibody by a cell expressing an antigen to which the antibodies bind. The antibodies of the present disclosure can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable regions. For instance, the polypeptide chain(s) may comprise VD1-(X1)$_n$-VD2-(X2)$_n$-Fc, wherein VD1 is a first variable region, VD2 is a second variable region, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable region polypeptides. The multivalent antibody herein may, for instance, comprise from about two to about eight light chain variable region polypeptides. The light chain variable region polypeptides contemplated here comprise a light chain variable region and, optionally, further comprise a $C_L$ domain.

Charge modifications are particularly useful in the context of a multispecific antibody, where amino acid substitutions in Fab molecules result in reducing the mispairing of light chains with non-matching heavy chains (Bence-Jones-type side products), which can occur in the production of Fab-based bi-/multispecific antigen binding molecules with a VH/VL exchange in one (or more, in case of molecules comprising more than two antigen-binding Fab molecules) of their binding arms (see also PCT publication no. WO 2015/150447, particularly the examples therein, incorporated herein by reference in its entirety).

Accordingly, in particular embodiments, an antibody comprised in the therapeutic agent comprises
(a) a first Fab molecule which specifically binds to a first antigen
(b) a second Fab molecule which specifically binds to a second antigen, and wherein the variable domains VL and VH of the Fab light chain and the Fab heavy chain are replaced by each other,
wherein the first antigen is an activating T cell antigen and the second antigen is a target cell antigen, or the first antigen is a target cell antigen and the second antigen is an activating T cell antigen; and
wherein
i) in the constant domain CL of the first Fab molecule under a) the amino acid at position 124 is substituted by a positively charged amino acid (numbering according to Kabat), and wherein in the constant domain CH1 of the first Fab molecule under a) the amino acid at position 147 or the amino acid at position 213 is substituted by a negatively charged amino acid (numbering according to Kabat EU index); or
ii) in the constant domain CL of the second Fab molecule under b) the amino acid at position 124 is substituted by a positively charged amino acid (numbering according to Kabat), and wherein in the constant domain CH1 of the second Fab molecule under b) the amino acid at position 147 or the amino acid at position 213 is substituted by a negatively charged amino acid (numbering according to Kabat EU index).

The antibody may not comprise both modifications mentioned under i) and ii). The constant domains CL and CH1 of the second Fab molecule are not replaced by each other (i.e., remain unexchanged).

In another embodiment of the antibody, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 or the amino acid at position 213 is substituted independently by glutamic acid (E), or aspartic acid (D) (numbering according to Kabat EU index).

In a further embodiment, in the constant domain CL of the first Fab molecule under a) the amino acid at position 124 is substituted independently by lysine (K), arginine (R) or histidine (H) (numbering according to Kabat), and in the constant domain CH1 of the first Fab molecule under a) the amino acid at position 147 is substituted independently by glutamic acid (E), or aspartic acid (D) (numbering according to Kabat EU index).

In a particular embodiment, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)) and the amino acid at position 123 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more particular embodiment, in the constant domain CL of the first Fab molecule under a) the amino acid at position 124 is substituted by lysine (K) (numbering according to Kabat) and the amino acid at position 123 is substituted by lysine (K) or arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

In an even more particular embodiment, in the constant domain CL of the first Fab molecule under a) the amino acid at position 124 is substituted by lysine (K) (numbering according to Kabat) and the amino acid at position 123 is substituted by arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

F. Chimeric Antigen Receptors

Artificial T cell receptors (also known as chimeric T cell receptors, chimeric immunoreceptors, chimeric antigen receptors (CARs)) are engineered receptors, which graft an arbitrary specificity onto an immune effector cell. Typically, these receptors are used to graft the specificity of a monoclonal antibody onto a T cell, with transfer of their coding sequence facilitated by retroviral vectors. In this way, a large number of target-specific T cells can be generated for adoptive cell transfer. Phase I clinical studies of this approach show efficacy.

The most common form of these molecules are fusions of single-chain variable fragments (scFv) derived from monoclonal antibodies, fused to CD3-zeta transmembrane and endodomain Such molecules result in the transmission of a zeta signal in response to recognition by the scFv of its target. An example of such a construct is 14g2a-Zeta, which is a fusion of a scFv derived from hybridoma 14g2a (which recognizes disialoganglioside GD2). When T cells express this molecule (usually achieved by oncoretroviral vector transduction), they recognize and kill target cells that express GD2 (e.g., neuroblastoma cells). To target malignant B cells, investigators have redirected the specificity of T cells using a chimeric immunoreceptor specific for the B-lineage molecule, CD19.

The variable portions of an immunoglobulin heavy and light chain are fused by a flexible linker to form a scFv. This scFv is preceded by a signal peptide to direct the nascent protein to the endoplasmic reticulum and subsequent surface expression (this is cleaved). A flexible spacer allows to the scFv to orient in different directions to enable antigen binding. The transmembrane domain is a typical hydrophobic alpha helix usually derived from the original molecule of the signaling endodomain which protrudes into the cell and transmits the desired signal.

Type I proteins are in fact two protein domains linked by a transmembrane alpha helix in between. The cell membrane lipid bilayer, through which the transmembrane domain passes, acts to isolate the inside portion (endodomain) from the external portion (ectodomain). It is not so surprising that attaching an ectodomain from one protein to an endodomain of another protein results in a molecule that combines the recognition of the former to the signal of the latter.

Ectodomain. A signal peptide directs the nascent protein into the endoplasmic reticulum. This is essential if the receptor is to be glycosylated and anchored in the cell membrane. Any eukaryotic signal peptide sequence usually works fine. Generally, the signal peptide natively attached to the amino-terminal most component is used (e.g., in a scFv with orientation light chain-linker-heavy chain, the native signal of the light-chain is used The antigen recognition domain is usually an scFv. There are however many alternatives. An antigen recognition domain from native T-cell receptor (TCR) alpha and beta single chains have been described, as have simple ectodomains (e.g., CD4 ectodomain to recognize HIV infected cells) and more exotic recognition components such as a linked cytokine (which leads to recognition of cells bearing the cytokine receptor). In fact, almost anything that binds a given target with high affinity can be used as an antigen recognition region.

A spacer region links the antigen binding domain to the transmembrane domain. It should be flexible enough to allow the antigen binding domain to orient in different directions to facilitate antigen recognition. The simplest form is the hinge region from IgG1. Alternatives include the $CH_2CH_3$ region of immunoglobulin and portions of CD3. For most scFv based constructs, the IgG1 hinge suffices. However, the best spacer often has to be determined empirically.

Transmembrane domain. The transmembrane domain is a hydrophobic alpha helix that spans the membrane. Generally, the transmembrane domain from the most membrane proximal component of the endodomain is used. Interestingly, using the CD3-zeta transmembrane domain may result in incorporation of the artificial TCR into the native TCR a factor that is dependent on the presence of the native CD3-zeta transmembrane charged aspartic acid residue. Different transmembrane domains result in different receptor stability. The CD28 transmembrane domain results in a brightly expressed, stable receptor.

Endodomain. This is the "business-end" of the receptor. After antigen recognition, receptors cluster and a signal is transmitted to the cell. The most commonly used endodomain component is CD3-zeta which contains 3 ITAMs. This transmits an activation signal to the T cell after antigen is bound. CD3-zeta may not provide a fully competent activation signal and additional co-stimulatory signaling is needed.

"First-generation" CARs typically had the intracellular domain from the CD3 ξ-chain, which is the primary transmitter of signals from endogenous TCRs. "Second-generation" CARs add intracellular signaling domains from various costimulatory protein receptors (e.g., CD28, 41BB, ICOS) to the cytoplasmic tail of the CAR to provide additional signals to the T cell. Preclinical studies have indicated that the second generation of CAR designs improves the antitumor activity of T cells. More recent, "third-generation" CARs combine multiple signaling domains, such as CD3z-CD28-41BB or CD3z-CD28-OX40, to further augment potency.

G. ADCs

Antibody Drug Conjugates or ADCs are a new class of highly potent biopharmaceutical drugs designed as a targeted therapy for the treatment of people with infectious disease. ADCs are complex molecules composed of an antibody (a whole mAb or an antibody fragment such as a single-chain variable fragment, or scFv) linked, via a stable chemical linker with labile bonds, to a biological active cytotoxic/anti-viral payload or drug. Antibody Drug Conjugates are examples of bioconjugates and immunoconjugates.

By combining the unique targeting capabilities of monoclonal antibodies with the cancer-killing ability of cytotoxic drugs, antibody-drug conjugates allow sensitive discrimination between healthy and diseased tissue. This means that, in contrast to traditional systemic approaches, antibody-drug conjugates target and attack the infected cell so that healthy cells are less severely affected.

In the development ADC-based anti-tumor therapies, an anticancer drug (e.g., a cell toxin or cytotoxin) is coupled to an antibody that specifically targets a certain cell marker (e.g., a protein that, ideally, is only to be found in or on infected cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cell or impairs viral replication. Due to this targeting, ideally the drug has lower side effects and gives a wider therapeutic window than other agents.

A stable link between the antibody and cytotoxic/antiviral agent is a crucial aspect of an ADC. Linkers are based on chemical motifs including disulfides, hydrazones or peptides (cleavable), or thioethers (non-cleavable) and control the distribution and delivery of the cytotoxic agent to the target cell. Cleavable and non-cleavable types of linkers have been proven to be safe in preclinical and clinical trials. Brentuximab vedotin includes an enzyme-sensitive cleavable linker that delivers the potent and highly toxic antimicrotubule agent Monomethyl auristatin E or MMAE, a synthetic antineoplastic agent, to human specific CD30-positive malignant cells. Because of its high toxicity MMAE, which inhibits cell division by blocking the polymerization of tubulin, cannot be used as a single-agent chemotherapeutic drug. However, the combination of MMAE linked to an anti-CD30 monoclonal antibody (cAC10, a cell membrane protein of the tumor necrosis factor or TNF receptor) proved to be stable in extracellular fluid, cleavable by cathepsin and safe for therapy. Trastuzumab emtansine, the other approved ADC, is a combination of the microtubule-formation inhibitor mertansine (DM-1), a derivative of the Maytansine, and antibody trastuzumab (Herceptin®/Genentech/Roche) attached by a stable, non-cleavable linker.

The availability of better and more stable linkers has changed the function of the chemical bond. The type of linker, cleavable or non-cleavable, lends specific properties to the cytotoxic (anti-cancer) drug. For example, a non-cleavable linker keeps the drug within the cell. As a result, the entire antibody, linker and cytotoxic agent enter the targeted cancer cell where the antibody is degraded to the level of an amino acid. The resulting complex—amino acid, linker and cytotoxic agent—now becomes the active drug. In contrast, cleavable linkers are catalyzed by enzymes in the host cell where it releases the cytotoxic agent.

Another type of cleavable linker, currently in development, adds an extra molecule between the cytotoxic/antiviral drug and the cleavage site. This linker technology allows researchers to create ADCs with more flexibility without worrying about changing cleavage kinetics. Researchers are also developing a new method of peptide cleavage based on Edman degradation, a method of sequencing amino acids in a peptide. Future direction in the development of ADCs also include the development of site-specific conjugation (TDCs) to further improve stability and therapeutic index and a emitting immunoconjugates and antibody-conjugated nanoparticles.

H. BiTES

Bi-specific T-cell engagers (BiTEs) are a class of artificial bispecific monoclonal antibodies that are investigated for the use as anti-cancer drugs. They direct a host's immune system, more specifically the T cells' cytotoxic activity, against infected cells. BiTE is a registered trademark of Micromet AG.

BiTEs are fusion proteins consisting of two single-chain variable fragments (scFvs) of different antibodies, or amino acid sequences from four different genes, on a single peptide chain of about 55 kilodaltons. One of the scFvs binds to T cells via the CD3 receptor, and the other to an infected cell via a specific molecule.

Like other bispecific antibodies, and unlike ordinary monoclonal antibodies, BiTEs form a link between T cells and target cells. This causes T cells to exert cytotoxic/antiviral activity on infected cells by producing proteins like perforin and granzymes, independently of the presence of MHC I or co-stimulatory molecules. These proteins enter infected cells and initiate the cell's apoptosis. This action mimics physiological processes observed during T cell attacks against infected cells.

I. Intrabodies

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

By virtue of their ability to enter cells, intrabodies have additional uses that other types of antibodies may not achieve. In the case of the present antibodies, the ability to interact with the MUC1 cytoplasmic domain in a living cell may interfere with functions associated with the MUC1 CD, such as signaling functions (binding to other molecules) or oligomer formation. In particular, it is contemplated that such antibodies can be used to inhibit MUC1 dimer formation.

J. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies are bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. ACTIVE/PASSIVE IMMUNIZATION AND TREATMENT/PREVENTION OF ENTEROVIRUS D68 INFECTION

A. Formulation and Administration

The present disclosure provides pharmaceutical compositions comprising anti-EV-D68 antibodies and antigens for generating the same. Such compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, intrarectal, vaginal, topical or delivered by mechanical ventilation.

Active vaccines are also envisioned where antibodies like those disclosed are produced in vivo in a subject at risk of EV-D68 infection. Such vaccines can be formulated for parenteral administration, e.g., formulated for injection via the intradermal, intravenous, intramuscular, subcutaneous, aerosol or even intraperitoneal routes. Administration by intradermal and intramuscular routes are contemplated. The vaccine could alternatively be administered by a topical route directly to the mucosa, for example by nasal drops, inhalation, by nebulizer, or via intrarectal or vaginal delivery. Pharmaceutically acceptable salts include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

2. ADCC

Antibody-dependent cell-mediated cytotoxicity (ADCC) is an immune mechanism leading to the lysis of antibody-coated target cells by immune effector cells. The target cells are cells to which antibodies or fragments thereof comprising an Fc region specifically bind, generally via the protein part that is N-terminal to the Fc region. By "antibody having increased/reduced antibody dependent cell-mediated cytotoxicity (ADCC)" is meant an antibody having increased/reduced ADCC as determined by any suitable method known to those of ordinary skill in the art.

As used herein, the term "increased/reduced ADCC" is defined as either an increase/reduction in the number of target cells that are lysed in a given time, at a given concentration of antibody in the medium surrounding the target cells, by the mechanism of ADCC defined above, and/or a reduction/increase in the concentration of antibody, in the medium surrounding the target cells, required to achieve the lysis of a given number of target cells in a given time, by the mechanism of ADCC. The increase/reduction in ADCC is relative to the ADCC mediated by the same antibody produced by the same type of host cells, using the same standard production, purification, formulation and storage methods (which are known to those skilled in the art), but that has not been engineered. For example the increase in ADCC mediated by an antibody produced by host cells engineered to have an altered pattern of glycosylation (e.g., to express the glycosyltransferase, GnTIII, or other glycosyltransferases) by the methods described herein, is relative to the ADCC mediated by the same antibody produced by the same type of non-engineered host cells.

3. CDC

Complement-dependent cytotoxicity (CDC) is a function of the complement system. It is the processes in the immune system that kill pathogens by damaging their membranes without the involvement of antibodies or cells of the immune system. There are three main processes. All three insert one or more membrane attack complexes (MAC) into the pathogen which cause lethal colloid-osmotic swelling, i.e., CDC. It is one of the mechanisms by which antibodies or antibody fragments have an anti-viral effect.

IV. ANTIBODY CONJUGATES

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine[211], [14]carbon, [51]chromium, [36]chlorine, [57]cobalt, [58]cobalt, copper[67], [152]Eu, gallium[67], [3]hydrogen, iodine[123], iodine[125], iodine[131], indium[111], [59]iron, [32]phosphorus, rhenium[186], rhenium[188], [75]selenium, [35]sulphur, technicium[99m] and/or yttrium[90]. [125]I is often being preferred for use in certain embodiments, and technicium[99m] and/or indium[111] are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium[99m] by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Additional types of antibodies contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939,350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. IMMUNODETECTION METHODS

In still further embodiments, the present disclosure concerns immunodetection methods for binding, purifying, removing, quantifying and otherwise generally detecting EV-D68 and its associated antigens. While such methods can be applied in a traditional sense, another use will be in quality control and monitoring of vaccine and other virus stocks, where antibodies according to the present disclosure can be used to assess the amount or integrity (i.e., long term stability) of antigens in viruses. Alternatively, the methods may be used to screen various antibodies for appropriate/desired reactivity profiles.

Other immunodetection methods include specific assays for determining the presence of EV-D68 in a subject. A wide variety of assay formats are contemplated, but specifically those that would be used to detect EV-D68 in a fluid obtained from a subject, such as saliva, blood, plasma, sputum, semen, urine, respiratory droplets or aerosol. In particular, semen has been demonstrated as a viable sample for detecting EV-D68 (Purpura et al., 2016; Mansuy et al., 2016; Barzon et al., 2016; Gornet et al., 2016; Duffy et al., 2009; CDC, 2016; Halfon et al., 2010; Elder et al. 2005). The assays may be advantageously formatted for non-healthcare (home) use, including lateral flow assays (see below) analogous to home pregnancy tests. These assays may be packaged in the form of a kit with appropriate reagents and instructions to permit use by the subject of a family member.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of EV-D68 antibodies directed to specific parasite epitopes in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing EV-D68, and contacting the sample with a first antibody in accordance with the present disclosure, as the case may be, under conditions effective to allow the formation of immunocomplexes.

These methods include methods for purifying EV-D68 or related antigens from a sample. The antibody will preferably be linked to a solid support, such as in the form of a column matrix, and the sample suspected of containing the EV-D68 or antigenic component will be applied to the immobilized antibody. The unwanted components will be washed from the column, leaving the EV-D68 antigen immunocomplexed to the immobilized antibody, which is then collected by removing the organism or antigen from the column.

The immunobinding methods also include methods for detecting and quantifying the amount of EV-D68 or related components in a sample and the detection and quantification of any immune complexes formed during the binding process. Here, one would obtain a sample suspected of containing EV-D68 or its antigens and contact the sample with an antibody that binds EV-D68 or components thereof, followed by detecting and quantifying the amount of immune complexes formed under the specific conditions. In terms of antigen detection, the biological sample analyzed may be any sample that is suspected of containing EV-D68 or EV-D68 antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to EV-D68 or antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the EV-D68 or EV-D68 antigen is added to the wells. After binding and washing to remove non-specifically bound immune complexes, the bound antigen may be detected. Detection may be achieved by the addition of another anti-EV-D68 antibody that is linked to a detectable label. This type of ELISA is a simple "sandwich ELISA." Detection may also be achieved by the addition of a second anti-EV-D68 antibody, followed by the addition of a third antibody that has binding affinity for the second antibody, with the third antibody being linked to a detectable label.

In another exemplary ELISA, the samples suspected of containing the EV-D68 or EV-D68 antigen are immobilized onto the well surface and then contacted with the anti-EV-D68 antibodies of the disclosure. After binding and washing to remove non-specifically bound immune complexes, the bound anti-EV-D68 antibodies are detected. Where the initial anti-EV-D68 antibodies are linked to a detectable label, the immune complexes may be detected directly. Again, the immune complexes may be detected using a second antibody that has binding affinity for the first anti-EV-D68 antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present disclosure contemplates the use of competitive formats. This is particularly useful in the detection of EV-D68 antibodies in sample. In competition-based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventor proposes the use of labeled EV-D68 monoclonal antibodies to determine the amount of EV-D68 antibodies in a sample. The basic format would include contacting a known amount of EV-D68 monoclonal antibody (linked to a detectable label) with EV-D68 antigen or particle. The EV-D68 antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Lateral Flow Assays

Lateral flow assays, also known as lateral flow immunochromatographic assays, are simple devices intended to detect the presence (or absence) of a target analyte in sample (matrix) without the need for specialized and costly equipment, though many laboratory-based applications exist that are supported by reading equipment. Typically, these tests are used as low resources medical diagnostics, either for home testing, point of care testing, or laboratory use. A widely spread and well-known application is the home pregnancy test.

The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex. After a while, when more and more fluid has passed the stripes, particles accumulate and the stripe-area changes color. Typically there are at least two stripes: one (the control) that captures any particle and thereby shows that reaction conditions and technology worked fine, the second contains a specific capture molecule and only captures those particles onto which an analyte molecule has been immobilized. After passing these reaction zones, the fluid enters the final porous material—the wick—that simply acts as a waste container. Lateral Flow Tests can operate as either competitive or sandwich assays. Lateral flow assays are disclosed in U.S. Pat. No. 6,485,982.

D. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules;

pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

E. Immunodetection Kits

In still further embodiments, the present disclosure concerns immunodetection kits for use with the immunodetection methods described above. As the antibodies may be used to detect EV-D68 or EV-D68 antigens, the antibodies may be included in the kit. The immunodetection kits will thus comprise, in suitable container means, a first antibody that binds to EV-D68 or EV-D68 antigen, and optionally an immunodetection reagent.

In certain embodiments, the EV-D68 antibody may be pre-bound to a solid support, such as a column matrix and/or well of a microtiter plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the EV-D68 or EV-D68 antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

F. Vaccine and Antigen Quality Control Assays

The present disclosure also contemplates the use of antibodies and antibody fragments as described herein for use in assessing the antigenic integrity of a viral antigen in a sample. Biological medicinal products like vaccines differ from chemical drugs in that they cannot normally be characterized molecularly; antibodies are large molecules of significant complexity and have the capacity to vary widely from preparation to preparation. They are also administered to healthy individuals, including children at the start of their lives, and thus a strong emphasis must be placed on their quality to ensure, to the greatest extent possible, that they are efficacious in preventing or treating life-threatening disease, without themselves causing harm.

The increasing globalization in the production and distribution of vaccines has opened new possibilities to better manage public health concerns but has also raised questions about the equivalence and interchangeability of vaccines procured across a variety of sources. International standardization of starting materials, of production and quality control testing, and the setting of high expectations for regulatory oversight on the way these products are manufactured and used, have thus been the cornerstone for continued success. But it remains a field in constant change, and continuous technical advances in the field offer a promise of developing potent new weapons against the oldest public health threats, as well as new ones—malaria, pandemic influenza, and HIV, to name a few—but also put a great pressure on manufacturers, regulatory authorities, and the wider medical community to ensure that products continue to meet the highest standards of quality attainable.

Thus, one may obtain an antigen or vaccine from any source or at any point during a manufacturing process. The quality control processes may therefore begin with preparing a sample for an immunoassay that identifies binding of an antibody or fragment disclosed herein to a viral antigen. Such immunoassays are disclosed elsewhere in this document, and any of these may be used to assess the structural/antigenic integrity of the antigen. Standards for finding the sample to contain acceptable amounts of antigenically correct and intact antigen may be established by regulatory agencies.

Another important embodiment where antigen integrity is assessed is in determining shelf-life and storage stability. Most medicines, including vaccines, can deteriorate over time. Therefore, it is critical to determine whether, over time, the degree to which an antigen, such as in a vaccine, degrades or destabilizes such that is it no longer antigenic and/or capable of generating an immune response when administered to a subject. Again, standards for finding the sample to contain acceptable amounts of antigenically intact antigen may be established by regulatory agencies.

In certain embodiments, viral antigens may contain more than one protective epitope. In these cases, it may prove useful to employ assays that look at the binding of more than one antibody, such as 2, 3, 4, 5 or even more antibodies. These antibodies bind to closely related epitopes, such that they are adjacent or even overlap each other. On the other hand, they may represent distinct epitopes from disparate parts of the antigen. By examining the integrity of multiple epitopes, a more complete picture of the antigen's overall integrity, and hence ability to generate a protective immune response, may be determined.

Antibodies and fragments thereof as described in the present disclosure may also be used in a kit for monitoring the efficacy of vaccination procedures by detecting the presence of protective EV-D68 antibodies. Antibodies, antibody fragment, or variants and derivatives thereof, as described in the present disclosure may also be used in a kit for monitoring vaccine manufacture with the desired immunogenicity.

VI. EXAMPLES

The following examples are included to demonstrate preferred embodiments. It should be appreciated by those of skill in the art that the techniques disclosed in the examples that follow represent techniques discovered by the inventor to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Animals. Four-week-old male and female AG129 mice from a specific-pathogen-free colony maintained at the Utah Science Technology and Research (USTAR) building at Utah State University. The mice were bred and maintained on irradiated Teklad Rodent Diet (Harlan Teklad) and autoclaved tap water at the USTAR building of Utah State University.

Antibodies and Compound. The monoclonal antibody (mAb) EV-D68-228 was provided by James Crowe at Vanderbilt University Medical Center. EV-D68-228 was provided in solution at a concentration of 1.134 mg/ml and was diluted in sterile saline to doses of 10, 3, and 1 mg/kg for treatment. rRSV-90 was provided in solution at a concentration of 5 mg/ml and was used as a negative control antibody at a dose of 10 mg/kg. Intravenous immunoglobulin (IVIg, Carimune, CSL Behring, King of Prussia, PA) was purchased from a local pharmacy and was used as a comparator to the EV-D68-228 mAb. Guanidine HCl (guanidine) was obtained from Sigma-Aldrich (St. Louis, MO) and served as a positive control.

Virus. Enterovirus D68 was obtained from BEI Resources, NIAID, NIH: Enterovirus D68, US/MO/14-18949, NR-49130. The virus was serially passaged 30 times in the lungs of 4-week-old AG129 mice and then plaque-purified three times in Rhabdomyosarcoma (RD) cells obtained from the American Type Culture Collection (Manassas, VA). The resulting virus stock was amplified twice in RD cells to create a working stock. The virus used for infection was designated EV-D68 MP30 PP.

Experiment design. A total of 78 mice were randomized into 6 groups of 12 mice each with a group of 6 mice used for normal controls as shown in Table I. Mice were treated via intraperitoneal (IP) administration of EV-D68-228 mAb, IVIg, or placebo mAb 24 hours prior to infection. Mice were infected via intranasal (IN) instillation of $1 \times 10^{4.5}$ $CCID_{50}$ of EV-D68 MP30 PP in a 90 µl volume of MEM. Treatment with guanidine started 4 hours post-infection and continued twice daily for 5 days. Mice were weighed prior to treatment and daily thereafter. Four mice from each treatment group were euthanized on days 1, 3, and 5 post-infection for evaluation of lung virus titers, blood virus titers, and lung cytokine concentrations.

Lung Cytokine/Chemokine Evaluations. Each sample of lung homogenate was tested for cytokines and chemokines using a chemiluminescent ELISA-based assay according to the manufacturer's instructions (Quansys Biosciences Q-Plex™ Array, Logan, UT). The Quansys multiplex ELISA is a quantitative test in which 16 distinct capture antibodies have been applied to each well of a 96-well plate in a defined array. Each sample supernatant was tested at for the following: IL-1α, IL-1β, IL-2, IL-3, IL-4, IL-5, IL-6, IL-10, IL-12p70, IL-17, MCP-1, IFN-γ, TNFα, MIP-1α, GM-CSF, and RANTES. Definitions of abbreviations are: IL—interleukin; MCP—monocyte chemoattractant protein; IFN—interferon; TNF—tumor necrosis factor, MIP— macrophage inflammatory protein; GM-CSF—granulocyte/macrophage colony stimulating factor; and RANTES— regulated upon activation, normal T cell expressed and secreted.

Statistical analysis. All figures and statistical analyses were completed using Prism 8.0.2. (GraphPad Software Inc.). For each day post-infection, lung and blood virus titers from treated groups were compared to lung and blood titers from placebo-treated mice using a one-way analysis of variance (ANOVA). For each cytokine/chemokine, the concentrations from treated mice were compared to placebo-treated mice using a two-way ANOVA.

Ethics regulation of laboratory animals. This study was conducted in accordance with the approval of the Institutional Animal Care and Use Committee of Utah State University dated Mar. 2, 2019 (expires Mar. 1, 2022). The work was done in the AAALAC-accredited Laboratory Animal Research Center of Utah State University. The U. S. Government (National Institutes of Health) approval was renewed Mar. 9, 2018 (PHS Assurance No. D16-00468 [A3801-01]) in accordance to the National Institutes of Health Guide for the Care and Use of Laboratory Animals (Revision; 2011).

TABLE I

Experimental Design to Text Efficacy of EV-D68-228 for treatment of an EV-D68 respiratory infection in mice

| Number/Cage | Group No. | Infected | Compound | Dosage | Route | Treatment Schedule | Observations |
|---|---|---|---|---|---|---|---|
| 12 | 1 | Yes | rRSV-90 (Placebo) | 10 mg/kg | IP | Once, 24 hours pre-infection | 4 mice per group euthanized at days 1, 3, and 5 post-infection for lung virus titers, blood virus titers, and lung cytokines. |
| 12 | 3 | Yes | EV-D68-228 | 10 mg/kg | | | |
| 12 | 5 | Yes | EV-D68-228 | 3 mg/kg | | | |
| 12 | 7 | Yes | EV-D68-228 | 1 mg/kg | | | |
| 12 | 9 | Yes | IVIg (Carimune NF) | 10 mg/kg | | | |
| 12 | 11 | Yes | Guanidine | 100 mg/kg/day | | b.i.d. x 5 beginning 4 hours post-infection | |
| 6 | 2 | No | Normal Controls | — | — | — | 2 mice per group euthanized at days 1, 3, and 5 post-infection for lung cytokines. |

Example 2—Results

The objective of this study was to determine the efficacy of treatment with EV-D68-228 for an Enterovirus D68 (EV-D68) respiratory infection in four-week-old AG129 mice. This study determined the efficacy of an EV-D68-228 mAb for treatment of an EV-D68 respiratory infection in four-week-old AG129 mice.

Figure 3:
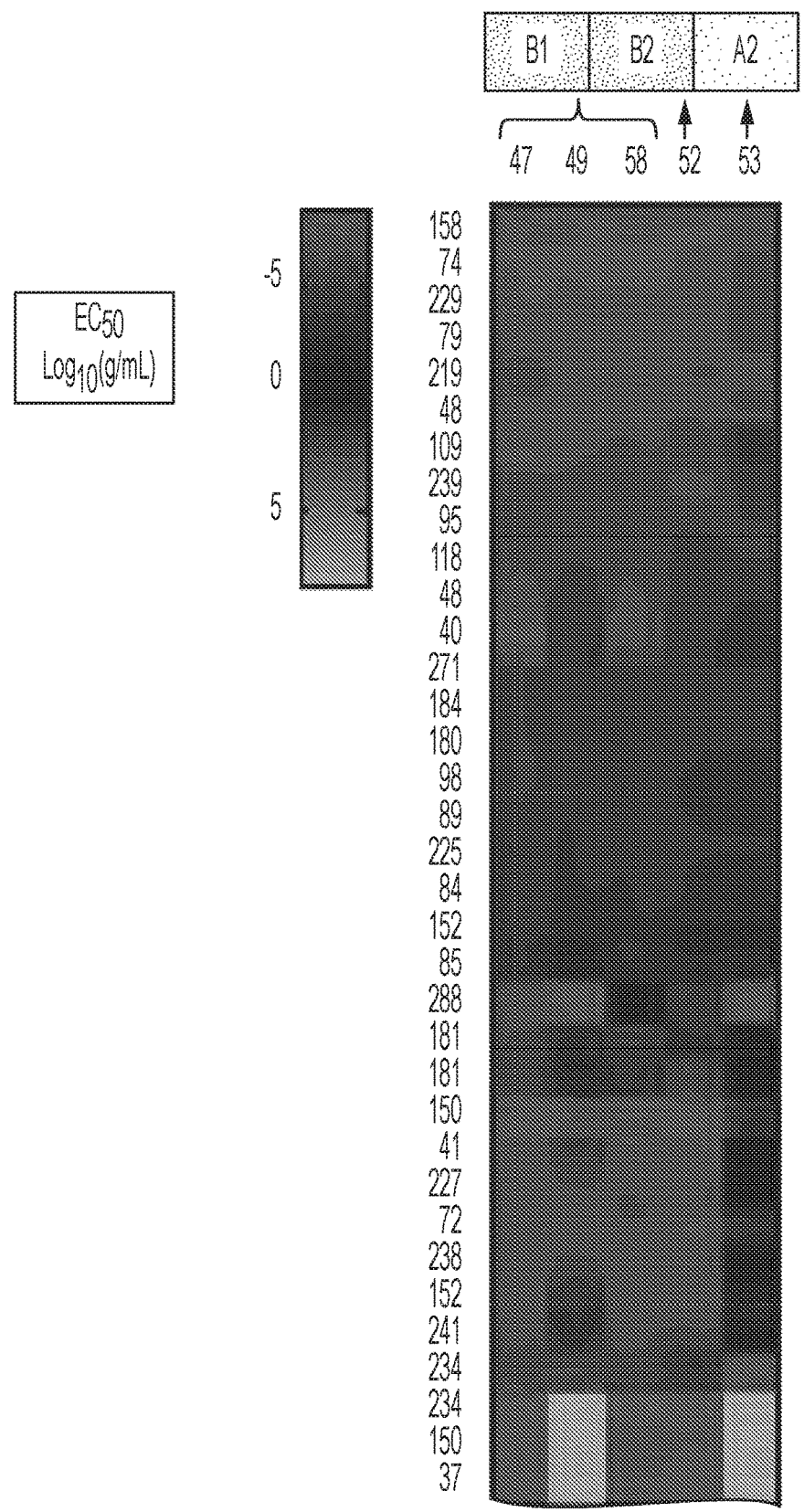
Figure 3:
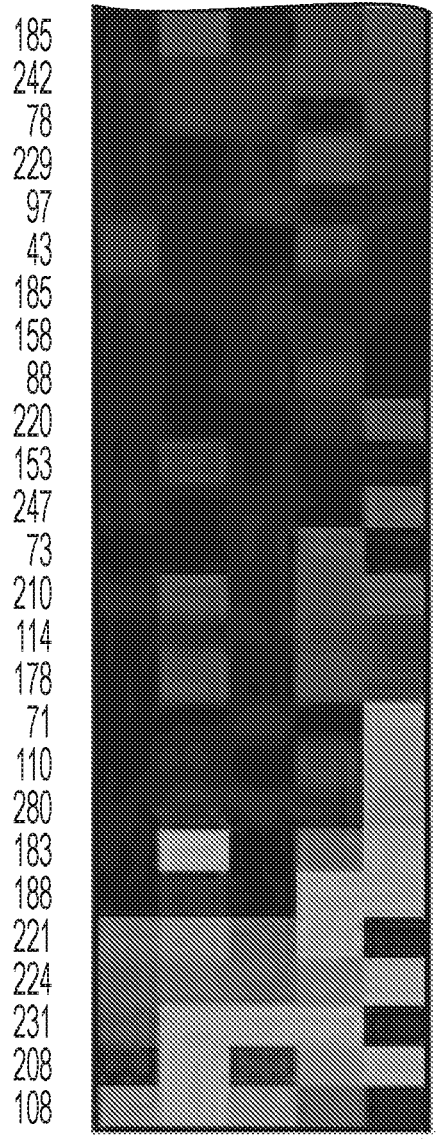
Figure 4:
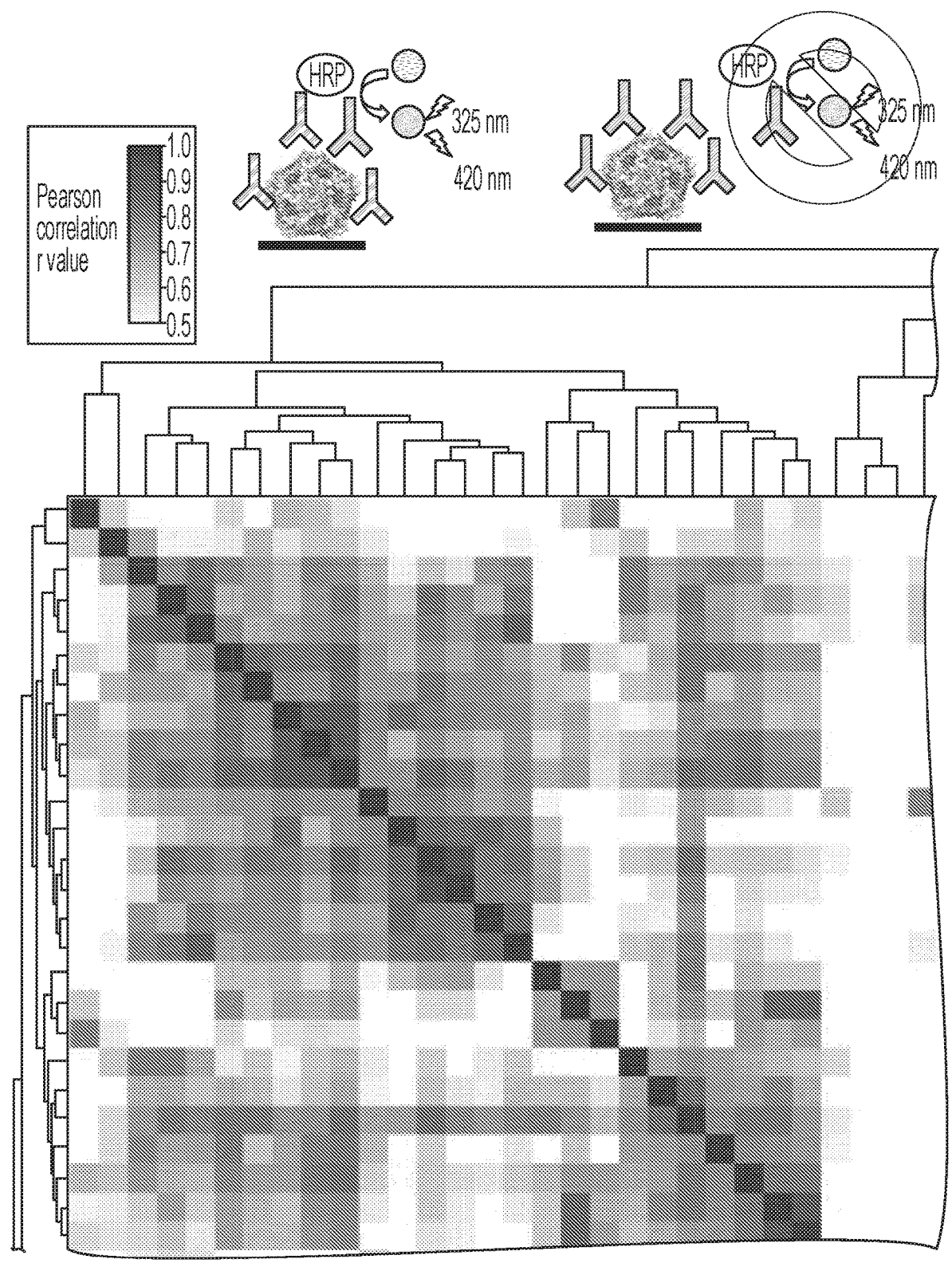
FIG. 4. Competition reveals at least four main surface epitopes. Using Pearson correlation, the inventors generated relatedness values as the colored readout to cluster. This relatedness helps to sort the antibodies, but not actual interference percentage. The inventors have now described three to four phenotypes, which can be related to each other. This permits identification of candidates for clinical development.
Figure 4:
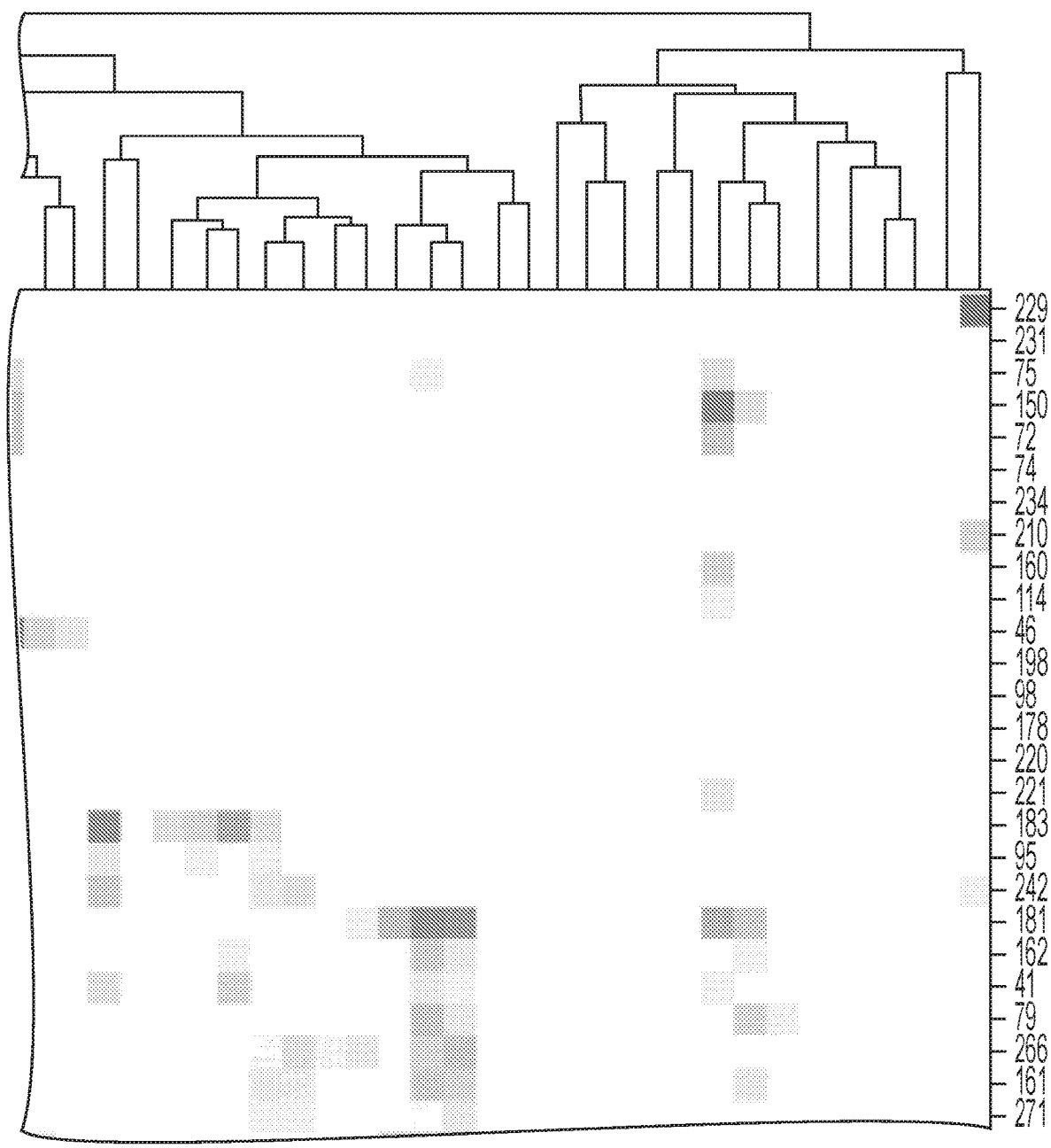
Figure 4:
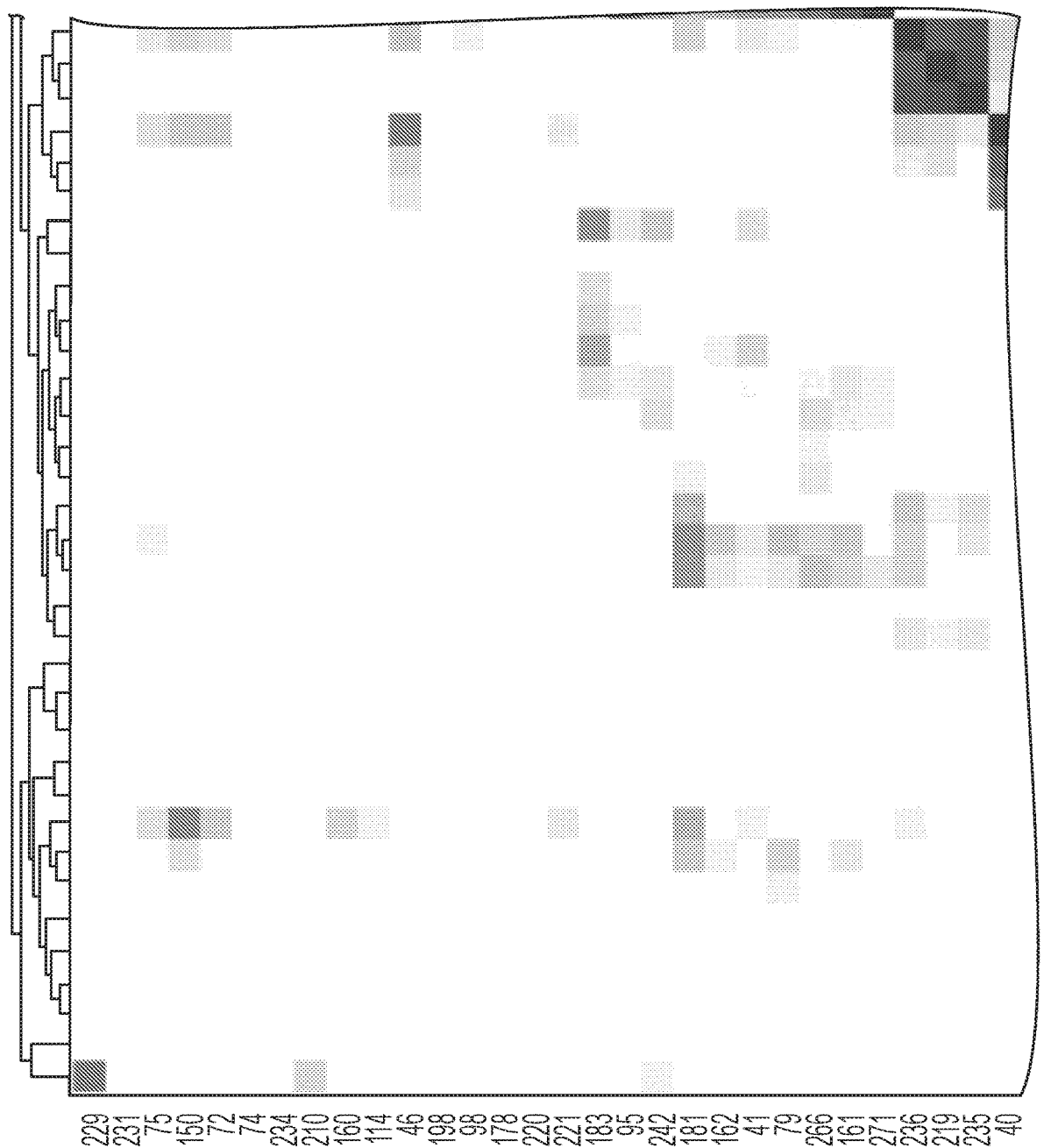
Figure 4:
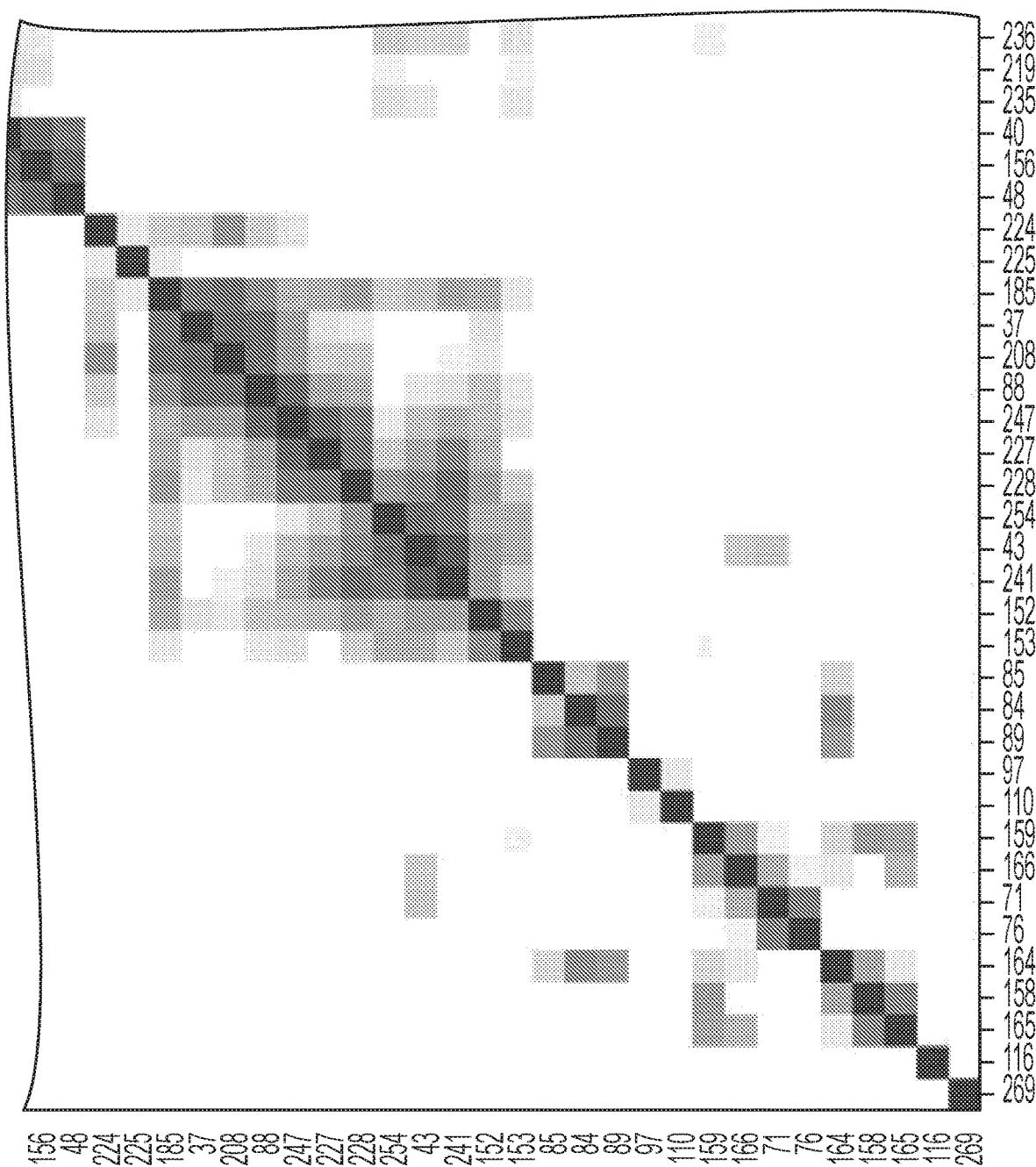
Figure 5:
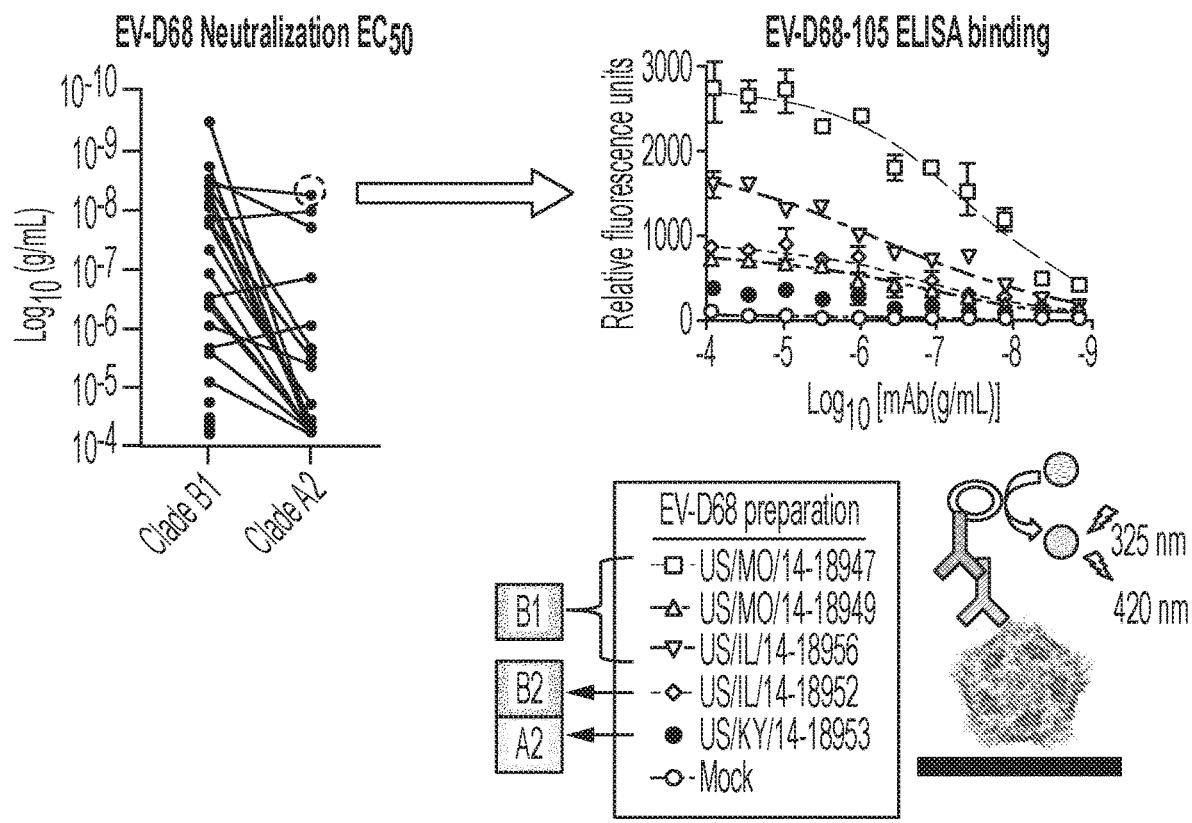
FIG. 5. Clinical candidates. In addition to neutralization, further characterization revealed additional clinical candidates. mAb 159 does not cross-react in ELISA or $CCID_{50}$, even though it is incredibly potent and does not bind to a mock preparation of virus. mAb 105 is still quite potent, but it cross-reacts quite well.
Figure 6:
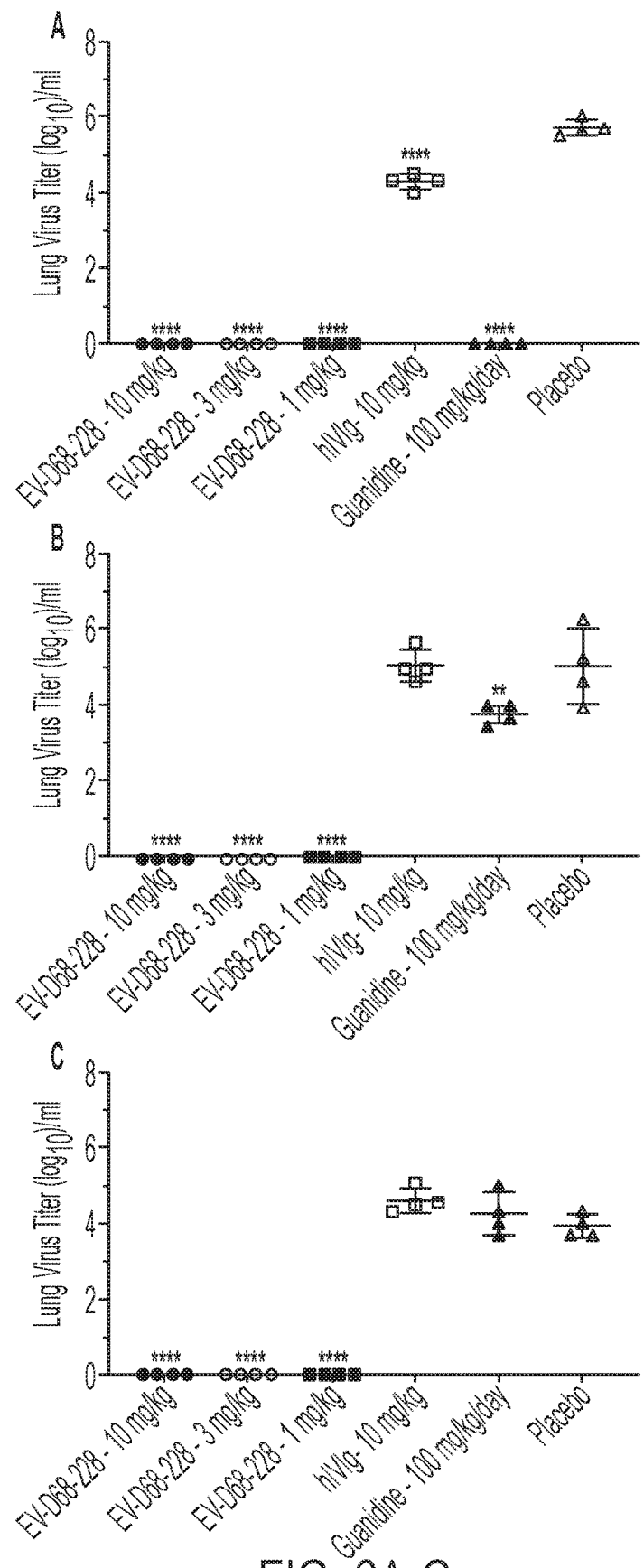
FIGS. 6A-C. Expt. NIA-1849. Lung virus titers of EV-D68-infected AG129 mice treated with EV-D68-228. Treatment with EV-D68-228 significantly reduced lung virus titers on day 1 (FIG. 6A), day 3 (FIG. 6B), and day 5 (FIG. 6C) post-infection. No lung virus titers were detected in mice treated with 10, 3, or 1 mg/kg of EV-D68-228 at days 1, 3, or 5 post-infection. Treatment with IVIg was able to reduce lung virus titers only on day 1 post-infection. Guanidine significantly reduced lung virus titers on days 1 and 3 but not day 5 post-infection. $P<0.01$, **$P<0.0001$ compared to placebo-treated mice.
Figure 7:
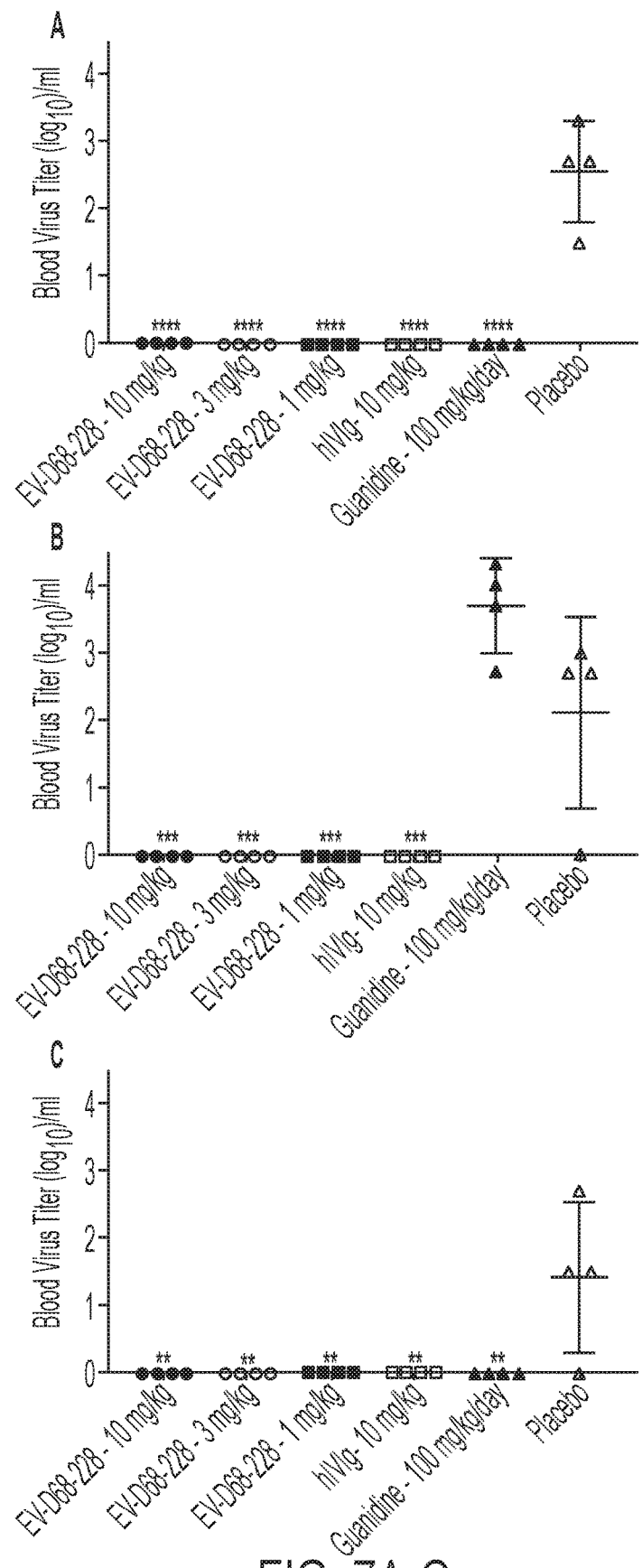
FIGS. 7A-C. Expt. NIA-1849. Blood virus titers of EV-D68-infected AG129 mice treated with EV-D68-228. Treatment with the EV-D68-228 mAb reduced blood virus titers at day 1 (FIG. 7A), day 3 (FIG. 7B), and day 5 (FIG. 7C) post-infection. Treatment with IVIg significantly reduced blood virus titers at days 1, 3, and 5 post-infection. Guanidine reduced blood virus titers on days 1 and 5 but not day 3 post-infection. P<0.01, *P<0.001, ****P<0.0001 compared to placebo-treated mice.
Figure 8:
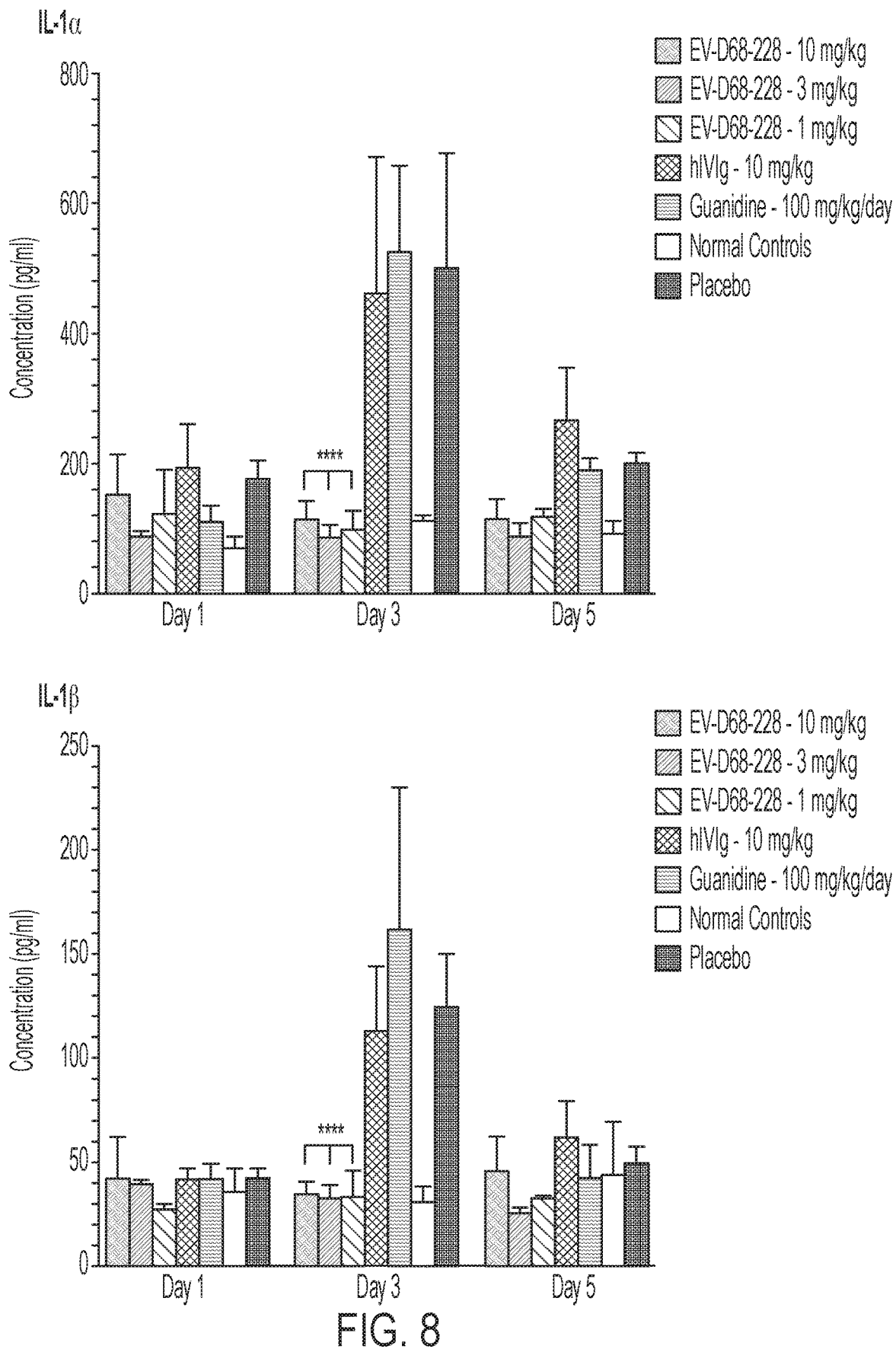
FIG. 8. Expt. NIA-1849. Lung concentrations of IL-1a and IL-1β from EV-D68-infected AG129 mice treated with EV-D68-228. Treatment with EV-D68-228 significantly reduced concentrations of IL-1a and IL-1β on day 3 post-infection compared to plac tions of IL-5 and IL-6 on day 3 post-infection compared to placebo-treated mice. Treatment with IVIg 24 hours post-infection significantly reduced lung concentrations of IL-5 and IL-6 on day 3 post-infection. (P<0.01, *P<0.001, ****P<0.0001 compared to placebo-treated mice). Designation of samples in graph corresponds left-to-right with vertical legend top-to-bottom.
Figure 9:
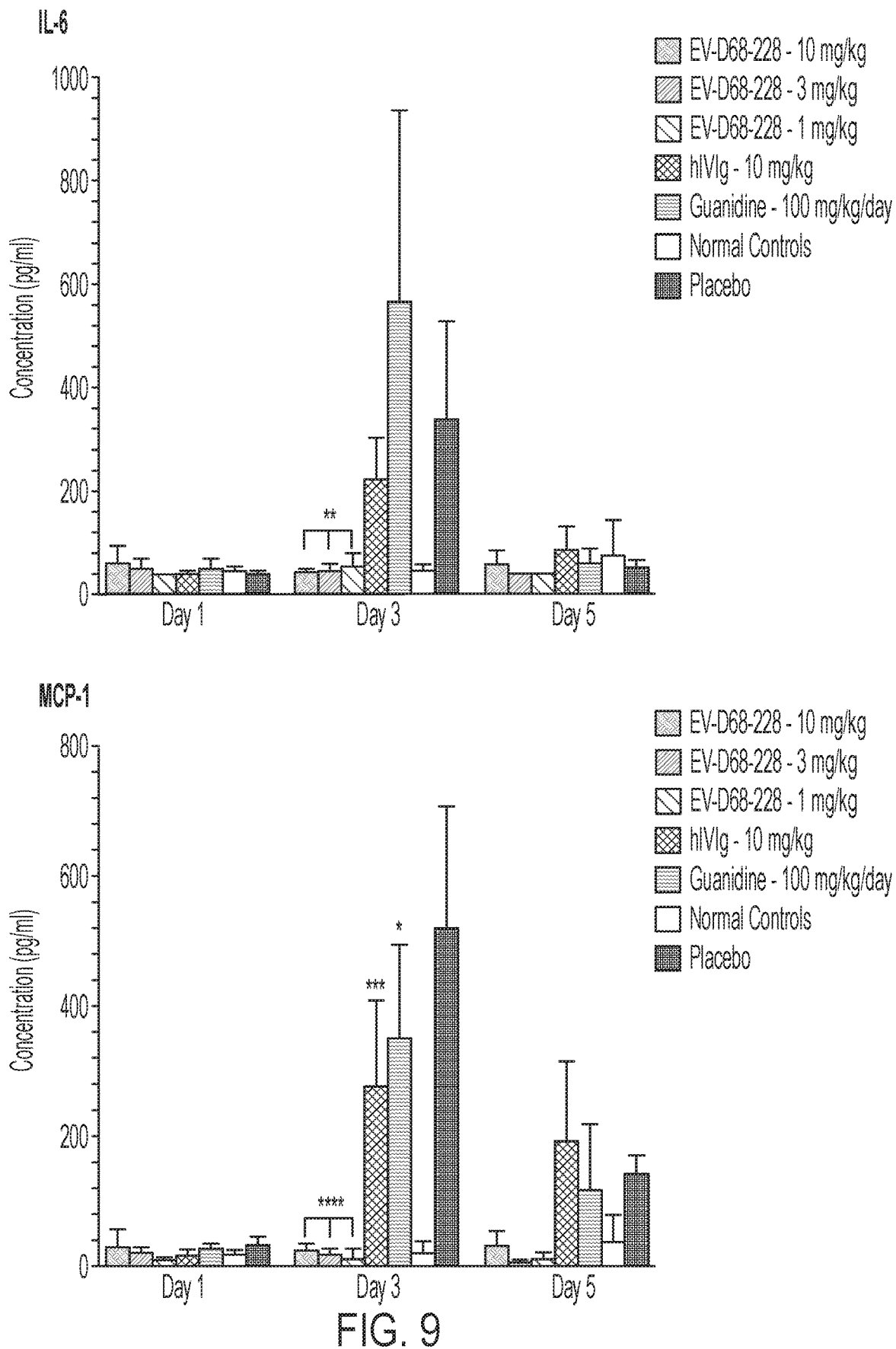
Figure 10:
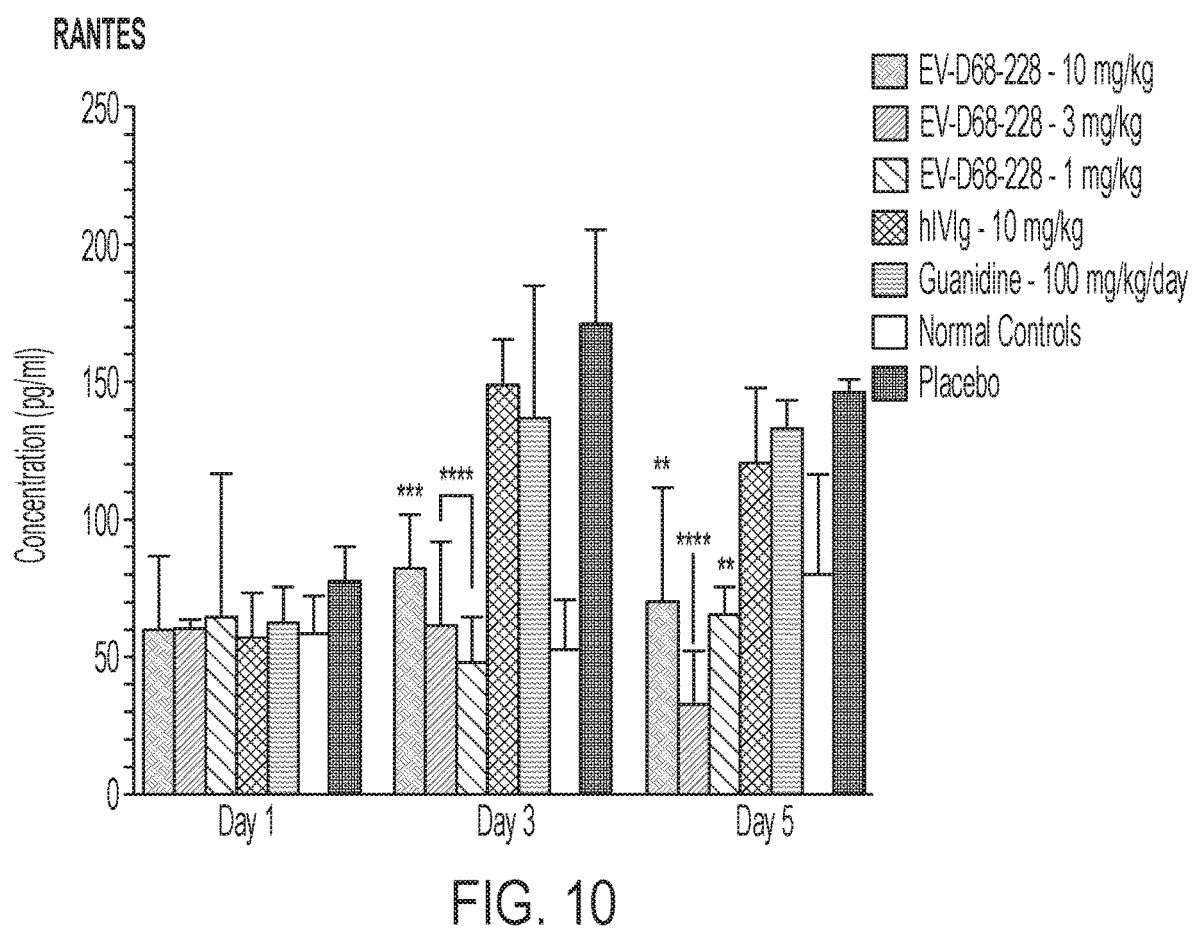
Figure 11:
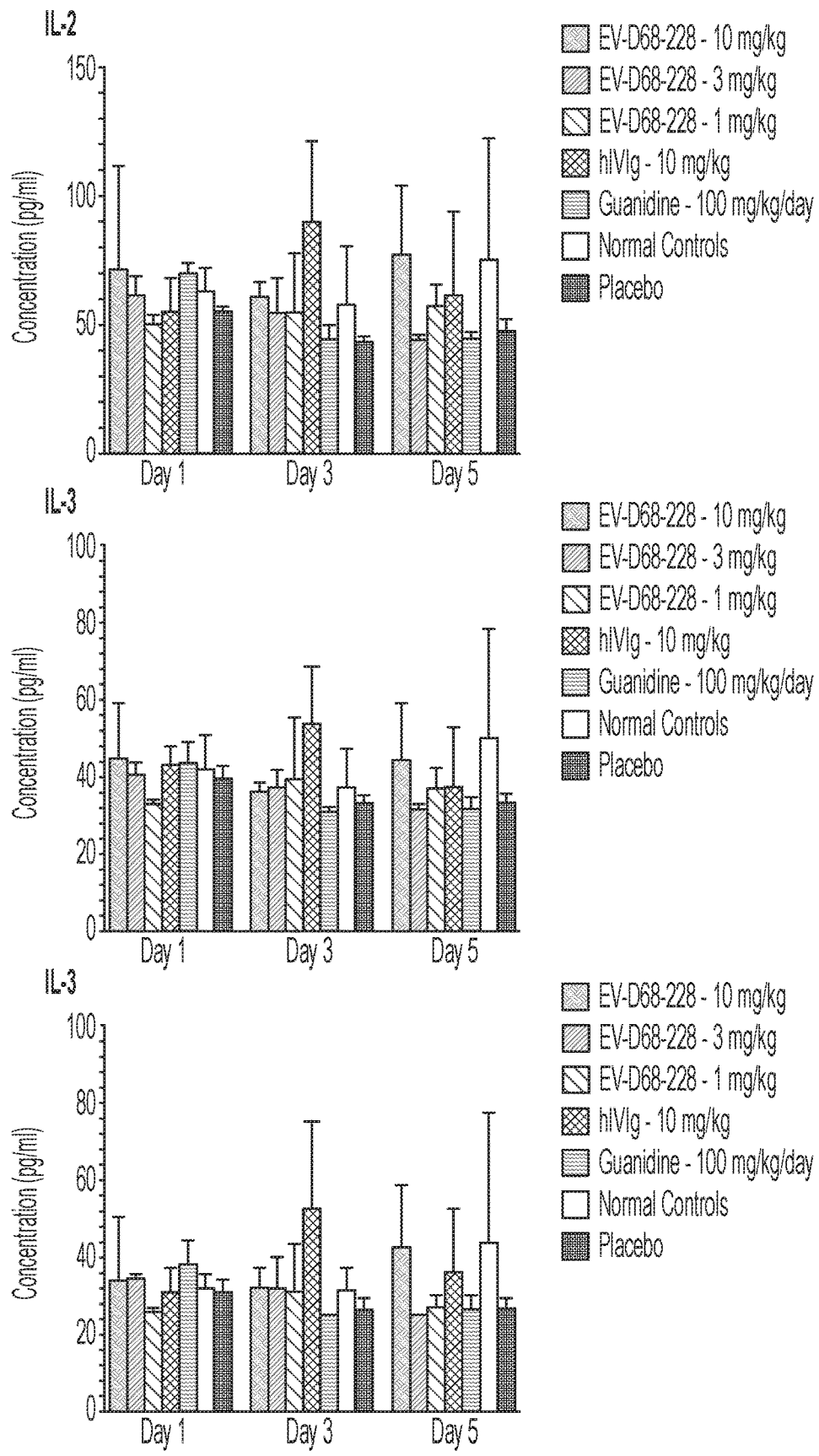
Figure 12:
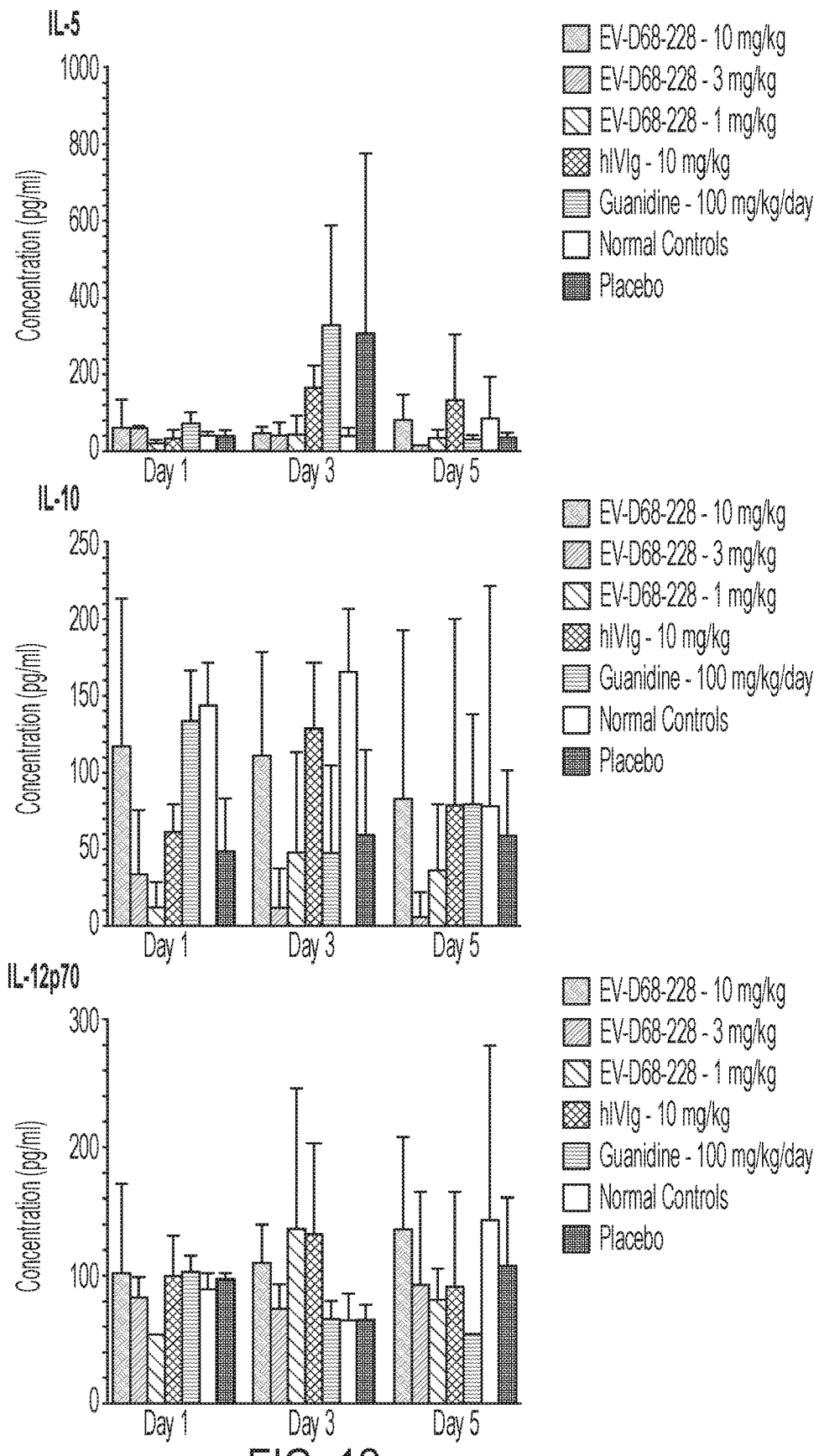
Figure 13:
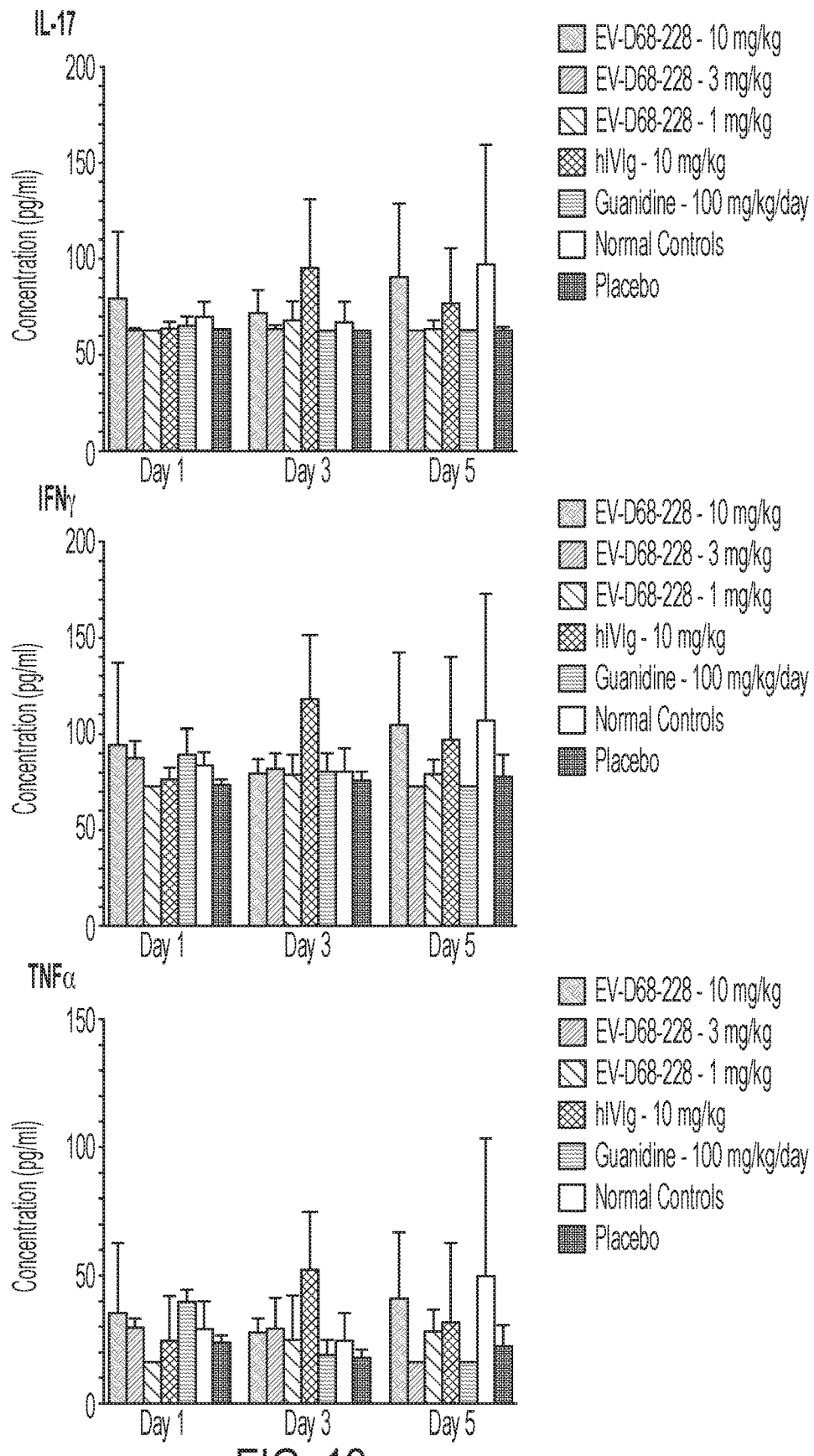

FIGS. 6A-C show lung virus titers for EV-D68-infected AG129 mice treated with EV-D68-228. No lung virus titers were detected at days 1, 3, or 5 post-infection in mice treated with doses of 10, 3, or 1 mg/kg of EV-D68-228. Treatment with a dose of 10 mg/kg of IVIg significantly reduced lung virus titers on day 1 post-infection, but not on days 3 or 5 post-infection. Guanidine treatment at a dose of 100 mg/kg/day significantly reduced lung virus titers on days 1 and 3 post-infection, but not on day 5 post-infection.

FIGS. 7A-C show blood virus titers for EV-D68-infected AG129 mice treated with EV-D68-228. No blood virus titers were detected at days 1, 3, or 5 post-infection in mice treated with doses of 10, 3, or 1 mg/kg of EV-D68-228. Treatment with IVIg at a dose of 10 mg/kg also reduced blood virus titers at days 1, 3, and 5 post-infection. Guanidine significantly reduced blood virus titers on days 1 and 5 but not day 3 post-infection.

FIG. 8 shows lung concentrations of IL-1α and IL-1β from EV-D68-infected AG129 mice treated with EV-D68-228. Treatment with EV-D68-228 significantly reduced concentrations of IL-1α and IL-1β on day 3 post-infection. Treatment with IVIg or guanidine did not significantly reduce lung concentrations of IL-1α or IL-1β.

Lung concentrations of IL-6 and MCP-1 from EV-D68-infected AG129 mice treated with EV-D68-228 are shown in FIG. 9. Treatment with EV-D68-228 significantly reduced concentrations of IL-6 and MCP-1 on day 3 post-infection. Treatment with IVIg or guanidine significantly reduced lung concentrations of MCP-1 but not IL-6 on day 3 post-infection.

Lung concentrations of RANTES from EV-D68-infected AG129 mice treated with EV-D68-228 are shown in FIG. 10. Treatment with EV-D68-228 significantly reduced concentrations of RANTES on days 3 and 5 post-infection compared to placebo-treated mice. Treatment with IVIg or guanidine did not significantly reduce lung concentrations of RANTES at days 1, 3, or 5 post-infection.

FIG. 11 shows lung concentrations of IL-2, IL-3, and IL-4 from EV-D68-infected AG129 mice treated with EV-D68-228. No significant changes in concentrations of IL-2, IL-3, or IL-4 were observed post-infection with EV-D68.

FIG. 12 shows lung concentrations of IL-5, IL-10, and IL-12p70 from EV-D68-infected AG129 mice treated with EV-D68-228. No significant changes in concentrations of IL-5, IL-10, or IL-12p70 were observed post-infection with EV-D68.

Lung concentrations of IL-17, IFNγ, and TNFα from EV-D68-infected AG129 mice treated with EV-D68-228 are shown in FIG. 13. No significant changes in concentrations of IL-17, IFNγ, or TNFα were observed post-infection with EV-D68.

Lung concentrations of MIP-1α and GM-CSF from EV-D68-infected AG129 mice treated with EV-D68-228 are shown in FIG. 14. No significant changes in concentrations of MIP-1α or GM-CSF were observed post-infection with EV-D68.

Example 3—Discussion

This study determined the efficacy of EV-D68-228, a mAb against EV-D68, for treatment of a respiratory infection caused by EV-D68 in four-week-old AG129 mice.

Doses of 10, 3, and 1 mg/kg of EV-D68-228 were highly effective at reducing lung virus titers, blood virus titers, and pro-inflammatory cytokines caused by EV-D68 infection. Lung concentrations of IL-1α, IL-1β, IL-6, MCP-1, and RANTES were significantly reduced by treatment with EV-D68-228.

EV-D68-228 was highly effective at preventing infection with EV-D68

Example 4—Materials and Methods

Animals. Ten-day-old AG129 mice from a specific-pathogen-free colony maintained at the Utah Science Technology and Research (USTAR) building at Utah State University. The mice were bred and maintained on irradiated Teklad Rodent Diet (Harlan Teklad) and autoclaved tap water at the USTAR building of Utah State University.

Antibodies and Compound. The monoclonal antibody (mAb) EV-D68-228 was provided by James Crowe at Vanderbilt University Medical Center. EV-D68-228 was provided in solution at a concentration of 1.134 mg/ml and was diluted in sterile saline to doses of 10, 3, and 1 mg/kg for treatment. rRSV-90 was provided in solution at a concentration of 5 mg/ml and was used as a negative control antibody at a dose of 10 mg/kg. Intravenous immunoglobulin (IVIg, Carimune, CSL Behring, King of Prussia, PA) was purchased from a local pharmacy and was used as a comparator to the EV-D68-228 mAb. Guanidine HCl (guanidine) was obtained from Sigma-Aldrich (St. Louis, MO) and served as a positive control.

Virus. Enterovirus D68 was obtained from BEI Resources, NIAID, NIH: Enterovirus D68, US/MO/14-18949, NR-49130. The virus was serially passaged 30 times in the lungs of 4-week-old AG129 mice and then plaque-purified three times in Rhabdomyosarcoma (RD) cells obtained from the American Type Culture Collection (Manassas, VA). The resulting virus stock was amplified twice in RD cells to create a working stock. The virus used for infection was designated EV-D68 MP30 PP.

Experiment design. A total of 42 mice were randomized into 7 groups of 6 mice each as shown in Table II. Mice were treated via intraperitoneal (IP) administration of EV-D68-228 mAb, IVIg, or placebo mAb 24 hours prior to infection. Mice were infected via intraperitoneal (IP) administration of $1\times10^{6.5}$ $CCID_{50}$ of EV-D68 MP30 PP in a 100 μl volume of MEM. Treatment with guanidine started 4 hours post-infection and continued twice daily for 5 days. Mice were weighed prior to treatment and daily thereafter. All mice were observed daily for morbidity, mortality, and neurological scores through day 21. Neurological scores (NS) were recorded as follows: NS0—no observable paralysis, NS1—abnormal splay of hindlimb but normal or slightly slower gait, NS2—hindlimb partially collapsed and foot drags during use for forward motion, NS3—rigid paralysis of hindlimb and hindlimb is not used for forward motion, NS4—rigid paralysis in hindlimbs and no forward motion. Any animals observed with a score of NS4 were humanely euthanized.

Statistical analysis. Kaplan-Meier survival curves were generated Prism 8.0.2. (GraphPad Software Inc.). Survival curves were compared using the Log-rank (Mantel-Cox) test followed by a Gehan-Breslow-Wilcoxon test. For each day post-infection, blood virus titers from treated groups were compared to lung and blood titers from placebo-treated mice using a one-way analysis of variance (ANOVA). Mean body weights were compared using a one-way ANOVA. Neurological scores were compared using a Kruskal-Wallis test followed by a Dunn's multiple comparisons test.

Ethics regulation of laboratory animals. This study was conducted in accordance with the approval of the Institutional Animal Care and Use Committee of Utah State University dated Mar. 2, 2019 (expires Mar. 1, 2022). The work was done in the AAALAC-accredited Laboratory Animal Research Center of Utah State University. The U. S. Government (National Institutes of Health) approval was renewed Mar. 9, 2018 (PHS Assurance No. D16-00468 [A3801-01]) in accordance to the National Institutes of Health Guide for the Care and Use of Laboratory Animals (Revision; 2011).

Figure 18:
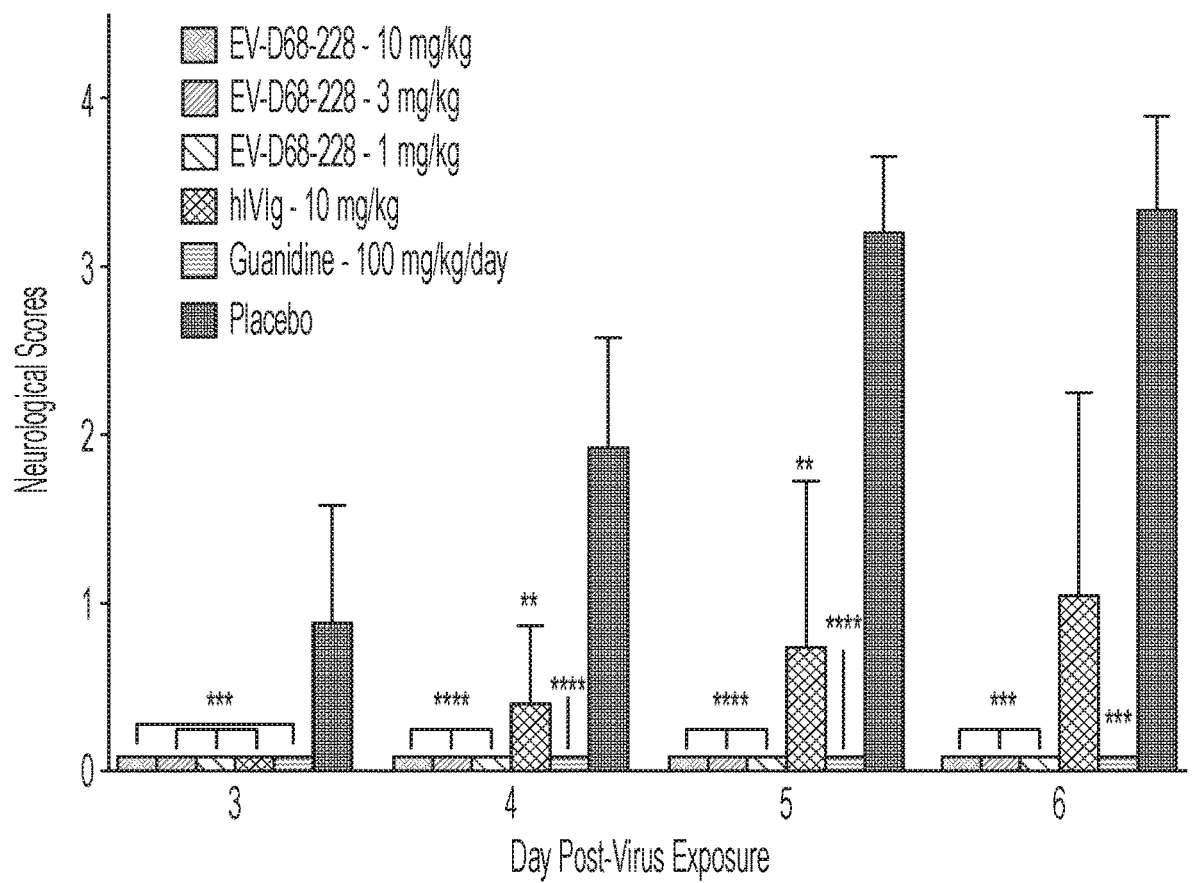

Neurological scores in 10-day-old AG129 mice infected with EV-D68 and treated with EV-D68-228, IVIg, or guanidine are shown in FIG. 18. No neurological scores were observed in mice treated with doses of 10, 3, or 1 mg/kg of the EV-D68-228 Ab. Neurological scores were observed in mice treated with IVIg at a dose of 10 mg/kg on days 4, 5, and 6 post-infection. However, neurological scores in mice treated with IVIg were significantly reduced compared to placebo-treated mice. No neurological scores were observed in the mice treated with guanidine at a dose of 100 mg/kg/day.

TABLE II

Experimental Design to Text Efficacy of EV-D68-228 for treatment of an EV-D68 neurological infection in mice

| Number/Cage | Group No. | Infected | Compound | Dosage | Route | Treatment Schedule | Observations |
|---|---|---|---|---|---|---|---|
| 6 | 1 | Yes | rRSV-90 (Placebo) | 10 mg/kg | IP | Once, 24 hours pre-infection | Mice observed daily for survival, |
| 6 | 3 | Yes | EV-D68-228 | 10 mg/kg | | | body weights, |
| 6 | 5 | Yes | EV-D68-228 | 3 mg/kg | | | and neurological |
| 6 | 7 | Yes | EV-D68-228 | 1 mg/kg | | | scores. |
| 6 | 9 | Yes | IVIg (Carimune NF) | 10 mg/kg | | | Blood collected from 3 mice per |
| 6 | 11 | Yes | Guanidine | 100 mg/kg/day | | b.i.d. x 5 beginning 4 hours post-infection | group on days 1, 3, and 5 post-infecton for blood virus titers. |
| 6 | 2 | No | Normal Controls | — | — | — | Observed for normal weight gain. |

Example 5—Results

The objective of this study was to determine the efficacy of treatment with EV-D68-228 for an Enterovirus D68 (EV-D68) neurological infection in 10-day-old AG129 mice. This study determined the efficacy of an EV-D68-228 mAb for treatment of an EV-D68 neurological infection in 10-day-old AG129 mice.

Figure 15:
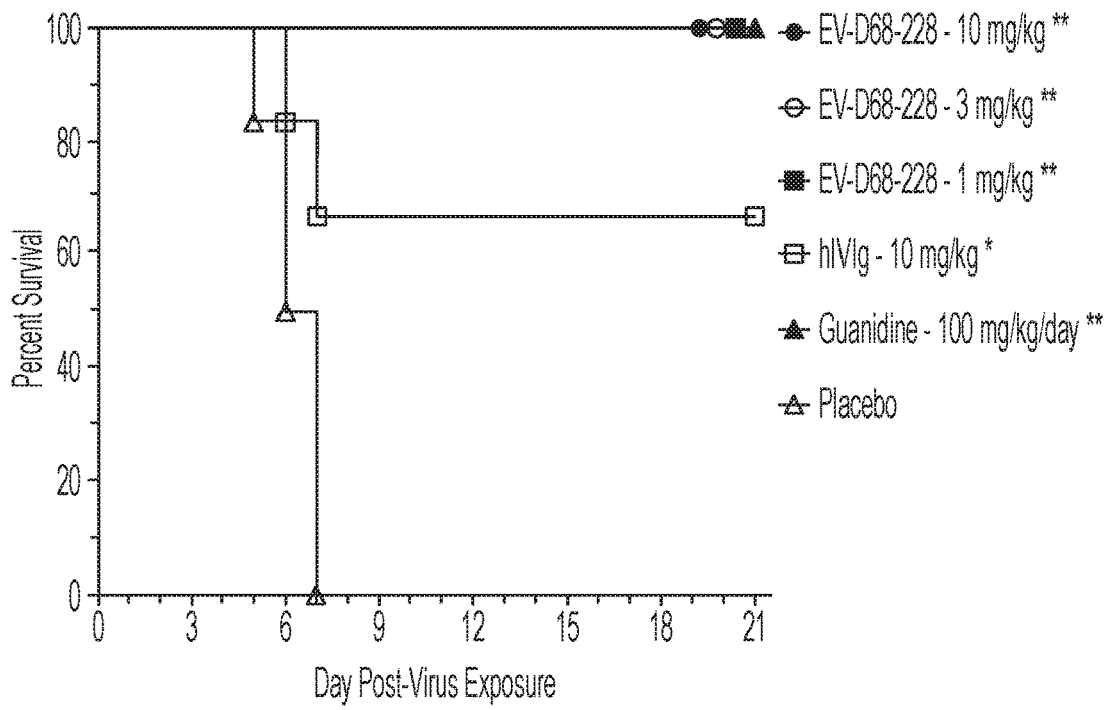

FIG. 15 shows Kaplan-Meier survival curves for 10-day-old AG129 mice infected with EV-D68 and treated with EV-D68-228, IVIg, or guanidine. Doses of 10, 3, or 1 mg/kg of EV-D68-228 provided 100% protection from mortality in each group of six mice infected with EV-D68. Two of six mice that were treated with IVIg at a dose of 10 mg/kg did not survive the infection. Treatment with guanidine at a dose of 100 mg/kg/day protected all six mice from mortality.

Figure 16:
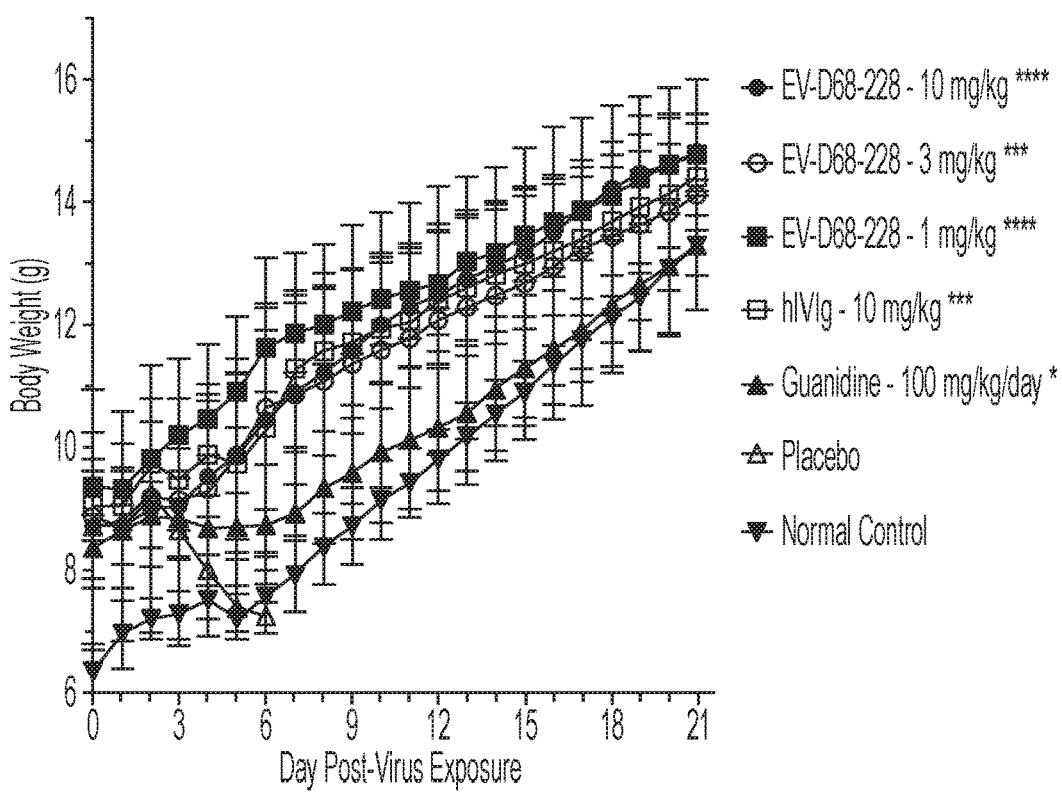

FIG. 16 shows mean body weights for 10-day-old AG129 mice infected with EV-D68 and treated with EV-D68-228, IVIg, or guanidine. Doses of 10, 3, or 1 mg/kg protected mice from infection-associated weight loss. A dose of 10 mg/kg of IVIg also protected mice from weight loss. In addition, guanidine at a dose of 100 mg/kg/day protected mice from weight loss.

Figure 17:
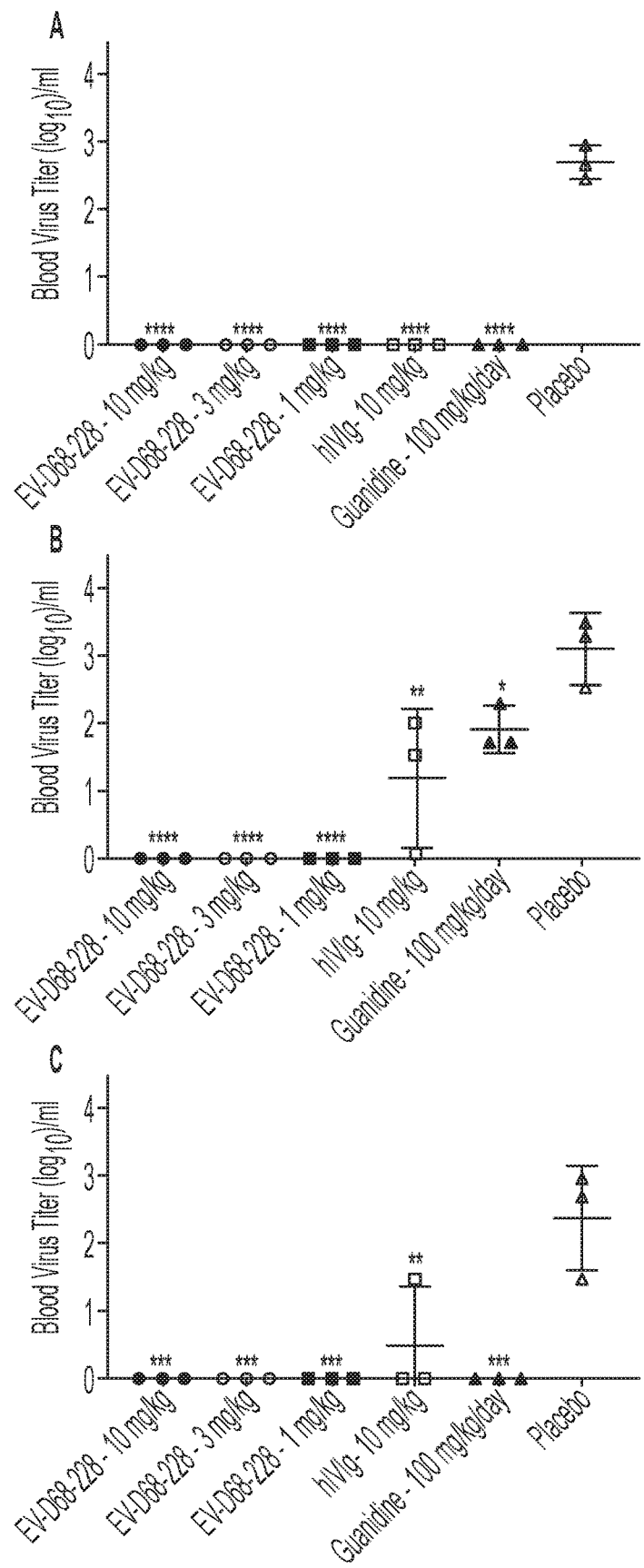

FIGS. 17A-C show blood virus titers for EV-D68-infected AG129 mice treated with EV-D68-228. No blood virus titers were detected at days 1, 3, or 5 post-infection in mice treated with doses of 10, 3, or 1 mg/kg of EV-D68-228. Treatment with IVIg at a dose of 10 mg/kg also reduced blood virus titers at days 1, 3, and 5 post-infection. Guanidine treatment at a dose of 100 mg/kg/day significantly reduced blood virus titers on days 1, 3, and 5 post-infection.

Example 6—Discussion

This study determined the efficacy of EV-D68-228, a mAb against EV-D68, for treatment of a neurological infection caused by EV-D68 in 10-day-old AG129 mice.

Doses of 10, 3, and 1 mg/kg of EV-D68-228 provided protection from mortality and weight loss in EV-D68-infected mice. In addition, no blood virus titers were detected at days 1, 3, or 5 post-infection in mice treated with EV-D68-228. No paralysis, as measured by neurological scores, was observed in mice treated with doses of 10, 3, or 1 mg/kg of EV-D68-228.

EV-D68-228 appeared to provide protection from EV-D68 infection compared to commercial IVIg as indicated by survival, blood virus titers, and neurological scores observed in mice treated with IVIg at a dose of 10 mg/kg.

EV-D68-228 provided equivalent protection from mortality and paralysis when compared to treatment with the positive control, guanidine. However, while blood virus titers were still detected in guanidine-treated mice on day 3 post-infection, no virus was detected in the blood of mice treated with EV-D68-228 at doses of 10, 3, or 1 mg/kg at days 1, 3, or 5 post-infection.

Example 7—Efficacy of EV-D68-228 on Respiratory Infection in Mice

Materials and Methods

Animals. Four-week-old male and female AG129 mice from a specific-pathogen-free colony maintained at the Utah Science Technology and Research (USTAR) building at Utah State University. The mice were bred and maintained on irradiated Teklad Rodent Diet (Harlan Teklad) and autoclaved tap water at the USTAR building of Utah State University.

Antibodies and Compound. The monoclonal antibody (mAb) EV-D68-228 was provided by James Crowe at Vanderbilt University Medical Center. EV-D68-228 was provided in solution at a concentration of 1.134 mg/ml and was diluted in sterile saline to doses of 10 or 1 mg/kg for treatment. rRSV-90 was provided in solution at a concentration of 5 mg/ml and was used as a negative control antibody at a dose of 10 mg/kg. Intravenous immunoglobulin (IVIg, Carimune, CSL Behring, King of Prussia, PA) was purchased from a local pharmacy and was used as a comparator to the EV-D68-228 mAb.

Virus. Enterovirus D68 was obtained from BEI Resources, NIAID, NIH: Enterovirus D68, US/MO/14-18949, NR-49130. The virus was serially passaged 30 times in the lungs of 4-week-old AG129 mice and then plaque-purified three times in Rhabdomyosarcoma (RD) cells obtained from the American Type Culture Collection (Manassas, VA). The resulting virus stock was amplified twice in RD cells to create a working stock. The virus used for infection was designated EV-D68 MP30 PP.

Experiment design. A total of 52 mice were randomized into 6 groups of 8 mice each with a group of 4 mice used for normal controls as shown in Table C. Mice were treated via intraperitoneal (IP) administration of EV-D68-228 mAb, IVIg, or placebo mAb at 4, 24, or 48 hours post-infection. Mice were infected via intranasal (IN) instillation of 1×104.5 CCID50 of EV-D68 MP30 PP in a 90 µl volume of MEM. Mice were weighed prior to treatment and daily thereafter. Four mice from each treatment group were euthanized on days 3 and 5 post-infection for evaluation of lung virus titers, blood virus titers, and lung cytokine concentrations.

Lung Cytokine/Chemokine Evaluations. Each sample of lung homogenate was tested for cytokines and chemokines using a chemiluminescent ELISA-based assay according to the manufacturer's instructions (Quansys Biosciences Q-Plex™ Array, Logan, UT). The Quansys multiplex ELISA is a quantitative test in which 16 distinct capture antibodies have been applied to each well of a 96-well plate in a defined array. Each sample supernatant was tested at for the following: IL-1α, IL-1β, IL-2, IL-3, IL-4, IL-5, IL-6, IL-10, IL-12p70, IL-17, MCP-1, IFN-γ, TNFα, MIP-1α, GM-CSF, and RANTES. Definition of abbreviations are: IL—interleukin; MCP—monocyte chemoattractant protein; IFN—interferon; TNF—tumor necrosis factor, MIP—macrophage inflammatory 3 protein; GM-CSF—granulocyte/macrophage colony stimulating factor; and RANTES—regulated upon activation, normal T cell expressed and secreted.

Statistical analysis. All figures and statistical analyses were completed using Prism 8.2.0. (GraphPad Software Inc.). For each day post-infection, lung and blood virus titers from treated groups were compared to lung and blood titers from placebo-treated mice using a one-way analysis of variance (ANOVA). For each cytokine/chemokine, the concentrations from treated mice were compared to placebo-treated mice using a two-way ANOVA.

Ethics regulation of laboratory animals. This study was conducted in accordance with the approval of the Institutional Animal Care and Use Committee of Utah State University. The work was done in the AAALAC-accredited Laboratory Animal Research Center of Utah State University. The U.S. Government (National Institutes of Health) approval was renewed (PHS Assurance No. D16-00468 [A3801-01]) in accordance to the National Institutes of Health Guide for the Care and Use of Laboratory Animals (Revision; 2011).

TABLE C

Expt. NIA-1869. Experimental Design - Therapeutic Efficacy of EV-D68-228 for treatment of an EV-D68 respiratory infection in mice.

| Number/Cage | Group No. | Infected | Compound | Dosage | Route | Treatment Schedule | Observations |
|---|---|---|---|---|---|---|---|
| 12 | 1 | Yes | rRSV-90 (Placebo) | 10 mg/kg | IP | Once, 24 hours post-infection | 4 mice per group euthanized at days 3 and 5 post-infection for lung virus titers, blood virus titers, and lung cytokines. |
| 12 | 3 | Yes | EV-D68-228 | 10 mg/kg | | Once, 4 hours post-infection | |
| 12 | 5 | Yes | EV-D68-228 | 10 mg/kg | | Once, 24 hours post-infection | |
| 12 | 7 | Yes | EV-D68-228 | 10 mg/kg | | Once, 48 hours post-infection | |
| 12 | 9 | Yes | EV-D68-228 | 1 mg/kg | | | |
| 12 | 11 | Yes | IVIg (Carimune NF) | 10 mg/kg | | Once, 24 hours post-infection | |
| 4 | 2 | No | Normal Controls | — | — | — | 2 mice per group euthanized at days 3 and 5 post-infection for lung cytokines. |

Results and Discussion

This study determined the therapeutic efficacy of an EV-D68-228 mAb for treatment of an EV-D68 respiratory infection in four-week-old AG129 mice.

Figure 19:
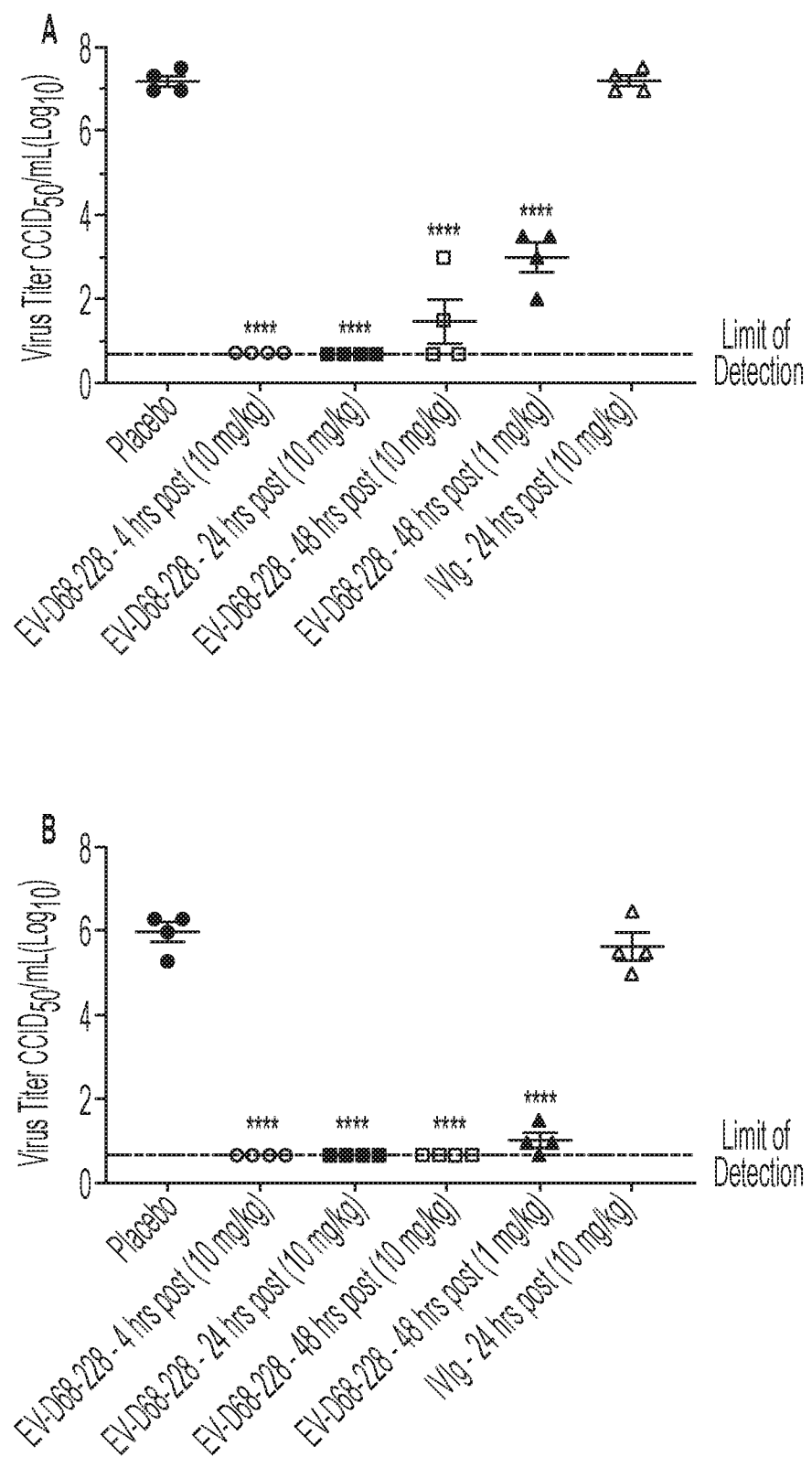

FIG. 19 shows lung virus titers for EV-D68-infected AG129 mice treated post-infection with EV-D68-228. No lung virus titers were detected at days 3 or 5 post-infection in mice treated with doses of 10 mg/kg of EV-D68-228 when treatment started at 4 or 24 hours after infection. In mice treated 48 hours post-infection, a dose of 10 mg/kg of EV-D68-228 significantly reduced lung virus titers on days 3 and 5 post-infection. Even a dose of 1 mg/kg given 48 hours post-infection significantly reduced lung virus titers on days 3 and 5 post-infection. Treatment with a dose of 10 mg/kg of IVIg given 24 hours post-infection did not significantly reduce lung virus titers on days 3 or 5 post-infection.

Figure 20:
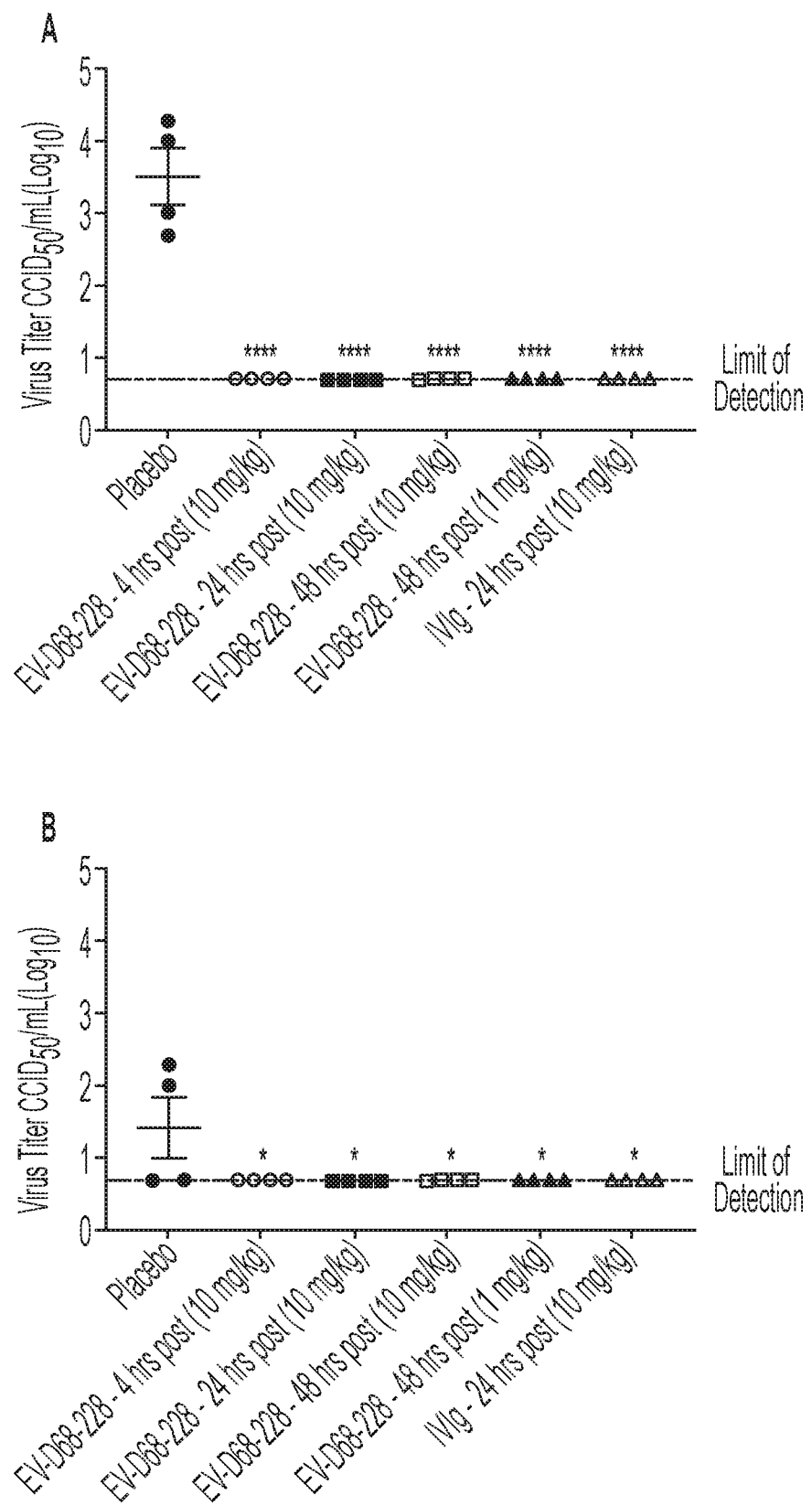
Figure 24:
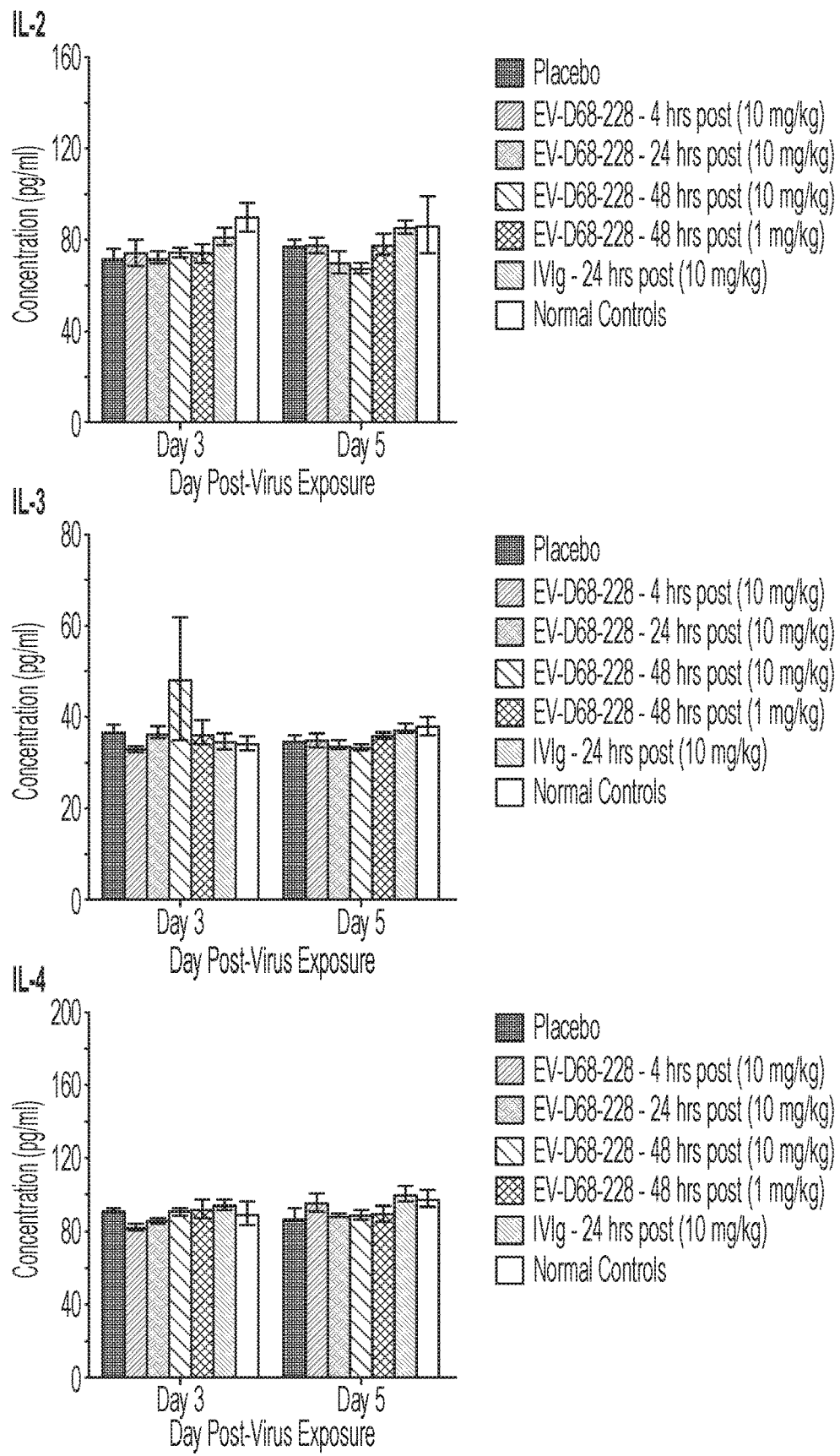
FIG. 24. Expt. NIA-1869. Lung concentrations of IL-2, IL-3, and IL-4 from EV-D68-infected AG129 mice treated post-infection with EV-D68-228. No significant changes in concentrations of IL-2, IL-3, or IL-4 were observed after infection with EV-D68. Designation of samples in graph corresponds left-to-right with vertical legend top-to-bottom.
Figure 25:
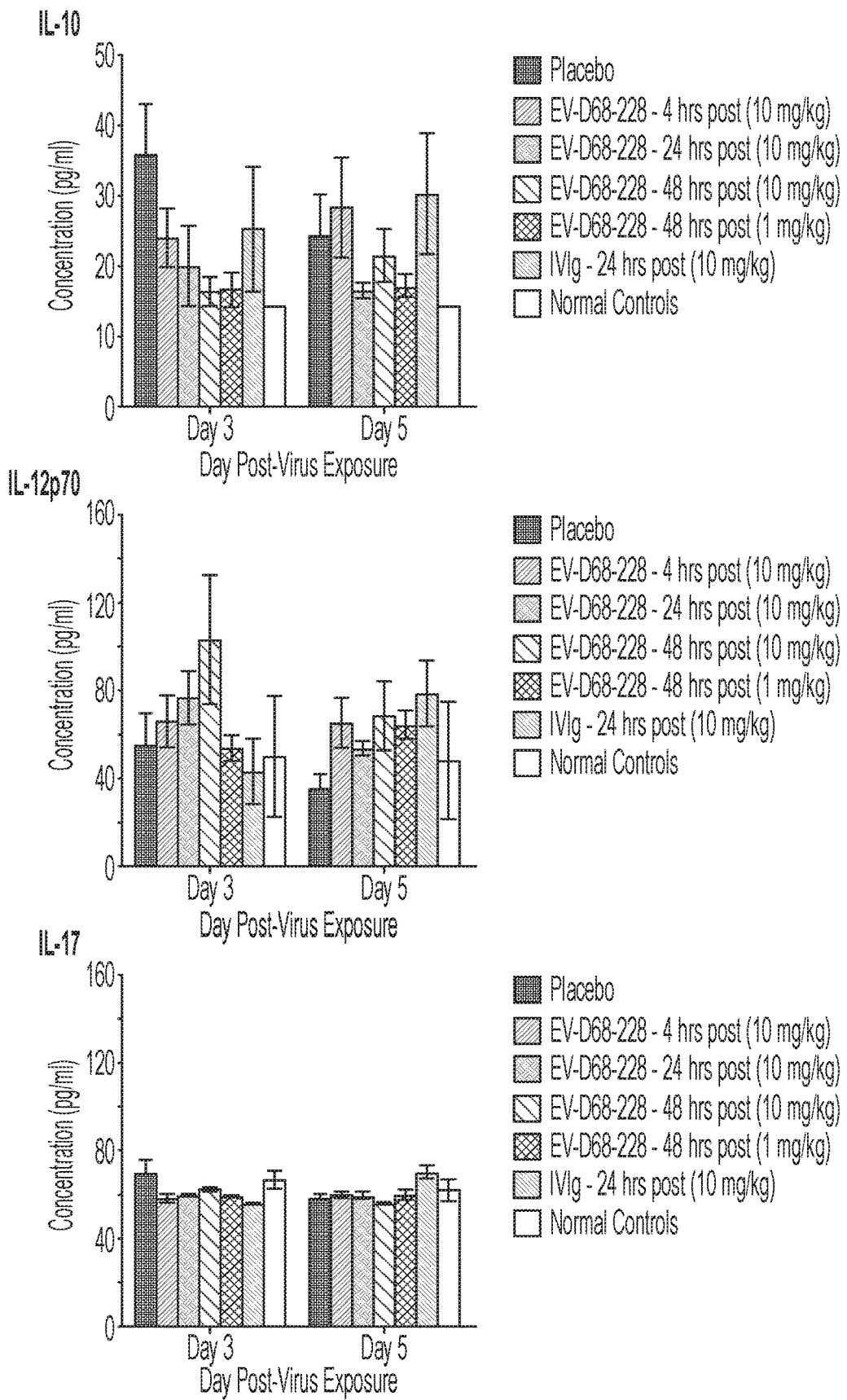
FIG. 25. Expt. NIA-1869. Lung concentrations of IL-10, IL-12p70, and IL-17 from EV-D68-infected AG129 mice treated post-infection with EV-D68-228. No significant changes in concentrations of IL-5, IL-10, or IL-12p70 were observed after infection with EV-D68. Designation of samples in graph corresponds left-to-right with vertical legend top-to-bottom.

FIG. 20 shows blood virus titers for EV-D68-infected AG129 mice treated post-infection with EV-D68-228. No blood virus titers were detected at days 3 or 5 post-infection in mice treated with doses of 10 mg/kg of EV-D68-228 at 4, 24, or 48 hours after infection. A lower dose of 1 mg/kg of EV-D68-228 given 48 hours post-infection reduced blood virus titers below the limit of detection. Treatment with IVIg at a dose of 10 mg/kg also reduced blood virus titers at days 3, and 5 post-infection.

FIG. 21 shows lung concentrations of IL-1α and IL-1β from EV-D68-infected AG129 mice treated post-infection with EV-D68-228. Therapeutic treatment with EV-D68-228 significantly reduced concentrations of IL-1α and IL-1β on days 3 and 5 post-infection. Treatment with IVIg significantly reduced lung concentrations of IL-1α or IL-1β, but only on day 3 post-infection.

Lung concentrations of IL-5 and IL-6 from EV-D68-infected AG129 mice treated post-infection with EV-D68-228 are shown in FIG. 224. Therapeutic treatment with EV-D68-228 significantly reduced concentrations of IL-5 and IL-6 on day 3 post-infection. Treatment with IVIg 24 hours post-infection significantly reduced lung concentrations of IL-5 and IL-6 on day 3 post-infection.

Lung concentrations of MCP-1 and RANTES from EV-D68-infected AG129 mice treated post-infection with EV-D68-228 are shown in FIG. 23. Therapeutic treatment with EV-D68-228 significantly reduced lung concentrations of MCP-1 and RANTES on days 3 and 5 post-infection compared to placebo-treated mice. Treatment with IVIg significantly reduced lung concentrations of MCP-1 on day 3 post-infection and reduced concentrations of RANTES on days 3 and 5 post-infection.

FIG. 24 shows lung concentrations of IL-2, IL-3, and IL-4 from EV-D68-infected AG129 mice treated post-infection with EV-D68-228. No significant changes in concentrations of IL-2, IL-3, or IL-4 were observed post-infection with EV-D68.

FIG. 25 shows lung concentrations of IL-10, IL-12p70, and IL-17 from EV-D68-infected AG129 mice treated post-infection with EV-D68-228. No significant changes in concentrations of IL-10, IL-12p70, or IL-17 were observed after infection with EV-D68.

Lung concentrations of IFNγ and TNFα from EV-D68-infected AG129 mice treated post-infection with EV-D68-228 are shown in FIG. 26. No significant changes in concentrations of IFNγ or TNFα were observed after infection with EV-D68.

Lung concentrations of MIP-1α and GM-CSF from EV-D68-infected AG129 mice treated post-infection with EV-D68-228 are shown in FIG. 27. No significant changes in concentrations of MIP-1α or GM-CSF were observed following infection with EV-D68.

Thus, this study determined the therapeutic efficacy of EV-D68-228, a mAb against EV-D68, for treatment of a respiratory infection caused by EV-D68 in four-week-old AG129 mice. Doses of 10 and 1 mg/kg of EV-D68-228 were highly effective at reducing lung virus titers, blood virus titers, and pro-inflammatory cytokines caused by EV-D68 infection when administered within 48 hours post-infection. Lung concentrations of IL-1α, IL-1β, IL-5, IL-6, MCP-1, and RANTES were significantly reduced by treatment with EV-D68-228. As EV-D68-228 was highly effective as a therapeutic treatment for an EV-D68 respiratory infection in AG129 mice, plethysmography could be used in future studies to determine the impact of EV-D68-228 treatment on lung function.

Example 8—Efficacy of EV-D68-228 on Respiratory Infection in Mice

Materials and Methods

The objective of this study was to determine the therapeutic efficacy of treatment with EV-D68-228 for an Enterovirus D68 (EV-D68) neurological infection in 10-day-old AG129 mice.

Animals. Ten-day-old AG129 mice from a specific-pathogen-free colony maintained at the Utah Science Technology and Research (USTAR) building at Utah State University. The mice were bred and maintained on irradiated Teklad Rodent Diet (Harlan Teklad) and autoclaved tap water at the USTAR building of Utah State University.

Antibodies and Compound. The monoclonal antibody (mAb) EV-D68-228 was provided by James Crowe at Vanderbilt University Medical Center. EV-D68-228 was provided in solution at a concentration of 1.134 mg/ml and was diluted in sterile saline to doses of 10 mg/kg for treatment. rRSV-90 was provided in solution at a concentration of 5 mg/ml and was used as a negative control antibody at a dose of 10 mg/kg. Intravenous immunoglobulin (IVIg, Carimune, CSL Behring, King of Prussia, PA) was purchased from a local pharmacy and was used as a comparator to the EV-D68-228 mAb.

Virus. Enterovirus D68 was obtained from BEI Resources, NIAID, NIH: Enterovirus D68, US/MO/14-18949, NR-49130. The virus was serially passaged 30 times in the lungs of 4-week-old AG129 mice and then plaque-purified three times in Rhabdomyosarcoma (RD) cells obtained from the American Type Culture Collection (Manassas, VA). The resulting virus stock was amplified twice in RD cells to create a working stock. The virus used for infection was designated EV-D68 MP30 PP.

Experiment design. A total of 42 mice were randomized into 6 groups of 6 treated-mice each with one group of 9 mice to account for deaths prior to treatment each as shown in Table D. One group of 3 mice was used as normal controls. Mice were infected via intraperitoneal (IP) administration of $1\times10^{6.5}$ CCID50 of EV-D68 MP30 PP in a 100 μl volume of MEM. Mice were treated via intraperitoneal (IP) administration of EV-D68-228 mAb at 24, 48, 72, or 120 hours post-infection. Treatment with IVIg or placebo Ab was given once 24 hours post-infection. Mice were weighed prior to treatment and daily thereafter. All mice were observed daily for morbidity, mortality, and neurological scores through day 21. Neurological scores (NS) were recorded as follows: NS0—no observable paralysis, NS1—abnormal splay of hindlimb but normal or slightly slower gait, NS2—hindlimb partially collapsed and foot drags during use for forward motion, NS3—rigid paralysis of hindlimb and hindlimb is not used for forward motion, NS4—rigid paralysis in hindlimbs and no forward motion. Any animals observed with a score of NS4 were humanely euthanized.

Statistical analysis. Kaplan-Meier survival curves were generated Prism 8.2.0. (GraphPad Software Inc.). Survival curves were compared using the Log-rank (Mantel-Cox) test followed by a Gehan-Breslow-Wilcoxon test. For each day post-infection, blood virus titers from treated groups were compared to lung and blood titers from placebo-treated mice using a one-way analysis of variance (ANOVA). Mean body weights were compared using a one-way ANOVA. Neurological scores were compared using a Kruskal-Wallis test followed by a Dunn's multiple comparisons test.

Ethics regulation of laboratory animals. This study was conducted in accordance with the approval of the Institutional Animal Care and Use Committee of Utah State University. The work was done in the AAALAC-accredited Laboratory Animal Research Center of Utah State University. The U. S. Government (National Institutes of Health) approval was renewed (PHS Assurance No. D16-00468 [A3801-01]) in accordance to the National Institutes of Health Guide for the Care and Use of Laboratory Animals (Revision; 2011).

4, and 5 were significantly reduced in mice treated 24 hours post-infection with EV-D68-228 at a dose of 10 mg/kg. IVIg at a dose of 10 mg/kg given 24 hours post-infection reduced neurological scores at days 3, 4, and 5 post-infection. No comparisons in neurological score were completed after day 5 post-infection due to the death of all the placebo-treated mice.

Thus, this study determined the therapeutic efficacy of EV-D68-228, a mAb against EV-D68, for treatment of a neurological infection caused by EV-D68 in 10-day-old

TABLE D

Expt. NIA-1870. Experimental Design - Therapeutic efficacy of EV-D68-228 for treatment of an EV-D68 neurological infection in mice.

| Number/ Cage | Group No. | Infected | Compound | Dosage | Route | Treatment Schedule | Observations |
| --- | --- | --- | --- | --- | --- | --- | --- |
| 6 | 1 | Yes | rRSV-90 (Placebo) | 10 mg/kg | IP | Once, 24 hours post-infection | Mice observed daily for survival, body weights, and neurological scores. Blood collected from 3 mice per group on days 1, 3, 5, and 7 post-infection for blood virus titers. |
| 6 | 3 | Yes | EV-D68-228 | 10 mg/kg | | Once, 24 hours post-infection | |
| 6 | 5 | Yes | EV-D68-228 | | | Once, 48 hours post-infection | |
| 6 | 7 | Yes | EV-D68-228 | | | Once, 72 hours post-infection | |
| 9 | 9 | Yes | EV-D68-228) | | | Once, 120 hours post-infection | |
| 6 | 11 | Yes | IVIg (Carimune NF) | 10 mg/kg | | Once, 24 hours post-infections | |
| 3 | 2 | No | Normal Controls | — | — | — | Observed for normal weight gain. |

Results and Discussion

This study determined the efficacy of an EV-D68-228 mAb for therapeutic treatment of an EV-D68 neurological infection in 10-day-old AG129 mice.

Figure 28:
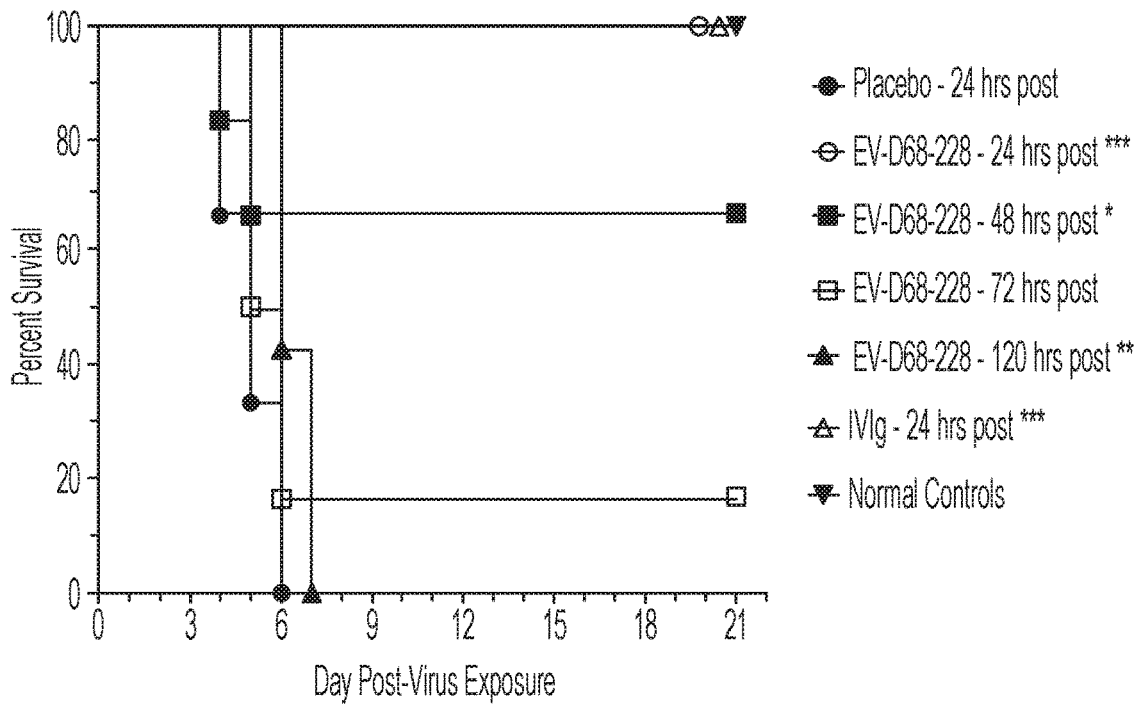
FIG. 28. Expt. NIA-1870. Survival of 10-day-old AG129 mice infected with EV-D68 and treated post-infection with EV-D68-228. (n=6 mice/group, n=7 mice/group treated 120 hours post-infection). Treatment with a dose of 10 mg/kg of EV-D68-228 completely protected mice from mortality at 24 hours post-infection. Treatment with EV-D68-228 at 48 hours post-infection protected four of six mice from mortality. Only one of six mice treated 72 hours post-infection with EV-D68-228 survived the infection. Despite none of the seven mice surviving in the group treated 120 hours post-infection with EV-D68-228, the survival curve was different than colored 2D projections of the viral surface were created with RIVEM. Virus surface residues facing any atoms from the Fab molecules within a distance of 4 Å are outlined in light blue (VP1), light green (VP2) and light red (VP3). The canyon region is outlined in yellow. Scale bars in (FIG. 34A) and (FIG. 34C) indicate radial distance measured in Å.

FIG. 28 shows Kaplan-Meier survival curves for 10-day-old AG129 mice infected with EV-D68 and treated post-infection with EV-D68-228. With a single administration of EV-D68-228 at a dose of 10 mg/kg, a significant survival benefit was observed in mice treated at 24, 48, and 120 hours post-infection. The difference in survival benefit in the mice treated 120 hours post-infection was due to an increase in the day of death as all seven mice that were treated still succumbed to the infection. A dose of 10 mg/kg of IVIg completely protected mice from mortality when administered 24 hours post-infection.

Figure 29:
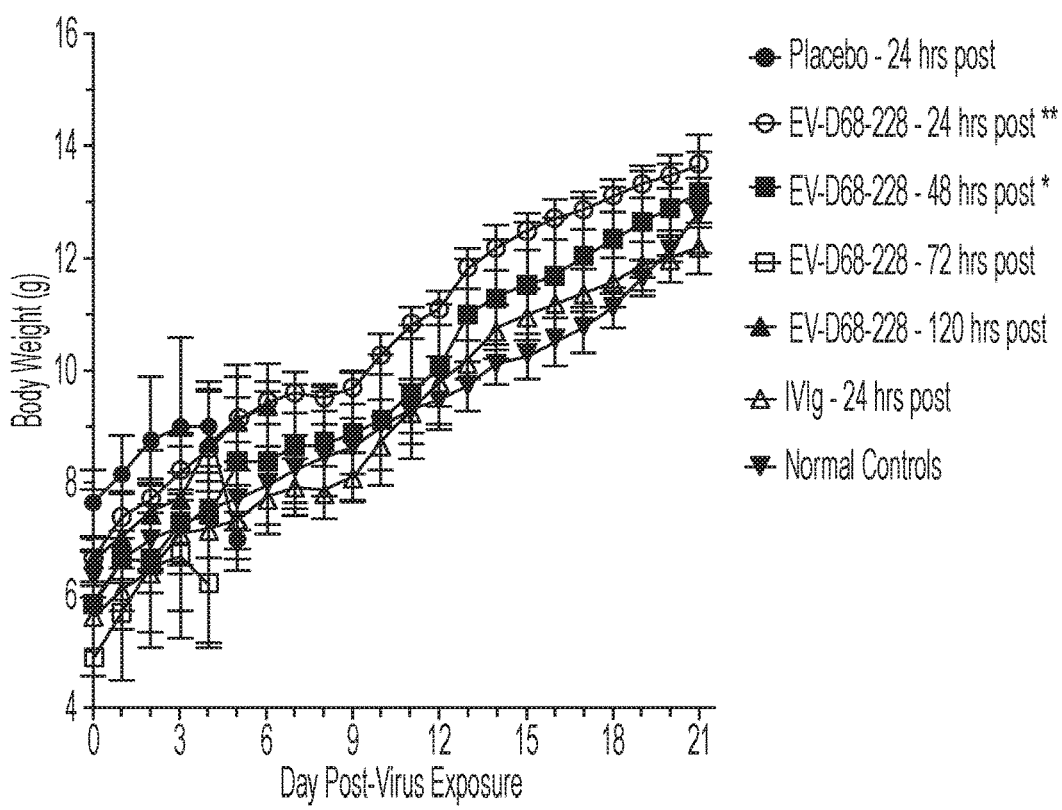

FIG. 29 shows mean body weights for 10-day-old AG129 mice infected with EV-D68 and treated post-infection with EV-D68-228. A single dose of 10 mg/kg of EV-D68-228 protected mice from infection-associated weight loss when administered 24 or 48 hours after infection. A single administration of IVIg administered 24 hours post-infection did not protect mice from weight loss.

Figure 30:
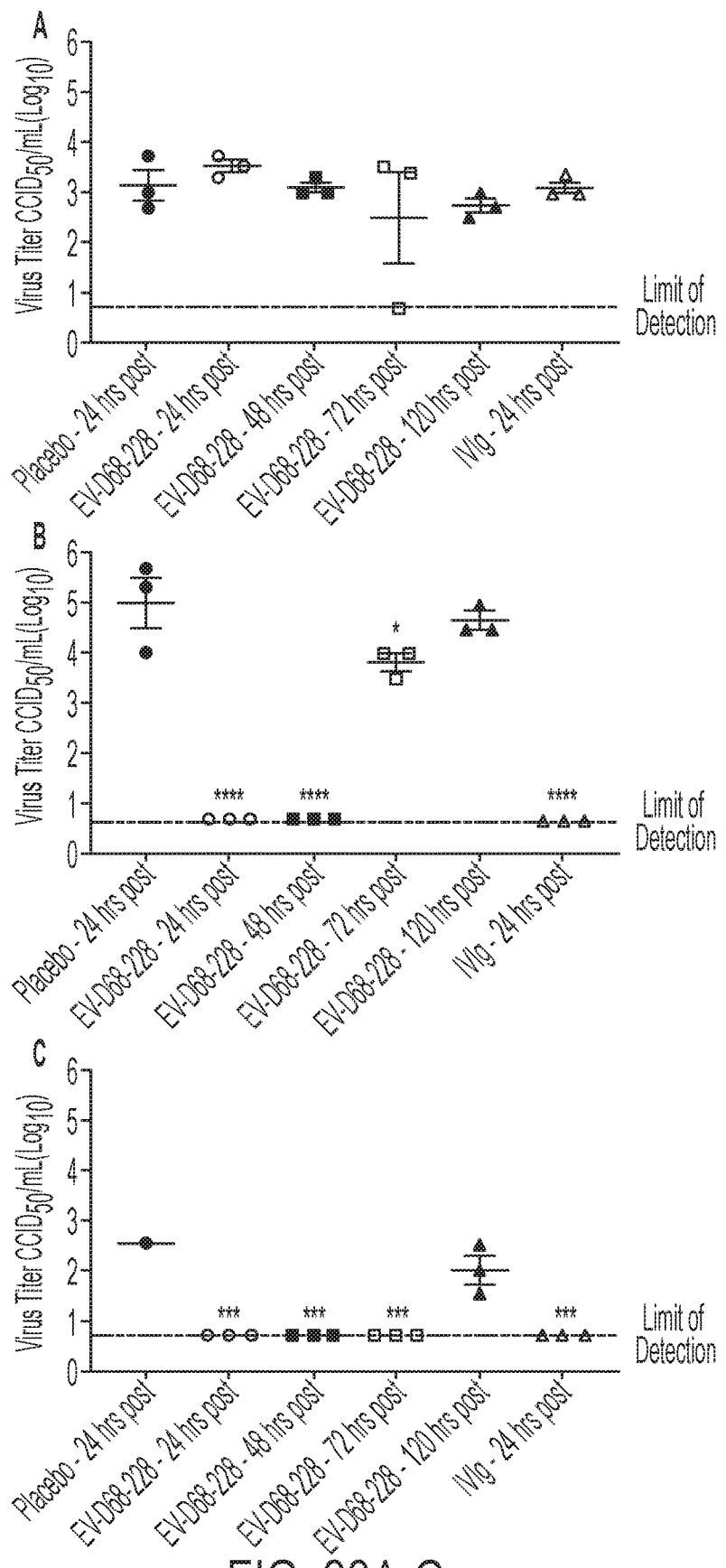

FIGS. 30A-C shows blood virus titers for EV-D68-infected AG129 mice treated post-infection with EV-D68-228. A single administration of 10 mg/kg of EV-D68-228 at 24, 48, or 72 hours post-infection significantly reduced blood virus titers at days 3 and 5 post-infection. Treatment with IVIg at a dose of 10 mg/kg 24 hours after infection reduced blood virus titers at days 3 and 5 post-infection. No virus titers were detected in any of the surviving mice at day seven post-infection.

Figure 31:
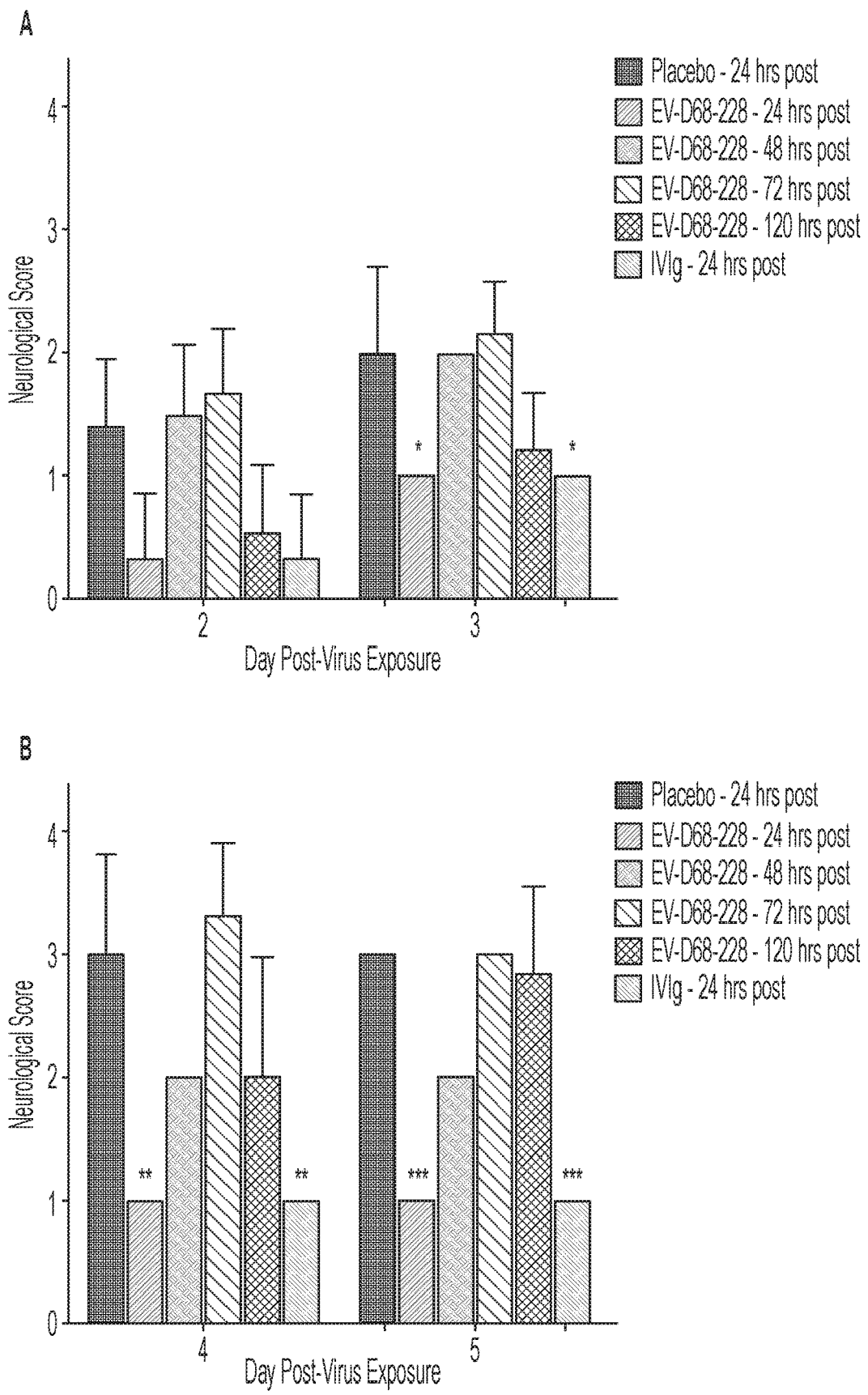
Figure 32:
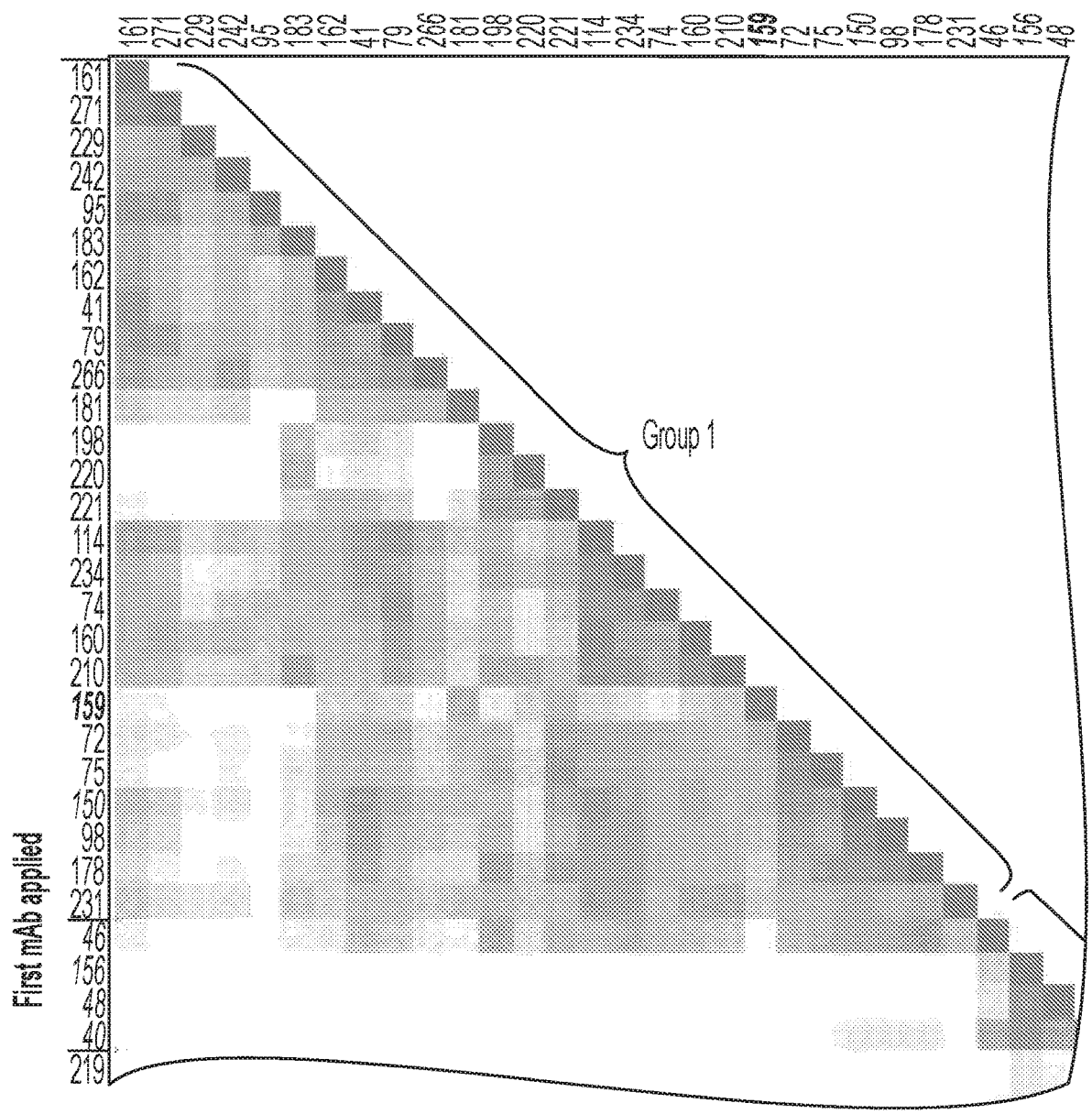
Figure 32:
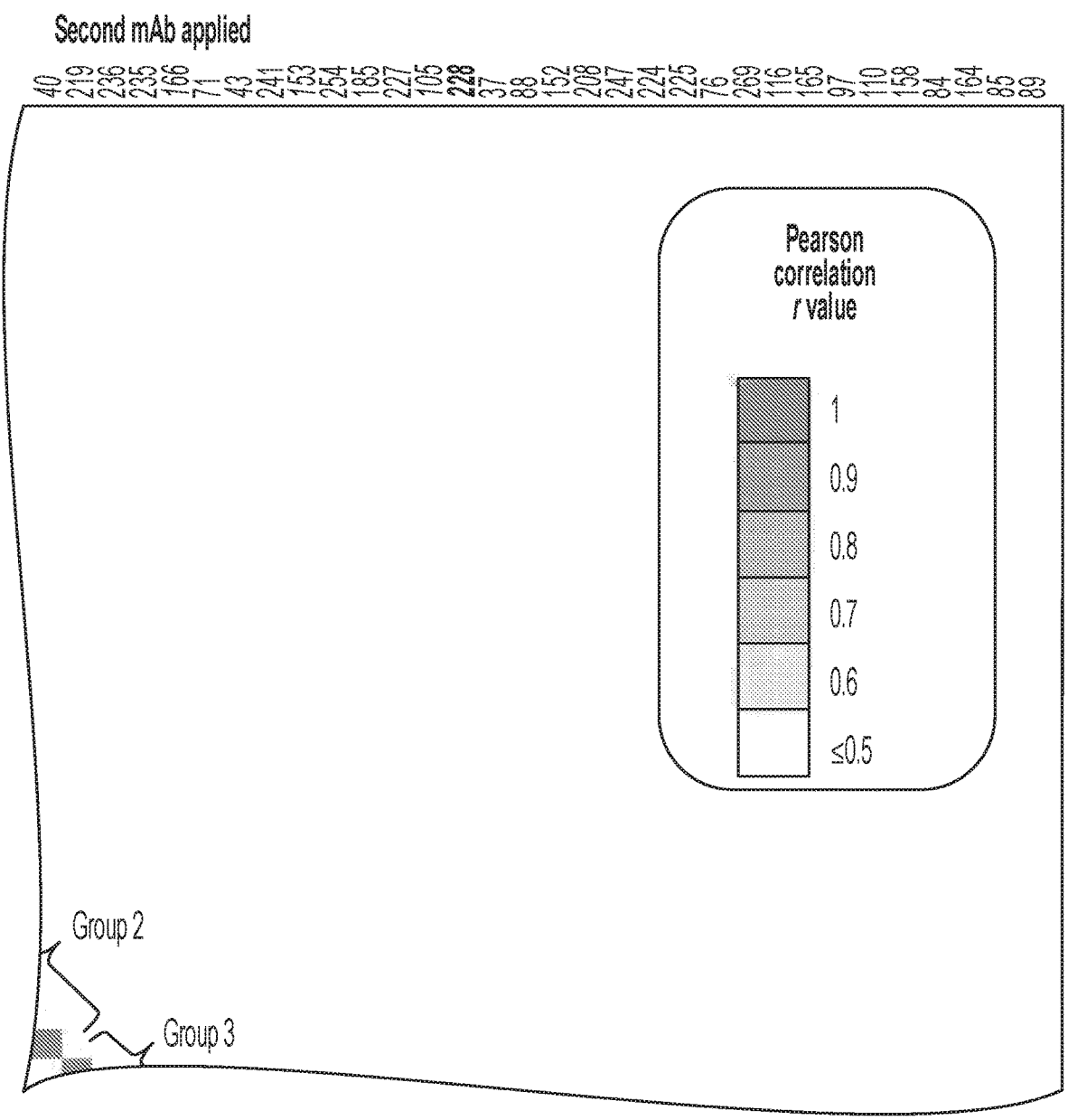
Figure 32:
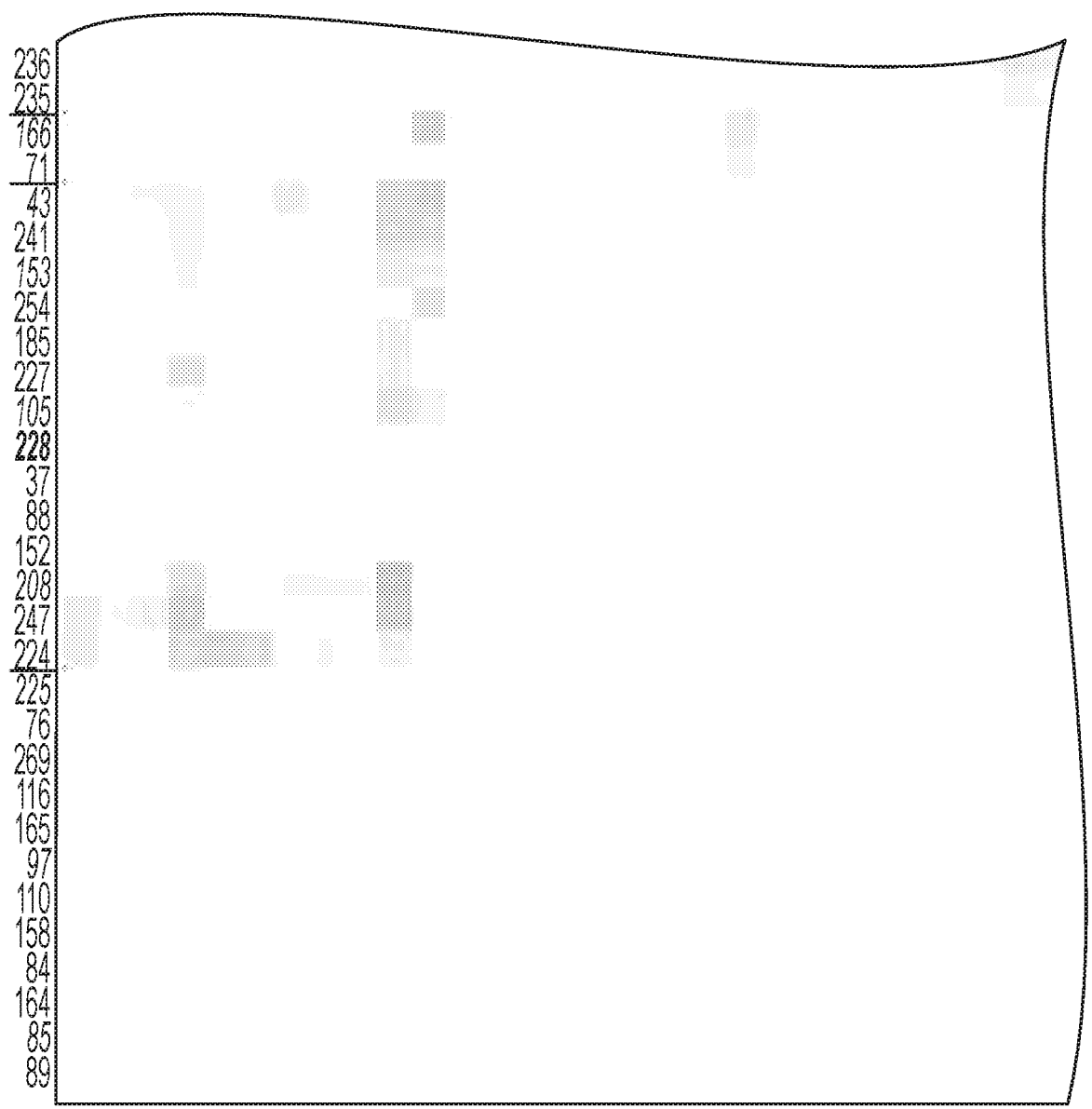
Figure 32:
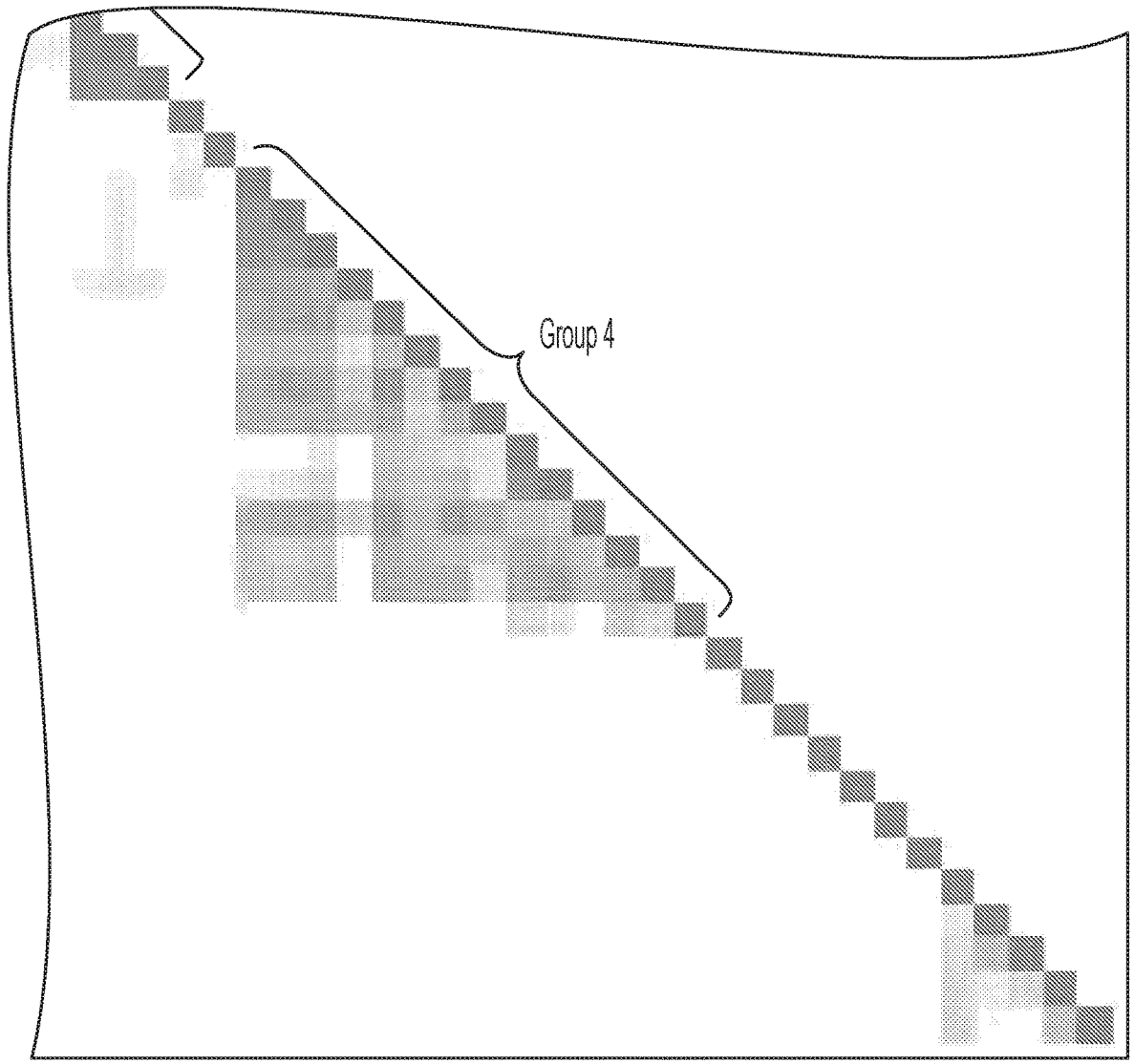

Neurological scores in 10-day-old AG129 mice infected with EV-D68 and treated post-infection with EV-D68-228 are shown in FIGS. 31A-B. Neurological scores on days 3, AG129 mice. When administered within 48 hours post-infection, a single dose of 10 mg/kg of EV-D68-228 protected mice from mortality and weight loss. A significant reduction in blood virus titers was observed in mice treated within 72 hours post-infection. A reduction in paralysis as measured by neurological scores was observed in mice treated with 10 mg/kg of EV-D68 at 24 hours post-infection. As EV-D68-228 could be used as a prophylactic therapy during an outbreak of EV-D68, determining the efficacy of EV-D68-228 when administered at various time points prior to infection would be beneficial.

Example 9—Materials and Methods

Study design. The inventors designed this study to try to identify any antibodies that humans can make in response to EV-D68 infection. Therefore, they used live virus isolates in an indirect ELISA screen to identify B cells secreting EV-D68-binding antibodies, and then electrofused those B cells with myeloma cells to create monoclonal antibody secreting hybridomas. The inventors then characterized the neutralization and binding properties of these individual mAbs in vitro using $CCID_{50}$, ELISA, and cryo-EM based techniques. They pursued in vivo experiments to generate pre-clinical data supporting the development of mAb EV68-228 as a prophylactic and/or therapeutic agent in humans. For this purpose, they studied the effectiveness of mAb EV68-228 at protecting mice from EV-D68 infection as compared to human IVIG, which is widely used to treat humans with AFM based on theoretical benefit, but this IVIG treatment so far has not been proven to be effective. An advantage of the AG129 murine model of infection is that the inventors could measure the effect of antibody treatment in both respiratory and neurologic models of infection.

Cell lines. RD cells (human, female origin) were obtained from the American Type Culture Collection (ATCC CCL-136). RD cells were cultured in 5% $CO_2$ at 37° C. in Dulbecco's Modified Eagle Medium (DMEM) (ThermoFisher Scientific) supplemented with 10% heat inactivated fetal bovine serum (HI-FBS; HyClone), 1 mM sodium pyruvate and 1% penicillin-streptomycin-amphotericin B (ThermoFisher Scientific). For structural studies, RD cells were cultured in DMEM (Sigma-Aldrich) supplemented with 10% HI-FBS (Sigma-Aldrich) and nonessential amino acids (NEAA, Life Technologies). The ExpiCHO (hamster, female origin) cell line was purchased from ThermoFisher Scientific and cultured according to the manufacturer's protocol. The HMMA2.5 line is a non-secreting mouse-human heteromyeloma cell line (sex information is not available) that was generated by fusing a murine myeloma cell line with a human myeloma cell line (Posner et al., 1987). This cell line was cultured as described previously (Yu et al., 2008). All cell lines were tested on a monthly basis for *Mycoplasma* and found to be negative in all cases.

Viruses. See Table K for a list of the virus isolates used in this study. EV-D68 isolates were propagated for two generations in RD cell monolayer cultures for use in enzyme linked immunosorbent assays (ELISAs) described below. RD cell monolayers were inoculated with a given virus isolate and monitored until 70 to 90% cell death was observed. This cell culture flask then was frozen to −80° C., thawed, and the contents scraped and collected into a 50 mL conical tube. This preparation was sonicated three times for 20 s in an inverted cup sonicator at maximum power settings (Fisherbrand), vortexed for 30 s, and then sonicated two more times for 20 s. Cell debris was pelleted, and the virus-containing supernatant was spun over a 30% sucrose in PBS (w/v) cushion at 10° C. for four hrs at 100,000×g. Supernatant was discarded, and the pellet allowed to soak in 0.01% (w/v) bovine serum albumin (BSA) in NTE buffer (20 mM Tris, 120 mM NaCl, 1 mM EDTA pH 8.0) overnight at 4° C. The resuspended pellet then was clarified further by centrifugation at 10,000×g for 10 min, before storage of virus aliquots at −80° C. until ready for use.

For structural studies the US/MO/14-18947 isolate was used. Virus was passaged in RD cells and stored at −80° C. before large scale propagation. RD cells were grown to 80% confluency and were infected with EV-D68 at a multiplicity of infection of 0.01. Two days post-infection, the cells were collected together with the supernatant and spun down. The cell pellets were collected and after multiple freeze/thaw cycles spun down to remove cell debris. All supernatants were combined and pelleted at 210,000×g for 2 hours. The pellets were incubated and resuspended in 250 mM HEPES (pH=7.5), 250 mM NaCl buffer, then supplemented with final concentration 5 mM $MgCl_2$, 0.01 mg/mL DNAse (Sigma-Aldrich), 0.8 mg/mL trypsin, 15 mM EDTA and 1% (w/v) n-lauryl-sarcosine. The sample was then pelleted at 210,000×g for 2 hours, resuspended, and loaded onto a potassium tartrate gradient (10 to 40%, w/v) for the last round of ultracentrifugation at 160,000×g for 2 hours. The purified virus sample, which was observed as a blue band in the middle of the tube, was extracted and buffered exchanged into 20 mM Tris, 120 mM NaCl, 1 mM EDTA (pH=8.0) buffer to remove potassium tartrate.

Detection of virus load by $CCID_{50}$ assay. Titration of virus stocks or virus in murine blood or lung samples was performed by $CCID_{50}$ assay in RD cell culture monolayers. Briefly, increasing 10-fold dilutions of the samples were applied to RD cell monolayers in triplicate wells (50 µL) of a 96 well plate, incubated for five days in 5% $CO_2$ at 33° C., and then fixed with 1% paraformaldehyde and stained with crystal violet. Wells with any cytopathic effect were scored as positive for virus, and titers were determined using a formula based on the Spearman-Kaerber equation (Ramakrishnan, 2016); the limit of detection was 136 $CCID_{50}$/mL.

Virus neutralization assay. Virus neutralization assays were performed in a $CCID_{50}$ format using the indicated viruses, essentially as described previously for poliovirus (Weldon et al., 2016). Virus was incubated with increasing concentrations of mAb in duplicate for one hr at 33° C., then each suspension was added to a monolayer of RD cells in technical quadruplicate wells (50 µL) of a 96-well plate. After five days incubation in 5% $CO_2$ at 33° C., cells were fixed with 1% paraformaldehyde and stained with crystal violet. Wells with any cytopathic effect were scored as positive for virus, and half maximal inhibitory concentrations ($IC_{50}$) were determined using a formula based on the Spearman-Kaerber equation (Ramakrishnan, 2016); the limits of detection were 57 µg/mL to 4.8 pg/mL.

Mouse models. Ten-day old (neurologic model) or four-week old (respiratory model) male and female AG129 mice (deficient in receptors for interferon $\alpha/\beta$ and $\gamma$) were obtained from a specific-pathogen-free colony maintained at the Utah Science Technology and Research (USTAR) building at Utah State University. The mice were bred and maintained on irradiated Teklad Rodent Diet (Harlan Teklad) and autoclaved tap water at the US TAR building of Utah State University. This study was conducted in accordance with the approval of the Institutional Animal Care and Use Committee of Utah State University dated Mar. 2, 2019 (expires Mar. 1, 2022). The work was done in the AAALAC-accredited Laboratory Animal Research Center of Utah State University. The U. S. Government (National Institutes of Health) approval was renewed Mar. 9, 2018 (PHS Assurance No. D16-00468[A3801-01]) in accordance with the National Institutes of Health Guide for the Care and Use of Laboratory Animals (Revision; 2011).

Antibody and control treatments were diluted in PBS and administered by intraperitoneal injection at indicated time points before or after EV-D68 inoculation. Guanidine HCl (Sigma-Aldrich) served as a positive control for treatment (Hurst et al., 2019), started 4 hours post-infection and continued twice daily for 5 days. A suspension of mouse adapted EV-D68 was administered by intraperitoneal injection (neurologic model; $10^{6.5}$ $CCID_{50}$ in a 100 µL volume of MEM) or intranasal instillation (respiratory model; $10^{4.5}$ $CCID_{50}$ in a 90 µL volume of MEM). Mice were weighed prior to treatment and daily thereafter. Mice were euthanized humanely at indicated time points post-infection for measurement of lung virus titers, blood virus titers, or lung cytokine concentrations, as indicated. For the neurologic model, all mice were observed daily for morbidity, mortality, and neurological scores through day 21. Neurological scores (NS) were recorded as follows: NS0—no observable paralysis, NS1—abnormal splay of hindlimb but normal or slightly slower gait, NS2—hindlimb partially collapsed and foot drags during use for forward motion, NS3—rigid paralysis of hindlimb and hindlimb is not used for forward motion, NS4—rigid paralysis in hindlimbs and no forward motion. Any animals observed with a score of NS4 were euthanized humanely.

Lung cytokine/chemokine evaluations. Each sample of lung homogenate was tested for cytokines and chemokines using quantitative chemiluminescent ELISA-based assays according to the manufacturer's instructions (Quansys Biosciences Q-Plex™ Array, Logan, UT). The Quansys multiplex ELISA is a quantitative test in which 16 distinct capture antibodies are applied to each well of a 96-well plate in a defined array.

Generation of human monoclonal antibodies (mAbs). Subjects were identified from the Childhood Onset of Asthma (COAST) birth cohort (Lemanske, 2002) who had laboratory documented EV-D68 upper respiratory tract infections (Bochkov et al., 2014). After written informed consent was obtained, peripheral blood was collected and stored at room temperature until peripheral blood mononuclear cells (PBMCs) could be purified using SepMate tubes (Stemcell Technologies), per the manufacturer's protocol, and then cryopreserved in 10% (v/v) dimethyl sulfoxide (DMSO) in fetal bovine serum (FBS) and stored in the vapor phase of liquid nitrogen. Lymphoblastoid cell lines (LCLs) were generated as described previously (Smith and Crowe, 2015) from memory B cells within the PBMCs by mixing with Epstein-Barr virus, cell cycle checkpoint kinase 2 (chk2) inhibitor (Sigma-Aldrich), CpG (Sigma-Aldrich), and cyclosporin A (Sigma-Aldrich) in Medium A (STEM-CELL Technologies). One week later, LCLs were counted and then expanded on a feeder layer of γ-irradiated, human PBMCs from an unrelated donor. In one more week, LCL supernatants were screened for the presence of EV-D68-reactive IgG by indirect ELISA using live EV-D68 virus as the antigen, comprising cell culture grown EV-D68 virus generated from a 2014 clinical isolate. LCLs from wells containing virus-reactive antibodies were fused to HMMA2.5 myeloma cells by electrofusion, as previously described (Yu et al., 2008). After the fusion reaction, hybridoma lines were cultured in a selection medium containing HAT media supplements (Sigma-Aldrich) and ouabain (Sigma-Aldrich) in 384-well plates before screening of supernatants for antibody production. Two weeks later, supernatants from the resulting hybridoma cell lines were screened by indirect ELISA with live virus as antigen, and cell lines from wells with EV-D68-reactive antibodies were expanded in culture and then cloned by single-cell flow cytometric sorting into 384-well cell culture plates. These cloned cells were expanded in Medium E until about 50% confluent in 12-well tissue culture treated plates (Corning) and their supernatants screened for virus binding by ELISA. Wells with the highest signal in ELISA were selected as the mAb-producing hybridoma cell lines for further use.

MAb isotype and gene sequence analysis. The isotype and subclass of secreted antibodies were determined using mouse anti-human IgG1, IgG2, IgG3 or IgG4 antibodies conjugated with horseradish peroxidase (Southern Biotech). Antibody heavy- and light-chain variable region genes were sequenced from RNA obtained from hybridoma lines that had been cloned biologically by flow cytometric sorting. Total RNA was extracted using the RNeasy Mini kit (Qiagen). A modified 5' RACE (Rapid Amplification of cDNA Ends) approach was used (Turchaninova et al., 2016). Briefly, 5 µL total RNA was mixed with cDNA synthesis primer mix (10 µM each) and incubated for 2 min at 70° C. and then decrease the incubation temperature to 42° C. to anneal the synthesis primers (1 to 3 min). After incubation, a mixture containing 5× first-strand buffer (Clontech), DTT (20 mM), 5' template switch oligo (10 µM), dNTP solution (10 mM each) and 10×SMARTScribe Reverse Transcriptase (Clontech) was added to the primer-annealed total RNA reaction and incubated for 60 min at 42° C. The first-strand synthesis reaction was purified using the Ampure Size Select Magnetic Bead Kit at a ratio of 1.8× (Beckman Coulter). Following, a single PCR amplification reaction containing 5 µL first-strand cDNA, 2×Q5 High Fidelity Mastermix (NEB), dNTP (10 mM each), forward universal primer (10 µM) and reverse primer mix (0.2 µM each in heavy-chain mix, 0.2 µM each in light-chain mix) were subjected to thermal cycling with the following conditions: initial denaturation for 90 s followed by 30 cycles of denaturation at 98° C. for 10 s, annealing at 60° C. for 20 s, and extension at 72° C. for 40 s, followed by a final extension step at 72° C. for 4 min. All primer sequences used in this protocol were described previously ((Turchaninova et al., 2016). The first PCR reaction was purified using the AMPure Size Select Magnetic Bead Kit at a ratio of 0.6× (Beckman Coulter) Amplicon libraries were then prepared according to the Multiplex SMRT Sequencing protocol (Pacific Biosciences) and sequenced on a Sequel platform instrument (Pacific Biosciences). Raw sequencing data was demultiplexed and circular consensus sequences (CCS) were determined using the SMRT Analysis tool suite (Pacific Biosciences). The identities of gene segments, complementarity-determining regions (CDRs), and mutations from germline genes were determined by alignment using the ImMunoGeneTics database (Giudicelli and Lefranc, 2011).

Antibody production and purification. For hybridoma-derived mAb, hybridoma cells were grown to exhaustion in Hybridoma SFM (1×) serum free medium (Gibco). For recombinant mAb production, cDNA encoding the genes of heavy and light chains were synthesized and cloned into a DNA plasmid expression vector encoding a full-length IgG1 protein (McLean et al., 2000) and transformed into E. coli cells. MAb proteins were produced after transient transfection of ExpiCHO cells following the manufacturer's protocol. The resulting secreted IgGs were purified from filtered culture supernatants by fast protein liquid chromatography (FPLC) on an ÅKTA instrument using a Protein G column (GE Healthcare Life Sciences). Purified mAbs were buffer exchanged into PBS, filtered using sterile 0.45-µm pore size filter devices (Millipore), concentrated, and stored in aliquots at −80° C. until use. An aliquot of each mAb also was biotinylated directly in 96-well format using the EZ-Link NHS-PEG$_4$-biotin kit (ThermoFisher Scientific) with a 20-fold molar excess of biotin to mAb, followed by buffer exchange back to PBS using a desalting plate (Zeba, 7 kDa cutoff). Hybridoma-derived mAbs were used in in vitro experiments, and recombinant mAbs were used in in vivo experiments. Pooled human immunoglobulin was purchased as intravenous immunoglobulin (IVIG, Carimune, CSL Behring, King of Prussia, PA). RSV90 is a recombinant human IgG1 mAb produced in the inventors' laboratory that was used as a negative control, placebo mAb in mouse experiments. Polyclonal anti-VP1, -VP2, and -VP3 antibodies used in western blot were purchased from Genetex.

Fab fragment production. Fab fragments were generated and purified via Pierce Fab Preparation Kit (ThermoFisher Scientific). The Immobilized Papain vial spin column and Zeba Spin Desalting Column were equilibrated with digestion buffer (35 mg cysteine·HCl per 10 mL of supplied Fab Digestion Buffer, pH ~7.0) before use. The NAb Protein A Plus Spin Column was equilibrated with PBS buffer before use. The original IgG samples were passed through the Zeba Spin Desalting Column, and 0.5 mL of the prepared IgG samples were applied on the Immobilized Papain vial and incubated at 37° C. for 5 hours Fab digestion. Then the final Fab fragments were buffer exchanged to PBS and stored at 4° C.

EV-D68-specific ELISA. Wells of medium binding, black fluorescent immunoassay microtiter plates (Greiner Bio-One) were coated with virus stocks diluted in 100 mM bicarbonate/carbonate buffer, pH 9.6 and incubated at 4° C.

overnight. Plates were blocked with 2% BSA in Dulbecco's phosphate-buffered saline (DPBS) containing 0.05% Tween-20 (DPBS-T) for 1 hr. For mAb screening assays, hybridoma culture supernatants were added to the wells and incubated for 2 hr at ambient temperature. The bound antibodies were detected using Fc-specific goat anti-human IgG conjugated with HRP (Southern Biotech) and QuantaBlu fluorogenic peroxidase substrate (ThermoFisher Scientific). After 20 min, 100 mM glycine (pH 10.5) was added to quench the reaction, and the emission was measured at 420 nm after excitement at 325 nm using a Synergy H1 microplate reader (Biotek). For dose-response and cross-reactivity assays, serial dilutions of purified mAbs were applied to the wells in duplicate technical replicates and mAb binding was detected as above; the experiments were performed at least three times. For the competition ELISA, microtiter plates were first coated with virus, and then a purified mAb was added at 100 µg/mL and allowed to incubate at 33° C. for 3 hr. Then, a biotinylated mAb was spiked into this mixture at a final concentration of 5 µg/mL and allowed to incubate at ambient temperature for 1.5 hr. After a wash and 30 min of incubation with avidin-peroxidase (ThermoFisher Scientific), mAb binding was detected as above.

Western blot. B1 clade virus preparation was mixed with denaturing and reducing loading buffer, boiled at 100° C. for 5 min, and then run on an SDS-PAGE gel along with Novex sharp pre-stained protein standard (ThermoFisher Scientific). Protein was transferred to a membrane, blocked in blocking buffer (Li-Cor), and then cut into strips so that individual lanes could be stained with purified mAb in blocking buffer. An IRDye 800CW-conjugated goat anti-human secondary antibody (Li-Cor) was used to detect mAb binding. Strips were reassembled to visualize molecular weight and imaged on an Odyssey CLx near infrared imager (Li-Cor).

Cryo-EM sample preparation and data collection. For both EV-D68:Fab EV68-159 and EV-D68:Fab EV68-228 complexes, purified EV-D68 viruses and Fabs were mixed at a molar ratio of 1:200. After incubating at room temperature for 45 to 60 min, 3.5 µL of virus-Fab mixture sample were added to a glow-discharged 400 mesh lacey carbon film copper grid (Ted Pella Inc.). Grids were plunge frozen (Cryoplunge 3 system, Gatan) in liquid ethane after being blotted for 3.5 s in 75 to 80% humidity. Cryo-EM datasets were collected on a 300 kV Titan Krios Microscope (Thermo Fisher Scientific). For the EV-D68:Fab EV68-228 dataset, movies were collected using the program Leginon (Subway et al., 2005) with a K3 Direct Detection Camera (Gatan) at a magnification of 64,000×, resulting in a super resolution pixel size of 0.662 Å, with a defocus range from 0.7 to 2 µm. A total electron dose of 44.2 electrons/Å$^2$ over 2.6 seconds of exposure was recorded over 50 frames. The EV-D68:Fab EV68-159 dataset was acquired with a K2 Summit direct electron detector (Gatan) at a nominal magnification of 81,000×, resulting in a super resolution pixel size of 0.874 Å, a defocus range from 0.7 to 3.5 µm. A total electron dose of 31.4 electrons/Å$^2$ over 12 seconds of exposure was split into 60 frames. Overall, 462 movies and 732 movies were acquired for the EV-D68:Fab EV68-228 and EV-D68:Fab EV68-159 datasets, respectively.

Image processing. For both datasets, motion correction was performed on the raw movie frames via MotionCor2 (Zheng et al., 2017b) as implemented in Appion (Lander et al., 2009) during data collection. The contrast transfer function (CTF) was estimated on the aligned frames with CTFFIND4 (Rohou and Grigorieff, 2015). Particle picking templates were generated using the Appion Manual Picker (Lander et al., 2009) and templates for auto picking were obtained through 2-dimensional (2D) classification in XMIPP (Sorzano et al., 2004). These templates were then used for auto-picking in FindEM (Roseman, 2004) and particles were extracted using RELION. These particles were then subjected to multiple rounds of 2D and 3D classifications in RELION (Scheres, 2012). This resulted in 20,194 and 30,554 particles for the EV-D68:Fab EV68-228 and EV-D68:Fab EV68-159 datasets which were selected for final 3D icosahedral reconstructions using the program JSPR following the gold-standard refinement method (Guo and Jiang, 2014). The final resolutions for both maps were estimated based on a gold-standard Fourier shell correlation cutoff of 0.143 (Scheres and Chen, 2012). Map sharpening was done in RELION (Scheres, 2012) post-processing. Data collection parameters and related items are summarized in Table G.

Model building, refinement and analysis. The same methods were used for the atomic structures of both EV-D68:Fab EV68-159 and EV-D68:Fab EV68-228. The X-ray crystallography model of the EV-D68 Fermon strain (PDB code: 4WM8) was selected as a starting reference for model building and was manually fitted into the density maps using the program Chimera (Pettersen et al., 2004). Using the initial fitting as a basis, the models were rebuilt in Coot (Emsley et al., 2010) and refined using real-space-refinement in PHENIX (Adams et al., 2010) to correct for outliers and poorly fitted rotamers. Chimera (Pettersen et al., 2004), Coot (Emsley et al., 2010) and CCP4i2-PISA (Potterton et al., 2018) were used to determine the binding interface residues. The final atomic models were validated in MolProbity (Chen et al., 2012). Refinement statistics are described in Table G.

Selection of neutralization escape mutant virus. A clade B1 EV-D68 isolate was passaged under selection with increasing amounts of purified mAb in RD cells. After incubating mAb and virus for 1 hr at 33° C., this mixture was added to a cell monolayer for 2 hr at 33° C. The monolayer then was rinsed thrice, and mAb containing medium was added back. This culture was incubated at 33° C. until at least 70% cytopathic effect was observed (cells lifted off of plate), at which point the cells and supernatant together were collected and frozen to −80° C. This sample was thawed and sonicated in the same microfuge tube in an inverted cup sonicator at maximum power 3×20 s, vortexed for 30 s at maximum power, and sonicated again 2×20 s. Cellular debris was clarified for 10 min at 10,000×g. Then the virus-containing supernatant was mixed 1:1 with fresh medium containing mAb at higher concentration. Over three passages, mAb concentration was increased from 5 to 50 to 500 ng/mL. Viral RNA was harvested using TRI Reagent and Direct-zol RNA MiniPrep kit (Zymo Research). In triplicate, the inventors generated cDNA templates, from which a 3,080 bp amplicon covering the P1 region of the viral genome was generated with the PrimeScript One Step RT-PCR Kit Ver. 2 (Takara) and primers 5'—CCTCCGGCCCCTGAAT (Fwd; SEQ ID NO: 641) and 5'—CCATTGAATCCCTGGGCCTT (Rev; SEQ ID NO: 642). They used a Pacific Biosciences (PacBio) next generation sequencing platform to generate sequences of each of the three replicates. 2,000 reads of each sequencing run were used to quantitate the percentage of reads in which each mutation was observed. Mutations were determined as compared to a wild-type consensus sequence of all of the reads from the negative control selection mAb selection.

Quantification and statistical analysis. Technical and biological replicates are indicated in the methods and figure legends. Statistical analyses were performed using Prism v8 (GraphPad).

Competition-binding assay. ELISA fluorescence values were normalized to a percentage of maximal binding determined from a control well without an irrelevant prior competing mAb added. The Pearson correlation of each biotinylated mAb to each other biotinylated mAb was calculated using the median inhibition percentage from three different experiments using the corn method of the Pandas Python package (McKinney, 2010). Hierarchical clustering was then performed on these Pearson correlations using the clustermap method of the Seaborn Python package. The clustering information was exported in newick format and imported into Interactive Tree of Life v4 (Letunic and Bork, 2019), which was used to display the hierarchically-clustered heatmap before importation into Excel (Microsoft) for final display.

Antibody ELISA binding experiments. $EC_{50}$ values for mAb binding were determined after log transformation of antibody concentration using four-parameter sigmoidal dose-response nonlinear regression analysis constrained to a bottom value of zero and top value less than the maximal fluorescent value of the mAb with the highest saturation fluorescence value.

Virus assays. MAb $IC_{50}$ values were calculated using a formula based on the Spearman-Kaerber equation (Ramkrishnan, 2016). Viral titers in murine plasma and lungs were compared using a one-way analysis of variance (ANOVA) and Dunnett's multiple comparisons test, with a single pooled variance. A value of $p<0.05$ was considered significant.

Lung cytokine/chemokine evaluations. For each cytokine/chemokine, the concentrations from treated mice were compared to placebo-treated mice using a Brown-Forsythe one-way ANOVA test and Dunnett's T3 multiple comparisons test, with individual variances computed for each comparison. This analysis was chosen because the inventors did not assume equal standard deviations for each measurement.

In vivo protection studies. Survival curves were generated using the Kaplan-Meier method and curves compared using the log rank test (Mantel-Cox). Neurologic scores were compared using a chi-square test.

Example 10—Results

After obtaining written informed consent, twelve subjects who had previous documented EV-D68 respiratory tract infections during the 2014 outbreak in the U.S. donated blood, from which the inventors isolated peripheral blood mononuclear cells (PBMCs). The subjects were 12 to 15 years old when infected and 16 to 18 years old at time of blood collection. Each subject had a history of EV-D68-associated respiratory disease, and none had symptoms of AFM (Table E). The collected PBMCs were transformed in vitro by inoculation with Epstein-Barr virus to generate memory B cell derived lymphoblastoid cell lines (LCLs), which secrete antibodies. LCL culture supernatants were used in an indirect ELISA to screen for the presence of EV-D68-reactive IgGs. The inventors selected cultures with antibodies that bound to laboratory-grown live virus preparations of EV-D68 generated from 2014 clinical isolates but that did not bind to a similarly prepared uninfected cell supernatant. After electrofusion of LCLs secreting EV-D68-specific antibodies with a non-secreting myeloma cell line, the resulting hybridoma cells were single-cell sorted to generate clonal hybridomas secreting fully human mAbs (Table F).

The inventors sought to determine how many major antigenic sites on the virus surface are bound by human mAbs made in response to natural infection. To identify groups of antibodies that recognized similar epitopes, they determined whether the mAbs could compete with the binding of each of the other mAbs to live virus in an indirect ELISA. For competition-binding experiments, virus was coated directly onto an ELISA plate and then incubated with high concentrations of one unlabeled mAb. Next, mAbs labeled by biotinylation were added at a lower concentration, and the ability of the second mAb to bind the virus in the presence of the first mAb was determined. The inventors then used a Pearson correlation with the inhibition data to determine the relatedness of the antibody binding patterns to each other and identified four main competition-binding groups (FIG. 32), which they termed groups 1 to 4. They used each mAb to stain a western blot of EV-D68 preparations and found that nearly all mAbs in competition-binding groups 2 and 3 bound to linear epitopes in the VP1 protein, whereas only a single other mAb bound to any protein in the virus preparation (FIG. 40).

During the 2014 EV-D68 outbreak in the U.S., nearly all viral isolates were of the newly emergent B1 clade, with fewer detections of virus from the closely related B2 or distantly related D clades (Tan et al., 2016). All but one of the subjects for this study were infected with B1 clade isolates (Table E). Since 2014, B3 clade viruses have dominated, and B1 clade viruses are no longer circulating (Dyrdak et al., 2019); in 2018 all EV-D68 isolates sequenced by the U.S. Centers for Disease Control and Prevention were from the B3 clade (Kujawski et al., 2019). The inventors first measured the in vitro neutralization capability of each mAb in a 50% cell culture infectious dose ($CCID_{50}$) assay using a B1 clade EV-D68 isolate (FIG. 33A). Twenty-eight mAbs demonstrated neutralization with a half maximal inhibitory concentration ($IC_{50}$) below 50 μg/mL, with mAb EV68-159 exhibiting the strongest neutralization at an $IC_{50}$ value of 0.32 ng/mL (FIG. 41). The inventors further tested the 21 most potently neutralizing mAbs against a D clade isolate and found that 11 mAbs neutralized that virus, with 7 of those exhibiting at least a ten-fold decrease in potency by $IC_{50}$ value for the heterologous virus. The Fermon strain is an isolate from 1962 and is so distantly related to modern EV-D68 isolates that it does not fit into the clade classification scheme (Tan et al., 2016). Nine mAbs neutralized the Fermon laboratory reference strain, but less potently than they inhibited the contemporary B1 clade virus.

Recognizing that neutralization assays may underestimate cross-reactivity, the inventors used the same indirect ELISA approach described above to generate half-maximal effective concentrations ($EC_{50}$) of purified mAb for binding to representative EV-D68 isolates from the B1, B2, or D clades (FIGS. 33B-C, and FIG. 42). Of the mAbs with $EC_{50}$ values for binding of ≤1 μg/mL to B1 clade isolates, all bound to a B2 clade isolate, whereas about half also bound to a D clade isolate (FIG. 33B and FIG. 41). An additional class of mAbs was observed that bound weakly in general but cross-reacted to viruses from all clades tested.

To date, structural studies of antibody-EV-D68 interactions have been limited to murine mAbs (Zheng et al., 2019). The inventors selected two potently neutralizing human mAbs, the clade-specific mAb EV68-159 and the highly cross-reactive mAb EV68-228, to make immune complexes with antigen binding fragments (Fabs) and a B1 clade EV-D68 isolate for cryo-electron microscopy (cryo-EM) studies. The final density maps attained a resolution of 2.9 Å (EV68-159) or 3.1 Å (EV68-228) (FIG. 34A, FIG. 43, FIG. 44, and Table G). The structures revealed two distinct binding sites: EV68-159 attached around the three-fold axes of symmetry, whereas EV68-228 bound around the five-fold axes between depressions that form the canyon regions (FIGS. 34A-C, FIG. 45). Thus, for each Fab, a total of 60 copies bound to the virus particle. The Fab variable domains, which interacted with the viral surface, displayed strong densities similar to the viral capsid proteins, and an atomic model of each Fab was built together with the four viral capsid proteins. In contrast, the Fab constant domains, which are located further from the viral surface, displayed weaker densities and were excluded from atomic model building. The backbone of the polypeptide chains and the majority of amino acid side chains are well-ordered in the density maps, demonstrating the critical features of the binding interface between virus particle and Fab molecule.

Figure 35:
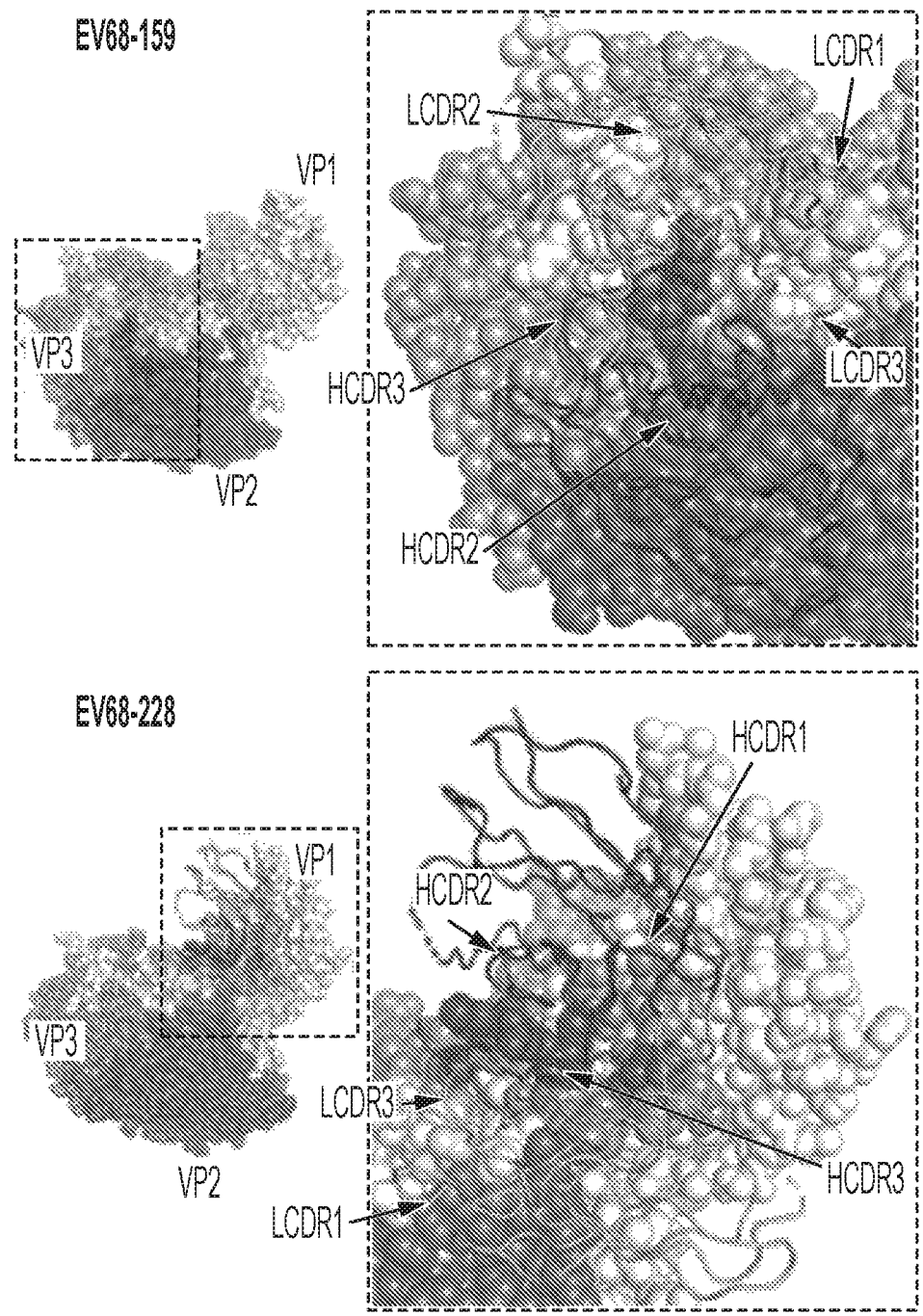
FIG. 35. Close-up view of the binding interfaces of EV68-159 and EV68-228. The viral capsid is shown as surface and the Fab is shown in a cartoon representation. VP1, VP2 and VP3 are colored in white, dark grey and silver, respectively. Heavy or light chains are colored in orange or yellow, respectively. Viral residues making interactions are colored based on the heavy and light chains, and the color intensities vary based on which of the VPs. The heavy and light chain complementarity-determining regions (HCDR and LCDR, respectively) involved in the binding interfaces are shown with arrows.
Figure 36:
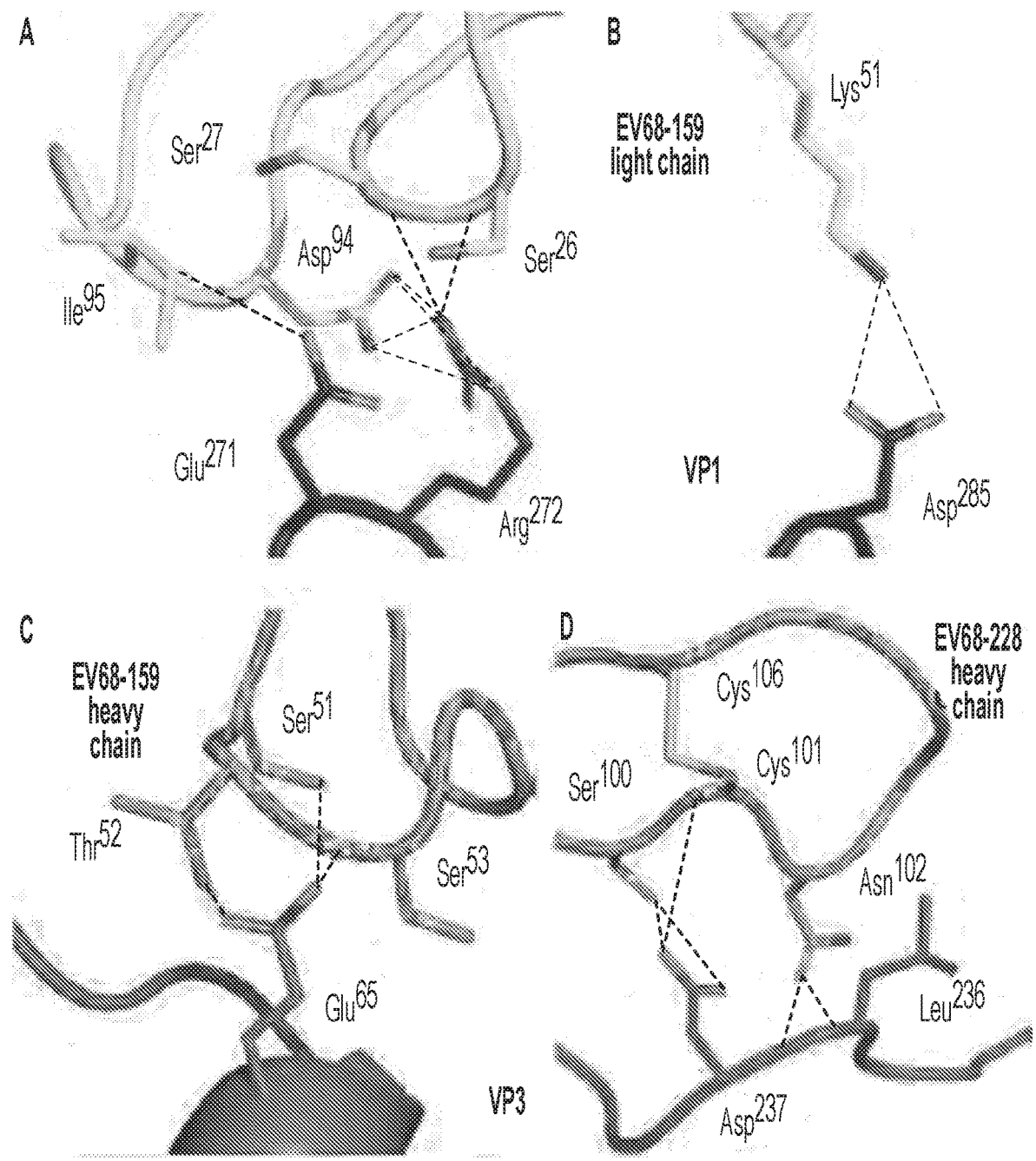
FIGS. 36A-D. Molecular detail of virion-Fab interactions. Representative interactions at the binding interface of EV-D68:Fab EV68-159 (FIGS. 36A-C) and EV-D68:Fab EV68-228 (FIG. 36D). Hydrogen bonds are colored in cyan and salt bridges are colored in magenta.
Figure 46:
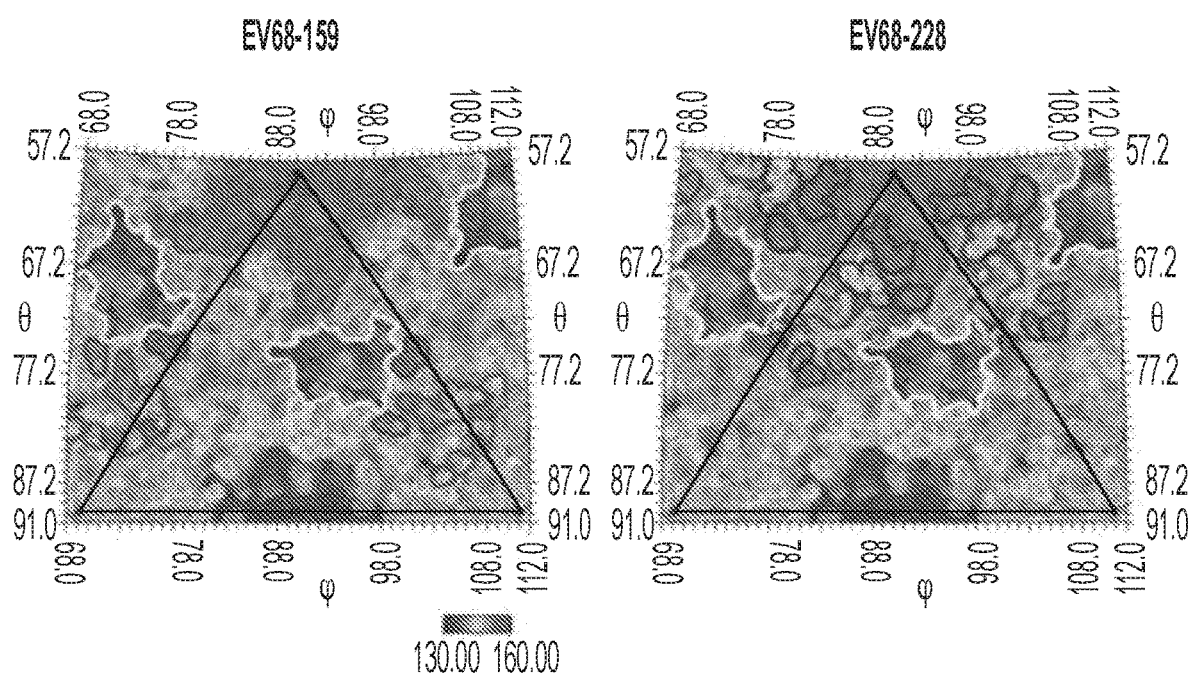
FIG. 46. Roadmaps showing an enlarged view of the Fab footprints. The radially colored 2D projection of the viral surface was created with RIVEM. Virus surface residues facing any atoms from the Fab molecules within a distance of 4 Å are outlined in light blue (VP1), light green (VP2) and light red (VP3). The canyon region is outlined in yellow.

For both models, the viral surface residues that were facing and within a 4 Å distance from the Fab were identified as the footprint (FIG. 34C, FIG. 46, and Table H). The footprints show that both Fab molecules sit within one protomer. In the EV-D68:Fab EV68-159 complex, each Fab masked a viral surface area around 990 Å$^2$. At the binding interface (FIG. 35), essential interactions were found between the EV68-159 light chain and three residues on the C-terminus of VP1: Glu271 and Arg272 (FIG. 36A) and Asp285 (FIG. 36B). Residues Glu271 and Arg272 formed hydrogen bonds with CDR3 and CDR1. Arg272 and Asp285 formed salt bridges with CDR3 and CDR2 residues, respectively. The heavy chain of EV68-159 contributed 77% of the masked surface areas. A series of hydrogen bonds was found between the heavy chain complementarity-determining region 2 (CDR2) and CDR3 and the VP3 N-terminal loop before the B-β strand (βB) (FIG. 36C).

In the EV-D68:Fab EV68-228 complex, each Fab masked approximately 1,170 Å$^2$ of the viral capsid surface. Similar to EV68-159, the heavy chain of the EV68-228 Fab dominated the interaction with the viral capsid by masking around 84% of the surface area. The binding interface (FIG. 35) was stabilized mainly by hydrogen bonds formed between the heavy chain CDRs and the VP1βB as well as the VP3 C-terminus (FIG. 36D). The light chain CDR1 interacted with the VP2 EF loop. In addition, hydrogen bonds formed between the heavy chain framework region (FR) 3 and the VP1 DE loop. Furthermore, a salt bridge formed between the light chain CDR3 and the VP1 C-terminus. Overall, the EV68-228 Fab bound the viral surface around the five-fold axes and recognized the classical picornavirus neutralizing immunogenic sites (NIms) NIm-IB (VP1 DE loop) and NIm-II (VP2 EF loop) (Rossmann et al., 1985).

Figure 47:
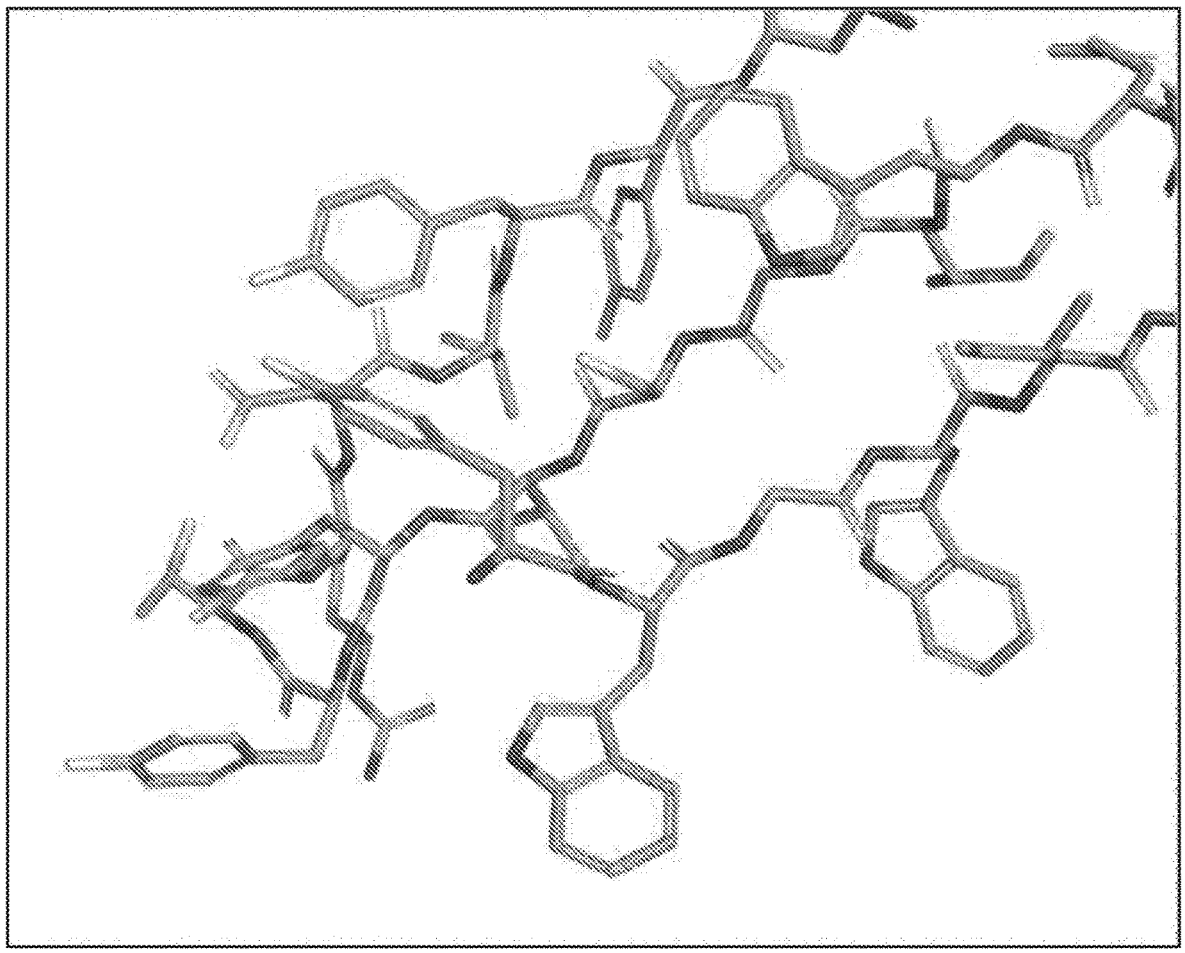
FIG. 47. Bulky side chains of the EV68-228 Fab heavy chain. This view shows an example of bulky side chains forming a hydrophobic interaction network to stabilize the EV68-228 Fab, which also is seen in the structure of the EV68-159 Fab.

Bulky side chains were found at the interface for both Fabs and act to stabilize the structures through hydrophobic interaction networks (FIG. 47). Furthermore, disulfide bonds also were detected around CDR1 and CDR3 in heavy and light chains. Another pair of cysteines, Cys101 and Cys106, were found within the CDR3 of the EV68-228 heavy chain and were at the correct distance and orientation to form a disulfide bond (FIG. 36D). Specifically, when the contour levels were reduced, the densities of the two cysteine side chains connected. As described above for the EV-D68:Fab EV68-228 complex, hydrogen bonds were observed between the heavy chain CDR3 and the VP3 C-terminal residues adjacent to the canyon involving Cys101, forming both a hydrogen bond and a disulfide bond. These cysteine residues play critical roles in stabilizing both Fab structure and the virus-Fab binding interface.

Figure 37:
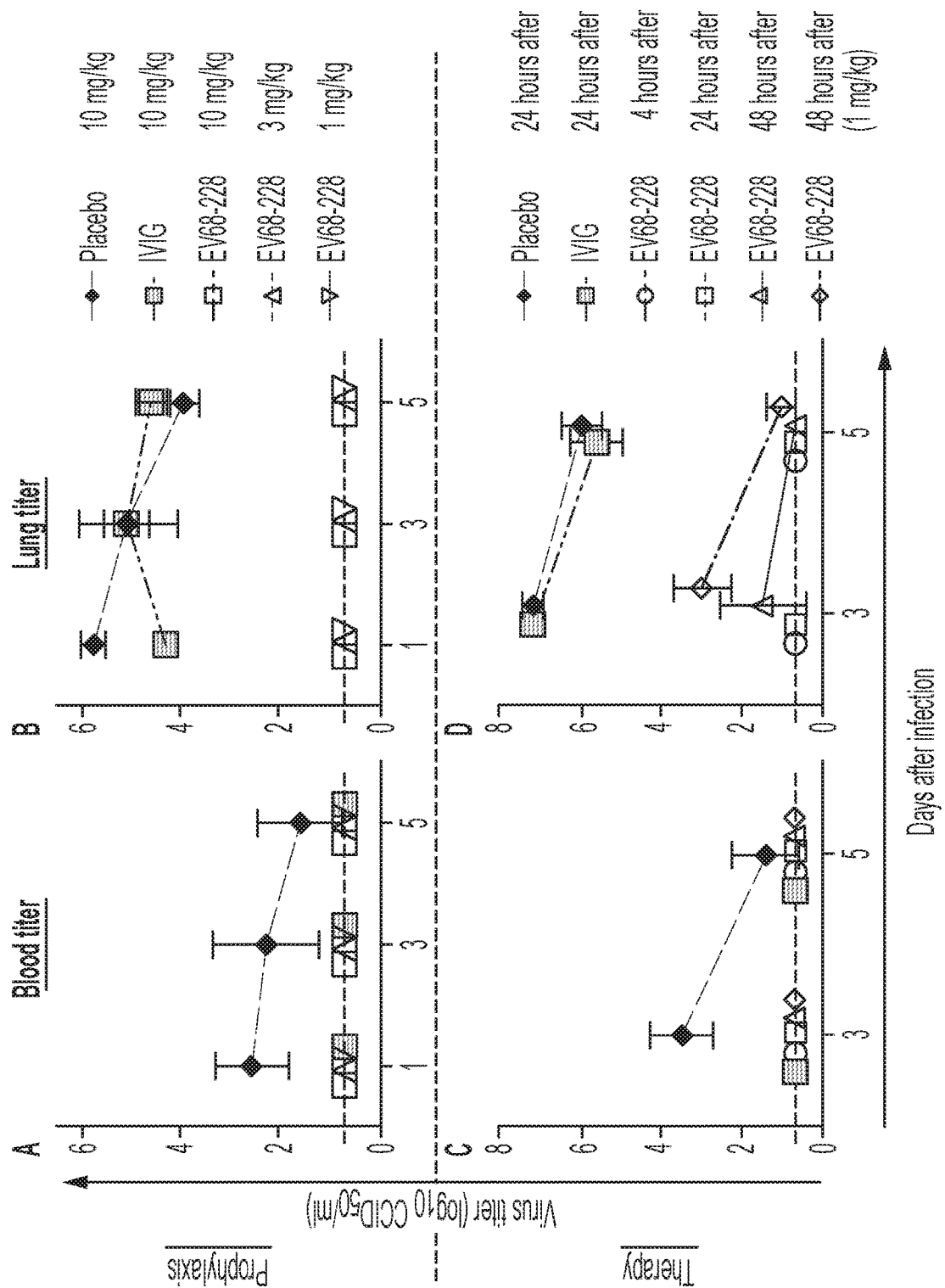
FIGS. 37A-D. MAb EV68-228 protects mice from EV-D68-induced respiratory disease, when used as either prophylaxis or therapy. Four-week-old AG129 strain mice (n=4 per time point) were inoculated with mouse-adapted B1 clade EV-D68 intranasally; antibody was administered intraperitoneally; and viral titers for indicated tissue were measured by a $CCID_{50}$ assay.
Figure 38:
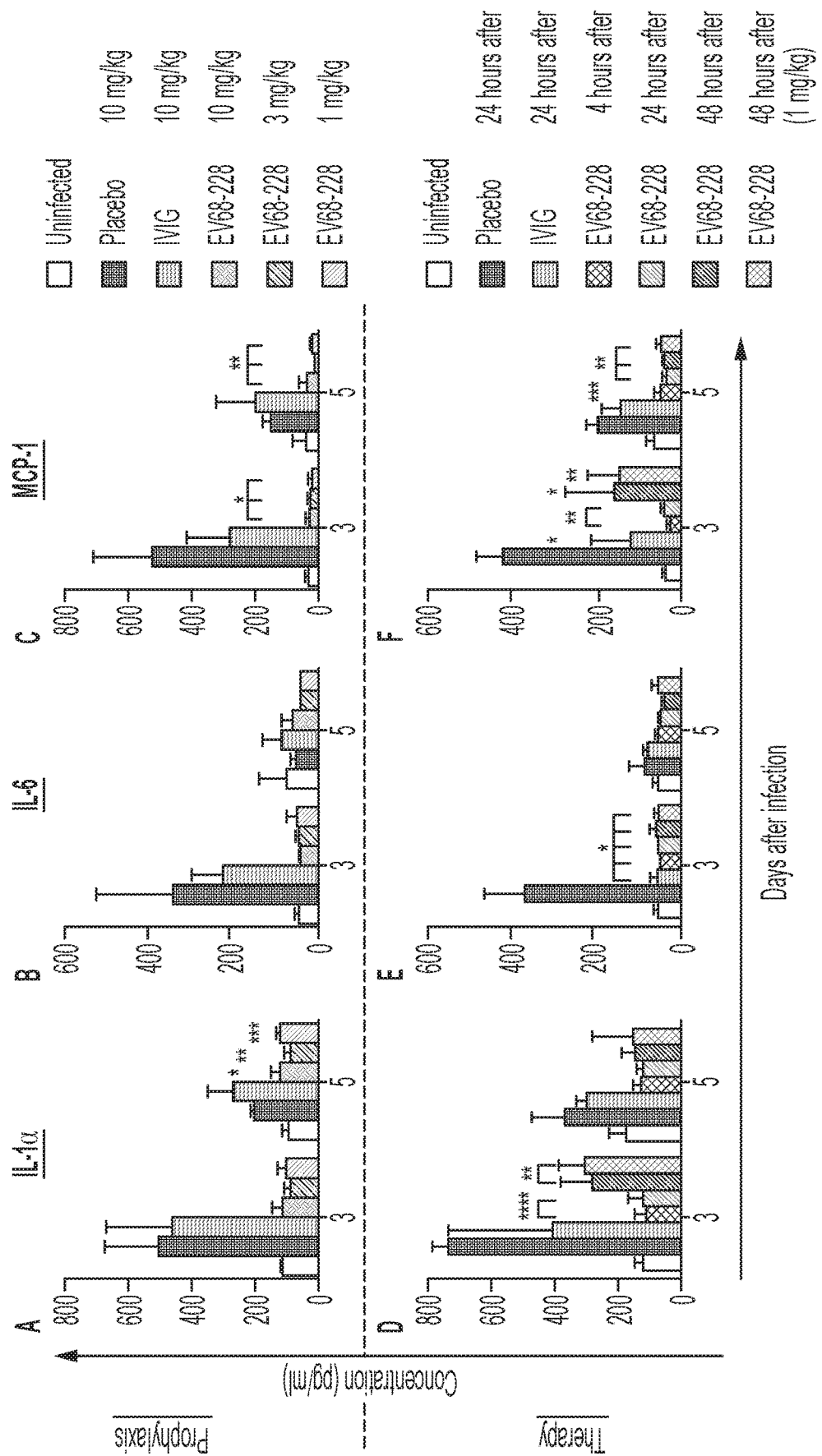
FIGS. 38A-F. MAb EV68-228 decreases lung inflammation in EV-D68 infected mice. Four-week-old AG129 mice (n=4 per time point) (FIGS. 38A-C) were inoculated with virus intranasally 24 hours after indicated dose of antibody or (FIGS. 38D-F) were inoculated with virus intranasally followed by 10 mg/kg (except where indicated) of antibody 4, 24, or 48 hours later, then cytokines were measured at indicated time points. Cytokines were quantified from lung homogenates using an ELISA. Values from the treatment groups were compared to the placebo group for each time point using a one-way ANOVA with Dunnett's T3 multiple comparisons test (*$P<0.05$, $P<0.01$, *$P<0.001$, ****$P<0.0001$). IL—interleukin; MCP—monocyte chemoattractant protein. Designation of samples in graph corresponds left-to-right with vertical legend top-to-bottom.

The inventors next sought to determine if the potently neutralizing and highly cross-reactive human mAb EV68-228 could prevent or treat infection and disease in small animal models of EV-D68 infection. They tested for this antiviral activity in vivo using two different established models of infection causing either respiratory or AFM-like neurologic disease in AG129 strain mice that are deficient in receptors for interferon α/β and γ (Evans et al., 2019; Hurst et al., 2019). First, the inventors tested whether antibodies could reduce viremia and lung virus replication in the respiratory model of infection. MAb EV68-228 administered systemically as prophylaxis a day before virus inoculation provided sterilizing immunity in the blood (FIG. 37A) and lungs (FIG. 37B) at each of the concentrations tested, whereas human IVIG only sterilized the blood. Induction of pro-inflammatory cytokine secretion was inhibited in the lungs of EV68-228 treated mice (FIGS. 38A-C). When used as treatment given at increasing times after virus inoculation, again all treatments were highly effective at sterilizing the blood (FIG. 37C), but only EV68-228 had efficacy in the lungs (FIG. 37D). The inventors similarly observed reduced pro-inflammatory cytokine levels in the lungs of EV68-228-treated mice (FIGS. 38D-F).

Figure 39:
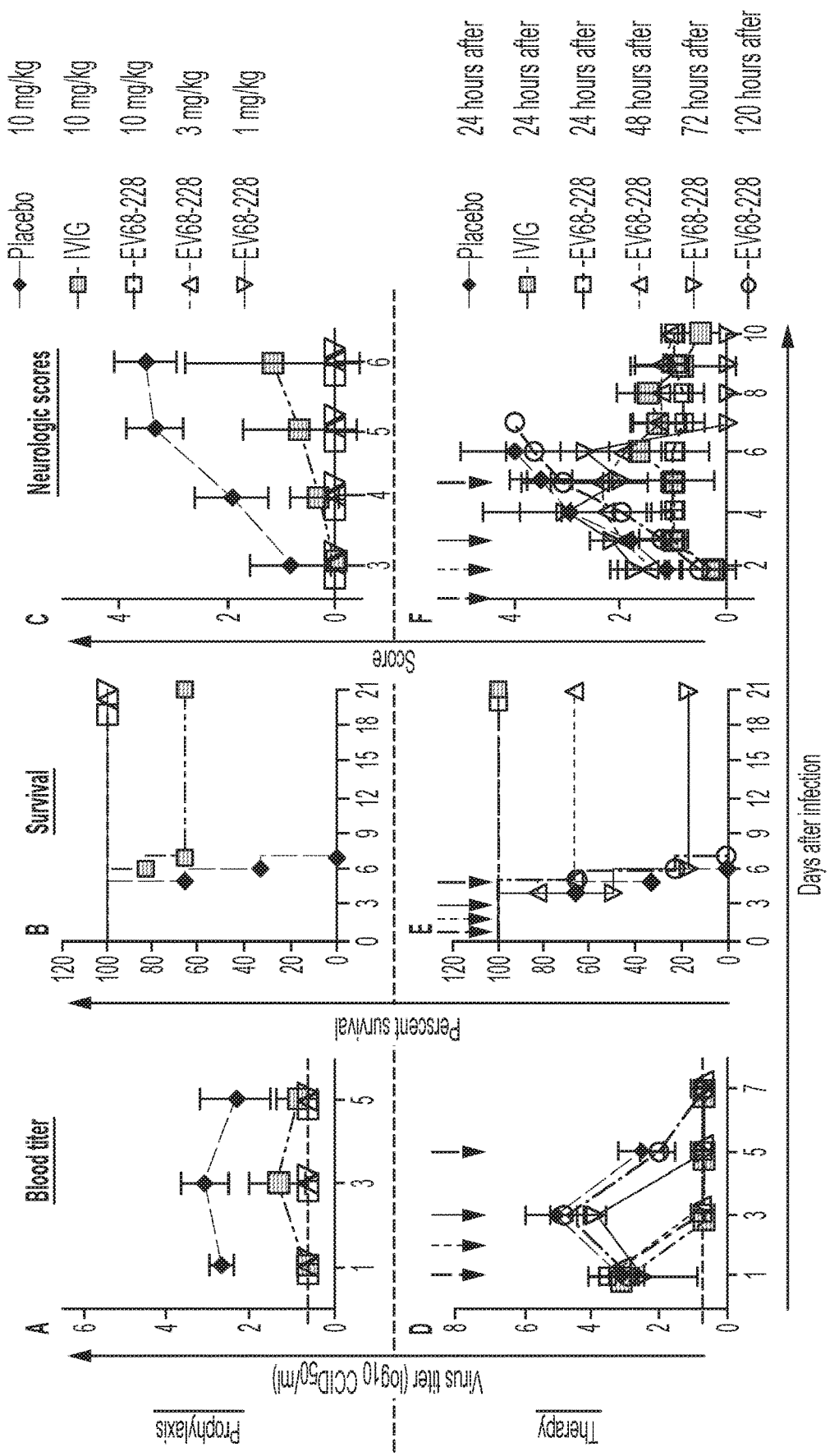
FIGS. 39A-F. MAb EV68-228 protects mice from EV-D68-induced neurologic disease, when used as either prophylaxis or therapy. Ten-day-old mice were inoculated with mouse-adapted B1 clade EV-D68 intraperitoneally; antibody was administered intraperitoneally; and viral titers for indicated tissue were measured by a $CCID_{50}$ assay.

Next the inventors assessed the effect of passive transfer of antibodies in a neurologic model of infection that mimics AFM disease. EV68-228 prophylaxis provided sterilizing immunity of the blood (FIG. 39A) and complete protection from death (FIG. 39B) or development of any neurologic disease (FIG. 39C), whereas IVIG immunity protected only partially. Given therapeutically, EV68-228 treatment sterilized the blood within 24 hours of administration (FIG. 39D) at each of the time points given. EV68-228 improved survival (FIG. 39E) and neurologic disease when given as late as 48 hours after infection; when given at 72 hours post-infection, the mouse that survived improved clinically (FIG. 39F and Table I).

TABLE E

Characteristics of subjects who provided peripheral blood mononuclear cells

| Subject | Age at donation[1] | Gender[2] | Ethnicity[3] | Race[4] | GenBank accession numbers for virus isolate | Virus Clade | Illness date | Donation date | Symptoms[5] | Severity[6] |
|---|---|---|---|---|---|---|---|---|---|---|
| 1 | 18 | F | Unk. | W | KX255352 | B1 | Aug. 11, 2014 | Dec. 27, 2017 | R, H | Mod. |
|   |    |   |      |   | KX255415 | B1 |               |               |      |      |
| 2 | 17 | F | NHL | B & W | Kχ255378 | B1 | Sep. 5, 2014 | Aug. 7, 2017 | NR | NR |
| 3 | 17 | M | NHL | W | KX255367 | B1 | Sep. 11, 2014 | Aug. 1, 2017 | NR | Mild |
| 4 | 17 | M | NHL | W | KX255385 | B1 | Sep. 11, 2014 | Jul. 19, 2017 | C, R, H, SP | Mild |
|   |    |   |      |   | KX433163 |    |               |               |      |      |

TABLE E-continued

Characteristics of subjects who provided peripheral blood mononuclear cells

| Subject | Age at donation[1] | Gender[2] | Ethnicity[3] | Race[4] | GenBank accession numbers for virus isolate | Virus Clade | Illness date | Donation date | Symptoms[5] | Severity[6] |
|---|---|---|---|---|---|---|---|---|---|---|
| 5 | 16 | M | NHL | W | KX255382 | B1 | Aug. 3, 2014 | Jul. 12, 2017 | NR | NR |
| 6 | 17 | F | NHL | W | KX255364 | B1 | Aug. 13, 2014 | Jul. 5, 2017 | C, R | Mod. |
|   |   |   |   |   | KX255373 | B1 |   |   |   |   |
| 7 | 17 | M | NHL | W | KX433162 | A1 | Aug, 7, 2012 | Jun. 21, 2017 | C, R, H, W | Severe |
| 8 | 17 | M | NHL | W | KX255407 | B1 | Sep. 23, 2014 | Jun. 19, 2017 | C, R, H, W | Mild |
| 9 | 17 | M | NHL | W | KX255379 | B1 | Sep. 26, 2014 | Jun. 8, 2017 | C, R | Mild |
| 10 | 18 | F | NHL | W | KX255411 | B1 | Sep. 4, 2014 | Jun. 6, 2017 | C | Mild |
| 11 | 18 | F | NHL | W | KX255390 | B1 | Jul. 18, 2014 | May 30, 2017 | C, H, R, W | Mod. |
|   |   |   |   |   | KX255362 | B1 |   |   |   |   |
|   |   |   |   |   | KX255403 | B1 |   |   |   |   |
| 12 | 18 | M | NHL | W | KX255389 | B1 | Sep. 26, 2014 | Jan. 22, 2018 | C, R, W | Mod. |

[1] Age in years;
[2] F: female, M: male;
[3] Unk.: unknown, NHL: not Hispanic or Latino;
[4] B: black, W: white;
[5] C: cough, H: hoarse, R: rhinitis, SP: sinus pain, W: wheeze, NR: not recorded;
6Mod.: moderate, NR: not recorded.

TABLE F

Sequence characteristics of human mAbs

| Clone | Heavy chain | | | | Light chain | | |
|---|---|---|---|---|---|---|---|
|  | V gene | J gene | D gene | CDR1 | V gene | J gene | CDR3 |
| EV68-37 | V3-30*04 | J4*02 | D6-13*01 | ARPTLPYSNNWYAPEY (SEQ ID NO: 259) | LV3-10*01 | LJ2*01 | SSTDSSGNPVL (SEQ ID NO: 451) |
| EV68-40 | V3-23*04 | J4*02 | D6-6*01 | AKVVRIAAVLYYFDY (SEQ ID NO: 262) | KV3-11*01 | KJ5*01 | QQRSSWPIT (SEQ ID NO: 454) |
| EV68-41 | V3-23*04 | J3*02 | D1-1*01 | ARVKSTTGTTALVFDI (SEQ ID NO: 265) | LV8-61*01 | LJ3*02 | GLYMGSGIWI (SEQ ID NO: 457) |
| EV68-43 | V3-30*03 | J6*02 | D4*17*01 | AKDKHGDFDYYGVDV (SEQ ID NO: 268) | KV1-12*01 | KJ1*01 | QQADSFPRT (SEQ ID NO: 460) |
| EV68-46 | V3-30*03 | J4*02 | D1-26*01 | ARRRPGSFPGLCDY (SEQ ID NO: 271) | KV3-5*03 | KJ2*01 | QQHNSYSYT (SEQ ID NO: 463) |
| EV68-48 | V1-69*06 | J3*01 | D5-12*01 | ARMYSGHDGVDV (SEQ ID NO: 274) | KV3-11*01 | KJ1*01 | QQRSTWPPGM (SEQ ID NO: 466) |
| EV68-71 | V3-39*01 | J3*02 | D4-17*01 | ARHLTHLYGDYVTPDALDI (SEQ ID NO: 277) | KV3-20*01 | KJ1*01 | QQYSNSRLT (SEQ ID NO: 469) |
| EV68-72 | V3-48*02 | J5*02 | D3-3*01 | ARAHGRIVNSGVVISRFDP (SEQ ID NO: 280) | LV2-14*01 | LJ2*01 | SSYTTSNTLVV (SEQ ID NO: 472) |
| EV68-74 | V1-2*02 | J4*02 | D2-2*01 | ARMGCRSDRCYSTNYNFDQ (SEQ ID NO: 283) | LV3-21*02 | LJ2*01 | QVWDSGIDVV (SEQ ID NO: 475) |
| EV68-75 | V3-21*01 | J4*02 | D6-6*01 | ARERGHSTSSSYFDS (SEQ ID NO: 286) | LV3-21*01 | LJ3*01 | RVWDSDTDHRV (SEQ ID NO: 478) |
| EV68-76 | V3-15*01 | J4*02 | D3-22*01 | STGPYYYDTSGYPQPFDY (SEQ ID NO: 289) | LV3-1*01 | LJ2*01 | QAWDSSTVV (SEQ ID NO: 481) |
| EV68-79 | V3-21*01 | J6*02 | D3-9*01 | ARDRPIMEGEGLDELTGYYVYQYYAMDV (SEQ ID NO: 643) | ND | ND | ND |
| EV68-84 | V1-2*02 | J4*02 | D5-24*01 | ARAGRNGYDY (SEQ ID NO: 295) | LV3-25*03 | LJ2*01 | QSGDSSGTYLV (SEQ ID NO: 487) |
| EV68-85 | V3-23*01 | J4*02 | D4-11*01 | TVPWGNYNDYVSDY (SEQ ID NO: 298) | KV3-11*01 | KJ5*01 | HQHSTWPRGT (SEQ ID NO: 490) |

TABLE F-continued

Sequence characteristics of human mAbs

| Clone | Heavy chain | | | | Light chain | | |
|---|---|---|---|---|---|---|---|
| | V gene | J gene | D gene | CDR1 | V gene | J gene | CDR3 |
| EV68-88 | V3-30-3*01 | J4*02 | D6-13*01 | ARHFLPYSSSWYQGFNY (SEQ ID NO: 301) | LV6-57*01 | LJ2*01 | QSYDNSNRAVV (SEQ ID NO: 493) |
| EV68-89 | V3-33*01 | J4*02 | D4-17*01 | ARGVPYGDTLTGLVY (SEQ ID NO: 304) | LV6-57*01 | LJ3*02 | QSYDNSDRV (SEQ ID NO: 496) |
| EV68-95 | V2-26*01 | J4*01 | D2-15*01 | ARLLVAGTFLPSHYFDY (SEQ ID NO: 307) | LV3-21*01 | LJ2*01 | QVWDSSRNHPV (SEQ ID NO: 499) |
| EV68-97 | V3-48*01 | J4*02 | D2-15*01 | IRQVGADFSGRGFDY (SEQ ID NO: 310) | LV3-1*01 | LJ3*02 | QAWDSSTAV (SEQ ID NO: 502) |
| EV68-98 | V3-48*01 | J3*02 | D1-14*01 | ATARHITNDGFDI (SEQ ID NO: 314) | KV1-9*01 | KJ3*01 | QQLNSHPRMFT (SEQ ID NO: 505) |
| EV68-105 | V4-38-2*01 | J4*02 | D2-21*02 | ARGPGHCYGDDDCYAYYFDQ (SEQ ID NO: 316) | KV1-12*01 | KJ3*01 | QQANSFPFT (SEQ ID NO: 508) |
| EV68-110 | V1-69*06 | J4*02 | D2-8*01 | ARSLPYCTNDVCSNQNTFDY (SEQ ID NO: 316) | LV3-25*03 | LJ2*01 | QSADSSGTYVV (SEQ ID NO: 511) |
| EV68-114 | V3-23*01 | J4*02 | D4-17*01 | VRRFPMTTVTSFDS (SEQ ID NO: 325) | LV2-11*01 | LJ2*01 | GAYAGFNAL (SEQ ID NO: 517) |
| EV68-116 | V3-7*03 | J4*01 | D2-2*01 | VREGVRRVVVRSTGYFDF (SEQ ID NO: 328) | LV3-16*01 | LJ3*02 | YSTDSSGYQRA (SEQ ID NO: 520) |
| EV68-150 | V4-31*03 | J5*02 | D2-21*02 | ARHVVTASGWFDP (SEQ ID NO: 331) | KV3-11*01 | KJ2*01 | QQRSRWPPPYT (SEQ ID NO: 523) |
| EV68-152 | V3-30-3*01 | J6*02 | D3-22*01 | ARVTADYYESSGKVF (SEQ ID NO: 337) | KV1-5*03 | KJ1*01 | QQYQTFSWT (SEQ ID NO: 529) |
| EV68-153 | ND | ND | ND | ND | LV1-47*01 | LJ2*01 | AAWDDRLSGVV (SEQ ID NO: 644) |
| EV68-156 | V4-59*01 | J1*01 | D2-8*02 | ARGSMPHI (SEQ ID NO: 346) | LV1-47*01 | LJ1*01 | AAWDDSLKAPV (SEQ ID NO: 538) |
| EV68-158 | V3-23*01 | J3*02 | D3-22*01 | AKDSHSMIVVDHAFDI (SEQ ID NO: 352) | LV3-21*02 | LJ1*01 | QVWDSYNVHYV (SEQ ID NO: 544) |
| EV68-159 | V3-21*01 | J4*02 | D1-14*01 | AREEGFRAYNLY (SEQ ID NO: 355) | LV1-47*01 | LJ2*01 | AAWDDILSGVV (SEQ ID NO: 547) |
| EV68-160 | V3-30*04 | J4*02 | D2-8*01 | ARDWDRLVRSAVGY (SEQ ID NO: 358) | LV2-11*01 | LJ3*02 | CSYAGTYTWV (SEQ ID NO: 550) |
| EV68-161 | V4-61*01 | J6*02 | D3-3*01 | ERRLRILSIERNYYAMDV (SEQ ID NO: 361) | KV3-20*01 | KJ1*01 | QQYGSPWT (SEQ ID NO: 553) |
| EV68-162 | V3-30-3*01 | J6*02 | D2-15*01 | ARDHVPPKDCSDGNCHSDYGMDV (SEQ ID NO: 364) | KV1-5*03 | KJ2*01 | QQHNSYSYT (SEQ ID NO: 556) |
| EV68-164 | V3-48*02 | J6*02 | D3-10*01 | ARVYTMLRGASMDV (SEQ ID NO: 370) | KV3-11*01 | KJ3*01 | QLRITWPPIFT (SEQ ID NO: 562) |
| EV68-165 | V1-2*02 | J4*02 | D2-2*01 | ARVKCSSANCYGNFDY (SEQ ID NO: 373) | LV2-8*01 | LJ2*01 | SSYAGSNNLV (SEQ ID NO: 565) |
| EV68-166 | V5-51*01 | J5*01 | D5-12*01 | ARQTTQNSGYDRWFDS (SEQ ID NO: 376) | LV1-44*01 | LJ3*02 | AAWDDSLNGWV (SEQ ID NO: 568) |
| EV68-178 | ND | ND | ND | ND | KV1-5*03 | KJ1*01 | QQYNSYPLT (SEQ ID NO: 645) |
| EV68-183 | V3-23*01 | J4*02 | D3-3*01 | AISVPLLRFLEWPQHPFDF (SEQ ID NO: 379) | KV3-15*01 | KJ1*01 | HQYINWPPWT (SEQ ID NO: 571) |
| EV63-183 | V3-21*01 | J4*02 | D4-11*01 | VRPTMTTVTNFDS (SEQ ID NO: 382) | LV2-11*01 | LJ3*02 | CSHAGSHTWV (SEQ ID NO: 574) |
| EV68-185 | V3-30*03 | J3*02 | D3-22*01 | PKVIPHPYYDSSGDDAFDI (SEQ ID NO: 385) | KV3-15*03 | KJ5*01 | QQYSKLPIT (SEQ ID NO: 577) |

TABLE F-continued

Sequence characteristics of human mAbs

| | Heavy chain | | | | Light chain | | |
|---|---|---|---|---|---|---|---|
| Clone | V gene | J gene | D gene | CDR1 | V gene | J gene | CDR3 |
| EV68-208 | V1-69*01 | J4*03 | D3-10*01 | ARFISTASYVPGTFEDV (SEQ ID NO: 391) | KV3-11*01 | KJ2*02 | QQRSDWPPGT (SEQ ID NO: 583) |
| EV68-210 | V3-21*01 | J4*02 | D4-17*01 | ARMVRNTVTAFDY (SEQ ID NO: 394) | LV2-23*02 | LJ3*02 | CSYGGNNSWM (SEQ ID NO: 586) |
| EV68-219 | V1-24*01 | J4*02 | D2-21*01 | ATWGVEVVNGRRDYFDS (SEQ ID NO: 397) | LV3-25*03 | LJ2*01 | QSADNTRITV (SEQ ID NO: 589) |
| EV68-220 | V3-48*03 | J3*01 | D3-22*01 | ARDVRDCSALTCPRRGDAFDF (SEQ ID NO: 400) | KV2-30*01 | KJ3*01 | MQGTHWPRT (SEQ ID NO: 592) |
| EV68-221 | V3-21*01 | J4*02 | D2-15*01 | VKVGGSKHQYYFDY (SEQ ID NO: 403) | LV1-44*01 | LJ2*01 | AAWDDSLNGVV (SEQ ID NO: 595) |
| EV68-224 | V1-18*01 | J4*02 | D2-2*02 | ARERCSTSTCYSRYADY (SEQ ID NO: 406) | KV1-39*01 | KJ1*01 | QQSYRSPRT (SEQ ID NO: 598) |
| EV68-225 | V3-48*03 | J3*02 | D3-9*01 | MREGLTYYDSTI (SEQ ID NO: 409) | LV4-69*01 | LJ3*02 | QTWGTGFRV (SEQ ID NO: 601) |
| EV68-227 | V3-9*01 | J3*02 | D3-16*01 | AKDDYEGAGFDI (SEQ ID NO: 412) | KV3-11*01 | KJ5*01 | QQRSNWPIT (SEQ ID NO: 604) |
| EV68-228 | V4-38-2*02 | J4*02 | D2-15*01 | VRHEGSCNDGSCYGSFVDN (SEQ ID NO: 415) | KV1-12*01 | KJ4*01 | QQADSFIT (SEQ ID NO: 607) |
| EV68-229 | ND | ND | ND | ND | KV3-11*01 | KJ4*01 | QQRSNWPPLT (SEQ ID NO: 646) |
| EV68-231 | V3-23*01 | J2*01 | D2-21*02 | ARGGTFHNWYFDL (SEQ ID NO: 418) | KV3-15*01 | KJ1*01 | QQYKNWPRT (SEQ ID NO: 610) |
| EV68-234 | V3-23*01 | J6*03 | D5-12*01 | AKGTITYSYYYMAV (SEQ ID NO: 421) | KV3-20*01 | KJ4*01 | QQYGTSIT (SEQ ID NO: 613) |
| EV68-235 | V1-24*01 | J4-02 | D2-21*01 | ATWGIEVVNGRDEFFDS (SEQ ID NO: 424) | LV3-25*03 | LJ2*01 | QSADTRITV (SEQ ID NO: 616) |
| EV68-236 | V1-24*01 | J4-02 | D2-21*01 | ATWGVAVVSGRRDYFDS (SEQ ID NO: 427) | LV3-25*03 | LJ2*01 | QTADIKYTV (SEQ ID NO: 619) |
| EV68-241 | V4-30-4*01 | J5*02 | D3-3*01 | ARAYAYEFWSGYPNWFDP (SEQ ID NO: 430) | KV1-39*01 | KJ1*01 | QQSYSPPWT (SEQ ID NO: 622) |
| EV68-242 | ND | ND | ND | ND | KV1-5*03 | KJ1*01 | QQYNSLPWT (SEQ ID NO: 647) |
| EV68-247 | V3-30*01 | J4*02 | D2-2*01 | ARGLGYCSGTGGSCTPFEY (SEQ ID NO: 433) | KV1-39*01 | KJ4*01 | QQSDSAPPT (SEQ ID NO: 625) |
| EV68-254 | V4-34*02 | J5*02 | D2-2*01 | VRVPRRGFEGSFGFCDD-TACRYGHTWFDP (SEQ ID NO: 436) | KV1-39*01 | KJ1*01 | QQSYLTPPT (SEQ ID NO: 628) |
| EV68-266 | V3-11*01 | J2*01 | D2-8*02 | AGSKVGYTTGRRNWYFDL (SEQ ID NO: 442) | LV2-8*01 | LJ2*01 | SSYAGNNNLV (SEQ ID NO: 634) |
| EV68-269 | V1-46*01 | J3*02 | D2-2*02 | ARDLVVVVPVEMSRRAFDI (SEQ ID NO: 445) | LV3-21*02 | LJ2*01 | QVWDSTTDHGV (SEQ ID NO: 637) |
| EV68-271 | V1-2*06 | J4*02 | D3-16*02 | ARDYRDDYMWGSYRPLDY (SEQ ID NO: 448) | KV3-11*01 | KJ4*01 | QQRSNGLT (SEQ ID NO: 640) |

Sequence characteristics as identified by the International ImMunoGeneTics (IMGT) Information System, world-wide-web at imgt.org. When IMGT could not rule out multiple genes, the first call is listed.
ND: not determined.

TABLE G

Cryo-EM data acquisition parameters and refinement statistics

| | EV-D68: Fab EV68-159 | EV-D68: Fab EV68-228 |
|---|---|---|
| Cryo-EM data acqusition and processing | | |
| Magnification | 81,000X | 64,000X |
| Camera | K2 Summit direct electron detector (Gatan) | K3 Direct Detection Camera (Gatan) |
| Voltage (kV) | 300 | 300 |
| Pixel size (Å) | 0.874 | 0.662 |
| Defocus range (μm) | 0.7-3.5 | 0.7-2.0 |
| Total electron dose (electrons/Å2) | 31.4 | 44.2 |
| Particles picked | 42,078 | 27,390 |
| Particles used | 30,554 | 20,194 |
| Map resolution (FSC threshold = 0.143) | 2.9 | 3.1 |
| Model building and refinement | | |
| Model building reference (PDB code) | 4WM8 | 4WM8 |
| MolProbity score | 1.93 | 1.96 |
| Clash score | 9.05 | 8.7 |
| Rotamer outliers (%) | 0.46 | 0.00 |
| R.m.s. deviations | | |
| Bond length (Å) | 0.005 | 0.005 |
| Bond angles (°) | 0.691 | 0.689 |
| Ramachandran plot (%) | | |
| Favored | 93.08 | 91.70 |
| Allowed | 6.92 | 8.20 |
| Outliers | 0.00 | 0.10 |

TABLE H

Structural contact amino acid residues of EV-D68 and respective Fabs

| Viral amino acid | Fab amino arid | Potential interactions |
|---|---|---|
| EV68-159 | | |
| VP1: GLU271 | L: ILE95 | Hydrogen bond |
| VP1: ARG272 | L: SER26 | Hydrogen bond |
| | L: SER27 | Hydrogen bond |
| | L: ASP94 | Salt bridge |
| VP1: ASP285 | L: LYS51 | Salt bridge |
| VP3: GLU59 | H: ARG102 | Hydrogen bond |
| VP3: SER60 | H: GLY100 | Hydrogen bond |
| VP3: MET64 | H: TYR56 | Hydrogen bond |
| VP3: GLU65 | H: SER51 | Hydrogen bond |
| | H: THR52 | Hydrogen bond |
| | H: SER53 | Hydrogen bond |
| EV68-228 | | |
| VP1: LYS71 | H: SER30 | Hydrogen bond |
| VP1: ARG72 | H: TYR-27 | Hydrogen bond |
| VP1: SER73 | H: ASN31 | Hydrogen bond |
| VP1: GLY129 | H: SER73 | Hydrogen bond |
| VP1: LYS268 | L: ASP92 | Salt bridge |
| VP2: ASN136 | L: SER30 | Hydrogen bond |
| VP3: GLY234 | H: ASN102 | Hydrogen bond |
| VP3: LEU236 | H: ASN102 | Hydrogen bond |
| VP3: ASP237 | H: TYR34 | Hydrogen bond |
| | H: SER100 | Hydrogen bond |
| | H: CYS101 | Hydrogen bond |
| | H: ASN102 | Hydrogen bond |
| VP3: HIS238 | H: TYR53 | Hydrogen bond |
| | H: TYR54 | Hydrogen bond |
| VP3: GLU243 | H: TYR33 | Hydrogen bond |

Heavy and light chains are labeled as H and L, respectively. Notably, only direct interactions that are clearly observed in the electron density maps at high resolution are listed. This differs from contact residues highlighted in the roadmaps (FIG. 34C and FIG. 46), which use a 4 Å cutoff for displaying the overall footprint at maximum hydrogen bonding distance.

Table I – Neurologic scores of individual mice treated with antibody after EV-68 inoculation

101

| Day | Placebo - 24 hrs post | | | | | |
|-----|---|---|---|---|---|---|
| 2 | 1 | 2 | 1 | 1 | 2 | 0 |
| 3 | 2 | 2 | 2 | 1 | 3 | 1 |
| 4 | 3 | 3 | 4 | 2 | 4 | 2 |
| 5 | 4 | 4 |   | 3 |   | 3 |
| 6 |   |   |   | 4 |   | 4 |
| 7 |   |   |   |   |   |   |
| 8 |   |   |   |   |   |   |
| 9 |   |   |   |   |   |   |
| 10 |  |   |   |   |   |   |

102

| Day | EV-D68-228 - 24 hrs post | | | | | |
|-----|---|---|---|---|---|---|
| 2 | 0 | 1 | 1 | 0 | 0 | 0 |
| 3 | 1 | 1 | 1 | 1 | 1 | 1 |
| 4 | 1 | 1 | 1 | 1 | 1 | 1 |
| 5 | 1 | 1 | 1 | 1 | 1 | 1 |
| 6 | 1 | 1 | 1 | 1 | 1 | 1 |
| 7 | 1 | 1 | 0 | 1 | 1 | 1 |
| 8 | 1 | 1 | 0 | 1 | 1 | 1 |
| 9 | 1 | 1 | 1 | 1 | 1 | 1 |
| 10 | 1 | 1 | 1 | 1 | 1 | 1 |

| Day | EV-D68-228 - 48 hrs post | | | | | |
|-----|---|---|---|---|---|---|
| 2 | 1 | 2 | 1 | 1 | 2 | 2 |
| 3 | 2 | 2 | 2 | 2 | 2 | 2 |
| 4 | 2 | 2 | 2 | 2 | 2 | 4 |
| 5 | 2 | 2 | 2 | 2 | 4 |   |
| 6 | 2 | 2 | 2 | 2 |   |   |
| 7 | 1 | 2 | 1 | 1 |   |   |
| 8 | 1 | 2 | 1 | 1 |   |   |
| 9 | 1 | 2 | 1 | 1 |   |   |
| 10 | 1 | 1 | 1 | 1 |   |   |

| Day | EV-D68-228 - 72 hrs post | | | | | |
|-----|---|---|---|---|---|---|
| 2 | 1 | 2 | 2 | 1 | 2 | 2 |
| 3 | 2 | 3 | 2 | 2 | 2 | 2 |
| 4 | 4 | 0 | 3 | 3 | 4 | 4 |
| 5 |   | 0 | 3 | 3 |   |   |
| 6 |   | 0 | 4 | 4 |   |   |
| 7 |   | 0 |   |   |   |   |
| 8 |   | 0 |   |   |   |   |
| 9 |   | 0 |   |   |   |   |
| 10 |  | 0 |   |   |   |   |

| Day | EV-D68-228 - 120 hrs post | | | | | | | | |
|-----|---|---|---|---|---|---|---|---|---|
| 2 | 1 | 0 | 1 | 0 | 1 | 1 | 1 | 0 | 0 |
| 3 | 1 | 1 | 1 | 2 | 1 | 1 | 1 | 2 | 1 |
| 4 | 1 | 1 | 2 | 3 | 2 | 3 | 2 | 2 | 3 |
| 5 | 2 | 2 | 3 | 3 | 3 | 4 | 3 | 4 | 4 |
| 6 | 3 | 4 | 4 | 3 | 4 |   | 4 |   |   |
| 7 | 4 |   |   | 4 |   |   |   |   |   |
| 8 |   |   |   |   |   |   |   |   |   |
| 9 |   |   |   |   |   |   |   |   |   |
| 10 |  |   |   |   |   |   |   |   |   |

| Day | IVIg - 24 hrs post | | | | |
|-----|---|---|---|---|---|
| 2 | 0 | 1 | 0 | 0 | 1 |
| 3 | 1 | 1 | 1 | 1 | 1 |
| 4 | 1 | 1 | 1 | 1 | 1 |
| 5 | 1 | 1 | 1 | 1 | 1 |
| 6 | 2 | 2 | 1 | 1 | 2 |
| 7 | 1 | 2 | 2 | 1 | 1 |
| 8 | 1 | 2 | 2 | 1 | 2 |
| 9 | 0 | 2 | 2 | 0 | 1 |
| 10 | 0 | 1 | 1 | 0 | 0 |

Each column is the data from an individual mouse within the indicated treatment group corresponding to the graph in FIG. 39F. Day represents the number of days after EV-D68 inoculation the score was determined. Mice were sacrificed or already dead upon a score of 4, so no further scores are listed in days after a 4 was recorded. Underlined scores indicate instances of a mouse improving clinically.

TABLE J

Neutralization escape amino acid mutants

| Position | Amino acid WT[3] | Mutant | Average percent of reads[1] RSV-90 | EV68-159 | EV68-228 | Contact residue[2] EV68-159 | EV68-228 |
|---|---|---|---|---|---|---|---|
| VP2 135 | HIS | TYR | 0 | 13 | 0 |  | Adjacent |
| VP2 139 | ALA | THR | 20 | 2 | 3 |  | Adjacent |
| VP3 42 | SER | ASN | 7 | 15 | 3 |  |  |
| VP1 71 | LYS | MET | 12 | 11 | 33 |  | Contact |
| VP1 126 | ALA | VAL | 1 | 3 | 0 |  |  |
| VP1 157 | LYS | GLU | 6 | 17 | 4 |  |  |
| VP1 270 | ARG | LYS | 1 | 0 | 1 | Adjacent |  |

[1]Each of the mAbs listed was used as selection for three passages of EV-D68 in RD cell culture, with RSV-90 being the same negative control mAb used as placebo treatment for in vivo experiments. For each treatment, the structural genes were sequenced using next generation sequencing in 3 technical replicates with 2000 sequences analyzed per replicate. Numbers listed are the average of these replicates.
[2]Contact residues as determined by cryo-EM structures from this manuscript, which are virus amino acids located within 4 Å of Fab amino acids. Adjacent refers to amino acids that are immediately adjacent to contact residues.
[3]WT: wild-type. Represents the consensus sequence of the RSV-90 selected virus sequences.

TABLE K

EV-68 isolates used

| Strain name | Abbreviation | Clade | Source | Source ID | GenBank Accession | Pubmed ID |
|---|---|---|---|---|---|---|
| US/MO/14-18947 | MO/47 | B1 | BEI | NR-49129 | KM851225 | 25414503 |
| US/MO/14-18949 | MO/49 | B1 | BEI | NR-49130 | KM851227 | 25414503 |
| US/IL/14-18956 | IL/56 | B1 | BEI | NR-49133 | MK268345 | 25414503 |
| US/IL/14-18952 | IL/52 | B2 | BEI | NR-49131 | KM851230 | 25414503 |
| US/KY/14-18953 | KY/53 | D | BEI | NR-49132 | KM851231 | 25414503 |
| Fermon | Fer. | 1962 reference strain | ATCC | VR-1826 | AY426531 | 15302951 |
| Mouse adapted US/MO/14-18949 |  | B1 | Hurst and Tarbet, USU | NA | MH708882 | 30521834 |

ATCC: American Type Culture Collection; BEI: Biodefense and Emerging Infections Research Resources Repository, NIAID, NIH; USU: Utah State University; NA: not applicable.

Example 11—Discussion

Figure 40:
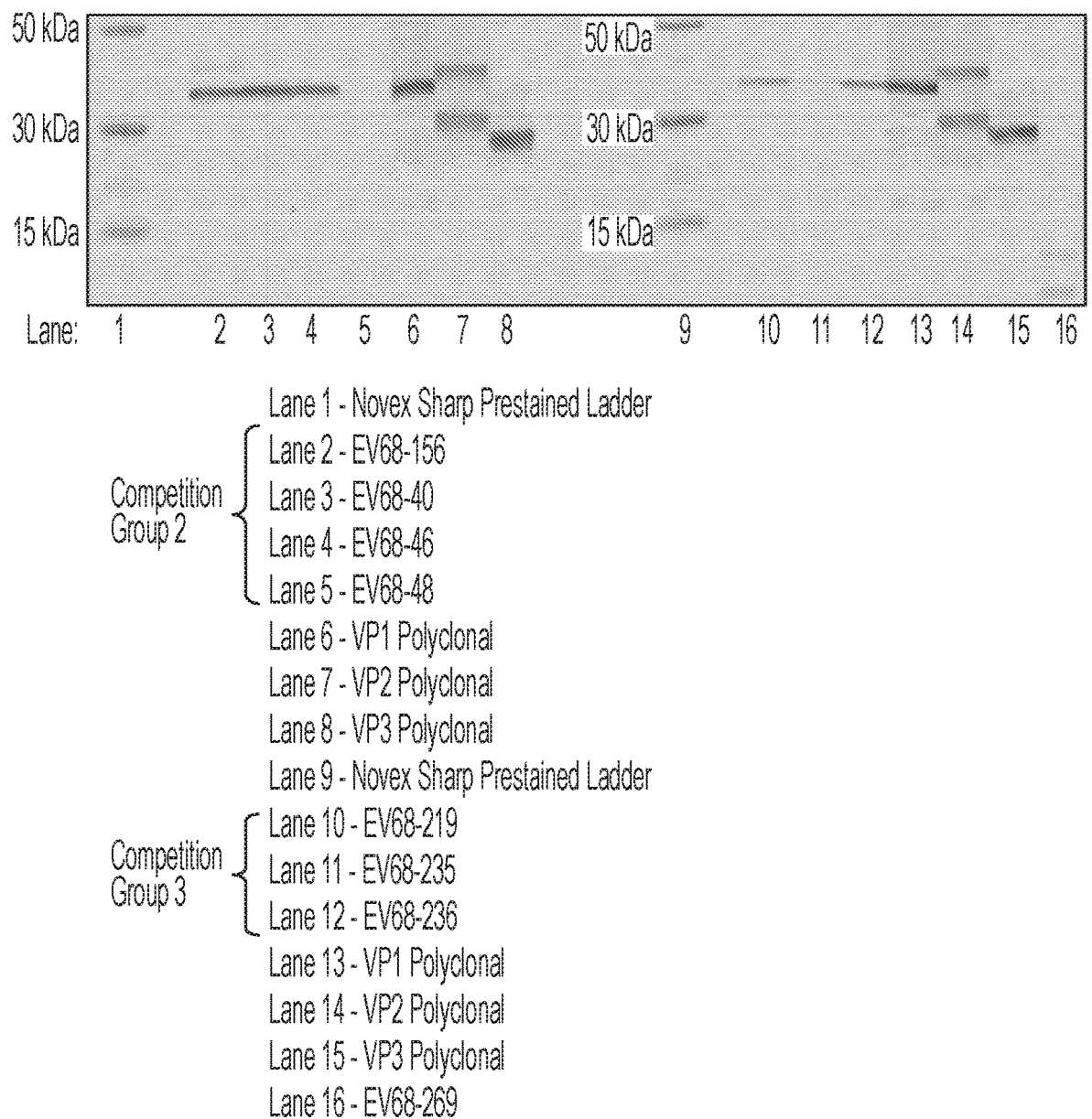
FIG. 40. Western blot data. All mAbs were tested for the ability to stain B1 clade virus by western blot. All positive results are shown.

These studies reveal diverse features of the human B cell response to EV-D68 infection. The inventors attempted to be unbiased in their approach to isolating these mAbs, using live virus isolates as the screening antigen. The diversity in antibody phenotypes that they recovered may be a result of this strategy, as the inventors observed a broad range of cross-reactivity among clades of EV-D68, both with binding and neutralization. Interestingly, strong binding to live virus particles did not necessarily predict high neutralizing potency. Of the competition-binding groups observed, only groups 2 and 3 exhibited uniformity in phenotype. MAbs in both groups were cross-reactive, but group 2 mAbs neutralized virus whereas group 3 mAbs did not. Nearly all of the group 2 and 3 mAbs bound to VP1 in western blot (FIGS. 40 and 41), suggesting that they bind to linear epitopes. Notably, the competition-binding studies used full-length IgG molecules, so the competition seen is functional as would occur in human tissues and does not necessarily indicate that there are only four structurally distinct epitopes on the viral surface.

The lack of western blot reactivity of EV68-159 and EV68-228 correlates with the findings in the structural studies that show both epitopes span all three major viral surface proteins. The conformation-dependent nature of the epitopes of these two potently neutralizing mAbs is notable because recent diagnostic advances using peptide microarray (Mishra et al., 2019) and phage library (Schubert et al., 2019) technologies scanned for antibodies in the cerebrospinal fluid of patients with AFM that recognize linear epitopes. Detection of antibodies recognizing linear epitopes currently can be used in valuable diagnostic tools; however, these studies reveal these tests are at best only partially informative about the quality of antibody response these patients make in response to enterovirus infection. The structures also suggest the molecular basis for antibody-mediated neutralization. By contacting all three structural proteins within a protomer, both mAbs appear capable of inhibiting dynamic structural transitions necessary for infection, which are poorly understood.

The disulfide bond in the CDR3 of EV68-228 heavy chain is a structural moiety the inventors have now observed in broadly neutralizing antiviral human mAbs for a number of viruses, including both hepatitis C (Flyak et al., 2018) and influenza A virus (Bangaru et al., 2019). The intervening four to five amino acids between cysteines forms a smaller structured loop at the most distal tip of the full CDR3 loop, stabilizing the CDR3 in a preconfigured state optimal for binding the viral antigen. For EV68-228 specifically, the Cys101 also directly interacts with VP3 via a hydrogen bond, so the cysteine participates in both CDR3 loop stabilization and interaction with target.

The three VP1 residues that interact with EV68-159 light chain (Glu271, Arg272 and Asp285) and Glu59 on the N-terminal loop of VP3, which interacts with EV68-159 heavy chain, are adjacent to the sialic acid receptor binding site (Liu et al., 2015), suggesting that the EV68-159 Fab may block virus from binding sialic acid receptors. In particular, these three VP1 residues are located on a 22-amino acid VP1 C-terminal peptide that is bound by antibodies found in the cerebrospinal fluid of patients with AFM (Mishra et al., 2019; Schubert et al., 2019). Furthermore, the interaction of the EV68-159 Fab heavy chain with the VP3 N-terminal loop may prevent the virus from uncoating, since the N-termini of the four VPs contribute to capsid stability (Filman et al., 1989). EV68-228 may prevent the virus from uncoating by binding VP1βB, inhibiting the externalization of the N-terminus of VP1 that is required for entry. In addition, the antibody footprint includes residues on the C-terminus of VP3, which is not part of a classical NIm. These residues are adjacent to the canyon receptor binding site, suggesting that mAb EV68-228 also may block virus binding to receptors.

Finally, at a time when poliovirus types 2 and 3 have been eradicated, AFM is on the rise, and the role of EV-D68 in causing epidemics of this paralytic disease is increasingly evident. Given how well prophylaxis with human mAb EV68-228 works in vivo, these data suggest that an effective EV-D68 vaccine might prevent AFM disease. Indeed, recent studies indicate that virus-like particle (Zhang et al., 2018a; Dai et al., 2018) and inactivated EV-D68 (Patel et al., 2016) vaccine candidates are immunogenic and protective against infection in mice. However, a study of cotton rats vaccinated with inactivated EV-D68 suggested that they may have suffered worse respiratory disease upon subsequent EV-D68 infection (Messacar et al., 2016). While this finding could suggest the possibility of antibody-dependent enhancement (ADE) of EV-D68 infection, in mice the inventors did not observe ADE caused by polyclonal or monoclonal antibodies, within the range of antibody concentrations they tested. Also, the prospect of using mAb EV68-228 as a therapy early during EV-D68 infection is appealing, especially since this antibody potently neutralizes a diverse set of viral isolates without obvious autoreactive binding to human cell materials (FIG. 33C). Even though IVIG protected mice from AFM-like disease due to EV-D68 in prior in vivo studies (Hixon et al., 2017a), so far IVIG has not been shown to confer benefit for humans with AFM (Messacar et al., 2016). However, IVIG is a complex mixture of polyclonal antibodies with only a small fraction that recognize EV-D68. MAb prophylaxis or therapy for EV-D68 associated AFM is more promising than IVIG because of the high specificity, high potency, and lower antibody dose that can be used. It is possible, however, that a cocktail of mAbs directed at multiple epitopes may be more protective than mAb monotherapy. A mAb cocktail theoretically would provide a higher barrier to emergence of mAb resistant virus, but the inventors did not observe resistance in vivo (FIGS. 37A-D and FIGS. 39A-F). Even under conditions optimized for selecting EV68-228 resistant viruses in vitro, the inventors could only identify virus genomes with mutations of unclear significance (Table J). In the absence of a reverse genetics system for making recombinant viruses with these mutations, they were unable to verify specifically if these mutations caused escape from neutralization. Therefore, they find emergence of resistance during potential therapeutic use unlikely. These experiments also provide hope for therapeutic efficacy in patients with severe respiratory disease due to EV-D68, which is the clinical syndrome that brought the 2014 EV-D68 outbreak to the attention of public health authorities prior to recognition of the association with AFM (Midgley et al., 2014). Overall, the studies presented here show that natural EV-D68 infection of humans induces B cells encoding broad and potently neutralizing antibodies that can prevent or treat infection and disease in both the respiratory tract and the nervous system.

Example 12

The objective of this study was to determine the efficacy of treatment with tobacco-produced EV68-228 for an Enterovirus D68 (EV-D68) respiratory infection in four-week-old AG129 mice.

Materials and Methods

Animals. Four-week-old male and female AG129 mice from a specific-pathogen-free colony maintained at the Utah Science Technology and Research (USTAR) building at Utah State University. The mice were bred and maintained on irradiated Teklad Rodent Diet (Harlan Teklad) and autoclaved tap water.

Antibodies and Compound. The monoclonal antibody (mAb) EV68-228 produced in tobacco plants (EV68-228-TP) as well as Chinese hamster ovary (CHO) cells (EV68-228-CHO) was provided by the inventors. Both the tobacco-produced and CHO antibodies were provided as solutions and were dosed at a concentration of 10 mg/kg. A tobacco-produced anti-HIV (Anti-HIV-TP) antibody was used as a negative control antibody at a dose of 10 mg/kg. Intravenous immunoglobulin (HIVIg, Carimune, CSL Behring, King of Prussia, PA) was purchased from a local pharmacy and was used as a positive control.

Virus. Enterovirus D68 was obtained from BEI Resources, NIAID, NIH: Enterovirus D68, US/MO/14-18949, NR-49130. The virus was serially passaged 30 times in the lungs of 4-week-old AG129 mice and then plaque-purified three times in Rhabdomyosarcoma (RD) cells obtained from the American Type Culture Collection (Manassas, VA). The resulting virus stock was amplified twice in RD cells to create a working stock. The virus used for infection was designated EV-D68 MP30 PP.

Experiment design. A total of 118 mice were randomized into 4 groups of 12 mice, 8 groups of 8, and an additional group of 6 mice used for normal controls as shown in Table 1. Mice were treated via intraperitoneal (IP) administration of EV68-228 mAb, HIVIg, or placebo mAb at 24 hours pre-infection or, 24- or 48-hours post-infection. Mice were infected via intranasal (IN) instillation of $1\times10^{45}$ $CCID_{50}$ of EV-D68 MP30 PP in a 90 µl volume of MEM. Mice were weighed prior to treatment and daily thereafter. Four mice from each treatment group were euthanized on days 1, 3 and 5 post-infection for evaluation of lung virus titers, blood virus titers, and lung cytokine concentrations. For the mice treated 24- and 48-hours post-infection, samples were only collected on days 3 and 5 post-infection.

Lung Cytokine/Chemokine Evaluations. Each sample of lung homogenate was tested for cytokines and chemokines using a chemiluminescent ELISA-based assay according to the manufacturer's instructions (Quansys Biosciences Q-Plex™ Array, Logan, UT). The Quansys multiplex ELISA is a quantitative test in which 16 distinct capture antibodies have been applied to each well of a 96-well plate in a defined array. Each sample supernatant was tested for the following: IL-1α, IL-1β, IL-2, IL-3, IL-4, IL-5, IL-6, IL-10, IL-12p70, IL-17, MCP-1, IFN-γ, TNFα, MIP-1α, GM-CSF, and RANTES. Definition of abbreviations are: IL-interleukin; MCP—monocyte chemoattractant protein; IFN—interferon; TNF—tumor necrosis factor, MIP—macrophage inflammatory protein; GM-CSF—granulocyte/macrophage colony stimulating factor; and RANTES—regulated upon activation, normal T cell expressed and secreted.

Statistical analysis. All figures and statistical analyses were completed using Prism 8.4.2. (GraphPad Software Inc.). For each day post-infection, lung and blood virus titers from treated groups were compared to lung and blood titers from placebo-treated mice using a one-way analysis of variance (ANOVA). For each cytokine/chemokine, the concentrations from treated mice were compared to placebo-treated mice using a two-way ANOVA.

Ethics regulation of laboratory animals. This study was conducted in accordance with the approval of the Institutional Animal Care and Use Committee of Utah State University dated Mar. 2, 2019 (expires Mar. 1, 2022). The work performed done in the AAALAC-accredited Laboratory Animal Research Center of Utah State University. The U.S. Government (National Institutes of Health) approval was renewed Mar. 9, 2018 (PHS Assurance No. D16-00468 [A3801-01]) in accordance to the National Institutes of Health Guide for the Care and Use of Laboratory Animals (Revision; 2011).

Results and Discussion

This study determined the efficacy of a tobacco-produced EV68-228 mAb for treatment of an EV-D68 respiratory infection in four-week-old AG129 mice.

Figure 48:
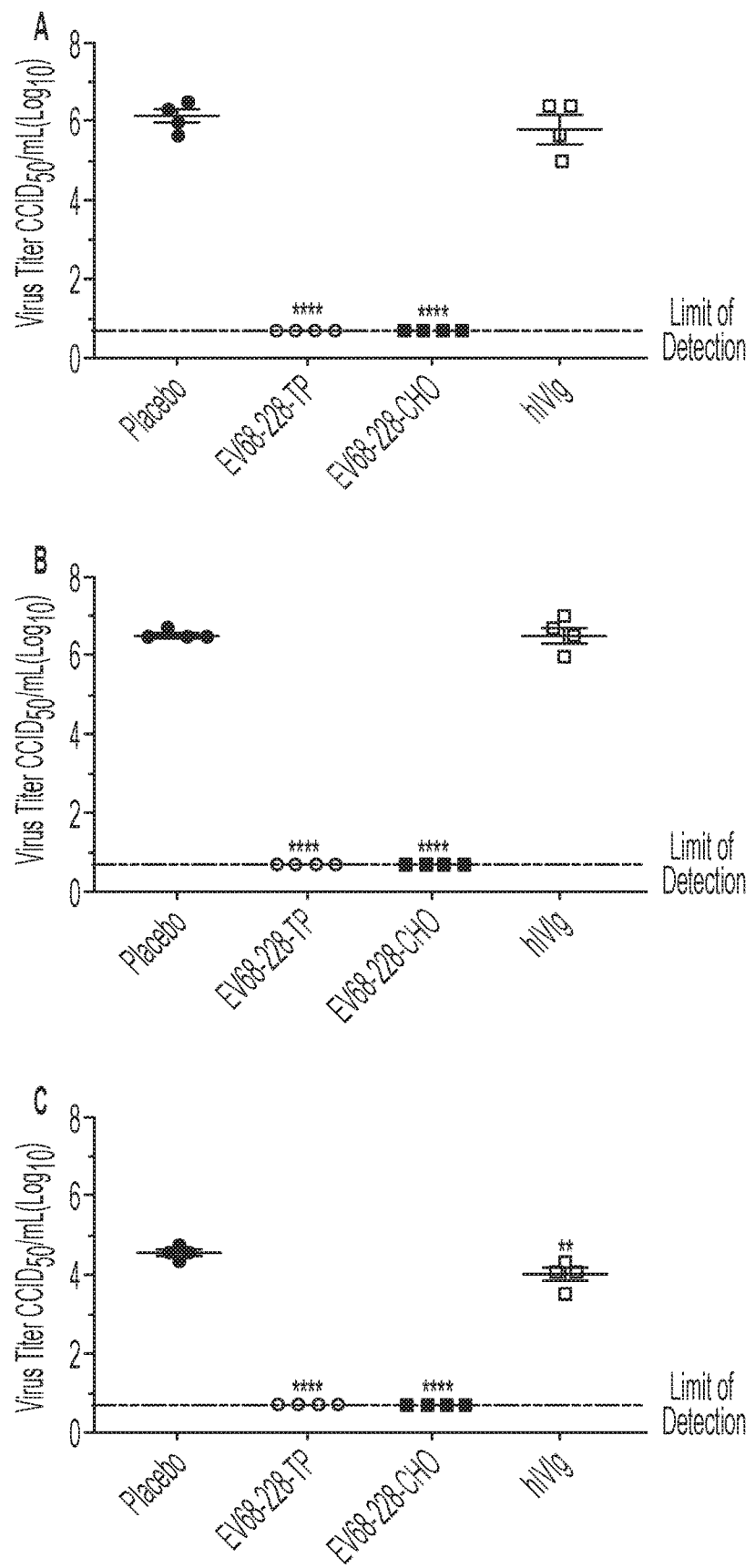
FIGS. 48A-C. Expt. NIA-1930. Lung virus titers of EV-D68-infected AG129 mice treated 24 hours pre-infection with EV68-228-TP or EV68-228-CHO. Lung virus titers are shown on day 1 (FIG. 48A), day 3 (FIG. 48B), and day 5

FIGS. 48A-C show lung virus titers for EV-D68-infected AG129 mice treated 24 hours pre-infection with EV68-228-TP or EV68-228-CHO. No lung virus titers were detected at days 1, 3, or 5 post-infection in mice treated with doses of 10 mg/kg of EV68-228-TP or EV68-228-CHO. Treatment with a dose of 10 mg/kg of HIVIg only significantly reduced lung virus titers on day 5 post-infection.

Figure 49:
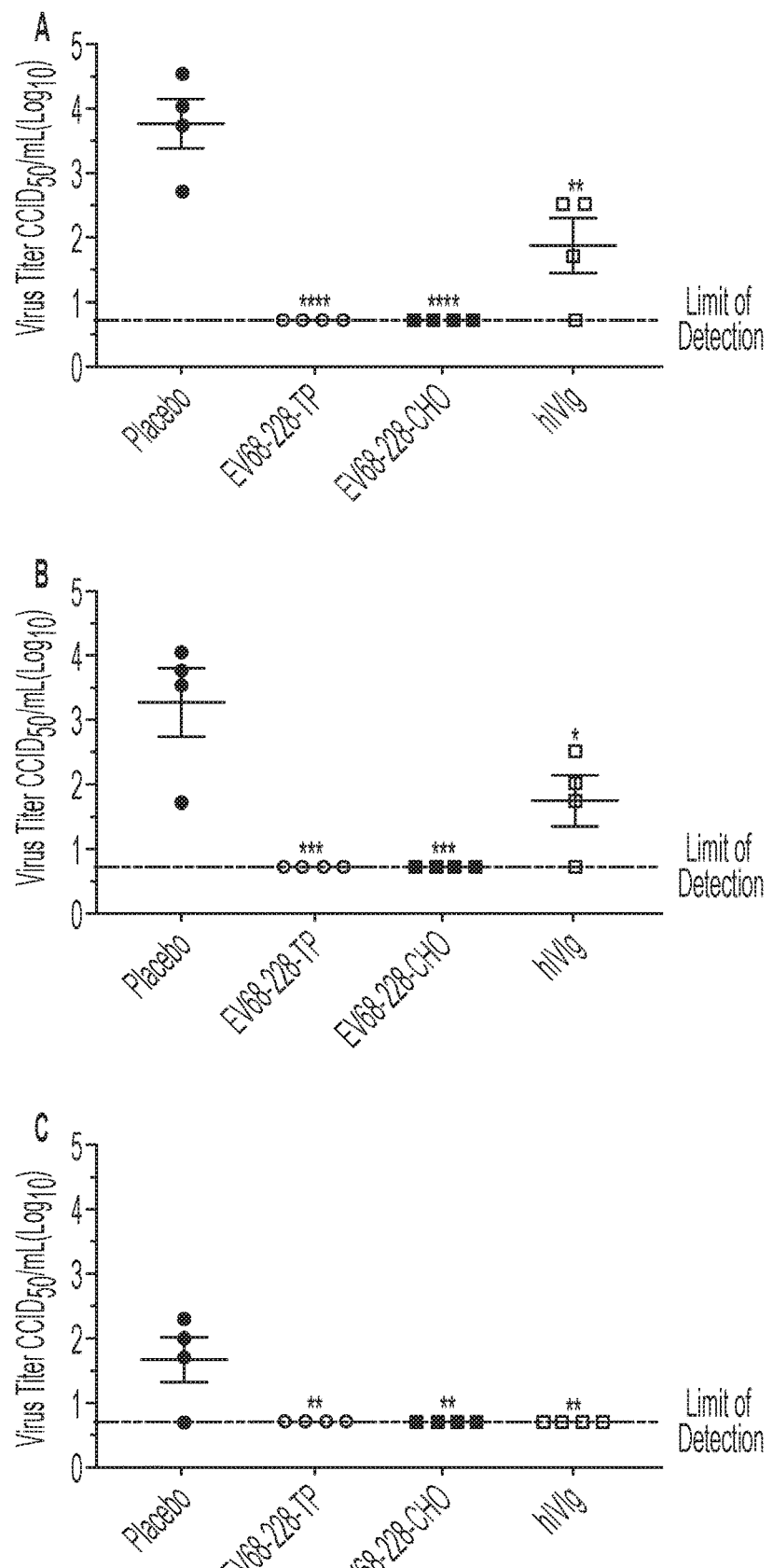
FIGS. 49A-C. Expt. NIA-1930. Blood virus titers of EV-D68-infected AG129 mice treated 24 hours pre-infection with EV68-228-TP or EV68-228-CHO. Blood virus titers are shown at day 1 (FIG. 49A), day 3 (FIG. 49B), and day 5 (FIG. 49C) post-infection. No virus was detected in the blood of mice treated with 10 mg/kg of EV68-228-TP or EV68-228-CHO on days 1, 3, or 5 post-infection. Treatment with 10 mg/kg of hIVIg significantly reduced blood virus titers at days 1,3, and 5 post-infection. (*P<0.05, P<0.01, *P<0.001, ****P<0.0001 compared to placebo-treated mice.)

FIGS. 49A-C show blood virus titers for EV-D68-infected AG129 mice treated 24 hours pre-infection with EV68-228-TP or EV68-228-CHO. No blood virus titers were detected at days 1, 3, or 5 post-infection in mice treated with doses of 10 mg/kg of EV68-228-TP or EV68-228-CHO. Treatment with hIVIg at a dose of 10 mg/kg also reduced blood virus titers at days 1, 3, and 5 post-infection.

Figure 50:
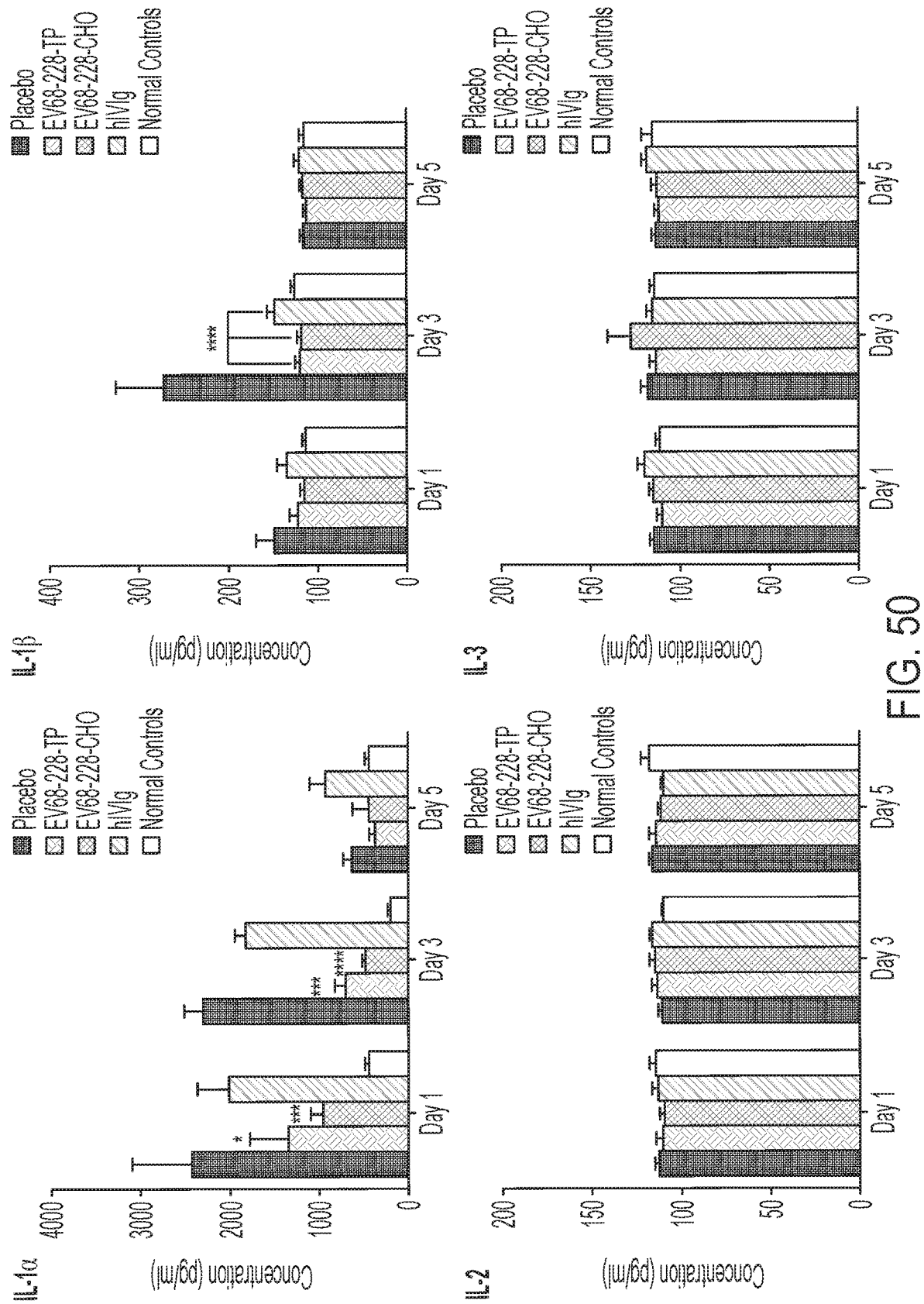
FIG. 50. Expt. NIA-1930. Lung concentrations of IL-1α, IL-1β, IL-2, and IL-3 from EV-D68-infected AG129 mice treated 24 hours pre-infection with EV68-228-TP or EV68-228-CHO. Treatment with 10 mg/kg of EV68-228-TP or EV68-228-CHO significantly reduced concentrations of IL-1α on days 1, 3, and 5 post-infection. Treatment with 10 mg/kg of EV68-228-TP or EV68-228-CHO also reduced concentrations of IL-1β on day 3 post-infection. Treatment with hIVIg only significantly reduced lung concentrations of IL-1β on day 3 post-infection. No significant changes were observed in concentrations of IL-2 or IL-3 following infection. (*P<0.05, *P<0.001, **P<0.0001 compared to placebo-treated mice). Designation of samples in graph corresponds left-to-right with vertical legend top-to-bottom.

FIG. 50 shows lung concentrations of IL-1α, IL-1β, IL-2, and IL-3 from EV-D68-infected AG129 mice treated 24 hours pre-infection with EV68-228-TP or EV68-228-CHO. Significant reductions in lung concentration of IL-1α were observed on days 1 and 3 post-infection in mice treated with EV68-228-TP as well as mice treated with EV68-228-CHO. Both the tobacco-produced and the CHO-produced treatments reduced concentrations of IL-1β at day 3 post-infection. Treatment with hIVIg did not significantly affect lung cytokine concentrations of IL-1α or IL-1β. No significant changes in lung concentrations of IL-2 or IL-3 were observed post-infection with EV-D68.

Figure 51:
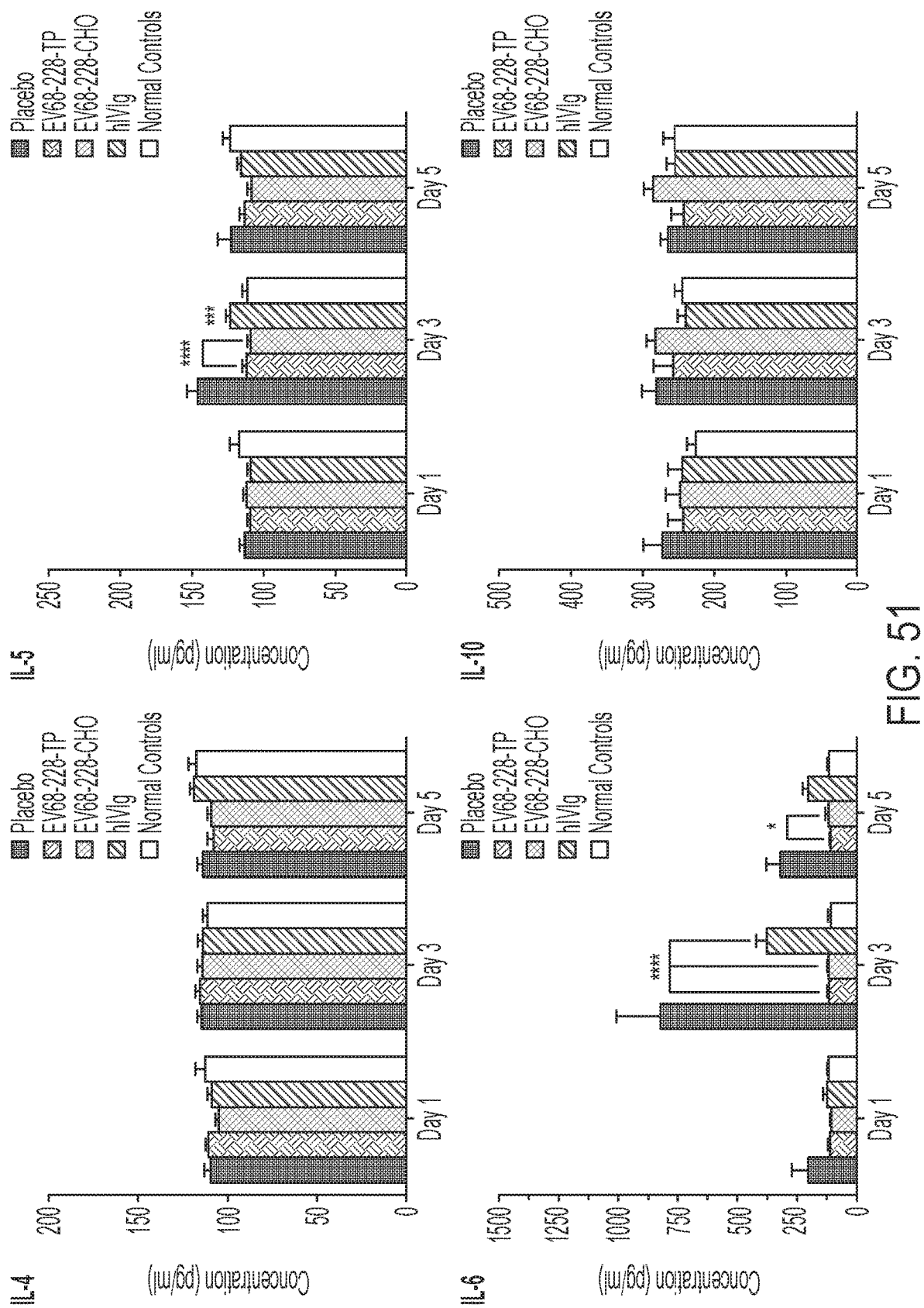
FIG. 51. Expt. NIA-1930. Lung concentrations of IL-4, IL-5, IL-6, and IL-10 from EV-D68-infected AG129 mice treated 24 hours pre-infection with EV68-228-TP or EV68-228-CHO. Treatment with 10 mg/kg of EV68-228-TP or EV68-228-CHO significantly reduced concentrations of IL-5 on day 3 post-infection and IL-6 on days 3 and 5 post-infection. Treatment with 10 mg/kg of hIVIg significantly reduced lung concentrations of IL-5 and IL-6 on day 3 post-infection. No significant changes were observed in concentrations of IL-4 or IL-10 following infection. (*P<0.05, *P<0.001, **P<0.0001 compared to placebo-treated mice). Designation of samples in graph corresponds left-to-right with vertical legend top-to-bottom.

Lung concentrations of Il-4, IL-5, IL-6, and IL-10 from EV-D68-infected AG129 mice treated 24 hours pre-infection with EV68-228-TP or EV68-228-CHO are shown in FIG. 51. Treatment with 10 mg/kg of EV68-228-TP or EV68-228-CHO significantly reduced concentrations of IL-5 on day 3 post-infection and reduced concentrations of IL-6 on days 3 and 5 post-infection. Treatment with hIVIg significantly reduced lung concentrations of IL-5 and IL-6 on day

TABLE L

Expt. NIA-1930/Experimental Design: Efficacy of EV68-228-TP for treatment of an EV-D68 respiratory infection in mice

| No./Cage | Group No. | Infected | Treatment | Dose | Treatment Schedule | Route | Observations |
|---|---|---|---|---|---|---|---|
| 12 | 1 | Yes | Anti-HIV-TP* | 10 mg/kg | Once, 24 hours pre-infection | IP | 4 mice/group sacrificed at days 1, 3, and 5 post-infection for: lung virus titers, and lung cytokines. |
| 12 | 2 | Yes | EV68-228-TP | | | | |
| 12 | 3 | Yes | EV68-228-CHO | | | | |
| 12 | 4 | Yes | hIVIg | | | | |
| 8 | 5 | Yes | Anti-HIV-TP* | 10 mg/kg | Once, 24 hours post-infection | IP | 4 mice/group sacrificed at days 3 and 5 post-infection for: lung virus titers, and lung cytokines. |
| 8 | 6 | Yes | EV68-228-TP | | | | |
| 8 | 7 | Yes | EV68-228-CHO | | | | |
| 8 | 8 | Yes | hIVIg | | | | |
| 8 | 9 | Yes | Anti-HIV-TP* | 10 mg/kg | Once, 48 hours post-infection | IP | |
| 8 | 10 | Yes | EV68-228-TP | | | | |
| 8 | 11 | Yes | EV68-228-CHO | | | | |
| 8 | 12 | Yes | hIVIg | | | | |
| 6 | 13 | No | Normal Controls | — | — | — | 2 mice/group sacrificed at days 1, 3, and 5 for normal cytokine controls |

3 post-infection. No significant changes in lung concentrations of IL-4 or IL-10 were observed after infection with EV-D68.

Figure 52:
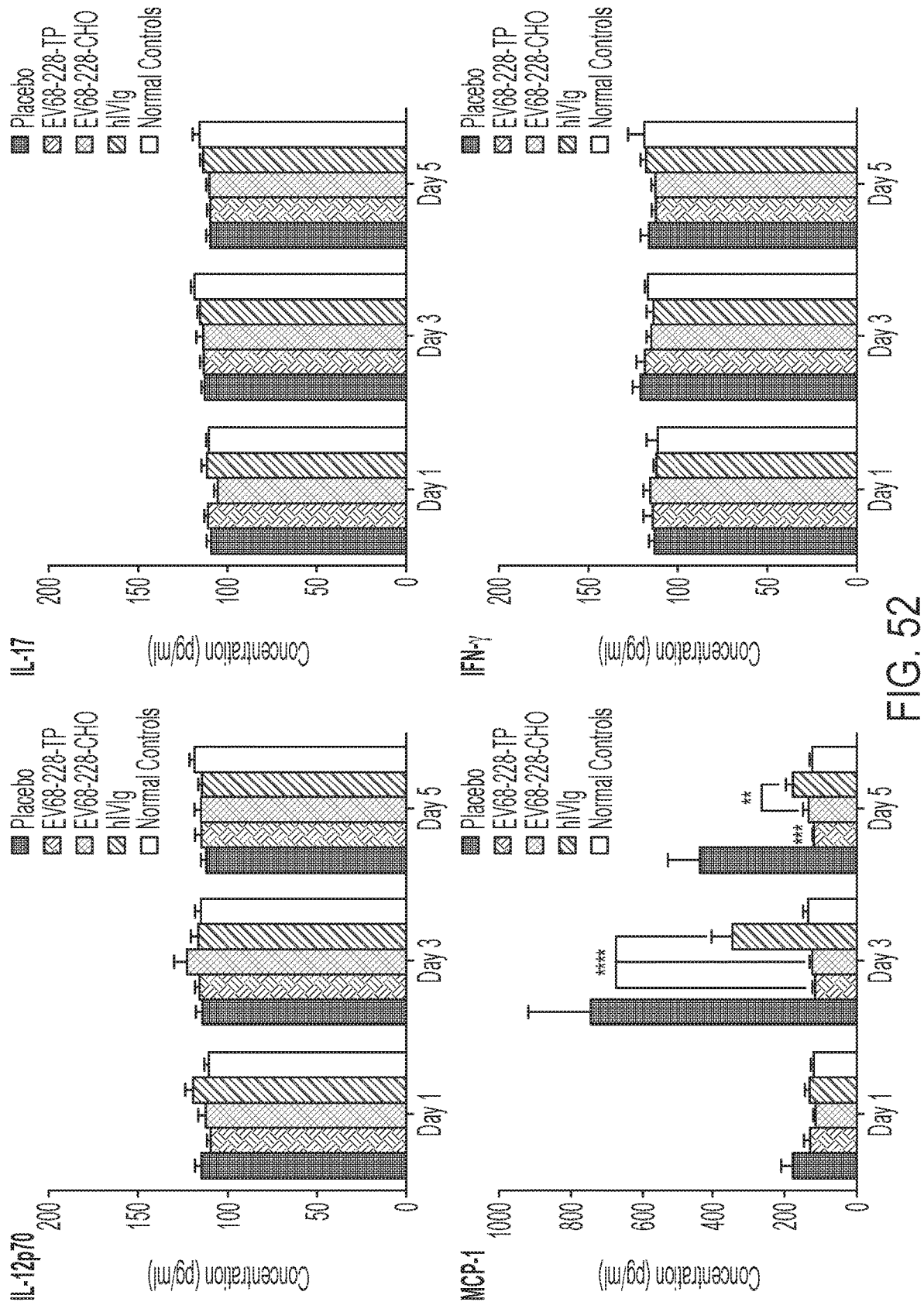
FIG. 52. Expt. NIA-1930. Lung concentrations of IL-12p70, IL-17, MCP-1, and IFN-γ from EV-D68-infected AG129 mice treated 24 hours pre-infection with EV68-228-TP or EV68-228-CHO. Treatment with 10 mg/kg of EV68-228-TP or EV68-228-CHO significantly reduced concentrations of MCP-1 on days 3 and 5 post-infection. Treatment with 10 mg/kg of hIVIg significantly reduced lung concentrations of MCP-1 at day 3 and 5 post-infection. No significant changes were observed in concentrations of IL-12p70, IL-17, or IFN-γ following infection. (P<0.01, *P<0.001, ****P<0.0001 compared to placebo-treated mice). Designation of samples in graph corresponds left-to-right with vertical legend top-to-bottom.

FIG. 52 shows lung concentrations of IL-12p70, IL-17, MCP-1, and IFNγ from EV-D68-infected AG129 mice treated 24 hours pre-infection with EV68-228-TP or EV68-228-CHO. Treatment with 10 mg/kg of EV68-228-TP or EV68-228-CHO significantly reduced lung concentrations of MCP-1 days 3 and 5 post-infection. Treatment with hIVIg significantly reduced lung concentrations of MCP-1 on days 3 and 5 post-infection. No significant changes in concentrations of IL-12p70, IL-17, or IFNγ were observed after infection with EV-D68.

Figure 53:
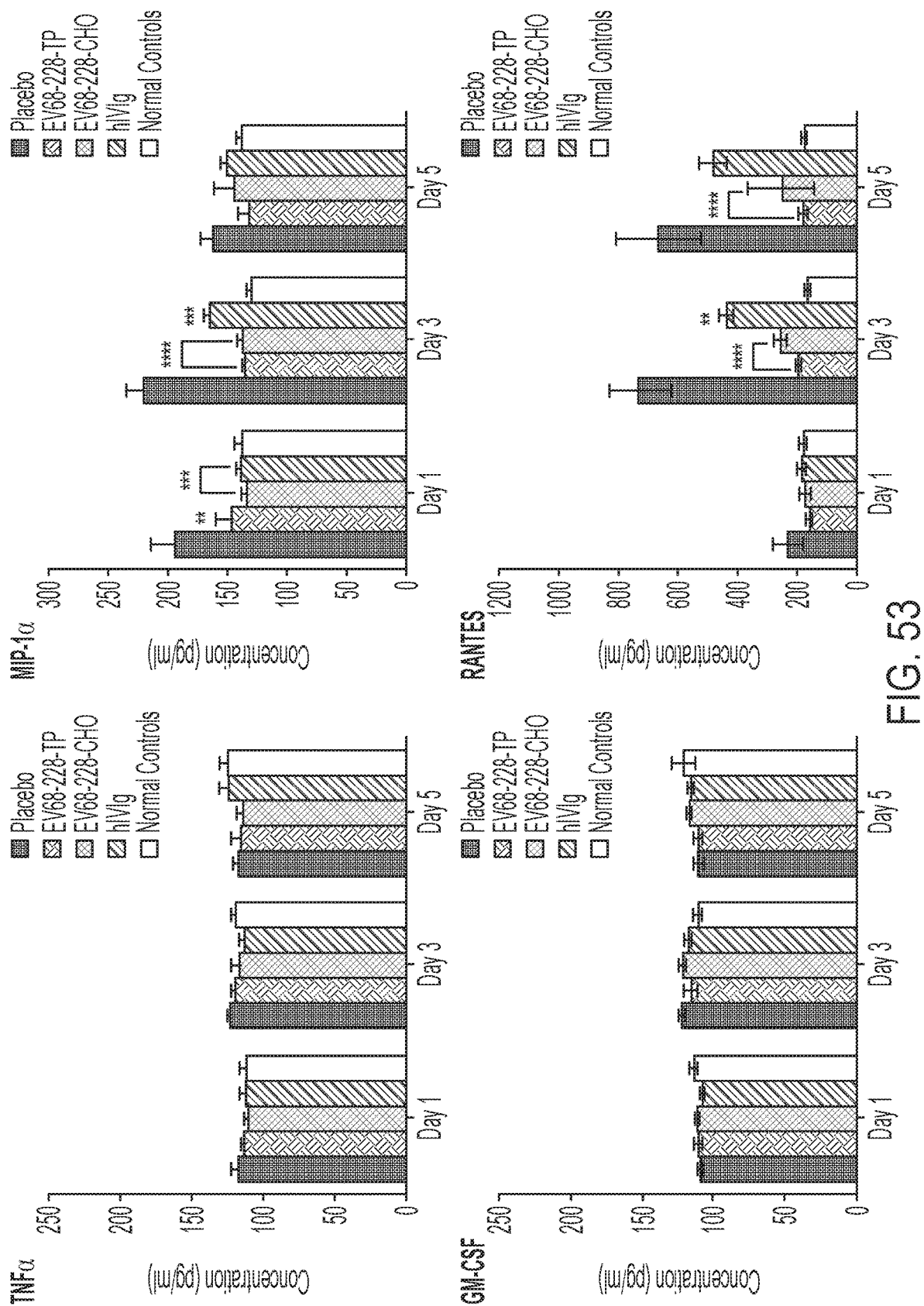
FIG. 53. Expt. NIA-1930. Lung concentrations of TNFα, MIP-1α, GM-CSF, and RANTES from EV-D68-infected AG129 mice treated 24 hours pre-infection with EV68-228-TP or EV68-228-CHO. Treatment with 10 mg/kg of EV68-228-TP or EV68-228-CHO significantly reduced lung concentrations of MIP-1α on days 1 and 3 post-infection and reduced concentrations of RANTES on days 3 and 5 post-infection. A 10 mg/kg dose of hIVIG significantly reduced concentrations of MIP-1α on days 1 and 3 post-infection and also reduced concentrations of RANTES on day 3 post-infection. No significant changes in concentrations of TNFα or GM-CSF were observed after infection with EV-D68. (P<0.01, *P<0.001, P<0.0001 compared to placebo-treated mice). Designation of samples in graph corresponds left-to-right with vertical legend top-to-bottom.

FIG. 53 shows lung concentrations of TNFα, MIP-1α, GM-CSF, and RANTES from EV-D68-infected AG129 mice treated 24 hours pre-infection with EV68-228-TP or EV68-228-CHO. Treatment with 10 mg/kg of EV68-228-TP or EV68-228-CHO reduced lung virus concentrations of MIP-1α on days 1 and 3 post-infection and reduced concentrations of RANTES on days 3 and 5 post-infection. A 10 mg/kg dose of hIVIg reduced lung concentrations of MIP-1α on days 1 and 3 post-infection and reduced concentrations of RANTES on day 3 post-infection. No significant changes in concentrations of TNFα or GM-CSF were observed after infection with EV-D68.

Figure 54:
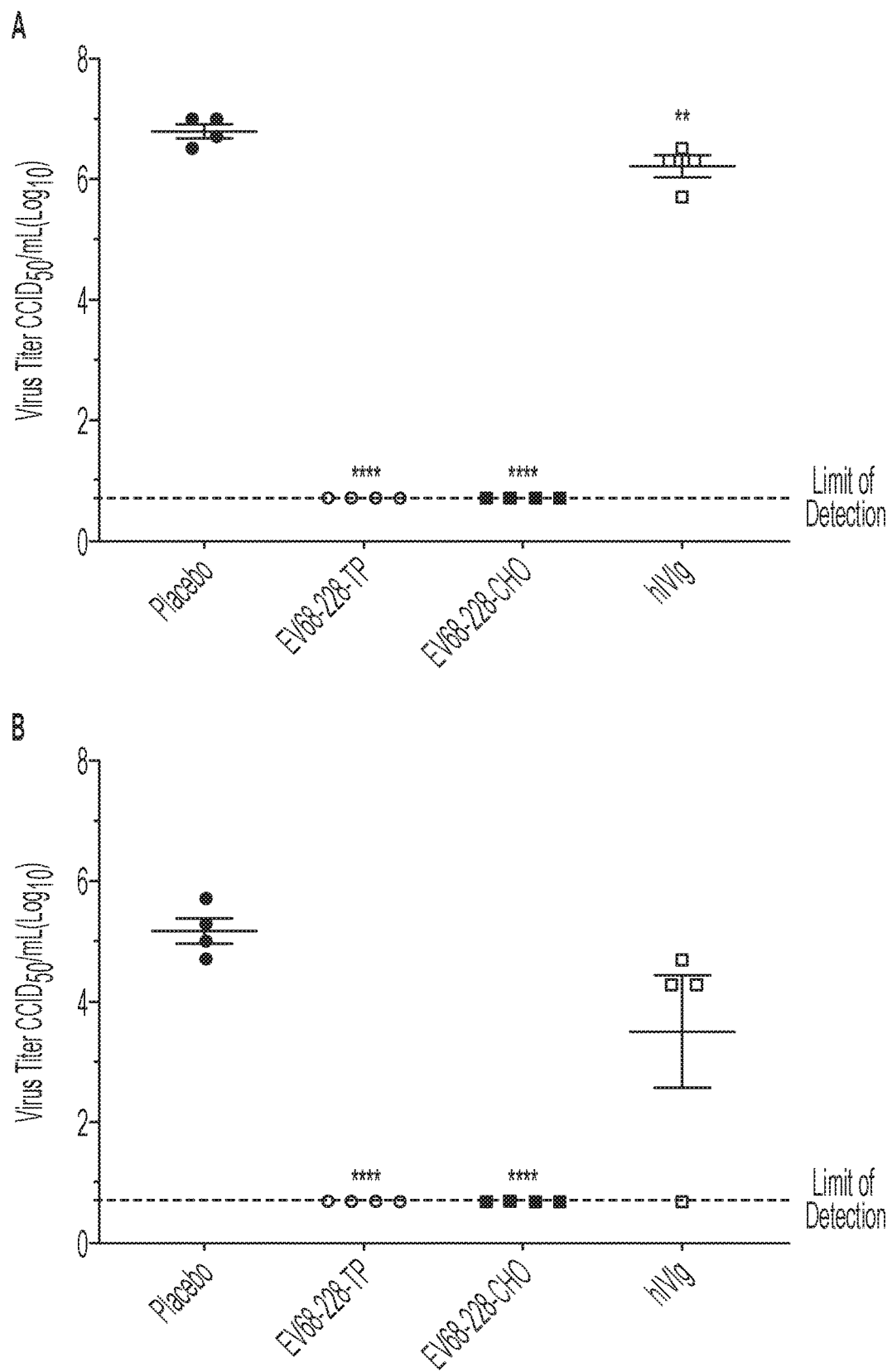
FIGS. 54A-B. Expt. NIA-1930. Lung virus titers of EV-D68-infected AG129 mice treated 24 hours post-infection with EV68-228-TP or EV68-228-CHO. Lung virus titers are shown on day 3 (FIG. 54A) and day 5 (FIG. 54B) post-infection. No lung virus titers were detected in mice treated with 10 mg/kg of EV68-228-TP or EV68-228-CHO at days 3 or 5 post-infection. Treatment with 10 mg/kg of hIVIg only significantly reduced lung virus titers on day 3 post-infection. (P<0.01, *P<0.001, ****P<0.0001 compared to placebo-treated mice.)

FIGS. 54A-B show lung virus titers for EV-D68-infected AG129 mice treated 24 hours post-infection with EV68-228-TP or EV68-228-CHO. No lung virus titers were detected at days 3 or 5 post-infection in mice treated with doses of 10 mg/kg of EV68-228-TP or EV68-228-CHO. Treatment with a dose of 10 mg/kg of HIVIg only significantly reduced lung virus titers on day 3 post-infection.

Figure 55:
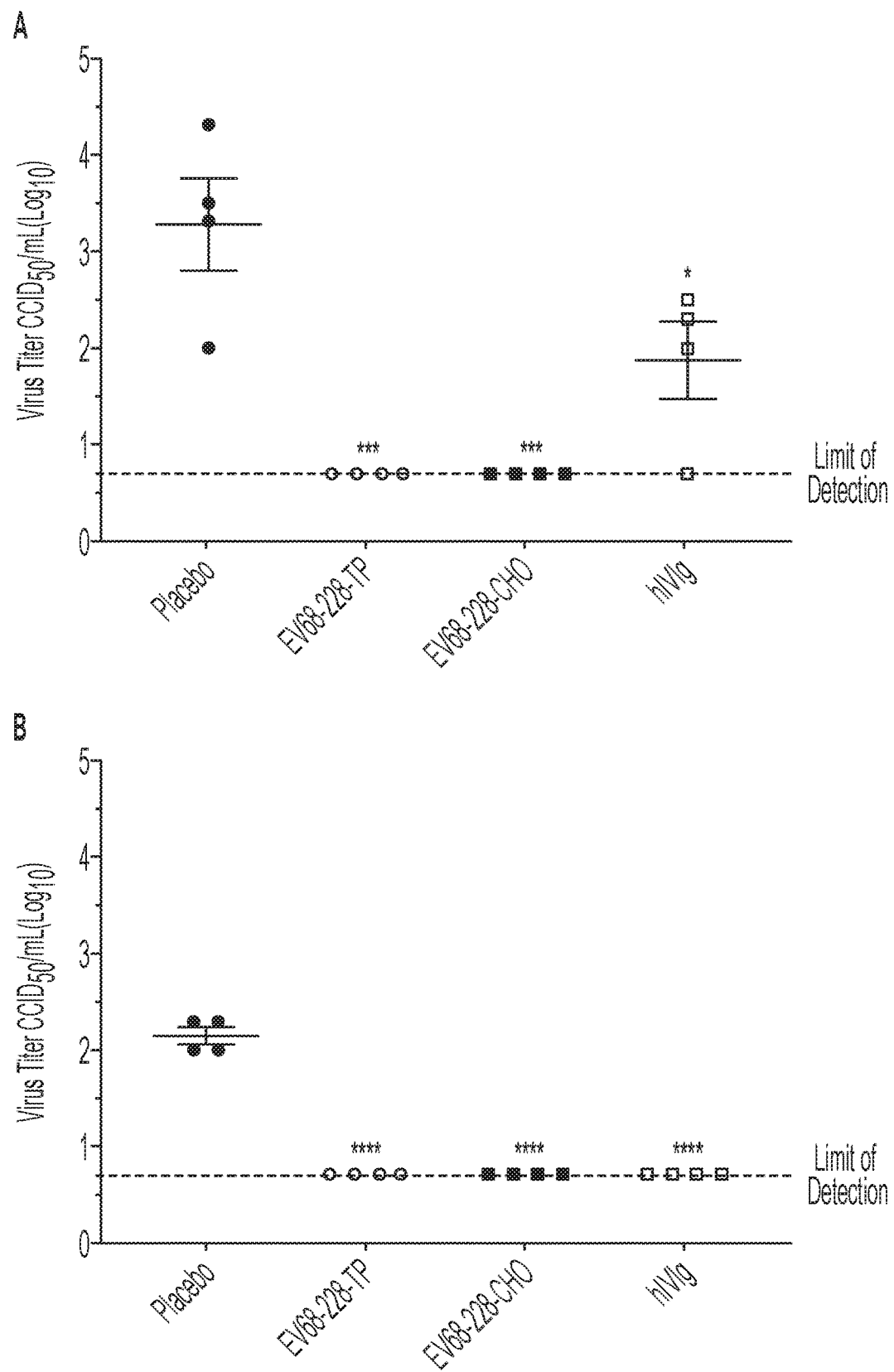
FIGS. 55A-B. Expt. NIA-1930. Blood virus titers of EV-D68-infected AG129 mice treated 24 hours post-infection with EV68-228-TP or EV68-228-CHO. Blood virus titers are shown at day 3 (FIG. 55A) and day 5 (FIG. 55B) post-infection. No virus was detected in the blood of mice treated with 10 mg/kg of EV68-228-TP or EV68-228-CHO on days 3 or 5 post-infection. Treatment with 10 mg/kg of hIVIg significantly reduced blood virus titers at days 3 and 5 post-infection. (*P<0.05, *P<0.001, **P<0.0001 compared to placebo-treated mice.)

FIGS. 55A-B show blood virus titers for EV-D68-infected AG129 mice treated 24 hours post-infection with EV68-228-TP or EV68-228-CHO. No blood virus titers were detected at days 3 or 5 post-infection in mice treated with doses of 10 mg/kg of EV68-228-TP or EV68-228-CHO. Treatment with hIVIg at a dose of 10 mg/kg also reduced blood virus titers at days 3 and 5 post-infection.

Figure 56:
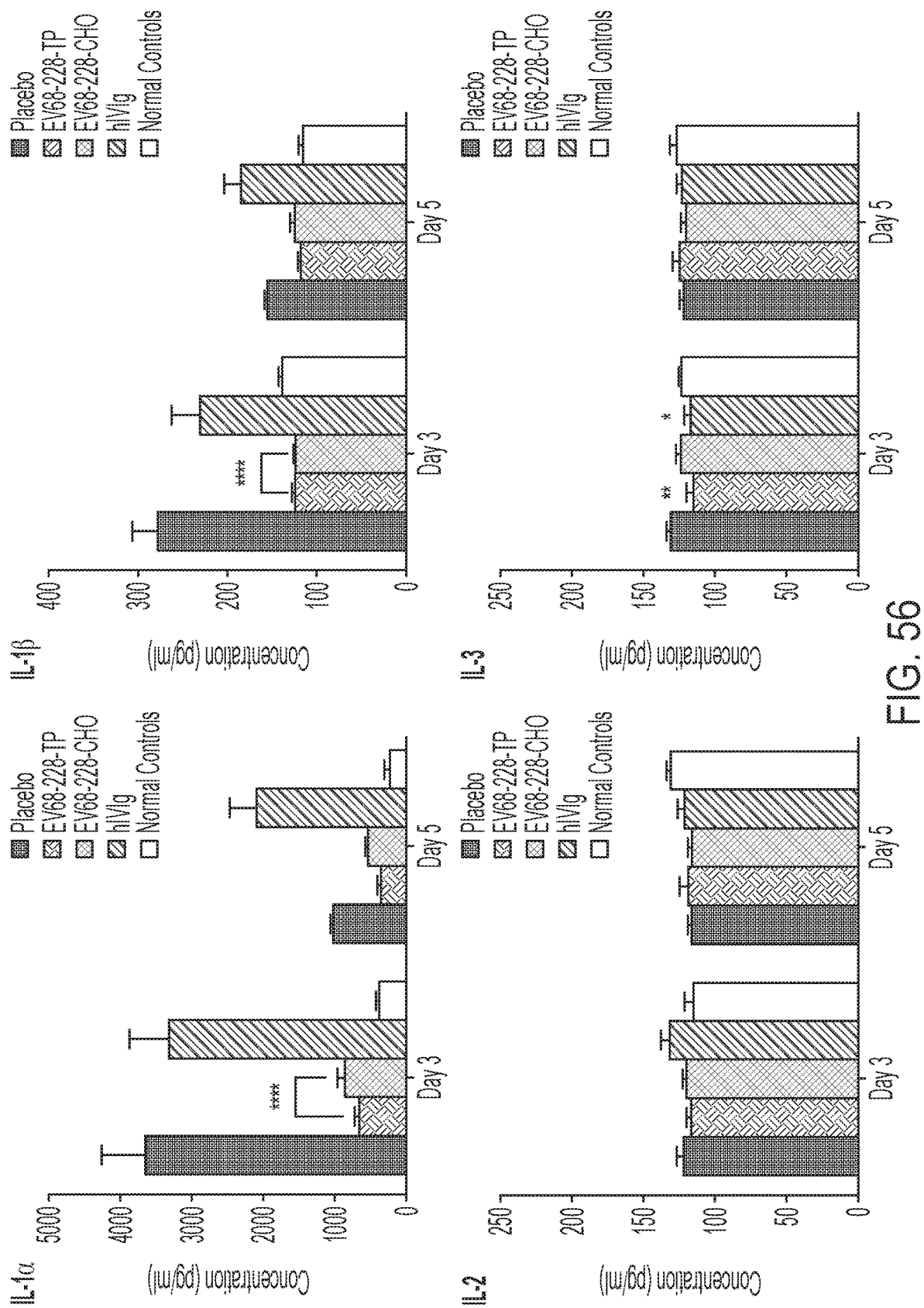
FIG. 56. Expt. NIA-1930. Lung concentrations of IL-1α, IL-1β, IL-2, and IL-3 from EV-D68-infected AG129 mice treated 24 hours post-infection with EV68-228-TP or EV68-228-CHO. Treatment with 10 mg/kg of EV68-228-TP or EV68-228-CHO significantly reduced concentrations of IL-1α and IL-1β on day 3 post-infection. Concentrations of IL-3 were significantly reduced in mice treated with EV68-228-TP as well as mice treated with hIVIg on day 3 post-infection. No significant changes were observed in concentrations of IL-2 following infection. (*P<0.05, P<0.01, **P<0.0001 compared to placebo-treated mice). Designation of samples in graph corresponds left-to-right with vertical legend top-to-bottom.

FIG. 56 shows lung concentrations of IL-1c, IL-1β, IL-2, and IL-3 from EV-D68-infected AG129 mice treated 24 hours post-infection with EV68-228-TP or EV68-228-CHO. Significant reductions in lung concentrations of IL-1c and IL-1β were observed on day 3 post-infection in mice treated with EV68-228-TP as well as mice treated with EV68-228-CHO. Treatment with hIVIg did not significantly affect lung cytokine concentrations of IL-1α or IL-1β. Concentrations of IL-3 were significantly reduced in mice treated with EV68-228-TP as well as mice treated with hIVIg on day 3 post-infection. No significant changes in lung concentrations of IL-2 were observed post-infection with EV-D68.

Figure 57:
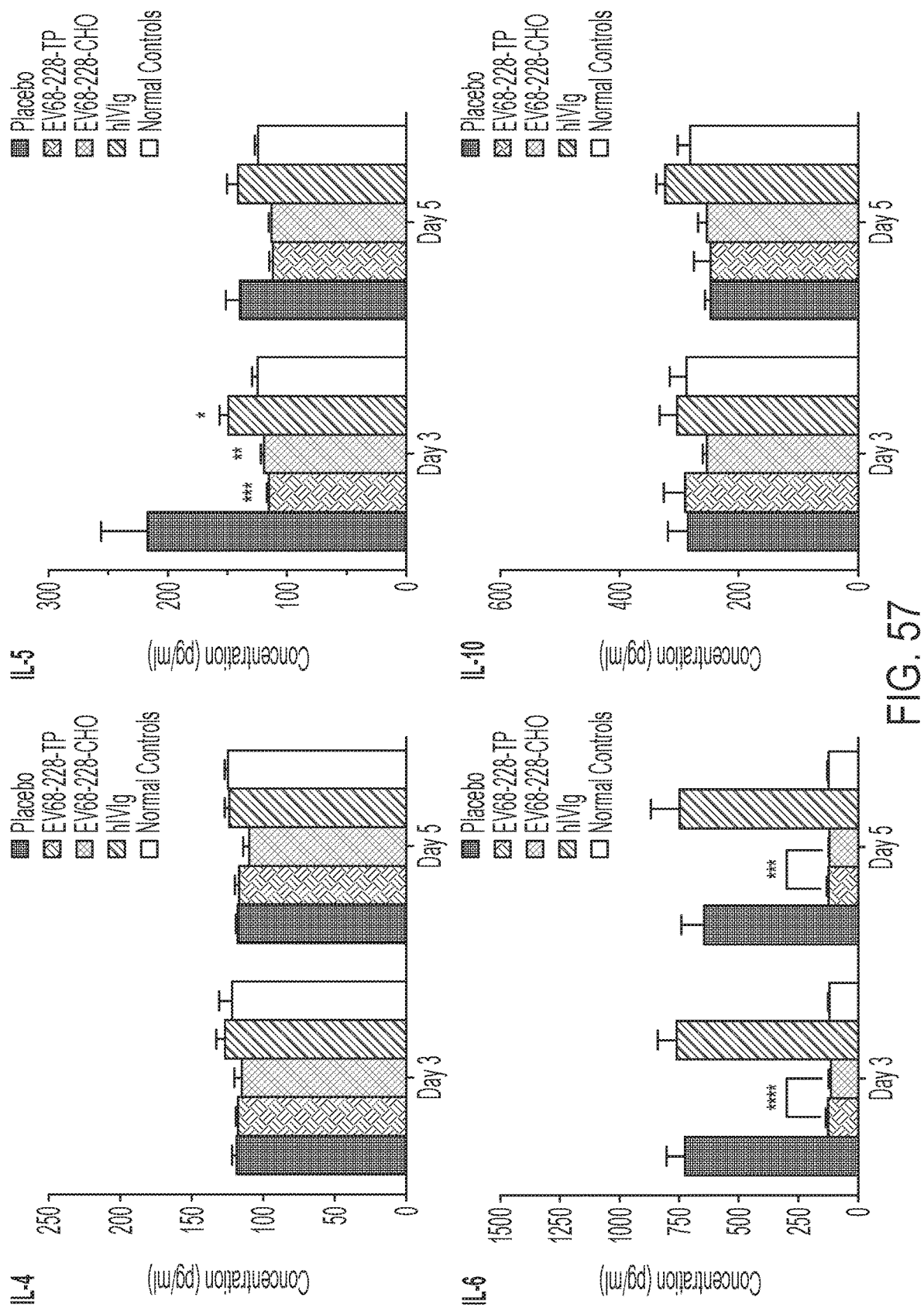
FIG. 57. Expt. NIA-1930. Lung concentrations of IL-4, IL-5, IL-6, and IL-10 from EV-D68-infected AG129 mice treated 24 hours post-infection with EV68-228-TP or EV68-228-CHO. Treatment with 10 mg/kg of EV68-228-TP or EV68-228-CHO significantly reduced concentrations of IL-5 on day 3 post-infection and IL-6 on days 3 and 5 post-infection. Treatment with 10 mg/kg of hIVIg significantly reduced lung concentrations of IL-5 on day 3 post-infection. No significant changes were observed in concentrations of IL-4 or IL-10 following infection. (*P<0.05, P<0.01, *P<0.001, ****P<0.0001 compared to placebo-treated mice). Designation of samples in graph corresponds left-to-right with vertical legend top-to-bottom.

Lung concentrations of 11-4, IL-5, IL-6, and IL-10 from EV-D68-infected AG129 mice treated 24 hours post-infection with EV68-228-TP or EV68-228-CHO are shown in FIG. 57. Treatment with 10 mg/kg of EV68-228-TP or EV68-228-CHO significantly reduced concentrations of IL-5 on day 3 post-infection and reduced concentrations of IL-6 on days 3 and 5 post-infection. Treatment with hIVIg significantly reduced lung concentrations of IL-5 on day 3 post-infection. No significant changes in concentrations of IL-4 or IL-10 in the lung tissue were observed after infection with EV-D68.

Figure 58:
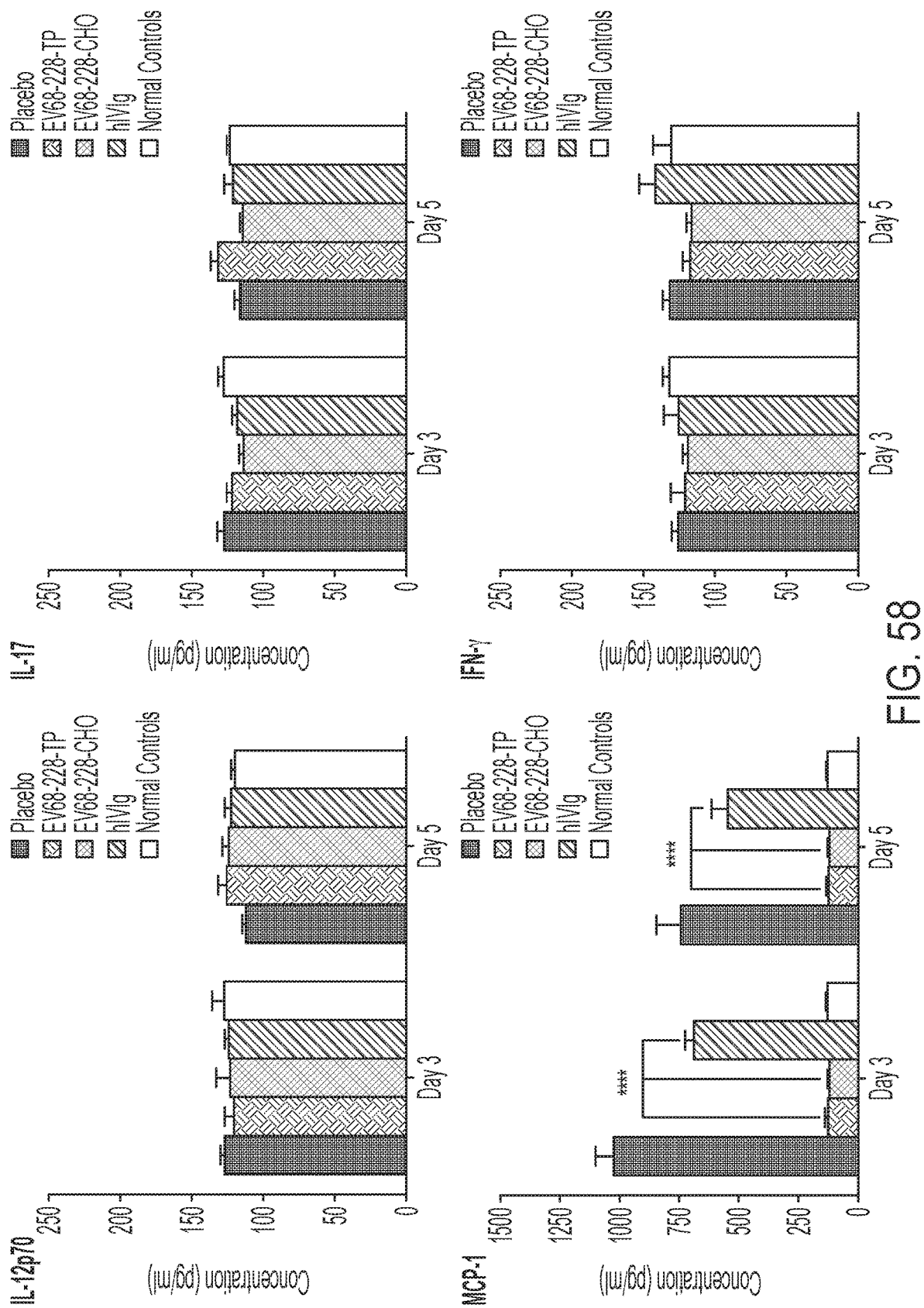
FIG. 58. Expt. NIA-1930. Lung concentrations of IL-12p70, IL-17, MCP-1, and IFN-γ from EV-D68-infected AG129 mice treated 24 hours post-infection with EV68-228-TP or EV68-228-CHO. Treatment with 10 mg/kg of EV68-228-TP or EV68-228-CHO significantly reduced concentrations of MCP-1 on days 3 and 5 post-infection. Treatment with 10 mg/kg of hIVIg significantly reduced lung concentrations of MCP-1 at day 3 and 5 post-infection. No significant changes were observed in concentrations of IL-12p70, IL-17, or IFN-γ following infection. (****P<0.0001 compared to placebo-treated mice). Designation of samples in graph corresponds left-to-right with vertical legend top-to-bottom.

FIG. 58 shows lung concentrations of IL-12p70, IL-17, MCP-1, and IFNγ from EV-D68-infected AG129 mice treated 24 hours post-infection with EV68-228-TP or EV68-228-CHO. Treatment with 10 mg/kg of EV68-228-TP or EV68-228-CHO significantly reduced lung concentrations of MCP-1 days 3 and 5 post-infection. Treatment with hIVIg significantly reduced lung concentrations of MCP-1 on days 3 and 5 post-infection. No significant changes in concentrations of IL-12p70, IL-17, or IFNγ were observed after infection with EV-D68.

Figure 59:
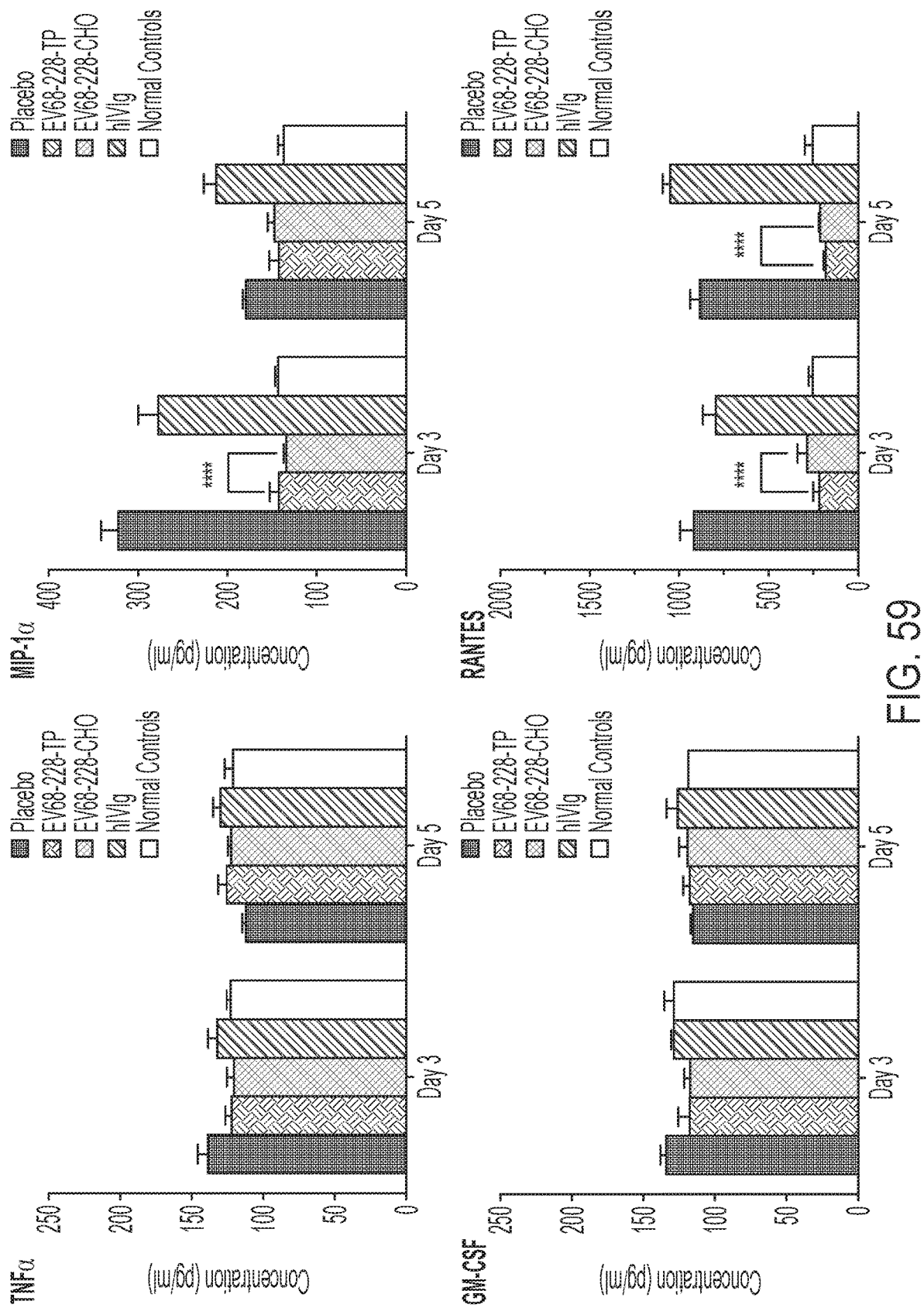
FIG. 59. Expt. NIA-1930. Lung concentrations of TNFα, MIP-1α, GM-CSF, and RANTES from EV-D68-infected AG129 mice treated 24 hours post-infection with EV68-

FIG. 59 shows lung concentrations of TNFα, MIP-1α, GM-CSF, and RANTES from EV-D68-infected AG129 mice treated 24 hours post-infection with EV68-228-TP or EV68-228-CHO. Treatment with 10 mg/kg of EV68-228-TP or EV68-228-CHO reduced lung virus concentrations of MIP-1α on day 3 post-infection and reduced concentrations of RANTES on days 3 and 5 post-infection. A 10 mg/kg dose of hIVIg did not significantly reduce lung concentrations of MIP-1α or RANTES post-infection. No significant changes in concentrations of TNFα or GM-CSF were observed after infection with EV-D68.

FIGS. 60A-B show lung virus titers for EV-D68-infected AG129 mice treated 48 hours post-infection with EV68-228-TP or EV68-228-CHO. Only treatment with the 10 mg/kg dose of EV68-228-CHO reduced lung virus titers when treatment was given 48 hours after infection. Neither treatment with 10 mg/kg of EV68-228-TP or hIVIg significantly reduced lung virus titers when treatment was administered 48 hours after infection.

FIGS. 61A-B show blood virus titers for EV-D68-infected AG129 mice treated 48 hours post-infection with EV68-228-TP or EV68-228-CHO. No blood virus titers were detected at days 3 or 5 post-infection in mice treated with doses of 10 mg/kg of EV68-228-TP or EV68-228-CHO. Treatment with hIVIg at a dose of 10 mg/kg also reduced blood virus titers at days 3 and 5 post-infection.

FIG. 62 shows lung concentrations of IL-1α, IL-1β, IL-2, and IL-3 from EV-D68-infected AG129 mice treated 48 hours post-infection with EV68-228-TP or EV68-228-CHO. Significant reductions in lung concentrations of IL-1α and IL-1β were observed on day 3 post-infection in mice treated with EV68-228-CHO but not in the mice treated with EV68-228-TP. Treatment with hIVIg did not significantly affect lung cytokine concentrations of IL-1α or IL-1β. No significant changes in lung concentrations of IL-2 or IL-3 were observed post-infection with EV-D68.

Lung concentrations of Il-4, IL-5, IL-6, and IL-10 from EV-D68-infected AG129 mice treated 48 hours post-infection with EV68-228-TP or EV68-228-CHO are shown in FIG. 63. Treatment with 10 mg/kg of EV68-228-CHO significantly reduced concentrations of IL-6 on day 3 post-infection. Treatment with EV68-228-TP or hIVIg did not significantly reduce lung concentrations of IL-6. No significant changes in concentrations of IL-4, IL-5, or IL-10 in the lung tissue were observed after infection with EV-D68.

FIG. 64 shows lung concentrations of IL-12p70, IL-17, MCP-1, and IFNγ from EV-D68-infected AG129 mice treated 48 hours post-infection with EV68-228-TP or EV68-228-CHO. When treatment was administered 48 hours after infection, no significant changes were observed in lung concentrations of IL-12p70, IL-17, MCP-1, or IFNγ in mice infected with EV-D68.

FIG. 65 shows lung concentrations of TNFα, MIP-1α, GM-CSF, and RANTES from EV-D68-infected AG129 mice treated 48 hours post-infection with EV68-228-TP or EV68-228-CHO. When treatment was administered 48 hours after infection, no significant changes were observed in lung concentrations of TNFα, MIP-1α, GM-CSF, or RANTES in mice infected with EV-D68.

Conclusions

This study determined the efficacy of a tobacco-produced EV68-228 mAb against EV-D68 for treatment of a respiratory infection caused by EV-D68 in four-week-old AG129 mice. The CHO-produced EV68-228 Ab was used as a comparator.

When treatment was administered either 24 hours pre-infection or 24 hours post-infection, the tobacco-produced Ab produced similar reductions in lung virus titers, blood virus titers, and lung cytokine concentrations when compared to the CHO-produced Ab.

When administered 48 hours post-infection, slight differences in the efficacy of the Abs were observed. The CHO-produced Ab was able to significantly reduce lung virus titers on days 3 and 5 post-infection while the tobacco-produced Ab was not able to reduce lung virus titers at either day 3 or 5 post-infection. Both the tobacco-produced and CHO-produced Abs were able to reduce blood virus titers on days 3 and 5 post-infection. In addition, the CHO-produced Ab significantly reduced lung concentrations of IL-1α, IL-1β, and IL-6 while the tobacco-produced Ab did not produce similar reductions in cytokine concentrations.

These differences in lung virus titers and lung cytokine concentrations were only observed when treatment was administered 48 hours after infection and the variability may be due to the limits of Ab treatment post-infection. However, in the previous study (NIA-1869) evaluating post-treatment of an EV-D68 respiratory infection with the CHO-produced antibody, a dose of 1 mg/kg was able to reduce lung concentrations of IL-1α, IL-1β, IL-5, MCP-1 and RANTES. Additional studies would be valuable to determine if there are significant differences between the tobacco-produced and the CHO-produced antibody.

Example 13

The objective of this study was to determine the efficacy of treatment with tobacco-produced EV68-228 antibody for an Enterovirus D68 (EV-D68) neurological infection in 10-day-old AG129 mice. Antibody produced in Chinese hamster ovary cells was used as a comparator for efficacy.

Materials and Methods

Animals. Ten-day-old AG129 mice from a specific-pathogen-free colony maintained at the Utah Science Technology and Research (USTAR) building at Utah State University. The mice were bred and maintained on irradiated Teklad Rodent Diet (Harlan Teklad) and autoclaved tap water at the USTAR building of Utah State University.

Antibodies and Compound. The monoclonal antibody (mAb) EV68-228 produced in tobacco plants (EV68-228-TP) as well as Chinese hamster ovary (CHO) cells (EV68-228-CHO) was provided by the inventors at Vanderbilt University Medical Center. Both the tobacco-produced and CHO antibodies were provided as solutions and were dosed at a concentration of 10 mg/kg. A tobacco-produced anti-HIV (Anti-HIV-TP) antibody was used as a negative control antibody at a dose of 10 mg/kg. Intravenous immunoglobulin (IVIg, Carimune, CSL Behring, King of Prussia, PA) was purchased from a local pharmacy and was used as a positive control.

Virus. Enterovirus D68 was obtained from BEI Resources, NIAID, NIH: Enterovirus D68, US/MO/14-18949, NR-49130. The virus was serially passaged 30 times in the lungs of 4-week-old AG129 mice and then plaque-purified three times in Rhabdomyosarcoma (RD) cells obtained from the American Type Culture Collection (Manassas, VA). The resulting virus stock was amplified twice in RD cells to create a working stock. The virus used for infection was designated EV-D68 MP30 PP.

Experiment design. A total of 125 mice were randomized into 12 groups of 10 mice each as shown in Table 1 with an additional 5 mice used as normal controls for weight gain. Mice were treated via intraperitoneal (IP) administration of EV68-228-TP or EV68-228-CHO, IVIg, or placebo 24 hours before, 24- or 48-hours post-infection. Mice were infected via intraperitoneal (IP) administration of $1 \times 10^{6.5}$ $CCID_{50}$ of EV-D68 MP30 PP in a 0.1 mL volume of MEM. Mice were weighed prior to treatment and daily thereafter. Blood was collected from groups of 5 mice on days 1, 3, 5, and 7 post-infection for evaluation of blood virus titers. All mice were observed daily for morbidity, mortality, and neurological scores through day 21. Neurological scores (NS) were recorded as follows: NS0—no observable paralysis, NS1—abnormal splay of hindlimb but normal or slightly slower gait, NS2—hindlimb partially collapsed and foot drags during use for forward motion, NS3—rigid paralysis of hindlimb and hindlimb is not used for forward motion, NS4—rigid paralysis in hindlimbs and no forward motion. Any animals observed with a score of NS4 were humanely euthanized.

Statistical analysis. Kaplan-Meier survival curves were generated Prism 8.4.2. (GraphPad Software Inc.). Survival curves were compared using the Log-rank (Mantel-Cox) test followed by a Gehan-Breslow-Wilcoxon test. For each day post-infection, blood virus titers from treated groups were compared to lung and blood titers from placebo-treated mice using a one-way analysis of variance (ANOVA). Mean body weights were compared using a one-way ANOVA. Neurological scores were compared using a Kruskal-Wallis test followed by a Dunn's multiple comparisons test.

Ethics regulation of laboratory animals. This study was conducted in accordance with the approval of the Institutional Animal Care and Use Committee of Utah State University dated Mar. 2, 2019 (expires Mar. 1, 2022). The work was done in the AAALAC-accredited Laboratory Animal Research Center of Utah State University. The U. S. Government (National Institutes of Health) approval was renewed Mar. 9, 2018 (PHS Assurance No. D16-00468 [A3801-01]) in accordance to the National Institutes of Health Guide for the Care and Use of Laboratory Animals (Revision; 2011).

TABLE M

Expt. NIA-1931/Experimental Design: Efficacy of EV68-228-TP for treatment of an EV-D68 neurological infection in mice

| No./Cage | Group No. | Infected | Compound | Dosage | Route | Treatment Schedule | Observations |
|---|---|---|---|---|---|---|---|
| 10 | 1 | Yes | Anti-HIV-TP (Placebo) | 10 mg/kg | IP | Once, 24 hours pre-infection | Mice observed daily for survival, body weights, and |
| 10 | 2 | Yes | EV68-228-TP | | | | |

TABLE M-continued

Expt. NIA-1931/Experimental Design: Efficacy of EV68-228-TP for treatment of an EV-D68 neurological infection in mice

| No./Cage | Group No. | Infected | Compound | Dosage | Route | Treatment Schedule | Observations |
|---|---|---|---|---|---|---|---|
| 10 | 3 | Yes | EV68-228-CHO | | | | neurological scores. |
| 10 | 4 | Yes | hIVIg | | | | Blood collected |
| 10 | 5 | Yes | Anti-HIV-TP (Placebo) | 10 mg/kg | IP | Once, 24 hours post-infection | from 5 mice per group on days 1, |
| 10 | 6 | Yes | EV68-228-TP | | | | 3, 5, and 7 post- |
| 10 | 7 | Yes | EV68-228-CHO | | | | infection for blood |
| 10 | 8 | Yes | hIVIg | | | | virus titers. |
| 10 | 9 | Yes | Anti-HIV-TP (Placebo) | 10 mg/kg | IP | Once, 48 hours post-infection | |
| 10 | 10 | Yes | EV68-228-TP | | | | |
| 10 | 11 | Yes | EV68-228-CHO | | | | |
| 10 | 12 | Yes | hIVIg | | | | |
| 5 | 13 | No | Normal Controls | — | — | — | Observed for normal weight gain |

Results and Discussion

This study determined the efficacy of a tobacco-produced EV68-228 mAb for treatment of an EV-D68 neurological infection in 10-day-old AG129 mice.

FIG. 66 shows Kaplan-Meier survival curves for 10-day-old AG129 mice infected with EV-D68 and treated 24 hours pre-infection with EV68-228-TP or EV68-228-CHO. Both the EV68-228-TP or EV68-228-CHO treatment 24 hours prior to infection provided complete protection from mortality. A single 10 mg/kg dose of hIVIG protected eight of ten mice (80%) from mortality. Nine of the ten placebo-treated mice succumbed to the infection.

FIG. 67 shows percentages of initial body weights for 10-day-old AG129 mice infected with EV-D68 and treated 24 hours prior to infection with EV68-228-TP or EV68-228-CHO. No significant protection from weight loss was observed in mice treated 24 hours pre-infection with EV68-228-TP or EV68-228-CHO since the one surviving mouse in the placebo-treated group gained weight after recovering from infection.

FIG. 68A-B show blood virus titers on days 1 and 3 post-infection for EV-D68-infected AG129 mice treated 24 hours pre-infection with EV68-228-TP or EV68-228-CHO. No blood virus titers were detected at days 1 or 3 post-infection in mice treated with a dose of 10 mg/kg of EV68-228-TP or EV68-228-CHO. Treatment with IVIg at a dose of 10 mg/kg also reduced blood virus titers at day 3 post-infection.

FIGS. 69A-B show blood virus titers on days 5 and 7 post-infection for EV-D68-infected AG129 mice treated 24 hours pre-infection with EV68-228-TP or EV68-228-CHO. No blood virus titers were detected at day 5 post-infection in mice treated with a dose of 10 mg/kg of EV68-228-TP or EV68-228-CHO. Treatment with IVIg at a dose of 10 mg/kg did not significantly reduce blood virus titers at days 5 post-infection. No virus was detected in the blood of any of the treatment groups at day 7 post-infection.

Neurological scores on days 2-10 post-infection in 10-day-old AG129 mice infected with EV-D68 and treated 24 hours pre-infection with EV68-228-TP or EV68-228-CHO are shown in FIGS. 70A-B. No neurological scores were observed in mice treated with a dose of 10 mg/kg of EV68-228-TP or EV68-228-CHO at any day post-infection. In addition, no neurological scores were observed in mice treated with IVIg at a dose of 10 mg/kg at any time post-infection. No significant reductions in neurological scores were observed after day 7 post-infection because the only surviving placebo-treated mouse did not display any signs of paralysis.

Kaplan-Meier survival curves of 10-day-old AG129 mice infected with EV-D68 and treated 24 hours post-infection with EV68-228-TP or EV68-228-CHO are shown in FIG. 71. Treatment with a 10 mg/kg dose of EV68-228-TP or EV68-228-CHO 24 hours after infection completely protected mice from mortality. A single dose of hIVIg given 24 hours after infection also protected all ten mice (100%) from mortality. Eight of the ten placebo-treated mice succumbed to the infection.

FIG. 72 shows percentages of initial body weights for 10-day-old AG129 mice infected with EV-D68 and treated 24 hours after infection with EV68-228-TP or EV68-228-CHO. No significant protection from weight loss was observed in mice treated 24 hours pre-infection with EV68-228-TP or EV68-228-CHO since two surviving mice in the placebo-treated group gained weight infection.

Blood virus titers on days 1 and 3 post-infection from 10-day-old mice infected with EV-D68 and treated 24 hours after infection with EV68-228-TP or EV68-228-CHO are shown in FIGS. 73A-B. No significant reduction in blood virus titers were observed on day 1 post-infection since the treatment was administered 24 hours after infection. On day 3 post-infection, treatment with EV68-228-TP and EV68-228-CHO significantly reduced blood virus titers. Treatment with hIVIg 24 hours after infection significantly reduced blood virus titers on day 3 post-infection.

Blood virus titers on days 5 and 7 post-infection from 10-day-old mice infected with EV-D68 and treated 24 hours after infection with EV68-228-TP or EV68-228-CHO are shown in FIGS. 74A-B. No virus was detected in the blood of mice treated 24 hours after infection with EV68-228-TP or EV68-228-CHO, however, only two placebo-treated mice were still alive for collection of blood and virus was not detected in the blood of either animal. Due to the lack of virus titers in placebo-treated animals, no statistical significance could be determined for any of the treatment groups. No virus was detected in the blood of any of the groups at day 7 post-infection.

FIGS. 75A-B show neurological scores on days 2-9 post-infection in 10-day-old AG129 mice treated 24 hours post-infection with EV68-228-TP or EV68-228-CHO. Treatment with EV68-228-TP or EV68-228-CHO 24 hours after infection significantly reduced signs of paralysis as indicated by reduced neurological scores at days 2-9 post-infection. A single 10 mg/kg dose of hIVIg 24 hours after infection reduced neurological scores at days 2 and 3 post-infection but did not improve the outcome for the remainder of the study.

Neurological scores on days 10-17 post-infection in 10-day-old AG129 mice treated 24 hours after infection with EV68-228-TP or EV68-228-CHO are shown in FIGS. 76A-B. Both EV68-228-TP and EV68-228-CHO significantly reduced neurological scores on days 10-15 post-infection. The administration of hIVIg did not significantly reduce neurological scores at days 10-17 post-infection.

FIG. 77 shows Kaplan-Meier survival curves for 10-day-old AG129 mice infected with EV-D68 and treated 48 hours post-infection with EV68-228-TP or EV68-228-CHO. Treatment with EV68-228-TP at a dose of 10 mg/kg protected nine of ten mice (90%) from mortality. Eight of ten mice (80%) survived the infection with treated 48 hours after infection with EV68-228-CHO. A single 10 mg/kg dose of hIVIG protected six of ten mice (60%) from mortality. One of the ten placebo-treated mice survived the infection.

FIG. 78 shows percentages of initial body weights for 10-day-old AG129 mice infected with EV-D68 and treated 48 hours after infection with EV68-228-TP or EV68-228-CHO. No significant protection from weight loss was observed in mice treated 24 hours pre-infection with EV68-228-TP or EV68-228-CHO as the one surviving mouse in the placebo-treated group gained weight following infection.

FIGS. 79A-B show blood virus titers on days 1 and 3 post-infection for EV-D68-infected AG129 mice treated 48 hours post-infection with EV68-228-TP or EV68-228-CHO. On day 1 post-infection, none of the treatment groups were significantly different since no treatments had occurred at that point. At day 3 post-infection, blood virus titers were lower in mice treated with 10 mg/kg of EV68-228-TP or EV68-228-CHO although the differences were not statistically significant. This is likely due to treatment being administered just 24 hours prior to the blood collection on day 3. Treatment with IVIg at a dose of 10 mg/kg did not significantly reduce blood virus titers at day 1 or day 3 post-infection.

FIGS. 80A-B show blood virus titers on days 5 and 7 post-infection for EV-D68-infected AG129 mice treated 48 hours post-infection with EV68-228-TP or EV68-228-CHO. No blood virus titers were detected at day 5 post-infection in mice treated with a dose of 10 mg/kg of EV68-228-TP or EV68-228-CHO. Treatment with IVIg at a dose of 10 mg/kg did not significantly reduce blood virus titers at days 5 post-infection. No virus was detected in the blood of any of the treatment groups at day 7 post-infection.

Neurological scores on days 3-10 post-infection in 10-day-old AG129 mice infected with EV-D68 and treated 48 hours post-infection with EV68-228-TP or EV68-228-CHO are shown in FIGS. 81A-B. Treatment with 10 mg/kg of EV68-228-TP significantly reduced neurological scores at days 3-5 post-infection. Treatment with 10 mg/kg of EV68-228-CHO significantly reduced neurological scores on days 3-6 post-infection. Neurological scores were significantly reduced in mice treated with 10 mg/kg of hIVIG on days 3-5 post-infection. No significant reduction in neurological scores were observed in any of the treatment groups on days 7-10 post-infection.

Conclusions

This study determined the efficacy of a tobacco-produced EV68-228 mAb against EV-D68 neurological infection 10-day-old AG129 mice.

The tobacco-produced mAb provided similar protection from mortality compared to the CHO-produced mAb when treatment was administered 24 hours prior to infection as well as 24 or 48 hours after infection.

In addition, similar reductions in blood virus titers were observed in mice treated with both EV68-228-TP and EV68-228-CHO mAbs in 10-day-old AG129 mice infected with EV-D68.

Similar protection from paralysis as indicated by reductions in neurological scores was observed in mice treated with EV68-228-TP as well as EV68-228-CHO.

In summary, the tobacco-produced EV68-228 provided similar protection from mortality, reductions in blood virus titers, and protection from paralysis when compared to the CHO-produced EV68-228.

TABLE 1

NUCLEOTIDE SEQUENCES FOR ANTIBODY VARIABLE REGIONS

| Clone | SEQ ID NO: | Chain | Variable Sequence Region |
|---|---|---|---|
| EV-D68-37 | 1 | heavy | CAGGTGCAGCTGGTGGAGTCTGGGGGAGGCGTGGTCCAGCCTGGGAGGTCCCTGAGACTCTCATGTGCAGCCTCTGGATTCATCTTCAGTCGCTACGCTCTGCACTGGGTCCGCCAGGCTCCAGGCAAGGGGCTGGACTGGGTGGCAGTTATATCATATGATGCAAGAAATTCATATTACACAGACTCCGTGAAGGGCCGATTCACCATCTCCAGAGACAATTCCAAAAACACGCTGTTTCTGCAGATGAACAGTCTGAGAGCTGACGACACGGCTGTCTATTACTGTGCGAGACCGACTTTGCCCTACAGCAACAACTGGTACGCGCCTGAATACTGGGGCCAGGGAACCCTGGTCACCGTCTCCTCA |
| | 2 | light | TCCTATGAGCTGACACAGCCACCCTCGGTGTCAGTGTCCCCAGGACAAACGGCCAGGATCACCTGCTCTGGAGATGCATTACCAAAAAAATATGCTTCTTGGTACCAGCAGAAGTCAGGCCAGGCCCCTGTGCTGGTCATCTATGAAGACACCAAACGACCCTCCGGGATCCCTGAGAGATTCTCTGGCTCCAGCTCAGGGACAATGGCCACCTTGACTATCAGTGGGGCCCAGGTGGAAGATGAAAGTGACTACTACTGTTCCTCGACAGACAGCAGTGGTAATCCTGTGCTATTCGGCGGAGGGACCAAGTTGACCGTCCTA |
| EV-D68- | 3 | heavy | GAGGTGCAGCTGGTAGAGTCTGGGGGAGACTTGGTACAGCCTGGGGGGTCCCTGAGACTCTCCTGTGCAGCCTCTGGAT |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| 40 | | | TCTCCTTTAGCAGCTATGCCATGGCCTGGGTCCGCCAGGC<br>TCCAGGGAAGGGGCTGCAGTGGGTCTCATCTATTAGTGGT<br>AACGGTAATGGGAGATCCTATGCAGATTCTCTGAAGGGCC<br>GGTTCACCACCTCCAAAGACCTTTCCAAGTATACCCTGTAT<br>CTGCAAATGAACAATCTGAGACCCGAGGACACGGCCATAT<br>ATTACTGTGCGAAAGTTGTCCGTATAGCAGCTGTTTTGTAT<br>TACTTTGACTATTGGGGCCCGGGAACCCAGGTTACCGTCT<br>CCTCA |
| | 4 | light | GAAATTGTGTTGACACAGTCTCCAGCCACCCTGTCTTTGTC<br>TCCAGGGGAAAGAGCCACCCTCTCCTGCAGGGCCAGTCA<br>GAGTGTTAGCACCTACTTAGCCTGGTACCAACAAAAGCCTG<br>GCCAGGCTCCCAGGCTCCTCATCTATGAAGCATCCACCAG<br>GGCCACTGGCATCCCAGCCAGGTTCAGTGGCAGTGGGTCT<br>GGGACAGACTTCACTCTCATCATCAGCAGCCTAGAGCCTG<br>AAGATTTTGCAGTTTATCACTGTCAGCAGCGCAGCTCCTGG<br>CCGATCACCTTCGGCCAAGGGACACGACTGGAGATTGAA |
| EV-<br>D68-<br>41 | 5 | heavy | GACGTGCAGCTGGTGGAGTCTGGGGGGGGCTTGGTACAG<br>CCTGGGGGGTCCCTGAGACTCTCCTGTGCTGCCTCTGGAT<br>TCACTTTTAGCAACTATGCCATGACCTGGGTCCGCCAGGCT<br>CTAGGGAAGGGGCTGGAGTGGGTCTCTTCTATTAGTGGTA<br>GTGGTGGCCTCACATATTTCGCACACTCCGTGAAGGGCCG<br>GCTCACCATCTCCAGAGACAACTCCAAGAATACCCTCTATC<br>TGCAAATGAGCAGCCTGAGAGCCGAAGACACGGCCGTATA<br>TTACTGTGCGAGAGTGAAAAGTACAACTGGAACGACGGCG<br>TTAGTTTTTGATATCTGGGGCCAAGGGACAATGGTCACCGT<br>CTCTTCG |
| | 6 | light | CAGACTGTGGTGACCCAGGAGCCATCGTTCTCAGTGTCCC<br>CTGGAGGGACAGTCACACTCACTTGTGGCTTGAGTTCTGG<br>CTCAGTCTCTAGTAGTTACTACCCCAGTTGGTACCAGCAGA<br>CCCCAGGCCAGGCTCCACGCACGCTCATCTACAGTATAAA<br>CAGACGTTCTTCTGGGGTCCCTGATCGCTTCTCTGGCTTCA<br>TCCTTGGGAACAAAGCTGCCCTCACCATCAGGGGGGCCCA<br>GGCAGATGATGAATCTGATTATTACTGTGGGCTGTATATGG<br>GTAGTGGCATTTGGATCTTCGGCGGAGGGACCAAGCTGAC<br>CGTCCTA |
| EV-<br>D68-<br>43 | 7 | heavy | CAGGTGCAGCTGGTGGAGTCTGGGGGAGGCGTGGTCCAG<br>CCTGGGAGGTCCCTGAGACTCTCCTGTGCAGCCTCTGGAT<br>TCACCTTCATTAACTATGGCATGCACTGGGTCCGCCAGGCT<br>CCAGGCAAGGGGCTGGAGTGGGTGGCAGTTATATCAAATG<br>ATGGAAGTTATAACTACGATGCAGACTCCGTGAAGGGCCG<br>ATTCACCATCTCCAGAGACAATTCCAAGAACAAGGTTTATC<br>TACAAATGAACAGCCTGAGACCTGAGGACACGGCTGTGTA<br>TTTCTGTGCGAAAGACAAACACGGTGACTTCGACTACTACG<br>GTGTGGACGTCTGGGGCCAAGGGACCACGGTCACCGTCT<br>CCCCA |
| | 8 | light | GACGTCCAGATGACCCAGTCTCCATCTTCCGTGTCTGCATC<br>TATAGGAGACAGAGTCACCATCACTTGTCGGGCGGGTCAG<br>GGAATTAGCAGCTGGTTAGCCTGGTATCAGCAGAAACCAG<br>GGAAAGCCCCTAAGCTCCTGATCTATGCTGCATCCAATTTG<br>CAAAGTGGGGTCCCATCACGGTTCAGCGGCAGTGGATCTG<br>GGACAGATTTCACTCTCACCATCAGCAGCCTGCAGCCTGA<br>AGATTTTGGAACTTACTATTGTCAACAGGCTGACAGTTTCC<br>CTCGGACGTTCGGCCAAGGGACCAAGGTGGAAATCAAA |
| EV-<br>D68-<br>46 | 9 | heavy | CAGGTGCAGCTGGTGGAGTCTGGGGGAGGCGTGGTCCAG<br>CCTGGGAGGTCCCTGAGACTCTCCTGTGCAGCCTCTGGAT<br>TCACCTTCAGTAGTTATGGCATACACTGGGTCCGCCAGGC<br>TCCAGGCAAGGGGCTGGAGTGGGTGGCAGTTATATCCTAT<br>GATGGAAGTGATAACACCTATGCACCTTTTGTGAACGGCC<br>GATTCACCATCTCCAGAGACAATTCCAAGAACACGCTGTAT<br>CTGCAAATGAACAGCCTGAGAGCTGACGACACGGCTGTGT<br>ATTACTGTGCGAGGCGTCGGCCTGGGAGCTTCCCAGGACT<br>TTGCGACTACTGGGGCCAGGGAGCCCTGGTCACCGTCTCC<br>TCA |
| | 10 | light | GACATCCAGATGACCCAGTCGCCTTCCACTATGTCTGCTTC<br>TGTAGGAGACAGAGTCACCATCACTTGCCGGGCCAGTCAG<br>AGTATTAGTAAGTGGTTGGCCTGGTATCAGCAGAAGCCAG<br>GGAAAGCCCCTAAACTCCTGATCTATAAGGCGTCTACCTTA<br>CAAACTGGGGTCCCATCAAGGTTCAGCGGCAGTGGATCTG<br>GGACAGAATTCACTCTCACCATCAACAGCCTGCAGCCTGAT<br>GATTTTGCAACTTATTACTGCCAACAGCATAATAGTTATTCG<br>TACACTTTTGGCCAGGGGACCAAGGTGGAGATCAAG |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| EV-D68-48 | 11 | heavy | CAGGTGCAGCTGGTGCAGTCTGGGGCTGAGGTGAAGAAG<br>CCTGGGTCCTCGGTGAAGGTCTCCTGCAAGGCTTCTGGAG<br>GCAGCTTCAGCAGACTTACTATCATCTGGGTGCGGCAGGC<br>CCCTGGACAAGGGCTTGAGTGGATGGGAGGGCACATCCC<br>TATCTTTGGAACAACAAACTACGCACTGAAGTTCCAGGGCA<br>GAGTCACGATTACCGCGGACAAAACCACGAGCACAGCCTA<br>CATGGAGCTGAGCAGCCTGAGATCTGAGGACACGGCCATA<br>TATTACTGTGCGAGAATGTATAGTGGCCATGACGGCGTTGA<br>TGTCTGGGGCCAAGGGACACTGGTCACCGTCTCTTCA |
| | 12 | light | GAAATTGTGTTGACACAGTCTCCAGCCACCCTGTCTTTGTC<br>TCCAGGGGAAAGAGCCACCCTCTCCTGCAGGGCCAGTCA<br>GAGTGTTAGGAGCTACTTAGCCTGGTACCAACACAAACCT<br>GGCCAGGCTCCCAGGCTCCTCATCTATGATGCATCCAACA<br>GGGCCAAGGGCATCCCAGCCAGGTTCAGTGGCAGTGGGT<br>CTGGGACAGACTTCACTCTCACCATCAGCAGCCTAGAGCC<br>TGAAGATTTTGCAGTTTATTACTGTCAGCAGCGTAGCACCT<br>GGCCTCCGGGAATGTTCGGCCAAGGGACCAGGGTGGAAA<br>TCAAA |
| EV-D68-71 | 13 | heavy | CAGCTGCAGCTGCAGGAGTCGGGCCCAGGACTGGTGAAG<br>CATTCGGAGACCCTGTCCCTCACCTGCACTGTCTCTGGTG<br>GCTCCATCAGCAGTGGTTTTTACTACTGGGGCTGGATCCG<br>CCAGCCCCCAGGGAAGGGGCTAGAGTGGATTGGGACTAT<br>CTATGATAGTGGGAGAACCTATGACAACCCGTCCCTCAAG<br>AGTCGAGTCACCATATCCGCAGACACGTCCAAGAAGCAGT<br>TCTCACTGACACTGAGGTCTGCGACCGCCGCGGACACGG<br>CTGTGTATTTCTGTGCGAGACACCTTACCCACCTCTACGGT<br>GACTACGTCACCCCTGATGCTTTAGATATCTGGGGCCAAG<br>GGACAATGGTCACCGTCTCTTCA |
| | 14 | light | GAAATTGTGTTGACGCAGTCTCCAGGCACCCTGTCCTTGTC<br>TCCAGGGGAAAGAGCCACCCTCTCTTGCAGGGCCAGTCAG<br>AGCGTTAGTAGCAGCTTCTTAGCCTGGTACCAGCAGAAAC<br>CTGGCCAGGCTCCCAGGCTCCTCATCTATGGTGCGTCCAG<br>CAGGGCCACCGGCATCCCAGACAGGTTCAGAGGCAGTGG<br>GTCTGGGACAGACTTCACTCTCACCATCAGCAGACTGGAG<br>CCTGAAGATTTTGCAGTATATTACTGTCAGCAGTATAGTAA<br>CTCACGTCTGACGTTCGGCCAAGGGACCAAGGTGGAAATC<br>AAA |
| EV-D68-72 | 15 | heavy | GAGGTGCAGCTGGTGGAGTCTGGGGGAGGCTTGGTACAG<br>CCTGGGGGGTCCCTGAGACTCTCCTGTGCAGCCTCTGGAT<br>TCACCTTCACTACCTATAGCATGAACTGGGTCCGCCAGGCT<br>CCAGGGAAGGGGCTGGAGTGGATTTCATACATTAGTAGTG<br>GTAGTAGTAACATATACTACGCAGACTCTGTGAAGGGCCG<br>ATTCACCATCTCCAGAGACAATGCCAAGAACTCACTGAATC<br>TGCAAATGAGCAGCCTGAGAGACGAGGACACGGCTGTGTA<br>TTACTGTGCGAGAGCCCACGGACGTATAGTGAATTCTGGA<br>GTGGTTATTAGTAGGTTCGACCCCTGGGGCCAGGGAATCC<br>TGGTCACCGTCTCCTCA |
| | 16 | light | CAGTCTGCCCTGACTCAGCCTGCCTCCGTGTCTGGGTCTC<br>CTGGACAGTCGATCACCATCTCCTGCACTGGAACCAGCAG<br>TGACGTTGGTGGTTATAACTATGTCTCCTGGTACCAACTGC<br>ACCCAGGCAAAGCCCCCAAACTCATGATTTTTGAGGTCACT<br>TATCGGCCCTCAGGGGTTTCTAATCGCTTCTCTGGCTCCAA<br>GTCTGGCAACACGGCCTCCTGACCATCTCTGGGCTCCAG<br>GCTGAGGACGAGGCTGATTATTTCTGCAGCTCCTATACAAC<br>CAGCAACACTCTCGTGGTGTTCGGCGGAGGGACCAAGCTG<br>ACCGTCCTA |
| EV-D68-74 | 17 | heavy | CAGGTGCAGCTGGTGCAGTCTGGGGCTGAGGTGAAGAAG<br>CCTGGGGCCTCAGTGAAGGTCTCCTGTAGGACTTCTGGAT<br>ACACCTTCACGGCCTACTATATGCACTGGGTGCGACAGGC<br>CCCCGGACAAGGGCTGAGTGGATGGGAAGGATCAACCC<br>GAGCAGTGGTGGCGCACAGTATGCACGAAGTTTCAGGGC<br>AGGGTCACCATGACCAGGGACACGTCCATCAGCACAACCT<br>ACATGACCCTGAGCGGGCTGACATCTGACGACACGGCCGT<br>GTTTTACTGTGCGAGAATGGGTTGTCGTAGTGACCGGTGC<br>TATTCGACCAACTACAACTTTGACCAGTGGGGCCAGGGAA<br>CCCTGGTCACCGTCTCCTCA |
| | 18 | light | TCCTATGTGCTGACTCAGCCACCCTCGGTGTCAGTGGCCC<br>CAGGACAGACGGCCAGGATTCCCTGTGGGGGAAACAACAT<br>TGGAACTAAAAGTGTTCACTGGTACCAGCAGAAGCCAGGC<br>CAGGCCCCTGTGCTGGTCGTCTCTAATGACAGCGACCGGC<br>CCTCAGGGATCCCTGAGCGATTCTCTGGCTCCAAGTCTGG<br>GAACACGGCCACCCTGACCATCAGCAGGGTCGAAGCCGG |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| | | | GGATGAGGCCGACTATTATTGTCAGGTGTGGGATAGTGGT ATTGATGTCGTTTTCGGCGGAGGGACCAAGCTGACCGTCC TA |
| EV-D68-75 | 19 | heavy | GAGGTGCAGCTGGTGGAGTCTGGGGGAGGCCTGGTCAAG CCTGGGGGGTCCCTGAGACTCTCCTGTGCAGCCTCTGGAT TCACTATCAGTCCCTATGGCATGAACTGGGTCCGCCAGGC TCCAGGGAAGGGGCTGGAGTGGGTCTCATTCATTAGTAGT AGTAGTCGTTACACATATTACGCAGACTCAGTGAAGGGCC GTTTCACCATCTCCAGAGACAACGCCAAGAATTCACTGTCT CTGCAAATGAACAGCCTGAGAGCCGAGGACACGGCTGTGT ATTACTGTGCGAGAGAGAGGGCCATAGCACCTCGTCCTC ATACTTTGACTCCTGGGGCCAGGGAACCCTGGTCACCGTC TCCTCA |
| | 20 | light | TCCTATGTGCTGACTCAGCCACCCTCAGTGTCATTGGCCC CAGGAAAGACGGCCAGGATTACCTGTGGGGAAACAACAT TGGAACTAAAACTGTGAGCTGGTACCAGCAGAAGCCAGGC CAGGCCCCTGTGCTGGTCATGTATTATGATAGTGACCGGC CCTCAGGGATCCCTGAGCGATTCTCTGGCTCCAACTCTGG GAACACGGCCACCCTGACCATCAACAGGGTCGAGGCCGG GGATGAGGCCGACTATTACTGTCGGGTGTGGGATAGTGAT ACTGATCATCGAGTGTTCGGCGGGGGGACCAAGCTGACC GTCCTA |
| EV-D68-76 | 21 | heavy | GAGGTGCAGCTGGTGGAGTCTGGGGGAGGCTTGGTAAAG CCTGGGGGGTCCCTTAGACTCTCCTGTGCAGCCTCTGGAT TCACTTTCAGTAACGCCTGGATTAGCTGGGTCCGCCAGGC TCCAGGGAAGGGGCTGGAGTGGGTTGGCCGTATTCAAACC AAAACTGATGGAGGGACAACAGACTACGCTGCACCCGTGA AAGGCAGATTCACCATCTCAAGAGATGATTCAAAAAACACG TTGTATCTGCAAATGAACAGCCTGAAAACCGAGGACACAG CCTTGTATTATTGTAGCACAGGACCGTATTACTATGATACTA GTGGTTACCCCCAACCCTTTGACTACTGGGGCCAGGGAAC CCTGGTCACCGTCTCCTCA |
| | 22 | light | TCCTATGAGCTGACTCAGCCACCCTCAGTGTCCGTGTCCC CAGGACAGACAGCCAGCATCACCTGCTCTGGAGATAAATT GGGAGATAAATATGCTTGCTGGTATCAGCAGAAGCCAGGC CAGTCCCCTGTGCTGGTCATCTATCAAGATACCAAGCGGC CCTCAGGGATCCCTGAGCGATTCTCTGGCTCCAACTCTGG GAACACAGCCACTCTGACCATCAGCGGGACCCAGGCTATG GATGAGGCTGACTATTACTGTCAGGCGTGGGACAGCAGCA CTGTGGTATTCGGCGGAGGGACCAAGCTGACCGTCCTA |
| EV-D68-80 | 23 | heavy | GAGGTACAGATGGTGGAGTCTGGGGGAGGCCTGGTCAAG CCCGGGGGGTCCCTCAGACTCTCCTGTTCAGTCTCTGGAT TCGACTTCAGTAGATACACCATGAACTGGTTCCGCCAGGCT CCAGGGGAGGGGCTGAAGTGGGTCTCGTCCATTAGTAGTA CTAGTCTTTACACATTCTATGCGGACTCAGTGAAGGGCCGA TTCTCCATCTCCAGAGACAACGCCCAGGGTTCCCTGTCTCT ACAAATGAGCAGCCTGAGACCCGAAGATACGGCTGTCTAT TATTGTGCGAGAGTCGTTGGTCCCGCCGAGTTAGATTACT GGGGCCAGGGAGTGCTGGTCACCGTCTCCTCA |
| | 24 | light | GTCACCCAGTTGACCCAGTCTCCATCCTCCCTGTCTGCTTC TGTCGGGACAGAGTCACCATCACTTGCCGGGCAAGTCAG GACATTGGAGTTGACTTAGGTTGGTTTCAGCAGAGACCTG GGAAAGCCCCTAAACTCCTGATCTATGGTGCCTCCAGGTT GCAGAGTGGGGTCCCATCACGCTTCAGCGGGCGTGGATC TGGCACATTTTTCACTCTCACCATCAGCAGCCTGCAGCCTG AAGATTTTACAACTTACTTCTGTCTTCAAGATTATAATTACC CTTGGACGCTCGGCCAGGGGACCACGGTGGAGTCAAA |
| EV-D68-84 | 25 | heavy | CAGGTGCACCTGGTGCAGTCTGGGTCTGCGGTGAGGAAG CCTGGGGCCTCAGTGAAGGTCTCCTGCAAGGCTTCTGGAT ACACCTTCACCGACTACTATATTCACTGGGTGCGACAGGC CCCTGGACAAGGCCTTGAGTGGATGGGATGGATCAACCCT AAAACTGGTGGCTCAAATTATACACAGAGGTTTCAGGCCAG GGTCACCATGACCTGGGACACGTCCATCAGTACAGCCTAC ATGGAGTTGAGCAGGCTGAGATCTGACGACACGGCCGTGT ATTATTGTGCGAGGGCGGGCAGAAATGGCTACGACTACTG GGGCCAGGGAACCCTGGTCACCGTCTCCTCA |
| | 26 | light | TCCTATGAGCTGACACAGCCACCCTCGGTGTCAGTGTCCC CAGGACAGACGGCCAGGATCACCTGCTCTGCAGATGCATT GCCAAAGCAATATGCTTATTGGTACCAACAGAAGCCAGGC CAGGCCCCTGTGTTGATGATATATCAAGACACTGAGAGGC CCTCAGGGATCCCTGAGCGATTCTCTGGGTCCAGCTCAGG |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| | | | GACAACAGTCACGTTGACCATCAGTGGAGTCCAGGCAGAA GACGAGGCTGACTATTACTGTCAATCAGGAGACAGCAGTG GTACTTATCTAGTTTTCGGCGGAGGGACCAAGCTGACCGT CCTA |
| EV-D68-85 | 27 | heavy | GAGGTACAGCTCTTGGAGTCTGGGGGAGGCTTGGTACAGC CTGGGGGGTCCCTGAGACTCTCCTGTGCAGCCTCTGGATT CAAATTTAGAAACTATGCCATGACCTGGGTCCGCCAGGCT CCAGGGAAGGGGCTGGAGTGGGTCTCAACTATTACTAGTG GTGGTAGTACAGAGTACGCAGACGCCGTGAAGGGCCGGT TCATCATCTCCAGAGACAATTCCAAGAACACGTTATATTTG CAAATGAACAGCCTGAGAGCCGACGACACGGCCGTATATT ACTGTACAGTGCCGTGGGGTAACTACAATGACTACGTGTCT GACTACTGGGGCCAGGGAACCCTGGTCCCCGTCTCCTCA |
| | 28 | light | GAAGTTGTATTGACACAGTCTCCAGCCACCCTGTCTTTGTC TCCAGGGCAAAGAGCCACCCTCTCCTGCAGGGCCAGTCAG CGTGTTGGCAACTCCTTAGCCTGGTACCAACAAAAACCTG GCCAGGCTCCCAGCCTCCTCATCTATGATGCTTCCAAGAG GGCCACTGGCATCCCAGCCAGGTTCAGTGGCAGTGGGTCT GGGACAGACTTCACTCTCACCATCATCAGCCTAGAGTCTGA AGATTTTGCAGTTTATTACTGTCACCAACATAGCACCTGGC CTCGGGGGACCTTCGGCCAAGGGACACGACTGGAGATTAA A |
| EV-D68-88 | 29 | heavy | CAGGTGCACCTGGTTGAGTCTGGGGGAGGCGTGGTCCAG CCTGGGAGGTCCCTGAGACTCTCCTGTGCAGCCTCTGGAT TCATCTTCAGTAGATATCCTATGCACTGGGTCCGCCAGGCT CCAGGCAAGGGTCTGGAGTGGGTGGCACTTATATCATATG ATGGAAACAATAAATACTACGCAGACTCCGTGAAGGGCCG ATTCACCATCTCCAGAGACAATTCCAAGAACACGCTGTTTC TCCAAATGAACAGCCTGAGAGCTGAGGACACGGCTGTCTA TTACTGTGCGAGACATTTCCTCCCATATAGCAGTAGTTGGT ACCAGGGCTTTAACTACTGGGGCCAGGGAATCCTGGTCAC CGTCTCCTCA |
| | 30 | light | AATTTTATGCTGACTCAGCCCCACTCTGTGTCGGAGTCTCC GGGGAAGACGGTAACCATCTCCTGCACCCGCAGCAGTGG CAGCATTGCCACCAACTATGTGCAGTGGTACCAGCAGCGC CCGGGCAGTTCCCCCACCCCTATAATCTTTGAAGATAGTCA AAGACCGTCTGGGGTCCCTGATCGGTTCTCTGGCTCCATC GACAGCTCCTCCAATTCTGCCTCCCTCACCATCTCTGGACT GAGGACTGACGACGAGGCTGACTACTACTGTCAGTCTTAT GATAACAGCAATCGGGCTGTTGTATTCGGCGGAGGGACCA AGCTGACCGTCCTA |
| EV-D68-89 | 31 | heavy | CAGGTGCAGCTGGTGGAGTCTGGGGGAGGCGTGGTCCAG CCTGGGAGGTCCCTGAGACTCTCCTGTGAAGCGTCTGGAT TCCTCTTCAGTCGCTATGGCATGCACTGGGTCCGCCAGGC TCCAGGCAAGGGGCTGGACTGGGTGGCAGTTATATCGTAT GATGGAAATAAGAAATATTATGCAGACTCTGTGAAGGGCCG ATTCACCATCTCCAGAGACAATTCAAAGAACACGTTGTATC TGCAAGTGAACAGCCTGAGAGTCGAGGACACGGCTGTTTA TTACTGTGCGAGAGGTGTCCCGTACGGTGACACCCTTACA GGGCTTGTCTACTGGGGCCAGGGAACCCTGGTCACCGTCT CCTCA |
| | 32 | light | AATTTTATGCTGACTCAGCCGCACTCTGTGTCGGAGTCTCC GGGGAAGACGGTAACCATCTCCTGCACCCGCAGCAGTGG CACCATTGCCAGCAACTATGTGCAGTGGTACCAGCAGCGC CCGGGCAGTGCCCCCACCACTGTAATCTATGAGGATAACC AAAGACCCTCTGGGGTCCCTGATCGGTTCTCTGGCTCCAT CGACAGCTCCTCCAACTCTGCCTCCCTCACCATCTCTGGA CTGAAGACTGAGGACGAGGCTGACTACTACTGTCAGTCTT ATGATAACAGCGATCGGGTGTTCGGCGGAGGGACCAAGCT GACCGTCCTT |
| EV-D68-95 | 33 | heavy | CAGGTCACCTTGAAGGAGTCTGGTCCTGTGCTGGTGAAAC CCACAGAGACCCTCACGCTGACCTGCACCGTCTCTGGGTT CTCACTCAGGAACGCTAGAATGGGAGTGAGCTGGATCCGT CAGCCCCCAGGGAAGGCCCTGGAGTGGCTTGCACACATTT TTTCGAATGACGAAAAATCCTACAACACATCTCTGAAGAGC AGACTCTCCATCTCCAAGGACACCTCCAAAAGCCAGGTGG TCCTTACCATGACCAGCATGGACCCTTTGGACACAGCCAC ATATTTCTGTGCACGGCTACTGGTGGCTGGTACTTTCCTCC CCTCTCACTACTTTGACTACTGGGGCCAAGGAATCCTGGTC ACCGTCTCCTCA |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| | 34 | light | TCCTATGTGCTGACTCAGCCACCCTCAGTGTCAGTGACCC CAGGAAAGACGGCCAGGATTACCTGTGGGGGAAACAACAT TGGACTTAAAAGTGTCTTCTGGTACCAGGAGAGGCCAGAC CAGGCCCCTGTGGTGGTCATCTATTATGATAGCGCCCGGC CCCTCAGGGATCCCTGAGCGAATCTCTGGCTCCAAGTCTGG GAACACGGCCACCCTGACCATCACCAGGGTCGAAGCCGG GGATGAGGCCGACTATTTTTGTCAGGTGTGGGATAGTAGT CGTAATCATCCGGTCTTCGGCGGAGGGACCAAACTGACCG TCCTC |
| EV-D68-97 | 35 | heavy | GAGCTGCAGCTGGTGGAGTCTGGGGGAGGCTTGGTACAG CCTGGGGGGTCCCTGAGACTCTCCTGTGCAGCCTCTGGAT TCACCTTCAGTACCTATAGCATGAATTGGGTCCGCCAGGCT CCAGGGAAGGGGCTGGAGTGGGTTTCATACATTAGTAGTA GTAGTAGTACCATACAGTACGCAGACTCTGTGAAGGGCCG ATTCACCATCTCCAGAGACAATGCCAAGAACTCACTGTATC TGCAAATGAATAGCCTGAGAGCCGAAGACACGGCCGTGTA TTATTGTACGAGACAGGTCGGGGCGGATTTCAGTGGCCGC GGCTTTGACTACTGGGGCCAGGGAACCCTGCTCACCGTCT CCTCA |
| | 36 | light | TCCTATGAGCTGACTCAGCCACCCTCAGTGTCCGTGTCCC CAGGACAGACAGCCACCATCACCTGCTTTGGAGATAAATT GGGGGATAAATATGCTTGCTGGTATCAGCAGAAGCCAGGC CAGTCCCCTGTGTTGGTCATCTACCAAGATAGCAAGCGGC CCTCAGGGATCCCTGAGCGATTCTCTGGCTCCAAGTCTGG GAACACAGCCACTCTGACCATCAGCGGGACCCAGGCAATG GATGAGGCTGACTATTACT-GT-CAGGCGTGGGACAGCAGCACTGCAGTGTTCGGCGGAGGG ACCAAGCTGACCGTCCTC |
| EV-D68-98 | 37 | heavy | GAGGTACAACTAGTGGAGTCAGGGGGAGGCTTGGTACAG CCTGGGGGGTCCCTGAGACTCTCCTGTGCAGCCTCTGGAT TCAAGTTTTCCGTCTATGCCTTGAGTTGGGTCCGCCAGGCT CCAGGGAAGGGGCTGGAGTGGATTTCATATATTAGTAGTA GTGGTTCTACCATATATTATTCAGACTCTGTGAAGGGCCGA TTCACCATCTCCAGAGACAATGTCGGGAACTCACTGTTTGT GCAAATGAACAGCCTGAGAGCCGAGGACACGGGTATTTAT TACTGTGCGACAGCCCGCCACATCACCAATGATGGTTTTGA TATTTGGGGCCAAGGGACAATGGTCATCGTCTCTTCA |
| | 38 | light | GACATCCAGTTGACCCAGTCTCCATCCTTCCTGTCTGCATC TGTAGGAGACAGAGTCACCATCACTTGCCGGGCCAGTCAG GGCATTAGTAGGTTTTTAGCCTGGTATCAGCAGAAACCAGG GAAAGCCCCTAAGCTCCTGATCTATTCTGCGTCCACTTTAC AAAGGGGGGTCCCATCAAGGTTCAGCGGCAGTGGATTTGG GACAGATTTCACTCTCACAATCAGTAGCCTTCAGCCTGAAG ATTTTGCAACTTATTACTGTCAACAACTTAATAGTCACCCCC GAATGTTCACTTTCGGCCCTGGGACCACAGTGGATATCAA G |
| EV-D68-105 | 39 | heavy | CAGGTGCAGCTGCAGGAGTCGGGCCCAGGACTGGTGAAG CCTTCGGAGACCCTGTCCCTCACCTGCGCTGTGTCTGGTT ACTTAATCAGCAATGGTTACTACTGGGGCTGGATCCGGCA GCCCCCCGGGAAGGGGCTGGAGTGGATTGGGAGTATCTA TCATACTAGAAGCACCTACTACAACCCGTCCCTCAAGAGTC GAGTCAGCATCTCAGTAGACACGTCCAAGAACCGGTTCTC CCTGAGGCTGAGGTCTGTGACCGCCGCAGACACGGCCTTT TATTACTGTGCGAGAGGCCCAGGCCACTGTTATGGTGATG ACGACTGCTACGCGTACTACTTTGACCAGTGGGGCCAGGG AACCCCGGTCACCGTCTCCCCA |
| | 40 | light | GACATCCAGATGACCCAGTCTCCATCTTCCGTGTCTTCATC TGTAGGAGACAGAGTCACCATCACTTGTCGGGCGAGTCAG GGTATTAGCAACTGGTTAGCCTGGTATCAGCAGAACCCAG GGAAAGCTCCTAAACTCCTGATCTATGATGCCTCCAGTTTG CAAAGTGGGGTCCCATCAAGGTTCAGCGGCAGTGGATCTG GGACAGATTTCACTCTCACCATCAACAGCCTGCAGCCTGAA GATTTTGCAACTTACTATTGTCAACAGGCTAACAGTTTCCCT TTCACTTTCGGCCCTGGGACCAAAGTGGATATCAAA |
| EV-D68-110 | 41 | heavy | CAGGTGCAGCTGGTGCAGTCTGGGGCTGAGGTGAAGAAG CCTGGGTCCTCGGTGAAGGTCTCCTGCAAGGCTTCTGGAG GCACCTTCAGCAGGTTTGCTATCAGCTGGGTGCGACAGGC CCCTGGACAAGGGCTTCAGTGGATGGGAGGGATCCTCCCT ATCTTTGGTACAGCAAACTACGCACAGAAGTTCCAGGGCA GAGTCACGATTACCGCGGACACATCCACGAGCACAGCCTA CATGGAGCTGAGCAGCCTGAGATCTGAGGACACGGCCGT |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| | | | GTATTACTGTGCGAGATCCCTCCCCTATTGTACTAATGATG<br>TATGCTCAAACCAGAACACATTTGACTACTGGGGCCAGGG<br>AACCCTGGTCACCGTCTCCTCA |
| | 42 | light | TCCTATGAGCTGACACAGCCACCCTCGGTGTCAGTGTCCC<br>CAGGACAGGCGGCCAGGATCACCTGCTCTGGAGATGCATT<br>GCCTAAGCAATATGCTTATTGGTACCAGCAGAAGCCAGGC<br>CAGGCCCCTGTGTTGGTGATATATGAAGACAATAAGAGGC<br>CCTCAGGGATCCCTGAGCGATTCTCTGGCTCCAGCTCAGG<br>GACAACAGTCACGTTGACCATCAGTGGAGTCCAGGCAGAA<br>GACGAGGCTGACTATTACTGTCAATCAGCAGACAGCAGTG<br>GTACTTATGTGGTATTCGGCGGAGGGACCAAGCTGACCGT<br>CCTA |
| EV-D68-111 | 43 | heavy | CAGGTGCAGCTGCAGGAGTCGGGCCCAGGACTGGTGAAG<br>CCTTCACAGACCCTGTCCCTCACCTGCACTGTCTCTGGTG<br>GCTCCATCAGCAGTGGTGATTACTACTGGAGTTGGATCCG<br>CCAGCCCCCAGGGAAGGGCCTGGAGTGGATTGGGTACAT<br>CTATTACAGTGGGAGCACCTACTACAACCCGTCCCTCAAGA<br>GTCGAGTTACCATATCAGTAGACACGTCCAAGAACCAGTTC<br>TCCCTGAAGCTGAGCTCTGTGACTGCCGCAGACACGGCCG<br>TGTATTACTGTGCCAGCCGCTACGGTGACCCGATAGGGGA<br>CAACTGGTTCGACCCCTGGGGCCAGGGAACCCTGGTCAC<br>CGTCTCCTCA |
| | 44 | light | TCCTATGTGCTGACTCAGCCACCCTCAGTGTCAGTGACCC<br>CAGGAAAGACGGCCAGGATTACCTGTGGGGGAAACAACAT<br>TGGACTTAAAAGTGTCTTCTGGTACCAGGAGAGGCCAGAC<br>CAGGCCCCTGTGGTGGTCATCTATTATGATAGCGCCCGGC<br>CCTCAGGGATCCCTGAGCGAATCTCTGGCTCCAAGTCTGG<br>GAACACGGCCACCCTGACCATCACCAGGGTCGAAGCCGG<br>GGATGAGGCCGACTATTTTTGTCAGGTGTGGGATAGTAGT<br>CGTAATCATCCGGTCTTCGGCGGAGGGACCAAACTGACCG<br>TCCTC |
| EV-D68-114 | 45 | heavy | GAGGTGCAACTGTTGGAGTCGGGGGAGGCTTGGTGCAG<br>CCGGGGGGGTCCCTGAGACTCTCCTGCGCAGCCTCCGGA<br>TTCAGGTTTAGCTTCTATGGCATGACCTGGGTCCGCCAGG<br>CTCCAGGGAAGGGGCTGGAGTGGGTCTCAAGTATTAGTGG<br>TACTGGTGCTACCAGAAACTGCGCAGACTCCGTGAAGGGC<br>CGGTTCACCATCTCCAGAGACAACTCCAAGAACACGCTGT<br>ACCTGCAAATGGACAGCCTGAGAGTCGACGACACGGCCGT<br>TTTTTATTGTGTGAGACGGTTCCCGATGACCACGGTGACAA<br>GCTTTGACTCTTGGGGCCAGGGAACCCTGGTCACCGTCTC<br>CTCA |
| | 46 | light | CAGTCTGCCCTGACTCAGCCTCGCTCAGTGTCCGGGTCTC<br>CTGGACAGTCAGTCACCATCTCCTGCACTGGAACCAGCAG<br>TGATGTTGGTGGTTATAACTTTGTCTCCTGGTACCAACAAC<br>ACCCGGGCAAAGCCCCCAAACTCATGATTTTTGATGTCACT<br>GGGCGGCCCTCAGGGGTCCCTGATCGCTTCTCTGGCTCCA<br>AGTCTGGCAACACGGCCTCCCTGACCATCGCTGGGCTCCA<br>GGCTGAAGATGAGGCTGATTATTATTGTGGCGCATATGCG<br>GGCTTTAACGCTCTTTTCGGCGGAGGGACCAAACTGACCG<br>TCCTA |
| EV-D68-116 | 47 | heavy | GAGGTGCAGCTGGTGCAGTCGGGGGAGGCTTGGTCCGG<br>CCGGGGGGGTCCGTGAGACTCTCCTGTGTAGCCTCTGGAT<br>TCCCCTTCAATATGTTTTGGATGGGCTGGGTCCGCCAGACT<br>CCAGGGAAGGGACTGGAGTGGGTGGCCAATATAAAACAG<br>GATGGCAGTGAGAAATACTATGTCGACTCCGTGAAGGGCC<br>GATTCGCCATCTCCAGAGACAATGCCAAGAACTCTCTCTTT<br>CTTCAAATGGACAGCCTGAGTGTCGGGGACACGGCCATCT<br>ATTATTGTGTCAGAGAGGGGGTGCGAAGGGTCGTCGTACG<br>TAGTACCGGTTACTTCGACTTTTGGGGCCAGGGGACAGCTG<br>GTCACCGTCTCCTCA |
| | 48 | light | TCCTATGAGCTGACACAGCCACCCTCGATGTCAGTGTCCC<br>CAGGACAAACGGCCAGGATCACCTGCTCTGGAGATGCAGT<br>GCCAATAAAATATGTTTATTGGTACCAACAGAGGTCAGGCC<br>AGGCCCCTGTATTAGTCATCTATGAAGACGACAGACGACC<br>CTCCGGGATCTCTGAGAGATTCTCTGGCTCCAGTTCAGGG<br>ACAACGGCCACCTTGACTATCACTGGGGCCCAGGTGGAGG<br>ATGAAGGTGACTACTATTGCTATTCAACAGACAGTAGTGGT<br>TATCAGAGAGCGTTCGGCGGGGGGACCACGCTGACCGTC<br>CTA |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| EV-D68-150 | 49 | heavy | CGGGTGCAGCTGCAGGAGTCGGCCCCAGGACTGGTGAGG<br>CCTTCAGAGACCCTGTCCCTCACCTGCAGTGTCTCTGGTG<br>GCCCCATCAGCAATGGTCCTTATTACTGGAGCTGGATCCG<br>CCAGCACCCAGGGAAGGGCCTGGAGTGGATTGGATTCATC<br>TTTTACAGTGGGAGCACCAACTACAACCCGTCCCTCCGGG<br>GGCGCGTAACCATGGCAGTGGACACGTCTAAGAACCAGTT<br>CTCCCTGAGGCTGAACTCTGTGACTGCCGCGGACACGGCC<br>GTTTATTACTGTGCGAGACATGTGGTGACTGCGTCGGGGT<br>GGTTCGACCCCTGGGGCCAGGGAACCCTGGTCACCGTCT<br>CCTCA |
|  | 50 | light | GAAATTGTGTTGACACAGTCTCCAGCCACCCTGTCTTTGTC<br>TCCAGGGGAAAGAGCCACCCTCTCCTGCAGGGCCAGTCA<br>GAGTGTTGGCACCGACTTAGCCTGGTACCAACAGAAACCT<br>GGCCAGGCTCCCAGGGTCCTCATCTATGATGCATTCAAGA<br>GGGCCACTGGCATCCCAGCCAGGTTCAGTGGCAGTGGGT<br>CTGGGACAGAGTTCACTCTCACCATCAGCAGCCTCGAGCC<br>TGAAGATTTTGCAGTTTATTACTGTCAGCAGCGTAGCAGGT<br>GGCCTCCCCCGTACACTTTTGGCCAGGGGACCAAGCTGGA<br>GATCAAA |
| EV-D68-151 | 51 | heavy | CGGGTGCAGCTGCAGGAGTCGGCCCCAGGACTGGTGAGG<br>CCTTCAGAGACCCTGTCCCTCACCTGCAGTGTCTCTGGTG<br>GCCCCATCAGCAATGGTCCTTATTACTGGAGCTGGATCCG<br>CCAGCACCCAGGGAAGGGCCTGGAGTGGATTGGATTCATC<br>TTTTACAGTGGGAGCACCAACTACAACCCGTCCCTCCGGG<br>GGCGCGTAACCATGGCAGTGGACACGTCTAAGAACCAGTT<br>CTCCCTGAGGCTGAACTCTGTGACTGCCGCGGACACGGCC<br>GTTTATTACTGTGCGAGACATGTGGTGACTGCGTCGGGGT<br>GGTTCGACCCCTGGGGCCAGGGAACCCTGGTCACCGTCT<br>CCTCA |
|  | 52 | light | GAAATTGTGTTGACACAGTCTCCAGCCACCCTGTCTTTGTC<br>TCCAGGGGAAAGAGCCACCCTCTCCTGCAGGGCCAGTCA<br>GAGTGTTGGCACCGACTTAGCCTGGTACCAACAGAAACCT<br>GGCCAGGCTCCCAGGGTCCTCATCTATGATGCATTCAAGA<br>GGGCCACTGGCATCCCAGCCAGGTTCAGTGGCAGTGGGT<br>CTGGGACAGAGTTCACTCTCACCATCAGCAGCCTCGAGCC<br>TGAAGATTTTGCAGTTTATTACTGTCAGCAGCGTAGCAGGT<br>GGCCTCCCCCGTACACTTTTGGCCAGGGGACCAAGCTGGA<br>GATCAAA |
| EV-D68-152 | 53 | heavy | CAGGTGCATCTGGTGGAGTCTGGGGGAGGCGTGGTCCAG<br>CCTGGGAGGTCCCTGAGACTCTCCTGTGCAGACTCTGGAG<br>TCACCTTCAGTGACAATGCTTTGTACTGGGTCCGCCAGGCT<br>CCAGGCAAGGGGCTGGAGTGGGTCGCAGTTATCTCATATG<br>ATGGAAGCAGTAGATACTACGCAGACTCCGTGAGGGGCCG<br>GTTCACCATATCCAGAGACAATTCCAAGGACACGCTGTATC<br>TGCAAATGAACGACTGAGAGCTGAGGACACGGCTATTTAT<br>TACTGTGCGAGAGTCACAGCGGATTACTATGAGAGTAGTG<br>GCAAGGTGTTTTGGGGCCAGGGAGCCCTGGTCGTCGTCTC<br>CTCA |
|  | 54 | light | GACATCCAGATGACCCAGTCTCCTTCCACCCTGTCTGCATC<br>TGTGGGGGACAGAGTCTCCATCACTTGCCGGGCCAGTCAG<br>AGTGTTAGGAGCTGGTTGGCCTGGTATCAGCACAAACCAG<br>GGAAAGCCCCTAAACTCCTGATCTATAAGGCGTCTAGTTTA<br>GAAAGTGGGGTCCCATCAAGGTTCAGCGGCAGTGGATCTG<br>GGACAGAATTCACTCTCACCATCAGCAGCCTGCAGGCTGA<br>TGATTTTGCAACTTATTACTGCCAACAGTATCAGACTTTTC<br>CTGGACGTTCGGCCAAGGGACCACGGTGGAAGTCAAA |
| EV-D68-154 | 55 | heavy | CAGGTGCAGCTGCAGGAGTCGGGCCCAGCACTGGTGAAG<br>CCTTCGGAGACCCTGTCCCTCACCTGCACTGTCTCTGGTG<br>GCTCCATCAGTGATCACTACTGGAGCTGGATCCGGCAGCC<br>CCCAGGGAAGGGACTGGAGTGGATTGGCTACATCTATACC<br>AGTGGGACCACCAACTACAACCCCTCCCTCAAGAGTCGAG<br>TCACCATATCAGTAGACACATCCAAGAAGCAGTTCTCCCTG<br>AATCTGAGGTCTGTGACCGCCGCAGACACGGCCGTGTATT<br>ACTGTGCGAGAAGTCTAGAAACGGTGATCCGTTTCTACTAC<br>TACCACTACATGGACGTCTGGGGCAAAGGGACCACGGTGA<br>TCGTCTCATCA |
|  | 56 | light | GATATTGTGATGACTCAGTCTCCACTCTCCCTGCCCGTCAC<br>CCCTGGAGAGCCGGCCTCCATCTCCTGCAGGTCTAGTCAG<br>AGCCTCCTGCAGAGTGATGGGTACAGCTATTTGGATTGGT<br>ACCTGCAGAAGCCAGGGCAGTCTCCACAGCTCCTGATCTA<br>TTTGGGTTCTAATCGGGCCTCCGGGGTCCCTGACAGGTTC<br>AGTGTCATTGGATCAGGCACATATTTTACACTGAAAATCAG |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| | | | CAGAGTGGAGGCTGAGGATGTTGGCGTTTATTTCTGCATG<br>CAAGCTCTACAAACTCCGTGGACGTTCGGCCAAGGGACCA<br>AGGTGGAAATCAAA |
| EV-D68-155 | 57 | heavy | CAGGTGCAGCTGCAGGAGTCGGGCCCAGGACTGGTGAAG<br>CCTTCGGAGACCCTGTCCCTCACCTGCACTGTCGCTGGCG<br>GCTCCATCGGTGATTACCACTGGAACTGGATCCGGCAGCC<br>CGCCGGGAAGGGGCTGGAGTGGATTGGGCGTATACATAG<br>CAGTGGGAACACTGACTACAACCCCTCCCTCAAGAGTCGA<br>GTCACCATGTCAGTAGACACGTCCAAGAACCAGTTCTCCCT<br>GAAACTGAGGTCTGTGACCGCCGCGGACACGGCCGTGTAT<br>TACTGTGCGAGGCAAAATGTTTTTGATATCTGGGGCCAAGG<br>GACAATGGTCACCGTCTCTTCA |
| | 58 | light | GACATCGTGATGACCCAGTCTCCAGACTCCCTGGCTCTGT<br>CTCTGGGCGAGAGGGCCACCATCAACTGCAAGTCCAGCCA<br>GAGTGTTTTATTCAGCTCCAACAATAAGAACTACTTAGCTTG<br>GTACCAGCAGAAACCAGGACAGCCTCCTAAGTTGCTCATTT<br>ACTGGGCATCTACCCGGGAATCGGGGTCCCTGACCGATT<br>CAGTGGCAGCGGGTCTGAGACAGATTTCACTCTCACCATC<br>AGCAGCCTGCAGGCTGAAGATGTGGCAGTTTATTTCTGTCA<br>GCAATTTTATACTACTCCGCTCACTTTCGGCGGAGGGACCA<br>AGGTGGAGATCAAA |
| EV-D68-156 | 59 | heavy | CAGGTACAGATGCAGGAGTCGGGCCCAGGGCTGGTGAAG<br>GCTTCGGAGACCCTGTCCCTCACCTGCAGTGTCTCTGGTA<br>TCTCCATCAATAACTACTATTGGAGTTGGTTCCGCCAGCCC<br>CCCGGGAAGGGCCTGGAGTGGATCGGATATGTCTATTCTA<br>CTGGGAGTTCCAAGTACAATCCCTCCCTCGAGCGTCGAGC<br>CACCATGTCAGTAGACACGTCCAACAACAACTTCTCCCTGA<br>GGCTGACGTCTGTGACCACTGCGGACACGGCCGTCTACTA<br>CTGTGCGCGGGGAGTATGCCGCATATCTGGGGCCAGGG<br>CCTCCTGGTCACCGTCTCCTCA |
| | 60 | light | CAGTCTGTGCTGACTCAGCCACCCTCAGCGTCCGGGACCC<br>CCGGACAGAGGGTCACCATCTCCTGTTCTGGTAGCACCTC<br>CAACATCGAGACTAATTATGTATACTGGTACCAGCAGGTCC<br>CAGGAACGGCCCCCAAGCCCCTCGTCTATAGGAATGATCA<br>GCGCCCCTCGGGGGTCCCTGACCGATTCTCTGGCTCCAAG<br>TCTGGCACCTCGGCCTCCCTGGTCATCAGTGGGCTCCGGA<br>CCGAGGATGAGGCTGCTTATTATTGTGCAGCTTGGGATGA<br>CAGTCTGAAAGCTCCGGTCTTCGGAGCTGGGACCAAGGTC<br>GCCGTCCTC |
| EV-D68-157 | 61 | heavy | GAGGTGCAGCTGGTGGAGTCTGGGGGAGGCTTGATAAAG<br>CCGGGGGGGTCCCTTAGACTCTCCTGTGCAGCCTCTGGAA<br>TCACTTTCAGTAACGCCTGGATGAGCTGGGTCCGCCAGGC<br>TCCAGGGAAGGGGCTGGAATGGGTTGGCCGTATTGAAAGC<br>AAAATTGACGGTGGGACAATAGACTACGCTACACCCGTGA<br>AAGGCAGATTCACCATCTCAAGAGATGATTCAAAAAACACG<br>CTGTACCTGCAAATGAACAGCCTGAAAACCGAGGACACAG<br>CCGTCTATTACTGTACCACAGACCAGGGCTACTATGATAGA<br>AGTGGTTATTGGGTCGTCGGGAACCACTTTGACTACTGGG<br>GCCAGGGAATCCTGGTCACCGTCTCCTCA |
| | 62 | light | CAGTCTGTGCTGACGCAGCCGCCCTCAGTGTCTGGGGCC<br>CCAGGGCTGAGGGTCACCATCTCCTGTACTGGGAGCAGCA<br>CCAACATCGGGGCAGGTTATGATGTACACTGGTACCAGCA<br>CCTTCCAGGAACAGCCCCCAAACTCCTCATCTATGGTAACA<br>GCAATCGGCCCTCAGGGGTCCCTGACCGATTCTCTGGCTC<br>CAAGTCTGGCACCTCAGCCTCCCTGGCCATCACTGGGCTC<br>CAGGCTGACGATGCGGCTGATTATTACTGCCAGTCCTATG<br>ACAGAAGCCTGAGTACTTATGTCTTCGGAACTGGGACCAA<br>GGTCACCGTCCTA |
| EV-D68-158 | 63 | heavy | GAGGTGCAGCTGTTGGAGTCTGGGGGAGGCTTGGTACAG<br>CCTGGGGGGTCCCTGAGACTCTCCTGTGCAGCCTCTGGAT<br>TCACCTTTAGCAGCTATGCCATGAACTGGGTCCGCCAGGC<br>TCCAGGGAAGGGGCTGGAGTGGGTCTCAGGTATTAGTGGT<br>ACTACAGGTAGCACATACTACGCAGACTCCGTGAAGGGCC<br>GGTTCACCATCTCCAGAGACAATTCCAAGAACACGGTGCAT<br>CTGCAAATGAACAGCCTGAGAGCCGAGGACACGGCCGTAT<br>ATTACTGTGCGAAAGATTCTCACTCCATGATAGTAGTTGAT<br>CATGCTTTTGATATCTGGGGCCAAGGGACAATGGTCACCG<br>TCTCTTCA |
| | 64 | light | TCCTATGTGCTGACTCAGCCACCCTCGGTGTCAGTGGCCC<br>CAGGACAGACGGCCAGGATTACCTGTGGGGGAAACAATAT<br>TGGAACTAAAAGTGTGCACTGGTACCAGCAGAGGCCAGGC |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| | | | CAGGCCCCTGTGCTGGTCGTCTATGATGATAGCGACCGGC<br>CCTCAGGGATCCCTGAGCGATTCTCTGGCTCCAACTCTGG<br>GAACACGGCCACCCTGACCATCAGCAGGGTCGAAGCCGG<br>GGATGAGGCCGACTATTACTGTCAGGTGTGGGATAGTTAT<br>AATGTTCATTATGTCTTCGGAACAGGGACCAAGGTCACCGT<br>CCTA |
| EV-D68-159 | 65 | heavy | GAGGTGCAGCTGGTGGAGTCTGGGGGGGCCTGGTCAAG<br>CCGGGGGGGTCCCTGAGACTCTCCTGTGCAGCCTCTGGAT<br>TCACCTTCAGTACTTATATCATGACCTGGGTCCGCCAGGCC<br>CCAGGGAGGGGGCTGGAGTGGGTCTCATCCATTAGTACCA<br>GTAGTGTTTACACATTCTATGCAGATTCACTGAAGGGCCGG<br>TTCACCATCTCCAGAGACAACGCCAAGAATTCAGTGTATCT<br>GCAGATGAACAGCCTGAGAGCCGACGACACGGCTGTTTAT<br>TACTGTGCGAGGGAAGAAGGGTTTCGAGCTTATAACCTATA<br>CTGGGGCCAGGGAACCCTGGTCACTGTCTCCTCA |
| | 66 | light | CAGTCTGTGCTGACTCAGCCACCGTCAGCGTCTGGGACCC<br>CCGGGCAGAGGGTCACCATCTCTTGTTCTGGAAGCAGCTC<br>CAACATCGAATACAATTATGTTTACTGGTACCAGAAATTCCC<br>AGGAACGGCCCCCAAACTCCTCATCTATAAAAATAATCAGC<br>GGCCCTCAGGGGTCCCTGACCGATTCTCTGGCTCCAAGTC<br>TGGCACCTCAGCCTCCCTGGCCATTAGTGGGCTCCGGTCC<br>GAGGATGAGGGTGATTATTACTGTCAGCATGGGATGACA<br>TCCTGAGTGGTGTGGTTTTCGGCGGGGGGACCAAGCTGAC<br>CGTCCTC |
| EV-D68-160 | 67 | heavy | CAGGTGCAGCTGGTGGAGTCTGGGGGAGGCGTGGTCCAG<br>CCTGGGAGGTCCCAGAAACTCTCCTGTGCAGCCTCTGGAT<br>TCACGTTCAGTAGGTTTGGTATGCACTGGGTCCGCCAGGC<br>TCCAGGCAAGGGGCTGGAGTGGGTGGCAGTTATTTCGTTT<br>GATGGAAGTAATAGATACTACGCAGACTCCGTGAAGGGGC<br>GATTCACCATCACCAGAGACAATTCCAAGAACACATTGTAT<br>CTGCAAATGAACAACCTGAGACCTGAGGACACGGCTGTAT<br>ATTACTGCGCGAGAGATTGGGATAGGCTGGTTCGTTCGGC<br>GGTTGGCTACTGGGGCCAGGGAACCCTGGTCAGCGTCTC<br>CTCA |
| | 68 | light | CAGTCTGCCCTGACTCAGCCTCGCTCAGTGTCCGGGTCTC<br>CTGGACAGTCAGTCACCATCTCCTGCACTGGAACCAGTAAT<br>GATGTTGGTGGTTATAACTTTGTCTCCTGGTATCAGCAACA<br>CCCAGGCAAAGCCCCCAAACTAATGATTTTTGATGTCATTA<br>GGCGGCCCTCAGGGGTCCCTGGTCGCTTCTCTGGCTCCAA<br>GTCTGGCGACACGGCCTCCCTTATCATCTCTGGACTCCAG<br>GCTGAGGATGAGGCTGATTATTACTGCTGCTCATATGCAG<br>GCACCTACACCTGGGTATTCGGCGCAGGGACCACACTGAC<br>CGTCCTA |
| EV-D68-161 | 69 | heavy | CAGGTGCACCTGCAGGAGTCGGGCCCACGACTGGTGAAG<br>CCTTCGGAGACCCTGTCCCTCACCTGCACTGTCTCTGGTG<br>GCTCCGTCAGCACTGCCACTTACTACTGGAGCTGGATCCG<br>GCAGTCCCCAGGGAGGGGACTGGAGTGGATAGGATATATC<br>TATTCCAGTGGTAACACCAACTACAACCCCTCCCTTAAGAG<br>TCGAGTCACCATTTCTTTAGACACGCCCAACAACCAGCTCT<br>CCCTGACGTTGACCTCTGTGACCGCTGCGGACACGGCCAT<br>TTATTATTGTGAGAGGCGCTTACGTATTCTGAGTATTGAGA<br>GGAACTACTACGCTATGGACGTCTGGGGCCAAGGGACCCC<br>GGTCACCGTCTCCTCA |
| | 70 | light | GAAGTTGTGTTGACGCAGACTCCAGGCACCCTGTCTTTGT<br>CTCCGGGGAAGGAGCCACCCTCTCCTGCAGGGCCAGTC<br>AGAGGGTTGTCAACAACTACTTAGCCTGGTACCAGCAGAG<br>AGCTGGCCAGGCTCCCAGGCTCCTCATTTTTGGTGCATCC<br>AACAGGGCCACTGGCATCCCAGACAGGTTCAGTGGCAGTG<br>GGTCTGGGACAGACTTCACTCTCACCATCAGGAAGCTGGA<br>GCCCGAAGATTTTGCAGTGTATTACTGTCAACAATATGGTA<br>GCCCGTGGACGTTCGGCCACGGGACCAAGGTGGAAATGA<br>AA |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| EV-D68-162 | 71 | heavy | CAGGTGCAGCTGGTGGAGTCTGGGGGAGGCGTGGTCCAGCCTGGGAGGTCCCTGAGACTCTCCTGTGCAGCCTCTGGATTCACCTTCAGTAGTTATGCTATGCATTGGGTCCGCCAGGCTCCAGGCAGGGGGCTGGAGTGGGTGGCAGTTATATCATATGATGCAAGCAAGAAATACCACGCAGACTCCGTGAAGGGCCGATTCACAATCTCCAGAGACAGTTCCAAGAACACGCTGTTTCTGCAAATGAATAGCCTGAAACCTGAGGACACGGCTGTGTATTACTGTGCGAGAGATCATGTCCCCCCCAAGGATTGCAGTGATGGTAATTGCCACTCGGACTACGGTATGGACGTCTGGGGCCAAGGGACCACGGTCACCGTCTCCTCA |
| | 72 | light | GACATCCAGATGACCCAGTCGCCTTCCACTATGTCTGCTTCTGTAGGAGACAGAGTCACCATCACTTGCCGGGCCAGTCAGAGTATTAGTAAGTGGTTGGCCTGGTATCAGCAGAAGCCAGGGAAAGCCCCTAAACTCCTGATCTATAAGGCGTCTACCTTACAAACTGGGGTCCCATCAAGGTTCAGCGGCAGTGGATCTGGGACAGAATTCACTCTCACCATCAACAGCCTGCAGCCTGATGATTTTGCAACTTATTACTGCCAACAGCATAATAGTTATTCGTACACTTTTGGCCAGGGGACCAAGGTGGAGATCAAG |
| EV-D68-163 | 73 | heavy | CAGGTCCAGCTTGTGCAGTCTGGGGCTGAGGTGAAGAAGCCTGGGGCCTCAGTGAAGATTTCTTGCAAGGCTTCTGGATACTCCTTCACTAACTTTGCTGTGCATTGGGTGCGCCAGGCCCCCGGACAAAGACTTGAGTGGATGGGATGGATCAACCCTGGCAATAGAAACACAAAGTATTCACACAACTTTCAGGGCAGAGTCACCATTACCAGGGACACATCCGCGAACACAGCCTACATGGAACTGAGCAGCCTGAGATCTCAAGACACGGCTGTGTATTACTGTGCGAGACTTCCGATAGCAGCAGCTGGCAGGGGCTGGTTCGACCCCTGGGGCCAGGGAACCCTGGTCACCGTCTCCTCC |
| | 74 | light | GAAATTGTGTTGACGCAGTCTCCAGGCACCCTGTCTTTGTCTCCAGGGGAAAGAGCCACCCTCTCCTGCAGGGCCAGTCAGAGTGTTATCAGCACCTACTTAGCCTGGTACCAGCAGAGACCTGGCCAGGCTCCCAGGGTCCTCATCTATGATGTATCCACCAGGGCCACTGGCATCCCAGACAGGTTCAGTGGCAGTGGGTCTGGGACAGACTTCACTCTCACCATCAGCAGACTGGAGCCTGAAGATTTTGCAGTCTATTTCTGTCACCAGTATGGTAGTTCACCGGCGACGTTCGGCCAAGGGACCAAGGTGGAAATCAAA |
| EV-D68-164 | 75 | heavy | GAAGTGCAGCTGGTGGAGTCTGGGGGAGACTTGGTACAGCCTGGGGGGTCCCTGAGACTCTCCTGTGCAGCCTCTGGATTCACCTTCAATACTTATGGCATGAACTGGGTCCGCCAGGCTCCAGGGAAGGGACTGGAGTGGGTTTCATACATTAGTAGTGCCACCACTACCTTCTACTACGCAGACTCTGTGAGGGGCCGATTCACCATCTCCAGAGACAATGCCAAGAATTCACTATTTCTGCACATGAAGAGCCTGAGAGACGAAGCACGGCAGTTTATTACTGTGCGAGAGTCTATACTATGCTTCGCGGAGCGAGTATGGACGTCTGGGGCCACGGGACCACGGTCACCGTCTCCTCA |
| | 76 | light | GAAATTGTGTTGACACAGTCTCCAGCCACCCTGTCTTTGTCTCCAGGGGAAAGAGCCACCCTCTCCTGCAGGGCCAGTCAGAGTGTTGGCACCTACCTGGCCTGGTACCAACAGAAACCTGGCCAGGCTCCCAGGCTCCTCATCTATGATTCAGCCAACAGGGCCACTGGCATCCCAGCCCGGTTCAGTGGCAGTGGGTCTGGGACAGACTTCACTCTCACCATCAGCAGCCTAGAGCCTGAAGATTTTGCAGTTTATTACTGTCAGCTGCGCATCACCTGGCCTCCTATATTCACTTTCGGCCCTGGGACCAAAGTGGATGTCAAA |
| EV-D68-165 | 77 | heavy | CAGGTGCACCTGGTGCAGTCTGGGGCTGAGGTGAAGAAGTCTGGGGCCTCAGTGAAGGTCTCCTGCAAGACTTTTGGATACACCTTCACCGCCTACTATATGCACTGGGTGCGACAGGCCCCTGGACAGGGGCCTGAGTGGATGGGATGGATCAACCCTATCAGTGGTGGCACAAACTATGCACAGAAGTTTCAGGGCAGGGTCTCCATGACCAGGGACACGTCCATCAGCACAGCCTACATGGGCCTGAGCAGGCTGAGACCTGACGACACGGCCGTCTATTACTGTGCGAGAGTGAAGTGTAGTAGTGCCAACTGCTATGGGAACTTTGACTACTGGGGCCAGGGTACCCTGGTCACCGTCTCCTCA |
| | 78 | light | CAGTCTGCCCTGACTCAGCCTCCCTCCGCGTCCGGGTCTCCTGGAGAGTCAGTCACCATCTCCTGCACTGGAACCAGCAGTGACGTTGTGGGTTATAACTATGTCTCCTGGTACCAACAACCCCAGGCAAAGCCCCCAAACTCATGATTTATGAGGTCAGTAAGCGGCCCTCAGGGGTCCCTGATCGCTTCTCTGGCTCCAAGTCTGGCAACACGGCCTCCCTGACCGTCTCTGGGCTCCA |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| | | | GGCTGAGGATGAGGCTGATTATTACTGCAGCTCATATGCA<br>GGCAGCAACAATTTGGTATTCGGCGGAGGGACCAAGCTGA<br>CCGTCCTA |
| EV-D68-166 | 79 | heavy | GAGGTGCAGCTGGTGCAGTCTGGAGCAGAGGTGAAAAAG<br>CCCGGTGAGTCTCTGAAGATCTCCTGTAAGGGTTCTGGAT<br>ACAGGTTTACCAACTACCGGATCGGCTGGGTGCGCCAGAT<br>GCCCGGGAAAGGCCTGGAGTGGATGGGGATCATCTATCC<br>CGGTGGCTCTGATACCAGATACAGTCCGTCCCTCCAAGGC<br>CAGGTCACCATGTCAGTCGACAAGTCCATCAGCACCGCCT<br>ACCTGATGTGGAGCAGCCTGAAGGCCTCGGACACCGCCAT<br>GTATTACTGTGCTCGACAGACCACTCAAAATAGTGGCTACG<br>ATAGATGGTTTGACTCCTGGGGCCAGGGAACCCACGTCAC<br>CGTCTCCTCA |
| | 80 | light | CAGTCTGTACTGACTCAGCCACCCTCAGCGTCTGGGACCC<br>CCGGGCAGAGGGTCACCATCTCTTGTTCTGGAAGCACCTC<br>CAGCATCGGAAGTAATATTGTAAATTGGTACCAACACCTCC<br>CAGGAACGGCCCCCAAACTCCTCATCTATATTAATAATCAG<br>CGGCCCTCAGGGGTCCCTGACCGATTCTCTGGCTCCAAGT<br>CTGGCACCTCAGCCTCCCTGGCCATCAGTGGGCTCCAGTC<br>TGAGGATGAGGCTGACTATTACTGTGCAGCATGGGATGAC<br>AGCCTGAATGGTTGGGTGTTCGGCGGAGGGACCAAGCTG<br>ACCGTCCTG |
| EV-D68-181 | 81 | heavy | GAGGTGCAGGTGTTGGAGTCTGGGGGAGGCTTGGTACAG<br>CCTGGGGGGTCCCTGAGACTCTCCTGTGCAGCCTCTGGAA<br>TCACCTTTAGCAGGCATACTATGAGCTGGGTCCGCCAGGC<br>TCCAGGGAAGGGGCTGGAGTGGGTCTCAGCTATTAGTGG<br>GAGTGGTGGTAGCACATATCATGCAGACTCCGTGAAGGGC<br>CGCTTCACCATCTCCAGAGACAGTTCCAAGAGCACGCTGT<br>ATCTGCAAATGAACAGCCTGAGAGCCGAGGACACGGCCGT<br>TTATTACTGTGCGATCTCCGTGCCATTATTACGATTTTTGGA<br>GTGGTTTCAACACCCTTTTGACTTCTGGGGCCAGGGAACC<br>CTGGTCACCGTCTCCTCA |
| | 82 | light | GAAATAGTGATGACGCAGTCTCCAGCCTCCCTGTCTGTGT<br>CTCCAGGGGAAAGAGTCACCCTCTCCTGCAGGGCCAGTCA<br>GAGTGTTGGCAGCACCTTAGCCTGGTACCAGCACAAACCT<br>GGCCAGGCTCCCAGGCTCCTCATCTCTGGTGCATCCACCA<br>GGGCCACTGGTGTCCCAGCCAGGTTCAGTGGCAGTGGGT<br>CTGGGACAGAGTTCACTCTCACCATCAGCAGTCTGCAGTC<br>TGAAGATTTTGCAGTTTACTACTGTCACCAGTATATTAACTG<br>GCCTCCGTGGACGTTCGGCCAAGGGACCAAGGTGGAAAT<br>CAAA |
| EV-D68-183 | 83 | heavy | GAGGTGCGGCTGGTGGAGTCTGGGGGAGGCCTGGTCAAA<br>CCTGGGGGGTCCCTGAGACTCTCCTGTGCAGCCTCTGGAT<br>TCACCTTCAATACATATTCCATGAGCTGGGTCCGCCAGGCT<br>CCAGGGAAGGGGCTGGAGTGGGTCGCCTCCATTAGTAGTA<br>CCGGAAGTTACATATACAATGCAGACTCACTGAAGGGCCG<br>ATTCACCATCTCCAGAGACAACGCCAAGAACTCCCTGTTTC<br>TGCAAATGAACAGCCTGAGAGTCGAAGACACGGCTGTGTA<br>TTACTGTGTGAGATTCACCATGACTACAGTGACTAACTTTG<br>ACTCATGGGGCCAGGGAACCCTGGTCACCGTCTCCTCA |
| | 84 | light | CAGTCTGCCCTGACTCAGCCTCGCTCAGTGTCCGGGTCTC<br>CTGGACAGTCAGTCACCATCTCCTGCACTGGAACCAGCAG<br>TGATGTTGGTGCTTATAGCTATGTCTCCTGGTACCAACAAC<br>ACCCAGGCAAAGCCCCCAAACTCATGATTTATGATGTCTAC<br>AGGCGGCCCTCAGGGGTCCCTGGTCGCTTCTCTGGCTCCA<br>AGTCTGGCAACACGGCCTCCCTGACCGTCTCTGGGCTCCA<br>GGCTGAGGATGAGGCTGATTACTACTGCTGCTCACATGCA<br>GGCAGTCACACCTGGGTGTTCGGCGGAGGGACCAAGGTG<br>ACCGTCCTA |
| EV-D68-185 | 85 | heavy | CAGCTGCAGGTGGTGGCGTCTGGGGGAGGCGTGGTCCAG<br>CCTGGGAGGTCCCTGAGACTCTCCTGTAAAGCCTCTGGAT<br>TCACGTTCACCAATTATGGCATGCACTGGGTTCGCCAGGC<br>GCCAGGCAAGGGGCTGGAGTGGGTGGCTTTTATATCATAC<br>GATGGAGGTAATAAAATTTTATGCAGACTCTGTGAAGGGCCG<br>ATTCACCATCTCCAGAGACAATTCCAGGAACACGGTTTATC<br>TGCAAATGAACAGCCTGAGAGTGGCGGACACGGCTATGTA<br>TTACTGTCCGAAGGTCATCCCCCACCCGTATTATGATAGTA<br>GTGGTGATGATGCTTTTGATATCTGGGGCCAAGGGACAAT<br>GGTCGCCATTTCTTCA |
| | 86 | light | GAAATAGTGATGACGCAGTCTCCAGCCACCCTGTCTGTGT<br>CTCCAGGGGAAAGAGCCACCCTCTCCTGCTGGGCCAGTCA |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| | | | GAGTATTAGCCGCAACTTAGCCTGGTATCAGCAAAAACCTG<br>GCCAGGCTCCCCGACTCCTCATCTATGGTGCATCCACCAG<br>GGCCACTGGTATCCCCGCCAAGTTCAGTGGCAGTGGGTCT<br>GGGACAGACTTCACTCTCACCGTCAGCAGCCTGCAGTCTG<br>AAGACCTTGCAGTTTATTACTGTCAGCAGTATAGTAAGTTG<br>CCTATCACCTTCGGCCAAGGGACACGACTGGAGATTAAA |
| EV-D68-200 | 87 | heavy | GAGGTGCAGCTGGTGGAGTCTGGGGGAGGCTTGGTACAG<br>CCGGGGGGGTCCCTGAGACTCTCCTGTGCAGCCTCTGGAT<br>TCCCCTTTCAGTAGTTATAGCATGAGCTGGGTCCGCCAGGC<br>TCCAGGGAAGGGGCTGGAGTGGGTCTCATACATAAGTGGT<br>AGTGGTGGTGACATATACTACGCAGACTCTGTGAAGGGCC<br>GATTCACCATCTCCAGGGACAATGCCAGGAACTCACTGTCT<br>CTGCAAATGAACAGCCTGAGAGCCGACGACACGGCTGTGT<br>ATTACTGTGCGAGAGGGCTGGTAGCAACAACTGGTACAAG<br>GTACTTTGACTACTGGGGCCAGGGAACCCTGGTCACCGTC<br>TCCTCA |
| | 88 | light | GAAATTGTGTTGACACAGTCTCCAGCCACCCTGTCTTTGTC<br>TCCAGGGGAAAGAGCCACCCTCTCCTGCAGGGCCAGTCA<br>GAGTGTTAGGAGTTACTTAGCCTGGTACCAACAGAGACCT<br>GGCCAGGCTCCCAGGCTCCTCATCTACGATGCATCCAACA<br>GGGCCACTGGCATCCCAGTCAGGTTCAGTGGCAGTGGGT<br>CTGGGACAGACTTCACTCTCACCATCAGCAGCCTAGAGCC<br>TGAAGATTTTGCAGTTTATTACTGTCAGCAGCGTAGCTACT<br>GGCCTCCGTTCACTTTCGGCGGAGGGACCAAGGTGGAGAT<br>CAAA |
| EV-D68-208 | 89 | heavy | CAGGTGCAGCTGGTGCAGTCTGGGGCTGAGGTGAAGAAG<br>CCGGGGTCCTCGGTGAAGGTCTCCTGCAAGGCTTCTGGAG<br>GCACCTTCAGGAGGTTTGCTATCAGCTGGGTGCGACAGGC<br>CCCTGGACAAGGGCTTGAGTGGATGGGAGGGATCATCCCT<br>ATCCTAGGTAGAGGAAAGTACGCACAGAAGTTCCAGGGCA<br>GAGTCAGGATTACCGCGGACGAATCCACGAGCACAGCCTA<br>CATGGAGCTGAGCAGCCTGAGATCTGAAGACACGGCCGTG<br>TATTACTGTGCGAGATTTATTTCGACAGCCTCCTATGTTCC<br>GGGGACCTTCGAGGACGTCTGGGGCCAAGGGACCACGGT<br>CACCGTCTCCTCA |
| | 90 | light | GACATTGTGTTGACACAGTCTCCAGCCACCCTGTCTTTGTC<br>TCCAGGGGAAAGAGCCACCCTCTCCTGCAGGGCCAGTCA<br>GAGTGTTAGCAGCTACTTAGCCTGGTACCAACAGAAACCT<br>GGCCAGGCTCCCAGGCTCCTCATCTATGATGCATCCAACA<br>GGGCCGCTGGCATCCCAGCCAGGTTCAGTGGCAGTGGGT<br>CTGAGACAGACTTCACTCTCACCATCAGCAGCCTAGAGCC<br>TGAAGATGTTGCGGTTTATTACTGTCAGCAGCGTAGCGACT<br>GGCCTCCGGGGACTTTTGGCCAGGGGACCAACGTGGAGA<br>TCAAA |
| EV-D68-210 | 91 | heavy | GAGGTGCAGCTGGTGGAGTCTGGGGGAGGCCTGGTCAAG<br>CCGGGGGGGTCCCTGAGACTCTCCTGTGCAGCCTCTGGAT<br>TCACCTTCAGGAACTATAACATCAACTGGGTCCGCCAGGCT<br>CCAGGGAAGGGGCTGGAGTGGGTCTCATCCATTAGTAGTA<br>CTGGTAGTTACATACACTACGCAGATTAGTGAAGGGCCGA<br>TTCACCATCTCCAGAGACAACGCCAAGAACTCACTGTATCT<br>GCAAATGAACAGCCTGAGAGTCGAGGACACGGCTGTATAT<br>TACTGTGCGCGAATGGTTAGGAATACGGTGACTGCCTTTG<br>ACTACTGGGGCCAGGGAACCCTGGTCTCCGTCTCCTCA |
| | 92 | light | CAGTCTGCCCTGACTCAGCCTGCCTCCGTGTCTGGGTCTC<br>CTGGCCAGTCGATCACCATCTCCTGCACTGGAACCAGCAG<br>TGATGTTGGTGGCTATAACTTTGTCTCCTGGTACCAACAAC<br>AGCCAGGCAGAGCCCCCAAACTCCTTATTTATGAAGTCATT<br>AAGCGGCCCTCAGGGGTTTCTGATCGCTTCTCTGGCTCCA<br>AGTCTGGCGACACGGCCTCCCTGACAATCTCTGGGCTCCA<br>GGCTGAGGACGAGGCTGATTATTACTGCTGCTCATATGGG<br>GGTAACAACTCTTGGATGTTCGGCGGAGGGACCATGCTGA<br>CCGTCCTA |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| EV-D68-219 | 93 | heavy | CAGGTCCAGGTGGTACAGTCTGGGGCTGAGATGAAGAAGC<br>CTGGGGCCTCAGTGAAGGTCTCCTGCAAGGTTTCCGGATA<br>CAGGCTCATTGATTTACCCTTGCACTGGGTGCGACAGGCT<br>CCTGGAAAAGGGCTTGAGTGGATGGGACTTTTTGATCCTG<br>AAAAGGCTGAAGCCATCTACTCACAGAAATTCCAGGACAAG<br>GTCACCATAAGCGAGGACACATCTATCGACACAGCCTACAT<br>GGAACTGAACAGCCTGCGCTCTGAAGACACGGCCGTCTAC<br>TACTGTGCAACTTGGGGAGTTGAGGTGGTGAATGGGAGAA<br>GGGACTACTTTGACTCCTGGGGCCAGGGAACCCTGGTCAC<br>CGTCTCCTCA |
|  | 94 | light | TCCTATGAGCTGACACAGCCACCCTCGGTGTCAGTGTCCC<br>CAGGACAGACGGCCAGGATCACATGCTATGCAGATGTGTT<br>GTCAAACCAATATACTTACTGGTATCAACAGAAGCCAGGCC<br>AGGCCCCTGTGTTGGTGATATATAAAGACACTGAGAGGCC<br>CTCAGGGATCCCTGAGCGATTTGCTGGCTCCAGCTCAGGG<br>ACAACAGTCACCTTAGTCATCAATGGAGTCCGGGCAGAGG<br>ACGAGGCTTACTATTACTGTCAATCAGCCGACAACACCAGA<br>ATTACGGTTTTCGGCGGAGGGACCAAGCTGTCCGTCCTA |
| EV-D68-220 | 95 | heavy | GGGGTGCAGCTGGTGGAGTCTGGGGGAGGATTGATACAG<br>CCTGGAGGGTCCCTGAGACTCTCCTGTGCAGCCTCTGGAT<br>TCACCTTCAGTAGTTTTGAAATGAACTGGGTCCGCCAGGCT<br>CCAGGGAAGGGGCTGGAGTGGGTTTCATACATTAGTACTA<br>GTGGTAGTACCATATACTACGCAGACTCTGTCAAGGGCCG<br>ATTCACCATCTCCAGAGACAACGCCAGGAACTCACTGTCTC<br>TGCAAATGAACAGCCTGAGAGCCGAGGACACGGCTGTTTA<br>TTACTGTGCGAGAGACGTGAGGGATTGTAGTGCTCTTACG<br>TGCCCCCGAAGGGGAGATGCTTYTGATTTCTGGGGCCGTG<br>GGACAAGGGTCACCGTCTCTTCA |
|  | 96 | light | GATGTTGTGATGACTCAGTCTCCACTCTCCCTGCCCGTCAC<br>CCTTGGACAGTCGGCCTCCATCTCCTGCAGGTCTAGTCAA<br>AGCCTCGTATACAGTGATGGAAACACCTACTTGAATTGGTT<br>TCAGCAGAGGCCAGGCCAATCTCCAAGGCGCCTAATTTAT<br>AAGGTTTCTAACCGGGACTCTGGGGTCCCAGACAGATTCA<br>GCGGCAGTGGGTCAGGCACTGATTTCACACTGAAAATCAG<br>CAGGGTGGAGGCTGAGGATGTTGGGGTTTATTACTGCATG<br>CAAGGTACACACTGGCCTCGCACTTTCGGCCCTGGGACCA<br>AAGTGGATATCAAA |
| EV-D68-221 | 97 | heavy | GAGGTGCAGCTGGTGGAGTCTGGGGGAGGCCTGGTCAAG<br>CCCGGGGGGGTCCCTGAGACTCTCCTGTGCAGCCTCTGGAT<br>TCAGTTTCAGTGTCTATCCCATGAACTGGGTCCGCCAGGCT<br>CCAGGGAAGGGGCTGGAGTGGGTCTCATCCATAAGTAGTA<br>GTAGTCGTTACATATCCTACGCAGACTCACTGAGGGGTCG<br>AATCACCATCTCCAGAGACAACGCCAAGAACTCACTGTATC<br>TGCAAATGAACAGCCTGAGAGTCGAGGACACGGCTGTGTA<br>TTACTGTGTGAAAGTCGGGGGTAGCAAACACCAATACTACT<br>TTGACTACTGGGGCCAGGGATCCCTGGTCACCGTCTCCTC<br>A |
|  | 98 | light | CAGTCTGTGCTGACTCAGCCACCCTCAACGTCTGGGATCC<br>CCGGGCAGACGGTCACCATCTCTTGTTCTGGAAGCAGGTC<br>CAACATCGGAAGTTATACTGTTAACTGGTACGAGCAACTCC<br>CAGGAACGGCCCCCAAACTCGTCATCTTTAATAATAATCAG<br>CGTCCCTCAGGGGTCCCTGACCGATTCTCTGGCTCCAAGT<br>CTGGCACCTCAGCCTCCCTGGCCATCAGTGGGCTCCAGTC<br>TGAGGGTGAAGCTGATTATTACTGTGCAGCATGGGATGAC<br>AGCCTGAATGGTGTGGTTTTCGGCGGAGGGACCAAGCTGA<br>CCGTCCTA |
| EV-D68-224 | 99 | heavy | CAGGTTCAGTTGGTGCAGTCTGGAGCTGAGGTGAAGAGGC<br>CTGGGGCCTCAGTGAAGGTCTTCTGCAAGGCTTCTGGTTA<br>CACCTTTACGAATTATGACATCATCTGGGTGCGACAGGCCC<br>CTGGACAAGGGCTTGAGTGGGTGGGCTGGATCAGCACTTA<br>CAATGGTAACACAAACTATGAACAGAACCTCCAGGGCAGA<br>GTCACCATGACCACAGACACATCCACGAGCACAGCCTACA<br>TGGAGCTGAGGAGCCTGAGATCTGACGACACGGCCGTTTA<br>CTATTGTGCGAGAGAGCGTTGTAGTACTAGTACCTGCTATA<br>GTCGTTATGCTGACTACTGGGGCCAGGGAACCCTGGTCAC<br>CGTCTCCTCA |
|  | 100 | light | GACATCCAGATGACCCAGTCTCCATCCTCCCTGTCTGCATC<br>TGTGGGAGACAGAGTCACCATCACTTGCCGGGCAAGTCAG<br>AGCATTAATATCTATTTGAATTGGTATCAGCAAAAACCGGG<br>GAAAGCCCCTAAGGTCCTGATCTATGCTGCATCCAGTTTGC<br>AAAGTGGGGTCCCATCAAGGTTCGTGGCAGTGGGTCTGG<br>GACAGATTTCATCCTCACCATCAGCAGTCTGCAACCTGAAG |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| | | | ACTTTGCAACCTACTACTGTCAACAGAGTTACAGGTCCCCT CGGACGTTCGGCCAAGGGACCGAGGTGGAAATCAAA |
| EV-D68-225 | 101 | heavy | GAGGTGCAGCTGGTGGAGTCTGGGGGAGGCTTGGCACAG CCTGGAGAGTCCATGAGACTCTCCTGTGTAGCCTCTGGAT TCACCTTAAGTCGTTATGAAGTGAACTGGGTCCGCCAGGC TCCAGGGAAGGGGCTAGAGTGGCTTTCATACATTAGCAGT GGTGGTCCTTCCATATACTACGCAGACTCTGTGAAGGGCC GATTCACGATCTCCAGAAACAGCGCCGAGAACTCACTGGA ACTACAAATGTCCACCCTGAGGACCGAGGACACGGCTGTT TATTATTGTATGAGAGAGGGTCTTACTTATTATGATAGTACT ATTTGGGGCCAGGGAACCCTGGTCGCCGTCTCCTCA |
| | 102 | light | CAGAATGTGCTGACTCAATCGCCCTCTGCCTCTGCCTCCCT GGGAGCCTCGGTCAAACTCACCTGCACTCTGAACAGTGGG CACAGCAGATACGCCATCGCATGGCATCAACATCAGCCAC AGAGGGGCCCTCGGTTCCTGATGAAGATTAATAGTGATGG CAGACACATCAGGGGGGACGGCATCTCTGATCGCTTCTCA GGCTCCGCCTCTGGGGCTGAGCGTCATCTCACCATCTCCA GCCTCCAGCTGAGGATGAGGCTGACTATTATTGTCAGAC CTGGGGCACTGGCTTTCGGGTGTTCGGCGGAGGGACCAA ACTGACCGTCCTA |
| EV-D68-227 | 103 | heavy | GAAGTGCAGCTGGTGGAGTCTGGGGGAGGCTTGGTACAG CCTGGCAGGTCCCTGAGACTCTCCTGTGCAGCCTCTGGAT TCACCTTTGATGAATATGCCATGCACTGGGTCCGGCAAGTT CCAGGGAAGGGCCTGGAGTGGGTCTCAGGTATTAGTTGGA ATGGTGGTAGCAAAGGCTATGCGGACTCTGTGAAGGGCCG ATTCACCATCTCCAGAGATAACGCCAGGTATTCCCTGTCTC TGCAAATGAACAGTCTGAGAACTGAGGACACGGCCTTATAT TACTGCGCAAAAGATGATTACGAGGGGGCTGGTTTTGATAT CTGGGGCCAAGGGACAGTGGTCACCGTCTCTTCA |
| | 104 | light | GAAATTGTGTTGACACAGTCTCCAGCCACCCTGTCTTTGTC TCCAGGGGAAAGAGCCACCCTCTCCTGCAGGGCCAGTCA GAGTGTTAGCAGCTACTTAGGCTGGTACCAACAGAAATCTG GCCAGGCTCCCAGGCTCCTCATCTATGGTGCATCCAGCAG GGCCACTGGCATCCCAGCCAGGTTCAGTGGCAGTGGGTCT GGGACAGACTTCACTCTCACCATCAGCAGCCTAGAGCCTG AAGATTTTGCAATTTATTACTGTCAGCAGCGTAGCAACTGG CCTATCACCTTCGGCCAAGGGACACGACTGGAGATTAAA |
| EV-D68-228 | 105 | heavy | CAGGTGCAGCTGCAGGAGTCGGGCCCAGGACTGGTGAAG CCTTCGGAGACCCTGTCCCTCACCTGCACTGTCTCTGGCT ATTTAATTAGCAATGGTTACTACTGGGGCTGGATCCGGCAG TCCCCCGGGAAGGGGCTGGAGTGGATTGGGAGTATCTATT ATACTAGGGACACCTACTACAACTGGTCCCTCAAGAGTCGA ATCACCATATCAGTGGACACGTCCAAGAAACAGTTCTCCCT GAAGTTGTATTCTGTGACCGCCGCAGACACGGCCGTCTAT TACTGTGTGAGACATGAGGGTTCTTGCAATGATGGAAGCT GTTACGGCTCGTTCGTTGACAACTGGGGCCAGGGAACCCT GGTCACCGTCTCCTCA |
| | 106 | light | GACATCCAGATGACCCAGTCTCCATCTTCCGTGTCTGCATC TGTAGGAGACAGAGTGACCCTCACTTGTCGGGCGAGTCAG GATATTAGCAGCTGGTTAGCCTGGTATCAGCAGAAACCAG GGAAAGCCCCTAAGCTCCTGATCTATGCTGCATCCAGTTTG CAAAGTGGGGTCCCATCAAGGTTCAGCGGCAGTGGATCTG GGACAGATTTCACTCTCACCATCAGCAGCCTGCAGCCTGA AGATTTCGCAACTTACTTTTGTCAACAGGCTGACAGTTTCAT CACTTTCGGCGGAGGGACCAAGGTGGAGATCAAA |
| EV-D68-231 | 107 | heavy | GAGGTGCAACTGTTGGAGTCTGGGGGAGGCTTGGTACAG CCGGGGGGGTCCCTGAGACTCTCCTGTGCAGCCTCTGATT TCACCTTCAGCAGCTACACCATGGCCTGGGTCCGCCAGGC TCCAGGGAAGGGGCTTGAATGGGTCTCATCTATTAGTGGT GATGGTGTTAGCACAAAAAAACGCAGACTCCGTGAAGGGCC GATTCTCCGTCTCCAGAGACAATTCCAAGAACACACTTTTT CTGCAACTGAACAGTCTGAGAGCCGAGGACACGGCCTTTT ATTGTGTGCGAGGGGGGGACCTTCCATAACTGGTACTT CGATCTCTGGGGCCGTGGCGTCTTGGTCACTGTCTCCTCA |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| | 108 | light | GAAATAGTGATGACGCAGTCTCCAGCCACCCTGTCTGTGT<br>CTCCAGGGGAAACAGCCACCCTCTCCTGCAGGGCCAGTCA<br>GAGTATTGGCGACAACTTAGCCTGGTATCAGCAGAAACCT<br>GGCCAGGCTCCCAGGCTCCTCATCTCTGGTGCATCCACAA<br>GGGCCACTGATTTCCCAGCCAGGTTCCGTGGCAGTGGGTC<br>TGGGACAGAGTTCACTCTCACCATCAGCAGCCTGCAGTCT<br>GAAGACTTTGCAGTTTATTACTGTCAGCAGTATAAAAACTG<br>GCCTCGGACGTTCGGCCGAGGGACCAAGGTGGAAGTCAG<br>A |
| EV-D68-234 | 109 | heavy | GAGGTGCAGCTGTTGGAGTCTGGGGGAGGCTTGGTACAG<br>CCGGGGGGGTCCCTGAGACTCTCCTGTGCAGCCTCTGGAT<br>TCACCTTTAGCACCTATGCCATGAGCTGGGTCCGCCAGGC<br>TCCAGGGAAGGGGCCGGAGTGGGTCTCAGGTATTAGTGG<br>TAGTGGTGGTAGCACAAACTACGCAGACTCTGCGAAGGGC<br>CGGTTCACCATCTCCAGAGACAATTCCAAGAACACGCTGTA<br>TCTGCAAATGAACAGCCTGAGAGCCGAGGACACGGCCGTA<br>TATTATTGTGCGAAAGGGACCATTACTTACTCCTACTACTAC<br>ATGGCCGTCTGGGGCAAAGGGACCACGGTCACCGTCTCCT<br>CA |
| | 110 | light | GAAATTGTGTTGACGCAGTCTCCAGGCACCCTGTCTTTGTC<br>TCCAGGGGAAAGAGGCACCCTCTCCTGCAGGGCCAGTCA<br>GAGTGTTAGGAGCAGCTACTTAGCCTGGTACCAGCAGAGA<br>CCTGGCCAGGCTCCCAGGCTCCTCATCTATGGTGCATCCA<br>GCAGGGCCACTGGCATCCCAGACAGGTTCAGTGGCAGTG<br>GGTCTGGGACAGACTTCACGCTCACCATCGGCAGACTGGA<br>GCCTGAAGATTTTGCAGTGTATTACTGTCAGCAGTATGGTA<br>CCTCAATAACTTTCGGCGGAGGGACCAAGGTGGAGATCAA<br>A |
| EV-D68-235 | 111 | heavy | CAGGTCCAGGTGGTACAATCTGGGGCTGAGATGAGGAAGC<br>CTGGGGCCTCAGTGAGGGTCTCCTGCAAGGTTTCCGGATA<br>CAGGCTCACTGATTTACCCTTGCACTGGGTGCGACAGGCT<br>CCTGGAAAAGGGCTTGAATGGATTGGATTTGTTGATCTTGA<br>AAAGCGCGAAATCATCTACGCACAGAAATTTCAGGGCAAA<br>GTCACCATAACCGAGGACACATCTGCAGACACCGCCTACA<br>TGGAACTGAACAGCCTGCGATCTGAAGACACGGCCGTCTA<br>CTACTGTGCAACTTGGGGAATTGAGGTGGTGAATGGGAGG<br>GACGAATTCTTTGACTCCTGGGGCCAGGGAACCCTGGTCT<br>CCGTCTCCTCA |
| | 112 | light | TCCTATGAGCTGACACAGCCACCCTCGGTGTCAGTGTCCC<br>CAGGACAGACGGCCAGGATCACATGCTATGCAGATGTGTT<br>GTCAAAGCAATATACTTACTGGTATCAGCAGAAGCCAGGCC<br>AGGCCCCTGTGTTGGTGATATATAAAGACACTGAGAGGCC<br>CTCAGGGATCCCTGAGCGATTTGCTGGCTCCAGCTCAGGG<br>ACAACAGTCACCTTGATCATCAATGGAGTCCGGACAGAGG<br>ACGAGGCGTACTATTACTGTCAATCAGCCGACACCAGAATT<br>ACGGTTTTCGGCGGAGGGACCAAGCTGTCCGTCCTA |
| EV-D68-236 | 113 | heavy | CAGGTCCAGGTGGTCCAGTCTGGGGCTGAGATGAAGAAG<br>CCTGGGGCCTCAGTGAAGGTCTCCTGCAAGGTTTCCGGAT<br>ATAGTCTCAGTGATTTACCCTTGCACTGGGTGCGACAGGCT<br>CCTGGAAAAGGGCTTGAGTGGATGGGACTTTTTGATCCTAT<br>AAACGGTGAAATCATCTACGCACAGACATTCCAGGGCAAA<br>GTCACCATAAGCGAGGACACATCGATAGACACAGCCTACA<br>TGGAACTCAACAGCCTGCGATCTGAAGACACGGCCGTGTA<br>CTATTGTGCAACTTGGGGAGTTGCGGTGGTGAGTGGGAGA<br>AGGGACTACTTTGACTCCTGGGGCCAGGGAACCCTGGTCA<br>CCGTCTCCTCA |
| | 114 | light | TCCTATGAGCTGACACAGCCACCCTCGGTGTCAGTGTCCC<br>CAGGACAGACGGCCAGGATCACATGCTATGCAGCTGTATT<br>GTCAAACCAATATACTTACTGGTATCAACAGAAGCCAGGCC<br>AGGCCCCTGTTTTGGTGATATATAAAGACACTGAGAGGCC<br>CTCAGGGATCCCTGAGCGATTTGCTGGCTCCAGCTCAGGG<br>ACAACAGTCACCTTGATCATCAATGGAGTCCGGACAGAGG<br>ACGAGGCTTACTATTACTGTCAAACAGCCGACACCAAATAT<br>ACGGTTTTCGGCGGAGGGACCAAGCTGTCCGTCCTA |
| EV-D68-241 | 115 | heavy | CAGGTGCAGCTGCAGGAGTCGGGCCCAGGACTGGTGAAG<br>CCTTCACAGACCCTGTCCCTCACCTGCACTGTCTCTGGTG<br>GCTCCATCACCAGTGGTGATTACTACTGGAATTGGATCCGC<br>CAGCCCCCAGGGAAGGGCCTGGAGTGGATTGGGTACATC<br>TATCACAGTGGGACCACCTACTACAACCCGTCCCTCAAGA<br>GTCGAGTTACCATATCAGTAGACACGTCCAAGAACAGGTTC<br>TCCCTGAAGTTGTCCTCTGTGACTGCCGCAGACACGGCCG |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| | | | TGTATTTTTGTGCCAGAGCCTACGCTTATGAATTTTGGAGC<br>GGTTACCCTAACTGGTTCGACCCCTGGGGCCTGGGAACCC<br>TGGTCACCGTCTCATCA |
| | 116 | light | GACATCCAGATGACCCAGTCTCCATCCTCCCTGTCTGCATC<br>TGTTGGAGACAGAGTCACCATCACTTGCCGGGCAAGTCAG<br>CGCATTAGTACCTATGTAAATTGGTATCAGGTGAAAGCAGG<br>GACAGCCCCTAAGGTCCTGATCTATGCTGCGTCCAGTTTG<br>CAAACTGGGGTCCCATCAAGGTTCAGTGGCAGTGGATCTG<br>GGACAGATTTCACTCTCACCATTGTCAGTCTACAACCTGAA<br>GATTTTACAACCTACTTCTGTCAACAGAGTTACAGTCCCCC<br>GTGGACGTTCGGCCAAGGGACCAAGGTGGAAATCAAA |
| EV-<br>D68-<br>247 | 117 | heavy | CAGGTGCAGTTGGTGGAGTCTGGGGGAGGCTTGGTCCAG<br>CCTGGTAGGTCCCTGAGACTCTCCTGTGCAGCCTCTGGGT<br>TCATCTTCAATAGATATGCCATGCACTGGGTCCGCCAGGCT<br>CCAGGCAAGGGGCTCGAGTGGGTGGCTCTTATATCATATG<br>ATGGAATTAATAAATATTACGCAGACTCCGTGAAGGGCCGA<br>TTCTCCATCTCCAGAGACAATTCCAAGAGTACGCTGTATCT<br>GCAAATGAACAGCCTCAGAGCTGAGGACACGGCTATCTTT<br>TACTGTGCGAGAGGACTAGGATATTGTAGTGGTACCGGTG<br>GTAGCTGTACACCCTTTGAATATTGGGGCCAGGGAATCCT<br>GGTCACCGTCTCCTCA |
| | 118 | light | GACATCCAGATGACCCAGTCTCCACCCTCCCTGTCTGCAT<br>CTGTTGGAGACAGAGTCACCATCACTTGCCGGGCAAGTCA<br>GAGCATTAAGAAATATTTAAATTGGTATCAGCAGAAACCAG<br>GGAATGCCCCTAAGCTCCTCATCTATGGCGCATCCAATTTG<br>CAAACTGGGGTCCCATCAAGGTTCAGTGGCAGTGGATCTG<br>GGACAGATTTCGCTCTCTCCATCAGCAGTCTGGAAACTGAA<br>GATTTTGCAACTTACTACTGTCAACAGAGTGACAGTGCCCC<br>TCCCACTTTCGGCGGAGGGACCAAGGTGGAGTTCAAA |
| EV-<br>D68-<br>254 | 119 | heavy | CAGGTGCAGCTGCAACAGCGGGGCGCAGGGCTGTTGAAG<br>CCCTCGGAGACCCTGTCCCTTACCTGCGAAATCTATGGTG<br>CATCCCTCAATGATTACGACTGGACCTGGATCCGCCAGCC<br>CCCAGGGAAGAGGCTGGAGTGGATTGGGGTCATCAATCGT<br>CGTGACACTGTTGACTACAACCCGTCCCTCAAGAGTCGGG<br>TCACCCTCTCACTTGACACGTCCAAGAACCAACTTTCCCTG<br>AGTCTGAGTTCTGTGACCGCCGCGGACACGGCTGTTTATT<br>ACTGTGTGAGAGTCCCACGTCGGGGCTTTGAAGGGTCTTT<br>CGGATTTTGTGATGATACTGCCTGCCGCTACGGGCATACC<br>TGGTTCGACCCCTGGGGCCAGGGAACCCTGGTCACCGTCT<br>CCTCA |
| | 120 | light | GACATTCAGATGACCCAGTCTCCTTCCTCCCTGTCTGCATC<br>TGTTGGCGACAGAGTCACCATCACTTGCCGGGCAAGTCAG<br>AGTATTAGAGATTATTTAAATTGGTATCAACAAAGACCAGG<br>GAAAGCCCCTAAAGTCCTGATCTTTGCTGGTTCCCGTTTGG<br>AAAGTGGGGTCCCATCGAGGTTTAGAGGCCGTGGATCTGG<br>GACAGAATTCACTCTCACCATCAGCGATCTGCAACCTGAG<br>GATTTTGCAACTTACTACTGTCAACAGAGTTACCTTACACCT<br>CCGACATTCGGCCAAGGGACCACCGTCGATATCAAA |
| EV-<br>D68-<br>260 | 121 | heavy | CAGGTCACCTTGAAGGAGTCTGGTCCTGTGCTGGTGAAAC<br>CCACAGAGACCCTCACGCTGACCTGCACCGTCTCTGGATT<br>CTCACTCCGCAATGGTAGAATGGGTGTGAGCTGGATCCGT<br>CAGCCCCCAGGGAAGGCCCTGGAGTGGCTTGCACACATTT<br>TTGCGAGTGACGAAAAATCTTACAGTACATCTCAGAGGACC<br>AGGCTCTCCATCTCCAGGGACACCTCCAAAAGCCAAGTGG<br>TCCTTAGCATGACCGACATGGACCCTGTGGACACAGCCAC<br>ATATTACTGTGCGCGGATTTTGAAGTTTGGGACAATGAGGG<br>CCGCATACTACTTTGACTACTGGGGCCAGGGAGCCCTGGT<br>CCCCGTCTCCTCA |
| | 122 | light | TCCTATGTGCTGACTCAGCCACCCTCAGTGTCAGTGGCCC<br>CAGGAAAGACGGCCAGGATTACCTGTGGGGAATCAACAT<br>TGGAATTAGAACTGTACACTGGTACCAGCAGAAGCCAGGC<br>CAGGCCCCTATGTTGGTCATCTATTATGATAGCGACCGGC<br>CCTTAGGGATCCCTGAGCGATTCTCTGGCTCCAAGTCTGG<br>GAACACGGCCACCCTGACCATCAGCAGGGTCGAAGCCGG<br>GGATGAGGCCGACTATTACTGTCAGGTGTGGGATAGTAGT<br>AGTGATCATGTTGTATTCGGCGGAGGGACCAAGCTGACCG<br>CCCTA |
| EV-<br>D68-<br>266 | 123 | heavy | CAGGTGCACTTGGTGGAGTCTGGGGGAGGCTTGGTCAAG<br>CCTGGAGGGTCCCTGAGACTCTCCTGTGCAGTTTCTGGAT<br>TCACCTTCAGTGACTACTACATGAGCTGGATCCGCCAGGC<br>TCCGGGGAAGGGACTGGAGTGGCTTTCATACATTAGTAGT |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| | | | AGTGGTAGTACCATATACTACGCAGACTCTATGAAGGGCC<br>GATTCACCATCTCCAGGGACAACGCCAGGAACTCACTCTAT<br>CTGCAAATGAACAGCCTGAGAGTCGAGGACACGGCCTTTT<br>ATTACTGTGCGGGGTCAAAGGTTGGCTATACTACTGGTCG<br>AAGGAACTGGTACTTCGATCTCTGGGGCCGTGGCACCCTG<br>GTCACTGTCTCCTCA |
| | 124 | light | CAGTCTGCCCTGACTCAGCCTCCCTCCGCGTCCGGGTCTC<br>CTGGACAGTCAGTCACCATCTCCTGCACTGGAACCAGCAG<br>TGACGTTGGTGCTTATAACTATGTCTCCTGGTACCAACAGC<br>ACCCAGGCAAAGCCCCCAAACTCATGATTTATGAGGTCACT<br>AAGCGGCCCTCAGGGGTCCCTGATCGCTTCTCTGGCTCCA<br>AGTCTGGCAACACGGCCTCTCTGACCGTCTCTGGGCTCCA<br>GGCTGAGGATGAGGCTGATTATTACTGCAGCTCATATGCA<br>GGCAACAACAATTTAGTCTTCGGCGGAGGGACCAAGCTGA<br>CCGTCCTA |
| EV-<br>D68-<br>269 | 125 | heavy | CAGGTGCAGTTGCTGCAGTCTGGGTCTGAGGTGAGGAAAC<br>CTGGGGCCTCAGTGAACATTCACTGTAAGGCATCTGGATT<br>CACTTTCACCGACTTCTATTTACACTGGGTGCGACAGGCCC<br>CTGGACAAGGGCTTGAGTGGATGGGGATAATCAACCCTGA<br>AACCGGTGAGACAACCTACTCACAGAAGTTTCAGGGCAGA<br>GTCACCATGACCAGGGACACGTCCACGAGTGTAGTGAATC<br>TGGAAGTGAGGAGCCTGAGATCTGAGGACACGGCCATATA<br>TTACTGTGCGAGAGATCTCGTTGTCGTAGTCCCCGTTGAAA<br>TGTCTCGGCGTGCCTTTGACATTTGGGGCCAAGGGATTAT<br>GGTCACAGTCTCCTCA |
| | 126 | light | TCCTATGTGCTGACTCAGCCACCCTCGGTGTCAGTGGCCC<br>CAGGACAGACGGCCAGGATTCCCTGTGGGGCAACAACAT<br>TGAACGTAAAAGTGTCCACTGGTACCAGCAGAGGCCAGGC<br>CAGGCCCCTGTGTTGGTCGTCTATGATGATACTGTCCGGC<br>CCTCAGGTATCCCTGAGCGATTCTCTGGCTCCAACTCCGG<br>GAGCACGGCCACCCTGACCATCAGCAGGGTCGGAGCCGG<br>GGATGAGGGCGACTATTATTGTCAGGTGTGGGACAGCACC<br>ACTGACCATGGGGTCTTCGGCGGAGGGACCAAGCTGACC<br>GTCCTA |
| EV-<br>D68-<br>271 | 127 | heavy | CGGGTGCAGCTGGTGCAGTCTGGGGCTGAGGTGAAGAAG<br>CCTGGGGCCTCAGTGAAGGTCTCCTGTCAGACTTCTGGAT<br>ACATTTTCAGCGCCTACTACATCTATTGGGTGCGACAGGCC<br>CCTGGACAAGGACTTGAGTGGATGGGACGGATGAACGCTA<br>AGAGTGGAGGCGCAAACACTGCACAGCAGTTTCAGGGCAG<br>ACTCACCATGACCAGGGACATGTCCGTCAGCACAGCCTAC<br>ATGGAACTGAGCAGGCTGCGATCGGACGACACGGCCGTC<br>TATTATTGTGCGAGAGACTATAGGGATGACTACATGTGGGG<br>GAGTTATCGGCCTTTAGACTACTGGGGCCAGGGAACCCTG<br>GTCACCGTCTCCTCA |
| | 128 | light | GAAGTTGTGTTGACACAGTCTCCAGCCACCCTGTCTTTGTC<br>TCCAGGGGAAAGAGCCTCCCTCTCCTGCAGGGCCAGTCAG<br>AGTGTTAGCGGCTACTTAGCCTGGTACCAACACAAACCTG<br>GCCAGGCTCCCAGGCTCCTCATCTATGATGCATCCAACAG<br>GGCCGCTGGCATCCCAGCCAGGTTCCGTGGCAGTGGGTC<br>TGGGACAGACTTCACTCTCACCATCAGCAGCCTGGAGCCT<br>GAAGATTTTGCAGTTTATTTCTGTCAGCAGCGTAGCAACGG<br>GCTCACTTTCGGCGGAGGGACCAAGGTCGAGATCAAA |

TABLE 2

PROTEIN SEQUENCES FOR ANTIBODY VARIABLE REGIONS

| Clone | SEQ ID NO: | Chain | Variable Sequence |
|---|---|---|---|
| EV-<br>D68-<br>37 | 129 | heavy | QVQLVESGGGVVQPGRSLRLSCAASGFIFSRYALHWVRQ<br>APGKGLDWVAVISYDARNSYYTDSVKGRFTISRDNSKNTL<br>FLQMNSLRADDTAVYYCARPTLPYSNNWYAPEYWGQGTL<br>VTVSS |
| | 130 | light | SYELTQPPSVSVSPGQTARITCSGDALPKKYASWYQQKSG<br>QAPVLVIYEDTKRPSGIPERFSGSSSGTMATLTISGAQVED<br>ESDYYCSSTDSSGNPVLFGGGTKLTVL |
| EV-<br>D68- | 131 | heavy | EVQLVESGGDLVQPGGSLRLSCAASGFSFSSYAMAWVRQ<br>APGKGLQWVSSISGNGNGRSYADSLKGRFTTSKDLSKYTL |

TABLE 2-continued

PROTEIN SEQUENCES FOR ANTIBODY VARIABLE REGIONS

| Clone | SEQ ID NO: | Chain | Variable Sequence |
|---|---|---|---|
| 40 | | | YLQMNNLRPEDTAIYYCAKVVRIAAVLYYFDYWGPGTQVTVSS |
| | 132 | light | EIVLTQSPATLSLSPGERATLSCRASQSVSTYLAWYQQKPGQAPRLLIYEASTRATGIPARFSGSGSGTDFTLIISSLEPEDFAVYHCQQRSSWPITFGQGTRLEIE |
| EV-D68-41 | 133 | heavy | DVQLVESGGGLVQPGGSLRLSCAASGFTFSNYAMTWVRQALGKGLEWVSSISGSGGLTYFAHSVKGRLTISRDNSKNTLYLQMSSLRAEDTAVYYCARVKSTTGTTALVFDIWGQGTMVTVSS |
| | 134 | light | QTVVTQEPSFSVSPGGTVTLTCGLSSGSVSSSYYPSWYQQTPGQAPRTLIYSINRRSSGVPDRFSGFILGNKAALTIRGAQADDESDYYCGLYMGSGIWIFGGGTKLTVL |
| EV-D68-43 | 135 | heavy | QVQLVESGGGVVQPGRSLRLSCAASGFTFINYGMHWVRQAPGKGLEWVAVISNDGSYNYDADSVKGRFTISRDNSKNKVYLQMNSLRPEDTAVYFCAKDKHGDFDYYGVDVWGQGTTVTVSP |
| | 136 | light | DVQMTQSPSSVSASIGDRVTITCRAGQGISSWLAWYQQKPGKAPKLLIYAASNLQSGVPSRFSGSGSGTDFTLTISSLQPEDFGTYYCQQADSFPRTFGQGTKVEIK |
| EV-D68-46 | 137 | heavy | QVQLVESGGGVVQPGRSLRLSCAASGFTFSSYGIHWVRQAPGKGLEWVAVISYDGSDNTYAPFVNGRFTISRDNSKNTLYLQMNSLRADDTAVYYCARRRPGSFPGLCDYWGQGALVTVSS |
| | 138 | light | DIQMTQSPSTMSASVGDRVTITCRASQSISKWLAWYQQKPGKAPKLLIYKASTLQTGVPSRFSGSGSGTEFTLTINSLQPDDFATYYCQQHNSYSYTFGQGTKVEIK |
| EV-D68-48 | 139 | heavy | QVQLVQSGAEVKKPGSSVKVSCKASGGSFSRLTIIWVRQAPGQGLEWMGGHIPIFGTTNYALKFQGRVTITADKTTSTAYMELSSLRSEDTAIYYCARMYSGHDGVDVWGQGTLVTVSS |
| | 140 | light | EIVLTQSPATLSLSPGERATLSCRASQSVRSYLAWYQHKPGQAPRLLIYDASNRAKGIPARFSGSGSGTDFTLTISSLEPEDFAVYYCQQRSTWPPGMFGQGTRVEIK |
| EV-D68-71 | 141 | heavy | QLQLQESGPGLVKHSETLSLTCTVSGGSISSGFYYWGWIRQPPGKGLEWIGTIYDSGRTYDNPSLKSRVTISADTSKKQFSLTLRSATAADTAVYFCARHLTHLYGDYVTPDALDIWGQGTMVTVSS |
| | 142 | light | EIVLTQSPGTLSLSPGERATLSCRASQSVSSSFLAWYQQKPGQAPRLLIYGASSRATGIPDRFRGSGSGTDFTLTISRLEPEDFAVYYCQQYSNSRLTFGQGTKVEIK |
| EV-D68-72 | 143 | heavy | EVQLVESGGGLVQPGGSLRLSCAASGFTFTTYSMNWVRQAPGKGLEWISYISSGSSNIYYADSVKGRFTISRDNAKNSLNLQMSSLRDEDTAVYYCARAHGRIVNSGVVISRFDPWGQGILVTVSS |
| | 144 | light | QSALTQPASVSGSPGQSITISCTGTSSDVGGYNYVSWYQLHPGKAPKLMIFEVTYRPSGVSNRFSGSKSGNTASLTISGLQAEDEADYFCSSYTTSNTLVVFGGGTKLTVL |
| EV-D68-74 | 145 | heavy | QVQLVQSGAEVKKPGASVKVSCRTSGYTFTAYYMHWVRQAPGQGPEWMGRINPSSGGAQYAQKFQGRVTMTRDTSISTTYMTLSGLTSDDTAVFYCARMGCRSDRCYSTNYNFDQWGQGTLVTVSS |
| | 146 | light | SYVLTQPPSVSVAPGQTARIPCGGNNIGTKSVHWYQQKPGQAPVLVVSNDSRPSGIPERFSGSKSGNTATLTISRVEAGDEADYYCQVWDSGIDVVFGGGTKLTVL |
| EV-D68-75 | 147 | heavy | EVQLVESGGGLVKPGGSLRLSCAASGFTISPYGMNWVRQAPGKGLEWVSFISSSSRYTYYADSVKGRFTISRDNAKNSLSLQMNSLRAEDTAVYYCARERGHSTSSSYFDSWGQGTLVTVSS |
| | 148 | light | SYVLTQPPSVSLAPGKTARITCGGNNIGTKTVSWYQQKPGQAPVLVMYYDSRPSGIPERFSGSNSGNTATLTINRVEAGDEADYYCRVWDSDTDHRVFGGGTKLTVL |

TABLE 2-continued

PROTEIN SEQUENCES FOR ANTIBODY VARIABLE REGIONS

| Clone | SEQ ID NO: | Chain | Variable Sequence |
|---|---|---|---|
| EV-D68-76 | 149 | heavy | EVQLVESGGGLVKPGGSLRLSCAASGFTFSNAWISWVRQAPGKGLEWVGRIQTKTDGGTTDYAAPVKGRFTISRDDSKNTLYLQMNSLKTEDTALYYCSTGPYYYDTSGYPQPFDYWGQGTLVTVSS |
|  | 150 | light | SYELTQPPSVSVSPGQTASITCSGDKLGDKYACWYQQKPGQSPVLVIYQDTKRPSGIPERFSGSNSGNTATLTISGTQAMDEADYYCQAWDSSTVVFGGGTKLTVL |
| EV-D68-80 | 151 | heavy | EVQMVESGGGLVKPGGSLRLSCSVSGFDFSRYTMNWFRQAPGEGLKWVSSISSTSLYTFYADSVKGRFSISRDNAQGSLSLQMSSLRPEDTAVYYCARVVGPAELDYWGQGVLVTVSS |
|  | 152 | light | VTQLTQSPSSLSASVGDRVTITCRASQDIGVDLGWFQQRPGKAPKLLIYGASRLQSGVPSRFSGRGSGTFFTLTISSLQPEDFTTYFCLQDYNYPWTLGQGTTVGVK |
| EV-D68-84 | 153 | heavy | QVHLVQSGSAVRKPGASVKVSCKASGYTFTDYYIHWVRQAPGQGLEWMGWINPKTGGSNYTQRFQARVTMTWDTSISTAYMELSRLRSDDTAVYYCARAGRNGYDYWGQGTLVTVSS |
|  | 154 | light | SYELTQPPSVSVSPGQTARITCSADALPKQYAYWYQQKPGQAPVLMIYQDTERPSGIPERFSGSSSGTTVTLTISGVQAEDEADYYCQSGDSSGTYLVFGGGTKLTVL |
| EV-D68-85 | 155 | heavy | EVQLLESGGGLVQPGGSLRLSCAASGFKFRNYAMTWVRQAPGKGLEWVSTITSGGSTEYADAVKGRFIISRDNSKNTLYLQMNSLRADDTAVYYCTVPWGNYNDYVSDYWGQGTLVPVSS |
|  | 156 | light | EVVLTQSPATLSLSPGQRATLSCRASQRVGNSLAWYQQKPGQAPSLLIYDASKRATGIPARFSGSGSGTDFTLTIISLESEDFAVYYCHQHSTWPRGTFGQGTRLEIK |
| EV-D68-88 | 157 | heavy | QVHLVESGGGVVQPGRSLRLSCAASGFIFSRYPMHWVRQAPGKGLEWVALISYDGNNKYYADSVKGRFTISRDNSKNTLFLQMNSLRAEDTAVYYCARHFLPYSSSWYQGFNYWGQGILVTVSS |
|  | 158 | light | NFMLTQPHSVSESPGKTVTISCTRSSGSIATNYVQWYQQRPGSSPTPIIFEDSQRPSGVPDRFSGSIDSSSNSASLTISGLRTDDEADYYCQSYDNSNRAVVFGGGTKLTVL |
| EV-D68-89 | 159 | heavy | QVQLVESGGGVVQPGRSLRLSCEASGFLFSRYGMHWVRQAPGKGLDWVAVISYDGNKKYYADSVKGRFTISRDNSKNTLYLQVNSLRVEDTAVYYCARGVPYGDTLTGLVYWGQGTLVTVSS |
|  | 160 | light | NFMLTQPHSVSESPGKTVTISCTRSSGTIASNYVQWYQQRPGSAPTTVIYEDNQRPSGVPDRFSGSIDSSSNSASLTISGLKTEDEADYYCQSYDNSDRVFGGGTKLTVL |
| EV-D68-95 | 161 | heavy | QVTLKESGPVLVKPTETLTLTCTVSGFSLRNARMGVSWIRQPPGKALEWLAHIFSNDEKSYNTSLKSRLSISKDTSKSQVVLTMTSMDPLDTATYFCARLLVAGTFLPSHYFDYWGQGILVTVSS |
|  | 162 | light | SYVLTQPPSVSVTPGKTARITCGGNNIGLKSVFWYQERPDQAPVVVIYYDSARPSGIPERISGSKSGNTATLTITRVEAGDEADYFCQVWDSSRNHPVFGGGTKLTVL |
| EV-D68-97 | 163 | heavy | ELQLVESGGGLVQPGGSLRLSCAASGFTFSTYSMNWVRQAPGKGLEWVSYISSSSSTIQYADSVKGRFTISRDNAKNSLYLQMNSLRAEDTAVYYCTRQVGADFSGRGFDYWGQGTLLTVSS |
|  | 164 | light | SYELTQPPSVSVSPGQTATITCFGDKLGDKYACWYQQKPGQSPVLVIYQDSKRPSGIPERFSGSKSGNTATLTISGTQAMDEADYYCQAWDSSTAVFGGGTKLTVL |
| EV-D68-98 | 165 | heavy | EVQLVESGGGLVQPGGSLRLSCAASGFKFSVYALSWVRQAPGKGLEWISYISSSGSTIYYSDSVKGRFTISRDNVGNSLFVQMNSLRAEDTGIYYCATARHITNDGFDIWGQGTMVIVSS |
|  | 166 | light | DIQLTQSPSFLSASVGDRVTITCRASQGISRFLAWYQQKPGKAPKLLIYSASTLQRGVPSRFSGSGFGTDFTLTISSLQPEDFATYYCQQLNSHPRMFTFGPGTTVDIK |

TABLE 2-continued

PROTEIN SEQUENCES FOR ANTIBODY VARIABLE REGIONS

| Clone | SEQ ID NO: | Chain | Variable Sequence |
|---|---|---|---|
| EV-D68-105 | 167 | heavy | QVQLQESGPGLVKPSETLSLTCAVSGYLISNGYYWGWIRQ PPGKGLEWIGSIYHTRSTYYNPSLKSRVSISVDTSKNRFSL RLRSVTAADTAFYYCARGPGHCYGDDDCYAYYFDQWGQ GTPVTVSP |
| | 168 | light | DIQMTQSPSSVSSSVGDRVTITCRASQGISNWLAWYQQNP GKAPKLLIYDASSLQSGVPSRFSGSGSGTDFTLTINSLQPE DFATYYCQQANSFPFTFGPGTKVDIK |
| EV-D68-110 | 169 | heavy | QVQLVQSGAEVKKPGSSVKVSCKASGGTFSRFAISWVRQ APGQGLQWMGGILPIFGTANYAQKFQGRVTITADTSTSTA YMELSSLRSEDTAVYYCARSLPYCTNDVCSNQNTFDYWG QGTLVTVSS |
| | 170 | light | SYELTQPPSVSVSPGQAARITCSGDALPKQYAYWYQQKP GQAPVLVIYEDNKRPSGIPERFSGSSSGTTVTLTISGVQAE DEADYYCQSADSSGTYVVFGGGTKLTVL |
| EV-D68-111 | 171 | heavy | QVQLQESGPGLVKPSQTLSLTCTVSGGSISSGDYYWSWIR QPPGKGLEWIGYIYYSGSTYYNPSLKSRVTISVDTSKNQFS LKLSSVTAADTAVYYCASRYGDPIGDNWFDPWGQGTLVTV SS |
| | 172 | light | SYVLTQPPSVSVTPGKTARITCGGNNIGLKSVFWYQERPD QAPVVVIYYDSARPSGIPERISGSKSGNTATLTITRVEAGDE ADYFCQVWDSSRNHPVFGGGTKLTVL |
| EV-D68-114 | 173 | heavy | EVQLLESGGGLVQPGGSLRLSCAASGFRFSFYGMTWVRQ APGKGLEWVSSISGTGATRNCADSVKGRFTISRDNSKNTL YLQMDSLRVDDTAVFYCVRRFPMTTVTSFDSWGQGTLVT VSS |
| | 174 | light | QSALTQPRSVSGSPGQSVTISCTGTSSDVGGYNFVSWYQ QHPGKAPKLMIFDVTGRPSGVPDRFSGSKSGNTASLTIAG LQAEDEADYYCGAYAGFNALFGGGTKLTVL |
| EV-D68-116 | 175 | heavy | EVQLVQSGGGLVRPGGSVRLSCVASGFPFNMFWMGWVR QTPGKGLEWVANIKQDGSEKYYVDSVKGRFAISRDNAKNS LFLQMDSLSVGDTAIYYCVREGVRRVVVRSTGYFDFWGQ GQLVTVSS |
| | 176 | light | SYELTQPPSMSVSPGQTARITCSGDAVPIKYVYWYQQRSG QAPVLVIYEDDRRPSGISERFSGSSSGTTATLTITGAQVED EGDYYCYSTDSSGYQRAFGGGTTLTVL |
| EV-D68-150 | 177 | heavy | RVQLQESAPGLVRPSETLSLTCSVSGGPISNGPYYWSWIR QHPGKGLEWIGFIFYSGSTNYNPSLRGRVTMAVDTSKNQF SLRLNSVTAADTAVYYCARHVVTASGWFDPWGQGTLVTV SS |
| | 178 | light | EIVLTQSPATLSLSPGERATLSCRASQSVGTDLAWYQQKP GQAPRVLIYDAFKRATGIPARFSGSGSGTEFTLTISSLEPED FAVYYCQQRSRWPPPYTFGQGTKLEIK |
| EV-D68-151 | 179 | heavy | RVQLQESAPGLVRPSETLSLTCSVSGGPISNGPYYWSWIR QHPGKGLEWIGFIFYSGSTNYNPSLRGRVTMAVDTSKNQF SLRLNSVTAADTAVYYCARHVVTASGWFDPWGQGTLVTV SS |
| | 180 | light | EIVLTQSPATLSLSPGERATLSCRASQSVGTDLAWYQQKP GQAPRVLIYDAFKRATGIPARFSGSGSGTEFTLTISSLEPED FAVYYCQQRSRWPPPYTFGQGTKLEIK |
| EV-D68-152 | 181 | heavy | QVHLVESGGGVVQPGRSLRLSCADSGVTFSDNALYWVRQ APGKGLEWVAVISYDGSSRYYADSVRGRFTISRDNSKDTL YLQMNRLRAEDTAIYYCARVTADYYESSGKVFWGQGALVV VSS |
| | 182 | light | DIQMTQSPSTLSASVGDRVSITCRASQSVRSWLAWYQHKP GKAPKLLIYKASSLESGVPSRFSGSGSGTEFTLTISSLQAD DFATYYCQQYQTFSWTFGQGTTVEVK |
| EV-D68-154 | 183 | heavy | QVQLQESGPALVKPSETLSLTCTVSGGSISDHYWSWIRQP PGKGLEWIGYIYTSGTTNYNPSLKSRVTISVDTSKKQFSLNL RSVTAADTAVYYCARSLETVIRFYYHYMDVWGKGTTVIVS S |
| | 184 | light | DIVMTQSPLSLPVTPGEPASISCRSSQSLLQSDGYSYLDWY LQKPGQSPQLLIYLGSNRASGVPDRFSVIGSGTYFTLKISR VEAEDVGVYFCMQALQTPWTFGQGTKVEIK |
| EV-D68-155 | 185 | heavy | QVQLQESGPGLVKPSETLSLTCTVAGGSIGDHWNWIRQP AGKGLEWIGRIHSSGNTDYNPSLKSRVTMSVDTSKNQFSL KLRSVTAADTAVYYCARQNVFDIWGQGTMVTVSS |

TABLE 2-continued

PROTEIN SEQUENCES FOR ANTIBODY VARIABLE REGIONS

| Clone | SEQ ID NO: | Chain | Variable Sequence |
|---|---|---|---|
| | 186 | light | DIVMTQSPDSLALSLGERATINCKSSQSVLFSSNNKNYLAW YQQKPGQPPKLLIYWASTRESGVPDRFSGSGSETDFTLTIS SLQAEDVAVYFCQQFYTTPLTFGGGTKVEIK |
| EV-D68-156 | 187 | heavy | QVQMQESGPGLVKASETLSLTCSVSGISINNYYWSWFRQP PGKGLEWIGYVYSTGSSKYNPSLERRATMSVDTSNNNFSL RLTSVTTADTAVYYCARGSMPHIWGQGLLVTVSS |
| | 188 | light | QSVLTQPPSASGTPGQRVTISCSGSTSNIETNYVYWYQQV PGTAPKPLVYRNDQRPSGVPDRFSGSKSGTSASLVISGLR TEDEAAYYCAAWDDSLKAPVFGAGTKVAVL |
| EV-D68-157 | 189 | heavy | EVQLVESGGGLIKPGGSLRLSCAASGITFSNAWMSWVRQA PGKGLEWVGRIESKIDGGTIDYATPVKGRFTISRDDSKNTL YLQMNSLKTEDTAVYYCTTDQGYYDRSGYWVVGNHFDY WGQGILVTVSS |
| | 190 | light | QSVLTQPPSVSGAPGLRVTISCTGSSTNIGAGYDVHWYQH LPGTAPKLLIYGNSNRPSGVPDRFSGSKSGTSASLAITGLQ ADDAADYYCQSYDRSLSTYVFGTGTKVTVL |
| EV-D68-158 | 191 | heavy | EVQLLESGGGLVQPGGSLRLSCAASGFTFSSYAMNWVRQ APGKGLEWVSGISGTTGSTYYADSVKGRFTISRDNSKNTV HLQMNSLRAEDTAVYYCAKDSHSMIVVDHAFDIWGQGTM VTVSS |
| | 192 | light | SYVLTQPPSVSVAPGQTARITCGGNNIGTKSVHWYQQRPG QAPVLVVYDDSDRPSGIPERFSGSNSGNTATLTISRVEAGD EADYYCQVWDSYNVHYVFGTGTKVTVL |
| EV-D68-159 | 193 | heavy | EVQLVESGGGLVKPGGSLRLSCAASGFTFSTY1MTWVRQA PGRGLEWVSSISTSSVYTFYADSLKGRFTISRDNAKNSVYL QMNSLRADDTAVYYCAREEGFRAYNLYWGQGTLVTVSS |
| | 194 | light | QSVLTQPPSASGTPGQRVTISCSGSSSNIEYNYVYWYQKF PGTAPKLLIYKNNQRPSGVPDRFSGSKSGTSASLAISGLRS EDEGDYYCAAWDDILSGVVFGGGTKLTVL |
| EV-D68-160 | 195 | heavy | QVQLVESGGGVVQPGRSQKLSCAASGFTFSRFGMHWVR QAPGKGLEWVAVISFDGSNRYYADSVKGRFTITRDNSKNT LYLQMNNLRPEDTAVYYCARDWDRLVRSAVGYWGQGTLV SVSS |
| | 196 | light | QSALTQPRSVSGSPGQSVTISCTGTSNDVGGYNFVSWYQ QHPGKAPKLMIFDVIRRPSGVPGRFSGSKSGDTASLIISGL QAEDEADYYCCSYAGTYTWVFGAGTTLTVL |
| EV-D68-161 | 197 | heavy | QVHLQESGPRLVKPSETLSLTCTVSGGSVSTATYYWSWIR QSPGRGLEWIGYIYSSGNTNYNPSLKSRVTISLDTPNNQLS LTLTSVTAADTAIYYCERRLRILSIERNYYAMDVWGQGTPV TVSS |
| | 198 | light | EVVLTQTPGTLSLSPGEGATLSCRASQRVVNNYLAWYQQ RAGQAPRLLIFGASNRATGIPDRFSGSGSGTDFTLTIRKLE PEDFAVYYCQQYGSPWTFGHGTKVEMK |
| EV-D68-162 | 199 | heavy | QVQLVESGGGVVQPGRSLRLSCAASGFTFSSYAMHWVR QAPGRGLEWVAVISYDASKKYHADSVKGRFTISRDSSKNT LFLQMNSLKPEDTAVYYCARDHVPPKDCSDGNCHSDYGM DVWGQGTTVTVSS |
| | 200 | light | DIQMTQSPSTMSASVGDRVTITCRASQSISKWLAWYQQKP GKAPKLLIYKASTLQTGVPSRFSGSGSGTEFTLTINSLQPD DFATYYCQQHNSYSYTFGQGTKVEIK |
| EV-D68-163 | 201 | heavy | QVQLVQSGAEVKKPGASVKISCKASGYSFTNFAVHWVRQ APGQRLEWMGWINPGNRNTKYSHNFQGRVTITRDTSANT AYMELSSLRSQDTAVYYCARLPIAAAGRGWFDPWGQGTL VTVSS |
| | 202 | light | EIVLTQSPGTLSLSPGERATLSCRASQSVISTYLAWYQQRP GQAPRVLIYDVSTRATGIPDRFSGSGSGTDFTLTISRLEPE DFAVYFCHQYGSSPATFGQGTKVEIK |
| EV-D68-164 | 203 | heavy | EVQLVESGGDLVQPGGSLRLSCAASGFTFNTYGMNWVRQ APGKGLEWVSYISSATTTFYYADSVRGRFTISRDNAKNSLF LHMKSLRDEDTAVYYCARVYTMLRGASMDVWGHGTTVTV SS |
| | 204 | light | EIVLTQSPATLSLSPGERATLSCRASQSVGTYLAWYQQKP GQAPRLLIYDSANRATGIPARFSGSGSGTDFTLTISSLEPED FAVYYCQLRITWPPIFTFGPGTKVDVK |

TABLE 2-continued

PROTEIN SEQUENCES FOR ANTIBODY VARIABLE REGIONS

| Clone | SEQ ID NO: | Chain | Variable Sequence |
|---|---|---|---|
| EV-D68-165 | 205 | heavy | QVHLVQSGAEVKKSGASVKVSCKTFGYTFTAYYMHWVRQ APGQGPEWMGWINPISGGTNYAQKFQGRVSMTRDTSIST AYMGLSRLRPDDTAVYYCARVKCSSANCYGNFDYWGQG TLVTVSS |
| | 206 | light | QSALTQPPSASGSPGESVTISCTGTSSDVGGYNYVSWYQ QHPGKAPKLMIYEVSKRPSGVPDRFSGSKSGNTASLTVSG LQAEDEADYYCSSYAGSNNLVFGGGTKLTVL |
| EV-D68-166 | 207 | heavy | EVQLVQSGAEVKKPGESLKISCKGSGYRFTNYRIGWVRQM PGKGLEWMGIIYPGGSDTRYSPSLQGQVTMSVDKSISTAY LMWSSLKASDTAMYYCARQTTQNSGYDRWFDSWGQGTH VTVSS |
| | 208 | light | QSVLTQPPSASGTPGQRVTISCSGSTSSIGSNIVNWYQHLP GTAPKLLIYINNQRPSGVPDRFSGSKSGTSASLAISGLQSE DEADYYCAAWDDSLNGWVFGGGTKLTVL |
| EV-D68-181 | 209 | heavy | EVQVLESGGGLVQPGGSLRLSCAASGITFSRHTMSWVRQ APGKGLEWVSAISGSGGSTYHADSVKGRFTISRDSSKSTL YLQMNSLRAEDTAVYYCAISVPLLRFLEWFQHPFDFWGQG TLVTVSS |
| | 210 | light | EIVMTQSPASLSVSPGERVTLSCRASQSVGSTLAWYQHKP GQAPRLLISGASTRATGVPARFSGSGSGTEFTLTISSLQSE DFAVYYCHQYINWPPWTFGQGTKVEIK |
| EV-D68-183 | 211 | heavy | EVRLVESGGGLVKPGGSLRLSCAASGFTFNTYSMSWVRQ APGKGLEWVASISSTGSYIYNADSLKGRFTISRDNAKNSLF LQMNSLRVEDTAVYYCVRFTMTTVTNFDSWGQGTLVTVS S |
| | 212 | light | QSALTQPRSVSGSPGQSVTISCTGTSSDVGAYSYVSWYQ QHPGKAPKLMIYDVYRRPSGVPGRFSGSKSGNTASLTVSG LQAEDEADYYCCSHAGSHTWVFGGGTKVTVL |
| EV-D68-185 | 213 | heavy | QLQVVASGGGVVQPGRSLRLSCKASGFTFTNYGMHWVR QAPGKGLEWVAFISYDGGNKFYADSVKGRFTISRDNSRNT VYLQMNSLRVADTAMYYCPKVIPHPYYDSSGDDAFDIWGQ GTMVAISS |
| | 214 | light | EIVMTQSPATLSVSPGERATLSCWASQSISRNLAWYQQKP GQAPRLLIYGASTRATGIPAKFSGSGSGTDFTLIVSSLQSE DLAVYYCQQYSKLPITFGQGTRLEIK |
| EV-D68-200 | 215 | heavy | EVQLVESGGGLVQPGGSLRLSCAASGFPFSSYSMSWVRQ APGKGLEWVSYISGSGGDIYYADSVKGRFTISRDNARNSL SLQMNSLRADDTAVYYCARGLVATTGTRYFDYWGQGTLV TVSS |
| | 216 | light | EIVLTQSPATLSLSPGERATLSCRASQSVRSYLAWYQQRP GQAPRLLIYDASNRATGIPVRFSGSGSGTDFTLTISSLEPED FAVYYCQQRSYWPPFTFGGGTKVEIK |
| EV-D68-208 | 217 | heavy | QVQLVQSGAEVKKPGSSVKVSCKASGGTFRRFAISWVRQ APGQGLEWMGGIIPILGRGKYAQKFQGRVRITADESTSTAY MELSSLRSEDTAVYYCARFISTASYVPGTFEDVWGQGTTV TVSS |
| | 218 | light | DIVLTQSPATLSLSPGERATLSCRASQSVSSYLAWYQQKP GQAPRLLIYDASNRAAGIPARFSGSGSETDFTLTISSLEPED VAVYYCQQRSDWPPGTFGQGTNVEIK |
| EV-D68-210 | 219 | heavy | EVQLVESGGGLVKPGGSLRLSCAASGFTFRNYNINWVRQ APGKGLEWVSSISSTGSYIHYADLVKGRFTISRDNAKNSLY LQMNSLRVEDTAVYYCARMVRNTVTAFDYWGQGTLVSVS S |
| | 220 | light | QSALTQPASVSGSPGQSITISCTGTSSDVGGYNFVSWYQQ QPGRAPKLLIYEVIKRPSGVSDRFSGSKSGDTASLTISGLQ AEDEADYYCCSYGGNNSWMFGGGTMLTVL |
| EV-D68-219 | 221 | heavy | QVQVVQSGAEMKKPGASVKVSCKVSGYRLIDLPLHWVRQ APGKGLEWMGLFDPEKAEAIYSQKFQDKVTISEDTSIDTAY MELNSLRSEDTAVYYCATWGVEVVNGRRDYFDSWGQGT LVTVSS |
| | 222 | light | SYELTQPPSVSVSPGQTARITCYADVLSNQYTYWYQQKPG QAPVLVIYKDTERPSGIPERFAGSSSGTTVTLVINGVRAED EAYYYCQSADNTRITVFGGGTKLSVL |

TABLE 2-continued

PROTEIN SEQUENCES FOR ANTIBODY VARIABLE REGIONS

| Clone | SEQ ID NO: | Chain | Variable Sequence |
|---|---|---|---|
| EV-D68-220 | 223 | heavy | GVQLVESGGGLIQPGGSLRLSCAASGFTFSSFEMNWVRQAPGKGLEWVSYISTSGSTIYYADSVKGRFTISRDNARNSLSLQMNSLRAEDTAVYYCARDVRDCSALTCPRRGDAFDFWGRGTRVTVSS |
| | 224 | light | DVVMTQSPLSLPVTLGQSASISCRSSQSLVYSDGNTYLNWFQQRPGQSPRRLIYKVSNRDSGVPDRFSGSGSGTDFTLKISRVEAEDVGVYYCMQGTHWPRTFGPGTKVDIK |
| EV-D68-221 | 225 | heavy | EVQLVESGGGLVKPGGSLRLSCAASGFSFSVYPMNWVRQAPGKGLEWVSSISSSSRYISYADSLRGRITISRDNAKNSLYLQMNSLRVEDTAVYYCVKVGGSKHQYYFDYWGQGSLVTVSS |
| | 226 | light | QSVLTQPPSTSGIPGQTVTISCSGSRSNIGSYTVNWYEQLPGTAPKLVIFNNNQRPSGVPDRFSGSKSGTSASLAISGLQSEGEADYYCAAWDDSLNGVVFGGGTKLTVL |
| EV-D68-224 | 227 | heavy | QVQLVQSGAEVKRPGASVKVFCKASGYTFTNYDIIWVRQAPGQGLEWVGWISTYNGNTNYEQNLQGRVTMTTDTSTSTAYMELRSLRSDDTAVYYCARERCSTSTCYSRYADYWGQGTLVTVSS |
| | 228 | light | DIQMTQSPSSLSASVGDRVTITCRASQSINIYLNWYQQKPGKAPKVLIYAASSLQSGVPSRFRGSGSGTDFILTISSLQPEDFATYYCQQSYRSPRTFGQGTEVEIK |
| EV-D68-225 | 229 | heavy | EVQLVESGGGLAQPGESMRLSCVASGFTLSRYEVNWVRQAPGKGLEWLSYISSGGPSIYYADSVKGRFTISRNSAENSLELQMSTLRTEDTAVYYCMREGLTYYDSTIWGQGTLVAVSS |
| | 230 | light | QNVLTQSPSASASLGASVKLTCTLNSGHSRYAIAWHQHQPQRGPRFLMKINSDGRHIRGDGISDRFSGSASGAERHLTISSLQPEDEADYYCQTWGTGFRVFGGGTKLTVL |
| EV-D68-227 | 231 | heavy | EVQLVESGGGLVQPGRSLRLSCAASGFTFDEYAMHWVRQVPGKGLEWVSGISWNGGSKGYADSVKGRFTISRDNARYSLSLQMNSLRTEDTALYYCAKDDYEGAGFDIWGQGTVVTVSS |
| | 232 | light | EIVLTQSPATLSLSPGERATLSCRASQSVSSYLGWYQQKSGQAPRLLIYGASSRATGIPARFSGSGSGTDFTLTISSLEPEDFAIYYCQQRSNWPITFGQGTRLEIK |
| EV-D68-228 | 233 | heavy | QVQLQESGPGLVKPSETLSLTCTVSGYLISNGYYWGWIRQSPGKGLEWIGSIYYTRDTYYNWSLKSRITISVDTSKKQFSLKLYSVTAADTAVYYCVRHEGSCNDGSCYGSFVDNWGQGTLVTVSS |
| | 234 | light | DIQMTQSPSSVSASVGDRVTLTCRASQDISSWLAWYQQKPGKAPKLLIYAASSLQSGVPSRFSGSGSGTHFTLTISSLQPEDFATYFCQQADSFITFGGGTKVEIK |
| EV-D68-231 | 235 | heavy | EVQLLESGGGLVQPGGSLRLSCAASDFTFSSYTMAWVRQAPGKGLEWVSSISGDGVSTKNADSVKGRFSVSRDNSKNTLFLQLNSLRAEDTAFYYCARGGTFHNWYFDLWGRGVLVTVSS |
| | 236 | light | EIVMTQSPATLSVSPGETATLSCRASQSIGDNLAWYQQKPGQAPRLLISGASTRATDFPARFRGSGSGTEFTLTISSLQSEDFAVYYCQQYKNWPRTFGRGTKVEVR |
| EV-D68-234 | 237 | heavy | EVQLLESGGGLVQPGGSLRLSCAASGFTFSTYAMSWVRQAPGKGPEWVSGISGSGGSTNYADSAKGRFTISRDNSKNTLYLQMNSLRAEDTAVYYCAKGTITYSYYYMAVWGKGTTVTVSS |
| | 238 | light | EIVLTQSPGTLSLSPGERGTLSCRASQSVRSSYLAWYQQRPGQAPRLLIYGASSRATGIPDRFSGSGSGTDFTLTIGRLEPEDFAVYYCQQYGTSITFGGGTKVEIK |
| EV-D68-235 | 239 | heavy | QVQVVQSGAEMRKPGASVRVSCKVSGYRLTDLPLHWVRQAPGKGLEWIGFVDLEKREIIYAQKFQGKVTITEDTSADTAYMELNSLRSEDTAVYYCATWGIEVVNGRDEFFDSWGQGTLVSVSS |
| | 240 | light | SYELTQPPSVSVSPGQTARITCYADVLSKQYTYWYQQKPGQAPVLVIYKDTERPSGIPERFAGSSSGTTVTLIINGVRTEDEAYYYCQSADTRIVFGGGTKLSVL |
| EV-D68-236 | 241 | heavy | QVQVVQSGAEMKKPGASVKVSCKVSGYSLSDLPLHWVRQAPGKGLEWMGLFDPINGEIIYAQTFQGKVTISEDTSIDTAYMELNSLRSEDTAVYYCATWGVAVVSGRRDYFDSWGQGTLVTVSS |

TABLE 2-continued

PROTEIN SEQUENCES FOR ANTIBODY VARIABLE REGIONS

| Clone | SEQ ID NO: | Chain | Variable Sequence |
|---|---|---|---|
| | 242 | light | SYELTQPPSVSVSPGQTARITCYAAVLSNQYTYWYQQKPG QAPVLVIYKDTERPSGIPERFAGSSSGTTVTLIINGVRTEDE AYYYCQTADTKYTVFGGGTKLSVL |
| EV-D68-241 | 243 | heavy | QVQLQESGPGLVKPSQTLSLTCTVSGGSITSGDYYWNWIR QPPGKGLEWIGYIYHSGTTYYNPSLKSRVTISVDTSKNRFS LKLSSVTAADTAVYFCARAYAYEFWSGYPNWFDPWGLGT LVTVSS |
| | 244 | light | DIQMTQSPSSLSASVGDRVTITCRASQRISTYVNWYQVKA GTAPKVLIYAASSLQTGVPSRFSGSGSGTDFTLTIVSLQPE DFTTYFCQQSYSPPWTFGQGTKVEIK |
| EV-D68-247 | 245 | heavy | QVQLVESGGGLVQPGRSLRLSCAASGFIFNRYAMHWVRQ APGKGLEWVALISYDGINKYYADSVKGRFSISRDNSKSTLY LQMNSLRAEDTAIFYCARGLGYCSGTGGSCTPFEYWGQGI LVTVSS |
| | 246 | light | DIQMTQSPPSLSASVGDRVTITCRASQSIKKYLNWYQQKP GNAPKLLIYGASNLQTGVPSRFSGSGSGTDFALSISSLETE DFATYYCQQSDSAPPTFGGGTKVEFK |
| EV-D68-254 | 247 | heavy | QVQLQQRGAGLLKPSETLSLTCEIYGASLNDYDWTWIRQP PGKRLEWIGVINRRDTVDYNPSLKSRVTLSLDTSKNQLSLS LSSVTAADTAVYYCVRVPRRGFEGSFGFCDDTACRYGHT WFDPWGQGTLVTVSS |
| | 248 | light | DIQMTQSPSSLSASVGDRVTITCRASQSIRDYLNWYQQRP GKAPKVLIFAGSRLESGVPSRFRGRGSGTEFTLTISDLQPE DFATYYCQQSYLTPPTFGQGTTVDIK |
| EV-D68-260 | 249 | heavy | QVTLKESGPVLVKPTETLTLTCTVSGFSLRNGRMGVSWIR QPPGKALEWLAHIFASDEKSYSTSQRTRLSISRDTSKSQVV LSMTDMDPVDTATYYCARILKFGTMRAAYYFDYWGQGAL VPVSS |
| | 250 | light | SYVLTQPPSVSVAPGKTARITCGGINIGIRTVHWYQQKPGQ APMLVIYYDSDRPLGIPERFSGSKSGNTATLTISRVEAGDE ADYYCQVWDSSSDHVVFGGGTKLTAL |
| EV-D68-266 | 251 | heavy | QVHLVESGGGLVKPGGSLRLSCAVSGFTFSDYYMSWIRQ APGKGLEWLSYISSSGSTIYYADSMKGRFTISRDNARNSLY LQMNSLRVEDTAFYYCAGSKVGYTTGRRNWYFDLWGRG TLVTVSS |
| | 252 | light | QSALTQPPSASGSPGQSVTISCTGTSSDVGAYNYVSWYQ QHPGKAPKLMIYEVTKRPSGVPDRFSGSKSGNTASLTVSG LQAEDEADYYCSSYAGNNNLVFGGGTKLTVL |
| EV-D68-269 | 253 | heavy | QVQLLQSGSEVRKPGASVNIHCKASGFTFTDFYLHWVRQA PGQGLEWMGIINPETGETTYSQKFQGRVTMTRDTSTSVVN LEVRSLRSEDTAIYYCARDLVVVVPVEMSRRAFDIWGQGIM VTVSS |
| | 254 | light | SYVLTQPPSVSVAPGQTARIPCGGNNIERKSVHWYQQRP GQAPVLVVYDDTVRPSGIPERFSGSNSGSTATLTISRVGAG DEGDYYCQVWDSTTDHGVFGGGTKLTVL |
| EV-D68-271 | 255 | heavy | RVQLVQSGAEVKKPGASVKVSCQTSGYIFSAYYIYWVRQA PGQGLEWMGRMNAKSGGANTAQQFQGRLTMTRDMSVS TAYMELSRLRSDDTAVYYCARDYRDDYMWGSYRPLDYW GQGTLVTVSS |
| | 256 | light | EVVLTQSPATLSLSPGERASLSCRASQSVSGYLAWYQHKP GQAPRLLIYDASNRAAGIPARFRGSGSGTDFTLTISSLEPE DFAVYFCQQRSNGLTFGGGTKVEIK |

TABLE 3

CDR HEAVY CHAIN SEQUENCES

| Clone | CDRH1 (SEQ ID NO:) | CDRH2 (SEQ ID NO:) | CDRH3 (SEQ ID NO:) |
|---|---|---|---|
| EV-D68-37 | GFIFSRYA (257) | ISYDARNS (258) | ARPTLPYSNNWYAPEY (259) |
| EV-D68-40 | GFSFSSYA (260) | ISGNGNGR (261) | AKVVRIAAVLYYFDY (262) |

TABLE 3-continued

CDR HEAVY CHAIN SEQUENCES

| Clone | CDRH1 (SEQ ID NO:) | CDRH2 (SEQ ID NO:) | CDRH3 (SEQ ID NO:) |
|---|---|---|---|
| EV-D68-41 | GFTFSNYA (263) | ISGSGGLT (264) | ARVKSTTGTTALVFDI (265) |
| EV-D68-43 | GFTFINYG (266) | ISNDGSYN (267) | AKDKHGDFDYYGVDV (268) |
| EV-D68-46 | GFTFSSYG (269) | ISYDGSDN (270) | ARRRPGSFPGLCDY (271) |
| EV-D68-48 | GGSFSRLT (272) | HIPIFGTT (273) | ARMYSGHDGVDV (274) |
| EV-D68-71 | GGSISSGFYY (275) | IYDSGRT (276) | ARHLTHLYGDYVTPDALDI (277) |
| EV-D68-72 | GFTFTTYS (278) | ISSGSSNI (279) | ARAHGRIVNSGVVISRFDP (280) |
| EV-D68-74 | GYTFTAYY (281) | INPSSGGA (282) | ARMGCRSDRCYSTNYNFDQ (283) |
| EV-D68-75 | GFTISPYG (284) | ISSSSRYT (285) | ARERGHSTSSSYFDS (286) |
| EV-D68-76 | GFTFSNAW (287) | IQTKIDGGIT (288) | STGPYYYDTSGYPQPFDY (289) |
| EV-D68-80 | GFDFSRYT (290) | ISSTSLYT (291) | ARVVGPAELDY (292) |
| EV-D68-84 | GYTFTDYY (293) | INPKTGGS (294) | ARAGRNGYDY (295) |
| EV-D68-85 | GFKFRNYA (296) | ITSGGST (297) | TVPWGNYNDYVSDY (298) |
| EV-D68-88 | GFIFSRYP (299) | ISYDGNNK (300) | ARHFLPYSSSWYQGFNY (301) |
| EV-D68-89 | GFLFSRYG (302) | ISYDGNKK (303) | ARGVPYGDTLTGLVY (304) |
| EV-D68-95 | GFSLRNARMG (305) | IFSNDEK (306) | ARLLVAGTFLPSHYFDY (307) |
| EV-D68-97 | GFTFSTYS (308) | ISSSSSTI (309) | TRQVGADFSGRGFDY (310) |
| EV-D68-98 | GFKFSVYA (311) | ISSSGSTI (312) | ATARHITNDGFDI (313) |
| EV-D68-105 | GYLISNGYY (314) | IYHTRST (315) | ARGPGHCYGDDDCYAYYFDQ (316) |
| EV-D68-110 | GGTFSRFA (317) | ILPIFGTA (318) | ARSLPYCTNDVCSNQNTFDY (319) |
| EV-D68-111 | GGSISSGDYY (320) | IYYSGST (321) | ASRYGDPIGDNWFDP (322) |
| EV-D68-114 | GFRFSFYG (323) | ISGTGATR (324) | VRRFPMTTVTSFDS (325) |
| EV-D68-116 | GFPFNMFW (326) | IKQDGSEK (327) | VREGVRRVVVRSTGYFDF (328) |
| EV-D68-150 | GGPISNGPYY (329) | IFYSGST (330) | ARHVVTASGWFDP (331) |

TABLE 3-continued

CDR HEAVY CHAIN SEQUENCES

| Clone | CDRH1 (SEQ ID NO:) | CDRH2 (SEQ ID NO:) | CDRH3 (SEQ ID NO:) |
|---|---|---|---|
| EV-D68-151 | GGPISNGPYY (332) | IFYSGST (333) | ARHVVTASGWFDP (334) |
| EV-D68-152 | GVTFSDNA (335) | ISYDGSSR (336) | ARVTADYYESSGKVF (337) |
| EV-D68-154 | GGSISDHY (338) | IYTSGTT (339) | ARSLETVIRFYYYHYMDV (340) |
| EV-D68-155 | GGSIGDYH (341) | IHSSGNT (342) | ARQNVFDI (343) |
| EV-D68-156 | GISINNYY (344) | VYSTGSS (345) | ARGSMPHI (346) |
| EV-D68-157 | GITFSNAW (347) | IESKIDGGTI (348) | TTDQGYYDRSGYWVVGNHFDY (349) |
| EV-D68-158 | GFTFSSYA (350) | ISGTTGST (351) | AKDSHSMIVVDHAFDI (352) |
| EV-D68-159 | GFTFSTYI (353) | ISTSSVYT (354) | AREEGFRAYNLY (355) |
| EV-D68-160 | GFTFSRFG (356) | ISFDGSNR (357) | ARDWDRLVRSAVGY (358) |
| EV-D68-161 | GGSVSTATYY (359) | IYSSGNT (360) | ERRLRILSIERNYYAMDV (361) |
| EV-D68-162 | GFTFSSYA (362) | ISYDASKK (363) | ARDHVPPKDCSDGNCHSDYGMDV (364) |
| EV-D68-163 | GYSFTNFA (365) | INPGNRNT (366) | ARLPIAAAGRGWFDP (367) |
| EV-D68-164 | GFTFNTYG (368) | ISSATTTF (369) | ARVYTMLRGASMDV (370) |
| EV-D68-165 | GYTFTAYY (371) | INPISGGT (372) | ARVKCSSANCYGNFDY (373) |
| EV-D68-166 | GYRFTNYR (374) | IYPGGSDT (375) | ARQTTQNSGYDRWFDS (376) |
| EV-D68-181 | GITFSRHT (377) | ISGSGGST (378) | AISVPLLRFLEWFQHPFDF (379) |
| EV-D68-183 | GFTFNTYS (380) | ISSIGSYI (381) | VRFTMTTVTNFDS (382) |
| EV-D68-185 | GFTFTNYG (383) | ISYDGGNK (384) | PKVIPHPYYDSSGDDAFDI (385) |

TABLE 3-continued

CDR HEAVY CHAIN SEQUENCES

| Clone | CDRH1 (SEQ ID NO:) | CDRH2 (SEQ ID NO:) | CDRH3 (SEQ ID NO:) |
|---|---|---|---|
| EV-D68-200 | GFPFSSYS (386) | ISGSGGDI (387) | ARGLVATTGTRYFDY (388) |
| EV-D68-208 | GGTFRRFA (389) | IIPILGRG (390) | ARFISTASYVPGTFEDV (391) |
| EV-D68-210 | GFTFRNYN (392) | ISSIGSYI (393) | ARMVRNTVTAFDY (394) |
| EV-D68-219 | GYRLIDLP (395) | FDPEKAEA (396) | ATWGVEVVNGRRDYFDS (397) |
| EV-D68-220 | GFTFSSFE (398) | ISTSGSTI (399) | ARDVRDCSALTCPRRGDAFDF (400) |
| EV-D68-221 | GFSFSVYP (401) | ISSSSRYI (402) | VKVGGSKHQYYFDY (403) |
| EV-D68-224 | GYTFTNYD (404) | ISTYNGNT (405) | ARERCSTSTCYSRYADY (406) |
| EV-D68-225 | GFTLSRYE (407) | ISSGGPSI (408) | MREGLTYYDSTI (409) |
| EV-D68-227 | GFTFDEYA (410) | ISWNGGSK (411) | AKDDYEGAGFDI (412) |
| EV-D68-228 | GYLISNGYY (413) | IYYTRDT (414) | VRHEGSCNDGSCYGSFVDN (415) |
| EV-D68-231 | DFTFSSYT (416) | ISGDGVST (417) | ARGGTFHNWYFDL (418) |
| EV-D68-234 | GFTFSTYA (419) | ISGSGGST (420) | AKGTITYSYYYMAV (421) |
| EV-D68-235 | GYRLTDLP (422) | VDLEKREI (423) | ATWGIEVVNGRDEFFDS (424) |
| EV-D68-236 | GYSLSDLP (425) | FDPINGEI (426) | ATWGVAVVSGRRDYFDS (427) |
| EV-D68-241 | GGSITSGDYY (428) | IYHSGTT (429) | ARAYAYEFWSGYPNWFDP (430) |
| EV-D68-247 | GFIFNRYA (431) | ISYDGINK (432) | ARGLGYCSGTGGSCTPFEY (433) |
| EV-D68-254 | GASLNDYD (434) | INRRDTV (435) | VRVPRRGFEGSFGFCDDTACRYGHTWFDP (436) |
| EV-D68-260 | GFSLRNGRMG (437) | IFASDEK (438) | ARILKFGTMRAAYYFDY (439) |
| EV-D68-266 | GFTFSDYY (440) | ISSSGSTI (441) | AGSKVGYTTGRRNWYFDL (442) |

TABLE 3-continued

CDR HEAVY CHAIN SEQUENCES

| Clone | CDRH1 (SEQ ID NO:) | CDRH2 (SEQ ID NO:) | CDRH3 (SEQ ID NO:) |
|---|---|---|---|
| EV-D68-269 | GFTFTDFY (443) | INPETGET (444) | ARDLVVVPVEMSRRAFDI (445) |
| EV-D68-271 | GYIFSAYY (446) | MNAKSGGA (447) | ARDYRDDYMWGSYRPLDY (448) |

TABLE 4

CDR LIGHT CHAIN SEQUENCES

| Clone | CDRL1 (SEQ ID NO:) | CDRL2 (SEQ ID NO:) | CDRL3 (SEQ ID NO:) |
|---|---|---|---|
| EV-D68-37 | ALPKKY (449) | EDT (450) | SSTDSSGNPVL (451) |
| EV-D68-40 | QSVSTY (452) | EAS (453) | QQRSSWPIT (454) |
| EV-D68-41 | SGSVSSSYY (455) | SIN (456) | GLYMGSGIWI (457) |
| EV-D68-43 | QGISSW (458) | AAS (459) | QQADSFPRT (460) |
| EV-D68-46 | QSISKW (461) | KAS (462) | QQHNSYSYT (463) |
| EV-D68-48 | QSVRSY (464) | DAS (465) | QQRSTWPPGM (466) |
| EV-D68-71 | QSVSSSF (467) | GAS (468) | QQYSNSRLT (469) |
| EV-D68-72 | SSDVGGYNY (470) | EVT (471) | SSYTTSNTLVV (472) |
| EV-D68-74 | NIGTKS (473) | NDS (474) | QVWDSGIDVV (475) |
| EV-D68-75 | NIGTKT (476) | YDS (477) | RVWDSDTDHRV (478) |
| EV-D68-76 | KLGDKY (479) | QDT (480) | QAWDSSTVV (481) |
| EV-D68-80 | QDIGVD (482) | GAS (483) | LQDYNYPWT (484) |
| EV-D68-84 | ALPKQY (485) | QDT (486) | QSGDSSGTYLV (487) |
| EV-D68-85 | QRVGNS (488) | DAS (489) | HQHSTWPRGT (490) |
| EV-D68-88 | SGSIATNY (491) | EDS (492) | QSYDNSNRAVV (493) |
| EV-D68-89 | SGTIASNY (494) | EDN (495) | QSYDNSDRV (496) |
| EV-D68-95 | NIGLKS (497) | YDS (498) | QVWDSSRNHPV (499) |
| EV-D68-97 | KLGDKY (500) | QDS (501) | QAWDSSTAV (502) |
| EV-D68-98 | QGISRF (503) | SAS (504) | QQLNSHPRMFT (505) |
| EV-D68-105 | QGISNW (506) | DAS (507) | QQANSFPFT (508) |
| EV-D68-110 | ALPKQY (509) | EDN (510) | QSADSSGTYVV (511) |
| EV-D68-111 | NIGLKS (512) | YDS (513) | QVWDSSRNHPV (514) |
| EV-D68-114 | SSDVGGYNF (515) | DVT (516) | GAYAGFNAL (517) |
| EV-D68-116 | AVPIKY (518) | EDD (519) | YSTDSSGYQRA (520) |
| EV-D68-150 | QSVGTD (521) | DAF (522) | QQRSRWPPPYT (523) |
| EV-D68-151 | QSVGTD (524) | DAF (525) | QQRSRWPPPYT (526) |
| EV-D68-152 | QSVRSW (527) | KAS (528) | QQYQTFSWT (529) |
| EV-D68-154 | QSLLQSDGYSY (530) | LGS (531) | MQALQTPWT (532) |
| EV-D68-155 | QSVLFSSNNKNY (533) | WAS (534) | QQFYTTPLT (535) |
| EV-D68-156 | TSNIETNY (536) | RND (537) | AAWDDSLKAPV (538) |
| EV-D68-157 | STNIGAGYD (539) | GNS (540) | QSYDRSLSTYV (541) |
| EV-D68-158 | NIGTKS (542) | DDS (543) | QVWDSYNVHYV (544) |
| EV-D68-159 | SSNIEYNY (545) | KNN (546) | AAWDDILSGVV (547) |
| EV-D68-160 | SNDVGGYNF (548) | DVI (549) | CSYAGTYTWV (550) |
| EV-D68-161 | QRVVNNY (551) | GAS (552) | QQYGSPWT (553) |
| EV-D68-162 | QSISKW (554) | KAS (555) | QQHNSYSYT (556) |
| EV-D68-163 | QSVISTY (557) | DVS (558) | HQYGSSPAT (559) |

TABLE 4-continued

CDR LIGHT CHAIN SEQUENCES

| Clone | CDRL1 (SEQ ID NO:) | CDRL2 (SEQ ID NO:) | CDRL3 (SEQ ID NO:) |
|---|---|---|---|
| EV-D68-164 | QSVGTY (560) | DSA (561) | QLRITVVPPIFT (562) |
| EV-D68-165 | SSDVGGYNY (563) | EVS (564) | SSYAGSNNLV (565) |
| EV-D68-166 | TSSIGSNI (566) | INN (567) | AAWDDSLNGWV (568) |
| EV-D68-181 | QSVGST (569) | GAS (570) | HQYINWPPWT (571) |
| EV-D68-183 | SSDVGAYSY (572) | DVY (573) | CSHAGSHTWV (574) |
| EV-D68-185 | QSISRN (575) | GAS (576) | QQYSKLPIT (577) |
| EV-D68-200 | QSVRSY (578) | DAS (579) | QQRSYWPPFT (580) |
| EV-D68-208 | QSVSSY (581) | DAS (582) | QQRSDWPPGT (583) |
| EV-D68-210 | SSDVGGYNF (584) | EVI (585) | CSYGGNNSWM (586) |
| EV-D68-219 | VLSNQY (587) | KDT (588) | QSADNTRITV (589) |
| EV-D68-220 | QSLVYSDGNTY (590) | KVS (591) | MQGTHWPRT (592) |
| EV-D68-221 | RSNIGSYT (593) | NNN (594) | AAWDDSLNGVV (595) |
| EV-D68-224 | QSINIY (596) | AAS (597) | QQSYRSPRT (598) |
| EV-D68-225 | SGHSRYA (599) | INSDGRH (600) | QTWGTGFRV (601) |
| EV-D68-227 | QSVSSY (602) | GAS (603) | QQRSNWPIT (604) |
| EV-D68-228 | QDISSW (605) | AAS (606) | QQADSFIT (607) |
| EV-D68-231 | QSIGDN (608) | GAS (609) | QQYKNWPRT (610) |
| EV-D68-234 | QSVRSSY (611) | GAS (612) | QQYGTSIT (613) |
| EV-D68-235 | VLSKQY (614) | KDT (615) | QSADTRITV (616) |
| EV-D68-236 | VLSNQY (617) | KDT (618) | QTADTKYTV (619) |
| EV-D68-241 | QRISTY (620) | AAS (621) | QQSYSPPWT (622) |
| EV-D68-247 | QSIKKY (623) | GAS (624) | QQSDSAPPT (625) |
| EV-D68-254 | QSIRDY (626) | AGS (627) | QQSYLTPPT (628) |
| EV-D68-260 | NIGIRT (629) | YDS (630) | QVWDSSSDHVV (631) |
| EV-D68-266 | SSDVGAYNY (632) | EVT (633) | SSYAGNNNLV (634) |
| EV-D68-269 | NIERKS (635) | DDT (636) | QVWDSTTDHGV (637) |
| EV-D68-271 | QSVSGY (638) | DAS (639) | QQRSNGLT (640) |

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
U.S. Pat. No. 6,485,982
"Antibodies: A Laboratory Manual," Cold Spring Harbor Press, Cold Spring Harbor, NY, 1988.
Abbondanzo et al., *Am. J. Pediatr. Hematol. Oncol.*, 12(4), 480-489, 1990.
Allred et al., *Arch. Surg.*, 125(1), 107-113, 1990.
Atherton et al., *Biol. of Reproduction*, 32, 155-171, 1985.
Barzon et al., *Euro Surveill.* 2016 Aug. 11; 21(32).
Beltramello et al., *Cell Host Microbe* 8, 271-283, 2010.
Brown et al., *J. Immunol. Meth.*, 12; 130(1), :111-121, 1990.

Campbell, In: *Monoclonal Antibody Technology, Laboratory Techniques in Biochemistry and Molecular Biology*, Vol. 13, Burden and Von Knippenberg, Eds. pp. 75-83, Amsterdam, Elsevier, 1984.
Capaldi et al., *Biochem. Biophys. Res. Comm.*, 74(2):425-433, 1977.
De Jager et al., *Semin. Nucl. Med.* 23(2), 165-179, 1993.
Dholakia et al., *J. Biol. Chem.*, 264, 20638-20642, 1989.
Diamond et al., *J Virol* 77, 2578-2586, 2003.
Doolittle and Ben-Zeev, *Methods Mol. Biol.*, 109, :215-237, 1999.
Duffy et al., *N. Engl. J. Med.* 360, 2536-2543, 2009.
Elder et al. Infections, infertility and assisted reproduction. Part II: Infections in reproductive medicine & Part III: Infections and the assisted reproductive laboratory. Cambridge UK: Cambridge University Press; 2005.
Gefter et al., *Somatic Cell Genet.*, 3:231-236, 1977.
Gornet et al., *Semin Reprod Med.* 2016 September; 34(5): 285-292. Epub 2016 Sep. 14.
Gulbis and Galand, *Hum. Pathol.* 24(12), 1271-1285, 1993.
Halfon et al., *PLoS ONE* 2010; 5 (5) e10569
Hessell et al., *Nature* 449, 101-4, 2007.
Khatoon et al., *Ann. of Neurology*, 26, 210-219, 1989.
King et al., *J. Biol. Chem.*, 269, 10210-10218, 1989.
Kohler and Milstein, *Eur. J. Immunol.*, 6, 511-519, 1976.
Kohler and Milstein, *Nature*, 256, 495-497, 1975.
Kyte and Doolittle, *J. Mol. Biol.*, 157(1):105-132, 1982.
Mansuy et al., *Lancet Infect Dis.* 2016 October; 16(10): 1106-7.
Nakamura et al., In: *Enzyme Immunoassays: Heterogeneous and Homogeneous Systems*, Chapter 27, 1987.
O'Shannessy et al., *J. Immun. Meth.*, 99, 153-161, 1987.
Persic et al., *Gene* 187:1, 1997
Potter and Haley, *Meth. Enzymol.*, 91, 613-633, 1983.
Purpura et al., *Lancet Infect Dis.* 2016 October; 16(10): 1107-8. Epub 2016 Sep. 19. Remington's Pharmaceutical Sciences, 15th Ed., 3:624-652, 1990.
Tang et al., *J. Biol. Chem.*, 271:28324-28330, 1996.
Wawrzynczak & Thorpe, In: *Immunoconjugates, Antibody Conjugates In Radioimaging And Therapy Of Cancer*, Vogel (Ed.), NY, Oxford University Press, 28, 1987.
Zell et al., *J Gen Virol* 2017; 98:2421-2.
Oberste et al., *J Gen Virol* 2004; 85:2577-84.
Blomqvist et al., *J Clin Microbiol* 2002; 40:4218-23.
Schieble et al., *Am J Epidemiol* 1967; 85:297-310.
Khetsuriani et al., Centers for Disease Control, Prevention. Enterovirus surveillance—United States, 1970-2005. MMWR Surveill Summ 2006; 55:1-20.
Xiang and Wang, *Semin Respir Crit Care Med* 2016; 37:578-85.
Oermann et al., *Ann Am Thorac Soc* 2015; 12:775-81.
Biggs et al., *Clin Infect Dis* 2017; 65:315-23.
Orvedahl et al., *Pediatr Infect Dis J* 2016; 35:481-7.
Midgley et al., *Lancet Respir Med* 2015; 3:879-87.
Messacar et al., *Lancet* 2015; 385:1662-71.
Division of Viral Diseases NCH, Respiratory Diseases CDC, Division of Vector-Borne Diseases DoH-C P, et al. *MMWR Morb Mortal Wkly Rep* 2015; 63:1243-4.
Messacar et al., *Lancet Infect Dis* 2018; 18:e239-e47.
National Center for Immunization and Respiratory Diseases DoVD. AFM Investigation. Available at: world-wide-web at cdc.gov/acute-flaccid-myelitis/afm-surveillance.html.
Annual Review of Diseases Prioritized under the Research and Development Blueprint. 2018 (Geneva, Switzerland).
Vidor et al., Poliovirus Vaccine-Inactivated. In: Plotkin S A, MD, Orenstein W A, MD, DSc (HON), Offit P A, MD, Edwards K M, MD, eds. Plotkin's Vaccines. 7 ed. Philadelphia, PA: Elsevier, Inc., 2018:841-65.
Sutter et al., Poliovirus Vaccine-Live. In: Plotkin S A, MD, Orenstein W A, MD, DSc (HON), Offit P A, MD, Edwards K M, MD, eds. Plotkin's Vaccines. 7 ed. Philadelphia, PA: Elsevier, Inc., 2018:866-917.
Howard et al., *Open Forum Infect Dis* 2016; 3:ofw001.
Zhang et al., *J Clin Virol* 2015; 69:172-75.
Liu et al., *Science* 2015a; 347:71-4.
Imamura et al., *J Virol* 2014; 88:2374-84.
Miao et al., *J Clin Microbiol* 2009; 47:3108-13.
Lu et al., *Nat Rev Immunol* 2018; 18:46-61.
Hixon et al., *J Infect Dis* 2017a; 216:1245-53.
Hixon et al., *PLoS Pathog* 2017b; 13:e1006199.
Morrey et al., *Viruses* 2018; 10.
Zhang et al., *Viruses* 2018; 10.
Zheng et al., *Viruses* 2017a; 9.
Gagneux et al., *J Biol Chem* 2003; 278:48245-50.
Blanco et al., *J Virol* 2013; 87:2036-45.
Leigh et al., *Vaccine* 1995; 13:1468-73.
Walther et al., *PLoS Pathog* 2013; 9:e1003223.
Bern et al., *Mol Cell Proteomics* 2013; 12:996-1004.
Jia et al., *J Biol Chem* 2014; 289:28489-504.
Zhang et al., *Emerg Microbes Infect* 2018a; 7:3.
Crowe J E, Jr. *Cell Host Microbe* 2017; 22:193-206.
Karrron R, A. Respiratory Syncytial Virus Vaccines. In: Plotkin S A, MD, Orenstein W A, MD, DSc (HON), Offit P A, MD, Edwards K M, MD, eds. Plotkin's Vaccines. 7 ed. Philadelphia, PA: Elsevier, Inc., 2018: 943-9.
Strebel et al., In: Plotkin S A, MD, Orenstein W A, MD, DSc (HON), Offit P A, MD, Edwards K M, MD, eds. Plotkin's Vaccines. 7 ed. Philadelphia, PA: Elsevier, Inc., 2018: 579-618.
Tan, et al., *J Virol* 90, 1997-2007 (2016).
Dyrdak et al., *Virus Evol* 5, vez007 (2019).
Kujawski et al., *MMWR Morb Mortal Wkly Rep* 68, 277-280 (2019).
Zheng et al., *Nat Microbiol* 4, 124-133 (2019).
Rossmann et al., *Nature* 317, 145-153 (1985).
Evans et al., *Antiviral Res* 162, 61-70 (2019).
Hurst et al., *Virology* 526, 146-154 (2019).
Flyak et al., *Cell Host Microbe* 24, 703-716 e703 (2018).
Bangaru et al., *Cell* 177, 1136-1152 e1118 (2019).
Liu et al., *Nat Commun* 6, 8865 (2015b).
Filman et al., *EMBO J* 8, 1567-1579 (1989).
Dai et al., *Vaccine* 36, 653-659 (2018).
Patel et al., *PLoS One* 11, e0166336 (2016).
Messacar et al., *Ann Neurol* 80, 326-338 (2016).
Posner et al., *Hybridoma* 6, 611-625 (1987).
Yu et al., *J Immunol Methods* 336, 142-151 (2008).
M. A Ramakrishnan, *World J Virol* 5, 85-86 (2016).
Weldon et al., *Methods Mol Biol* 1387, 145-176 (2016).
R. F. Lemanske, Jr., *Pediatr Allergy Immunol* 13, 38-43 (2002).
Bochkov et al., *J Clin Microbiol* 52, 2461-2471 (2014).
S. A. Smith, J. E. Crowe, Jr., *Microbiol Spectr* 3, AID-0027-2014 (2015).
Turchaninova et al., *Nat Protoc* 11, 1599-1616 (2016).
V. Giudicelli, M. P. Lefranc, *Cold Spring Harb Protoc* 2011, 716-725 (2011).
McLean et al., *Mol Immunol* 37, 837-845 (2000).
Subway et al., *J Struct Biol* 151, 41-60 (2005).
Zheng et al., *Nat Methods* 14, 331-332 (2017b).
Lander et al., *J Struct Biol* 166, 95-102 (2009).
A. Rohou, N. Grigorieff, *J Struct Biol* 192, 216-221 (2015).
Sorzano et al., *J Struct Biol* 148, 194-204 (2004).
A. M. Roseman, *J Struct Biol* 145, 91-99 (2004).

S. H. Scheres, *J Struct Biol* 180, 519-530 (2012).
F. Guo, W. Jiang, *Methods Mol Biol* 1117, 401-443 (2014).
S. H. Scheres, S. Chen, *Nat Methods* 9, 853-854 (2012).
Pettersen et al., *J Comput Chem* 25, 1605-1612 (2004).
Emsley et al., *Acta Crystallogr D Biol Crystallogr* 66, 486-501 (2010).
Adams et al., *Acta Crystallogr D Biol Crystallogr* 66, 213-221 (2010).
Potterton et al., *Acta Crystallogr D Struct Biol* 74, 68-84 (2018).
Chen et al., in *International Tables for Crystallography*. (2012), vol. F, chap. 21.6, pp. 694-701.
W. McKinney, in *Python in Science Conference*, S. van der Walt, J. Millman, Eds. (Austin, Texas, 2010), pp. 51-56.
I. Letunic, P. Bork, *Nucleic Acids Res* 47, W256-W259 (2019).
Mishra et al., *MBio* 10, (2019).
Schubert et al., *Nat Med*, (2019).

What is claimed is:

1. A method of treating a subject infected with enterovirus D68 (EV-D68) or reducing the likelihood of infection of a subject at risk of contracting EV-D68, comprising delivering to said subject an antibody or antibody fragment comprising heavy chain CDR1-3 of SEQ ID NOS: 257, 258 and 259, and light chain CDR1-3 of SEQ ID NOS: 449, 450 and 451; heavy chain CDR1-3 of SEQ ID NOS: 260, 261 and 262, and light chain CDR1-3 of SEQ ID NOS: 452, 453 and 454; heavy chain CDR1-3 of SEQ ID NOS: 263, 264 and 265, and light chain CDR1-3 of SEQ ID NOS: 455, 456 and 457; heavy chain CDR1-3 of SEQ ID NOS: 266, 267 and 268, and light chain CDR1-3 of SEQ ID NOS: 458, 459 and 460; heavy chain CDR1-3 of SEQ ID NOS: 269, 270 and 271, and light chain CDR1-3 of SEQ ID NOS: 461, 462 and 463; heavy chain CDR1-3 of SEQ ID NOS: 272, 273 and 274, and light chain CDR1-3 of SEQ ID NOS: 464, 465 and 466; heavy chain CDR1-3 of SEQ ID NOS: 275, 276 and 277, and light chain CDR1-3 of SEQ ID NOS: 467, 468 and 469; heavy chain CDR1-3 of SEQ ID NOS: 278, 279 and 280, and light chain CDR1-3 of SEQ ID NOS: 470, 471 and 472; heavy chain CDR1-3 of SEQ ID NOS: 281, 282 and 283, and light chain CDR1-3 of SEQ ID NOS: 473, 474 and 475; heavy chain CDR1-3 of SEQ ID NOS: 284, 285 and 286, and light chain CDR1-3 of SEQ ID NOS: 476, 477 and 478; heavy chain CDR1-3 of SEQ ID NOS: 287, 288 and 289, and light chain CDR1-3 of SEQ ID NOS: 479, 480 and 481; heavy chain CDR1-3 of SEQ ID NOS: 290, 291 and 292, and light chain CDR1-3 of SEQ ID NOS: 482, 483 and 484; heavy chain CDR1-3 of SEQ ID NOS: 293, 294 and 295, and light chain CDR1-3 of SEQ ID NOS: 485, 486 and 487; heavy chain CDR1-3 of SEQ ID NOS: 296, 297 and 298, and light chain CDR1-3 of SEQ ID NOS: 488, 489 and 490; heavy chain CDR1-3 of SEQ ID NOS: 299, 300 and 301, and light chain CDR1-3 of SEQ ID NOS: 491, 492 and 493; heavy chain CDR1-3 of SEQ ID NOS: 302, 303 and 304, and light chain CDR1-3 of SEQ ID NOS: 494, 495 and 496; heavy chain CDR1-3 of SEQ ID NOS: 305, 306 and 307, and light chain CDR1-3 of SEQ ID NOS: 497, 498 and 499; heavy chain CDR1-3 of SEQ ID NOS: 308, 309 and 310, and light chain CDR1-3 of SEQ ID NOS: 500, 501 and 502; heavy chain CDR1-3 of SEQ ID NOS: 311, 312 and 313, and light chain CDR1-3 of SEQ ID NOS: 503, 504 and 505; heavy chain CDR1-3 of SEQ ID NOS: 314, 315 and 316, and light chain CDR1-3 of SEQ ID NOS: 506, 507 and 508; heavy chain CDR1-3 of SEQ ID NOS: 317, 318 and 319, and light chain CDR1-3 of SEQ ID NOS: 509, 510 and 511; heavy chain CDR1-3 of SEQ ID NOS: 320, 321 and 322, and light chain CDR1-3 of SEQ ID NOS: 512, 513 and 514; heavy chain CDR1-3 of SEQ ID NOS: 323, 324 and 325, and light chain CDR1-3 of SEQ ID NOS: 515, 516 and 517; heavy chain CDR1-3 of SEQ ID NOS: 326, 327 and 328, and light chain CDR1-3 of SEQ ID NOS: 518, 519 and 520; heavy chain CDR1-3 of SEQ ID NOS: 329, 330 and 331, and light chain CDR1-3 of SEQ ID NOS: 521, 522 and 523; heavy chain CDR1-3 of SEQ ID NOS: 332, 333 and 334, and light chain CDR1-3 of SEQ ID NOS: 524, 525 and 526; heavy chain CDR1-3 of SEQ ID NOS: 335, 336 and 337, and light chain CDR1-3 of SEQ ID NOS: 527, 528 and 529; heavy chain CDR1-3 of SEQ ID NOS: 338, 339 and 340, and light chain CDR1-3 of SEQ ID NOS: 530, 531 and 532; heavy chain CDR1-3 of SEQ ID NOS: 341, 342 and 343, and light chain CDR1-3 of SEQ ID NOS: 533, 534 and 535; heavy chain CDR1-3 of SEQ ID NOS: 344, 345 and 346, and light chain CDR1-3 of SEQ ID NOS: 536, 537 and 538; heavy chain CDR1-3 of SEQ ID NOS: 347, 348 and 349, and light chain CDR1-3 of SEQ ID NOS: 539, 540 and 541; heavy chain CDR1-3 of SEQ ID NOS: 350, 351 and 352, and light chain CDR1-3 of SEQ ID NOS: 542, 543 and 544; heavy chain CDR1-3 of SEQ ID NOS: 353, 354 and 355, and light chain CDR1-3 of SEQ ID NOS: 545, 546 and 547; heavy chain CDR1-3 of SEQ ID NOS: 356, 357 and 358, and light chain CDR1-3 of SEQ ID NOS: 548, 549 and 550; heavy chain CDR1-3 of SEQ ID NOS: 359, 360 and 361, and light chain CDR1-3 of SEQ ID NOS: 551, 552 and 553; heavy chain CDR1-3 of SEQ ID NOS: 362, 363 and 364, and light chain CDR1-3 of SEQ ID NOS: 554, 555 and 556; heavy chain CDR1-3 of SEQ ID NOS: 365, 366 and 367, and light chain CDR1-3 of SEQ ID NOS: 557, 558 and 559; heavy chain CDR1-3 of SEQ ID NOS: 368, 369 and 370, and light chain CDR1-3 of SEQ ID NOS: 560, 561 and 562; heavy chain CDR1-3 of SEQ ID NOS: 371, 372 and 373, and light chain CDR1-3 of SEQ ID NOS: 563, 564 and 565; heavy chain CDR1-3 of SEQ ID NOS: 374, 375 and 376, and light chain CDR1-3 of SEQ ID NOS: 566, 567 and 568; heavy chain CDR1-3 of SEQ ID NOS: 377, 378 and 379, and light chain CDR1-3 of SEQ ID NOS: 569, 570 and 571; heavy chain CDR1-3 of SEQ ID NOS: 380, 381 and 382, and light chain CDR1-3 of SEQ ID NOS: 572, 573 and 574; heavy chain CDR1-3 of SEQ ID NOS: 383, 384 and 385, and light chain CDR1-3 of SEQ ID NOS: 575, 576 and 577; heavy chain CDR1-3 of SEQ ID NOS: 386, 387 and 388, and light chain CDR1-3 of SEQ ID NOS: 578, 579 and 580; heavy chain CDR1-3 of SEQ ID NOS: 389, 390 and 391, and light chain CDR1-3 of SEQ ID NOS: 581, 582 and 583; heavy chain CDR1-3 of SEQ ID NOS: 392, 393 and 394, and light chain CDR1-3 of SEQ ID NOS: 584, 585 and 586; heavy chain CDR1-3 of SEQ ID NOS: 395, 396 and 397, and light chain CDR1-3 of SEQ ID NOS: 587, 588 and 589; heavy chain CDR1-3 of SEQ ID NOS: 398, 399 and 400, and light chain CDR1-3 of SEQ ID NOS: 590, 591 and 592; heavy chain CDR1-3 of SEQ ID NOS: 401, 402 and 403, and light chain CDR1-3 of SEQ ID NOS: 593, 594 and 595; heavy chain CDR1-3 of SEQ ID NOS: 404, 405 and 406, and light chain CDR1-3 of SEQ ID NOS: 596, 597 and 598; heavy chain CDR1-3 of SEQ ID NOS: 407, 408 and 409, and light chain CDR1-3 of SEQ ID NOS: 599, 600 and 601; heavy chain CDR1-3 of SEQ ID NOS: 410, 411 and 412, and light chain CDR1-3 of SEQ ID NOS: 602, 603 and 604; heavy chain CDR1-3 of SEQ ID NOS: 413, 414 and 415, and light chain CDR1-3 of SEQ ID NOS: 605, 606 and 607; heavy chain CDR1-3 of SEQ ID NOS: 416, 417 and 418, and light chain CDR1-3 of SEQ ID NOS: 608, 609 and 610; heavy chain CDR1-3 of SEQ ID NOS: 419, 420 and 421, and light chain CDR1-3 of SEQ ID NOS: 611, 612 and 613; heavy chain CDR1-3 of SEQ ID NOS: 422, 423 and 424, and light chain CDR1-3 of SEQ ID NOS: 614, 615 and 616; heavy chain CDR1-3 of SEQ ID NOS: 425, 426 and 427, and light chain CDR1-3 of SEQ ID NOS: 617, 618 and 619; heavy chain CDR1-3 of SEQ ID NOS: 428, 429 and 430, and light chain CDR1-3 of SEQ ID NOS: 620, 621 and 622; heavy chain CDR1-3 of SEQ ID NOS: 431, 432 and 433, and light chain CDR1-3 of SEQ ID NOS: 623, 624 and 625; heavy chain CDR1-3 of SEQ ID NOS: 434, 435 and 436, and light chain CDR1-3 of SEQ ID NOS: 626, 627 and 628; heavy chain CDR1-3 of SEQ ID NOS: 437, 438 and 439, and light chain CDR1-3 of SEQ ID NOS: 629, 630 and 631; heavy chain CDR1-3 of SEQ ID NOS: 440, 441 and 442, and light chain CDR1-3 of SEQ ID NOS: 632, 633 and 634; heavy chain CDR1-3 of SEQ ID NOS: 443, 444 and 445, and light chain CDR1-3 of SEQ ID NOS: 635, 636 and 637; or heavy chain CDR1-3 of SEQ ID NOS: 446, 447 and 448, and light chain CDR1-3 of SEQ ID NOS: 638, 639 and 640.

2. A method of detecting enterovirus D68 (EV-D68) infection in a subject comprising:
(a) contacting a sample from said subject with an antibody or antibody fragment comprising heavy chain CDR1-3 of SEQ ID NOS: 257, 258 and 259, and light chain CDR1-3 of SEQ ID NOS: 449, 450 and 451; heavy chain CDR1-3 of SEQ ID NOS: 260, 261 and 262, and light chain CDR1-3 of SEQ ID NOS: 452, 453 and 454; heavy chain CDR1-3 of SEQ ID NOS: 263, 264 and 265, and light chain CDR1-3 of SEQ ID NOS: 455, 456 and 457; heavy chain CDR1-3 of SEQ ID NOS: 266, 267 and 268, and light chain CDR1-3 of SEQ ID NOS: 458, 459 and 460; heavy chain CDR1-3 of SEQ ID NOS: 269, 270 and 271, and light chain CDR1-3 of SEQ ID NOS: 461, 462 and 463; heavy chain CDR1-3 of SEQ ID NOS: 272, 273 and 274, and light chain CDR1-3 of SEQ ID NOS: 464, 465 and 466; heavy chain CDR1-3 of SEQ ID NOS: 275, 276 and 277, and light chain CDR1-3 of SEQ ID NOS: 467, 468 and 469; heavy chain CDR1-3 of SEQ ID NOS: 278, 279 and 280, and light chain CDR1-3 of SEQ ID NOS: 470, 471 and 472; heavy chain CDR1-3 of SEQ ID NOS: 281, 282 and 283, and light chain CDR1-3 of SEQ ID NOS: 473, 474 and 475; heavy chain CDR1-3 of SEQ ID NOS: 284, 285 and 286, and light chain CDR1-3 of SEQ ID NOS: 476, 477 and 478; heavy chain CDR1-3 of SEQ ID NOS: 287, 288 and 289, and light chain CDR1-3 of SEQ ID NOS: 479, 480 and 481; heavy chain CDR1-3 of SEQ ID NOS: 290, 291 and 292, and light chain CDR1-3 of SEQ ID NOS: 482, 483 and 484; heavy chain CDR1-3 of SEQ ID NOS: 293, 294 and 295, and light chain CDR1-3 of SEQ ID NOS: 485, 486 and 487; heavy chain CDR1-3 of SEQ ID NOS: 296, 297 and 298, and light chain CDR1-3 of SEQ ID NOS: 488, 489 and 490; heavy chain CDR1-3 of SEQ ID NOS: 299, 300 and 301, and light chain CDR1-3 of SEQ ID NOS: 491, 492 and 493; heavy chain CDR1-3 of SEQ ID NOS: 302, 303 and 304, and light chain CDR1-3 of SEQ ID NOS: 494, 495 and 496; heavy chain CDR1-3 of SEQ ID NOS: 305, 306 and 307, and light chain CDR1-3 of SEQ ID NOS: 497, 498 and 499; heavy chain CDR1-3 of SEQ ID NOS: 308, 309 and 310, and light chain CDR1-3 of SEQ ID NOS: 500, 501 and 502; heavy chain CDR1-3 of SEQ ID NOS: 311, 312 and 313, and light chain CDR1-3 of SEQ ID NOS: 503, 504 and 505; heavy chain CDR1-3 of SEQ ID NOS: 314, 315 and 316, and light chain CDR1-3 of SEQ ID NOS: 506, 507 and 508; heavy chain CDR1-3 of SEQ ID NOS: 317, 318 and 319, and light chain CDR1-3 of SEQ ID NOS: 509, 510 and 511; heavy chain CDR1-3 of SEQ ID NOS: 320, 321 and 322, and light chain CDR1-3 of SEQ ID NOS: 512, 513 and 514; heavy chain CDR1-3 of SEQ ID NOS: 323, 324 and 325, and light chain CDR1-3 of SEQ ID NOS: 515, 516 and 517; heavy chain CDR1-3 of SEQ ID NOS: 326, 327 and 328, and light chain CDR1-3 of SEQ ID NOS: 518, 519 and 520; heavy chain CDR1-3 of SEQ ID NOS: 329, 330 and 331, and light chain CDR1-3 of SEQ ID NOS: 521, 522 and 523; heavy chain CDR1-3 of SEQ ID NOS: 332, 333 and 334, and light chain CDR1-3 of SEQ ID NOS: 524, 525 and 526; heavy chain CDR1-3 of SEQ ID NOS: 335, 336 and 347, and light chain CDR1-3 of SEQ ID NOS: 527, 528 and 529; heavy chain CDR1-3 of SEQ ID NOS: 338, 339 and 340, and light chain CDR1-3 of SEQ ID NOS: 530, 531 and 532; heavy chain CDR1-3 of SEQ ID NOS: 341, 342 and 343, and light chain CDR1-3 of SEQ ID NOS: 533, 534 and 535; heavy chain CDR1-3 of SEQ ID NOS: 344, 345 and 346, and light chain CDR1-3 of SEQ ID NOS: 536, 537 and 538; heavy chain CDR1-3 of SEQ ID NOS: 337, 348 and 349, and light chain CDR1-3 of SEQ ID NOS: 539, 540 and 541; heavy chain CDR1-3 of SEQ ID NOS: 350, 351 and 352, and light chain CDR1-3 of SEQ ID NOS: 542, 543 and 544; heavy chain CDR1-3 of SEQ ID NOS: 353, 354 and 355, and light chain CDR1-3 of SEQ ID NOS: 545, 546 and 547; heavy chain CDR1-3 of SEQ ID NOS: 356, 357 and 358, and light chain CDR1-3 of SEQ ID NOS: 548, 549 and 550; heavy chain CDR1-3 of SEQ ID NOS: 359, 360 and 361, and light chain CDR1-3 of SEQ ID NOS: 551, 552 and 553; heavy chain CDR1-3 of SEQ ID NOS: 362, 363 and 364, and light chain CDR1-3 of SEQ ID NOS: 554, 555 and 556; heavy chain CDR1-3 of SEQ ID NOS: 365, 366 and 367, and light chain CDR1-3 of SEQ ID NOS: 557, 558 and 559; heavy chain CDR1-3 of SEQ ID NOS: 368, 369 and 370, and light chain CDR1-3 of SEQ ID NOS: 560, 561 and 562; heavy chain CDR1-3 of SEQ ID NOS: 371, 372 and 373, and light chain CDR1-3 of SEQ ID NOS: 563, 564 and 565; heavy chain CDR1-3 of SEQ ID NOS: 374, 375 and 376, and light chain CDR1-3 of SEQ ID NOS: 566, 567 and 568; heavy chain CDR1-3 of SEQ ID NOS: 377, 378 and 379, and light chain CDR1-3 of SEQ ID NOS: 569, 570 and 571; heavy chain CDR1-3 of SEQ ID NOS: 380, 381 and 382, and light chain CDR1-3 of SEQ ID NOS: 572, 573 and 574; heavy chain CDR1-3 of SEQ ID NOS: 383, 384 and 385, and light chain CDR1-3 of SEQ ID NOS: 575, 576 and 577; heavy chain CDR1-3 of SEQ ID NOS: 386, 387 and 388, and light chain CDR1-3 of SEQ ID NOS: 578, 579 and 580; heavy chain CDR1-3 of SEQ ID NOS: 389, 390 and 391, and light chain CDR1-3 of SEQ ID NOS: 581, 582 and 583; heavy chain CDR1-3 of SEQ ID NOS: 392, 393 and 394, and light chain CDR1-3 of SEQ ID NOS: 584, 585 and 586; heavy chain CDR1-3 of SEQ ID NOS: 395, 396 and 397, and light chain CDR1-3 of SEQ ID NOS: 587, 588 and 589;

heavy chain CDR1-3 of SEQ ID NOS: 398, 399 and 400, and light chain CDR1-3 of SEQ ID NOS: 590, 591 and 592; heavy chain CDR1-3 of SEQ ID NOS: 401, 402 and 403, and light chain CDR1-3 of SEQ ID NOS: 593, 594 and 595; heavy chain CDR1-3 of SEQ ID NOS: 404, 405 and 406, and light chain CDR1-3 of SEQ ID NOS: 596, 597 and 598; heavy chain CDR1-3 of SEQ ID NOS: 407, 408 and 409, and light chain CDR1-3 of SEQ ID NOS: 599, 600 and 601; heavy chain CDR1-3 of SEQ ID NOS: 410, 411 and 412, and light chain CDR1-3 of SEQ ID NOS: 602, 603 and 604; heavy chain CDR1-3 of SEQ ID NOS: 413, 414 and 415, and light chain CDR1-3 of SEQ ID NOS: 605, 606 and 607; heavy chain CDR1-3 of SEQ ID NOS: 416, 417 and 418, and light chain CDR1-3 of SEQ ID NOS: 608, 609 and 610; heavy chain CDR1-3 of SEQ ID NOS: 419, 420 and 421, and light chain CDR1-3 of SEQ ID NOS: 611, 612 and 613; heavy chain CDR1-3 of SEQ ID NOS: 422, 423 and 424, and light chain CDR1-3 of SEQ ID NOS: 614, 615 and 616; heavy chain CDR1-3 of SEQ ID NOS: 425, 426 and 427, and light chain CDR1-3 of SEQ ID NOS: 617, 618 and 619; heavy chain CDR1-3 of SEQ ID NOS: 428, 429 and 430, and light chain CDR1-3 of SEQ ID NOS: 620, 621 and 622; heavy chain CDR1-3 of SEQ ID NOS: 431, 432 and 433, and light chain CDR1-3 of SEQ ID NOS: 623, 624 and 625; heavy chain CDR1-3 of SEQ ID NOS: 434, 435 and 436, and light chain CDR1-3 of SEQ ID NOS: 626, 627 and 628; heavy chain CDR1-3 of SEQ ID NOS: 437, 438 and 439, and light chain CDR1-3 of SEQ ID NOS: 629, 630 and 631; heavy chain CDR1-3 of SEQ ID NOS: 440, 441 and 442, and light chain CDR1-3 of SEQ ID NOS: 632, 633 and 634; heavy chain CDR1-3 of SEQ ID NOS: 443, 444 and 445, and light chain CDR1-3 of SEQ ID NOS: 635, 636 and 637; or heavy chain CDR1-3 of SEQ ID NOS: 446, 447 and 448, and light chain CDR1-3 of SEQ ID NOS: 638, 639 and 640; and (b) detecting EV-D68 in said sample by binding of said antibody or antibody fragment to a EV-D68 antigen in said sample.

3. The method of claim 2, wherein said sample is a body fluid.

4. The method of claim 2, wherein said sample is blood, sputum, tears, saliva, mucous or serum, semen, cervical or vaginal secretions, amniotic fluid, placental tissues, urine, exudate, transudate, respiratory droplets or aerosol, tissue scrapings or feces.

5. The method of claim 2, wherein detection comprises ELISA, RIA, lateral flow assay or Western blot.

6. The method of claim 2, further comprising performing steps (a) and (b) a second time and determining a change in EV-D68 antigen levels as compared to a previous assay.

7. The method of claim 2, wherein the antibody or antibody fragment is encoded by heavy and light chain variable regions comprising SEQ ID NOS: 1 and 2; SEQ ID NOS: 3 and 4; SEQ ID NOS: 5 and 6; SEQ ID NOS: 7 and 8; SEQ ID NOS: 9 and 10; SEQ ID NOS: 11 and 12; SEQ ID NOS: 13 and 14; SEQ ID NOS: 15 and 16; SEQ ID NOS: 17 and 18; SEQ ID NOS: 19 and 20; SEQ ID NOS: 21 and 22; SEQ ID NOS: 23 and 24; SEQ ID NOS: 25 and 26; SEQ ID NOS: 27 and 28; SEQ ID NOS: 29 and 30; SEQ ID NOS: 31 and 32; SEQ ID NOS: 33 and 34; SEQ ID NOS: 35 and 36; SEQ ID NOS: 37 and 38; SEQ ID NOS: 39 and 40; SEQ ID NOS: 41 and 42; SEQ ID NOS: 43 and 44; SEQ ID NOS: 45 and 46; SEQ ID NOS: 47 and 48; SEQ ID NOS: 49 and 50; SEQ ID NOS: 51 and 52; SEQ ID NOS: 53 and 54; SEQ ID NOS: 55 and 56; SEQ ID NOS: 57 and 58; SEQ ID NOS: 59 and 60; SEQ ID NOS: 61 and 62; SEQ ID NOS: 63 and 64; SEQ ID NOS: 65 and 66; SEQ ID NOS: 67 and 68; SEQ ID NOS: 69 and 70; SEQ ID NOS: 71 and 72; SEQ ID NOS: 73 and 74; SEQ ID NOS: 75 and 76; SEQ ID NOS: 77 and 78; SEQ ID NOS: 79 and 80; SEQ ID NOS: 81 and 82; SEQ ID NOS: 83 and 84; SEQ ID NOS: 85 and 86; SEQ ID NOS: 87 and 88; SEQ ID NOS: 89 and 90; SEQ ID NOS: 91 and 92; SEQ ID NOS: 93 and 94; SEQ ID NOS: 95 and 96; SEQ ID NOS: 97 and 98; SEQ ID NOS: 99 and 100; SEQ ID NOS: 101 and 102; SEQ ID NOS: 103 and 104; SEQ ID NOS: 105 and 106; SEQ ID NOS: 107 and 108; SEQ ID NOS: 109 and 110; SEQ ID NOS: 111 and 112; SEQ ID NOS: 113 and 114; SEQ ID NOS: 115 and 116; SEQ ID NOS: 117 and 118; SEQ ID NOS: 119 and 120; SEQ ID NOS: 121 and 122; SEQ ID NOS: 123 and 124; SEQ ID NOS: 125 and 126; or SEQ ID NOS: 127 and 128.

8. The method of claim 2, wherein said antibody or antibody fragment is encoded by heavy and light chain variable regions comprising SEQ ID NOS: 1 and 2; SEQ ID NOS: 3 and 4; SEQ ID NOS: 5 and 6; SEQ ID NOS: 7 and 8; SEQ ID NOS: 9 and 10; SEQ ID NOS: 11 and 12; SEQ ID NOS: 13 and 14; SEQ ID NOS: 15 and 16; SEQ ID NOS: 17 and 18; SEQ ID NOS: 19 and 20; SEQ ID NOS: 21 and 22; SEQ ID NOS: 23 and 24; SEQ ID NOS: 25 and 26; SEQ ID NOS: 27 and 28; SEQ ID NOS: 29 and 30; SEQ ID NOS: 31 and 32; SEQ ID NOS: 33 and 34; SEQ ID NOS: 35 and 36; SEQ ID NOS: 37 and 38; SEQ ID NOS: 39 and 40; SEQ ID NOS: 41 and 42; SEQ ID NOS: 43 and 44; SEQ ID NOS: 45 and 46; SEQ ID NOS: 47 and 48; SEQ ID NOS: 49 and 50; SEQ ID NOS: 51 and 52; SEQ ID NOS: 53 and 54; SEQ ID NOS: 55 and 56; SEQ ID NOS: 57 and 58; SEQ ID NOS: 59 and 60; SEQ ID NOS: 61 and 62; SEQ ID NOS: 63 and 64; SEQ ID NOS: 65 and 66; SEQ ID NOS: 67 and 68; SEQ ID NOS: 69 and 70; SEQ ID NOS: 71 and 72; SEQ ID NOS: 73 and 74; SEQ ID NOS: 75 and 76; SEQ ID NOS: 77 and 78; SEQ ID NOS: 79 and 80; SEQ ID NOS: 81 and 82; SEQ ID NOS: 83 and 84; SEQ ID NOS: 85 and 86; SEQ ID NOS: 87 and 88; SEQ ID NOS: 89 and 90; SEQ ID NOS: 91 and 92; SEQ ID NOS: 93 and 94; SEQ ID NOS: 95 and 96; SEQ ID NOS: 97 and 98; SEQ ID NOS: 99 and 100; SEQ ID NOS: 101 and 102; SEQ ID NOS: 103 and 104; SEQ ID NOS: 105 and 106; SEQ ID NOS: 107 and 108; SEQ ID NOS: 109 and 110; SEQ ID NOS: 111 and 112; SEQ ID NOS: 113 and 114; SEQ ID NOS: 115 and 116; SEQ ID NOS: 117 and 118; SEQ ID NOS: 119 and 120; SEQ ID NOS: 121 and 122; SEQ ID NOS: 123 and 124; SEQ ID NOS: 125 and 126; or SEQ ID NOS: 127 and 128.

9. The method of claim 2, wherein said antibody or antibody fragment comprises heavy and light chain variable sequences comprising SEQ ID NOS: 129 and 130; SEQ ID NOS: 131 and 132; SEQ ID NOS: 133 and 134; SEQ ID NOS: 135 and 136; SEQ ID NOS: 137 and 138; SEQ ID NOS: 139 and 140; SEQ ID NOS: 141 and 142; SEQ ID NOS: 143 and 144; SEQ ID NOS: 145 and 146; SEQ ID NOS: 147 and 148; SEQ ID NOS: 149 and 150; SEQ ID NOS: 151 and 152; SEQ ID NOS: 153 and 154; SEQ ID NOS: 155 and 156; SEQ ID NOS: 157 and 158; SEQ ID NOS: 159 and 160; SEQ ID NOS: 161 and 162; SEQ ID NOS: 163 and 164; SEQ ID NOS: 165 and 166; SEQ ID NOS: 167 and 168; SEQ ID NOS: 169 and 170; SEQ ID NOS: 171 and 172; SEQ ID NOS: 173 and 174; SEQ ID NOS: 175 and 176; SEQ ID NOS: 177 and 178; SEQ ID NOS: 179 and 180; SEQ ID NOS: 181 and 182; SEQ ID NOS: 183 and 184; SEQ ID NOS: 185 and 186; SEQ ID NOS: 187 and 188; SEQ ID NOS: 189 and 190; SEQ ID NOS: 191 and 192; SEQ ID NOS: 193 and 194; SEQ ID NOS: 195 and 196; SEQ ID NOS: 197 and 198; SEQ ID NOS: 199 and 200; SEQ ID NOS: 201 and 202; SEQ ID NOS: 203 and 204; SEQ ID NOS: 205 and 206; SEQ ID NOS: 207 and 208; SEQ ID NOS: 209 and 210; SEQ ID NOS: 211 and 212; SEQ ID NOS: 213 and 214; SEQ ID NOS: 215 and 216; SEQ ID NOS: 217 and 218; SEQ ID NOS: 219 and 220; SEQ ID NOS: 221 and 222; SEQ ID NOS: 223 and 224; SEQ ID NOS: 225 and 226; SEQ ID NOS: 227 and 228; SEQ ID NOS: 229 and 230; SEQ ID NOS: 231 and 232; SEQ ID NOS: 233 and 234; SEQ ID NOS: 235 and 236; SEQ ID NOS: 237 and 238; SEQ ID NOS: 239 and 240; SEQ ID NOS: 241 and 242; SEQ ID NOS: 243 and 244; SEQ ID NOS: 245 and 246; SEQ ID NOS: 247 and 248; SEQ ID NOS: 249 and 250; SEQ ID NOS: 251 and 252; SEQ ID NOS: 253 and 254; or SEQ ID NOS: 255 and 256.

10. The method of claim 2, wherein said antibody or antibody fragment comprises heavy and light chain variable sequences having 95% identity to SEQ ID NOS: 129 and 130; SEQ ID NOS: 131 and 132; SEQ ID NOS: 133 and 134; SEQ ID NOS: 135 and 136; SEQ ID NOS: 137 and 138; SEQ ID NOS: 139 and 140; SEQ ID NOS: 141 and 142; SEQ ID NOS: 143 and 144; SEQ ID NOS: 145 and 146; SEQ ID NOS: 147 and 148; SEQ ID NOS: 149 and 150; SEQ ID NOS: 151 and 152; SEQ ID NOS: 153 and 154; SEQ ID NOS: 155 and 156; SEQ ID NOS: 157 and 158; SEQ ID NOS: 159 and 160; SEQ ID NOS: 161 and 162; SEQ ID NOS: 163 and 164; SEQ ID NOS: 165 and 166; SEQ ID NOS: 167 and 168; SEQ ID NOS: 169 and 170; SEQ ID NOS: 171 and 172; SEQ ID NOS: 173 and 174; SEQ ID NOS: 175 and 176; SEQ ID NOS: 177 and 178; SEQ ID NOS: 179 and 180; SEQ ID NOS: 181 and 182; SEQ ID NOS: 183 and 184; SEQ ID NOS: 185 and 186; SEQ ID NOS: 187 and 188; SEQ ID NOS: 189 and 190; SEQ ID NOS: 191 and 192; SEQ ID NOS: 193 and 194; SEQ ID NOS: 195 and 196; SEQ ID NOS: 197 and 198; SEQ ID NOS: 199 and 200; SEQ ID NOS: 201 and 202; SEQ ID NOS: 203 and 204; SEQ ID NOS: 205 and 206; SEQ ID NOS: 207 and 208; SEQ ID NOS: 209 and 210; SEQ ID NOS: 211 and 212; SEQ ID NOS: 213 and 214; SEQ ID NOS: 215 and 216; SEQ ID NOS: 217 and 218; SEQ ID NOS: 219 and 220; SEQ ID NOS: 221 and 222; SEQ ID NOS: 223 and 224; SEQ ID NOS: 225 and 226; SEQ ID NOS: 227 and 228; SEQ ID NOS: 229 and 230; SEQ ID NOS: 231 and 232; SEQ ID NOS: 233 and 234; SEQ ID NOS: 235 and 236; SEQ ID NOS: 237 and 238; SEQ ID NOS: 239 and 240; SEQ ID NOS: 241 and 242; SEQ ID NOS: 243 and 244; SEQ ID NOS: 245 and 246; SEQ ID NOS: 247 and 248; SEQ ID NOS: 249 and 250; SEQ ID NOS: 251 and 252; SEQ ID NOS: 253 and 254; or SEQ ID NOS: 255 and 256.

11. The method of claim 2, wherein the antibody fragment is a recombinant scFv (single chain fragment variable) antibody, Fab fragment, F(ab')$_2$ fragment, or Fv fragment.

12. The method of claim 2, wherein the antibody or antibody fragment comprises heavy chain CDR1-3 of SEQ ID NOS: 314-316 and light chain CDR1-3 of SEQ ID NOS: 506-508 or heavy chain CDR1-3 of SEQ ID NOS: 413-415 and light chain CDR1-3 of SEQ ID NOS: 605-607.

13. The method of claim 2, wherein the antibody or antibody fragment comprises a heavy chain variable region of SEQ ID NO: 165 and a light chain variable region of SEQ ID NO: 166 or a heavy chain variable region of SEQ ID NO: 233 and a light chain variable region of SEQ ID NO: 234.

14. The method of claim 2, wherein the antibody or antibody fragment comprises heavy and light chain variable sequences having 95% identity to a heavy chain variable region of SEQ ID NO: 165 and a light chain variable region of SEQ ID NO: 166 or a heavy chain variable region of SEQ ID NO: 233 and a light chain variable region of SEQ ID NO: 234.

15. A monoclonal antibody or fragment thereof, wherein the antibody or antibody fragment comprises heavy chain CDR1-3 of SEQ ID NOS: 257, 258 and 259, and light chain CDR1-3 of SEQ ID NOS: 449, 450 and 451; heavy chain CDR1-3 of SEQ ID NOS: 260, 261 and 262, and light chain CDR1-3 of SEQ ID NOS: 452, 453 and 454; heavy chain CDR1-3 of SEQ ID NOS: 263, 264 and 265, and light chain CDR1-3 of SEQ ID NOS: 455, 456 and 457; heavy chain CDR1-3 of SEQ ID NOS: 266, 267 and 268, and light chain CDR1-3 of SEQ ID NOS: 458, 459 and 460; heavy chain CDR1-3 of SEQ ID NOS: 269, 270 and 271, and light chain CDR1-3 of SEQ ID NOS: 461, 462 and 463; heavy chain CDR1-3 of SEQ ID NOS: 272, 273 and 274, and light chain CDR1-3 of SEQ ID NOS: 464, 465 and 466; heavy chain CDR1-3 of SEQ ID NOS: 275, 276 and 277, and light chain CDR1-3 of SEQ ID NOS: 467, 468 and 469; heavy chain CDR1-3 of SEQ ID NOS: 278, 279 and 280, and light chain CDR1-3 of SEQ ID NOS: 470, 471 and 472; heavy chain CDR1-3 of SEQ ID NOS: 281, 282 and 283, and light chain CDR1-3 of SEQ ID NOS: 473, 474 and 475; heavy chain CDR1-3 of SEQ ID NOS: 284, 285 and 286, and light chain CDR1-3 of SEQ ID NOS: 476, 477 and 478; heavy chain CDR1-3 of SEQ ID NOS: 287, 288 and 289, and light chain CDR1-3 of SEQ ID NOS: 479, 480 and 481; heavy chain CDR1-3 of SEQ ID NOS: 290, 291 and 292, and light chain CDR1-3 of SEQ ID NOS: 482, 483 and 484; heavy chain CDR1-3 of SEQ ID NOS: 293, 294 and 295, and light chain CDR1-3 of SEQ ID NOS: 485, 486 and 487; heavy chain CDR1-3 of SEQ ID NOS: 296, 297 and 298, and light chain CDR1-3 of SEQ ID NOS: 488, 489 and 490; heavy chain CDR1-3 of SEQ ID NOS: 299, 300 and 301, and light chain CDR1-3 of SEQ ID NOS: 491, 492 and 493; heavy chain CDR1-3 of SEQ ID NOS: 302, 303 and 304, and light chain CDR1-3 of SEQ ID NOS: 494, 495 and 496; heavy chain CDR1-3 of SEQ ID NOS: 305, 306 and 307, and light chain CDR1-3 of SEQ ID NOS: 497, 498 and 499; heavy chain CDR1-3 of SEQ ID NOS: 308, 309 and 310, and light chain CDR1-3 of SEQ ID NOS: 500, 501 and 502; heavy chain CDR1-3 of SEQ ID NOS: 311, 312 and 313, and light chain CDR1-3 of SEQ ID NOS: 503, 504 and 505; heavy chain CDR1-3 of SEQ ID NOS: 314, 315 and 316, and light chain CDR1-3 of SEQ ID NOS: 506, 507 and 508; heavy chain CDR1-3 of SEQ ID NOS: 317, 318 and 319, and light chain CDR1-3 of SEQ ID NOS: 509, 510 and 511; heavy chain CDR1-3 of SEQ ID NOS: 320, 321 and 322, and light chain CDR1-3 of SEQ ID NOS: 512, 513 and 514; heavy chain CDR1-3 of SEQ ID NOS: 323, 324 and 325, and light chain CDR1-3 of SEQ ID NOS: 515, 516 and 517; heavy chain CDR1-3 of SEQ ID NOS: 326, 327 and 328, and light chain CDR1-3 of SEQ ID NOS: 518, 519 and 520; heavy chain CDR1-3 of SEQ ID NOS: 329, 330 and 331, and light chain CDR1-3 of SEQ ID NOS: 521, 522 and 523; heavy chain CDR1-3 of SEQ ID NOS: 332, 333 and 334, and light chain CDR1-3 of SEQ ID NOS: 524, 525 and 526; heavy chain CDR1-3 of SEQ ID NOS: 335, 336 and 337, and light chain CDR1-3 of SEQ ID NOS: 527, 528 and 529; heavy chain CDR1-3 of SEQ ID NOS: 338, 339 and 340, and light chain CDR1-3 of SEQ ID NOS: 530, 531 and 532; heavy chain CDR1-3 of SEQ ID NOS: 341, 342 and 343, and light chain CDR1-3 of SEQ ID NOS: 533, 534 and 535; heavy chain CDR1-3 of SEQ ID NOS: 344, 345 and 346, and light chain CDR1-3 of SEQ ID NOS: 536, 537 and 538; heavy chain CDR1-3 of SEQ ID NOS: 347, 348 and 349, and light chain CDR1-3 of SEQ ID NOS: 539, 540 and 541; heavy chain
CDR1-3 of SEQ ID NOS: 350, 351 and 352, and light chain
CDR1-3 of SEQ ID NOS: 542, 543 and 544; heavy chain
CDR1-3 of SEQ ID NOS: 353, 354 and 355, and light chain
CDR1-3 of SEQ ID NOS: 545, 546 and 547; heavy chain
CDR1-3 of SEQ ID NOS: 356, 357 and 358, and light chain
CDR1-3 of SEQ ID NOS: 548, 549 and 550; heavy chain
CDR1-3 of SEQ ID NOS: 359, 360 and 361, and light chain
CDR1-3 of SEQ ID NOS: 551, 552 and 553; heavy chain
CDR1-3 of SEQ ID NOS: 362, 363 and 364, and light chain
CDR1-3 of SEQ ID NOS: 554, 555 and 556; heavy chain
CDR1-3 of SEQ ID NOS: 365, 366 and 367, and light chain
CDR1-3 of SEQ ID NOS: 557, 558 and 559; heavy chain
CDR1-3 of SEQ ID NOS: 368, 369 and 370, and light chain
CDR1-3 of SEQ ID NOS: 560, 561 and 562; heavy chain
CDR1-3 of SEQ ID NOS: 371, 372 and 373, and light chain
CDR1-3 of SEQ ID NOS: 563, 564 and 565; heavy chain
CDR1-3 of SEQ ID NOS: 374, 375 and 376, and light chain
CDR1-3 of SEQ ID NOS: 566, 567 and 568; heavy chain
CDR1-3 of SEQ ID NOS: 377, 378 and 379, and light chain
CDR1-3 of SEQ ID NOS: 569, 570 and 571; heavy chain
CDR1-3 of SEQ ID NOS: 380, 381 and 382, and light chain
CDR1-3 of SEQ ID NOS: 572, 573 and 574; heavy chain
CDR1-3 of SEQ ID NOS: 383, 384 and 385, and light chain
CDR1-3 of SEQ ID NOS: 575, 576 and 577; heavy chain
CDR1-3 of SEQ ID NOS: 386, 387 and 388, and light chain
CDR1-3 of SEQ ID NOS: 578, 579 and 580; heavy chain
CDR1-3 of SEQ ID NOS: 389, 390 and 391, and light chain
CDR1-3 of SEQ ID NOS: 581, 582 and 583; heavy chain
CDR1-3 of SEQ ID NOS: 392, 393 and 394, and light chain
CDR1-3 of SEQ ID NOS: 584, 585 and 586; heavy chain
CDR1-3 of SEQ ID NOS: 395, 396 and 397, and light chain
CDR1-3 of SEQ ID NOS: 587, 588 and 589; heavy chain
CDR1-3 of SEQ ID NOS: 398, 399 and 400, and light chain
CDR1-3 of SEQ ID NOS: 590, 591 and 592; heavy chain
CDR1-3 of SEQ ID NOS: 401, 402 and 403, and light chain
CDR1-3 of SEQ ID NOS: 593, 594 and 595; heavy chain
CDR1-3 of SEQ ID NOS: 404, 405 and 406, and light chain
CDR1-3 of SEQ ID NOS: 596, 597 and 598; heavy chain
CDR1-3 of SEQ ID NOS: 407, 408 and 409, and light chain
CDR1-3 of SEQ ID NOS: 599, 600 and 601; heavy chain
CDR1-3 of SEQ ID NOS: 410, 411 and 412, and light chain
CDR1-3 of SEQ ID NOS: 602, 603 and 604; heavy chain
CDR1-3 of SEQ ID NOS: 413, 414 and 415, and light chain
CDR1-3 of SEQ ID NOS: 605, 606 and 607; heavy chain
CDR1-3 of SEQ ID NOS: 416, 417 and 418, and light chain
CDR1-3 of SEQ ID NOS: 608, 609 and 610; heavy chain
CDR1-3 of SEQ ID NOS: 419, 420 and 421, and light chain
CDR1-3 of SEQ ID NOS: 611, 612 and 613; heavy chain
CDR1-3 of SEQ ID NOS: 422, 423 and 424, and light chain
CDR1-3 of SEQ ID NOS: 614, 615 and 616; heavy chain
CDR1-3 of SEQ ID NOS: 425, 426 and 427, and light chain
CDR1-3 of SEQ ID NOS: 617, 618 and 619; heavy chain
CDR1-3 of SEQ ID NOS: 428, 429 and 430, and light chain
CDR1-3 of SEQ ID NOS: 620, 621 and 622; heavy chain
CDR1-3 of SEQ ID NOS: 431, 432 and 433, and light chain
CDR1-3 of SEQ ID NOS: 623, 624 and 625; heavy chain
CDR1-3 of SEQ ID NOS: 434, 435 and 436, and light chain
CDR1-3 of SEQ ID NOS: 626, 627 and 628; heavy chain
CDR1-3 of SEQ ID NOS: 437, 438 and 439, and light chain
CDR1-3 of SEQ ID NOS: 629, 630 and 631; heavy chain
CDR1-3 of SEQ ID NOS: 440, 441 and 442, and light chain
CDR1-3 of SEQ ID NOS: 632, 633 and 634; heavy chain
CDR1-3 of SEQ ID NOS: 443, 444 and 445, and light chain
CDR1-3 of SEQ ID NOS: 635, 636 and 637; or heavy chain
CDR1-3 of SEQ ID NOS: 446, 447 and 448, and light chain
CDR1-3 of SEQ ID NOS: 638, 639 and 640, wherein said antibody is a chimeric antibody or a bispecific antibody, and said antibody fragment is an scFv (single chain fragment variable).

16. The monoclonal antibody or fragment thereof of claim 15, wherein said antibody or antibody fragment is encoded by heavy and light chain variable sequences comprising SEQ ID NOS: 1 and 2; SEQ ID NOS: 3 and 4; SEQ ID NOS: 5 and 6; SEQ ID NOS: 7 and 8; SEQ ID NOS: 9 and 10; SEQ ID NOS: 11 and 12; SEQ ID NOS: 13 and 14; SEQ ID NOS: 15 and 16; SEQ ID NOS: 17 and 18; SEQ ID NOS: 19 and 20; SEQ ID NOS: 21 and 22; SEQ ID NOS: 23 and 24; SEQ ID NOS: 25 and 26; SEQ ID NOS: 27 and 28; SEQ ID NOS: 29 and 30; SEQ ID NOS: 31 and 32; SEQ ID NOS: 33 and 34; SEQ ID NOS: 35 and 36; SEQ ID NOS: 37 and 38; SEQ ID NOS: 39 and 40; SEQ ID NOS: 41 and 42; SEQ ID NOS: 43 and 44; SEQ ID NOS: 45 and 46; SEQ ID NOS: 47 and 48; SEQ ID NOS: 49 and 50; SEQ ID NOS: 51 and 52; SEQ ID NOS: 53 and 54; SEQ ID NOS: 55 and 56; SEQ ID NOS: 57 and 58; SEQ ID NOS: 59 and 60; SEQ ID NOS: 61 and 62; SEQ ID NOS: 63 and 64; SEQ ID NOS: 65 and 66; SEQ ID NOS: 67 and 68; SEQ ID NOS: 69 and 70; SEQ ID NOS: 71 and 72; SEQ ID NOS: 73 and 74; SEQ ID NOS: 75 and 76; SEQ ID NOS: 77 and 78; SEQ ID NOS: 79 and 80; SEQ ID NOS: 81 and 82; SEQ ID NOS: 83 and 84; SEQ ID NOS: 85 and 86; SEQ ID NOS: 87 and 88; SEQ ID NOS: 89 and 90; SEQ ID NOS: 91 and 92; SEQ ID NOS: 93 and 94; SEQ ID NOS: 95 and 96; SEQ ID NOS: 97 and 98; SEQ ID NOS: 99 and 100; SEQ ID NOS: 101 and 102; SEQ ID NOS: 103 and 104; SEQ ID NOS: 105 and 106; SEQ ID NOS: 107 and 108; SEQ ID NOS: 109 and 110; SEQ ID NOS: 111 and 112; SEQ ID NOS: 113 and 114; SEQ ID NOS: 115 and 116; SEQ ID NOS: 117 and 118; SEQ ID NOS: 119 and 120; SEQ ID NOS: 121 and 122; SEQ ID NOS: 123 and 124; SEQ ID NOS: 125 and 126; or SEQ ID NOS: 127 and 128.

17. The monoclonal antibody or fragment thereof of claim 15, wherein said antibody or antibody fragment is encoded by heavy and light chain variable sequences having at least 95% identity to SEQ ID NOS: 1 and 2; SEQ ID NOS: 3 and 4; SEQ ID NOS: 5 and 6; SEQ ID NOS: 7 and 8; SEQ ID NOS: 9 and 10; SEQ ID NOS: 11 and 12; SEQ ID NOS: 13 and 14; SEQ ID NOS: 15 and 16; SEQ ID NOS: 17 and 18; SEQ ID NOS: 19 and 20; SEQ ID NOS: 21 and 22; SEQ ID NOS: 23 and 24; SEQ ID NOS: 25 and 26; SEQ ID NOS: 27 and 28; SEQ ID NOS: 29 and 30; SEQ ID NOS: 31 and 32; SEQ ID NOS: 33 and 34; SEQ ID NOS: 35 and 36; SEQ ID NOS: 37 and 38; SEQ ID NOS: 39 and 40; SEQ ID NOS: 41 and 42; SEQ ID NOS: 43 and 44; SEQ ID NOS: 45 and 46; SEQ ID NOS: 47 and 48; SEQ ID NOS: 49 and 50; SEQ ID NOS: 51 and 52; SEQ ID NOS: 53 and 54; SEQ ID NOS: 55 and 56; SEQ ID NOS: 57 and 58; SEQ ID NOS: 59 and 60; SEQ ID NOS: 61 and 62; SEQ ID NOS: 63 and 64; SEQ ID NOS: 65 and 66; SEQ ID NOS: 67 and 68; SEQ ID NOS: 69 and 70; SEQ ID NOS: 71 and 72; SEQ ID NOS: 73 and 74; SEQ ID NOS: 75 and 76; SEQ ID NOS: 77 and 78; SEQ ID NOS: 79 and 80; SEQ ID NOS: 81 and 82; SEQ ID NOS: 83 and 84; SEQ ID NOS: 85 and 86; SEQ ID NOS: 87 and 88; SEQ ID NOS: 89 and 90; SEQ ID NOS: 91 and 92; SEQ ID NOS: 93 and 94; SEQ ID NOS: 95 and 96; SEQ ID NOS: 97 and 98; SEQ ID NOS: 99 and 100; SEQ ID NOS: 101 and 102; SEQ ID NOS: 103 and 104; SEQ ID NOS: 105 and 106; SEQ ID NOS: 107 and 108; SEQ ID NOS: 109 and 110; SEQ ID NOS: 111 and 112; SEQ ID NOS: 113 and 114; SEQ ID NOS: 115 and 116; SEQ ID NOS: 117 and 118; SEQ ID NOS: 119 and 120; SEQ ID NOS: 121 and 122; SEQ ID NOS: 123 and 124; SEQ ID NOS: 125 and 126; or SEQ ID NOS: 127 and 128.

18. The monoclonal antibody or fragment thereof of claim 15, wherein said antibody or antibody fragment comprises heavy and light chain variable sequences comprising SEQ ID NOS: 129 and 130; SEQ ID NOS: 131 and 132; SEQ ID NOS: 133 and 134; SEQ ID NOS: 135 and 136; SEQ ID NOS: 137 and 138; SEQ ID NOS: 139 and 140; SEQ ID NOS: 141 and 142; SEQ ID NOS: 143 and 144; SEQ ID NOS: 145 and 146; SEQ ID NOS: 147 and 148; SEQ ID NOS: 149 and 150; SEQ ID NOS: 151 and 152; SEQ ID NOS: 153 and 154; SEQ ID NOS: 155 and 156; SEQ ID NOS: 157 and 158; SEQ ID NOS: 159 and 160; SEQ ID NOS: 161 and 162; SEQ ID NOS: 163 and 164; SEQ ID NOS: 165 and 166; SEQ ID NOS: 167 and 168; SEQ ID NOS: 169 and 170; SEQ ID NOS: 171 and 172; SEQ ID NOS: 173 and 174; SEQ ID NOS: 175 and 176; SEQ ID NOS: 177 and 178; SEQ ID NOS: 179 and 180; SEQ ID NOS: 181 and 182; SEQ ID NOS: 183 and 184; SEQ ID NOS: 185 and 186; SEQ ID NOS: 187 and 188; SEQ ID NOS: 189 and 190; SEQ ID NOS: 191 and 192; SEQ ID NOS: 193 and 194; SEQ ID NOS: 195 and 196; SEQ ID NOS: 197 and 198; SEQ ID NOS: 199 and 200; SEQ ID NOS: 201 and 202; SEQ ID NOS: 203 and 204; SEQ ID NOS: 205 and 206; SEQ ID NOS: 207 and 208; SEQ ID NOS: 209 and 210; SEQ ID NOS: 211 and 212; SEQ ID NOS: 213 and 214; SEQ ID NOS: 215 and 216; SEQ ID NOS: 217 and 218; SEQ ID NOS: 219 and 220; SEQ ID NOS: 221 and 222; SEQ ID NOS: 223 and 224; SEQ ID NOS: 225 and 226; SEQ ID NOS: 227 and 228; SEQ ID NOS: 229 and 230; SEQ ID NOS: 231 and 232; SEQ ID NOS: 233 and 234; SEQ ID NOS: 235 and 236; SEQ ID NOS: 237 and 238; SEQ ID NOS: 239 and 240; SEQ ID NOS: 241 and 242; SEQ ID NOS: 243 and 244; SEQ ID NOS: 245 and 246; SEQ ID NOS: 247 and 248; SEQ ID NOS: 249 and 250; SEQ ID NOS: 251 and 252; SEQ ID NOS: 253 and 254; or SEQ ID NOS: 255 and 256.

19. The monoclonal antibody or fragment thereof of claim 15, wherein said antibody or antibody fragment comprises heavy and light chain variable sequences having 95% identity to SEQ ID NOS: 129 and 130; SEQ ID NOS: 131 and 132; SEQ ID NOS: 133 and 134; SEQ ID NOS: 135 and 136; SEQ ID NOS: 137 and 138; SEQ ID NOS: 139 and 140; SEQ ID NOS: 141 and 142; SEQ ID NOS: 143 and 144; SEQ ID NOS: 145 and 146; SEQ ID NOS: 147 and 148; SEQ ID NOS: 149 and 150; SEQ ID NOS: 151 and 152; SEQ ID NOS: 153 and 154; SEQ ID NOS: 155 and 156; SEQ ID NOS: 157 and 158; SEQ ID NOS: 159 and 160; SEQ ID NOS: 161 and 162; SEQ ID NOS: 163 and 164; SEQ ID NOS: 165 and 166; SEQ ID NOS: 167 and 168; SEQ ID NOS: 169 and 170; SEQ ID NOS: 171 and 172; SEQ ID NOS: 173 and 174; SEQ ID NOS: 175 and 176; SEQ ID NOS: 177 and 178; SEQ ID NOS: 179 and 180; SEQ ID NOS: 181 and 182; SEQ ID NOS: 183 and 184; SEQ ID NOS: 185 and 186; SEQ ID NOS: 187 and 188; SEQ ID NOS: 189 and 190; SEQ ID NOS: 191 and 192; SEQ ID NOS: 193 and 194; SEQ ID NOS: 195 and 196; SEQ ID NOS: 197 and 198; SEQ ID NOS: 199 and 200; SEQ ID NOS: 201 and 202; SEQ ID NOS: 203 and 204; SEQ ID NOS: 205 and 206; SEQ ID NOS: 207 and 208; SEQ ID NOS: 209 and 210; SEQ ID NOS: 211 and 212; SEQ ID NOS: 213 and 214; SEQ ID NOS: 215 and 216; SEQ ID NOS: 217 and 218; SEQ ID NOS: 219 and 220; SEQ ID NOS: 221 and 222; SEQ ID NOS: 223 and 224; SEQ ID NOS: 225 and 226; SEQ ID NOS: 227 and 228; SEQ ID NOS: 229 and 230; SEQ ID NOS: 231 and 232; SEQ ID NOS: 233 and 234; SEQ ID NOS: 235 and 236; SEQ ID NOS: 237 and 238; SEQ ID NOS: 239 and 240; SEQ ID NOS: 241 and 242; SEQ ID NOS: 243 and 244; SEQ ID NOS: 245 and 246; SEQ ID NOS: 247 and 248; SEQ ID NOS: 249 and 250; SEQ ID NOS: 251 and 252; SEQ ID NOS: 253 and 254; or SEQ ID NOS: 255 and 256.

20. The monoclonal antibody or fragment thereof of claim 15, wherein the antibody or antibody fragment comprises heavy chain CDR1-3 of SEQ ID NOS: 314-316 and light chain CDR1-3 of SEQ ID NOS: 506-508 or heavy chain CDR1-3 of SEQ ID NOS: 413-415 and light chain CDR1-3 of SEQ ID NOS: 605-607.

21. The monoclonal antibody or fragment thereof of claim 15, wherein the antibody or antibody fragment comprises a heavy chain variable region of SEQ ID NO: 165 and a light chain variable region of SEQ ID NO: 166 or a heavy chain variable region of SEQ ID NO: 233 and a light chain variable region of SEQ ID NO: 234.

22. The monoclonal antibody or fragment thereof of claim 15, wherein the antibody or antibody fragment comprises heavy and light chain variable sequences having 95% identity to a heavy chain variable region of SEQ ID NO: 165 and a light chain variable region of SEQ ID NO: 166 or a heavy chain variable region of SEQ ID NO: 233 and a light chain variable region of SEQ ID NO: 234.

23. A hybridoma or engineered cell encoding an antibody or antibody fragment, wherein the antibody or antibody fragment comprises heavy chain CDR1-3 of SEQ ID NOS: 257, 258 and 259, and light chain CDR1-3 of SEQ ID NOS: 449, 450 and 451; heavy chain CDR1-3 of SEQ ID NOS: 260, 261 and 262, and light chain CDR1-3 of SEQ ID NOS: 452, 453 and 454; heavy chain CDR1-3 of SEQ ID NOS: 263, 264 and 265, and light chain CDR1-3 of SEQ ID NOS: 455, 456 and 457; heavy chain CDR1-3 of SEQ ID NOS: 266, 267 and 268, and light chain CDR1-3 of SEQ ID NOS: 458, 459 and 460; heavy chain CDR1-3 of SEQ ID NOS: 269, 270 and 271, and light chain CDR1-3 of SEQ ID NOS: 461, 462 and 463; heavy chain CDR1-3 of SEQ ID NOS: 272, 273 and 274, and light chain CDR1-3 of SEQ ID NOS: 464, 465 and 466; heavy chain CDR1-3 of SEQ ID NOS: 275, 276 and 277, and light chain CDR1-3 of SEQ ID NOS: 467, 468 and 469; heavy chain CDR1-3 of SEQ ID NOS: 278, 279 and 280, and light chain CDR1-3 of SEQ ID NOS: 470, 471 and 472; heavy chain CDR1-3 of SEQ ID NOS: 281, 282 and 283, and light chain CDR1-3 of SEQ ID NOS: 473, 474 and 475; heavy chain CDR1-3 of SEQ ID NOS: 284, 285 and 286, and light chain CDR1-3 of SEQ ID NOS: 476, 477 and 478; heavy chain CDR1-3 of SEQ ID NOS: 287, 288 and 289, and light chain CDR1-3 of SEQ ID NOS: 479, 480 and 481; heavy chain CDR1-3 of SEQ ID NOS: 290, 291 and 292, and light chain CDR1-3 of SEQ ID NOS: 482, 483 and 484; heavy chain CDR1-3 of SEQ ID NOS: 293, 294 and 295, and light chain CDR1-3 of SEQ ID NOS: 485, 486 and 487; heavy chain CDR1-3 of SEQ ID NOS: 296, 297 and 298, and light chain CDR1-3 of SEQ ID NOS: 488, 489 and 490; heavy chain CDR1-3 of SEQ ID NOS: 299, 300 and 301, and light chain CDR1-3 of SEQ ID NOS: 491, 492 and 493; heavy chain CDR1-3 of SEQ ID NOS: 302, 303 and 304, and light chain CDR1-3 of SEQ ID NOS: 494, 495 and 496; heavy chain CDR1-3 of SEQ ID NOS: 305, 306 and 307, and light chain CDR1-3 of SEQ ID NOS: 497, 498 and 499; heavy chain CDR1-3 of SEQ ID NOS: 308, 309 and 310, and light chain CDR1-3 of SEQ ID NOS: 500, 501 and 502; heavy chain CDR1-3 of SEQ ID NOS: 311, 312 and 313, and light chain CDR1-3 of SEQ ID NOS: 503, 504 and 505; heavy chain CDR1-3 of SEQ ID NOS: 314, 315 and 316, and light chain CDR1-3 of SEQ ID NOS: 506, 507 and 508; heavy chain CDR1-3 of SEQ ID NOS: 317, 318 and 319, and light chain CDR1-3 of SEQ ID NOS:

509, 510 and 511; heavy chain CDR1-3 of SEQ ID NOS: 320, 321 and 322, and light chain CDR1-3 of SEQ ID NOS: 512, 513 and 514; heavy chain CDR1-3 of SEQ ID NOS: 323, 324 and 325, and light chain CDR1-3 of SEQ ID NOS: 515, 516 and 517; heavy chain CDR1-3 of SEQ ID NOS: 326, 327 and 328, and light chain CDR1-3 of SEQ ID NOS: 518, 519 and 520; heavy chain CDR1-3 of SEQ ID NOS: 329, 330 and 331, and light chain CDR1-3 of SEQ ID NOS: 521, 522 and 523; heavy chain CDR1-3 of SEQ ID NOS: 332, 333 and 334, and light chain CDR1-3 of SEQ ID NOS: 524, 525 and 526; heavy chain CDR1-3 of SEQ ID NOS: 335, 336 and 337, and light chain CDR1-3 of SEQ ID NOS: 527, 528 and 529; heavy chain CDR1-3 of SEQ ID NOS: 338, 339 and 340, and light chain CDR1-3 of SEQ ID NOS: 530, 531 and 532; heavy chain CDR1-3 of SEQ ID NOS: 341, 342 and 343, and light chain CDR1-3 of SEQ ID NOS: 533, 534 and 535; heavy chain CDR1-3 of SEQ ID NOS: 344, 345 and 346, and light chain CDR1-3 of SEQ ID NOS: 536, 537 and 538; heavy chain CDR1-3 of SEQ ID NOS: 347, 348 and 349, and light chain CDR1-3 of SEQ ID NOS: 539, 540 and 541; heavy chain CDR1-3 of SEQ ID NOS: 350, 351 and 352, and light chain CDR1-3 of SEQ ID NOS: 542, 543 and 544; heavy chain CDR1-3 of SEQ ID NOS: 353, 354 and 355, and light chain CDR1-3 of SEQ ID NOS: 545, 546 and 547; heavy chain CDR1-3 of SEQ ID NOS: 356, 357 and 358, and light chain CDR1-3 of SEQ ID NOS: 548, 549 and 550; heavy chain CDR1-3 of SEQ ID NOS: 359, 360 and 361, and light chain CDR1-3 of SEQ ID NOS: 551, 552 and 553; heavy chain CDR1-3 of SEQ ID NOS: 362, 363 and 364, and light chain CDR1-3 of SEQ ID NOS: 554, 555 and 556; heavy chain CDR1-3 of SEQ ID NOS: 365, 366 and 367, and light chain CDR1-3 of SEQ ID NOS: 557, 558 and 559; heavy chain CDR1-3 of SEQ ID NOS: 368, 369 and 370, and light chain CDR1-3 of SEQ ID NOS: 560, 561 and 562; heavy chain CDR1-3 of SEQ ID NOS: 371, 372 and 373, and light chain CDR1-3 of SEQ ID NOS: 563, 564 and 565; heavy chain CDR1-3 of SEQ ID NOS: 374, 375 and 376, and light chain CDR1-3 of SEQ ID NOS: 566, 567 and 568; heavy chain CDR1-3 of SEQ ID NOS: 377, 378 and 379, and light chain CDR1-3 of SEQ ID NOS: 569, 570 and 571; heavy chain CDR1-3 of SEQ ID NOS: 380, 381 and 382, and light chain CDR1-3 of SEQ ID NOS: 572, 573 and 574; heavy chain CDR1-3 of SEQ ID NOS: 383, 384 and 385, and light chain CDR1-3 of SEQ ID NOS: 575, 576 and 577; heavy chain CDR1-3 of SEQ ID NOS: 386, 387 and 388, and light chain CDR1-3 of SEQ ID NOS: 578, 579 and 580; heavy chain CDR1-3 of SEQ ID NOS: 389, 390 and 391, and light chain CDR1-3 of SEQ ID NOS: 581, 582 and 583; heavy chain CDR1-3 of SEQ ID NOS: 392, 393 and 394, and light chain CDR1-3 of SEQ ID NOS: 584, 585 and 586; heavy chain CDR1-3 of SEQ ID NOS: 395, 396 and 397, and light chain CDR1-3 of SEQ ID NOS: 587, 588 and 589; heavy chain CDR1-3 of SEQ ID NOS: 398, 399 and 400, and light chain CDR1-3 of SEQ ID NOS: 590, 591 and 592; heavy chain CDR1-3 of SEQ ID NOS: 401, 402 and 403, and light chain CDR1-3 of SEQ ID NOS: 593, 594 and 595; heavy chain CDR1-3 of SEQ ID NOS: 404, 405 and 406, and light chain CDR1-3 of SEQ ID NOS: 596, 597 and 598; heavy chain CDR1-3 of SEQ ID NOS: 407, 408 and 409, and light chain CDR1-3 of SEQ ID NOS: 599, 600 and 601; heavy chain CDR1-3 of SEQ ID NOS: 410, 411 and 412, and light chain CDR1-3 of SEQ ID NOS: 602, 603 and 604; heavy chain CDR1-3 of SEQ ID NOS: 413, 414 and 415, and light chain CDR1-3 of SEQ ID NOS: 605, 606 and 607; heavy chain CDR1-3 of SEQ ID NOS: 416, 417 and 418, and light chain CDR1-3 of SEQ ID NOS: 608, 609 and 610; heavy chain CDR1-3 of SEQ ID NOS: 419, 420 and 421, and light chain CDR1-3 of SEQ ID NOS: 611, 612 and 613; heavy chain CDR1-3 of SEQ ID NOS: 422, 423 and 424, and light chain CDR1-3 of SEQ ID NOS: 614, 615 and 616; heavy chain CDR1-3 of SEQ ID NOS: 425, 426 and 427, and light chain CDR1-3 of SEQ ID NOS: 617, 618 and 619; heavy chain CDR1-3 of SEQ ID NOS: 428, 429 and 430, and light chain CDR1-3 of SEQ ID NOS: 620, 621 and 622; heavy chain CDR1-3 of SEQ ID NOS: 431, 432 and 433, and light chain CDR1-3 of SEQ ID NOS: 623, 624 and 625; heavy chain CDR1-3 of SEQ ID NOS: 434, 435 and 436, and light chain CDR1-3 of SEQ ID NOS: 626, 627 and 628; heavy chain CDR1-3 of SEQ ID NOS: 437, 438 and 439, and light chain CDR1-3 of SEQ ID NOS: 629, 630 and 631; heavy chain CDR1-3 of SEQ ID NOS: 440, 441 and 442, and light chain CDR1-3 of SEQ ID NOS: 632, 633 and 634; heavy chain CDR1-3 of SEQ ID NOS: 443, 444 and 445, and light chain CDR1-3 of SEQ ID NOS: 635, 636 and 637; or heavy chain CDR1-3 of SEQ ID NOS: 446, 447 and 448, and light chain CDR1-3 of SEQ ID NOS: 638, 639 and 640.

24. The hybridoma or engineered cell of claim 23, wherein the antibody or antibody fragment comprises heavy chain CDR1-3 of SEQ ID NOS: 314-316 and light chain CDR1-3 of SEQ ID NOS: 506-508 or heavy chain CDR1-3 of SEQ ID NOS: 413-415 and light chain CDR1-3 of SEQ ID NOS: 605-607.

25. The hybridoma or engineered cell of claim 23, wherein the antibody or antibody fragment comprises a heavy chain variable region of SEQ ID NO: 165 and a light chain variable region of SEQ ID NO: 166 or a heavy chain variable region of SEQ ID NO: 233 and a light chain variable region of SEQ ID NO: 234.

26. The hybridoma or engineered cell of claim 23, wherein the antibody or antibody fragment comprises heavy and light chain variable sequences having 95% identity to a heavy chain variable region of SEQ ID NO: 165 and a light chain variable region of SEQ ID NO: 166 or a heavy chain variable region of SEQ ID NO: 233 and a light chain variable region of SEQ ID NO: 234.

* * * * *

SEQUENCE LISTING

<160> NUMBER OF SEQ ID NOS: 647

<210> SEQ ID NO 1
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 1
caggtgcagc tggtggagtc tgggggaggc gtggtccagc ctgggaggtc cctgagactc      60
tcatgtgcag cctctggatt catcttcagt cgctacgctc tgcactgggt ccgccaggct     120
ccaggcaagg ggctggactg ggtggcagtt atatcatatg atgcaagaaa ttcatattac     180
acagactccg tgaagggccg attcaccatc tccagagaca attccaaaaa cacgctgttt     240
ctgcagatga acagtctgag agctgacgac acggctgtct attactgtgc gagaccgact     300
ttgccctaca gcaacaactg gtacgcgcct gaatactggg gccagggaac cctggtcacc     360
gtctcctca                                                            369

<210> SEQ ID NO 2
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 2
tcctatgagc tgacacagcc accctcggtg tcagtgtccc caggacaaac ggccaggatc      60
acctgctctg gagatgcatt accaaaaaaa tatgcttctt ggtaccagca gaagtcaggc     120
caggcccctg tgctggtcat ctatgaagac accaaacgac cctccgggat ccctgagaga     180
ttctctggct ccagctcagg gacaatggcc accttgacta tcagtggggc caggtggaa      240 gatgaaagtg actactactg ttcctcgaca gacagcagtg gtaatcctgt gctattcggc     300
ggagggacca agttgaccgt ccta                                            324

<210> SEQ ID NO 3
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 3
gaggtgcagc tggtagagtc tgggggagac ttggtacagc ctgggggtc cctgagactc       60 tcctgtgcag cctctggatt ctcctttagc agctatgcca tggcctgggt ccgccaggct     120
ccagggaagg ggctgcagtg ggtctcatct attagtggta acggtaatgg agatcctat     180 gcagattctc tgaagggccg gttcaccacc tccaaagacc tttccaagta taccctgtat     240

```
ctgcaaatga caatctgag acccgaggac acggccatat attactgtgc gaaagttgtc    300
cgtatagcag ctgttttgta ttactttgac tattggggcc cgggaaccca ggttaccgtc    360
tcctca                                                                366
```

```
<210> SEQ ID NO 4
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 4
gaaattgtgt tgacacagtc tccagccacc ctgtctttgt ctccagggga aagagccacc     60
ctctcctgca gggccagtca gagtgttagc acctacttag cctggtacca acaaaagcct    120
ggccaggctc ccaggctcct catctatgaa gcatccacca gggccactgg catcccagcc    180
aggttcagtg gcagtgggtc tgggacagac ttcactctca tcatcagcag cctagagcct    240
gaagattttg cagtttatca ctgtcagcag cgcagctcct ggccgatcac cttcggccaa    300
gggacacgac tggagattga a                                              321
```

```
<210> SEQ ID NO 5
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 5
gacgtgcagc tggtggagtc tgggggggc ttggtacagc ctggggggtc cctgagactc      60
tcctgtgctg cctctggatt cacttttagc aactatgcca tgacctgggt ccgccaggct    120
ctagggaagg gctggagtg gtctcttct attagtggta gtggtggcct cacatatttc    180
gcacactccg tgaagggccg gctcaccatc tccagagaca actccaagaa taccctctat    240
ctgcaaatga gcagcctgag agccgaagac acggccgtat attactgtgc gagagtgaaa    300
agtacaactg gaacgacggc gttagttttt gatatctggg gccaagggac aatggtcacc    360
gtctcttcg                                                            369
```

```
<210> SEQ ID NO 6
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 6
cagactgtgg tgacccagga gccatcgttc tcagtgtccc ctggagggac agtcacactc     60
acttgtggct tgagttctgg ctcagtctct agtagttact accccagttg gtaccagcag    120
accccaggcc aggctccacg cacgctcatc tacagtataa acagacgttc ttctggggtc    180
cctgatcgct tctctggctt catccttggg aacaaagctg ccctcaccat cagggggggcc    240 caggcagatg atgaatctga ttattactgt gggctgtata tgggtagtgg catttggatc    300
ttcggcggag ggaccaagct gaccgtccta                                      330
```

```
<210> SEQ ID NO 7
<211> LENGTH: 366
<212> TYPE: DNA
<213> ORGANISM: Artificial sequence
```

```
<220> FEATURE:
<223> OTHER INFORMATION: Synthetic oligonucleotide

<400> SEQUENCE: 7
caggtgcagc tggtggagtc tggggggaggc gtggtccagc ctggaggtc cctgagactc      60 tcctgtgcag cctctggatt caccttcatt aactatggca tgcactgggt ccgccaggct     120
ccaggcaagg ggctggagtg ggtggcagtt atatcaaatg atggaagtta taactacgat     180
gcagactccg tgaagggccg attcaccatc tccagagaca attccaagaa caaggttttat    240 ctacaaatga acagcctgag acctgaggac acggctgtgt atttctgtgc gaaagacaaa     300
cacggtgact tcgactacta cggtgtggac gtctggggcc aagggaccac ggtcaccgtc     360
tcccca                                                                366

<210> SEQ ID NO 8
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 8
gacgtccaga tgacccagtc tccatcttcc gtgtctgcat ctataggaga cagagtcacc      60
atcacttgtc gggcgggtca gggaattagc agctggttag cctggtatca gcagaaacca    120
gggaaagccc ctaagctcct gatctatgct gcatccaatt tgcaaagtgg ggtcccatca    180
cggttcagcg gcagtggatc tgggacagat ttcactctca ccatcagcag cctgcagcct    240
gaagattttg aacttactat tgtcaacag gctgacagtt ccctcggac gttcggccaa       300 gggaccaagg tggaaatcaa a                                               321

<210> SEQ ID NO 9
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 9
caggtgcagc tggtggagtc tggggggaggc gtggtccagc ctggaggtc cctgagactc      60 tcctgtgcag cctctggatt caccttcagt agttatggca tacactgggt ccgccaggct    120
ccaggcaagg ggctggagtg ggtggcagtt atatcctatg atggaagtga taacacctat    180 gcacctttg tgaacggccg attcaccatc tccagagaca attccaagaa cacgctgtat     240
ctgcaaatga acagcctgag agctgacgac acggctgtgt attactgtgc gaggcgtcgg    300
cctgggagct tcccaggact ttgcgactac tggggccagg gagccctggt caccgtctcc    360
tca                                                                  363

<210> SEQ ID NO 10
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 10
gacatccaga tgacccagtc gccttccact atgtctgctt ctgtaggaga cagagtcacc      60
atcacttgcc gggccagtca gagtattagt agtggttgg cctggtatca gcagaagcca    120
```

```
gggaaagccc ctaaactcct gatctataag gcgtctacct tacaaactgg ggtcccatca      180
aggttcagcg gcagtggatc tgggacagaa ttcactctca ccatcaacag cctgcagcct      240
gatgattttg caacttatta ctgccaacag cataatagtt attcgtacac ttttggccag      300
gggaccaagg tggagatcaa g                                                321

<210> SEQ ID NO 11
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 11
caggtgcagc tggtgcagtc tggggctgag gtgaagaagc ctgggtcctc ggtgaaggtc      60
tcctgcaagg cttctggagg cagcttcagc agacttacta tcatctgggt gcggcaggcc     120
cctggacaag gcttgagtg gatgggaggg cacatccta tctttggaac aacaaactac      180
gcactgaagt tccagggcag agtcacgatt accgcgaca aaaccacgag cacagcctac      240
atggagctga gcagcctgag atctgaggac acggccatat attactgtgc gagaatgtat      300
agtggccatg acggcgttga tgtctggggc caagggacac tggtcaccgt ctcttca        357

<210> SEQ ID NO 12
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 12
gaaattgtgt tgacacagtc tccagccacc ctgtctttgt ctccagggga aagagccacc      60
ctctcctgca gggccagtca gagtgttagg agctacttag cctggtacca acacaaacct     120
ggccaggctc ccaggctcct catctatgat gcatccaaca gggccaaggg catcccagcc     180
aggttcagtg gcagtgggtc tgggacagac ttcactctca ccatcagcag cctagagcct     240
gaagattttg cagtttatta ctgtcagcag cgtagcacct ggcctccggg aatgttcggc     300
caagggacca gggtggaaat caaa                                             324

<210> SEQ ID NO 13
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 13
cagctgcagc tgcaggagtc gggcccagga ctggtgaagc attcggagac cctgtccctc      60
acctgcactg tctctggtgg ctccatcagc agtggttttt actactgggg ctggatccgc     120
cagcccccag ggaaggggct agagtggatt gggactatct atgatagtgg gagaacctat     180
gacaacccgt ccctcaagag tcgagtcacc atatccgcag acacgtccaa gaagcagttc     240
tcactgacac tgaggtctgc gaccgccgcg gacacggctg tgtatttctg tgcgagacac     300
cttacccacc tctacggtga ctacgtcacc cctgatgctt tagatatctg ggccaaggg      360 acaatggtca ccgtctcttc a                                                381

<210> SEQ ID NO 14
<211> LENGTH: 324
```

```
<212> TYPE: DNA
<213> ORGANISM: Artificial sequence
<220> FEATURE:
<223> OTHER INFORMATION: Synthetic oligonucleotide

<400> SEQUENCE: 14
gaaattgtgt tgacgcagtc tccaggcacc ctgtccttgt ctccagggga aagagccacc    60
ctctcttgca gggccagtca gagcgttagt agcagcttct tagcctggta ccagcagaaa   120
cctggccagg ctcccaggct cctcatctat ggtgcgtcca gcagggccac cggcatccca   180
gacaggttca gaggcagtgg gtctgggaca gacttcactc tcaccatcag cagactggag   240
cctgaagatt ttgcagtata ttactgtcag cagtatagta actcacgtct gacgttcggc   300
caagggacca aggtggaaat caaa                                          324

<210> SEQ ID NO 15
<211> LENGTH: 378
<212> TYPE: DNA
<213> ORGANISM: Artificial sequence
<220> FEATURE:
<223> OTHER INFORMATION: Synthetic oligonucleotide

<400> SEQUENCE: 15
gaggtgcagc tggtggagtc tgggggaggc ttggtacagc ctggggggtc cctgagactc    60
tcctgtgcag cctctggatt caccttcact acctatagca tgaactgggt ccgccaggct   120
ccagggaagg gctggagtg gatttcatac attagtagtg gtagtagtaa catatactac   180
gcagactctg tgaagggccg attcaccatc tccagagaca tgccaagaa ctcactgaat   240 ctgcaaatga gcagcctgag agacgaggac acggctgtgt attactgtgc gagagcccac   300
ggacgtatag tgaattctgg agtggttatt agtaggttcg accctgggg ccagggaatc    360 ctggtcaccg tctcctca                                                 378

<210> SEQ ID NO 16
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 16
cagtctgccc tgactcagcc tgcctccgtg tctgggtctc ctggacagtc gatcaccatc    60
tcctgcactg gaaccagcag tgacgttggt ggttataact atgtctcctg gtaccaactg   120
cacccaggca aagccccccaa actcatgatt tttgaggtca cttatcggcc ctcaggggtt   180
tctaatcgct tctctggctc caagtctggc aacacggcct ccctgaccat ctctgggctc   240
caggctgagg acgaggctga ttatttctgc agctcctata caaccagcaa cactctcgtg   300
gtgttcggcg gagggaccaa gctgaccgtc cta                                333

<210> SEQ ID NO 17
<211> LENGTH: 378
<212> TYPE: DNA
<213> ORGANISM: Artificial sequence
<220> FEATURE:
<223> OTHER INFORMATION: Synthetic oligonucleotide

<400> SEQUENCE: 17
caggtgcagc tggtgcagtc tggggctgag gtgaagaagc ctggggcctc agtgaaggtc    60
tcctgtagga cttctggata caccttcacg gcctactata tgcactgggt gcgacaggcc   120
```

```
cccggacaag ggcctgagtg gatgggaagg atcaacccga gcagtggtgg cgcacagtat    180
gcacagaagt tcagggcag ggtcaccatg accagggaca cgtccatcag cacaacctac    240
atgaccctga gcgggctgac atctgacgac acggccgtgt tttactgtgc gagaatgggt    300
tgtcgtagtg accggtgcta ttcgaccaac tacaactttg accagtgggg ccagggaacc    360
ctggtcaccg tctcctca                                                  378

<210> SEQ ID NO 18
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 18
tcctatgtgc tgactcagcc accctcggtg tcagtggccc caggacagac ggccaggatt    60
ccctgtgggg gaaacaacat tggaactaaa agtgttcact ggtaccagca gaagccaggc    120
caggcccctg tgctggtcgt ctctaatgac agcgaccggc cctcagggat ccctgagcga    180
ttctctggct ccaagtctgg gaacacggcc accctgacca tcagcagggt cgaagccggg    240
gatgaggccg actattattg tcaggtgtgg gatagtggta ttgatgtcgt tttcggcgga    300
gggaccaagc tgaccgtcct a                                              321

<210> SEQ ID NO 19
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 19
gaggtgcagc tggtggagtc tgggggaggc ctggtcaagc ctgggggtc cctgagactc     60 tcctgtgcag cctctggatt cactatcagt ccctatggca tgaactgggt ccgccaggct   120
ccagggaagg ggctggagtg ggtctcattc attagtagta gtagtcgtta cacatattac   180
gcagactcag tgaagggccg tttcaccatc tccagagaca cgccaagaa ttcactgtct    240 ctgcaaatga acagcctgag agccgaggac acggctgtgt attactgtgc gagagagagg   300
ggccatagca cctcgtcctc atactttgac tcctggggcc agggaaccct ggtcaccgtc   360
tcctca                                                              366

<210> SEQ ID NO 20
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 20
tcctatgtgc tgactcagcc accctcagtg tcattggccc caggaaagac ggccaggatt    60
acctgtgggg gaaacaacat tggaactaaa actgtgagct ggtaccagca gaagccaggc   120
caggcccctg tgctggtcat gtattatgat agtgaccggc cctcagggat ccctgagcga   180
ttctctggct ccaactctgg gaacacggcc accctgacca tcaacagggt cgaggccggg   240
gatgaggccg actattactg tcgggtgtgg gatagtgata ctgatcatcg agtgttcggc   300 gggggggacca agctgaccgt ccta                                         324
```

<210> SEQ ID NO 21
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 21

```
gaggtgcagc tggtggagtc tgggggaggc ttggtaaagc ctggggggtc ccttagactc    60
tcctgtgcag cctctggatt cactttcagt aacgcctgga ttagctgggt ccgccaggct   120
ccagggaagg ggctggagtg ggttggccgt attcaaacca aaactgatgg agggacaaca   180
gactacgctg cacccgtgaa aggcagattc accatctcaa gagatgattc aaaaaacacg   240
ttgtatctgc aaatgaacag cctgaaaacc gaggacacag ccttgtatta ttgtagcaca   300
ggaccgtatt actatgatac tagtggttac ccccaaccct ttgactactg gggccaggga   360
accctggtca ccgtctcctc a                                             381
```

<210> SEQ ID NO 22
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 22

```
tcctatgagc tgactcagcc accctcagtg tccgtgtccc caggacagac agccagcatc    60
acctgctctg gagataaatt gggagataaa tatgcttgct ggtatcagca gaagccaggc   120
cagtcccctg tgctggtcat ctatcaagat accaagcggc cctcagggat ccctgagcga   180
ttctctggct ccaactctgg gaacacagcc actctgacca tcagcgggac ccaggctatg   240
gatgaggctg actattactg tcaggcgtgg gacagcagca ctgtggtatt cggcggaggg   300
accaagctga ccgtccta                                                 318
```

<210> SEQ ID NO 23
<211> LENGTH: 354
<212> TYPE: DNA
<213> ORGANISM: Artificial sequence
<220> FEATURE:
<223> OTHER INFORMATION: Synthetic oligonucleotide

<400> SEQUENCE: 23

```
gaggtacaga tggtggagtc tgggggaggc ctggtcaagc cggggggtc cctcagactc     60
tcctgttcag tctctggatt cgacttcagt agatacacca tgaactggtt ccgccaggct   120
ccaggggagg ggctgaagtg ggtctcgtcc attagtagta ctagtcttta cacattctat   180
gcggactcag tgaagggccg attctccatc tccagagaca acgcccaggg ttccctgtct   240
ctacaaatga gcagcctgag acccgaagat acggctgtct attattgtgc gagagtcgtt   300
ggtcccgccg agttagatta ctggggccag ggagtgctgg tcaccgtctc ctca         354
```

<210> SEQ ID NO 24
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 24

```
gtcacccagt tgacccagtc tccatcctcc ctgtctgctt ctgtcgggga cagagtcacc    60
```

```
atcacttgcc gggcaagtca ggacattgga gttgacttag gttggtttca gcagagacct    120
gggaaagccc ctaaactcct gatctatggt gcctccaggt tgcagagtgg ggtcccatca    180
cgcttcagcg ggcgtggatc tggcacattt ttcactctca ccatcagcag cctgcagcct    240
gaagatttta caacttactt ctgtcttcaa gattataatt accottggac gctcggccag    300 gggaccacgg tgggagtcaa a                                              321
```

<210> SEQ ID NO 25
<211> LENGTH: 351
<212> TYPE: DNA
<213> ORGANISM: Artificial sequence
<220> FEATURE:
<223> OTHER INFORMATION: Synthetic oligonucleotide

<400> SEQUENCE: 25

```
caggtgcacc tggtgcagtc tggggtctgcg gtgaggaagc ctggggcctc agtgaaggtc     60
tcctgcaagg cttctggata caccttcacc gactactata ttcactgggt gcgacaggcc    120
cctggacaag gccttgagtg gatgggatgg atcaaccta aaactggtgg ctcaaattat    180
acacagaggt ttcaggccag ggtcaccatg acctgggaca cgtccatcag tacagcctac    240
atggagttga gcaggctgag atctgacgac acggccgtgt attattgtgc gagggcgggc    300
agaaatggct acgactactg gggccaggga accctggtca ccgtctcctc a             351
```

<210> SEQ ID NO 26
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 26

```
tcctatgagc tgacacagcc accctcggtg tcagtgtccc caggacagac ggccaggatc     60
acctgctctg cagatgcatt gccaaagcaa tatgcttatt ggtaccaaca gaagccaggc    120
caggcccctg tgttgatgat atatcaagac actgagaggc cctcagggat ccctgagcga    180
ttctctgggt ccagctcagg gacaacagtc acgttgacca tcagtggagt ccaggcagaa    240
gacgaggctg actattactg tcaatcagga gacagcagtg gtacttatct agttttcggc    300
ggagggacca agctgaccgt ccta                                           324
```

<210> SEQ ID NO 27
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 27

```
gaggtacagc tcttggagtc tgggggaggc ttggtacagc ctgggggtc cctgagactc      60 tcctgtgcag cctctggatt caaatttaga aactatgcca tgacctgggt ccgccaggct    120
ccagggaagg ggctggagtg ggtctcaact attactagtg gtggtagtac agagtacgca    180
gacgccgtga agggccggtt catcatctcc agagacaatt ccaagaacac gttatatttg    240
caaatgaaca gcctgagagc cgacgacacg gccgtatatt actgtacagt gccgtggggt    300
aactacaatg actacgtgtc tgactactgg ggccagggaa ccctggtccc cgtctcctca    360
```

<210> SEQ ID NO 28
<211> LENGTH: 324

```
<212> TYPE: DNA
<213> ORGANISM: Artificial sequence
<220> FEATURE:
<223> OTHER INFORMATION: Synthetic oligonucleotide

<400> SEQUENCE: 28
gaagttgtat tgacacagtc tccagccacc ctgtctttgt ctccagggca aagagccacc       60
ctctcctgca gggccagtca gcgtgttggc aactccttag cctggtacca acaaaaacct      120
ggccaggctc ccagcctcct catctatgat gcttccaaga gggccactgg catcccagcc      180
aggttcagtg gcagtgggtc tgggacagac ttcactctca ccatcatcag cctagagtct      240
gaagattttg cagtttatta ctgtcaccaa catagcacct ggcctcgggg gaccttcggc      300
caagggacac gactggagat taaa                                             324

<210> SEQ ID NO 29
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 29
caggtgcacc tggttgagtc tgggggaggc gtggtccagc ctgggaggtc cctgagactc       60
tcctgtgcag cctctggatt catcttcagt agatatccta tgcactgggt ccgccaggct      120 ccagcaagg gtctggagtg ggtggcactt atatcatatg atggaaacaa taaatactac       180
gcagactccg tgaagggccg attccaccatc tccagagaca attccaagaa cacgctgttt      240
ctccaaatga acagcctgag agctgaggac acggctgtct attactgtgc gagacatttc      300
ctcccatata gcagtagttg gtaccagggc tttaactact ggggccaggg aatcctggtc      360
accgtctcct ca                                                          372

<210> SEQ ID NO 30
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 30
aattttatgc tgactcagcc ccactctgtg tcggagtctc ggggaagac ggtaaccatc        60 tcctgcaccc gcagcagtgg cagcattgcc accaactatg tgcagtggta ccagcagcgc      120
ccgggcagtt cccccacccc tataatcttt gaagatagtc aaagaccgtc tggggtccct      180
gatcggttct ctggctccat cgacagctcc tccaattctg cctccctcac catctctgga      240
ctgaggactg acgacgaggc tgactactac tgtcagtctt atgataacag caatcgggct      300
gttgtattcg gcggagggac caagctgacc gtccta                                336

<210> SEQ ID NO 31
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 31
caggtgcagc tggtggagtc tgggggaggc gtggtccagc ctgggaggtc cctgagactc       60
tcctgtgaag cgtctggatt cctcttcagt cgctatggca tgcactgggt ccgccaggct      120
```

| | |
|---|---:|
| ccaggcaagg ggctggactg ggtggcagtt atatcgtatg atggaaataa gaaatattat | 180 |
| gcagactctg tgaagggccg attcaccatc tccagagaca attcaaagaa cacgttgtat | 240 |
| ctgcaagtga acagcctgag agtcgaggac acggctgttt attactgtgc gagaggtgtc | 300 |
| ccgtacggtg acacccttac agggcttgtc tactggggcc agggaaccct ggtcaccgtc | 360 |
| tcctca | 366 |

<210> SEQ ID NO 32
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 32

| | |
|---|---:|
| aattttatgc tgactcagcc gcactctgtg tcggagtctc cggggaagac ggtaaccatc | 60 |
| tcctgcaccc gcagcagtgg caccattgcc agcaactatg tgcagtggta ccagcagcgc | 120 |
| ccgggcagtg cccccaccac tgtaatctat gaggataacc aaagaccctc tggggtccct | 180 |
| gatcggttct ctggctccat cgacagctcc tccaactctg cctccctcac catctctgga | 240 |
| ctgaagactg aggacgaggc tgactactac tgtcagtctt atgataacag cgatcgggtg | 300 |
| ttcggcggag ggaccaagct gaccgtcctt | 330 |

<210> SEQ ID NO 33
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 33

| | |
|---|---:|
| caggtcacct tgaaggagtc tggtcctgtg ctggtgaaac ccacagagac cctcacgctg | 60 |
| acctgcaccg tctctgggtt ctcactcagg aacgctagaa tgggagtgag ctggatccgt | 120 |
| cagcccccag ggaaggccct ggagtggctt gcacacattt tttcgaatga cgaaaaatcc | 180 |
| tacaacacat ctctgaagag cagactctcc atctccaagg acacctccaa agccaggtg | 240 |
| gtccttacca tgaccagcat ggaccctttg gacacagcca catatttctg tgcacggcta | 300 |
| ctggtggctg gtactttcct cccctctcac tactttgact actggggcca aggaatcctg | 360 |
| gtcaccgtct cctca | 375 |

<210> SEQ ID NO 34
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 34

| | |
|---|---:|
| tcctatgtgc tgactcagcc accctcagtg tcagtgaccc caggaaagac ggccaggatt | 60 |
| acctgtgggg gaaacaacat tggacttaaa agtgtcttct ggtaccagga gaggccagac | 120 |
| cagcccctg tggtggtcat ctattatgat agcgcccggc cctcagggat ccctgagcga | 180 |
| atctctggct ccaagtctgg gaacacggcc accctgacca tcaccagggt cgaagccggg | 240 |
| gatgaggccg actattttg tcaggtgtgg gatagtagtc gtaatcatcc ggtcttcggc | 300 |
| ggagggacca aactgaccgt cctc | 324 |

```
<210> SEQ ID NO 35
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 35
gagctgcagc tggtggagtc tgggggaggc ttggtacagc ctgggggtc cctgagactc      60 tcctgtgcag cctctggatt caccttcagt acctatagca tgaattgggt ccgccaggct     120
ccagggaagg ggctggagtg ggtttcatac attagtagta gtagtagtac catacagtac    180
gcagactctg tgaagggccg attcaccatc tccagagaca tgccaagaa ctcactgtat     240 ctgcaaatga atagcctgag agccgaagac acggccgtgt attattgtac gagacaggtc    300
ggggcggatt tcagtggccg cggctttgac tactggggcc agggaaccct gctcaccgtc    360
tcctca                                                                366

<210> SEQ ID NO 36
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 36
tcctatgagc tgactcagcc accctcagtg tccgtgtccc caggacagac agccaccatc     60
acctgctttg agatatatt ggggataaa tatgcttgct ggtatcagca gaagccaggc    120
cagtcccctg tgttggtcat ctaccaagat agcaagcggc cctcagggat ccctgagcga    180
ttctctggct ccaagtctgg gaacacagcc actctgacca tcagcgggac ccaggcaatg    240
gatgaggctg actattactg tcaggcgtgg gacagcagca ctgcagtgtt cggcggaggg    300
accaagctga ccgtcctc                                                  318

<210> SEQ ID NO 37
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 37
gaggtacaac tagtggagtc agggggaggc ttggtacagc ctgggggtc cctgagactc      60 tcctgtgcag cctctggatt caagttttcc gtctatgcct tgagttgggt ccgccaggct    120
ccagggaagg ggctggagtg gatttcatat attagtagta gtggttctac catatattat    180
tcagactctg tgaagggccg attcaccatc tccagagaca tgtcgggaa ctcactgttt    240 gtgcaaatga acagcctgag agccgaggac acgggtattt attactgtgc gacagcccgc    300
cacatcacca atgatggttt tgatatttgg ggccaaggga caatggtcat cgtctcttca    360

<210> SEQ ID NO 38
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 38
gacatccagt tgacccagtc tccatccttc ctgtctgcat ctgtaggaga cagagtcacc     60
```

| | |
|---|---|
| atcacttgcc gggccagtca gggcattagt aggttttag cctggtatca gcagaaacca | 120 |
| gggaaagccc ctaagctcct gatctattct gcgtccactt tacaaagggg ggtcccatca | 180 |
| aggttcagcg gcagtggatt tgggacagat ttcactctca caatcagtag ccttcagcct | 240 |
| gaagattttg caacttatta ctgtcaacaa cttaatagtc accccgaat gttcactttc | 300 |
| ggccctggga ccacagtgga tatcaag | 327 |

```
<210> SEQ ID NO 39
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 39
```

| | |
|---|---|
| caggtgcagc tgcaggagtc gggcccagga ctggtgaagc cttcggagac cctgtccctc | 60 |
| acctgcgctg tgtctggtta cttaatcagc aatggttact actggggctg gatccggcag | 120 |
| cccccgggga aggggctgga gtggattggg agtatctatc atactagaag cacctactac | 180 |
| aacccgtccc tcaagagtcg agtcagcatc tcagtagaca cgtccaagaa ccggttctcc | 240 |
| ctgaggctga ggtctgtgac cgccgcagac acggcctttt attactgtgc gagaggccca | 300 |
| ggccactgtt atggtgatga cgactgctac gcgtactact ttgaccagtg gggccaggga | 360 |
| accccggtca ccgtctcccc a | 381 |

```
<210> SEQ ID NO 40
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 40
```

| | |
|---|---|
| gacatccaga tgacccagtc tccatcttcc gtgtcttcat ctgtaggaga cagagtcacc | 60 |
| atcacttgtc gggcgagtca gggtattagc aactggttag cctggtatca gcagaaccca | 120 |
| gggaaagctc ctaaactcct gatctatgat gcctccagtt tgcaaagtgg ggtcccatca | 180 |
| aggttcagcg gcagtggatc tgggacagat ttcactctca ccatcaacag cctgcagcct | 240 |
| gaagattttg caacttacta ttgtcaacag gctaacagtt tccctttcac tttcggccct | 300 |
| gggaccaaag tggatatcaa a | 321 |

```
<210> SEQ ID NO 41
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 41
```

| | |
|---|---|
| caggtgcagc tggtgcagtc tggggctgag gtgaagaagc ctgggtcctc ggtgaaggtc | 60 |
| tcctgcaagg cttctggagg caccttcagc aggtttgcta tcagctgggt gcgacaggcc | 120 |
| cctggacaag gcttcagtg gatgggaggg atcctcccta tctttggtac agcaaactac | 180 |
| gcacagaagt tccagggcag agtcacgatt accgcggaca catccacgag cacagcctac | 240 |
| atggagctga gcagcctgag atctgaggac acggccgtgt attactgtgc gagatccctc | 300 |
| ccctattgta ctaatgatgt atgctcaaac cagaacacat tgactactg gggccaggga | 360 |
| accctggtca ccgtctcctc a | 381 |

<210> SEQ ID NO 42
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 42

```
tcctatgagc tgacacagcc accctcggtg tcagtgtccc caggacaggc ggccaggatc      60
acctgctctg gagatgcatt gcctaagcaa tatgcttatt ggtaccagca gaagccaggc     120
caggcccctg tgttggtgat atatgaagac aataagaggc cctcagggat ccctgagcga     180
ttctctggct ccagctcagg gacaacagtc acgttgacca tcagtggagt ccaggcagaa     240
gacgaggctg actattactg tcaatcagca gacagcagtg gtacttatgt ggtattcggc     300
ggagggacca agctgaccgt ccta                                            324
```

<210> SEQ ID NO 43
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 43

```
caggtgcagc tgcaggagtc gggcccagga ctggtgaagc cttcacagac cctgtccctc      60
acctgcactg tctctggtgg ctccatcagc agtggtgatt actactggag ttggatccgc     120
cagcccccag ggaagggcct ggagtggatt gggtacatct attacagtgg gagcacctac     180
tacaacccgt ccctcaagag tcgagttacc atatcagtag acacgtccaa gaaccagttc     240
tccctgaagc tgagctctgt gactgccgca gacacggccg tgtattactg tgccagccgc     300
tacggtgacc cgataggga caactggttc gaccccggg ccagggaac cctggtcacc     360 gtctcctca                                                             369
```

<210> SEQ ID NO 44
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 44

```
tcctatgtgc tgactcagcc accctcagtg tcagtgaccc caggaaagac ggccaggatt      60
acctgtgggg gaaacaacat tggacttaaa agtgtcttct ggtaccagga gaggccagac     120
caggcccctg tgtggtcat ctattatgat agcgcccggc cctcagggat ccctgagcga     180
atctctggct ccaagtctgg gaacacggcc accctgacca tcaccagggt cgaagccggg     240
gatgaggccg actatttttg tcaggtgtgg gatagtagtc gtaatcatcc ggtcttcggc     300
ggagggacca aactgaccgt cctc                                            324
```

<210> SEQ ID NO 45
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 45

```
gaggtgcaac tgttggagtc ggggggaggc ttggtgcagc cggggggtc cctgagactc    60 tcctgcgcag cctccggatt caggtttagc ttctatggca tgacctgggt ccgccaggct   120
ccagggaagg ggctggagtg ggtctcaagt attagtggta ctggtgctac cagaaactgc   180
gcagactccg tgaagggccg gttcaccatc tccagagaca actccaagaa cacgctgtac   240
ctgcaaatgg acagcctgag agtcgacgac acggccgttt tttattgtgt gagacggttc   300
ccgatgacca cggtgacaag ctttgactct ggggccagg gaaccctggt caccgtctcc   360
tca                                                                 363

<210> SEQ ID NO 46
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 46
cagtctgccc tgactcagcc tcgctcagtg tccgggtctc ctggacagtc agtcaccatc    60
tcctgcactg gaaccagcag tgatgttggt ggttataact ttgtctcctg gtaccaacaa   120
cacccgggca aagcccccaa actcatgatt tttgatgtca ctgggcggcc ctcaggggtc   180
cctgatcgct tctctggctc caagtctggc aacacggcct ccctgaccat cgctgggctc   240
caggctgaag atgaggctga ttattattgt ggcgcatatg cgggctttaa cgctcttttc   300
ggcggaggga ccaaactgac cgtccta                                       327

<210> SEQ ID NO 47
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 47
gaggtgcagc tggtgcagtc ggggggaggc ttggtccggc cggggggtc cgtgagactc    60 tcctgtgtag cctctggatt cccccttcaat atgttttgga tgggctgggt ccgccagact   120
ccagggaagg gactggagtg ggtggccaat ataaaacagg atggcagtga aaatactat    180 gtcgactccg tgaagggccg attcgccatc tccagagaca atgccaagaa ctctctcttt   240
cttcaaatgg acagcctgag tgtcggggac acggccatct attattgtgt cagagagggg   300
gtgcgaaggg tcgtcgtacg tagtaccggt tacttcgact ttggggcca gggacagctg   360 gtcaccgtct cctca                                                    375

<210> SEQ ID NO 48
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 48
tcctatgagc tgacacagcc accctcgatg tcagtgtccc caggacaaac ggccaggatc    60
acctgctctg gagatgcagt gccaataaaa tatgtttatt ggtaccaaca gaggtcaggc   120
caggcccctg tattagtcat ctatgaagac gacagacgac cctccgggat ctctgagaga   180
ttctctggct ccagttcagg gacaacggcc accttgacta tcactggggc ccaggtggag   240
gatgaaggtg actactattg ctattcaaca gacagtagtg gttatcagag agcgttcggc   300
```

```
gggggggacca cgctgaccgt ccta                                       324
```

<210> SEQ ID NO 49
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 49

```
cgggtgcagc tgcaggagtc ggccccagga ctggtgaggc cttcagagac cctgtccctc    60
acctgcagtg tctctggtgg ccccatcagc aatggtcctt attactggag ctggatccgc   120
cagcacccag ggaagggcct ggagtggatt ggattcatct tttacagtgg gagcaccaac   180
tacaacccgt ccctccgggg gcgcgtaacc atggcagtgg acacgtctaa gaaccagttc   240
tccctgaggc tgaactctgt gactgccgcg gacacggccg tttattactg tgcgagacat   300
gtggtgactg cgtcggggtg gttcgacccc tggggccagg gaaccctggt caccgtctcc   360
tca                                                               363
```

<210> SEQ ID NO 50
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 50

```
gaaattgtgt tgacacagtc tccagccacc ctgtctttgt ctccagggga aagagccacc    60
ctctcctgca gggccagtca gagtgttggc accgacttag cctggtacca acagaaacct   120
ggccaggctc ccagggtcct catctatgat gcattcaaga gggccactgg catcccagcc   180
aggttcagtg gcagtgggtc tgggacagag ttcactctca ccatcagcag cctcgagcct   240
gaagattttg cagtttatta ctgtcagcag cgtagcaggt ggcctccccc gtacactttt   300
ggccagggga ccaagctgga gatcaaa                                     327
```

<210> SEQ ID NO 51
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 51

```
cgggtgcagc tgcaggagtc ggccccagga ctggtgaggc cttcagagac cctgtccctc    60
acctgcagtg tctctggtgg ccccatcagc aatggtcctt attactggag ctggatccgc   120
cagcacccag ggaagggcct ggagtggatt ggattcatct tttacagtgg gagcaccaac   180
tacaacccgt ccctccgggg gcgcgtaacc atggcagtgg acacgtctaa gaaccagttc   240
tccctgaggc tgaactctgt gactgccgcg gacacggccg tttattactg tgcgagacat   300
gtggtgactg cgtcggggtg gttcgacccc tggggccagg gaaccctggt caccgtctcc   360
tca                                                               363
```

<210> SEQ ID NO 52
<211> LENGTH: 327
<212> TYPE: DNA
<213> ORGANISM: Artificial sequence
<220> FEATURE:

<223> OTHER INFORMATION: Synthetic oligonucleotide

<400> SEQUENCE: 52

```
gaaattgtgt tgacacagtc tccagccacc ctgtctttgt ctccagggga aagagccacc      60
ctctcctgca gggccagtca gagtgttggc accgacttag cctggtacca acagaaacct     120
ggccaggctc ccagggtcct catctatgat gcattcaaga gggccactgg catcccagcc     180
aggttcagtg gcagtgggtc tgggacagag ttcactctca ccatcagcag cctgagcct      240
gaagattttg cagtttatta ctgtcagcag cgtagcaggt ggcctccccc gtacactttt     300
ggccagggga ccaagctgga gatcaaa                                         327
```

<210> SEQ ID NO 53
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 53

```
caggtgcatc tggtggagtc tggggaggc gtggtccagc ctgggaggtc cctgagactc      60
tcctgtgcag actctggagt caccttcagt gacaatgctt tgtactgggt ccgccaggct    120
ccaggcaagg ggctggagtg ggtcgcagtt atctcatatg atggaagcag tagatactac    180
gcagactccg tgaggggccg gttcaccata tccagagaca attccaagga cacgctgtat    240
ctgcaaatga acagactgag agctgaggac acggctattt attactgtgc gagagtcaca    300
gcggattact atgagagtag tggcaaggtg ttttggggcc agggagccct ggtcgtcgtc    360
tcctca                                                               366
```

<210> SEQ ID NO 54
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 54

```
gacatccaga tgacccagtc tccttccacc ctgtctgcat ctgtggggga cagagtctcc      60
atcacttgcc gggccagtca gagtgttagg agctggttgg cctggtatca gcacaaacca    120
gggaaagccc ctaaactcct gatctataag gcgtctagtt tagaaagtgg ggtcccatca    180
aggttcagcg gcagtggatc tgggacagaa ttcactctca ccatcagcag cctgcaggct    240
gatgattttg caacttatta ctgccaacag tatcagactt tttcctggac gttcggccaa    300
gggaccacgg tggaagtcaa a                                              321
```

<210> SEQ ID NO 55
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 55

```
caggtgcagc tgcaggagtc gggcccagca ctggtgaagc cttcggagac cctgtccctc      60
acctgcactg tctctggtgg ctccatcagt gatcactact ggagctggat ccggcagccc    120
ccagggaagg gactggagtg gattggctac atctatacca gtgggaccac caactacaac    180
ccctcccctca agagtcgagt caccatatca gtagacacat ccaagaagca gttctccctg    240
```

```
aatctgaggt ctgtgaccgc cgcagacacg gccgtgtatt actgtgcgag aagtctagaa      300
acggtgatcc gtttctacta ctaccactac atggacgtct ggggcaaagg gaccacggtg      360
atcgtctcat ca                                                          372
```

<210> SEQ ID NO 56
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 56

```
gatattgtga tgactcagtc tccactctcc ctgcccgtca cccctggaga gccggcctcc       60
atctcctgca ggtctagtca gagcctcctg cagagtgatg gtacagcta tttggattgg      120 tacctgcaga agccagggca gtctccacag ctcctgatct atttgggttc taatcgggcc     180
tccggggtcc ctgacaggtt cagtgtcatt ggatcaggca catattttac actgaaaatc     240
agcagagtgg aggctgagga tgttggcgtt tatttctgca tgcaagctct acaaactccg     300
tggacgttcg gccaagggac caaggtggaa atcaaa                               336
```

<210> SEQ ID NO 57
<211> LENGTH: 342
<212> TYPE: DNA
<213> ORGANISM: Artificial sequence
<220> FEATURE:
<223> OTHER INFORMATION: Synthetic oligonucleotide

<400> SEQUENCE: 57

```
caggtgcagc tgcaggagtc gggcccagga ctggtgaagc cttcggagac cctgtccctc       60
acctgcactg tcgctggcgg ctccatcggt gattaccact ggaactggat ccggcagccc     120
gccgggaagg ggctggagtg gattgggcgt atacatagca gtgggaacac tgactacaac     180
ccctccctca gagtcgagt caccatgtca gtagacacgt ccaagaacca gttctccctg      240
aaactgaggt ctgtgaccgc cgcggacacg gccgtgtatt actgtgcgag gcaaaatgtt     300
tttgatatct ggggccaagg gacaatggtc accgtctctt ca                        342
```

<210> SEQ ID NO 58
<211> LENGTH: 339
<212> TYPE: DNA
<213> ORGANISM: Artificial sequence
<220> FEATURE:
<223> OTHER INFORMATION: Synthetic oligonucleotide

<400> SEQUENCE: 58

```
gacatcgtga tgacccagtc tccagactcc ctggctctgt ctctgggcga gggggccacc      60
atcaactgca gtccagccca gagtgtttta ttcagctcca acaataagaa ctacttagct     120
tggtaccagc agaaaccagg acagcctcct aagttgctca tttactgggc atctacccgg     180
gaatccgggg tccctgaccg attcagtggc agcgggtctg agacagattt cactctcacc     240
atcagcagcc tgcaggctga agatgtggca gtttatttct gtcagcaatt ttatactact     300
ccgctcactt tcggcggagg gaccaaggtg gagatcaaa                            339
```

<210> SEQ ID NO 59
<211> LENGTH: 342
<212> TYPE: DNA
<213> ORGANISM: Artificial sequence
<220> FEATURE:

<223> OTHER INFORMATION: Synthetic oligonucleotide

<400> SEQUENCE: 59

| caggtacaga tgcaggagtc gggcccaggg ctggtgaagg cttcggagac cctgtccctc | 60 |
| acctgcagtg tctctggtat ctccatcaat aactactatt ggagttggtt ccgccagccc | 120 |
| cccgggaagg gcctggagtg gatcggatat gtctattcta ctgggagttc aagtacaat | 180 |
| ccctccctcg agcgtcgagc caccatgtca gtagacacgt ccaacaacaa cttctccctg | 240 |
| aggctgacgt ctgtgaccac tgcggacacg gccgtctact actgtgcgcg ggggagtatg | 300 |
| ccgcatatct ggggccaggg cctcctggtc accgtctcct ca | 342 |

<210> SEQ ID NO 60
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 60

| cagtctgtgc tgactcagcc accctcagcg tccgggaccc ccggacagag ggtcaccatc | 60 |
| tcctgttctg gtagcaccte caacatcgag actaattatg tatactggta ccagcaggtc | 120 |
| ccaggaacgg cccccaagcc cctcgtctat aggaatgatc agcgcccctc ggggtccct | 180 |
| gaccgattct ctggctccaa gtctggcacc tcggcctccc tggtcatcag tgggctccgg | 240 |
| accgaggatg aggctgctta ttattgtgca gcttgggatg acagtctgaa agctccggtc | 300 |
| ttcggagctg ggaccaaggt cgccgtcctc | 330 |

<210> SEQ ID NO 61
<211> LENGTH: 390
<212> TYPE: DNA
<213> ORGANISM: Artificial sequence
<220> FEATURE:
<223> OTHER INFORMATION: Synthetic oligonucleotide

<400> SEQUENCE: 61

| gaggtgcagc tggtggagtc tgggggaggc ttgataaagc cggggggtc ccttagactc | 60 |
| tcctgtgcag cctctggaat cactttcagt aacgcctgga tgagctgggt ccgccaggct | 120 |
| ccagggaagg ggctggaatg ggttggccgt attgaaagca aaattgacgg tgggacaata | 180 |
| gactacgcta cacccgtgaa aggcagattc accatctcaa gagatgattc aaaaaacacg | 240 |
| ctgtacctgc aaatgaacag cctgaaaacc gaggacacag ccgtctatta ctgtaccaca | 300 |
| gaccagggct actatgatag aagtggttat tgggtcgtcg ggaaccactt tgactactgg | 360 |
| ggccagggaa tcctggtcac cgtctcctca | 390 |

<210> SEQ ID NO 62
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 62

| cagtctgtgc tgacgcagcc gccctcagtg tctggggccc cagggctgag ggtcaccatc | 60 |
| tcctgtactg ggagcagcac caacatcggg gcaggttatg atgtacactg gtaccagcac | 120 |
| cttccaggaa cagcccccaa actcctcatc tatggtaaca gcaatcggcc ctcagggtc | 180 |
| cctgaccgat tctctggctc caagtctggc acctcagcct ccctggccat cactgggctc | 240 |

```
caggctgacg atgcggctga ttattactgc cagtcctatg acagaagcct gagtacttat    300
gtcttcggaa ctgggaccaa ggtcaccgtc cta                                 333

<210> SEQ ID NO 63
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 63
gaggtgcagc tgttggagtc tgggggaggc ttggtacagc ctgggggGtc cctgagactc    60
tcctgtgcag cctctggatt cacctttagc agctatgcca tgaactgggt ccgccaggct    120
ccagggaagg ggctggagtg ggtctcaggt attagtggta ctacaggtag cacatactac    180
gcagactccg tgaagggccg gttcaccatc tccagagaca attccaagaa cacggtgcat    240
ctgcaaatga acagcctgag agccgaggac acggccgtat attactgtgc gaaagattct    300
cactccatga tagtagttga tcatgctttt gatatctggg gccaagggac aatggtcacc    360
gtctcttca                                                             369

<210> SEQ ID NO 64
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 64
tcctatgtgc tgactcagcc accctcggtg tcagtggccc caggacagac ggccaggatt    60
acctgtgggg gaaacaatat tggaactaaa agtgtgcact ggtaccagca gaggccaggc    120
caggcccctg tgctggtcgt ctatgatgat agcgaccggc cctcaggGat ccctgagcga    180
ttctctggct ccaactctgg gaacacggcc accctgacca tcagcagggt cgaagccggg    240
gatgaggccg actattactg tcaggtgtgg gatagttata atgttcatta tgtcttcgga    300
acagggacca aggtcaccgt ccta                                            324

<210> SEQ ID NO 65
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 65
gaggtgcagc tggtggagtc tgggggggc ctggtcaagc cggggggGtc cctgagactc     60
tcctgtgcag cctctggatt caccttcagt acttatatca tgacctgggt ccgccaggcc    120
ccagggaggg ggctggagtg ggtctcatcc attagtacca gtagtgttta cacattctat    180
gcagattcac tgaagggccg gttcaccatc tccagagaca cgccaagaa ttcagtgtat     240 ctgcagatga acagcctgag agccgacgac acggctgttt attactgtgc gagggaagaa    300
gggtttcgag cttataaccct atactggggc cagggaaccc tggtcactgt ctcctca     357

<210> SEQ ID NO 66
<211> LENGTH: 330
<212> TYPE: DNA
<213> ORGANISM: Artificial sequence
<220> FEATURE:
```

<223> OTHER INFORMATION: Synthetic oligonucleotide

<400> SEQUENCE: 66

```
cagtctgtgc tgactcagcc accgtcagcg tctgggaccc ccgggcagag ggtcaccatc    60
tcttgttctg gaagcagctc caacatcgaa tacaattatg tttactggta ccagaaattc   120
ccaggaacgg cccccaaact cctcatctat aaaaataatc agcggccctc agggggtccct  180
gaccgattct ctggctccaa gtctggcacc tcagcctccc tggccattag tgggctccgg   240
tccgaggatg agggtgatta ttactgtgca gcatgggatg acatcctgag tggtgtggtt   300
ttcggcgggg ggaccaagct gaccgtcctc                                    330
```

<210> SEQ ID NO 67
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 67

```
caggtgcagc tggtggagtc tgggggaggc gtggtccagc ctgggaggtc cagaaactc     60
tcctgtgcag cctctggatt cacgttcagt aggtttggta tgcactgggt ccgccaggct   120
ccaggcaagg ggctggagtg ggtggcagtt atttcgtttg atggaagtaa tagatactac   180
gcagactccg tgaaggggcg attcaccatc accagagaca attccaagaa cacattgtat   240
ctgcaaatga caacctgag acctgaggac acggctgtat attactgcgc gagagattgg    300
gataggctgg ttcgttcggc ggttggctac tggggccagg gaaccctggt cagcgtctcc   360
tca                                                                 363
```

<210> SEQ ID NO 68
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 68

```
cagtctgccc tgactcagcc tcgctcagtg tccgggtctc ctggacagtc agtcaccatc    60
tcctgcactg gaaccagtaa tgatgttggt ggttataact ttgtctcctg gtatcagcaa   120
cacccaggca aagcccccaa actaatgatt tttgatgtca ttaggcggcc ctcaggggtc   180
cctggtcgct tctctggctc caagtctggc gacacggcct cccttatcat ctctggactc   240
caggctgagg atgaggctga ttattactgc tgctcatatg caggcaccta cacctgggta   300
ttcggcgcag ggaccacact gaccgtccta                                    330
```

<210> SEQ ID NO 69
<211> LENGTH: 378
<212> TYPE: DNA
<213> ORGANISM: Artificial sequence
<220> FEATURE:
<223> OTHER INFORMATION: Synthetic oligonucleotide

<400> SEQUENCE: 69

```
caggtgcacc tgcaggagtc gggcccacga ctggtgaagc cttcggagac cctgtccctc    60
acctgcactg tctctggtgg ctccgtcagc actgccactt actactggag ctggatccgg   120
cagtccccag ggaggggact ggagtggata ggatatatct attccagtgg taacaccaac   180
tacaacccct cccttaagag tcgagtcacc atttctttag acacgcccaa caaccagctc   240
```

```
tccctgacgt tgacctctgt gaccgctgcg gacacggcca tttattattg tgagaggcgc    300
ttacgtattc tgagtattga gaggaactac tacgctatgg acgtctgggg ccaagggacc    360
ccggtcaccg tctcctca                                                  378
```

<210> SEQ ID NO 70
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 70

```
gaagttgtgt tgacgcagac tccaggcacc ctgtctttgt ctccggggga aggagccacc    60
ctctcctgca gggccagtca gagggttgtc aacaactact tagcctggta ccagcagaga    120
gctggccagg ctcccaggct cctcattttt ggtgcatcca acagggccac tggcatccca    180
gacaggttca gtggcagtgg gtctgggaca gacttcactc tcaccatcag gaagctggag    240
cccgaagatt ttgcagtgta ttactgtcaa caatatggta gcccgtggac gttcggccac    300
gggaccaagg tggaaatgaa a                                              321
```

<210> SEQ ID NO 71
<211> LENGTH: 390
<212> TYPE: DNA
<213> ORGANISM: Artificial sequence
<220> FEATURE:
<223> OTHER INFORMATION: Synthetic oligonucleotide

<400> SEQUENCE: 71

```
caggtgcagc tggtggagtc tgggggaggc gtggtccagc ctgggaggtc cctgagactc    60
tcctgtgcag cctctggatt caccttcagt agttatgcta tgcattgggt ccgccaggct    120
ccaggcaggg gctggagtg gtggcagtt atatcatatg atggcaagca gaaataccac    180
gcagactccg tgaagggccg attcacaatc tccagagaca gttccaagaa cacgctgttt    240
ctgcaaatga atagcctgaa acctgaggac acggctgtgt attactgtgc gagagatcat    300
gtccccccca aggattgcag tgatggtaat tgccactcgg actacggtat ggacgtctgg    360
ggccaaggga ccacggtcac cgtctcctca                                     390
```

<210> SEQ ID NO 72
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 72

```
gacatccaga tgacccagtc gccttccact atgtctgctt ctgtaggaga cagagtcacc    60
atcacttgcc gggccagtca gagtattagt aagtggttgg cctggtatca gcagaagcca    120
gggaaagccc ctaaactcct gatctataag gcgtctacct tacaaactgg ggtcccatca    180
aggttcagcg gcagtggatc tgggacagaa ttcactctca ccatcaacag cctgcagcct    240
gatgattttg caacttatta ctgccaacag cataatagtt attcgtacac ttttggccag    300
gggaccaagg tggagatcaa g                                              321
```

<210> SEQ ID NO 73
<211> LENGTH: 366
<212> TYPE: DNA

<213> ORGANISM: Artificial sequence
<220> FEATURE:
<223> OTHER INFORMATION: Synthetic oligonucleotide

<400> SEQUENCE: 73

```
caggtccagc ttgtgcagtc tgggctgag gtgaagaagc ctggggcctc agtgaagatt      60
tcttgcaagg cttctggata ctccttcact aactttgctg tgcattgggt gcgccaggcc    120
cccggacaaa gacttgagtg gatgggatgg atcaaccctg caatagaaa cacaaagtat     180
tcacacaact ttcagggcag agtcaccatt accagggaca catccgcgaa cacagcctac    240
atggaactga gcagcctgag atctcaagac acggctgtgt attactgtgc gagacttccg    300
atagcagcag ctggcagggg ctggttcgac ccctggggcc agggaaccct ggtcaccgtc    360
tcctcc                                                                366
```

<210> SEQ ID NO 74
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 74

```
gaaattgtgt tgacgcagtc tccaggcacc ctgtctttgt ctccagggga aagagccacc     60
ctctcctgca gggccagtca gagtgttatc agcacctact tagcctggta ccagcagaga   120
cctggccagg ctcccagggt cctcatctat gatgtatcca ccagggccac tggcatccca   180
gacaggttca gtggcagtgg gtctgggaca gacttcactc tcaccatcag cagactggag   240
cctgaagatt ttgcagtcta tttctgtcac cagtatggta gttcaccggc gacgttcggc   300
caagggacca aggtggaaat caaa                                            324
```

<210> SEQ ID NO 75
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 75

```
gaagtgcagc tggtggagtc tgggggagac ttggtacagc ctggggggtc cctgagactc     60
tcctgtgcag cctctggatt caccttcaat acttatggca tgaactgggt ccgccaggct   120
ccagggaagg gactggagtg ggtttcatac attagtagtg ccaccactac cttctactac   180
gcagactctg tgaggggccg attcaccatc tccagagaca atgccaagaa ttcactattt   240
ctgcacatga gagcctgag agacgaagac acggcagttt attactgtgc gagagtctat    300
actatgcttc gcggagcgag tatggacgtc tggggccacg gaccacggt caccgtctcc   360
tca                                                                  363
```

<210> SEQ ID NO 76
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 76

```
gaaattgtgt tgacacagtc tccagccacc ctgtctttgt ctccaggga aagagccacc      60
ctctcctgca gggccagtca gagtgttggc acctacctgg cctggtacca acagaaacct   120
```
ggccaggctc ccaggctcct catctatgat tcagccaaca gggccactgg catcccagcc    180
cggttcagtg gcagtgggtc tgggacagac ttcactctca ccatcagcag cctagagcct    240
gaagattttg cagtttatta ctgtcagctg cgcatcacct ggcctcctat attcactttc    300
ggccctggga ccaaagtgga tgtcaaa                                        327

<210> SEQ ID NO 77
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 77
caggtgcacc tggtgcagtc tggggctgag gtgaagaagt ctggggcctc agtgaaggtc     60
tcctgcaaga cttttggata caccttcacc gcctactata tgcactgggt gcgacaggcc    120
cctggacagg ggcctgagtg gatgggatgg atcaaccccta tcagtggtgg cacaaactat    180
gcacagaagt ttcagggcag ggtctccatg accagggaca cgtccatcag cacagcctac    240
atgggcctga gcaggctgag acctgacgac acggccgtct attactgtgc gagagtgaag    300
tgtagtagtg ccaactgcta tggaactttt gactactggg gccagggtac cctggtcacc    360
gtctcctca                                                            369

<210> SEQ ID NO 78
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 78
cagtctgccc tgactcagcc tccctccgcg tccgggtctc ctggagagtc agtcaccatc     60
tcctgcactg gaaccagcag tgacgttggt ggttataact atgtctcctg gtaccaacaa    120
cacccaggca aagcccccaa actcatgatt tatgaggtca gtaagcggcc ctcaggggtc    180
cctgatcgct tctctggctc caagtctggc aacacggccc cctgaccgt ctctgggctc    240 caggctgagg atgaggctga ttattactgc agctcatatg caggcagcaa caatttggta    300
ttcggcggag ggaccaagct gaccgtccta                                     330

<210> SEQ ID NO 79
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 79
gaggtgcagc tggtgcagtc tggagcagag gtgaaaaagc ccggtgagtc tctgaagatc     60
tcctgtaagg gttctggata caggtttacc aactaccgga tcggctgggt gcgccagatg    120
cccgggaaag gcctggagtg gatgggggatc atctatcccg gtggctctga taccagatac    180
agtccgtccc tccaaggcca ggtcaccatg tcagtcgaca gtccatcag caccgcctac    240 ctgatgtgga gcagcctgaa ggcctcggac accgccatgt attactgtgc tcgacagacc    300
actcaaaata gtggctacga tagatggttt gactcctggg gccagggaac ccacgtcacc    360
gtctcctca                                                            369

<210> SEQ ID NO 80
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 80

```
cagtctgtac tgactcagcc accctcagcg tctgggaccc ccgggcagag ggtcaccatc      60
tcttgttctg gaagcacctc cagcatcgga agtaatattg taaattggta ccaacacctc     120
ccaggaacgg cccccaaact cctcatctat attaataatc agcggccctc agggtccct      180 gaccgattct ctggctccaa gtctggcacc tcagcctccc tggccatcag tgggctccag     240
tctgaggatg aggctgacta ttactgtgca gcatgggatg acagcctgaa tggttgggtg     300
ttcggcggag ggaccaagct gaccgtcctg                                      330
```

<210> SEQ ID NO 81
<211> LENGTH: 378
<212> TYPE: DNA
<213> ORGANISM: Artificial sequence
<220> FEATURE:
<223> OTHER INFORMATION: Synthetic oligonucleotide

<400> SEQUENCE: 81

```
gaggtgcagg tgttggagtc tgggggaggc ttggtacagc ctgggggtc cctgagactc       60 tcctgtgcag cctctggaat cacctttagc aggcatacta tgagctgggt ccgccaggct     120
ccagggaagg ggctggagtg gtctcagct attagtggga gtggtggtag cacatatcat      180
gcagactccg tgaagggccg cttcaccatc tccagagaca gttccaagag cacgctgtat     240
ctgcaaatga acagcctgag agccgaggac acggccgttt attactgtgc gatctccgtg     300
ccattattac gattttttgga gtggtttcaa caccttttg acttctgggg ccagggaacc     360
ctggtcaccg tctcctca                                                   378
```

<210> SEQ ID NO 82
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 82

```
gaaatagtga tgacgcagtc tccagcctcc ctgtctgtgt ctccagggga aagagtcacc      60
ctctcctgca gggccagtca gagtgttggc agcaccttag cctggtacca gcacaaacct     120
ggccaggctc ccaggctcct catctctggt gcatccacca gggccactgg tgtcccagcc     180
aggttcagtg gcagtgggtc tgggacagag ttcactctca ccatcagcag tctgcagtct     240
gaagattttg cagtttacta ctgtcaccag tatattaact ggcctccgtg gacgttcggc     300
caagggacca aggtggaaat caaa                                            324
```

<210> SEQ ID NO 83
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 83

```
gaggtgcggc tggtggagtc tgggggaggc ctggtcaaac ctggggggtc cctgagactc      60
```

```
tcctgtgcag cctctggatt caccttcaat acatattcca tgagctgggt ccgccaggct    120
ccagggaagg ggctggagtg ggtcgcctcc attagtagta ccggaagtta catatacaat    180
gcagactcac tgaagggccg attcaccatc tccagagaca acgccaagaa ctccctgttt    240
ctgcaaatga acagcctgag agtcgaagac acggctgtgt attactgtgt gagattcacc    300
atgactacag tgactaactt tgactcatgg ggccagggaa ccctggtcac cgtctcctca    360
```

<210> SEQ ID NO 84
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 84

```
cagtctgccc tgactcagcc tcgctcagtg tccgggtctc ctggacagtc agtcaccatc     60
tcctgcactg gaaccagcag tgatgttggt gcttatagct atgtctcctg gtaccaacaa    120
cacccaggca aagcccccaa actcatgatt tatgatgtct acaggcggcc ctcagggatc    180
cctggtcgct tctctggctc caagtctggc aacacggcct ccctgaccgt ctctgggctc    240
caggctgagg atgaggctga ttactactgc tgctcacatg caggcagtca cacctgggtg    300
ttcggcggag ggaccaaggt gaccgtccta                                     330
```

<210> SEQ ID NO 85
<211> LENGTH: 378
<212> TYPE: DNA
<213> ORGANISM: Artificial sequence
<220> FEATURE:
<223> OTHER INFORMATION: Synthetic oligonucleotide

<400> SEQUENCE: 85

```
cagctgcagg tggtggcgtc tgggggaggc gtggtccagc ctgggaggtc cctgagactc     60
tcctgtaaag cctctggatt cacgttcacc aattatggca tgcactgggt tcgccaggcg    120
ccaggcaagg ggctggagtg ggtggctttt atatcatacg atggaggtaa taaattttat    180
gcagactctg tgaagggccg attcaccatc tccagagaca attccaggaa cacggtttat    240
ctgcaaatga acagcctgag agtggcggac acggctatgt attactgtcc gaaggtcatc    300
ccccacccgt attatgatag tagtggtgat gatgcttttg atatctgggg ccaagggaca    360
atggtcgcca tttcttca                                                  378
```

<210> SEQ ID NO 86
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 86

```
gaaatagtga tgacgcagtc tccagccacc ctgtctgtgt ctccagggga aagagccacc     60
ctctcctgct gggccagtca gagtattagc cgcaacttag cctggtatca gcaaaaacct    120
ggccaggctc cccgactcct catctatggt gcatccacca gggccactgg tatccccgcc    180
aagttcagtg gcagtgggtc tgggacagac ttcactctca ccgtcagcag cctgcagtct    240
gaagaccttg cagtttatta ctgtcagcag tatagtaagt tgcctatcac cttcggccaa    300
gggacacgac tggagattaa a                                              321
```

<210> SEQ ID NO 87
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 87

| | | | | | |
|---|---|---|---|---|---|
| gaggtgcagc | tggtggagtc | tgggggaggc | ttggtacagc | cggggggggtc | cctgagactc | 60 |
| tcctgtgcag | cctctggatt | cccccttcagt | agttatagca | tgagctgggt | ccgccaggct | 120 |
| ccagggaagg | gctggagtg | ggtctcatac | ataagtggta | gtggtggtga | catatactac | 180 |
| gcagactctg | tgaagggccg | attcaccatc | tccagggaca | atgccaggaa | ctcactgtct | 240 |
| ctgcaaatga | acagcctgag | agccgacgac | acggctgtgt | attactgtgc | gagagggctg | 300 |
| gtagcaacaa | ctggtacaag | gtactttgac | tactgggggcc | agggaaccct | ggtcaccgtc | 360 |
| tcctca | | | | | | 366 |

<210> SEQ ID NO 88
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 88

| | | | | | |
|---|---|---|---|---|---|
| gaaattgtgt | tgacacagtc | tccagccacc | ctgtctttgt | ctccagggga | aagagccacc | 60 |
| ctctcctgca | gggccagtca | gagtgttagg | agttacttag | cctggtacca | acagagacct | 120 |
| ggccaggctc | ccaggctcct | catctacgat | gcatccaaca | gggccactgg | catcccagtc | 180 |
| aggttcagtg | gcagtgggtc | tgggacagac | ttcactctca | ccatcagcag | cctagagcct | 240 |
| gaagattttg | cagtttatta | ctgtcagcag | cgtagctact | ggcctccgtt | cactttcggc | 300 |
| ggagggacca | aggtggagat | caaa | | | | 324 |

<210> SEQ ID NO 89
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 89

| | | | | | |
|---|---|---|---|---|---|
| caggtgcagc | tggtgcagtc | tggggctgag | gtgaagaagc | cggggtcctc | ggtgaaggtc | 60 |
| tcctgcaagg | cttctggagg | caccttcagg | aggtttgcta | tcagctgggt | gcgacaggcc | 120 |
| cctggacaag | gcttgagtg | gatgggaggg | atcatcccta | tcctaggtag | aggaaagtac | 180 |
| gcacagaagt | tccagggcag | agtcaggatt | accgcggacg | aatccacgag | cacagcctac | 240 |
| atggagctga | gcagcctgag | atctgaagac | acggccgtgt | attactgtgc | gagatttatt | 300 |
| tcgacagcct | cctatgttcc | ggggaccttc | gaggacgtct | ggggccaagg | gaccacggtc | 360 |
| accgtctcct | ca | | | | | 372 |

<210> SEQ ID NO 90
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 90

```
gacattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccgctgg catcccagcc   180
aggttcagtg gcagtgggtc tgagacagac ttcactctca ccatcagcag cctagagcct   240
gaagatgttg cggtttatta ctgtcagcag cgtagcgact ggcctccggg gacttttggc   300
caggggacca acgtggagat caaa                                          324
```

<210> SEQ ID NO 91
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 91

```
gaggtgcagc tggtggagtc tgggggaggc ctggtcaagc cggggggttc cctgagactc    60
tcctgtgcag cctctggatt caccttcagg aactataaca tcaactgggt ccgccaggct   120
ccagggaagg ggctggagtg ggtctcatcc attagtagta ctggtagtta catacactac   180
gcagatttag tgaagggccg attcaccatc tccagagaca acgccaagaa ctcactgtat   240
ctgcaaatga acagcctgag agtcgaggac acggctgtat attactgtgc gcgaatggtt   300
aggaatacgg tgactgcctt tgactactgg ggccagggaa ccctggtctc cgtctcctca   360
```

<210> SEQ ID NO 92
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 92

```
cagtctgccc tgactcagcc tgcctccgtg tctgggtctc ctggccagtc gatcaccatc    60
tcctgcactg gaaccagcag tgatgttggt ggctataact ttgtctcctg gtaccaacaa   120
cagccaggca gagcccccaa actccttatt tatgaagtca ttaagcggcc ctcagggtt   180 tctgatcgct tctctggctc caagtctggc gacacggcct ccctgacaat ctctgggctc   240
caggctgagg acgaggctga ttattactgc tgctcatatg gggtaacaa ctcttggatg   300 ttcggcggag ggaccatgct gaccgtccta                                    330
```

<210> SEQ ID NO 93
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 93

```
caggtccagg tggtacagtc tggggctgag atgaagaagc ctggggcctc agtgaaggtc    60
tcctgcaagg tttccggata caggctcatt gatttaccct tgcactgggt gcgacaggct   120
cctggaaaag gcttgagtg gatgggactt tttgatcctg aaaaggctga agccatctac   180
tcacagaaat tccaggacaa ggtcaccata agcgaggaca catctatcga cacagcctac   240
atggaactga acagcctgcg ctctgaagac acggccgtct actactgtgc aacttgggga   300
gttgaggtgg tgaatgggag aagggactac tttgactcct ggggccaggg aaccctggtc   360
```
accgtctcct ca 372

<210> SEQ ID NO 94
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 94
tcctatgagc tgacacagcc accctcggtg tcagtgtccc caggacagac ggccaggatc 60
acatgctatg cagatgtgtt gtcaaaccaa tatacttact ggtatcaaca gaagccaggc 120
caggcccctg tgttggtgat atataaagac actgagaggc cctcagggat ccctgagcga 180
tttgctggct ccagctcagg gacaacagtc accttagtca tcaatggagt ccggcagag 240 gacgaggctt actattactg tcaatcagcc gacaacacca gaattacggt tttcggcgga 300
gggaccaagc tgtccgtcct a 321

<210> SEQ ID NO 95
<211> LENGTH: 384
<212> TYPE: DNA
<213> ORGANISM: Artificial sequence
<220> FEATURE:
<223> OTHER INFORMATION: Synthetic oligonucleotide

<400> SEQUENCE: 95
ggggtgcagc tggtggagtc tgggggagga ttgatacagc ctggagggtc cctgagactc 60
tcctgtgcag cctctggatt caccttcagt agttttgaaa tgaactgggt ccgccaggct 120
ccagggaagg gctggagtg ggtttcatac attagtacta gtggtagtac catatactac 180
gcagactctg tcaagggccg attcaccatc tccagagaca cgccaggaa ctcactgtct 240 ctgcaaatga acagcctgag agccgaggac acggctgttt attactgtgc gagagacgtg 300
agggattgta gtgctcttac gtgcccccga aggggagatg cttttgattt ctggggccgt 360
gggacaaggg tcaccgtctc ttca 384

<210> SEQ ID NO 96
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 96
gatgttgtga tgactcagtc tccactctcc ctgcccgtca cccttggaca gtcggcctcc 60
atctcctgca ggtctagtca aagcctcgta tacagtgatg gaaacaccta cttgaattgg 120
tttcagcaga ggccaggcca atctccaagg cgcctaattt ataaggtttc taaccgggac 180
tctggggtcc cagacagatt cagcggcagt gggtcaggca ctgatttcac actgaaaatc 240
agcagggtgg aggctgagga tgttggggtt tattactgca tgcaaggtac acactggcct 300
cgcactttcg gccctgggac caaagtggat atcaaa 336

<210> SEQ ID NO 97
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 97

```
gaggtgcagc tggtggagtc tgggggaggc ctggtcaagc cggggggtc cctgagactc    60 tcctgtgcag cctctggatt cagtttcagt gtctatccca tgaactgggt ccgccaggct   120
ccagggaagg ggctggagtg ggtctcatcc ataagtagta gtagtcgtta catatcctac   180
gcagactcac tgagggtcg aatcaccatc tccagagaca cgccaagaa ctcactgtat    240 ctgcaaatga acagcctgag agtcgaggac acggctgtgt attactgtgt gaaagtcggg   300
ggtagcaaac accaatacta ctttgactac tggggccagg gatccctggt caccgtctcc   360
tca                                                                363
```

<210> SEQ ID NO 98
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 98

```
cagtctgtgc tgactcagcc accctcaacg tctgggatcc ccgggcagac ggtcaccatc    60
tcttgttctg gaagcaggtc caacatcgga agttatactg ttaactggta cgagcaactc   120
ccaggaacgg cccccaaact cgtcatcttt aataataatc agcgtccctc aggggtccct   180
gaccgattct ctggctccaa gtctggcacc tcagcctccc tggccatcag tgggctccag   240
tctgagggtg aagctgatta ttactgtgca gcatgggatg acagcctgaa tggtgtggtt   300
ttcggcggag ggaccaagct gaccgtccta                                    330
```

<210> SEQ ID NO 99
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 99

```
caggttcagt tggtgcagtc tggagctgag gtgaagaggc ctggggcctc agtgaaggtc    60
ttctgcaagg cttctggtta caccttacg aattatgaca tcatctgggt gcgacaggcc   120
cctggacaag ggcttgagtg ggtgggctgg atcagcactt acaatggtaa cacaaactat   180
gaacagaacc tccagggcag agtcaccatg accacagaca tccacgag cacagcctac   240 atggagctga ggagcctgag atctgacgac acggccgttt actattgtgc gagagagcgt   300
tgtagtacta gtacctgcta tagtcgttat gctgactact ggggccaggg aaccctggtc   360
accgtctcct ca                                                      372
```

<210> SEQ ID NO 100
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 100

```
gacatccaga tgacccagtc tccatcctcc ctgtctgcat ctgtgggaga cagagtcacc    60
atcacttgcc gggcaagtca gagcattaat atctatttga attggtatca gcaaaaaccg   120
gggaaagccc ctaaggtcct gatctatgct gcatccagtt tgcaaagtgg ggtcccatca   180
aggttccgtg gcagtgggtc tgggacagat ttcatcctca ccatcagcag tctgcaacct   240
```

```
gaagactttg caacctacta ctgtcaacag agttacaggt ccccteggac gttcggccaa    300 gggaccgagg tggaaatcaa a                                              321
```

<210> SEQ ID NO 101
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 101

```
gaggtgcagc tggtggagtc tgggggaggc ttggcacagc ctggagagtc catgagactc    60
tcctgtgtag cctctggatt caccttaagt cgttatgaag tgaactgggt ccgccaggct    120
ccagggaagg ggctagagtg gctttcatac attagcagtg gtggtccttc catatactac    180
gcagactctg tgaagggccg attcacgatc tccagaaaca cgccgagaa ctcactggaa     240 ctacaaatgt ccaccctgag gaccgaggac acggctgttt attattgtat gagagagggt    300
cttacttatt atgatagtac tatttggggc cagggaaccc tggtcgccgt ctcctca      357
```

<210> SEQ ID NO 102
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 102

```
cagaatgtgc tgactcaatc gccctctgcc tctgcctccc tgggagcctc ggtcaaactc    60
acctgcactc tgaacagtgg gcacagcaga tacgccatcg catggcatca acatcagcca    120
cagaggggcc ctcggttcct gatgaagatt aatagtgatg cagacacat caggggggac    180 ggcatctctg atcgcttctc aggctccgcc tctgggctg agcgtcatct caccatctcc    240
agcctccagc tgaggatga ggctgactat tattgtcaga cctggggcac tggctttcgg    300
gtgttcggcg gagggaccaa actgaccgtc cta                                 333
```

<210> SEQ ID NO 103
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 103

```
gaagtgcagc tggtggagtc tgggggaggc ttggtacagc ctggcaggtc cctgagactc    60
tcctgtgcag cctctggatt cacctttgat gaatatgcca tgcactgggt ccggcaagtt    120
ccagggaagg gcctggagtg ggtctcaggt attagttgga atggtggtag caaaggctat    180
gcggactctg tgaagggccg attcaccatc tccagagata cgccaggta ttccctgtct    240 ctgcaaatga acagtctgag aactgaggac acggccttat attactgcgc aaaagatgat    300 tacgagggg ctggttttga tatctggggc caagggacag tggtcaccgt ctcttca       357
```

<210> SEQ ID NO 104
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 104

```
gaaattgtgt tgacacagtc tccagccacc ctgtctttgt ctccagggga aagagccacc      60
ctctcctgca gggccagtca gagtgttagc agctacttag ctggtacca acagaaatct     120 ggccaggctc ccaggctcct catctatggt gcatccagca gggccactgg catcccagcc    180
aggttcagtg gcagtgggtc tgggacagac ttcactctca ccatcagcag cctagagcct    240
gaagattttg caatttatta ctgtcagcag cgtagcaact ggcctatcac cttcggccaa    300
gggacacgac tggagattaa a                                              321

<210> SEQ ID NO 105
<211> LENGTH: 378
<212> TYPE: DNA
<213> ORGANISM: Artificial sequence
<220> FEATURE:
<223> OTHER INFORMATION: Synthetic oligonucleotide

<400> SEQUENCE: 105
caggtgcagc tgcaggagtc gggcccagga ctggtgaagc cttcggagac cctgtccctc     60
acctgcactg tctctggcta tttaattagc aatggttact actggggctg gatccggcag    120
tcccccggga aggggctgga gtggattggg agtatctatt atactaggga cacctactac    180
aactggtccc tcaagagtcg aatcaccata tcagtggaca cgtccaagaa acagttctcc    240
ctgaagttgt attctgtgac cgccgcagac acggccgtct attactgtgt gagacatgag    300
ggttcttgca atgatggaag ctgttacggc tcgttcgttg acaactgggg ccagggaacc    360
ctggtcaccg tctcctca                                                  378

<210> SEQ ID NO 106
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 106
gacatccaga tgacccagtc tccatcttcc gtgtctgcat ctgtaggaga cagagtgacc     60
ctcacttgtc gggcgagtca ggatattagc agctggttag cctggtatca gcagaaacca    120
gggaaagccc ctaagctcct gatctatgct gcatccagtt tgcaaagtgg ggtcccatca    180
aggttcagcg gcagtggatc tgggacacat ttcactctca ccatcagcag cctgcagcct    240
gaagatttcg caacttactt ttgtcaacag gctgacagtt tcatcacttt cggcggaggg    300
accaaggtgg agatcaaa                                                  318

<210> SEQ ID NO 107
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 107
gaggtgcaac tgttggagtc tgggggaggc ttggtacagc cggggggtc cctgagactc       60 tcctgtgcag cctctgattt caccttcagc agctacacca tggcctgggt ccgccaggct    120
ccagggaagg ggcttgaatg ggtctcatct attagtggtg atggtgttag cacaaaaaac    180
gcagactccg tgaagggccg attctccgtc tccagagaca attccaagaa cacactttt    240 ctgcaactga acagtctgag agccgaggac acggcctttt attactgtgc gagggggggg    300
```
accttccata actggtactt cgatctctgg ggccgtggcg tcttggtcac tgtctcctca    360

<210> SEQ ID NO 108
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 108
gaaatagtga tgacgcagtc tccagccacc ctgtctgtgt ctccagggga aacagccacc     60
ctctcctgca gggccagtca gagtattggc acaacttag cctggtatca gcagaaacct    120
ggccaggctc ccaggctcct catctctggt gcatccacaa gggccactga tttcccagcc    180
aggttccgtg gcagtgggtc tgggacagag ttcactctca ccatcagcag cctgcagtct    240
gaagactttg cagtttatta ctgtcagcag tataaaaact ggcctcggac gttcggccga    300
gggaccaagg tggaagtcag a                                              321

<210> SEQ ID NO 109
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 109
gaggtgcagc tgttggagtc tgggggaggc ttggtacagc cggggggtc cctgagactc      60 tcctgtgcag cctctggatt caccttagc acctatgcca tgagctgggt ccgccaggct    120
ccagggaagg ggccggagtg ggtctcaggt attagtggta gtggtggtag cacaaactac    180
gcagactctg cgaagggccg gttcaccatc tccagagaca attccaagaa cacgctgtat    240
ctgcaaatga acagcctgag agccgaggac acggccgtat attattgtgc gaaagggacc    300
attacttact cctactacta catggccgtc tggggcaaag gaccacggt caccgtctcc    360 tca                                                                  363

<210> SEQ ID NO 110
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 110
gaaattgtgt tgacgcagtc tccaggcacc ctgtctttgt ctccagggga agaggcacc      60 ctctcctgca gggccagtca gagtgttagg agcagctact agcctggta ccagcagaga    120 cctggccagg ctcccaggct cctcatctat ggtgcatcca gcagggccac tggcatccca    180
gacaggttca gtggcagtgg gtctgggaca gacttcacgc tcaccatcgg cagactggag    240
cctgaagatt ttgcagtgta ttactgtcag cagtatggta cctcaataac tttcggcgga    300
gggaccaagg tggagatcaa a                                              321

<210> SEQ ID NO 111
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 111

```
caggtccagg tggtacaatc tggggctgag atgaggaagc ctgggcctc  agtgagggtc    60 tcctgcaagg tttccggata caggctcact gatttaccct tgcactgggt gcgacaggct   120
cctggaaaag ggcttgaatg gattggattt gttgatcttg aaaagcgcga aatcatctac   180
gcacagaaat ttcagggcaa agtcaccata accgaggaca catctgcaga caccgcctac   240
atggaactga acagcctgcg atctgaagac acggccgtct actactgtgc aacttgggga   300
attgaggtgg tgaatgggag ggacgaattc tttgactcct ggggccaggg aaccctggtc   360
tccgtctcct ca                                                       372

<210> SEQ ID NO 112
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 112
tcctatgagc tgacacagcc accctcggtg tcagtgtccc caggacagac ggccaggatc    60
acatgctatg cagatgtgtt gtcaaagcaa tatacttact ggtatcagca gaagccaggc   120
caggcccctg tgttggtgat atataaagac actgagaggc cctcagggat ccctgagcga   180
tttgctggct ccagctcagg gacaacagtc accttgatca tcaatggagt ccggacagag   240
gacgaggcgt actattactg tcaatcagcc gacaccagaa ttacggtttt cggcggaggg   300
accaagctgt ccgtccta                                                 318

<210> SEQ ID NO 113
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 113
caggtccagg tggtccagtc tggggctgag atgaagaagc ctggggcctc agtgaaggtc    60
tcctgcaagg tttccggata tagtctcagt gatttaccct tgcactgggt gcgacaggct   120
cctggaaaag ggcttgagtg gatgggactt tttgatccta taaacggtga aatcatctac   180
gcacagacat tccagggcaa agtcaccata agcgaggaca catcgataga cacagcctac   240
atggaactca acagcctgcg atctgaagac acggccgtgt actattgtgc aacttgggga   300
gttgcggtgg tgagtgggag aagggactac tttgactcct ggggccaggg aaccctggtc   360
accgtctcct ca                                                       372

<210> SEQ ID NO 114
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 114
tcctatgagc tgacacagcc accctcggtg tcagtgtccc caggacagac ggccaggatc    60
acatgctatg cagctgtatt gtcaaaccaa tatacttact ggtatcaaca gaagccaggc   120
caggcccctg ttttggtgat atataaagac actgagaggc cctcagggat ccctgagcga   180
tttgctggct ccagctcagg gacaacagtc accttgatca tcaatggagt ccggacagag   240
```

```
gacgaggctt actattactg tcaaacagcc gacaccaaat atacggtttt cggcggaggg    300
accaagctgt ccgtccta                                                  318
```

<210> SEQ ID NO 115
<211> LENGTH: 378
<212> TYPE: DNA
<213> ORGANISM: Artificial sequence
<220> FEATURE:
<223> OTHER INFORMATION: Synthetic oligonucleotide

<400> SEQUENCE: 115

```
caggtgcagc tgcaggagtc gggcccagga ctggtgaagc cttcacagac cctgtccctc    60
acctgcactg tctctggtgg ctccatcacc agtggtgatt actactggaa ttggatccgc   120
cagcccccag ggaagggcct ggagtggatt gggtacatct atcacagtgg gaccacctac   180
tacaacccgt ccctcaagag tcgagttacc atatcagtag acacgtccaa gaacaggttc   240
tccctgaagt tgtcctctgt gactgccgca gacacggccg tgtattttg tgccagagcc    300 tacgcttatg aattttggag cggttaccct aactggttcg accctgggg cctgggaacc    360 ctggtcaccg tctcatca                                                 378
```

<210> SEQ ID NO 116
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 116

```
gacatccaga tgacccagtc tccatcctcc ctgtctgcat ctgttggaga cagagtcacc    60
atcacttgcc gggcaagtca gcgcattagt acctatgtaa attggtatca ggtgaaagca   120
gggacagccc ctaaggtcct gatctatgct gcgtccagtt tgcaaactgg ggtcccatca   180
aggttcagtg gcagtggatc tgggacagat ttcactctca ccattgtcag tctacaacct   240 gaagattta caacctactt ctgtcaacag agttacagtc ccccgtggac gttcggccaa    300
gggaccaagg tggaaatcaa a                                             321
```

<210> SEQ ID NO 117
<211> LENGTH: 378
<212> TYPE: DNA
<213> ORGANISM: Artificial sequence
<220> FEATURE:
<223> OTHER INFORMATION: Synthetic oligonucleotide

<400> SEQUENCE: 117

```
caggtgcagt tggtggagtc tgggggaggc ttggtccagc ctggtaggtc cctgagactc    60
tcctgtgcag cctctgggtt catcttcaat agatatgcca tgcactgggt ccgccaggct   120
ccaggcaagg ggctcgagtg gtggctctt atatcatatg atggaattaa taaatattac    180
gcagactccg tgaagggccg attctccatc tccagagaca attccaagag tacgctgtat   240
ctgcaaatga acagcctcag agctgaggac acggctatct tttactgtgc gagaggacta   300
ggatattgta gtggtaccgg tggtagctgt acacccttg aatattgggg ccagggaatc    360
ctggtcaccg tctcctca                                                 378
```

<210> SEQ ID NO 118
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 118

```
gacatccaga tgacccagtc tccaccctcc ctgtctgcat ctgttggaga cagagtcacc    60
atcacttgcc gggcaagtca gagcattaag aaatatttaa attggtatca gcagaaacca   120
gggaatgccc ctaagctcct catctatggc gcatccaatt tgcaaactgg ggtcccatca   180
aggttcagtg gcagtggatc tgggacagat ttcgctctct ccatcagcag tctgaaaact   240
gaagattttg caacttacta ctgtcaacag agtgacagtg cccctcccac tttcggcgga   300
gggaccaagg tggagttcaa a                                             321
```

<210> SEQ ID NO 119
<211> LENGTH: 405
<212> TYPE: DNA
<213> ORGANISM: Artificial sequence
<220> FEATURE:
<223> OTHER INFORMATION: Synthetic oligonucleotide

<400> SEQUENCE: 119

```
caggtgcagc tgcaacagcg gggcgcaggg ctgttgaagc cctcggagac cctgtccctt    60
acctgcgaaa tctatggtgc atccctcaat gattacgact ggacctggat ccgccagccc   120
ccagggaaga ggctggagtg gattggggtc atcaatcgtc gtgacactgt tgactacaac   180
ccgtccctca agagtcgggt caccctctca cttgacacgt ccaagaacca actttccctg   240
agtctgagtt ctgtgaccgc cgcggacacg gctgtttatt actgtgtgag agtcccacgt   300
cggggctttg aagggtcttt cggattttgt gatgatactg cctgccgcta cgggcatacc   360
tggttcgacc cctggggcca gggaaccctg gtcaccgtct cctca                   405
```

<210> SEQ ID NO 120
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 120

```
gacattcaga tgacccagtc tccttcctcc ctgtctgcat ctgttggcga cagagtcacc    60
atcacttgcc gggcaagtca gagtattaga gattatttaa attggtatca acaaagacca   120
gggaaagccc ctaaagtcct gatctttgct ggttcccgtt tggaaagtgg ggtcccatcg   180
aggtttagag gccgtggatc tgggacagaa ttcactctca ccatcagcga tctgcaacct   240
gaggattttg caacttacta ctgtcaacag agttacctta cacctccgac attcggccaa   300
gggaccaccg tcgatatcaa a                                             321
```

<210> SEQ ID NO 121
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 121

```
caggtcacct tgaaggagtc tggtcctgtg ctggtgaaac ccacagagac cctcacgctg    60
acctgcaccg tctctggatt ctcactccgc aatggtagaa tgggtgtgag ctggatccgt   120
cagccccag ggaaggccct ggagtggctt gcacacattt ttgcgagtga cgaaaaatct   180
```

```
tacagtacat ctcagaggac caggctctcc atctccaggg acacctccaa aagccaagtg      240
gtccttagca tgaccgacat ggaccctgtg gacacagcca catattactg tgcgcggatt      300
ttgaagtttg ggacaatgag ggccgcatac tactttgact actggggcca gggagccctg      360
gtccccgtct cctca                                                      375

<210> SEQ ID NO 122
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 122
tcctatgtgc tgactcagcc accctcagtg tcagtggccc caggaaagac ggccaggatt       60
acctgtgggg gaatcaacat tggaattaga actgtacact ggtaccagca gaagccaggc      120
caggccccta tgttggtcat ctattatgat agcgaccggc ccttagggat ccctgagcga      180
ttctctggct ccaagtctgg gaacacggcc accctgacca tcagcagggt cgaagccggg      240
gatgaggccg actattactg tcaggtgtgg gatagtagta gtgatcatgt tgtattcggc      300
ggagggacca agctgaccgc ccta                                             324

<210> SEQ ID NO 123
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 123
caggtgcact tggtggagtc tgggggaggc ttggtcaagc ctggagggtc cctgagactc       60
tcctgtgcag tttctggatt caccttcagt gactactaca tgagctggat ccgccaggct      120
ccggggaagg gactggagtg gctttcatac attagtagta gtggtagtac catatactac      180
gcagactcta tgaagggccg attcaccatc tccagggaca acgccaggaa ctcactctat      240
ctgcaaatga acagcctgag agtcgaggac acggccttt attactgtgc ggggtcaaag      300
gttggctata ctactggtcg aaggaactgg tacttcgatc tctggggccg tggcaccctg      360
gtcactgtct cctca                                                      375

<210> SEQ ID NO 124
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 124
cagtctgccc tgactcagcc tccctccgcg tccgggtctc ctggacagtc agtcaccatc       60
tcctgcactg gaaccagcag tgacgttggt gcttataact atgtctcctg gtaccaacag      120
cacccaggca aagcccccaa actcatgatt tatgaggtca ctaagcggcc ctcaggggtc      180
cctgatcgct tctctggctc caagtctggc aacacggcct ctctgaccgt ctctgggctc      240
caggctgagg atgaggctga ttattactgc agctcatatg caggcaacaa caatttagtc      300
ttcggcggag ggaccaagct gaccgtccta                                       330

<210> SEQ ID NO 125
<211> LENGTH: 378
```

```
<212> TYPE: DNA
<213> ORGANISM: Artificial sequence
<220> FEATURE:
<223> OTHER INFORMATION: Synthetic oligonucleotide

<400> SEQUENCE: 125
caggtgcagt tgctgcagtc tgggtctgag gtgaggaaac ctggggcctc agtgaacatt      60
cactgtaagg catctggatt cactttcacc gacttctatt tacactgggt gcgacaggcc    120
cctggacaag ggcttgagtg gatggggata atcaaccctg aaaccggtga dacaacctac    180
tcacagaagt ttcagggcag agtcaccatg accagggaca cgtccacgag tgtagtgaat    240
ctggaagtga ggagcctgag atctgaggac acggccatat attactgtgc gagagatctc    300
gttgtcgtag tccccgttga aatgtctcgg cgtgcctttg acatttgggg ccaagggatt    360
atggtcacag tctcctca                                                  378

<210> SEQ ID NO 126
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 126
tcctatgtgc tgactcagcc accctcggtg tcagtggccc caggacagac ggccaggatt      60
ccctgtgggg gcaacaacat tgaacgtaaa agtgtccact ggtaccagca gaggccaggc    120
caggcccctg tgttggtcgt ctatgatgat actgtccggc cctcaggtat ccctgagcga    180
ttctctggct ccaactccgg gagcacggcc accctgacca tcagcagggt cggagccggg    240
gatgagggcg actattattg tcaggtgtgg gacagcacca ctgaccatgg ggtcttcggc    300
ggagggacca agctgaccgt ccta                                           324

<210> SEQ ID NO 127
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 127
cgggtgcagc tggtgcagtc tggggctgag gtgaagaagc ctggggcctc agtgaaggtc      60
tcctgtcaga cttctggata cattttcagc gcctactaca tctattgggt gcgacaggcc    120
cctggacaag gacttgagtg gatgggacgg atgaacgcta agagtggagg cgcaaacact    180
gcacagcagt ttcagggcag actcaccatg accagggaca tgtccgtcag cacagcctac    240
atggaactga gcaggctgcg atcggacgac acggccgtct attattgtgc gagagactat    300
agggatgact acatgtgggg gagttatcgg cctttagact actggggcca gggaaccctg    360
gtcaccgtct cctca                                                     375

<210> SEQ ID NO 128
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 128
gaagttgtgt tgacacagtc tccagccacc ctgtctttgt ctccagggga aagagcctcc      60
```

```
ctctcctgca gggccagtca gagtgttagc ggctacttag cctggtacca acacaaacct    120
ggccaggctc ccaggctcct catctatgat gcatccaaca gggccgctgg catcccagcc    180
aggttccgtg gcagtgggtc tgggacagac ttcactctca ccatcagcag cctggagcct    240
gaagattttg cagtttattt ctgtcagcag cgtagcaacg ggctcacttt cggcggaggg    300
accaaggtcg agatcaaa                                                  318
```

<210> SEQ ID NO 129
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 129

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Arg Tyr
            20                  25                  30

Ala Leu His Trp Val Arg Gln Ala Pro Gly Lys Gly Leu Asp Trp Val
        35                  40                  45

Ala Val Ile Ser Tyr Asp Ala Arg Asn Ser Tyr Tyr Thr Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Asp Asp Thr Ala Val Tyr Tyr Cys
                85                  90                  95

Ala Arg Pro Thr Leu Pro Tyr Ser Asn Asn Trp Tyr Ala Pro Glu Tyr
            100                 105                 110

Trp Gly Gln Gly Thr Leu Val Thr Val Ser Ser
        115                 120

<210> SEQ ID NO 130
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 130

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Ser Trp Tyr Gln Gln Lys Ser Gly Gln Ala Pro Val Leu Val Ile Tyr
            35                  40                  45

Glu Asp Thr Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ser Asp Tyr Tyr Cys Ser Ser Thr Asp Ser Ser Gly Asn Pro
                85                  90                  95

Val Leu Phe Gly Gly Gly Thr Lys Leu Thr Val Leu
            100                 105

<210> SEQ ID NO 131
<211> LENGTH: 122
<212> TYPE: PRT

<213> ORGANISM: Artificial sequence
<220> FEATURE:
<223> OTHER INFORMATION: Synthetic polypeptide

<400> SEQUENCE: 131

```
Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Met Ala Trp Val Arg Gln Ala Pro Gly Lys Gly Leu Gln Trp Val
        35                  40                  45

Ser Ser Ile Ser Gly Asn Gly Asn Gly Arg Ser Tyr Ala Asp Ser Leu
    50                  55                  60

Lys Gly Arg Phe Thr Thr Ser Lys Asp Leu Ser Lys Tyr Thr Leu Tyr
65                  70                  75                  80

Leu Gln Met Asn Asn Leu Arg Pro Glu Asp Thr Ala Ile Tyr Tyr Cys
                85                  90                  95

Ala Lys Val Val Arg Ile Ala Ala Val Leu Tyr Tyr Phe Asp Tyr Trp
            100                 105                 110

Gly Pro Gly Thr Gln Val Thr Val Ser Ser
        115                 120
```

<210> SEQ ID NO 132
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 132

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Thr Tyr
            20                  25                  30

Leu Ala Trp Tyr Gln Gln Lys Pro Gly Gln Ala Pro Arg Leu Leu Ile
        35                  40                  45

Tyr Glu Ala Ser Thr Arg Ala Thr Gly Ile Pro Ala Arg Phe Ser Gly
    50                  55                  60

Ser Gly Ser Gly Thr Asp Phe Thr Leu Ile Ile Ser Ser Leu Glu Pro
65                  70                  75                  80

Glu Asp Phe Ala Val Tyr His Cys Gln Gln Arg Ser Ser Trp Pro Ile
                85                  90                  95

Thr Phe Gly Gln Gly Thr Arg Leu Glu Ile Glu
            100                 105
```

<210> SEQ ID NO 133
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 133

```
Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Thr Trp Val Arg Gln Ala Leu Gly Lys Gly Leu Glu Trp Val
        35                  40                  45
```

```
Ser Ser Ile Ser Gly Ser Gly Gly Leu Thr Tyr Phe Ala His Ser Val
    50                  55                  60

Lys Gly Arg Leu Thr Ile Ser Arg Asp Asn Ser Lys Asn Thr Leu Tyr
 65                  70                  75                  80

Leu Gln Met Ser Ser Leu Arg Ala Glu Asp Thr Ala Val Tyr Tyr Cys
                 85                  90                  95

Ala Arg Val Lys Ser Thr Thr Gly Thr Thr Ala Leu Val Phe Asp Ile
            100                 105                 110

Trp Gly Gln Gly Thr Met Val Thr Val Ser Ser
            115                 120

<210> SEQ ID NO 134
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 134

Gln Thr Val Val Thr Gln Glu Pro Ser Phe Ser Val Ser Pro Gly Gly
 1               5                  10                  15

Thr Val Thr Leu Thr Cys Gly Leu Ser Ser Gly Ser Val Ser Ser Ser
            20                  25                  30

Tyr Tyr Pro Ser Trp Tyr Gln Gln Thr Pro Gly Gln Ala Pro Arg Thr
        35                  40                  45

Leu Ile Tyr Ser Ile Asn Arg Arg Ser Ser Gly Val Pro Asp Arg Phe
    50                  55                  60

Ser Gly Phe Ile Leu Gly Asn Lys Ala Ala Leu Thr Ile Arg Gly Ala
 65                  70                  75                  80

Gln Ala Asp Asp Glu Ser Asp Tyr Tyr Cys Gly Leu Tyr Met Gly Ser
                 85                  90                  95

Gly Ile Trp Ile Phe Gly Gly Gly Thr Lys Leu Thr Val Leu
            100                 105                 110

<210> SEQ ID NO 135
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 135

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ile Asn Tyr
            20                  25                  30

Gly Met His Trp Val Arg Gln Ala Pro Gly Lys Gly Leu Glu Trp Val
        35                  40                  45

Ala Val Ile Ser Asn Asp Gly Ser Tyr Asn Tyr Asp Ala Asp Ser Val
    50                  55                  60

Lys Gly Arg Phe Thr Ile Ser Arg Asp Asn Ser Lys Asn Lys Val Tyr
 65                  70                  75                  80

Leu Gln Met Asn Ser Leu Arg Pro Glu Asp Thr Ala Val Tyr Phe Cys
                 85                  90                  95

Ala Lys Asp Lys His Gly Asp Phe Asp Tyr Tyr Gly Val Asp Val Trp
            100                 105                 110

Gly Gln Gly Thr Thr Val Thr Val Ser Pro
```

<210> SEQ ID NO 136
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 136

Asp Val Gln Met Thr Gln Ser Pro Ser Ser Val Ser Ala Ser Ile Gly
1               5                   10                  15

Asp Arg Val Thr Ile Thr Cys Arg Ala Gly Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Gly Thr Tyr Tyr Cys Gln Gln Ala Asp Ser Phe Pro Arg
                85                  90                  95

Thr Phe Gly Gln Gly Thr Lys Val Glu Ile Lys
            100                 105

<210> SEQ ID NO 137
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 137

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Ile His Trp Val Arg Gln Ala Pro Gly Lys Gly Leu Glu Trp Val
        35                  40                  45

Ala Val Ile Ser Tyr Asp Gly Ser Asp Asn Thr Tyr Ala Pro Phe Val
    50                  55                  60

Asn Gly Arg Phe Thr Ile Ser Arg Asp Asn Ser Lys Asn Thr Leu Tyr
65                  70                  75                  80

Leu Gln Met Asn Ser Leu Arg Ala Asp Thr Ala Val Tyr Tyr Cys
                85                  90                  95

Ala Arg Arg Arg Pro Gly Ser Phe Pro Gly Leu Cys Asp Tyr Trp Gly
            100                 105                 110

Gln Gly Ala Leu Val Thr Val Ser Ser
        115                 120

<210> SEQ ID NO 138
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 138

Asp Ile Gln Met Thr Gln Ser Pro Ser Thr Met Ser Ala Ser Val Gly
1               5                   10                  15

```
Asp Arg Val Thr Ile Thr Cys Arg Ala Ser Gln Ser Ile Ser Lys Trp
                20                  25                  30

Leu Ala Trp Tyr Gln Gln Lys Pro Gly Lys Ala Pro Lys Leu Leu Ile
        35                  40                  45

Tyr Lys Ala Ser Thr Leu Gln Thr Gly Val Pro Ser Arg Phe Ser Gly
 50                  55                  60

Ser Gly Ser Gly Thr Glu Phe Thr Leu Thr Ile Asn Ser Leu Gln Pro
 65                  70                  75                  80

Asp Asp Phe Ala Thr Tyr Tyr Cys Gln Gln His Asn Ser Tyr Ser Tyr
                85                  90                  95

Thr Phe Gly Gln Gly Thr Lys Val Glu Ile Lys
                100                 105

<210> SEQ ID NO 139
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 139

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Ser Phe Ser Arg Leu
                20                  25                  30

Thr Ile Ile Trp Val Arg Gln Ala Pro Gly Gln Gly Leu Glu Trp Met
        35                  40                  45

Gly Gly His Ile Pro Ile Phe Gly Thr Thr Asn Tyr Ala Leu Lys Phe
 50                  55                  60

Gln Gly Arg Val Thr Ile Thr Ala Asp Lys Thr Thr Ser Thr Ala Tyr
 65                  70                  75                  80

Met Glu Leu Ser Ser Leu Arg Ser Glu Asp Thr Ala Ile Tyr Tyr Cys
                85                  90                  95

Ala Arg Met Tyr Ser Gly His Asp Gly Val Asp Val Trp Gly Gln Gly
                100                 105                 110

Thr Leu Val Thr Val Ser Ser
        115

<210> SEQ ID NO 140
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 140

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Arg Ser Tyr
                20                  25                  30

Leu Ala Trp Tyr Gln His Lys Pro Gly Gln Ala Pro Arg Leu Leu Ile
        35                  40                  45

Tyr Asp Ala Ser Asn Arg Ala Lys Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Thr Trp Pro Pro
```

```
                    85                  90                  95

Gly Met Phe Gly Gln Gly Thr Arg Val Glu Ile Lys
            100                 105

<210> SEQ ID NO 141
<211> LENGTH: 127
<212> TYPE: PRT
<213> ORGANISM: Artificial sequence
<220> FEATURE:
<223> OTHER INFORMATION: Synthetic polypeptide

<400> SEQUENCE: 141

Gln Leu Gln Leu Gln Glu Ser Gly Pro Gly Leu Val Lys His Ser Glu
1               5                   10                  15

Thr Leu Ser Leu Thr Cys Thr Val Ser Gly Gly Ser Ile Ser Ser Gly
            20                  25                  30

Phe Tyr Tyr Trp Gly Trp Ile Arg Gln Pro Pro Gly Lys Gly Leu Glu
        35                  40                  45

Trp Ile Gly Thr Ile Tyr Asp Ser Gly Arg Thr Tyr Asp Asn Pro Ser
    50                  55                  60

Leu Lys Ser Arg Val Thr Ile Ser Ala Asp Thr Ser Lys Lys Gln Phe
65                  70                  75                  80

Ser Leu Thr Leu Arg Ser Ala Thr Ala Ala Asp Thr Ala Val Tyr Phe
                85                  90                  95

Cys Ala Arg His Leu Thr His Leu Tyr Gly Asp Tyr Val Thr Pro Asp
            100                 105                 110

Ala Leu Asp Ile Trp Gly Gln Gly Thr Met Val Thr Val Ser Ser
        115                 120                 125

<210> SEQ ID NO 142
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 142

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Arg
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Asn Ser Arg
                85                  90                  95

Leu Thr Phe Gly Gln Gly Thr Lys Val Glu Ile Lys
            100                 105

<210> SEQ ID NO 143
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 143
```

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Thr Thr Tyr
            20                  25                  30

Ser Met Asn Trp Val Arg Gln Ala Pro Gly Lys Gly Leu Glu Trp Ile
            35                  40                  45

Ser Tyr Ile Ser Ser Gly Ser Ser Asn Ile Tyr Tyr Ala Asp Ser Val
        50                  55                  60

Lys Gly Arg Phe Thr Ile Ser Arg Asp Asn Ala Lys Asn Ser Leu Asn
65                  70                  75                  80

Leu Gln Met Ser Ser Leu Arg Asp Glu Asp Thr Ala Val Tyr Tyr Cys
                85                  90                  95

Ala Arg Ala His Gly Arg Ile Val Asn Ser Gly Val Val Ile Ser Arg
            100                 105                 110

Phe Asp Pro Trp Gly Gln Gly Ile Leu Val Thr Val Ser Ser
        115                 120                 125

<210> SEQ ID NO 144
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 144

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Leu His Pro Gly Lys Ala Pro Lys Leu
            35                  40                  45

Met Ile Phe Glu Val Thr Tyr Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ser Ser Tyr Thr Thr Ser
                85                  90                  95

Asn Thr Leu Val Val Phe Gly Gly Gly Thr Lys Leu Thr Val Leu
            100                 105                 110

<210> SEQ ID NO 145
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 145

Gln Val Gln Leu Val Gln Ser Gly Ala Glu Val Lys Lys Pro Gly Ala
1               5                   10                  15

Ser Val Lys Val Ser Cys Arg Thr Ser Gly Tyr Thr Phe Thr Ala Tyr
            20                  25                  30

Tyr Met His Trp Val Arg Gln Ala Pro Gly Gln Gly Pro Glu Trp Met
            35                  40                  45

Gly Arg Ile Asn Pro Ser Ser Gly Gly Ala Gln Tyr Ala Gln Lys Phe
        50                  55                  60

Gln Gly Arg Val Thr Met Thr Arg Asp Thr Ser Ile Ser Thr Thr Tyr

```
                65                  70                  75                  80
Met Thr Leu Ser Gly Leu Thr Ser Asp Asp Thr Ala Val Phe Tyr Cys
                    85                  90                  95

Ala Arg Met Gly Cys Arg Ser Asp Arg Cys Tyr Ser Thr Asn Tyr Asn
            100                 105                 110

Phe Asp Gln Trp Gly Gln Gly Thr Leu Val Thr Val Ser Ser
        115                 120                 125

<210> SEQ ID NO 146
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 146

Ser Tyr Val Leu Thr Gln Pro Pro Ser Val Ser Val Ala Pro Gly Gln
1               5                   10                  15

Thr Ala Arg Ile Pro Cys Gly Gly Asn Asn Ile Gly Thr Lys Ser Val
            20                  25                  30

His Trp Tyr Gln Gln Lys Pro Gly Gln Ala Pro Val Leu Val Val Ser
        35                  40                  45

Asn Asp Ser Asp Arg Pro Ser Gly Ile Pro Glu Arg Phe Ser Gly Ser
    50                  55                  60

Lys Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Gly Ile Asp Val
                85                  90                  95

Val Phe Gly Gly Gly Thr Lys Leu Thr Val Leu
            100                 105

<210> SEQ ID NO 147
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 147

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Ile Ser Pro Tyr
            20                  25                  30

Gly Met Asn Trp Val Arg Gln Ala Pro Gly Lys Gly Leu Glu Trp Val
        35                  40                  45

Ser Phe Ile Ser Ser Ser Arg Tyr Thr Tyr Tyr Ala Asp Ser Val
    50                  55                  60

Lys Gly Arg Phe Thr Ile Ser Arg Asp Asn Ala Lys Asn Ser Leu Ser
65                  70                  75                  80

Leu Gln Met Asn Ser Leu Arg Ala Glu Asp Thr Ala Val Tyr Tyr Cys
                85                  90                  95

Ala Arg Glu Arg Gly His Ser Thr Ser Ser Tyr Phe Asp Ser Trp
            100                 105                 110

Gly Gln Gly Thr Leu Val Thr Val Ser Ser
        115                 120

<210> SEQ ID NO 148
<211> LENGTH: 108
```

<212> TYPE: PRT
<213> ORGANISM: Artificial sequence
<220> FEATURE:
<223> OTHER INFORMATION: Synthetic polypeptide

<400> SEQUENCE: 148

Ser Tyr Val Leu Thr Gln Pro Pro Ser Val Ser Leu Ala Pro Gly Lys
1               5                   10                  15

Thr Ala Arg Ile Thr Cys Gly Gly Asn Asn Ile Gly Thr Lys Thr Val
            20                  25                  30

Ser Trp Tyr Gln Gln Lys Pro Gly Gln Ala Pro Val Leu Val Met Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Asn Arg Val Glu Ala Gly
65                  70                  75                  80

Asp Glu Ala Asp Tyr Tyr Cys Arg Val Trp Asp Ser Asp Thr Asp His
                85                  90                  95

Arg Val Phe Gly Gly Gly Thr Lys Leu Thr Val Leu
            100                 105

<210> SEQ ID NO 149
<211> LENGTH: 127
<212> TYPE: PRT
<213> ORGANISM: Artificial sequence
<220> FEATURE:
<223> OTHER INFORMATION: Synthetic polypeptide

<400> SEQUENCE: 149

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Ile Ser Trp Val Arg Gln Ala Pro Gly Lys Gly Leu Glu Trp Val
        35                  40                  45

Gly Arg Ile Gln Thr Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Leu Tyr
                85                  90                  95

Tyr Cys Ser Thr Gly Pro Tyr Tyr Asp Thr Ser Gly Tyr Pro Gln
            100                 105                 110

Pro Phe Asp Tyr Trp Gly Gln Gly Thr Leu Val Thr Val Ser Ser
        115                 120                 125

<210> SEQ ID NO 150
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 150

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr

```
                 35                  40                  45

Gln Asp Thr Lys Arg Pro Ser Gly Ile Pro Glu Arg Phe Ser Gly Ser
         50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Thr Val Val
                 85                  90                  95

Phe Gly Gly Gly Thr Lys Leu Thr Val Leu
            100                 105

<210> SEQ ID NO 151
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 151

Glu Val Gln Met Val Glu Ser Gly Gly Gly Leu Val Lys Pro Gly Gly
 1               5                  10                  15

Ser Leu Arg Leu Ser Cys Ser Val Ser Gly Phe Asp Phe Ser Arg Tyr
             20                  25                  30

Thr Met Asn Trp Phe Arg Gln Ala Pro Gly Glu Gly Leu Lys Trp Val
         35                  40                  45

Ser Ser Ile Ser Ser Thr Ser Leu Tyr Thr Phe Tyr Ala Asp Ser Val
 50                  55                  60

Lys Gly Arg Phe Ser Ile Ser Arg Asp Asn Ala Gln Gly Ser Leu Ser
 65                  70                  75                  80

Leu Gln Met Ser Ser Leu Arg Pro Glu Asp Thr Ala Val Tyr Tyr Cys
             85                  90                  95

Ala Arg Val Val Gly Pro Ala Glu Leu Asp Tyr Trp Gly Gln Gly Val
            100                 105                 110

Leu Val Thr Val Ser Ser
        115

<210> SEQ ID NO 152
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 152

Val Thr Gln Leu Thr Gln Ser Pro Ser Ser Leu Ser Ala Ser Val Gly
 1               5                  10                  15

Asp Arg Val Thr Ile Thr Cys Arg Ala Ser Gln Asp Ile Gly Val Asp
             20                  25                  30

Leu Gly Trp Phe Gln Gln Arg Pro Gly Lys Ala Pro Lys Leu Leu Ile
         35                  40                  45

Tyr Gly Ala Ser Arg Leu Gln Ser Gly Val Pro Ser Arg Phe Ser Gly
         50                  55                  60

Arg Gly Ser Gly Thr Phe Phe Thr Leu Thr Ile Ser Ser Leu Gln Pro
 65                  70                  75                  80

Glu Asp Phe Thr Thr Tyr Phe Cys Leu Gln Asp Tyr Asn Tyr Pro Trp
             85                  90                  95

Thr Leu Gly Gln Gly Thr Thr Val Gly Val Lys
            100                 105
```

-continued

<210> SEQ ID NO 153
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 153

```
Gln Val His Leu Val Gln Ser Gly Ser Ala Val Arg Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile Asn Pro Lys Thr Gly Gly Ser Asn Tyr Thr Gln Arg Phe
    50                  55                  60

Gln Ala Arg Val Thr Met Thr Trp Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ala Gly Arg Asn Gly Tyr Asp Tyr Trp Gly Gln Gly Thr Leu
            100                 105                 110

Val Thr Val Ser Ser
        115
```

<210> SEQ ID NO 154
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 154

```
Ser Tyr Glu Leu Thr Gln Pro Pro Ser Val Ser Val Ser Pro Gly Gln
1               5                   10                  15

Thr Ala Arg Ile Thr Cys Ser Ala Asp Ala Leu Pro Lys Gln Tyr Ala
            20                  25                  30

Tyr Trp Tyr Gln Gln Lys Pro Gly Gln Ala Pro Val Leu Met Ile Tyr
        35                  40                  45

Gln Asp Thr Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Gly Asp Ser Ser Gly Thr Tyr
                85                  90                  95

Leu Val Phe Gly Gly Gly Thr Lys Leu Thr Val Leu
            100                 105
```

<210> SEQ ID NO 155
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 155

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Lys Phe Arg Asn Tyr
```

```
            20                  25                  30
Ala Met Thr Trp Val Arg Gln Ala Pro Gly Lys Gly Leu Glu Trp Val
            35                  40                  45

Ser Thr Ile Thr Ser Gly Gly Ser Thr Glu Tyr Ala Asp Ala Val Lys
            50                  55                  60

Gly Arg Phe Ile Ile Ser Arg Asp Asn Ser Lys Asn Thr Leu Tyr Leu
65                      70                  75                  80

Gln Met Asn Ser Leu Arg Ala Asp Asp Thr Ala Val Tyr Tyr Cys Thr
                85                  90                  95

Val Pro Trp Gly Asn Tyr Asn Asp Tyr Val Ser Asp Tyr Trp Gly Gln
                100                 105                 110

Gly Thr Leu Val Pro Val Ser Ser
            115                 120

<210> SEQ ID NO 156
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 156

Glu Val Val Leu Thr Gln Ser Pro Ala Thr Leu Ser Leu Ser Pro Gly
1               5                   10                  15

Gln Arg Ala Thr Leu Ser Cys Arg Ala Ser Gln Arg Val Gly Asn Ser
            20                  25                  30

Leu Ala Trp Tyr Gln Gln Lys Pro Gly Gln Ala Pro Ser Leu Leu Ile
            35                  40                  45

Tyr Asp Ala Ser Lys Arg Ala Thr Gly Ile Pro Ala Arg Phe Ser Gly
            50                  55                  60

Ser Gly Ser Gly Thr Asp Phe Thr Leu Thr Ile Ile Ser Leu Glu Ser
65                  70                  75                  80

Glu Asp Phe Ala Val Tyr Tyr Cys His Gln His Ser Thr Trp Pro Arg
                85                  90                  95

Gly Thr Phe Gly Gln Gly Thr Arg Leu Glu Ile Lys
                100                 105

<210> SEQ ID NO 157
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 157

Gln Val His Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Arg Tyr
            20                  25                  30

Pro Met His Trp Val Arg Gln Ala Pro Gly Lys Gly Leu Glu Trp Val
            35                  40                  45

Ala Leu Ile Ser Tyr Asp Gly Asn Asn Lys Tyr Tyr Ala Asp Ser Val
            50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95
```

-continued

Ala Arg His Phe Leu Pro Tyr Ser Ser Ser Trp Tyr Gln Gly Phe Asn
            100                 105                 110

Tyr Trp Gly Gln Gly Ile Leu Val Thr Val Ser Ser
        115                 120

<210> SEQ ID NO 158
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 158

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Thr Asn
            20                  25                  30

Tyr Val Gln Trp Tyr Gln Gln Arg Pro Gly Ser Ser Pro Thr Pro Ile
        35                  40                  45

Ile Phe Glu Asp Ser Gln Arg Pro Ser Gly Val Pro Asp Arg Phe Ser
    50                  55                  60

Gly Ser Ile Asp Ser Ser Asn Ser Ala Ser Leu Thr Ile Ser Gly
65                  70                  75                  80

Leu Arg Thr Asp Asp Glu Ala Asp Tyr Tyr Cys Gln Ser Tyr Asp Asn
                85                  90                  95

Ser Asn Arg Ala Val Val Phe Gly Gly Gly Thr Lys Leu Thr Val Leu
            100                 105                 110

<210> SEQ ID NO 159
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 159

Gln Val Gln Leu Val Glu Ser Gly Gly Val Val Gln Pro Gly Arg
1               5                   10                  15

Ser Leu Arg Leu Ser Cys Glu Ala Ser Gly Phe Leu Phe Ser Arg Tyr
            20                  25                  30

Gly Met His Trp Val Arg Gln Ala Pro Gly Lys Gly Leu Asp Trp Val
        35                  40                  45

Ala Val Ile Ser Tyr Asp Gly Asn Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Val Asn Ser Leu Arg Val Glu Asp Thr Ala Val Tyr Tyr Cys
                85                  90                  95

Ala Arg Gly Val Pro Tyr Gly Asp Thr Leu Thr Gly Leu Val Tyr Trp
            100                 105                 110

Gly Gln Gly Thr Leu Val Thr Val Ser Ser
        115                 120

<210> SEQ ID NO 160
<211> LENGTH: 110
<212> TYPE: PRT
<213> ORGANISM: Artificial sequence
<220> FEATURE:
<223> OTHER INFORMATION: Synthetic polypeptide

```
<400> SEQUENCE: 160

Asn Phe Met Leu Thr Gln Pro His Ser Val Ser Glu Ser Pro Gly Lys
1               5                   10                  15

Thr Val Thr Ile Ser Cys Thr Arg Ser Ser Gly Thr Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Asn
                85                  90                  95

Ser Asp Arg Val Phe Gly Gly Gly Thr Lys Leu Thr Val Leu
            100                 105                 110

<210> SEQ ID NO 161
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 161

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Arg Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Asn Thr Ser
    50                  55                  60

Leu Lys Ser Arg Leu Ser Ile Ser Lys Asp Thr Ser Lys Ser Gln Val
65                  70                  75                  80

Val Leu Thr Met Thr Ser Met Asp Pro Leu Asp Thr Ala Thr Tyr Phe
                85                  90                  95

Cys Ala Arg Leu Leu Val Ala Gly Thr Phe Leu Pro Ser His Tyr Phe
            100                 105                 110

Asp Tyr Trp Gly Gln Gly Ile Leu Val Thr Val Ser Ser
        115                 120                 125

<210> SEQ ID NO 162
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 162

Ser Tyr Val Leu Thr Gln Pro Pro Ser Val Ser Val Thr Pro Gly Lys
1               5                   10                  15

Thr Ala Arg Ile Thr Cys Gly Gly Asn Asn Ile Gly Leu Lys Ser Val
            20                  25                  30

Phe Trp Tyr Gln Glu Arg Pro Asp Gln Ala Pro Val Val Val Ile Tyr
        35                  40                  45

Tyr Asp Ser Ala Arg Pro Ser Gly Ile Pro Glu Arg Ile Ser Gly Ser
    50                  55                  60
```

Lys Ser Gly Asn Thr Ala Thr Leu Thr Ile Thr Arg Val Glu Ala Gly
65                  70                  75                  80

Asp Glu Ala Asp Tyr Phe Cys Gln Val Trp Asp Ser Ser Arg Asn His
                85                  90                  95

Pro Val Phe Gly Gly Gly Thr Lys Leu Thr Val Leu
            100                 105

<210> SEQ ID NO 163
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 163

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Gln Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Thr Arg Gln Val Gly Ala Asp Phe Ser Gly Arg Gly Phe Asp Tyr Trp
            100                 105                 110

Gly Gln Gly Thr Leu Leu Thr Val Ser Ser
        115                 120

<210> SEQ ID NO 164
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 164

Ser Tyr Glu Leu Thr Gln Pro Pro Ser Val Ser Val Ser Pro Gly Gln
1               5                   10                  15

Thr Ala Thr Ile Thr Cys Phe Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Lys Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
            85                  90                  95

Phe Gly Gly Gly Thr Lys Leu Thr Val Leu
            100                 105

<210> SEQ ID NO 165
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 165

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Lys Phe Ser Val Tyr
            20                  25                  30

Ala Leu Ser Trp Val Arg Gln Ala Pro Gly Lys Gly Leu Glu Trp Ile
        35                  40                  45

Ser Tyr Ile Ser Ser Ser Gly Ser Thr Ile Tyr Tyr Ser Asp Ser Val
    50                  55                  60

Lys Gly Arg Phe Thr Ile Ser Arg Asp Asn Val Gly Asn Ser Leu Phe
65                  70                  75                  80

Val Gln Met Asn Ser Leu Arg Ala Glu Asp Thr Gly Ile Tyr Tyr Cys
                85                  90                  95

Ala Thr Ala Arg His Ile Thr Asn Asp Gly Phe Asp Ile Trp Gly Gln
            100                 105                 110

Gly Thr Met Val Ile Val Ser Ser
        115                 120

<210> SEQ ID NO 166
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 166

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Arg Phe
            20                  25                  30

Leu Ala Trp Tyr Gln Gln Lys Pro Gly Lys Ala Pro Lys Leu Leu Ile
        35                  40                  45

Tyr Ser Ala Ser Thr Leu Gln Arg Gly Val Pro Ser Arg Phe Ser Gly
    50                  55                  60

Ser Gly Phe Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Ser His Pro Arg
                85                  90                  95

Met Phe Thr Phe Gly Pro Gly Thr Thr Val Asp Ile Lys
            100                 105

<210> SEQ ID NO 167
<211> LENGTH: 127
<212> TYPE: PRT
<213> ORGANISM: Artificial sequence
<220> FEATURE:
<223> OTHER INFORMATION: Synthetic polypeptide

<400> SEQUENCE: 167

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Leu Ile Ser Asn Gly
            20                  25                  30

Tyr Tyr Trp Gly Trp Ile Arg Gln Pro Pro Gly Lys Gly Leu Glu Trp
        35                  40                  45

```
Ile Gly Ser Ile Tyr His Thr Arg Ser Thr Tyr Tyr Asn Pro Ser Leu
        50                  55                  60

Lys Ser Arg Val Ser Ile Ser Val Asp Thr Ser Lys Asn Arg Phe Ser
 65                  70                  75                  80

Leu Arg Leu Arg Ser Val Thr Ala Ala Asp Thr Ala Phe Tyr Tyr Cys
                85                  90                  95

Ala Arg Gly Pro Gly His Cys Tyr Gly Asp Asp Cys Tyr Ala Tyr
                100                 105                 110

Tyr Phe Asp Gln Trp Gly Gln Gly Thr Pro Val Thr Val Ser Pro
            115                 120                 125

<210> SEQ ID NO 168
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 168

Asp Ile Gln Met Thr Gln Ser Pro Ser Ser Val Ser Ser Val Gly
 1               5                  10                  15

Asp Arg Val Thr Ile Thr Cys Arg Ala Ser Gln Gly Ile Ser Asn Trp
                20                  25                  30

Leu Ala Trp Tyr Gln Gln Asn Pro Gly Lys Ala Pro Lys Leu Leu Ile
            35                  40                  45

Tyr Asp Ala Ser Ser Leu Gln Ser Gly Val Pro Ser Arg Phe Ser Gly
        50                  55                  60

Ser Gly Ser Gly Thr Asp Phe Thr Leu Thr Ile Asn Ser Leu Gln Pro
 65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys
                100                 105

<210> SEQ ID NO 169
<211> LENGTH: 127
<212> TYPE: PRT
<213> ORGANISM: Artificial sequence
<220> FEATURE:
<223> OTHER INFORMATION: Synthetic polypeptide

<400> SEQUENCE: 169

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Arg Phe
                20                  25                  30

Ala Ile Ser Trp Val Arg Gln Ala Pro Gly Gln Gly Leu Gln Trp Met
            35                  40                  45

Gly Gly Ile Leu Pro Ile Phe Gly Thr Ala Asn Tyr Ala Gln Lys Phe
        50                  55                  60

Gln Gly Arg Val Thr Ile Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Ser Leu Pro Tyr Cys Thr Asn Asp Val Cys Ser Asn Gln Asn
                100                 105                 110

Thr Phe Asp Tyr Trp Gly Gln Gly Thr Leu Val Thr Val Ser Ser
            115                 120                 125
```

<210> SEQ ID NO 170
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 170

```
Ser Tyr Glu Leu Thr Gln Pro Pro Ser Val Ser Val Ser Pro Gly Gln
1               5                   10                  15

Ala Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Glu Asp Asn Lys Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Val Val Phe Gly Gly Gly Thr Lys Leu Thr Val Leu
            100                 105
```

<210> SEQ ID NO 171
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 171

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Ser Arg Tyr Gly Asp Pro Ile Gly Asp Asn Trp Phe Asp Pro
            100                 105                 110

Trp Gly Gln Gly Thr Leu Val Thr Val Ser Ser
        115                 120
```

<210> SEQ ID NO 172
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 172

```
Ser Tyr Val Leu Thr Gln Pro Pro Ser Val Ser Val Thr Pro Gly Lys
1               5                   10                  15
```

```
Thr Ala Arg Ile Thr Cys Gly Gly Asn Asn Ile Gly Leu Lys Ser Val
            20                  25                  30

Phe Trp Tyr Gln Glu Arg Pro Asp Gln Ala Pro Val Val Val Ile Tyr
        35                  40                  45

Tyr Asp Ser Ala Arg Pro Ser Gly Ile Pro Glu Arg Ile Ser Gly Ser
 50                  55                  60

Lys Ser Gly Asn Thr Ala Thr Leu Thr Ile Thr Arg Val Glu Ala Gly
 65                  70                  75                  80

Asp Glu Ala Asp Tyr Phe Cys Gln Val Trp Asp Ser Ser Arg Asn His
                85                  90                  95

Pro Val Phe Gly Gly Gly Thr Lys Leu Thr Val Leu
                100                 105
```

<210> SEQ ID NO 173
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 173

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Arg Phe Ser Phe Tyr
            20                  25                  30

Gly Met Thr Trp Val Arg Gln Ala Pro Gly Lys Gly Leu Glu Trp Val
        35                  40                  45

Ser Ser Ile Ser Gly Thr Gly Ala Thr Arg Asn Cys Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asp Ser Leu Arg Val Asp Thr Ala Val Phe Tyr Cys
                85                  90                  95

Val Arg Arg Phe Pro Met Thr Thr Val Thr Ser Phe Asp Ser Trp Gly
                100                 105                 110

Gln Gly Thr Leu Val Thr Val Ser Ser
            115                 120
```

<210> SEQ ID NO 174
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 174

```
Gln Ser Ala Leu Thr Gln Pro Arg Ser Val Ser Gly Ser Pro Gly Gln
 1               5                   10                  15

Ser Val Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Met Ile Phe Asp Val Thr Gly Arg Pro Ser Gly Val Pro Asp Arg Phe
 50                  55                  60

Ser Gly Ser Lys Ser Gly Asn Thr Ala Ser Leu Thr Ile Ala Gly Leu
 65                  70                  75                  80

Gln Ala Glu Asp Glu Ala Asp Tyr Tyr Cys Gly Ala Tyr Ala Gly Phe
                85                  90                  95
```

Asn Ala Leu Phe Gly Gly Gly Thr Lys Leu Thr Val Leu
            100                 105

<210> SEQ ID NO 175
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 175

Glu Val Gln Leu Val Gln Ser Gly Gly Leu Val Arg Pro Gly Gly
1               5                   10                  15

Ser Val Arg Leu Ser Cys Val Ala Ser Gly Phe Pro Phe Asn Met Phe
            20                  25                  30

Trp Met Gly Trp Val Arg Gln Thr Pro Gly Lys Gly Leu Glu Trp Val
            35                  40                  45

Ala Asn Ile Lys Gln Asp Gly Ser Glu Lys Tyr Tyr Val Asp Ser Val
        50                  55                  60

Lys Gly Arg Phe Ala Ile Ser Arg Asp Asn Ala Lys Asn Ser Leu Phe
65                  70                  75                  80

Leu Gln Met Asp Ser Leu Ser Val Gly Asp Thr Ala Ile Tyr Tyr Cys
                85                  90                  95

Val Arg Glu Gly Val Arg Arg Val Val Arg Ser Thr Gly Tyr Phe
            100                 105                 110

Asp Phe Trp Gly Gln Gly Gln Leu Val Thr Val Ser Ser
        115                 120                 125

<210> SEQ ID NO 176
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 176

Ser Tyr Glu Leu Thr Gln Pro Pro Ser Met Ser Val Ser Pro Gly Gln
1               5                   10                  15

Thr Ala Arg Ile Thr Cys Ser Gly Asp Ala Val Pro Ile Lys Tyr Val
            20                  25                  30

Tyr Trp Tyr Gln Gln Arg Ser Gly Gln Ala Pro Val Leu Val Ile Tyr
            35                  40                  45

Glu Asp Asp Arg Arg Pro Ser Gly Ile Ser Glu Arg Phe Ser Gly Ser
        50                  55                  60

Ser Ser Gly Thr Thr Ala Thr Leu Thr Ile Thr Gly Ala Gln Val Glu
65                  70                  75                  80

Asp Glu Gly Asp Tyr Tyr Cys Tyr Ser Thr Asp Ser Ser Gly Tyr Gln
                85                  90                  95

Arg Ala Phe Gly Gly Gly Thr Lys Leu Thr Val Leu
            100                 105

<210> SEQ ID NO 177
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 177

```
Arg Val Gln Leu Gln Glu Ser Ala Pro Gly Leu Val Arg Pro Ser Glu
1               5                   10                  15

Thr Leu Ser Leu Thr Cys Ser Val Ser Gly Gly Pro Ile Ser Asn Gly
            20                  25                  30

Pro Tyr Tyr Trp Ser Trp Ile Arg Gln His Pro Gly Lys Gly Leu Glu
        35                  40                  45

Trp Ile Gly Phe Ile Phe Tyr Ser Gly Ser Thr Asn Tyr Asn Pro Ser
50                  55                  60

Leu Arg Gly Arg Val Thr Met Ala Val Asp Thr Ser Lys Asn Gln Phe
65                  70                  75                  80

Ser Leu Arg Leu Asn Ser Val Thr Ala Ala Asp Thr Ala Val Tyr Tyr
                85                  90                  95

Cys Ala Arg His Val Val Thr Ala Ser Gly Trp Phe Asp Pro Trp Gly
                100                 105                 110

Gln Gly Thr Leu Val Thr Val Ser Ser
            115                 120
```

<210> SEQ ID NO 178
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 178

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Thr Asp
            20                  25                  30

Leu Ala Trp Tyr Gln Gln Lys Pro Gly Gln Ala Pro Arg Val Leu Ile
        35                  40                  45

Tyr Asp Ala Phe Lys Arg Ala Thr Gly Ile Pro Ala Arg Phe Ser Gly
50                  55                  60

Ser Gly Ser Gly Thr Glu Phe Thr Leu Thr Ile Ser Ser Leu Glu Pro
65                  70                  75                  80

Glu Asp Phe Ala Val Tyr Tyr Cys Gln Gln Arg Ser Arg Trp Pro Pro
                85                  90                  95

Pro Tyr Thr Phe Gly Gln Gly Thr Lys Leu Glu Ile Lys
                100                 105
```

<210> SEQ ID NO 179
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 179

```
Arg Val Gln Leu Gln Glu Ser Ala Pro Gly Leu Val Arg Pro Ser Glu
1               5                   10                  15

Thr Leu Ser Leu Thr Cys Ser Val Ser Gly Gly Pro Ile Ser Asn Gly
            20                  25                  30

Pro Tyr Tyr Trp Ser Trp Ile Arg Gln His Pro Gly Lys Gly Leu Glu
        35                  40                  45

Trp Ile Gly Phe Ile Phe Tyr Ser Gly Ser Thr Asn Tyr Asn Pro Ser
50                  55                  60

Leu Arg Gly Arg Val Thr Met Ala Val Asp Thr Ser Lys Asn Gln Phe
65                  70                  75                  80
```

Ser Leu Arg Leu Asn Ser Val Thr Ala Ala Asp Thr Ala Val Tyr Tyr
            85                  90                  95

Cys Ala Arg His Val Val Thr Ala Ser Gly Trp Phe Asp Pro Trp Gly
            100                 105                 110

Gln Gly Thr Leu Val Thr Val Ser Ser
        115                 120

<210> SEQ ID NO 180
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 180

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Thr Asp
            20                  25                  30

Leu Ala Trp Tyr Gln Gln Lys Pro Gly Gln Ala Pro Arg Val Leu Ile
        35                  40                  45

Tyr Asp Ala Phe Lys Arg Ala Thr Gly Ile Pro Ala Arg Phe Ser Gly
    50                  55                  60

Ser Gly Ser Gly Thr Glu Phe Thr Leu Thr Ile Ser Ser Leu Glu Pro
65                  70                  75                  80

Glu Asp Phe Ala Val Tyr Tyr Cys Gln Gln Arg Ser Arg Trp Pro Pro
                85                  90                  95

Pro Tyr Thr Phe Gly Gln Gly Thr Lys Leu Glu Ile Lys
            100                 105

<210> SEQ ID NO 181
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 181

Gln Val His Leu Val Glu Ser Gly Gly Val Val Gln Pro Gly Arg
1               5                   10                  15

Ser Leu Arg Leu Ser Cys Ala Asp Ser Gly Val Thr Phe Ser Asp Asn
            20                  25                  30

Ala Leu Tyr Trp Val Arg Gln Ala Pro Gly Lys Gly Leu Glu Trp Val
        35                  40                  45

Ala Val Ile Ser Tyr Asp Gly Ser Ser Arg Tyr Tyr Ala Asp Ser Val
    50                  55                  60

Arg Gly Arg Phe Thr Ile Ser Arg Asp Asn Ser Lys Asp Thr Leu Tyr
65                  70                  75                  80

Leu Gln Met Asn Arg Leu Arg Ala Glu Asp Thr Ala Ile Tyr Tyr Cys
                85                  90                  95

Ala Arg Val Thr Ala Asp Tyr Tyr Glu Ser Ser Gly Lys Val Phe Trp
            100                 105                 110

Gly Gln Gly Ala Leu Val Val Val Ser Ser
        115                 120

<210> SEQ ID NO 182
<211> LENGTH: 107
<212> TYPE: PRT

```
<213> ORGANISM: Artificial sequence
<220> FEATURE:
<223> OTHER INFORMATION: Synthetic polypeptide

<400> SEQUENCE: 182

Asp Ile Gln Met Thr Gln Ser Pro Ser Thr Leu Ser Ala Ser Val Gly
1               5                   10                  15

Asp Arg Val Ser Ile Thr Cys Arg Ala Ser Gln Ser Val Arg Ser Trp
            20                  25                  30

Leu Ala Trp Tyr Gln His Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Ala
65                  70                  75                  80

Asp Asp Phe Ala Thr Tyr Tyr Cys Gln Gln Tyr Gln Thr Phe Ser Trp
                85                  90                  95

Thr Phe Gly Gln Gly Thr Thr Val Glu Val Lys
            100                 105

<210> SEQ ID NO 183
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 183

Gln Val Gln Leu Gln Glu Ser Gly Pro Ala Leu Val Lys Pro Ser Glu
1               5                   10                  15

Thr Leu Ser Leu Thr Cys Thr Val Ser Gly Gly Ser Ile Ser Asp His
            20                  25                  30

Tyr Trp Ser Trp Ile Arg Gln Pro Pro Gly Lys Gly Leu Glu Trp Ile
        35                  40                  45

Gly Tyr Ile Tyr Thr Ser Gly Thr Thr Asn Tyr Asn Pro Ser Leu Lys
    50                  55                  60

Ser Arg Val Thr Ile Ser Val Asp Thr Ser Lys Lys Gln Phe Ser Leu
65                  70                  75                  80

Asn Leu Arg Ser Val Thr Ala Ala Asp Thr Ala Val Tyr Tyr Cys Ala
                85                  90                  95

Arg Ser Leu Glu Thr Val Ile Arg Phe Tyr Tyr Tyr His Tyr Met Asp
            100                 105                 110

Val Trp Gly Lys Gly Thr Thr Val Ile Val Ser Ser
        115                 120

<210> SEQ ID NO 184
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 184

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Gln Ser
            20                  25                  30

Asp Gly Tyr Ser Tyr Leu Asp Trp Tyr Leu Gln Lys Pro Gly Gln Ser
        35                  40                  45
```

```
Pro Gln Leu Leu Ile Tyr Leu Gly Ser Asn Arg Ala Ser Gly Val Pro
    50                  55                  60

Asp Arg Phe Ser Val Ile Gly Ser Gly Thr Tyr Phe Thr Leu Lys Ile
65                  70                  75                  80

Ser Arg Val Glu Ala Glu Asp Val Gly Val Tyr Phe Cys Met Gln Ala
                85                  90                  95

Leu Gln Thr Pro Trp Thr Phe Gly Gln Gly Thr Lys Val Glu Ile Lys
                100                 105                 110

<210> SEQ ID NO 185
<211> LENGTH: 114
<212> TYPE: PRT
<213> ORGANISM: Artificial sequence
<220> FEATURE:
<223> OTHER INFORMATION: Synthetic polypeptide

<400> SEQUENCE: 185

Gln Val Gln Leu Gln Glu Ser Gly Pro Gly Leu Val Lys Pro Ser Glu
1               5                   10                  15

Thr Leu Ser Leu Thr Cys Thr Val Ala Gly Gly Ser Ile Gly Asp Tyr
                20                  25                  30

His Trp Asn Trp Ile Arg Gln Pro Ala Gly Lys Gly Leu Glu Trp Ile
            35                  40                  45

Gly Arg Ile His Ser Ser Gly Asn Thr Asp Tyr Asn Pro Ser Leu Lys
        50                  55                  60

Ser Arg Val Thr Met Ser Val Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Arg Gln Asn Val Phe Asp Ile Trp Gly Gln Gly Thr Met Val Thr Val
                100                 105                 110

Ser Ser

<210> SEQ ID NO 186
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 186

Asp Ile Val Met Thr Gln Ser Pro Asp Ser Leu Ala Leu Ser Leu Gly
1               5                   10                  15

Glu Arg Ala Thr Ile Asn Cys Lys Ser Ser Gln Ser Val Leu Phe Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Glu Thr Asp Phe Thr Leu Thr
65                  70                  75                  80

Ile Ser Ser Leu Gln Ala Glu Asp Val Ala Val Tyr Phe Cys Gln Gln
                85                  90                  95

Phe Tyr Thr Thr Pro Leu Thr Phe Gly Gly Gly Thr Lys Val Glu Ile
                100                 105                 110

Lys
```

<210> SEQ ID NO 187
<211> LENGTH: 114
<212> TYPE: PRT
<213> ORGANISM: Artificial sequence
<220> FEATURE:
<223> OTHER INFORMATION: Synthetic polypeptide

<400> SEQUENCE: 187

Gln Val Gln Met Gln Glu Ser Gly Pro Gly Leu Val Lys Ala Ser Glu
1               5                   10                  15

Thr Leu Ser Leu Thr Cys Ser Val Ser Gly Ile Ser Ile Asn Asn Tyr
            20                  25                  30

Tyr Trp Ser Trp Phe Arg Gln Pro Pro Gly Lys Gly Leu Glu Trp Ile
        35                  40                  45

Gly Tyr Val Tyr Ser Thr Gly Ser Ser Lys Tyr Asn Pro Ser Leu Glu
    50                  55                  60

Arg Arg Ala Thr Met Ser Val Asp Thr Ser Asn Asn Phe Ser Leu
65                  70                  75                  80

Arg Leu Thr Ser Val Thr Thr Ala Asp Thr Ala Val Tyr Cys Ala
            85                  90                  95

Arg Gly Ser Met Pro His Ile Trp Gly Gln Gly Leu Leu Val Thr Val
            100                 105                 110

Ser Ser

<210> SEQ ID NO 188
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 188

Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Glu Thr Asn
            20                  25                  30

Tyr Val Tyr Trp Tyr Gln Gln Val Pro Gly Thr Ala Pro Lys Pro Leu
        35                  40                  45

Val Tyr Arg Asn Asp Gln Arg Pro Ser Gly Val Pro Asp Arg Phe Ser
    50                  55                  60

Gly Ser Lys Ser Gly Thr Ser Ala Ser Leu Val Ile Ser Gly Leu Arg
65                  70                  75                  80

Thr Glu Asp Glu Ala Ala Tyr Tyr Cys Ala Ala Trp Asp Asp Ser Leu
                85                  90                  95

Lys Ala Pro Val Phe Gly Ala Gly Thr Lys Val Ala Val Leu
            100                 105                 110

<210> SEQ ID NO 189
<211> LENGTH: 130
<212> TYPE: PRT
<213> ORGANISM: Artificial sequence
<220> FEATURE:
<223> OTHER INFORMATION: Synthetic polypeptide

<400> SEQUENCE: 189

Glu Val Gln Leu Val Glu Ser Gly Gly Gly Leu Ile Lys Pro Gly Gly
1               5                   10                  15

Ser Leu Arg Leu Ser Cys Ala Ala Ser Gly Ile Thr Phe Ser Asn Ala
            20                  25                  30

```
Trp Met Ser Trp Val Arg Gln Ala Pro Gly Lys Gly Leu Glu Trp Val
            35                  40                  45

Gly Arg Ile Glu Ser Lys Ile Asp Gly Gly Thr Ile Asp Tyr Ala Thr
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Gln Gly Tyr Tyr Asp Arg Ser Gly Tyr Trp Val
            100                 105                 110

Val Gly Asn His Phe Asp Tyr Trp Gly Gln Gly Ile Leu Val Thr Val
            115                 120                 125

Ser Ser
    130

<210> SEQ ID NO 190
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 190

Gln Ser Val Leu Thr Gln Pro Pro Ser Val Ser Gly Ala Pro Gly Leu
1               5                   10                  15

Arg Val Thr Ile Ser Cys Thr Gly Ser Ser Thr Asn Ile Gly Ala Gly
            20                  25                  30

Tyr Asp Val His Trp Tyr Gln His Leu Pro Gly Thr Ala Pro Lys Leu
            35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Asp Asp Ala Ala Asp Tyr Tyr Cys Gln Ser Tyr Asp Arg Ser
                85                  90                  95

Leu Ser Thr Tyr Val Phe Gly Thr Gly Thr Lys Val Thr Val Leu
            100                 105                 110

<210> SEQ ID NO 191
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 191

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ser Gly Ile Ser Gly Thr Thr Gly Ser Thr Tyr Tyr Ala Asp Ser Val
    50                  55                  60

Lys Gly Arg Phe Thr Ile Ser Arg Asp Asn Ser Lys Asn Thr Val His
65                  70                  75                  80

Leu Gln Met Asn Ser Leu Arg Ala Glu Asp Thr Ala Val Tyr Tyr Cys
```

85                  90                  95

Ala Lys Asp Ser His Ser Met Ile Val Val Asp His Ala Phe Asp Ile
                    100                 105                 110

Trp Gly Gln Gly Thr Met Val Thr Val Ser Ser
            115                 120

<210> SEQ ID NO 192
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 192

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Thr Lys Ser Val
            20                  25                  30

His Trp Tyr Gln Gln Arg Pro Gly Gln Ala Pro Val Leu Val Val Tyr
        35                  40                  45

Asp Asp Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Tyr Asn Val His
                85                  90                  95

Tyr Val Phe Gly Thr Gly Thr Lys Val Thr Val Leu
            100                 105

<210> SEQ ID NO 193
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 193

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ile Met Thr Trp Val Arg Gln Ala Pro Gly Arg Gly Leu Glu Trp Val
        35                  40                  45

Ser Ser Ile Ser Thr Ser Ser Val Tyr Thr Phe Tyr Ala Asp Ser Leu
50                  55                  60

Lys Gly Arg Phe Thr Ile Ser Arg Asp Asn Ala Lys Asn Ser Val Tyr
65                  70                  75                  80

Leu Gln Met Asn Ser Leu Arg Ala Asp Asp Thr Ala Val Tyr Tyr Cys
                85                  90                  95

Ala Arg Glu Glu Gly Phe Arg Ala Tyr Asn Leu Tyr Trp Gly Gln Gly
            100                 105                 110

Thr Leu Val Thr Val Ser Ser
        115

<210> SEQ ID NO 194
<211> LENGTH: 110
<212> TYPE: PRT
<213> ORGANISM: Artificial sequence
<220> FEATURE:

<223> OTHER INFORMATION: Synthetic polypeptide

<400> SEQUENCE: 194

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Glu Tyr Asn
            20                  25                  30

Tyr Val Tyr Trp Tyr Gln Lys Phe Pro Gly Thr Ala Pro Lys Leu Leu
        35                  40                  45

Ile Tyr Lys Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Gly Asp Tyr Tyr Cys Ala Ala Trp Asp Asp Ile Leu
                85                  90                  95

Ser Gly Val Val Phe Gly Gly Gly Thr Lys Leu Thr Val Leu
            100                 105                 110

<210> SEQ ID NO 195
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 195

Gln Val Gln Leu Val Glu Ser Gly Gly Gly Val Val Gln Pro Gly Arg
1               5                   10                  15

Ser Gln Lys Leu Ser Cys Ala Ala Ser Gly Phe Thr Phe Ser Arg Phe
            20                  25                  30

Gly Met His Trp Val Arg Gln Ala Pro Gly Lys Gly Leu Glu Trp Val
        35                  40                  45

Ala Val Ile Ser Phe Asp Gly Ser Asn Arg Tyr Tyr Ala Asp Ser Val
    50                  55                  60

Lys Gly Arg Phe Thr Ile Thr Arg Asp Asn Ser Lys Asn Thr Leu Tyr
65                  70                  75                  80

Leu Gln Met Asn Asn Leu Arg Pro Glu Asp Thr Ala Val Tyr Tyr Cys
                85                  90                  95

Ala Arg Asp Trp Asp Arg Leu Val Arg Ser Ala Val Gly Tyr Trp Gly
            100                 105                 110

Gln Gly Thr Leu Val Ser Val Ser Ser
        115                 120

<210> SEQ ID NO 196
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 196

Gln Ser Ala Leu Thr Gln Pro Arg Ser Val Ser Gly Ser Pro Gly Gln
1               5                   10                  15

Ser Val Thr Ile Ser Cys Thr Gly Thr Ser Asn Asp Val Gly Gly Tyr
            20                  25                  30

Asn Phe Val Ser Trp Tyr Gln Gln His Pro Gly Lys Ala Pro Lys Leu
        35                  40                  45

Met Ile Phe Asp Val Ile Arg Arg Pro Ser Gly Val Pro Gly Arg Phe

```
                  50                  55                  60

Ser Gly Ser Lys Ser Gly Asp Thr Ala Ser Leu Ile Ile Ser Gly Leu
 65                  70                  75                  80

Gln Ala Glu Asp Glu Ala Asp Tyr Tyr Cys Cys Ser Tyr Ala Gly Thr
                 85                  90                  95

Tyr Thr Trp Val Phe Gly Ala Gly Thr Thr Leu Thr Val Leu
                100                 105                 110

<210> SEQ ID NO 197
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 197

Gln Val His Leu Gln Glu Ser Gly Pro Arg Leu Val Lys Pro Ser Glu
 1               5                  10                  15

Thr Leu Ser Leu Thr Cys Thr Val Ser Gly Gly Ser Val Ser Thr Ala
                 20                  25                  30

Thr Tyr Tyr Trp Ser Trp Ile Arg Gln Ser Pro Gly Arg Gly Leu Glu
                 35                  40                  45

Trp Ile Gly Tyr Ile Tyr Ser Ser Gly Asn Thr Asn Tyr Asn Pro Ser
 50                  55                  60

Leu Lys Ser Arg Val Thr Ile Ser Leu Asp Thr Pro Asn Asn Gln Leu
 65                  70                  75                  80

Ser Leu Thr Leu Thr Ser Val Thr Ala Ala Asp Thr Ala Ile Tyr Tyr
                 85                  90                  95

Cys Glu Arg Arg Leu Arg Ile Leu Ser Ile Glu Arg Asn Tyr Tyr Ala
                100                 105                 110

Met Asp Val Trp Gly Gln Gly Thr Pro Val Thr Val Ser Ser
                115                 120                 125

<210> SEQ ID NO 198
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 198

Glu Val Val Leu Thr Gln Thr Pro Gly Thr Leu Ser Leu Ser Pro Gly
 1               5                  10                  15

Glu Gly Ala Thr Leu Ser Cys Arg Ala Ser Gln Arg Val Val Asn Asn
                 20                  25                  30

Tyr Leu Ala Trp Tyr Gln Gln Arg Ala Gly Gln Ala Pro Arg Leu Leu
                 35                  40                  45

Ile Phe Gly Ala Ser Asn Arg Ala Thr Gly Ile Pro Asp Arg Phe Ser
 50                  55                  60

Gly Ser Gly Ser Gly Thr Asp Phe Thr Leu Thr Ile Arg Lys Leu Glu
 65                  70                  75                  80

Pro Glu Asp Phe Ala Val Tyr Tyr Cys Gln Gln Tyr Gly Ser Pro Trp
                 85                  90                  95

Thr Phe Gly His Gly Thr Lys Val Glu Met Lys
                100                 105

<210> SEQ ID NO 199
<211> LENGTH: 130
```

```
<212> TYPE: PRT
<213> ORGANISM: Artificial sequence
<220> FEATURE:
<223> OTHER INFORMATION: Synthetic polypeptide

<400> SEQUENCE: 199

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Arg Gly Leu Glu Trp Val
        35                  40                  45

Ala Val Ile Ser Tyr Asp Ala Ser Lys Lys Tyr His Ala Asp Ser Val
    50                  55                  60

Lys Gly Arg Phe Thr Ile Ser Arg Asp Ser Ser Lys Asn Thr Leu Phe
65                  70                  75                  80

Leu Gln Met Asn Ser Leu Lys Pro Glu Asp Thr Ala Val Tyr Tyr Cys
                85                  90                  95

Ala Arg Asp His Val Pro Pro Lys Asp Cys Ser Asp Gly Asn Cys His
            100                 105                 110

Ser Asp Tyr Gly Met Asp Val Trp Gly Gln Gly Thr Thr Val Thr Val
        115                 120                 125

Ser Ser
    130

<210> SEQ ID NO 200
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 200

Asp Ile Gln Met Thr Gln Ser Pro Ser Thr Met Ser Ala Ser Val Gly
1               5                   10                  15

Asp Arg Val Thr Ile Thr Cys Arg Ala Ser Gln Ser Ile Ser Lys Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Gln Thr Gly Val Pro Ser Arg Phe Ser Gly
    50                  55                  60

Ser Gly Ser Gly Thr Glu Phe Thr Leu Thr Ile Asn Ser Leu Gln Pro
65                  70                  75                  80

Asp Asp Phe Ala Thr Tyr Tyr Cys Gln Gln His Asn Ser Tyr Ser Tyr
                85                  90                  95

Thr Phe Gly Gln Gly Thr Lys Val Glu Ile Lys
            100                 105

<210> SEQ ID NO 201
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 201

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Asn Phe
```

```
            20                  25                  30

Ala Val His Trp Val Arg Gln Ala Pro Gly Gln Arg Leu Glu Trp Met
            35                  40                  45

Gly Trp Ile Asn Pro Gly Asn Arg Asn Thr Lys Tyr Ser His Asn Phe
        50                  55                  60

Gln Gly Arg Val Thr Ile Thr Arg Asp Thr Ser Ala Asn Thr Ala Tyr
 65                  70                  75                  80

Met Glu Leu Ser Ser Leu Arg Ser Gln Asp Thr Ala Val Tyr Tyr Cys
                85                  90                  95

Ala Arg Leu Pro Ile Ala Ala Gly Arg Gly Trp Phe Asp Pro Trp
            100                 105                 110

Gly Gln Gly Thr Leu Val Thr Val Ser Ser
            115                 120

<210> SEQ ID NO 202
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 202

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ile Ser Thr
            20                  25                  30

Tyr Leu Ala Trp Tyr Gln Gln Arg Pro Gly Gln Ala Pro Arg Val Leu
        35                  40                  45

Ile Tyr Asp Val Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Phe Cys His Gln Tyr Gly Ser Ser Pro
                85                  90                  95

Ala Thr Phe Gly Gln Gly Thr Lys Val Glu Ile Lys
            100                 105

<210> SEQ ID NO 203
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 203

Glu Val Gln Leu Val Glu Ser Gly Gly Asp Leu Val Gln Pro Gly Gly
 1               5                  10                  15

Ser Leu Arg Leu Ser Cys Ala Ala Ser Gly Phe Thr Phe Asn Thr Tyr
            20                  25                  30

Gly Met Asn Trp Val Arg Gln Ala Pro Gly Lys Gly Leu Glu Trp Val
        35                  40                  45

Ser Tyr Ile Ser Ser Ala Thr Thr Thr Phe Tyr Tyr Ala Asp Ser Val
    50                  55                  60

Arg Gly Arg Phe Thr Ile Ser Arg Asp Asn Ala Lys Asn Ser Leu Phe
 65                  70                  75                  80

Leu His Met Lys Ser Leu Arg Asp Glu Asp Thr Ala Val Tyr Tyr Cys
                85                  90                  95
```

Ala Arg Val Tyr Thr Met Leu Arg Gly Ala Ser Met Asp Val Trp Gly
            100                 105                 110

His Gly Thr Thr Val Thr Val Ser Ser
        115                 120

<210> SEQ ID NO 204
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 204

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Thr Tyr
            20                  25                  30

Leu Ala Trp Tyr Gln Gln Lys Pro Gly Gln Ala Pro Arg Leu Leu Ile
        35                  40                  45

Tyr Asp Ser Ala Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Leu Arg Ile Thr Trp Pro Pro
                85                  90                  95

Ile Phe Thr Phe Gly Pro Gly Thr Lys Val Asp Val Lys
            100                 105

<210> SEQ ID NO 205
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 205

Gln Val His Leu Val Gln Ser Gly Ala Glu Val Lys Lys Ser Gly Ala
1               5                   10                  15

Ser Val Lys Val Ser Cys Lys Thr Phe Gly Tyr Thr Phe Thr Ala Tyr
            20                  25                  30

Tyr Met His Trp Val Arg Gln Ala Pro Gly Gln Gly Pro Glu Trp Met
        35                  40                  45

Gly Trp Ile Asn Pro Ile Ser Gly Gly Thr Asn Tyr Ala Gln Lys Phe
    50                  55                  60

Gln Gly Arg Val Ser Met Thr Arg Asp Thr Ser Ile Ser Thr Ala Tyr
65                  70                  75                  80

Met Gly Leu Ser Arg Leu Arg Pro Asp Asp Thr Ala Val Tyr Tyr Cys
                85                  90                  95

Ala Arg Val Lys Cys Ser Ser Ala Asn Cys Tyr Gly Asn Phe Asp Tyr
            100                 105                 110

Trp Gly Gln Gly Thr Leu Val Thr Val Ser Ser
        115                 120

<210> SEQ ID NO 206
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 206

Gln Ser Ala Leu Thr Gln Pro Pro Ser Ala Ser Gly Ser Pro Gly Glu
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Leu Val Phe Gly Gly Gly Thr Lys Leu Thr Val Leu
            100                 105                 110

<210> SEQ ID NO 207
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 207

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Thr Asn Tyr
            20                  25                  30

Arg Ile Gly Trp Val Arg Gln Met Pro Gly Lys Gly Leu Glu Trp Met
        35                  40                  45

Gly Ile Ile Tyr Pro Gly Gly Ser Asp Thr Arg Tyr Ser Pro Ser Leu
    50                  55                  60

Gln Gly Gln Val Thr Met Ser Val Asp Lys Ser Ile Ser Thr Ala Tyr
65                  70                  75                  80

Leu Met Trp Ser Ser Leu Lys Ala Ser Asp Thr Ala Met Tyr Tyr Cys
                85                  90                  95

Ala Arg Gln Thr Thr Gln Asn Ser Gly Tyr Asp Arg Trp Phe Asp Ser
            100                 105                 110

Trp Gly Gln Gly Thr His Val Thr Val Ser Ser
        115                 120

<210> SEQ ID NO 208
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 208

Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Ser Ile Gly Ser Asn
            20                  25                  30

Ile Val Asn Trp Tyr Gln His Leu Pro Gly Thr Ala Pro Lys Leu Leu
        35                  40                  45

Ile Tyr Ile Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu
            100                 105                 110

<210> SEQ ID NO 209
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 209

Glu Val Gln Val Leu Glu Ser Gly Gly Gly Leu Val Gln Pro Gly Gly
1               5                   10                  15

Ser Leu Arg Leu Ser Cys Ala Ala Ser Gly Ile Thr Phe Ser Arg His
                20                  25                  30

Thr Met Ser Trp Val Arg Gln Ala Pro Gly Lys Gly Leu Glu Trp Val
            35                  40                  45

Ser Ala Ile Ser Gly Ser Gly Gly Ser Thr Tyr His Ala Asp Ser Val
        50                  55                  60

Lys Gly Arg Phe Thr Ile Ser Arg Asp Ser Ser Lys Ser Thr Leu Tyr
65                  70                  75                  80

Leu Gln Met Asn Ser Leu Arg Ala Glu Asp Thr Ala Val Tyr Tyr Cys
                85                  90                  95

Ala Ile Ser Val Pro Leu Leu Arg Phe Leu Glu Trp Phe Gln His Pro
            100                 105                 110

Phe Asp Phe Trp Gly Gln Gly Thr Leu Val Thr Val Ser Ser
        115                 120                 125

<210> SEQ ID NO 210
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 210

Glu Ile Val Met Thr Gln Ser Pro Ala Ser Leu Ser Val Ser Pro Gly
1               5                   10                  15

Glu Arg Val Thr Leu Ser Cys Arg Ala Ser Gln Ser Val Gly Ser Thr
                20                  25                  30

Leu Ala Trp Tyr Gln His Lys Pro Gly Gln Ala Pro Arg Leu Leu Ile
            35                  40                  45

Ser Gly Ala Ser Thr Arg Ala Thr Gly Val Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys His Gln Tyr Ile Asn Trp Pro Pro
                85                  90                  95

Trp Thr Phe Gly Gln Gly Thr Lys Val Glu Ile Lys
            100                 105

<210> SEQ ID NO 211
<211> LENGTH: 120
<212> TYPE: PRT
<213> ORGANISM: Artificial sequence

```
<220> FEATURE:
<223> OTHER INFORMATION: Synthetic polypeptide

<400> SEQUENCE: 211

Glu Val Arg Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ser Met Ser Trp Val Arg Gln Ala Pro Gly Lys Gly Leu Glu Trp Val
        35                  40                  45

Ala Ser Ile Ser Ser Thr Gly Ser Tyr Ile Tyr Asn Ala Asp Ser Leu
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Val Glu Asp Thr Ala Val Tyr Tyr Cys
                85                  90                  95

Val Arg Phe Thr Met Thr Thr Val Thr Asn Phe Asp Ser Trp Gly Gln
            100                 105                 110

Gly Thr Leu Val Thr Val Ser Ser
            115                 120

<210> SEQ ID NO 212
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 212

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ala Tyr
            20                  25                  30

Ser Tyr Val Ser Trp Tyr Gln Gln His Pro Gly Lys Ala Pro Lys Leu
        35                  40                  45

Met Ile Tyr Asp Val Tyr Arg Arg Pro Ser Gly Val Pro Gly Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Cys Ser His Ala Gly Ser
                85                  90                  95

His Thr Trp Val Phe Gly Gly Gly Thr Lys Val Thr Val Leu
            100                 105                 110

<210> SEQ ID NO 213
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 213

Gln Leu Gln Val Val Ala Ser Gly Gly Gly Val Val Gln Pro Gly Arg
1               5                   10                  15

Ser Leu Arg Leu Ser Cys Lys Ala Ser Gly Phe Thr Phe Thr Asn Tyr
            20                  25                  30

Gly Met His Trp Val Arg Gln Ala Pro Gly Lys Gly Leu Glu Trp Val
        35                  40                  45
```

Ala Phe Ile Ser Tyr Asp Gly Gly Asn Lys Phe Tyr Ala Asp Ser Val
    50                  55                  60

Lys Gly Arg Phe Thr Ile Ser Arg Asp Asn Ser Arg Asn Thr Val Tyr
65                  70                  75                  80

Leu Gln Met Asn Ser Leu Arg Val Ala Asp Thr Ala Met Tyr Tyr Cys
                85                  90                  95

Pro Lys Val Ile Pro His Pro Tyr Tyr Asp Ser Ser Gly Asp Asp Ala
                100                 105                 110

Phe Asp Ile Trp Gly Gln Gly Thr Met Val Ala Ile Ser Ser
                115                 120                 125

<210> SEQ ID NO 214
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 214

Glu Ile Val Met Thr Gln Ser Pro Ala Thr Leu Ser Val Ser Pro Gly
1               5                   10                  15

Glu Arg Ala Thr Leu Ser Cys Trp Ala Ser Gln Ser Ile Ser Arg Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Lys Phe Ser Gly
    50                  55                  60

Ser Gly Ser Gly Thr Asp Phe Thr Leu Thr Val Ser Ser Leu Gln Ser
65                  70                  75                  80

Glu Asp Leu Ala Val Tyr Tyr Cys Gln Gln Tyr Ser Lys Leu Pro Ile
                85                  90                  95

Thr Phe Gly Gln Gly Thr Arg Leu Glu Ile Lys
                100                 105

<210> SEQ ID NO 215
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 215

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
            20                  25                  30

Ser Met Ser Trp Val Arg Gln Ala Pro Gly Lys Gly Leu Glu Trp Val
        35                  40                  45

Ser Tyr Ile Ser Gly Ser Gly Asp Ile Tyr Ala Asp Ser Val
    50                  55                  60

Lys Gly Arg Phe Thr Ile Ser Arg Asp Asn Ala Arg Asn Ser Leu Ser
65                  70                  75                  80

Leu Gln Met Asn Ser Leu Arg Asp Asp Thr Ala Val Tyr Tyr Cys
                85                  90                  95

Ala Arg Gly Leu Val Ala Thr Thr Gly Thr Arg Tyr Phe Asp Tyr Trp
                100                 105                 110

Gly Gln Gly Thr Leu Val Thr Val Ser Ser
                115                 120

```
<210> SEQ ID NO 216
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 216

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Tyr
            20                  25                  30

Leu Ala Trp Tyr Gln Gln Arg Pro Gly Gln Ala Pro Arg Leu Leu Ile
        35                  40                  45

Tyr Asp Ala Ser Asn Arg Ala Thr Gly Ile Pro Val Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Tyr Trp Pro Pro
                85                  90                  95

Phe Thr Phe Gly Gly Gly Thr Lys Val Glu Ile Lys
            100                 105

<210> SEQ ID NO 217
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 217

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Arg Phe
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Arg Gly Lys Tyr Ala Gln Lys Phe
    50                  55                  60

Gln Gly Arg Val Arg Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Ile Ser Thr Ala Ser Tyr Val Pro Gly Thr Phe Glu Asp
            100                 105                 110

Val Trp Gly Gln Gly Thr Thr Val Thr Val Ser Ser
        115                 120

<210> SEQ ID NO 218
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 218

Asp Ile Val Leu Thr Gln Ser Pro Ala Thr Leu Ser Leu Ser Pro Gly
1               5                   10                  15
```

```
Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Ala Gly Ile Pro Ala Arg Phe Ser Gly
    50                  55                  60

Ser Gly Ser Glu Thr Asp Phe Thr Leu Thr Ile Ser Ser Leu Glu Pro
65                  70                  75                  80

Glu Asp Val Ala Val Tyr Tyr Cys Gln Gln Arg Ser Asp Trp Pro Pro
                85                  90                  95

Gly Thr Phe Gly Gln Gly Thr Asn Val Glu Ile Lys
            100                 105

<210> SEQ ID NO 219
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 219

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Asn Tyr
            20                  25                  30

Asn Ile Asn Trp Val Arg Gln Ala Pro Gly Lys Gly Leu Glu Trp Val
        35                  40                  45

Ser Ser Ile Ser Ser Thr Gly Ser Tyr Ile His Tyr Ala Asp Leu Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Ala Arg Met Val Arg Asn Thr Val Thr Ala Phe Asp Tyr Trp Gly Gln
            100                 105                 110

Gly Thr Leu Val Ser Val Ser Ser
        115                 120

<210> SEQ ID NO 220
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 220

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln Pro Gly Arg Ala Pro Lys Leu
        35                  40                  45

Leu Ile Tyr Glu Val Ile Lys Arg Pro Ser Gly Val Ser Asp Arg Phe
    50                  55                  60

Ser Gly Ser Lys Ser Gly Asp Thr Ala Ser Leu Thr Ile Ser Gly Leu
65                  70                  75                  80

Gln Ala Glu Asp Glu Ala Asp Tyr Tyr Cys Cys Ser Tyr Gly Gly Asn
                85                  90                  95
```

Asn Ser Trp Met Phe Gly Gly Gly Thr Met Leu Thr Val Leu
            100                 105                 110

<210> SEQ ID NO 221
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 221

Gln Val Gln Val Val Gln Ser Gly Ala Glu Met Lys Lys Pro Gly Ala
1               5                   10                  15

Ser Val Lys Val Ser Cys Lys Val Ser Gly Tyr Arg Leu Ile Asp Leu
            20                  25                  30

Pro Leu His Trp Val Arg Gln Ala Pro Gly Lys Gly Leu Glu Trp Met
        35                  40                  45

Gly Leu Phe Asp Pro Glu Lys Ala Glu Ala Ile Tyr Ser Gln Lys Phe
    50                  55                  60

Gln Asp Lys Val Thr Ile Ser Glu Asp Thr Ser Ile Asp Thr Ala Tyr
65                  70                  75                  80

Met Glu Leu Asn Ser Leu Arg Ser Glu Asp Thr Ala Val Tyr Tyr Cys
                85                  90                  95

Ala Thr Trp Gly Val Glu Val Val Asn Gly Arg Arg Asp Tyr Phe Asp
            100                 105                 110

Ser Trp Gly Gln Gly Thr Leu Val Thr Val Ser Ser
        115                 120

<210> SEQ ID NO 222
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 222

Ser Tyr Glu Leu Thr Gln Pro Pro Ser Val Ser Val Ser Pro Gly Gln
1               5                   10                  15

Thr Ala Arg Ile Thr Cys Tyr Ala Asp Val Leu Ser Asn Gln Tyr Thr
            20                  25                  30

Tyr Trp Tyr Gln Gln Lys Pro Gly Gln Ala Pro Val Leu Val Ile Tyr
        35                  40                  45

Lys Asp Thr Glu Arg Pro Ser Gly Ile Pro Glu Arg Phe Ala Gly Ser
    50                  55                  60

Ser Ser Gly Thr Thr Val Thr Leu Val Ile Asn Gly Val Arg Ala Glu
65                  70                  75                  80

Asp Glu Ala Tyr Tyr Tyr Cys Gln Ser Ala Asp Asn Thr Arg Ile Thr
                85                  90                  95

Val Phe Gly Gly Gly Thr Lys Leu Ser Val Leu
            100                 105

<210> SEQ ID NO 223
<211> LENGTH: 128
<212> TYPE: PRT
<213> ORGANISM: Artificial sequence
<220> FEATURE:
<223> OTHER INFORMATION: Synthetic polypeptide

<400> SEQUENCE: 223

```
Gly Val Gln Leu Val Glu Ser Gly Gly Leu Ile Gln Pro Gly Gly
1               5                   10                  15

Ser Leu Arg Leu Ser Cys Ala Ala Ser Gly Phe Thr Phe Ser Ser Phe
            20                  25                  30

Glu Met Asn Trp Val Arg Gln Ala Pro Gly Lys Gly Leu Glu Trp Val
        35                  40                  45

Ser Tyr Ile Ser Thr Ser Gly Ser Thr Ile Tyr Tyr Ala Asp Ser Val
    50                  55                  60

Lys Gly Arg Phe Thr Ile Ser Arg Asp Asn Ala Arg Asn Ser Leu Ser
65                  70                  75                  80

Leu Gln Met Asn Ser Leu Arg Ala Glu Asp Thr Ala Val Tyr Tyr Cys
                85                  90                  95

Ala Arg Asp Val Arg Asp Cys Ser Ala Leu Thr Cys Pro Arg Arg Gly
                100                 105                 110

Asp Ala Phe Asp Phe Trp Gly Arg Gly Thr Arg Val Thr Val Ser Ser
            115                 120                 125
```

<210> SEQ ID NO 224
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 224

```
Asp Val Val Met Thr Gln Ser Pro Leu Ser Leu Pro Val Thr Leu Gly
1               5                   10                  15

Gln Ser Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Arg Thr Phe Gly Pro Gly Thr Lys Val Asp Ile Lys
                100                 105                 110
```

<210> SEQ ID NO 225
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 225

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Val Tyr
            20                  25                  30

Pro Met Asn Trp Val Arg Gln Ala Pro Gly Lys Gly Leu Glu Trp Val
        35                  40                  45

Ser Ser Ile Ser Ser Ser Arg Tyr Ile Tyr Ala Asp Ser Leu
    50                  55                  60

Arg Gly Arg Ile Thr Ile Ser Arg Asp Asn Ala Lys Asn Ser Leu Tyr
65                  70                  75                  80
```

```
Leu Gln Met Asn Ser Leu Arg Val Glu Asp Thr Ala Val Tyr Tyr Cys
                 85                  90                  95

Val Lys Val Gly Gly Ser Lys His Gln Tyr Tyr Phe Asp Tyr Trp Gly
            100                 105                 110

Gln Gly Ser Leu Val Thr Val Ser Ser
        115                 120
```

<210> SEQ ID NO 226
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 226

```
Gln Ser Val Leu Thr Gln Pro Pro Ser Thr Ser Gly Ile Pro Gly Gln
1               5                   10                  15

Thr Val Thr Ile Ser Cys Ser Gly Ser Arg Ser Asn Ile Gly Ser Tyr
            20                  25                  30

Thr Val Asn Trp Tyr Glu Gln Leu Pro Gly Thr Ala Pro Lys Leu Val
        35                  40                  45

Ile Phe Asn Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Gly Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110
```

<210> SEQ ID NO 227
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 227

```
Gln Val Gln Leu Val Gln Ser Gly Ala Glu Val Lys Arg Pro Gly Ala
1               5                   10                  15

Ser Val Lys Val Phe Cys Lys Ala Ser Gly Tyr Thr Phe Thr Asn Tyr
            20                  25                  30

Asp Ile Ile Trp Val Arg Gln Ala Pro Gly Gln Gly Leu Glu Trp Val
        35                  40                  45

Gly Trp Ile Ser Thr Tyr Asn Gly Asn Thr Asn Tyr Glu Gln Asn Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Arg Cys Ser Thr Ser Thr Cys Tyr Ser Arg Tyr Ala Asp
            100                 105                 110

Tyr Trp Gly Gln Gly Thr Leu Val Thr Val Ser Ser
        115                 120
```

<210> SEQ ID NO 228
<211> LENGTH: 107
<212> TYPE: PRT

```
<213> ORGANISM: Artificial sequence
<220> FEATURE:
<223> OTHER INFORMATION: Synthetic polypeptide

<400> SEQUENCE: 228

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ile Tyr
            20                  25                  30

Leu Asn Trp Tyr Gln Gln Lys Pro Gly Lys Ala Pro Lys Val Leu Ile
        35                  40                  45

Tyr Ala Ala Ser Ser Leu Gln Ser Gly Val Pro Ser Arg Phe Arg Gly
50                  55                  60

Ser Gly Ser Gly Thr Asp Phe Ile Leu Thr Ile Ser Ser Leu Gln Pro
65                  70                  75                  80

Glu Asp Phe Ala Thr Tyr Tyr Cys Gln Gln Ser Tyr Arg Ser Pro Arg
                85                  90                  95

Thr Phe Gly Gln Gly Thr Glu Val Glu Ile Lys
            100                 105

<210> SEQ ID NO 229
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 229

Glu Val Gln Leu Val Glu Ser Gly Gly Gly Leu Ala Gln Pro Gly Glu
1               5                   10                  15

Ser Met Arg Leu Ser Cys Val Ala Ser Gly Phe Thr Leu Ser Arg Tyr
            20                  25                  30

Glu Val Asn Trp Val Arg Gln Ala Pro Gly Lys Gly Leu Glu Trp Leu
        35                  40                  45

Ser Tyr Ile Ser Ser Gly Gly Pro Ser Ile Tyr Tyr Ala Asp Ser Val
    50                  55                  60

Lys Gly Arg Phe Thr Ile Ser Arg Asn Ser Ala Glu Asn Ser Leu Glu
65                  70                  75                  80

Leu Gln Met Ser Thr Leu Arg Thr Glu Asp Thr Ala Val Tyr Tyr Cys
                85                  90                  95

Met Arg Glu Gly Leu Thr Tyr Tyr Asp Ser Thr Ile Trp Gly Gln Gly
            100                 105                 110

Thr Leu Val Ala Val Ser Ser
        115

<210> SEQ ID NO 230
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 230

Gln Asn Val Leu Thr Gln Ser Pro Ser Ala Ser Ala Ser Leu Gly Ala
1               5                   10                  15

Ser Val Lys Leu Thr Cys Thr Leu Asn Ser Gly His Ser Arg Tyr Ala
            20                  25                  30

Ile Ala Trp His Gln Gln Pro Gln Arg Gly Pro Arg Phe Leu Met
        35                  40                  45
```

```
Lys Ile Asn Ser Asp Gly Arg His Ile Arg Gly Asp Gly Ile Ser Asp
 50                  55                  60

Arg Phe Ser Gly Ser Ala Ser Gly Ala Glu Arg His Leu Thr Ile Ser
 65                  70                  75                  80

Ser Leu Gln Pro Glu Asp Glu Ala Asp Tyr Tyr Cys Gln Thr Trp Gly
                 85                  90                  95

Thr Gly Phe Arg Val Phe Gly Gly Gly Thr Lys Leu Thr Val Leu
            100                 105                 110

<210> SEQ ID NO 231
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 231

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Glu Tyr
                 20                  25                  30

Ala Met His Trp Val Arg Gln Val Pro Gly Lys Gly Leu Glu Trp Val
             35                  40                  45

Ser Gly Ile Ser Trp Asn Gly Gly Ser Lys Gly Tyr Ala Asp Ser Val
         50                  55                  60

Lys Gly Arg Phe Thr Ile Ser Arg Asp Asn Ala Arg Tyr Ser Leu Ser
 65                  70                  75                  80

Leu Gln Met Asn Ser Leu Arg Thr Glu Asp Thr Ala Leu Tyr Tyr Cys
                 85                  90                  95

Ala Lys Asp Asp Tyr Glu Gly Ala Gly Phe Asp Ile Trp Gly Gln Gly
            100                 105                 110

Thr Val Val Thr Val Ser Ser
        115

<210> SEQ ID NO 232
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 232

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                 20                  25                  30

Leu Gly Trp Tyr Gln Gln Lys Ser Gly Gln Ala Pro Arg Leu Leu Ile
             35                  40                  45

Tyr Gly Ala Ser Ser Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Ile Tyr Tyr Cys Gln Gln Arg Ser Asn Trp Pro Ile
                 85                  90                  95

Thr Phe Gly Gln Gly Thr Arg Leu Glu Ile Lys
            100                 105
```

-continued

```
<210> SEQ ID NO 233
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 233

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Leu Ile Ser Asn Gly
            20                  25                  30

Tyr Tyr Trp Gly Trp Ile Arg Gln Ser Pro Gly Lys Gly Leu Glu Trp
        35                  40                  45

Ile Gly Ser Ile Tyr Tyr Thr Arg Asp Thr Tyr Tyr Asn Trp Ser Leu
    50                  55                  60

Lys Ser Arg Ile Thr Ile Ser Val Asp Thr Ser Lys Lys Gln Phe Ser
65                  70                  75                  80

Leu Lys Leu Tyr Ser Val Thr Ala Ala Asp Thr Ala Val Tyr Tyr Cys
                85                  90                  95

Val Arg His Glu Gly Ser Cys Asn Asp Gly Ser Cys Tyr Gly Ser Phe
            100                 105                 110

Val Asp Asn Trp Gly Gln Gly Thr Leu Val Thr Val Ser Ser
        115                 120                 125

<210> SEQ ID NO 234
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 234

Asp Ile Gln Met Thr Gln Ser Pro Ser Ser Val Ser Ala Ser Val Gly
1               5                   10                  15

Asp Arg Val Thr Leu Thr Cys Arg Ala Ser Gln Asp Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr His Phe Thr Leu Thr Ile Ser Ser Leu Gln Pro
65                  70                  75                  80

Glu Asp Phe Ala Thr Tyr Phe Cys Gln Gln Ala Asp Ser Phe Ile Thr
                85                  90                  95

Phe Gly Gly Gly Thr Lys Val Glu Ile Lys
            100                 105

<210> SEQ ID NO 235
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 235

Glu Val Gln Leu Leu Glu Ser Gly Gly Gly Leu Val Gln Pro Gly Gly
1               5                   10                  15

Ser Leu Arg Leu Ser Cys Ala Ala Ser Asp Phe Thr Phe Ser Ser Tyr
            20                  25                  30
```

Thr Met Ala Trp Val Arg Gln Ala Pro Gly Lys Gly Leu Glu Trp Val
            35                  40                  45

Ser Ser Ile Ser Gly Asp Gly Val Ser Thr Lys Asn Ala Asp Ser Val
     50                  55                  60

Lys Gly Arg Phe Ser Val Ser Arg Asp Asn Ser Lys Asn Thr Leu Phe
 65                  70                  75                  80

Leu Gln Leu Asn Ser Leu Arg Ala Glu Asp Thr Ala Phe Tyr Tyr Cys
                 85                  90                  95

Ala Arg Gly Gly Thr Phe His Asn Trp Tyr Phe Asp Leu Trp Gly Arg
            100                 105                 110

Gly Val Leu Val Thr Val Ser Ser
            115                 120

<210> SEQ ID NO 236
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 236

Glu Ile Val Met Thr Gln Ser Pro Ala Thr Leu Ser Val Ser Pro Gly
 1               5                  10                  15

Glu Thr Ala Thr Leu Ser Cys Arg Ala Ser Gln Ser Ile Gly Asp Asn
             20                  25                  30

Leu Ala Trp Tyr Gln Gln Lys Pro Gly Gln Ala Pro Arg Leu Leu Ile
         35                  40                  45

Ser Gly Ala Ser Thr Arg Ala Thr Asp Phe Pro Ala Arg Phe Arg Gly
     50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Lys Asn Trp Pro Arg
                 85                  90                  95

Thr Phe Gly Arg Gly Thr Lys Val Glu Val Arg
            100                 105

<210> SEQ ID NO 237
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 237

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
             20                  25                  30

Ala Met Ser Trp Val Arg Gln Ala Pro Gly Lys Gly Pro Glu Trp Val
         35                  40                  45

Ser Gly Ile Ser Gly Ser Gly Gly Ser Thr Asn Tyr Ala Asp Ser Ala
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Thr Ile Thr Tyr Ser Tyr Tyr Tyr Met Ala Val Trp Gly

Lys Gly Thr Thr Val Thr Val Ser Ser
        115                 120

<210> SEQ ID NO 238
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 238

Glu Ile Val Leu Thr Gln Ser Pro Gly Thr Leu Ser Leu Ser Pro Gly
1               5                   10                  15

Glu Arg Gly Thr Leu Ser Cys Arg Ala Ser Gln Ser Val Arg Ser Ser
            20                  25                  30

Tyr Leu Ala Trp Tyr Gln Gln Arg Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Gly Arg Leu Glu
65                  70                  75                  80

Pro Glu Asp Phe Ala Val Tyr Tyr Cys Gln Gln Tyr Gly Thr Ser Ile
                85                  90                  95

Thr Phe Gly Gly Gly Thr Lys Val Glu Ile Lys
            100                 105

<210> SEQ ID NO 239
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 239

Gln Val Gln Val Val Gln Ser Gly Ala Glu Met Arg Lys Pro Gly Ala
1               5                   10                  15

Ser Val Arg Val Ser Cys Lys Val Ser Gly Tyr Arg Leu Thr Asp Leu
            20                  25                  30

Pro Leu His Trp Val Arg Gln Ala Pro Gly Lys Gly Leu Glu Trp Ile
        35                  40                  45

Gly Phe Val Asp Leu Glu Lys Arg Glu Ile Ile Tyr Ala Gln Lys Phe
50                  55                  60

Gln Gly Lys Val Thr Ile Thr Glu Asp Thr Ser Ala Asp Thr Ala Tyr
65                  70                  75                  80

Met Glu Leu Asn Ser Leu Arg Ser Glu Asp Thr Ala Val Tyr Tyr Cys
                85                  90                  95

Ala Thr Trp Gly Ile Glu Val Val Asn Gly Arg Asp Glu Phe Phe Asp
            100                 105                 110

Ser Trp Gly Gln Gly Thr Leu Val Ser Val Ser Ser
        115                 120

<210> SEQ ID NO 240
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 240

```
Ser Tyr Glu Leu Thr Gln Pro Pro Ser Val Ser Val Ser Pro Gly Gln
1               5                   10                  15

Thr Ala Arg Ile Thr Cys Tyr Ala Asp Val Leu Ser Lys Gln Tyr Thr
            20                  25                  30

Tyr Trp Tyr Gln Gln Lys Pro Gly Gln Ala Pro Val Leu Val Ile Tyr
            35                  40                  45

Lys Asp Thr Glu Arg Pro Ser Gly Ile Pro Glu Arg Phe Ala Gly Ser
50                  55                  60

Ser Ser Gly Thr Thr Val Thr Leu Ile Ile Asn Gly Val Arg Thr Glu
65                  70                  75                  80

Asp Glu Ala Tyr Tyr Cys Gln Ser Ala Asp Thr Arg Ile Thr Val
                85                  90                  95

Phe Gly Gly Gly Thr Lys Leu Ser Val Leu
            100                 105
```

<210> SEQ ID NO 241
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 241

```
Gln Val Gln Val Val Gln Ser Gly Ala Glu Met Lys Lys Pro Gly Ala
1               5                   10                  15

Ser Val Lys Val Ser Cys Lys Val Ser Gly Tyr Ser Leu Ser Asp Leu
            20                  25                  30

Pro Leu His Trp Val Arg Gln Ala Pro Gly Lys Gly Leu Glu Trp Met
            35                  40                  45

Gly Leu Phe Asp Pro Ile Asn Gly Glu Ile Ile Tyr Ala Gln Thr Phe
50                  55                  60

Gln Gly Lys Val Thr Ile Ser Glu Asp Thr Ser Ile Asp Thr Ala Tyr
65                  70                  75                  80

Met Glu Leu Asn Ser Leu Arg Ser Glu Asp Thr Ala Val Tyr Tyr Cys
                85                  90                  95

Ala Thr Trp Gly Val Ala Val Val Ser Gly Arg Arg Asp Tyr Phe Asp
            100                 105                 110

Ser Trp Gly Gln Gly Thr Leu Val Thr Val Ser Ser
            115                 120
```

<210> SEQ ID NO 242
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 242

```
Ser Tyr Glu Leu Thr Gln Pro Pro Ser Val Ser Val Ser Pro Gly Gln
1               5                   10                  15

Thr Ala Arg Ile Thr Cys Tyr Ala Ala Val Leu Ser Asn Gln Tyr Thr
            20                  25                  30

Tyr Trp Tyr Gln Gln Lys Pro Gly Gln Ala Pro Val Leu Val Ile Tyr
            35                  40                  45

Lys Asp Thr Glu Arg Pro Ser Gly Ile Pro Glu Arg Phe Ala Gly Ser
50                  55                  60

Ser Ser Gly Thr Thr Val Thr Leu Ile Ile Asn Gly Val Arg Thr Glu
```

```
                 65                  70                  75                  80
Asp Glu Ala Tyr Tyr Tyr Cys Gln Thr Ala Asp Thr Lys Tyr Thr Val
                    85                  90                  95

Phe Gly Gly Gly Thr Lys Leu Ser Val Leu
                100                 105

<210> SEQ ID NO 243
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 243

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Gly
                20                  25                  30

Asp Tyr Tyr Trp Asn Trp Ile Arg Gln Pro Pro Gly Lys Gly Leu Glu
            35                  40                  45

Trp Ile Gly Tyr Ile Tyr His Ser Gly Thr Thr Tyr Tyr Asn Pro Ser
    50                  55                  60

Leu Lys Ser Arg Val Thr Ile Ser Val Asp Thr Ser Lys Asn Arg Phe
65                  70                  75                  80

Ser Leu Lys Leu Ser Ser Val Thr Ala Ala Asp Thr Ala Val Tyr Phe
                85                  90                  95

Cys Ala Arg Ala Tyr Ala Tyr Glu Phe Trp Ser Gly Tyr Pro Asn Trp
                100                 105                 110

Phe Asp Pro Trp Gly Leu Gly Thr Leu Val Thr Val Ser Ser
            115                 120                 125

<210> SEQ ID NO 244
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 244

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Arg Ile Ser Thr Tyr
                20                  25                  30

Val Asn Trp Tyr Gln Val Lys Ala Gly Thr Ala Pro Lys Val Leu Ile
            35                  40                  45

Tyr Ala Ala Ser Ser Leu Gln Thr Gly Val Pro Ser Arg Phe Ser Gly
    50                  55                  60

Ser Gly Ser Gly Thr Asp Phe Thr Leu Thr Ile Val Ser Leu Gln Pro
65                  70                  75                  80

Glu Asp Phe Thr Thr Tyr Phe Cys Gln Gln Ser Tyr Ser Pro Pro Trp
                85                  90                  95

Thr Phe Gly Gln Gly Thr Lys Val Glu Ile Lys
                100                 105

<210> SEQ ID NO 245
<211> LENGTH: 126
<212> TYPE: PRT
<213> ORGANISM: Artificial sequence
<220> FEATURE:
```

<223> OTHER INFORMATION: Synthetic polypeptide

<400> SEQUENCE: 245

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Ile Phe Asn Arg Tyr
            20                  25                  30

Ala Met His Trp Val Arg Gln Ala Pro Gly Lys Gly Leu Glu Trp Val
        35                  40                  45

Ala Leu Ile Ser Tyr Asp Gly Ile Asn Lys Tyr Tyr Ala Asp Ser Val
    50                  55                  60

Lys Gly Arg Phe Ser Ile Ser Arg Asp Asn Ser Lys Ser Thr Leu Tyr
65                  70                  75                  80

Leu Gln Met Asn Ser Leu Arg Ala Glu Asp Thr Ala Ile Phe Tyr Cys
                85                  90                  95

Ala Arg Gly Leu Gly Tyr Cys Ser Gly Thr Gly Gly Ser Cys Thr Pro
            100                 105                 110

Phe Glu Tyr Trp Gly Gln Gly Ile Leu Val Thr Val Ser Ser
        115                 120                 125

<210> SEQ ID NO 246
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 246

Asp Ile Gln Met Thr Gln Ser Pro Pro Ser Leu Ser Ala Ser Val Gly
1               5                   10                  15

Asp Arg Val Thr Ile Thr Cys Arg Ala Ser Gln Ser Ile Lys Lys Tyr
            20                  25                  30

Leu Asn Trp Tyr Gln Gln Lys Pro Gly Asn Ala Pro Lys Leu Leu Ile
        35                  40                  45

Tyr Gly Ala Ser Asn Leu Gln Thr Gly Val Pro Ser Arg Phe Ser Gly
    50                  55                  60

Ser Gly Ser Gly Thr Asp Phe Ala Leu Ser Ile Ser Ser Leu Glu Thr
65                  70                  75                  80

Glu Asp Phe Ala Thr Tyr Tyr Cys Gln Gln Ser Asp Ser Ala Pro Pro
                85                  90                  95

Thr Phe Gly Gly Gly Thr Lys Val Glu Phe Lys
            100                 105

<210> SEQ ID NO 247
<211> LENGTH: 135
<212> TYPE: PRT
<213> ORGANISM: Artificial sequence
<220> FEATURE:
<223> OTHER INFORMATION: Synthetic polypeptide

<400> SEQUENCE: 247

Gln Val Gln Leu Gln Gln Arg Gly Ala Gly Leu Leu Lys Pro Ser Glu
1               5                   10                  15

Thr Leu Ser Leu Thr Cys Glu Ile Tyr Gly Ala Ser Leu Asn Asp Tyr
            20                  25                  30

Asp Trp Thr Trp Ile Arg Gln Pro Pro Gly Lys Arg Leu Glu Trp Ile
        35                  40                  45

Gly Val Ile Asn Arg Arg Asp Thr Val Asp Tyr Asn Pro Ser Leu Lys

```
                     50                  55                  60

Ser Arg Val Thr Leu Ser Leu Asp Thr Ser Lys Asn Gln Leu Ser Leu
 65                  70                  75                  80

Ser Leu Ser Ser Val Thr Ala Ala Asp Thr Ala Val Tyr Tyr Cys Val
                 85                  90                  95

Arg Val Pro Arg Arg Gly Phe Glu Gly Ser Phe Gly Phe Cys Asp Asp
            100                 105                 110

Thr Ala Cys Arg Tyr Gly His Thr Trp Phe Asp Pro Trp Gly Gln Gly
        115                 120                 125

Thr Leu Val Thr Val Ser Ser
        130                 135

<210> SEQ ID NO 248
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 248

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Arg Asp Tyr
             20                  25                  30

Leu Asn Trp Tyr Gln Gln Arg Pro Gly Lys Ala Pro Lys Val Leu Ile
         35                  40                  45

Phe Ala Gly Ser Arg Leu Glu Ser Gly Val Pro Ser Arg Phe Arg Gly
     50                  55                  60

Arg Gly Ser Gly Thr Glu Phe Thr Leu Thr Ile Ser Asp Leu Gln Pro
 65                  70                  75                  80

Glu Asp Phe Ala Thr Tyr Tyr Cys Gln Gln Ser Tyr Leu Thr Pro Pro
                 85                  90                  95

Thr Phe Gly Gln Gly Thr Thr Val Asp Ile Lys
            100                 105

<210> SEQ ID NO 249
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 249

Gln Val Thr Leu Lys Glu Ser Gly Pro Val Leu Val Lys Pro Thr Glu
  1               5                  10                  15

Thr Leu Thr Leu Thr Cys Thr Val Ser Gly Phe Ser Leu Arg Asn Gly
             20                  25                  30

Arg Met Gly Val Ser Trp Ile Arg Gln Pro Pro Gly Lys Ala Leu Glu
         35                  40                  45

Trp Leu Ala His Ile Phe Ala Ser Asp Glu Lys Ser Tyr Ser Thr Ser
     50                  55                  60

Gln Arg Thr Arg Leu Ser Ile Ser Arg Asp Thr Ser Lys Ser Gln Val
 65                  70                  75                  80

Val Leu Ser Met Thr Asp Met Asp Pro Val Asp Thr Ala Thr Tyr Tyr
                 85                  90                  95

Cys Ala Arg Ile Leu Lys Phe Gly Thr Met Arg Ala Ala Tyr Tyr Phe
            100                 105                 110
```

```
Asp Tyr Trp Gly Gln Gly Ala Leu Val Pro Val Ser Ser
        115                 120                 125

<210> SEQ ID NO 250
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 250

Ser Tyr Val Leu Thr Gln Pro Pro Ser Val Ser Val Ala Pro Gly Lys
1               5                   10                  15

Thr Ala Arg Ile Thr Cys Gly Gly Ile Asn Ile Gly Ile Arg Thr Val
            20                  25                  30

His Trp Tyr Gln Gln Lys Pro Gly Gln Ala Pro Met Leu Val Ile Tyr
        35                  40                  45

Tyr Asp Ser Asp Arg Pro Leu Gly Ile Pro Glu Arg Phe Ser Gly Ser
    50                  55                  60

Lys Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Ala Leu
            100                 105

<210> SEQ ID NO 251
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 251

Gln Val His Leu Val Glu Ser Gly Gly Gly Leu Val Lys Pro Gly Gly
1               5                   10                  15

Ser Leu Arg Leu Ser Cys Ala Val Ser Gly Phe Thr Phe Ser Asp Tyr
            20                  25                  30

Tyr Met Ser Trp Ile Arg Gln Ala Pro Gly Lys Gly Leu Glu Trp Leu
        35                  40                  45

Ser Tyr Ile Ser Ser Ser Gly Ser Thr Ile Tyr Tyr Ala Asp Ser Met
    50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Val Glu Asp Thr Ala Phe Tyr Tyr Cys
                85                  90                  95

Ala Gly Ser Lys Val Gly Tyr Thr Thr Gly Arg Arg Asn Trp Tyr Phe
            100                 105                 110

Asp Leu Trp Gly Arg Gly Thr Leu Val Thr Val Ser Ser
        115                 120                 125

<210> SEQ ID NO 252
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 252

Gln Ser Ala Leu Thr Gln Pro Pro Ser Ala Ser Gly Ser Pro Gly Gln
```

```
                1               5                  10                 15
            Ser Val Thr Ile Ser Cys Thr Gly Thr Ser Ser Asp Val Gly Ala Tyr
                            20                 25                 30

Asn Tyr Val Ser Trp Tyr Gln Gln His Pro Gly Lys Ala Pro Lys Leu
                            35                 40                 45

Met Ile Tyr Glu Val Thr Lys Arg Pro Ser Gly Val Pro Asp Arg Phe
                    50                 55                 60

Ser Gly Ser Lys Ser Gly Asn Thr Ala Ser Leu Thr Val Ser Gly Leu
             65                 70                 75                 80

Gln Ala Glu Asp Glu Ala Asp Tyr Tyr Cys Ser Ser Tyr Ala Gly Asn
                            85                 90                 95

Asn Asn Leu Val Phe Gly Gly Gly Thr Lys Leu Thr Val Leu
                            100                105                110
```

<210> SEQ ID NO 253
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 253

```
            Gln Val Gln Leu Leu Gln Ser Gly Ser Glu Val Arg Lys Pro Gly Ala
             1               5                  10                 15

Ser Val Asn Ile His Cys Lys Ala Ser Gly Phe Thr Phe Thr Asp Phe
                            20                 25                 30

Tyr Leu His Trp Val Arg Gln Ala Pro Gly Gln Gly Leu Glu Trp Met
                            35                 40                 45

Gly Ile Ile Asn Pro Glu Thr Gly Glu Thr Thr Tyr Ser Gln Lys Phe
                    50                 55                 60

Gln Gly Arg Val Thr Met Thr Arg Asp Thr Ser Thr Ser Val Val Asn
             65                 70                 75                 80

Leu Glu Val Arg Ser Leu Arg Ser Glu Asp Thr Ala Ile Tyr Tyr Cys
                            85                 90                 95

Ala Arg Asp Leu Val Val Val Pro Val Glu Met Ser Arg Arg Ala
                            100                105                110

Phe Asp Ile Trp Gly Gln Gly Ile Met Val Thr Val Ser Ser
                    115                120                125
```

<210> SEQ ID NO 254
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 254

```
            Ser Tyr Val Leu Thr Gln Pro Pro Ser Val Ser Val Ala Pro Gly Gln
             1               5                  10                 15

Thr Ala Arg Ile Pro Cys Gly Gly Asn Asn Ile Glu Arg Lys Ser Val
                            20                 25                 30

His Trp Tyr Gln Gln Arg Pro Gly Gln Ala Pro Val Leu Val Val Tyr
                            35                 40                 45

Asp Asp Thr Val Arg Pro Ser Gly Ile Pro Glu Arg Phe Ser Gly Ser
                    50                 55                 60

Asn Ser Gly Ser Thr Ala Thr Leu Thr Ile Ser Arg Val Gly Ala Gly
             65                 70                 75                 80
```

```
Asp Glu Gly Asp Tyr Tyr Cys Gln Val Trp Asp Ser Thr Thr Asp His
                85                  90                  95

Gly Val Phe Gly Gly Gly Thr Lys Leu Thr Val Leu
            100                 105

<210> SEQ ID NO 255
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 255

Arg Val Gln Leu Val Gln Ser Gly Ala Glu Val Lys Lys Pro Gly Ala
1               5                   10                  15

Ser Val Lys Val Ser Cys Gln Thr Ser Gly Tyr Ile Phe Ser Ala Tyr
            20                  25                  30

Tyr Ile Tyr Trp Val Arg Gln Ala Pro Gly Gln Gly Leu Glu Trp Met
            35                  40                  45

Gly Arg Met Asn Ala Lys Ser Gly Gly Ala Asn Thr Ala Gln Gln Phe
    50                  55                  60

Gln Gly Arg Leu Thr Met Thr Arg Asp Met Ser Val Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Arg Asp Asp Tyr Met Trp Gly Ser Tyr Arg Pro Leu
            100                 105                 110

Asp Tyr Trp Gly Gln Gly Thr Leu Val Thr Val Ser Ser
            115                 120                 125

<210> SEQ ID NO 256
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 256

Glu Val Val Leu Thr Gln Ser Pro Ala Thr Leu Ser Leu Ser Pro Gly
1               5                   10                  15

Glu Arg Ala Ser Leu Ser Cys Arg Ala Ser Gln Ser Val Ser Gly Tyr
            20                  25                  30

Leu Ala Trp Tyr Gln His Lys Pro Gly Gln Ala Pro Arg Leu Leu Ile
            35                  40                  45

Tyr Asp Ala Ser Asn Arg Ala Ala Gly Ile Pro Ala Arg Phe Arg Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Phe Cys Gln Gln Arg Ser Asn Gly Leu Thr
                85                  90                  95

Phe Gly Gly Gly Thr Lys Val Glu Ile Lys
            100                 105

<210> SEQ ID NO 257
<211> LENGTH: 8
<212> TYPE: PRT
<213> ORGANISM: Artificial sequence
<220> FEATURE:
<223> OTHER INFORMATION: Synthetic peptide
```

```
<400> SEQUENCE: 257

Gly Phe Ile Phe Ser Arg Tyr Ala
1               5

<210> SEQ ID NO 258
<211> LENGTH: 8
<212> TYPE: PRT
<213> ORGANISM: Artificial sequence
<220> FEATURE:
<223> OTHER INFORMATION: Synthetic peptide

<400> SEQUENCE: 258

Ile Ser Tyr Asp Ala Arg Asn Ser
1               5

<210> SEQ ID NO 259
<211> LENGTH: 16
<212> TYPE: PRT
<213> ORGANISM: Artificial sequence
<220> FEATURE:
<223> OTHER INFORMATION: Synthetic peptide

<400> SEQUENCE: 259

Ala Arg Pro Thr Leu Pro Tyr Ser Asn Asn Trp Tyr Ala Pro Glu Tyr
1               5                   10                  15

<210> SEQ ID NO 260
<211> LENGTH: 8
<212> TYPE: PRT
<213> ORGANISM: Artificial sequence
<220> FEATURE:
<223> OTHER INFORMATION: Synthetic peptide

<400> SEQUENCE: 260

Gly Phe Ser Phe Ser Ser Tyr Ala
1               5

<210> SEQ ID NO 261
<211> LENGTH: 8
<212> TYPE: PRT
<213> ORGANISM: Artificial sequence
<220> FEATURE:
<223> OTHER INFORMATION: Synthetic peptide

<400> SEQUENCE: 261

Ile Ser Gly Asn Gly Asn Gly Arg
1               5

<210> SEQ ID NO 262
<211> LENGTH: 15
<212> TYPE: PRT
<213> ORGANISM: Artificial sequence
<220> FEATURE:
<223> OTHER INFORMATION: Synthetic peptide

<400> SEQUENCE: 262

Ala Lys Val Val Arg Ile Ala Ala Val Leu Tyr Tyr Phe Asp Tyr
1               5                   10                  15

<210> SEQ ID NO 263
<211> LENGTH: 8
<212> TYPE: PRT
<213> ORGANISM: Artificial sequence
<220> FEATURE:
<223> OTHER INFORMATION: Synthetic peptide

<400> SEQUENCE: 263
```

```
Gly Phe Thr Phe Ser Asn Tyr Ala
1               5

<210> SEQ ID NO 264
<211> LENGTH: 8
<212> TYPE: PRT
<213> ORGANISM: Artificial sequence
<220> FEATURE:
<223> OTHER INFORMATION: Synthetic peptide

<400> SEQUENCE: 264

Ile Ser Gly Ser Gly Gly Leu Thr
1               5

<210> SEQ ID NO 265
<211> LENGTH: 16
<212> TYPE: PRT
<213> ORGANISM: Artificial sequence
<220> FEATURE:
<223> OTHER INFORMATION: Synthetic peptide

<400> SEQUENCE: 265

Ala Arg Val Lys Ser Thr Thr Gly Thr Thr Ala Leu Val Phe Asp Ile
1               5                   10                  15

<210> SEQ ID NO 266
<211> LENGTH: 8
<212> TYPE: PRT
<213> ORGANISM: Artificial sequence
<220> FEATURE:
<223> OTHER INFORMATION: Synthetic peptide

<400> SEQUENCE: 266

Gly Phe Thr Phe Ile Asn Tyr Gly
1               5

<210> SEQ ID NO 267
<211> LENGTH: 8
<212> TYPE: PRT
<213> ORGANISM: Artificial sequence
<220> FEATURE:
<223> OTHER INFORMATION: Synthetic peptide

<400> SEQUENCE: 267

Ile Ser Asn Asp Gly Ser Tyr Asn
1               5

<210> SEQ ID NO 268
<211> LENGTH: 15
<212> TYPE: PRT
<213> ORGANISM: Artificial sequence
<220> FEATURE:
<223> OTHER INFORMATION: Synthetic peptide

<400> SEQUENCE: 268

Ala Lys Asp Lys His Gly Asp Phe Asp Tyr Tyr Gly Val Asp Val
1               5                   10                  15

<210> SEQ ID NO 269
<211> LENGTH: 8
<212> TYPE: PRT
<213> ORGANISM: Artificial sequence
<220> FEATURE:
<223> OTHER INFORMATION: Synthetic peptide

<400> SEQUENCE: 269
```

```
Gly Phe Thr Phe Ser Ser Tyr Gly
1               5

<210> SEQ ID NO 270
<211> LENGTH: 8
<212> TYPE: PRT
<213> ORGANISM: Artificial sequence
<220> FEATURE:
<223> OTHER INFORMATION: Synthetic peptide

<400> SEQUENCE: 270

Ile Ser Tyr Asp Gly Ser Asp Asn
1               5

<210> SEQ ID NO 271
<211> LENGTH: 14
<212> TYPE: PRT
<213> ORGANISM: Artificial sequence
<220> FEATURE:
<223> OTHER INFORMATION: Synthetic peptide

<400> SEQUENCE: 271

Ala Arg Arg Arg Pro Gly Ser Phe Pro Gly Leu Cys Asp Tyr
1               5                   10

<210> SEQ ID NO 272
<211> LENGTH: 8
<212> TYPE: PRT
<213> ORGANISM: Artificial sequence
<220> FEATURE:
<223> OTHER INFORMATION: Synthetic peptide

<400> SEQUENCE: 272

Gly Gly Ser Phe Ser Arg Leu Thr
1               5

<210> SEQ ID NO 273
<211> LENGTH: 8
<212> TYPE: PRT
<213> ORGANISM: Artificial sequence
<220> FEATURE:
<223> OTHER INFORMATION: Synthetic peptide

<400> SEQUENCE: 273

His Ile Pro Ile Phe Gly Thr Thr
1               5

<210> SEQ ID NO 274
<211> LENGTH: 12
<212> TYPE: PRT
<213> ORGANISM: Artificial sequence
<220> FEATURE:
<223> OTHER INFORMATION: Synthetic peptide

<400> SEQUENCE: 274

Ala Arg Met Tyr Ser Gly His Asp Gly Val Asp Val
1               5                   10

<210> SEQ ID NO 275
<211> LENGTH: 10
<212> TYPE: PRT
<213> ORGANISM: Artificial sequence
<220> FEATURE:
<223> OTHER INFORMATION: Synthetic peptide

<400> SEQUENCE: 275

Gly Gly Ser Ile Ser Ser Gly Phe Tyr Tyr
```

```
<210> SEQ ID NO 276
<211> LENGTH: 7
<212> TYPE: PRT
<213> ORGANISM: Artificial sequence
<220> FEATURE:
<223> OTHER INFORMATION: Synthetic peptide

<400> SEQUENCE: 276

Ile Tyr Asp Ser Gly Arg Thr
1               5

<210> SEQ ID NO 277
<211> LENGTH: 19
<212> TYPE: PRT
<213> ORGANISM: Artificial sequence
<220> FEATURE:
<223> OTHER INFORMATION: Synthetic peptide

<400> SEQUENCE: 277

Ala Arg His Leu Thr His Leu Tyr Gly Asp Tyr Val Thr Pro Asp Ala
1               5                   10                  15

Leu Asp Ile

<210> SEQ ID NO 278
<211> LENGTH: 8
<212> TYPE: PRT
<213> ORGANISM: Artificial sequence
<220> FEATURE:
<223> OTHER INFORMATION: Synthetic peptide

<400> SEQUENCE: 278

Gly Phe Thr Phe Thr Thr Tyr Ser
1               5

<210> SEQ ID NO 279
<211> LENGTH: 8
<212> TYPE: PRT
<213> ORGANISM: Artificial sequence
<220> FEATURE:
<223> OTHER INFORMATION: Synthetic peptide

<400> SEQUENCE: 279

Ile Ser Ser Gly Ser Ser Asn Ile
1               5

<210> SEQ ID NO 280
<211> LENGTH: 19
<212> TYPE: PRT
<213> ORGANISM: Artificial sequence
<220> FEATURE:
<223> OTHER INFORMATION: Synthetic peptide

<400> SEQUENCE: 280

Ala Arg Ala His Gly Arg Ile Val Asn Ser Gly Val Val Ile Ser Arg
1               5                   10                  15

Phe Asp Pro

<210> SEQ ID NO 281
<211> LENGTH: 8
<212> TYPE: PRT
<213> ORGANISM: Artificial sequence
<220> FEATURE:
<223> OTHER INFORMATION: Synthetic peptide
```

```
<400> SEQUENCE: 281

Gly Tyr Thr Phe Thr Ala Tyr Tyr
1               5

<210> SEQ ID NO 282
<211> LENGTH: 8
<212> TYPE: PRT
<213> ORGANISM: Artificial sequence
<220> FEATURE:
<223> OTHER INFORMATION: Synthetic peptide

<400> SEQUENCE: 282

Ile Asn Pro Ser Ser Gly Gly Ala
1               5

<210> SEQ ID NO 283
<211> LENGTH: 19
<212> TYPE: PRT
<213> ORGANISM: Artificial sequence
<220> FEATURE:
<223> OTHER INFORMATION: Synthetic peptide

<400> SEQUENCE: 283

Ala Arg Met Gly Cys Arg Ser Asp Arg Cys Tyr Ser Thr Asn Tyr Asn
1               5                   10                  15

Phe Asp Gln

<210> SEQ ID NO 284
<211> LENGTH: 8
<212> TYPE: PRT
<213> ORGANISM: Artificial sequence
<220> FEATURE:
<223> OTHER INFORMATION: Synthetic peptide

<400> SEQUENCE: 284

Gly Phe Thr Ile Ser Pro Tyr Gly
1               5

<210> SEQ ID NO 285
<211> LENGTH: 8
<212> TYPE: PRT
<213> ORGANISM: Artificial sequence
<220> FEATURE:
<223> OTHER INFORMATION: Synthetic peptide

<400> SEQUENCE: 285

Ile Ser Ser Ser Ser Arg Tyr Thr
1               5

<210> SEQ ID NO 286
<211> LENGTH: 15
<212> TYPE: PRT
<213> ORGANISM: Artificial sequence
<220> FEATURE:
<223> OTHER INFORMATION: Synthetic peptide

<400> SEQUENCE: 286

Ala Arg Glu Arg Gly His Ser Thr Ser Ser Ser Tyr Phe Asp Ser
1               5                   10                  15

<210> SEQ ID NO 287
<211> LENGTH: 8
<212> TYPE: PRT
<213> ORGANISM: Artificial sequence
<220> FEATURE:
<223> OTHER INFORMATION: Synthetic peptide
```

<400> SEQUENCE: 287

Gly Phe Thr Phe Ser Asn Ala Trp
1               5

<210> SEQ ID NO 288
<211> LENGTH: 10
<212> TYPE: PRT
<213> ORGANISM: Artificial sequence
<220> FEATURE:
<223> OTHER INFORMATION: Synthetic peptide

<400> SEQUENCE: 288

Ile Gln Thr Lys Thr Asp Gly Gly Thr Thr
1               5                   10

<210> SEQ ID NO 289
<211> LENGTH: 18
<212> TYPE: PRT
<213> ORGANISM: Artificial sequence
<220> FEATURE:
<223> OTHER INFORMATION: Synthetic peptide

<400> SEQUENCE: 289

Ser Thr Gly Pro Tyr Tyr Tyr Asp Thr Ser Gly Tyr Pro Gln Pro Phe
1               5                   10                  15

Asp Tyr

<210> SEQ ID NO 290
<211> LENGTH: 8
<212> TYPE: PRT
<213> ORGANISM: Artificial sequence
<220> FEATURE:
<223> OTHER INFORMATION: Synthetic peptide

<400> SEQUENCE: 290

Gly Phe Asp Phe Ser Arg Tyr Thr
1               5

<210> SEQ ID NO 291
<211> LENGTH: 8
<212> TYPE: PRT
<213> ORGANISM: Artificial sequence
<220> FEATURE:
<223> OTHER INFORMATION: Synthetic peptide

<400> SEQUENCE: 291

Ile Ser Ser Thr Ser Leu Tyr Thr
1               5

<210> SEQ ID NO 292
<211> LENGTH: 11
<212> TYPE: PRT
<213> ORGANISM: Artificial sequence
<220> FEATURE:
<223> OTHER INFORMATION: Synthetic peptide

<400> SEQUENCE: 292

Ala Arg Val Val Gly Pro Ala Glu Leu Asp Tyr
1               5                   10

<210> SEQ ID NO 293
<211> LENGTH: 8
<212> TYPE: PRT
<213> ORGANISM: Artificial sequence
<220> FEATURE:

<223> OTHER INFORMATION: Synthetic peptide

<400> SEQUENCE: 293

Gly Tyr Thr Phe Thr Asp Tyr Tyr
1               5

<210> SEQ ID NO 294
<211> LENGTH: 8
<212> TYPE: PRT
<213> ORGANISM: Artificial sequence
<220> FEATURE:
<223> OTHER INFORMATION: Synthetic peptide

<400> SEQUENCE: 294

Ile Asn Pro Lys Thr Gly Gly Ser
1               5

<210> SEQ ID NO 295
<211> LENGTH: 10
<212> TYPE: PRT
<213> ORGANISM: Artificial sequence
<220> FEATURE:
<223> OTHER INFORMATION: Synthetic peptide

<400> SEQUENCE: 295

Ala Arg Ala Gly Arg Asn Gly Tyr Asp Tyr
1               5                   10

<210> SEQ ID NO 296
<211> LENGTH: 8
<212> TYPE: PRT
<213> ORGANISM: Artificial sequence
<220> FEATURE:
<223> OTHER INFORMATION: Synthetic peptide

<400> SEQUENCE: 296

Gly Phe Lys Phe Arg Asn Tyr Ala
1               5

<210> SEQ ID NO 297
<211> LENGTH: 7
<212> TYPE: PRT
<213> ORGANISM: Artificial sequence
<220> FEATURE:
<223> OTHER INFORMATION: Synthetic peptide

<400> SEQUENCE: 297

Ile Thr Ser Gly Gly Ser Thr
1               5

<210> SEQ ID NO 298
<211> LENGTH: 14
<212> TYPE: PRT
<213> ORGANISM: Artificial sequence
<220> FEATURE:
<223> OTHER INFORMATION: Synthetic peptide

<400> SEQUENCE: 298

Thr Val Pro Trp Gly Asn Tyr Asn Asp Tyr Val Ser Asp Tyr
1               5                   10

<210> SEQ ID NO 299
<211> LENGTH: 8
<212> TYPE: PRT
<213> ORGANISM: Artificial sequence
<220> FEATURE:
<223> OTHER INFORMATION: Synthetic peptide

```
<400> SEQUENCE: 299

Gly Phe Ile Phe Ser Arg Tyr Pro
1               5

<210> SEQ ID NO 300
<211> LENGTH: 8
<212> TYPE: PRT
<213> ORGANISM: Artificial sequence
<220> FEATURE:
<223> OTHER INFORMATION: Synthetic peptide

<400> SEQUENCE: 300

Ile Ser Tyr Asp Gly Asn Asn Lys
1               5

<210> SEQ ID NO 301
<211> LENGTH: 17
<212> TYPE: PRT
<213> ORGANISM: Artificial sequence
<220> FEATURE:
<223> OTHER INFORMATION: Synthetic peptide

<400> SEQUENCE: 301

Ala Arg His Phe Leu Pro Tyr Ser Ser Ser Trp Tyr Gln Gly Phe Asn
1               5                   10                  15
Tyr

<210> SEQ ID NO 302
<211> LENGTH: 8
<212> TYPE: PRT
<213> ORGANISM: Artificial sequence
<220> FEATURE:
<223> OTHER INFORMATION: Synthetic peptide

<400> SEQUENCE: 302

Gly Phe Leu Phe Ser Arg Tyr Gly
1               5

<210> SEQ ID NO 303
<211> LENGTH: 8
<212> TYPE: PRT
<213> ORGANISM: Artificial sequence
<220> FEATURE:
<223> OTHER INFORMATION: Synthetic peptide

<400> SEQUENCE: 303

Ile Ser Tyr Asp Gly Asn Lys Lys
1               5

<210> SEQ ID NO 304
<211> LENGTH: 15
<212> TYPE: PRT
<213> ORGANISM: Artificial sequence
<220> FEATURE:
<223> OTHER INFORMATION: Synthetic peptide

<400> SEQUENCE: 304

Ala Arg Gly Val Pro Tyr Gly Asp Thr Leu Thr Gly Leu Val Tyr
1               5                   10                  15

<210> SEQ ID NO 305
<211> LENGTH: 10
<212> TYPE: PRT
<213> ORGANISM: Artificial sequence
<220> FEATURE:
```

<223> OTHER INFORMATION: Synthetic peptide

<400> SEQUENCE: 305

Gly Phe Ser Leu Arg Asn Ala Arg Met Gly
1               5                   10

<210> SEQ ID NO 306
<211> LENGTH: 7
<212> TYPE: PRT
<213> ORGANISM: Artificial sequence
<220> FEATURE:
<223> OTHER INFORMATION: Synthetic peptide

<400> SEQUENCE: 306

Ile Phe Ser Asn Asp Glu Lys
1               5

<210> SEQ ID NO 307
<211> LENGTH: 17
<212> TYPE: PRT
<213> ORGANISM: Artificial sequence
<220> FEATURE:
<223> OTHER INFORMATION: Synthetic peptide

<400> SEQUENCE: 307

Ala Arg Leu Leu Val Ala Gly Thr Phe Leu Pro Ser His Tyr Phe Asp
1               5                   10                  15

Tyr

<210> SEQ ID NO 308
<211> LENGTH: 8
<212> TYPE: PRT
<213> ORGANISM: Artificial sequence
<220> FEATURE:
<223> OTHER INFORMATION: Synthetic peptide

<400> SEQUENCE: 308

Gly Phe Thr Phe Ser Thr Tyr Ser
1               5

<210> SEQ ID NO 309
<211> LENGTH: 8
<212> TYPE: PRT
<213> ORGANISM: Artificial sequence
<220> FEATURE:
<223> OTHER INFORMATION: Synthetic peptide

<400> SEQUENCE: 309

Ile Ser Ser Ser Ser Ser Thr Ile
1               5

<210> SEQ ID NO 310
<211> LENGTH: 15
<212> TYPE: PRT
<213> ORGANISM: Artificial sequence
<220> FEATURE:
<223> OTHER INFORMATION: Synthetic peptide

<400> SEQUENCE: 310

Thr Arg Gln Val Gly Ala Asp Phe Ser Gly Arg Gly Phe Asp Tyr
1               5                   10                  15

<210> SEQ ID NO 311
<211> LENGTH: 8
<212> TYPE: PRT
<213> ORGANISM: Artificial sequence

```
<220> FEATURE:
<223> OTHER INFORMATION: Synthetic peptide

<400> SEQUENCE: 311

Gly Phe Lys Phe Ser Val Tyr Ala
1               5

<210> SEQ ID NO 312
<211> LENGTH: 8
<212> TYPE: PRT
<213> ORGANISM: Artificial sequence
<220> FEATURE:
<223> OTHER INFORMATION: Synthetic peptide

<400> SEQUENCE: 312

Ile Ser Ser Ser Gly Ser Thr Ile
1               5

<210> SEQ ID NO 313
<211> LENGTH: 13
<212> TYPE: PRT
<213> ORGANISM: Artificial sequence
<220> FEATURE:
<223> OTHER INFORMATION: Synthetic peptide

<400> SEQUENCE: 313

Ala Thr Ala Arg His Ile Thr Asn Asp Gly Phe Asp Ile
1               5                   10

<210> SEQ ID NO 314
<211> LENGTH: 9
<212> TYPE: PRT
<213> ORGANISM: Artificial sequence
<220> FEATURE:
<223> OTHER INFORMATION: Synthetic peptide

<400> SEQUENCE: 314

Gly Tyr Leu Ile Ser Asn Gly Tyr Tyr
1               5

<210> SEQ ID NO 315
<211> LENGTH: 7
<212> TYPE: PRT
<213> ORGANISM: Artificial sequence
<220> FEATURE:
<223> OTHER INFORMATION: Synthetic peptide

<400> SEQUENCE: 315

Ile Tyr His Thr Arg Ser Thr
1               5

<210> SEQ ID NO 316
<211> LENGTH: 20
<212> TYPE: PRT
<213> ORGANISM: Artificial sequence
<220> FEATURE:
<223> OTHER INFORMATION: Synthetic peptide

<400> SEQUENCE: 316

Ala Arg Gly Pro Gly His Cys Tyr Gly Asp Asp Cys Tyr Ala Tyr
1               5                   10                  15

Tyr Phe Asp Gln
            20

<210> SEQ ID NO 317
<211> LENGTH: 8
```

```
<212> TYPE: PRT
<213> ORGANISM: Artificial sequence
<220> FEATURE:
<223> OTHER INFORMATION: Synthetic peptide

<400> SEQUENCE: 317

Gly Gly Thr Phe Ser Arg Phe Ala
1               5

<210> SEQ ID NO 318
<211> LENGTH: 8
<212> TYPE: PRT
<213> ORGANISM: Artificial sequence
<220> FEATURE:
<223> OTHER INFORMATION: Synthetic peptide

<400> SEQUENCE: 318

Ile Leu Pro Ile Phe Gly Thr Ala
1               5

<210> SEQ ID NO 319
<211> LENGTH: 20
<212> TYPE: PRT
<213> ORGANISM: Artificial sequence
<220> FEATURE:
<223> OTHER INFORMATION: Synthetic peptide

<400> SEQUENCE: 319

Ala Arg Ser Leu Pro Tyr Cys Thr Asn Asp Val Cys Ser Asn Gln Asn
1               5                   10                  15

Thr Phe Asp Tyr
            20

<210> SEQ ID NO 320
<211> LENGTH: 10
<212> TYPE: PRT
<213> ORGANISM: Artificial sequence
<220> FEATURE:
<223> OTHER INFORMATION: Synthetic peptide

<400> SEQUENCE: 320

Gly Gly Ser Ile Ser Ser Gly Asp Tyr Tyr
1               5                   10

<210> SEQ ID NO 321
<211> LENGTH: 7
<212> TYPE: PRT
<213> ORGANISM: Artificial sequence
<220> FEATURE:
<223> OTHER INFORMATION: Synthetic peptide

<400> SEQUENCE: 321

Ile Tyr Tyr Ser Gly Ser Thr
1               5

<210> SEQ ID NO 322
<211> LENGTH: 15
<212> TYPE: PRT
<213> ORGANISM: Artificial sequence
<220> FEATURE:
<223> OTHER INFORMATION: Synthetic peptide

<400> SEQUENCE: 322

Ala Ser Arg Tyr Gly Asp Pro Ile Gly Asp Asn Trp Phe Asp Pro
1               5                   10                  15
```

```
<210> SEQ ID NO 323
<211> LENGTH: 8
<212> TYPE: PRT
<213> ORGANISM: Artificial sequence
<220> FEATURE:
<223> OTHER INFORMATION: Synthetic peptide

<400> SEQUENCE: 323

Gly Phe Arg Phe Ser Phe Tyr Gly
1               5

<210> SEQ ID NO 324
<211> LENGTH: 8
<212> TYPE: PRT
<213> ORGANISM: Artificial sequence
<220> FEATURE:
<223> OTHER INFORMATION: Synthetic peptide

<400> SEQUENCE: 324

Ile Ser Gly Thr Gly Ala Thr Arg
1               5

<210> SEQ ID NO 325
<211> LENGTH: 14
<212> TYPE: PRT
<213> ORGANISM: Artificial sequence
<220> FEATURE:
<223> OTHER INFORMATION: Synthetic peptide

<400> SEQUENCE: 325

Val Arg Arg Phe Pro Met Thr Thr Val Thr Ser Phe Asp Ser
1               5                   10

<210> SEQ ID NO 326
<211> LENGTH: 8
<212> TYPE: PRT
<213> ORGANISM: Artificial sequence
<220> FEATURE:
<223> OTHER INFORMATION: Synthetic peptide

<400> SEQUENCE: 326

Gly Phe Pro Phe Asn Met Phe Trp
1               5

<210> SEQ ID NO 327
<211> LENGTH: 8
<212> TYPE: PRT
<213> ORGANISM: Artificial sequence
<220> FEATURE:
<223> OTHER INFORMATION: Synthetic peptide

<400> SEQUENCE: 327

Ile Lys Gln Asp Gly Ser Glu Lys
1               5

<210> SEQ ID NO 328
<211> LENGTH: 18
<212> TYPE: PRT
<213> ORGANISM: Artificial sequence
<220> FEATURE:
<223> OTHER INFORMATION: Synthetic peptide

<400> SEQUENCE: 328

Val Arg Glu Gly Val Arg Arg Val Val Arg Ser Thr Gly Tyr Phe
1               5                   10                  15

Asp Phe
```

<210> SEQ ID NO 329
<211> LENGTH: 10
<212> TYPE: PRT
<213> ORGANISM: Artificial sequence
<220> FEATURE:
<223> OTHER INFORMATION: Synthetic peptide

<400> SEQUENCE: 329

Gly Gly Pro Ile Ser Asn Gly Pro Tyr Tyr
1               5                   10

<210> SEQ ID NO 330
<211> LENGTH: 7
<212> TYPE: PRT
<213> ORGANISM: Artificial sequence
<220> FEATURE:
<223> OTHER INFORMATION: Synthetic peptide

<400> SEQUENCE: 330

Ile Phe Tyr Ser Gly Ser Thr
1               5

<210> SEQ ID NO 331
<211> LENGTH: 13
<212> TYPE: PRT
<213> ORGANISM: Artificial sequence
<220> FEATURE:
<223> OTHER INFORMATION: Synthetic peptide

<400> SEQUENCE: 331

Ala Arg His Val Val Thr Ala Ser Gly Trp Phe Asp Pro
1               5                   10

<210> SEQ ID NO 332
<211> LENGTH: 10
<212> TYPE: PRT
<213> ORGANISM: Artificial sequence
<220> FEATURE:
<223> OTHER INFORMATION: Synthetic peptide

<400> SEQUENCE: 332

Gly Gly Pro Ile Ser Asn Gly Pro Tyr Tyr
1               5                   10

<210> SEQ ID NO 333
<211> LENGTH: 7
<212> TYPE: PRT
<213> ORGANISM: Artificial sequence
<220> FEATURE:
<223> OTHER INFORMATION: Synthetic peptide

<400> SEQUENCE: 333

Ile Phe Tyr Ser Gly Ser Thr
1               5

<210> SEQ ID NO 334
<211> LENGTH: 13
<212> TYPE: PRT
<213> ORGANISM: Artificial sequence
<220> FEATURE:
<223> OTHER INFORMATION: Synthetic peptide

<400> SEQUENCE: 334

Ala Arg His Val Val Thr Ala Ser Gly Trp Phe Asp Pro
1               5                   10

<210> SEQ ID NO 335
<211> LENGTH: 8
<212> TYPE: PRT
<213> ORGANISM: Artificial sequence
<220> FEATURE:
<223> OTHER INFORMATION: Synthetic peptide

<400> SEQUENCE: 335

Gly Val Thr Phe Ser Asp Asn Ala
1               5

<210> SEQ ID NO 336
<211> LENGTH: 8
<212> TYPE: PRT
<213> ORGANISM: Artificial sequence
<220> FEATURE:
<223> OTHER INFORMATION: Synthetic peptide

<400> SEQUENCE: 336

Ile Ser Tyr Asp Gly Ser Ser Arg
1               5

<210> SEQ ID NO 337
<211> LENGTH: 15
<212> TYPE: PRT
<213> ORGANISM: Artificial sequence
<220> FEATURE:
<223> OTHER INFORMATION: Synthetic peptide

<400> SEQUENCE: 337

Ala Arg Val Thr Ala Asp Tyr Tyr Glu Ser Ser Gly Lys Val Phe
1               5                   10                  15

<210> SEQ ID NO 338
<211> LENGTH: 8
<212> TYPE: PRT
<213> ORGANISM: Artificial sequence
<220> FEATURE:
<223> OTHER INFORMATION: Synthetic peptide

<400> SEQUENCE: 338

Gly Gly Ser Ile Ser Asp His Tyr
1               5

<210> SEQ ID NO 339
<211> LENGTH: 7
<212> TYPE: PRT
<213> ORGANISM: Artificial sequence
<220> FEATURE:
<223> OTHER INFORMATION: Synthetic peptide

<400> SEQUENCE: 339

Ile Tyr Thr Ser Gly Thr Thr
1               5

<210> SEQ ID NO 340
<211> LENGTH: 18
<212> TYPE: PRT
<213> ORGANISM: Artificial sequence
<220> FEATURE:
<223> OTHER INFORMATION: Synthetic peptide

<400> SEQUENCE: 340

Ala Arg Ser Leu Glu Thr Val Ile Arg Phe Tyr Tyr Tyr His Tyr Met
1               5                   10                  15

Asp Val

<210> SEQ ID NO 341
<211> LENGTH: 8
<212> TYPE: PRT
<213> ORGANISM: Artificial sequence
<220> FEATURE:
<223> OTHER INFORMATION: Synthetic peptide

<400> SEQUENCE: 341

Gly Gly Ser Ile Gly Asp Tyr His
1               5

<210> SEQ ID NO 342
<211> LENGTH: 7
<212> TYPE: PRT
<213> ORGANISM: Artificial sequence
<220> FEATURE:
<223> OTHER INFORMATION: Synthetic peptide

<400> SEQUENCE: 342

Ile His Ser Ser Gly Asn Thr
1               5

<210> SEQ ID NO 343
<211> LENGTH: 8
<212> TYPE: PRT
<213> ORGANISM: Artificial sequence
<220> FEATURE:
<223> OTHER INFORMATION: Synthetic peptide

<400> SEQUENCE: 343

Ala Arg Gln Asn Val Phe Asp Ile
1               5

<210> SEQ ID NO 344
<211> LENGTH: 8
<212> TYPE: PRT
<213> ORGANISM: Artificial sequence
<220> FEATURE:
<223> OTHER INFORMATION: Synthetic peptide

<400> SEQUENCE: 344

Gly Ile Ser Ile Asn Asn Tyr Tyr
1               5

<210> SEQ ID NO 345
<211> LENGTH: 7
<212> TYPE: PRT
<213> ORGANISM: Artificial sequence
<220> FEATURE:
<223> OTHER INFORMATION: Synthetic peptide

<400> SEQUENCE: 345

Val Tyr Ser Thr Gly Ser Ser
1               5

<210> SEQ ID NO 346
<211> LENGTH: 8
<212> TYPE: PRT
<213> ORGANISM: Artificial sequence
<220> FEATURE:
<223> OTHER INFORMATION: Synthetic peptide

<400> SEQUENCE: 346

Ala Arg Gly Ser Met Pro His Ile
1               5

```
<210> SEQ ID NO 347
<211> LENGTH: 8
<212> TYPE: PRT
<213> ORGANISM: Artificial sequence
<220> FEATURE:
<223> OTHER INFORMATION: Synthetic peptide

<400> SEQUENCE: 347

Gly Ile Thr Phe Ser Asn Ala Trp
1               5

<210> SEQ ID NO 348
<211> LENGTH: 10
<212> TYPE: PRT
<213> ORGANISM: Artificial sequence
<220> FEATURE:
<223> OTHER INFORMATION: Synthetic peptide

<400> SEQUENCE: 348

Ile Glu Ser Lys Ile Asp Gly Gly Thr Ile
1               5                   10

<210> SEQ ID NO 349
<211> LENGTH: 21
<212> TYPE: PRT
<213> ORGANISM: Artificial sequence
<220> FEATURE:
<223> OTHER INFORMATION: Synthetic peptide

<400> SEQUENCE: 349

Thr Thr Asp Gln Gly Tyr Tyr Asp Arg Ser Gly Tyr Trp Val Val Gly
1               5                   10                  15

Asn His Phe Asp Tyr
            20

<210> SEQ ID NO 350
<211> LENGTH: 8
<212> TYPE: PRT
<213> ORGANISM: Artificial sequence
<220> FEATURE:
<223> OTHER INFORMATION: Synthetic peptide

<400> SEQUENCE: 350

Gly Phe Thr Phe Ser Ser Tyr Ala
1               5

<210> SEQ ID NO 351
<211> LENGTH: 8
<212> TYPE: PRT
<213> ORGANISM: Artificial sequence
<220> FEATURE:
<223> OTHER INFORMATION: Synthetic peptide

<400> SEQUENCE: 351

Ile Ser Gly Thr Thr Gly Ser Thr
1               5

<210> SEQ ID NO 352
<211> LENGTH: 16
<212> TYPE: PRT
<213> ORGANISM: Artificial sequence
<220> FEATURE:
<223> OTHER INFORMATION: Synthetic peptide

<400> SEQUENCE: 352

Ala Lys Asp Ser His Ser Met Ile Val Val Asp His Ala Phe Asp Ile
1               5                   10                  15
```

```
<210> SEQ ID NO 353
<211> LENGTH: 8
<212> TYPE: PRT
<213> ORGANISM: Artificial sequence
<220> FEATURE:
<223> OTHER INFORMATION: Synthetic peptide

<400> SEQUENCE: 353

Gly Phe Thr Phe Ser Thr Tyr Ile
1               5

<210> SEQ ID NO 354
<211> LENGTH: 8
<212> TYPE: PRT
<213> ORGANISM: Artificial sequence
<220> FEATURE:
<223> OTHER INFORMATION: Synthetic peptide

<400> SEQUENCE: 354

Ile Ser Thr Ser Ser Val Tyr Thr
1               5

<210> SEQ ID NO 355
<211> LENGTH: 12
<212> TYPE: PRT
<213> ORGANISM: Artificial sequence
<220> FEATURE:
<223> OTHER INFORMATION: Synthetic peptide

<400> SEQUENCE: 355

Ala Arg Glu Glu Gly Phe Arg Ala Tyr Asn Leu Tyr
1               5                   10

<210> SEQ ID NO 356
<211> LENGTH: 8
<212> TYPE: PRT
<213> ORGANISM: Artificial sequence
<220> FEATURE:
<223> OTHER INFORMATION: Synthetic peptide

<400> SEQUENCE: 356

Gly Phe Thr Phe Ser Arg Phe Gly
1               5

<210> SEQ ID NO 357
<211> LENGTH: 8
<212> TYPE: PRT
<213> ORGANISM: Artificial sequence
<220> FEATURE:
<223> OTHER INFORMATION: Synthetic peptide

<400> SEQUENCE: 357

Ile Ser Phe Asp Gly Ser Asn Arg
1               5

<210> SEQ ID NO 358
<211> LENGTH: 14
<212> TYPE: PRT
<213> ORGANISM: Artificial sequence
<220> FEATURE:
<223> OTHER INFORMATION: Synthetic peptide

<400> SEQUENCE: 358

Ala Arg Asp Trp Asp Arg Leu Val Arg Ser Ala Val Gly Tyr
1               5                   10
```

<210> SEQ ID NO 359
<211> LENGTH: 10
<212> TYPE: PRT
<213> ORGANISM: Artificial sequence
<220> FEATURE:
<223> OTHER INFORMATION: Synthetic peptide

<400> SEQUENCE: 359

Gly Gly Ser Val Ser Thr Ala Thr Tyr Tyr
1               5                   10

<210> SEQ ID NO 360
<211> LENGTH: 7
<212> TYPE: PRT
<213> ORGANISM: Artificial sequence
<220> FEATURE:
<223> OTHER INFORMATION: Synthetic peptide

<400> SEQUENCE: 360

Ile Tyr Ser Ser Gly Asn Thr
1               5

<210> SEQ ID NO 361
<211> LENGTH: 18
<212> TYPE: PRT
<213> ORGANISM: Artificial sequence
<220> FEATURE:
<223> OTHER INFORMATION: Synthetic peptide

<400> SEQUENCE: 361

Glu Arg Arg Leu Arg Ile Leu Ser Ile Glu Arg Asn Tyr Tyr Ala Met
1               5                   10                  15

Asp Val

<210> SEQ ID NO 362
<211> LENGTH: 8
<212> TYPE: PRT
<213> ORGANISM: Artificial sequence
<220> FEATURE:
<223> OTHER INFORMATION: Synthetic peptide

<400> SEQUENCE: 362

Gly Phe Thr Phe Ser Ser Tyr Ala
1               5

<210> SEQ ID NO 363
<211> LENGTH: 8
<212> TYPE: PRT
<213> ORGANISM: Artificial sequence
<220> FEATURE:
<223> OTHER INFORMATION: Synthetic peptide

<400> SEQUENCE: 363

Ile Ser Tyr Asp Ala Ser Lys Lys
1               5

<210> SEQ ID NO 364
<211> LENGTH: 23
<212> TYPE: PRT
<213> ORGANISM: Artificial sequence
<220> FEATURE:
<223> OTHER INFORMATION: Synthetic peptide

<400> SEQUENCE: 364

Ala Arg Asp His Val Pro Pro Lys Asp Cys Ser Asp Gly Asn Cys His
1               5                   10                  15

```
Ser Asp Tyr Gly Met Asp Val
            20

<210> SEQ ID NO 365
<211> LENGTH: 8
<212> TYPE: PRT
<213> ORGANISM: Artificial sequence
<220> FEATURE:
<223> OTHER INFORMATION: Synthetic peptide

<400> SEQUENCE: 365

Gly Tyr Ser Phe Thr Asn Phe Ala
1               5

<210> SEQ ID NO 366
<211> LENGTH: 8
<212> TYPE: PRT
<213> ORGANISM: Artificial sequence
<220> FEATURE:
<223> OTHER INFORMATION: Synthetic peptide

<400> SEQUENCE: 366

Ile Asn Pro Gly Asn Arg Asn Thr
1               5

<210> SEQ ID NO 367
<211> LENGTH: 15
<212> TYPE: PRT
<213> ORGANISM: Artificial sequence
<220> FEATURE:
<223> OTHER INFORMATION: Synthetic peptide

<400> SEQUENCE: 367

Ala Arg Leu Pro Ile Ala Ala Ala Gly Arg Gly Trp Phe Asp Pro
1               5                   10                  15

<210> SEQ ID NO 368
<211> LENGTH: 8
<212> TYPE: PRT
<213> ORGANISM: Artificial sequence
<220> FEATURE:
<223> OTHER INFORMATION: Synthetic peptide

<400> SEQUENCE: 368

Gly Phe Thr Phe Asn Thr Tyr Gly
1               5

<210> SEQ ID NO 369
<211> LENGTH: 8
<212> TYPE: PRT
<213> ORGANISM: Artificial sequence
<220> FEATURE:
<223> OTHER INFORMATION: Synthetic peptide

<400> SEQUENCE: 369

Ile Ser Ser Ala Thr Thr Thr Phe
1               5

<210> SEQ ID NO 370
<211> LENGTH: 14
<212> TYPE: PRT
<213> ORGANISM: Artificial sequence
<220> FEATURE:
<223> OTHER INFORMATION: Synthetic peptide

<400> SEQUENCE: 370
```

Ala Arg Val Tyr Thr Met Leu Arg Gly Ala Ser Met Asp Val
1               5                   10

<210> SEQ ID NO 371
<211> LENGTH: 8
<212> TYPE: PRT
<213> ORGANISM: Artificial sequence
<220> FEATURE:
<223> OTHER INFORMATION: Synthetic peptide

<400> SEQUENCE: 371

Gly Tyr Thr Phe Thr Ala Tyr Tyr
1               5

<210> SEQ ID NO 372
<211> LENGTH: 8
<212> TYPE: PRT
<213> ORGANISM: Artificial sequence
<220> FEATURE:
<223> OTHER INFORMATION: Synthetic peptide

<400> SEQUENCE: 372

Ile Asn Pro Ile Ser Gly Gly Thr
1               5

<210> SEQ ID NO 373
<211> LENGTH: 16
<212> TYPE: PRT
<213> ORGANISM: Artificial sequence
<220> FEATURE:
<223> OTHER INFORMATION: Synthetic peptide

<400> SEQUENCE: 373

Ala Arg Val Lys Cys Ser Ser Ala Asn Cys Tyr Gly Asn Phe Asp Tyr
1               5                   10                  15

<210> SEQ ID NO 374
<211> LENGTH: 8
<212> TYPE: PRT
<213> ORGANISM: Artificial sequence
<220> FEATURE:
<223> OTHER INFORMATION: Synthetic peptide

<400> SEQUENCE: 374

Gly Tyr Arg Phe Thr Asn Tyr Arg
1               5

<210> SEQ ID NO 375
<211> LENGTH: 8
<212> TYPE: PRT
<213> ORGANISM: Artificial sequence
<220> FEATURE:
<223> OTHER INFORMATION: Synthetic peptide

<400> SEQUENCE: 375

Ile Tyr Pro Gly Gly Ser Asp Thr
1               5

<210> SEQ ID NO 376
<211> LENGTH: 16
<212> TYPE: PRT
<213> ORGANISM: Artificial sequence
<220> FEATURE:
<223> OTHER INFORMATION: Synthetic peptide

<400> SEQUENCE: 376

Ala Arg Gln Thr Thr Gln Asn Ser Gly Tyr Asp Arg Trp Phe Asp Ser

```
<210> SEQ ID NO 377
<211> LENGTH: 8
<212> TYPE: PRT
<213> ORGANISM: Artificial sequence
<220> FEATURE:
<223> OTHER INFORMATION: Synthetic peptide

<400> SEQUENCE: 377

Gly Ile Thr Phe Ser Arg His Thr
1               5

<210> SEQ ID NO 378
<211> LENGTH: 8
<212> TYPE: PRT
<213> ORGANISM: Artificial sequence
<220> FEATURE:
<223> OTHER INFORMATION: Synthetic peptide

<400> SEQUENCE: 378

Ile Ser Gly Ser Gly Gly Ser Thr
1               5

<210> SEQ ID NO 379
<211> LENGTH: 19
<212> TYPE: PRT
<213> ORGANISM: Artificial sequence
<220> FEATURE:
<223> OTHER INFORMATION: Synthetic peptide

<400> SEQUENCE: 379

Ala Ile Ser Val Pro Leu Leu Arg Phe Leu Glu Trp Phe Gln His Pro
1               5                   10                  15

Phe Asp Phe

<210> SEQ ID NO 380
<211> LENGTH: 8
<212> TYPE: PRT
<213> ORGANISM: Artificial sequence
<220> FEATURE:
<223> OTHER INFORMATION: Synthetic peptide

<400> SEQUENCE: 380

Gly Phe Thr Phe Asn Thr Tyr Ser
1               5

<210> SEQ ID NO 381
<211> LENGTH: 8
<212> TYPE: PRT
<213> ORGANISM: Artificial sequence
<220> FEATURE:
<223> OTHER INFORMATION: Synthetic peptide

<400> SEQUENCE: 381

Ile Ser Ser Thr Gly Ser Tyr Ile
1               5

<210> SEQ ID NO 382
<211> LENGTH: 13
<212> TYPE: PRT
<213> ORGANISM: Artificial sequence
<220> FEATURE:
<223> OTHER INFORMATION: Synthetic peptide

<400> SEQUENCE: 382
```

Val Arg Phe Thr Met Thr Thr Val Thr Asn Phe Asp Ser
1               5                   10

<210> SEQ ID NO 383
<211> LENGTH: 8
<212> TYPE: PRT
<213> ORGANISM: Artificial sequence
<220> FEATURE:
<223> OTHER INFORMATION: Synthetic peptide

<400> SEQUENCE: 383

Gly Phe Thr Phe Thr Asn Tyr Gly
1               5

<210> SEQ ID NO 384
<211> LENGTH: 8
<212> TYPE: PRT
<213> ORGANISM: Artificial sequence
<220> FEATURE:
<223> OTHER INFORMATION: Synthetic peptide

<400> SEQUENCE: 384

Ile Ser Tyr Asp Gly Gly Asn Lys
1               5

<210> SEQ ID NO 385
<211> LENGTH: 19
<212> TYPE: PRT
<213> ORGANISM: Artificial sequence
<220> FEATURE:
<223> OTHER INFORMATION: Synthetic peptide

<400> SEQUENCE: 385

Pro Lys Val Ile Pro His Pro Tyr Tyr Asp Ser Ser Gly Asp Asp Ala
1               5                   10                  15

Phe Asp Ile

<210> SEQ ID NO 386
<211> LENGTH: 8
<212> TYPE: PRT
<213> ORGANISM: Artificial sequence
<220> FEATURE:
<223> OTHER INFORMATION: Synthetic peptide

<400> SEQUENCE: 386

Gly Phe Pro Phe Ser Ser Tyr Ser
1               5

<210> SEQ ID NO 387
<211> LENGTH: 8
<212> TYPE: PRT
<213> ORGANISM: Artificial sequence
<220> FEATURE:
<223> OTHER INFORMATION: Synthetic peptide

<400> SEQUENCE: 387

Ile Ser Gly Ser Gly Gly Asp Ile
1               5

<210> SEQ ID NO 388
<211> LENGTH: 15
<212> TYPE: PRT
<213> ORGANISM: Artificial sequence
<220> FEATURE:
<223> OTHER INFORMATION: Synthetic peptide

<400> SEQUENCE: 388

Ala Arg Gly Leu Val Ala Thr Thr Gly Thr Arg Tyr Phe Asp Tyr
1               5                   10                  15

<210> SEQ ID NO 389
<211> LENGTH: 8
<212> TYPE: PRT
<213> ORGANISM: Artificial sequence
<220> FEATURE:
<223> OTHER INFORMATION: Synthetic peptide

<400> SEQUENCE: 389

Gly Gly Thr Phe Arg Arg Phe Ala
1               5

<210> SEQ ID NO 390
<211> LENGTH: 8
<212> TYPE: PRT
<213> ORGANISM: Artificial sequence
<220> FEATURE:
<223> OTHER INFORMATION: Synthetic peptide

<400> SEQUENCE: 390

Ile Ile Pro Ile Leu Gly Arg Gly
1               5

<210> SEQ ID NO 391
<211> LENGTH: 17
<212> TYPE: PRT
<213> ORGANISM: Artificial sequence
<220> FEATURE:
<223> OTHER INFORMATION: Synthetic peptide

<400> SEQUENCE: 391

Ala Arg Phe Ile Ser Thr Ala Ser Tyr Val Pro Gly Thr Phe Glu Asp
1               5                   10                  15

Val

<210> SEQ ID NO 392
<211> LENGTH: 8
<212> TYPE: PRT
<213> ORGANISM: Artificial sequence
<220> FEATURE:
<223> OTHER INFORMATION: Synthetic peptide

<400> SEQUENCE: 392

Gly Phe Thr Phe Arg Asn Tyr Asn
1               5

<210> SEQ ID NO 393
<211> LENGTH: 8
<212> TYPE: PRT
<213> ORGANISM: Artificial sequence
<220> FEATURE:
<223> OTHER INFORMATION: Synthetic peptide

<400> SEQUENCE: 393

Ile Ser Ser Thr Gly Ser Tyr Ile
1               5

<210> SEQ ID NO 394
<211> LENGTH: 13
<212> TYPE: PRT
<213> ORGANISM: Artificial sequence
<220> FEATURE:
<223> OTHER INFORMATION: Synthetic peptide

```
<400> SEQUENCE: 394

Ala Arg Met Val Arg Asn Thr Val Thr Ala Phe Asp Tyr
1               5                   10

<210> SEQ ID NO 395
<211> LENGTH: 8
<212> TYPE: PRT
<213> ORGANISM: Artificial sequence
<220> FEATURE:
<223> OTHER INFORMATION: Synthetic peptide

<400> SEQUENCE: 395

Gly Tyr Arg Leu Ile Asp Leu Pro
1               5

<210> SEQ ID NO 396
<211> LENGTH: 8
<212> TYPE: PRT
<213> ORGANISM: Artificial sequence
<220> FEATURE:
<223> OTHER INFORMATION: Synthetic peptide

<400> SEQUENCE: 396

Phe Asp Pro Glu Lys Ala Glu Ala
1               5

<210> SEQ ID NO 397
<211> LENGTH: 17
<212> TYPE: PRT
<213> ORGANISM: Artificial sequence
<220> FEATURE:
<223> OTHER INFORMATION: Synthetic peptide

<400> SEQUENCE: 397

Ala Thr Trp Gly Val Glu Val Val Asn Gly Arg Arg Asp Tyr Phe Asp
1               5                   10                  15

Ser

<210> SEQ ID NO 398
<211> LENGTH: 8
<212> TYPE: PRT
<213> ORGANISM: Artificial sequence
<220> FEATURE:
<223> OTHER INFORMATION: Synthetic peptide

<400> SEQUENCE: 398

Gly Phe Thr Phe Ser Ser Phe Glu
1               5

<210> SEQ ID NO 399
<211> LENGTH: 8
<212> TYPE: PRT
<213> ORGANISM: Artificial sequence
<220> FEATURE:
<223> OTHER INFORMATION: Synthetic peptide

<400> SEQUENCE: 399

Ile Ser Thr Ser Gly Ser Thr Ile
1               5

<210> SEQ ID NO 400
<211> LENGTH: 21
<212> TYPE: PRT
<213> ORGANISM: Artificial sequence
<220> FEATURE:
<223> OTHER INFORMATION: Synthetic peptide
```

<400> SEQUENCE: 400

Ala Arg Asp Val Arg Asp Cys Ser Ala Leu Thr Cys Pro Arg Arg Gly
1               5                   10                  15

Asp Ala Phe Asp Phe
            20

<210> SEQ ID NO 401
<211> LENGTH: 8
<212> TYPE: PRT
<213> ORGANISM: Artificial sequence
<220> FEATURE:
<223> OTHER INFORMATION: Synthetic peptide

<400> SEQUENCE: 401

Gly Phe Ser Phe Ser Val Tyr Pro
1               5

<210> SEQ ID NO 402
<211> LENGTH: 8
<212> TYPE: PRT
<213> ORGANISM: Artificial sequence
<220> FEATURE:
<223> OTHER INFORMATION: Synthetic peptide

<400> SEQUENCE: 402

Ile Ser Ser Ser Ser Arg Tyr Ile
1               5

<210> SEQ ID NO 403
<211> LENGTH: 14
<212> TYPE: PRT
<213> ORGANISM: Artificial sequence
<220> FEATURE:
<223> OTHER INFORMATION: Synthetic peptide

<400> SEQUENCE: 403

Val Lys Val Gly Gly Ser Lys His Gln Tyr Tyr Phe Asp Tyr
1               5                   10

<210> SEQ ID NO 404
<211> LENGTH: 8
<212> TYPE: PRT
<213> ORGANISM: Artificial sequence
<220> FEATURE:
<223> OTHER INFORMATION: Synthetic peptide

<400> SEQUENCE: 404

Gly Tyr Thr Phe Thr Asn Tyr Asp
1               5

<210> SEQ ID NO 405
<211> LENGTH: 8
<212> TYPE: PRT
<213> ORGANISM: Artificial sequence
<220> FEATURE:
<223> OTHER INFORMATION: Synthetic peptide

<400> SEQUENCE: 405

Ile Ser Thr Tyr Asn Gly Asn Thr
1               5

<210> SEQ ID NO 406
<211> LENGTH: 17
<212> TYPE: PRT
<213> ORGANISM: Artificial sequence

```
<220> FEATURE:
<223> OTHER INFORMATION: Synthetic peptide

<400> SEQUENCE: 406

Ala Arg Glu Arg Cys Ser Thr Ser Thr Cys Tyr Ser Arg Tyr Ala Asp
1               5                   10                  15
Tyr

<210> SEQ ID NO 407
<211> LENGTH: 8
<212> TYPE: PRT
<213> ORGANISM: Artificial sequence
<220> FEATURE:
<223> OTHER INFORMATION: Synthetic peptide

<400> SEQUENCE: 407

Gly Phe Thr Leu Ser Arg Tyr Glu
1               5

<210> SEQ ID NO 408
<211> LENGTH: 8
<212> TYPE: PRT
<213> ORGANISM: Artificial sequence
<220> FEATURE:
<223> OTHER INFORMATION: Synthetic peptide

<400> SEQUENCE: 408

Ile Ser Ser Gly Gly Pro Ser Ile
1               5

<210> SEQ ID NO 409
<211> LENGTH: 12
<212> TYPE: PRT
<213> ORGANISM: Artificial sequence
<220> FEATURE:
<223> OTHER INFORMATION: Synthetic peptide

<400> SEQUENCE: 409

Met Arg Glu Gly Leu Thr Tyr Tyr Asp Ser Thr Ile
1               5                   10

<210> SEQ ID NO 410
<211> LENGTH: 8
<212> TYPE: PRT
<213> ORGANISM: Artificial sequence
<220> FEATURE:
<223> OTHER INFORMATION: Synthetic peptide

<400> SEQUENCE: 410

Gly Phe Thr Phe Asp Glu Tyr Ala
1               5

<210> SEQ ID NO 411
<211> LENGTH: 8
<212> TYPE: PRT
<213> ORGANISM: Artificial sequence
<220> FEATURE:
<223> OTHER INFORMATION: Synthetic peptide

<400> SEQUENCE: 411

Ile Ser Trp Asn Gly Gly Ser Lys
1               5

<210> SEQ ID NO 412
<211> LENGTH: 12
<212> TYPE: PRT
```

```
<213> ORGANISM: Artificial sequence
<220> FEATURE:
<223> OTHER INFORMATION: Synthetic peptide

<400> SEQUENCE: 412

Ala Lys Asp Asp Tyr Glu Gly Ala Gly Phe Asp Ile
1               5                   10

<210> SEQ ID NO 413
<211> LENGTH: 9
<212> TYPE: PRT
<213> ORGANISM: Artificial sequence
<220> FEATURE:
<223> OTHER INFORMATION: Synthetic peptide

<400> SEQUENCE: 413

Gly Tyr Leu Ile Ser Asn Gly Tyr Tyr
1               5

<210> SEQ ID NO 414
<211> LENGTH: 7
<212> TYPE: PRT
<213> ORGANISM: Artificial sequence
<220> FEATURE:
<223> OTHER INFORMATION: Synthetic peptide

<400> SEQUENCE: 414

Ile Tyr Tyr Thr Arg Asp Thr
1               5

<210> SEQ ID NO 415
<211> LENGTH: 19
<212> TYPE: PRT
<213> ORGANISM: Artificial sequence
<220> FEATURE:
<223> OTHER INFORMATION: Synthetic peptide

<400> SEQUENCE: 415

Val Arg His Glu Gly Ser Cys Asn Asp Gly Ser Cys Tyr Gly Ser Phe
1               5                   10                  15

Val Asp Asn

<210> SEQ ID NO 416
<211> LENGTH: 8
<212> TYPE: PRT
<213> ORGANISM: Artificial sequence
<220> FEATURE:
<223> OTHER INFORMATION: Synthetic peptide

<400> SEQUENCE: 416

Asp Phe Thr Phe Ser Ser Tyr Thr
1               5

<210> SEQ ID NO 417
<211> LENGTH: 8
<212> TYPE: PRT
<213> ORGANISM: Artificial sequence
<220> FEATURE:
<223> OTHER INFORMATION: Synthetic peptide

<400> SEQUENCE: 417

Ile Ser Gly Asp Gly Val Ser Thr
1               5

<210> SEQ ID NO 418
<211> LENGTH: 13
```

<212> TYPE: PRT
<213> ORGANISM: Artificial sequence
<220> FEATURE:
<223> OTHER INFORMATION: Synthetic peptide

<400> SEQUENCE: 418

Ala Arg Gly Gly Thr Phe His Asn Trp Tyr Phe Asp Leu
1               5                   10

<210> SEQ ID NO 419
<211> LENGTH: 8
<212> TYPE: PRT
<213> ORGANISM: Artificial sequence
<220> FEATURE:
<223> OTHER INFORMATION: Synthetic peptide

<400> SEQUENCE: 419

Gly Phe Thr Phe Ser Thr Tyr Ala
1               5

<210> SEQ ID NO 420
<211> LENGTH: 8
<212> TYPE: PRT
<213> ORGANISM: Artificial sequence
<220> FEATURE:
<223> OTHER INFORMATION: Synthetic peptide

<400> SEQUENCE: 420

Ile Ser Gly Ser Gly Gly Ser Thr
1               5

<210> SEQ ID NO 421
<211> LENGTH: 14
<212> TYPE: PRT
<213> ORGANISM: Artificial sequence
<220> FEATURE:
<223> OTHER INFORMATION: Synthetic peptide

<400> SEQUENCE: 421

Ala Lys Gly Thr Ile Thr Tyr Ser Tyr Tyr Tyr Met Ala Val
1               5                   10

<210> SEQ ID NO 422
<211> LENGTH: 8
<212> TYPE: PRT
<213> ORGANISM: Artificial sequence
<220> FEATURE:
<223> OTHER INFORMATION: Synthetic peptide

<400> SEQUENCE: 422

Gly Tyr Arg Leu Thr Asp Leu Pro
1               5

<210> SEQ ID NO 423
<211> LENGTH: 8
<212> TYPE: PRT
<213> ORGANISM: Artificial sequence
<220> FEATURE:
<223> OTHER INFORMATION: Synthetic peptide

<400> SEQUENCE: 423

Val Asp Leu Glu Lys Arg Glu Ile
1               5

<210> SEQ ID NO 424
<211> LENGTH: 17
<212> TYPE: PRT

```
<213> ORGANISM: Artificial sequence
<220> FEATURE:
<223> OTHER INFORMATION: Synthetic peptide

<400> SEQUENCE: 424

Ala Thr Trp Gly Ile Glu Val Val Asn Gly Arg Asp Glu Phe Phe Asp
1               5                   10                  15
Ser

<210> SEQ ID NO 425
<211> LENGTH: 8
<212> TYPE: PRT
<213> ORGANISM: Artificial sequence
<220> FEATURE:
<223> OTHER INFORMATION: Synthetic peptide

<400> SEQUENCE: 425

Gly Tyr Ser Leu Ser Asp Leu Pro
1               5

<210> SEQ ID NO 426
<211> LENGTH: 8
<212> TYPE: PRT
<213> ORGANISM: Artificial sequence
<220> FEATURE:
<223> OTHER INFORMATION: Synthetic peptide

<400> SEQUENCE: 426

Phe Asp Pro Ile Asn Gly Glu Ile
1               5

<210> SEQ ID NO 427
<211> LENGTH: 17
<212> TYPE: PRT
<213> ORGANISM: Artificial sequence
<220> FEATURE:
<223> OTHER INFORMATION: Synthetic peptide

<400> SEQUENCE: 427

Ala Thr Trp Gly Val Ala Val Val Ser Gly Arg Arg Asp Tyr Phe Asp
1               5                   10                  15
Ser

<210> SEQ ID NO 428
<211> LENGTH: 10
<212> TYPE: PRT
<213> ORGANISM: Artificial sequence
<220> FEATURE:
<223> OTHER INFORMATION: Synthetic peptide

<400> SEQUENCE: 428

Gly Gly Ser Ile Thr Ser Gly Asp Tyr Tyr
1               5                   10

<210> SEQ ID NO 429
<211> LENGTH: 7
<212> TYPE: PRT
<213> ORGANISM: Artificial sequence
<220> FEATURE:
<223> OTHER INFORMATION: Synthetic peptide

<400> SEQUENCE: 429

Ile Tyr His Ser Gly Thr Thr
1               5
```

```
<210> SEQ ID NO 430
<211> LENGTH: 18
<212> TYPE: PRT
<213> ORGANISM: Artificial sequence
<220> FEATURE:
<223> OTHER INFORMATION: Synthetic peptide

<400> SEQUENCE: 430

Ala Arg Ala Tyr Ala Tyr Glu Phe Trp Ser Gly Tyr Pro Asn Trp Phe
1               5                   10                  15
Asp Pro

<210> SEQ ID NO 431
<211> LENGTH: 8
<212> TYPE: PRT
<213> ORGANISM: Artificial sequence
<220> FEATURE:
<223> OTHER INFORMATION: Synthetic peptide

<400> SEQUENCE: 431

Gly Phe Ile Phe Asn Arg Tyr Ala
1               5

<210> SEQ ID NO 432
<211> LENGTH: 8
<212> TYPE: PRT
<213> ORGANISM: Artificial sequence
<220> FEATURE:
<223> OTHER INFORMATION: Synthetic peptide

<400> SEQUENCE: 432

Ile Ser Tyr Asp Gly Ile Asn Lys
1               5

<210> SEQ ID NO 433
<211> LENGTH: 19
<212> TYPE: PRT
<213> ORGANISM: Artificial sequence
<220> FEATURE:
<223> OTHER INFORMATION: Synthetic peptide

<400> SEQUENCE: 433

Ala Arg Gly Leu Gly Tyr Cys Ser Gly Thr Gly Gly Ser Cys Thr Pro
1               5                   10                  15
Phe Glu Tyr

<210> SEQ ID NO 434
<211> LENGTH: 8
<212> TYPE: PRT
<213> ORGANISM: Artificial sequence
<220> FEATURE:
<223> OTHER INFORMATION: Synthetic peptide

<400> SEQUENCE: 434

Gly Ala Ser Leu Asn Asp Tyr Asp
1               5

<210> SEQ ID NO 435
<211> LENGTH: 7
<212> TYPE: PRT
<213> ORGANISM: Artificial sequence
<220> FEATURE:
<223> OTHER INFORMATION: Synthetic peptide

<400> SEQUENCE: 435

Ile Asn Arg Arg Asp Thr Val
```

<210> SEQ ID NO 436
<211> LENGTH: 29
<212> TYPE: PRT
<213> ORGANISM: Artificial sequence
<220> FEATURE:
<223> OTHER INFORMATION: Synthetic peptide

<400> SEQUENCE: 436

Val Arg Val Pro Arg Arg Gly Phe Glu Gly Ser Phe Gly Phe Cys Asp
1               5                   10                  15

Asp Thr Ala Cys Arg Tyr Gly His Thr Trp Phe Asp Pro
            20                  25

<210> SEQ ID NO 437
<211> LENGTH: 10
<212> TYPE: PRT
<213> ORGANISM: Artificial sequence
<220> FEATURE:
<223> OTHER INFORMATION: Synthetic peptide

<400> SEQUENCE: 437

Gly Phe Ser Leu Arg Asn Gly Arg Met Gly
1               5                   10

<210> SEQ ID NO 438
<211> LENGTH: 7
<212> TYPE: PRT
<213> ORGANISM: Artificial sequence
<220> FEATURE:
<223> OTHER INFORMATION: Synthetic peptide

<400> SEQUENCE: 438

Ile Phe Ala Ser Asp Glu Lys
1               5

<210> SEQ ID NO 439
<211> LENGTH: 17
<212> TYPE: PRT
<213> ORGANISM: Artificial sequence
<220> FEATURE:
<223> OTHER INFORMATION: Synthetic peptide

<400> SEQUENCE: 439

Ala Arg Ile Leu Lys Phe Gly Thr Met Arg Ala Ala Tyr Tyr Phe Asp
1               5                   10                  15

Tyr

<210> SEQ ID NO 440
<211> LENGTH: 8
<212> TYPE: PRT
<213> ORGANISM: Artificial sequence
<220> FEATURE:
<223> OTHER INFORMATION: Synthetic peptide

<400> SEQUENCE: 440

Gly Phe Thr Phe Ser Asp Tyr Tyr
1               5

<210> SEQ ID NO 441
<211> LENGTH: 8
<212> TYPE: PRT
<213> ORGANISM: Artificial sequence
<220> FEATURE:
<223> OTHER INFORMATION: Synthetic peptide

```
<400> SEQUENCE: 441

Ile Ser Ser Ser Gly Ser Thr Ile
1               5

<210> SEQ ID NO 442
<211> LENGTH: 18
<212> TYPE: PRT
<213> ORGANISM: Artificial sequence
<220> FEATURE:
<223> OTHER INFORMATION: Synthetic peptide

<400> SEQUENCE: 442

Ala Gly Ser Lys Val Gly Tyr Thr Thr Gly Arg Arg Asn Trp Tyr Phe
1               5                   10                  15

Asp Leu

<210> SEQ ID NO 443
<211> LENGTH: 8
<212> TYPE: PRT
<213> ORGANISM: Artificial sequence
<220> FEATURE:
<223> OTHER INFORMATION: Synthetic peptide

<400> SEQUENCE: 443

Gly Phe Thr Phe Thr Asp Phe Tyr
1               5

<210> SEQ ID NO 444
<211> LENGTH: 8
<212> TYPE: PRT
<213> ORGANISM: Artificial sequence
<220> FEATURE:
<223> OTHER INFORMATION: Synthetic peptide

<400> SEQUENCE: 444

Ile Asn Pro Glu Thr Gly Glu Thr
1               5

<210> SEQ ID NO 445
<211> LENGTH: 19
<212> TYPE: PRT
<213> ORGANISM: Artificial sequence
<220> FEATURE:
<223> OTHER INFORMATION: Synthetic peptide

<400> SEQUENCE: 445

Ala Arg Asp Leu Val Val Val Pro Val Glu Met Ser Arg Arg Ala
1               5                   10                  15

Phe Asp Ile

<210> SEQ ID NO 446
<211> LENGTH: 8
<212> TYPE: PRT
<213> ORGANISM: Artificial sequence
<220> FEATURE:
<223> OTHER INFORMATION: Synthetic peptide

<400> SEQUENCE: 446

Gly Tyr Ile Phe Ser Ala Tyr Tyr
1               5

<210> SEQ ID NO 447
<211> LENGTH: 8
<212> TYPE: PRT
```

```
<213> ORGANISM: Artificial sequence
<220> FEATURE:
<223> OTHER INFORMATION: Synthetic peptide

<400> SEQUENCE: 447

Met Asn Ala Lys Ser Gly Gly Ala
1               5

<210> SEQ ID NO 448
<211> LENGTH: 18
<212> TYPE: PRT
<213> ORGANISM: Artificial sequence
<220> FEATURE:
<223> OTHER INFORMATION: Synthetic peptide

<400> SEQUENCE: 448

Ala Arg Asp Tyr Arg Asp Asp Tyr Met Trp Gly Ser Tyr Arg Pro Leu
1               5                   10                  15

Asp Tyr

<210> SEQ ID NO 449
<211> LENGTH: 6
<212> TYPE: PRT
<213> ORGANISM: Artificial sequence
<220> FEATURE:
<223> OTHER INFORMATION: Synthetic peptide

<400> SEQUENCE: 449

Ala Leu Pro Lys Lys Tyr
1               5

<210> SEQ ID NO 450

<400> SEQUENCE: 450

000

<210> SEQ ID NO 451
<211> LENGTH: 11
<212> TYPE: PRT
<213> ORGANISM: Artificial sequence
<220> FEATURE:
<223> OTHER INFORMATION: Synthetic peptide

<400> SEQUENCE: 451

Ser Ser Thr Asp Ser Ser Gly Asn Pro Val Leu
1               5                   10

<210> SEQ ID NO 452
<211> LENGTH: 6
<212> TYPE: PRT
<213> ORGANISM: Artificial sequence
<220> FEATURE:
<223> OTHER INFORMATION: Synthetic peptide

<400> SEQUENCE: 452

Gln Ser Val Ser Thr Tyr
1               5

<210> SEQ ID NO 453

<400> SEQUENCE: 453

000

<210> SEQ ID NO 454
```

```
<211> LENGTH: 9
<212> TYPE: PRT
<213> ORGANISM: Artificial sequence
<220> FEATURE:
<223> OTHER INFORMATION: Synthetic peptide

<400> SEQUENCE: 454

Gln Gln Arg Ser Ser Trp Pro Ile Thr
1               5

<210> SEQ ID NO 455
<211> LENGTH: 9
<212> TYPE: PRT
<213> ORGANISM: Artificial sequence
<220> FEATURE:
<223> OTHER INFORMATION: Synthetic peptide

<400> SEQUENCE: 455

Ser Gly Ser Val Ser Ser Ser Tyr Tyr
1               5

<210> SEQ ID NO 456

<400> SEQUENCE: 456

000

<210> SEQ ID NO 457
<211> LENGTH: 10
<212> TYPE: PRT
<213> ORGANISM: Artificial sequence
<220> FEATURE:
<223> OTHER INFORMATION: Synthetic peptide

<400> SEQUENCE: 457

Gly Leu Tyr Met Gly Ser Gly Ile Trp Ile
1               5                   10

<210> SEQ ID NO 458
<211> LENGTH: 6
<212> TYPE: PRT
<213> ORGANISM: Artificial sequence
<220> FEATURE:
<223> OTHER INFORMATION: Synthetic peptide

<400> SEQUENCE: 458

Gln Gly Ile Ser Ser Trp
1               5

<210> SEQ ID NO 459

<400> SEQUENCE: 459

000

<210> SEQ ID NO 460
<211> LENGTH: 9
<212> TYPE: PRT
<213> ORGANISM: Artificial sequence
<220> FEATURE:
<223> OTHER INFORMATION: Synthetic peptide

<400> SEQUENCE: 460

Gln Gln Ala Asp Ser Phe Pro Arg Thr
1               5

<210> SEQ ID NO 461
```

```
<211> LENGTH: 6
<212> TYPE: PRT
<213> ORGANISM: Artificial sequence
<220> FEATURE:
<223> OTHER INFORMATION: Synthetic peptide

<400> SEQUENCE: 461

Gln Ser Ile Ser Lys Trp
1               5

<210> SEQ ID NO 462

<400> SEQUENCE: 462

000

<210> SEQ ID NO 463
<211> LENGTH: 9
<212> TYPE: PRT
<213> ORGANISM: Artificial sequence
<220> FEATURE:
<223> OTHER INFORMATION: Synthetic peptide

<400> SEQUENCE: 463

Gln Gln His Asn Ser Tyr Ser Tyr Thr
1               5

<210> SEQ ID NO 464
<211> LENGTH: 6
<212> TYPE: PRT
<213> ORGANISM: Artificial sequence
<220> FEATURE:
<223> OTHER INFORMATION: Synthetic peptide

<400> SEQUENCE: 464

Gln Ser Val Arg Ser Tyr
1               5

<210> SEQ ID NO 465

<400> SEQUENCE: 465

000

<210> SEQ ID NO 466
<211> LENGTH: 10
<212> TYPE: PRT
<213> ORGANISM: Artificial sequence
<220> FEATURE:
<223> OTHER INFORMATION: Synthetic peptide

<400> SEQUENCE: 466

Gln Gln Arg Ser Thr Trp Pro Pro Gly Met
1               5                   10

<210> SEQ ID NO 467
<211> LENGTH: 7
<212> TYPE: PRT
<213> ORGANISM: Artificial sequence
<220> FEATURE:
<223> OTHER INFORMATION: Synthetic peptide

<400> SEQUENCE: 467

Gln Ser Val Ser Ser Ser Phe
1               5

<210> SEQ ID NO 468
```

<400> SEQUENCE: 468

000

<210> SEQ ID NO 469
<211> LENGTH: 9
<212> TYPE: PRT
<213> ORGANISM: Artificial sequence
<220> FEATURE:
<223> OTHER INFORMATION: Synthetic peptide

<400> SEQUENCE: 469

Gln Gln Tyr Ser Asn Ser Arg Leu Thr
1               5

<210> SEQ ID NO 470
<211> LENGTH: 9
<212> TYPE: PRT
<213> ORGANISM: Artificial sequence
<220> FEATURE:
<223> OTHER INFORMATION: Synthetic peptide

<400> SEQUENCE: 470

Ser Ser Asp Val Gly Gly Tyr Asn Tyr
1               5

<210> SEQ ID NO 471

<400> SEQUENCE: 471

000

<210> SEQ ID NO 472
<211> LENGTH: 11
<212> TYPE: PRT
<213> ORGANISM: Artificial sequence
<220> FEATURE:
<223> OTHER INFORMATION: Synthetic peptide

<400> SEQUENCE: 472

Ser Ser Tyr Thr Thr Ser Asn Thr Leu Val Val
1               5                   10

<210> SEQ ID NO 473
<211> LENGTH: 6
<212> TYPE: PRT
<213> ORGANISM: Artificial sequence
<220> FEATURE:
<223> OTHER INFORMATION: Synthetic peptide

<400> SEQUENCE: 473

Asn Ile Gly Thr Lys Ser
1               5

<210> SEQ ID NO 474

<400> SEQUENCE: 474

000

<210> SEQ ID NO 475
<211> LENGTH: 10
<212> TYPE: PRT
<213> ORGANISM: Artificial sequence
<220> FEATURE:
<223> OTHER INFORMATION: Synthetic peptide

```
<400> SEQUENCE: 475

Gln Val Trp Asp Ser Gly Ile Asp Val Val
1               5                   10

<210> SEQ ID NO 476
<211> LENGTH: 6
<212> TYPE: PRT
<213> ORGANISM: Artificial sequence
<220> FEATURE:
<223> OTHER INFORMATION: Synthetic peptide

<400> SEQUENCE: 476

Asn Ile Gly Thr Lys Thr
1               5

<210> SEQ ID NO 477

<400> SEQUENCE: 477

000

<210> SEQ ID NO 478
<211> LENGTH: 11
<212> TYPE: PRT
<213> ORGANISM: Artificial sequence
<220> FEATURE:
<223> OTHER INFORMATION: Synthetic peptide

<400> SEQUENCE: 478

Arg Val Trp Asp Ser Asp Thr Asp His Arg Val
1               5                   10

<210> SEQ ID NO 479
<211> LENGTH: 6
<212> TYPE: PRT
<213> ORGANISM: Artificial sequence
<220> FEATURE:
<223> OTHER INFORMATION: Synthetic peptide

<400> SEQUENCE: 479

Lys Leu Gly Asp Lys Tyr
1               5

<210> SEQ ID NO 480

<400> SEQUENCE: 480

000

<210> SEQ ID NO 481
<211> LENGTH: 9
<212> TYPE: PRT
<213> ORGANISM: Artificial sequence
<220> FEATURE:
<223> OTHER INFORMATION: Synthetic peptide

<400> SEQUENCE: 481

Gln Ala Trp Asp Ser Ser Thr Val Val
1               5

<210> SEQ ID NO 482
<211> LENGTH: 6
<212> TYPE: PRT
<213> ORGANISM: Artificial sequence
<220> FEATURE:
<223> OTHER INFORMATION: Synthetic peptide
```

```
<400> SEQUENCE: 482

Gln Asp Ile Gly Val Asp
1               5

<210> SEQ ID NO 483

<400> SEQUENCE: 483

000

<210> SEQ ID NO 484
<211> LENGTH: 9
<212> TYPE: PRT
<213> ORGANISM: Artificial sequence
<220> FEATURE:
<223> OTHER INFORMATION: Synthetic peptide

<400> SEQUENCE: 484

Leu Gln Asp Tyr Asn Tyr Pro Trp Thr
1               5

<210> SEQ ID NO 485
<211> LENGTH: 6
<212> TYPE: PRT
<213> ORGANISM: Artificial sequence
<220> FEATURE:
<223> OTHER INFORMATION: Synthetic peptide

<400> SEQUENCE: 485

Ala Leu Pro Lys Gln Tyr
1               5

<210> SEQ ID NO 486

<400> SEQUENCE: 486

000

<210> SEQ ID NO 487
<211> LENGTH: 11
<212> TYPE: PRT
<213> ORGANISM: Artificial sequence
<220> FEATURE:
<223> OTHER INFORMATION: Synthetic peptide

<400> SEQUENCE: 487

Gln Ser Gly Asp Ser Ser Gly Thr Tyr Leu Val
1               5                   10

<210> SEQ ID NO 488
<211> LENGTH: 6
<212> TYPE: PRT
<213> ORGANISM: Artificial sequence
<220> FEATURE:
<223> OTHER INFORMATION: Synthetic peptide

<400> SEQUENCE: 488

Gln Arg Val Gly Asn Ser
1               5

<210> SEQ ID NO 489

<400> SEQUENCE: 489

000
```

```
<210> SEQ ID NO 490
<211> LENGTH: 10
<212> TYPE: PRT
<213> ORGANISM: Artificial sequence
<220> FEATURE:
<223> OTHER INFORMATION: Synthetic peptide

<400> SEQUENCE: 490

His Gln His Ser Thr Trp Pro Arg Gly Thr
1               5                   10

<210> SEQ ID NO 491
<211> LENGTH: 8
<212> TYPE: PRT
<213> ORGANISM: Artificial sequence
<220> FEATURE:
<223> OTHER INFORMATION: Synthetic peptide

<400> SEQUENCE: 491

Ser Gly Ser Ile Ala Thr Asn Tyr
1               5

<210> SEQ ID NO 492

<400> SEQUENCE: 492

000

<210> SEQ ID NO 493
<211> LENGTH: 11
<212> TYPE: PRT
<213> ORGANISM: Artificial sequence
<220> FEATURE:
<223> OTHER INFORMATION: Synthetic peptide

<400> SEQUENCE: 493

Gln Ser Tyr Asp Asn Ser Asn Arg Ala Val Val
1               5                   10

<210> SEQ ID NO 494
<211> LENGTH: 8
<212> TYPE: PRT
<213> ORGANISM: Artificial sequence
<220> FEATURE:
<223> OTHER INFORMATION: Synthetic peptide

<400> SEQUENCE: 494

Ser Gly Thr Ile Ala Ser Asn Tyr
1               5

<210> SEQ ID NO 495

<400> SEQUENCE: 495

000

<210> SEQ ID NO 496
<211> LENGTH: 9
<212> TYPE: PRT
<213> ORGANISM: Artificial sequence
<220> FEATURE:
<223> OTHER INFORMATION: Synthetic peptide

<400> SEQUENCE: 496

Gln Ser Tyr Asp Asn Ser Asp Arg Val
1               5
```

-continued

```
<210> SEQ ID NO 497
<211> LENGTH: 6
<212> TYPE: PRT
<213> ORGANISM: Artificial sequence
<220> FEATURE:
<223> OTHER INFORMATION: Synthetic peptide

<400> SEQUENCE: 497

Asn Ile Gly Leu Lys Ser
1               5

<210> SEQ ID NO 498

<400> SEQUENCE: 498

000

<210> SEQ ID NO 499
<211> LENGTH: 11
<212> TYPE: PRT
<213> ORGANISM: Artificial sequence
<220> FEATURE:
<223> OTHER INFORMATION: Synthetic peptide

<400> SEQUENCE: 499

Gln Val Trp Asp Ser Ser Arg Asn His Pro Val
1               5                   10

<210> SEQ ID NO 500
<211> LENGTH: 6
<212> TYPE: PRT
<213> ORGANISM: Artificial sequence
<220> FEATURE:
<223> OTHER INFORMATION: Synthetic peptide

<400> SEQUENCE: 500

Lys Leu Gly Asp Lys Tyr
1               5

<210> SEQ ID NO 501

<400> SEQUENCE: 501

000

<210> SEQ ID NO 502
<211> LENGTH: 9
<212> TYPE: PRT
<213> ORGANISM: Artificial sequence
<220> FEATURE:
<223> OTHER INFORMATION: Synthetic peptide

<400> SEQUENCE: 502

Gln Ala Trp Asp Ser Ser Thr Ala Val
1               5

<210> SEQ ID NO 503
<211> LENGTH: 6
<212> TYPE: PRT
<213> ORGANISM: Artificial sequence
<220> FEATURE:
<223> OTHER INFORMATION: Synthetic peptide

<400> SEQUENCE: 503

Gln Gly Ile Ser Arg Phe
1               5
```

```
<210> SEQ ID NO 504

<400> SEQUENCE: 504

000

<210> SEQ ID NO 505
<211> LENGTH: 11
<212> TYPE: PRT
<213> ORGANISM: Artificial sequence
<220> FEATURE:
<223> OTHER INFORMATION: Synthetic peptide

<400> SEQUENCE: 505

Gln Gln Leu Asn Ser His Pro Arg Met Phe Thr
1               5                   10

<210> SEQ ID NO 506
<211> LENGTH: 6
<212> TYPE: PRT
<213> ORGANISM: Artificial sequence
<220> FEATURE:
<223> OTHER INFORMATION: Synthetic peptide

<400> SEQUENCE: 506

Gln Gly Ile Ser Asn Trp
1               5

<210> SEQ ID NO 507

<400> SEQUENCE: 507

000

<210> SEQ ID NO 508
<211> LENGTH: 9
<212> TYPE: PRT
<213> ORGANISM: Artificial sequence
<220> FEATURE:
<223> OTHER INFORMATION: Synthetic peptide

<400> SEQUENCE: 508

Gln Gln Ala Asn Ser Phe Pro Phe Thr
1               5

<210> SEQ ID NO 509
<211> LENGTH: 6
<212> TYPE: PRT
<213> ORGANISM: Artificial sequence
<220> FEATURE:
<223> OTHER INFORMATION: Synthetic peptide

<400> SEQUENCE: 509

Ala Leu Pro Lys Gln Tyr
1               5

<210> SEQ ID NO 510

<400> SEQUENCE: 510

000

<210> SEQ ID NO 511
<211> LENGTH: 11
<212> TYPE: PRT
<213> ORGANISM: Artificial sequence
<220> FEATURE:
<223> OTHER INFORMATION: Synthetic peptide
```

<400> SEQUENCE: 511

Gln Ser Ala Asp Ser Ser Gly Thr Tyr Val Val
1               5                   10

<210> SEQ ID NO 512
<211> LENGTH: 6
<212> TYPE: PRT
<213> ORGANISM: Artificial sequence
<220> FEATURE:
<223> OTHER INFORMATION: Synthetic peptide

<400> SEQUENCE: 512

Asn Ile Gly Leu Lys Ser
1               5

<210> SEQ ID NO 513

<400> SEQUENCE: 513

000

<210> SEQ ID NO 514
<211> LENGTH: 11
<212> TYPE: PRT
<213> ORGANISM: Artificial sequence
<220> FEATURE:
<223> OTHER INFORMATION: Synthetic peptide

<400> SEQUENCE: 514

Gln Val Trp Asp Ser Ser Arg Asn His Pro Val
1               5                   10

<210> SEQ ID NO 515
<211> LENGTH: 9
<212> TYPE: PRT
<213> ORGANISM: Artificial sequence
<220> FEATURE:
<223> OTHER INFORMATION: Synthetic peptide

<400> SEQUENCE: 515

Ser Ser Asp Val Gly Gly Tyr Asn Phe
1               5

<210> SEQ ID NO 516

<400> SEQUENCE: 516

000

<210> SEQ ID NO 517
<211> LENGTH: 9
<212> TYPE: PRT
<213> ORGANISM: Artificial sequence
<220> FEATURE:
<223> OTHER INFORMATION: Synthetic peptide

<400> SEQUENCE: 517

Gly Ala Tyr Ala Gly Phe Asn Ala Leu
1               5

<210> SEQ ID NO 518
<211> LENGTH: 6
<212> TYPE: PRT
<213> ORGANISM: Artificial sequence
<220> FEATURE:
<223> OTHER INFORMATION: Synthetic peptide

<400> SEQUENCE: 518

Ala Val Pro Ile Lys Tyr
1               5

<210> SEQ ID NO 519

<400> SEQUENCE: 519

000

<210> SEQ ID NO 520
<211> LENGTH: 11
<212> TYPE: PRT
<213> ORGANISM: Artificial sequence
<220> FEATURE:
<223> OTHER INFORMATION: Synthetic peptide

<400> SEQUENCE: 520

Tyr Ser Thr Asp Ser Ser Gly Tyr Gln Arg Ala
1               5                   10

<210> SEQ ID NO 521
<211> LENGTH: 6
<212> TYPE: PRT
<213> ORGANISM: Artificial sequence
<220> FEATURE:
<223> OTHER INFORMATION: Synthetic peptide

<400> SEQUENCE: 521

Gln Ser Val Gly Thr Asp
1               5

<210> SEQ ID NO 522

<400> SEQUENCE: 522

000

<210> SEQ ID NO 523
<211> LENGTH: 11
<212> TYPE: PRT
<213> ORGANISM: Artificial sequence
<220> FEATURE:
<223> OTHER INFORMATION: Synthetic peptide

<400> SEQUENCE: 523

Gln Gln Arg Ser Arg Trp Pro Pro Pro Tyr Thr
1               5                   10

<210> SEQ ID NO 524
<211> LENGTH: 6
<212> TYPE: PRT
<213> ORGANISM: Artificial sequence
<220> FEATURE:
<223> OTHER INFORMATION: Synthetic peptide

<400> SEQUENCE: 524

Gln Ser Val Gly Thr Asp
1               5

<210> SEQ ID NO 525

<400> SEQUENCE: 525

000

```
<210> SEQ ID NO 526
<211> LENGTH: 11
<212> TYPE: PRT
<213> ORGANISM: Artificial sequence
<220> FEATURE:
<223> OTHER INFORMATION: Synthetic peptide

<400> SEQUENCE: 526

Gln Gln Arg Ser Arg Trp Pro Pro Pro Tyr Thr
1               5                   10

<210> SEQ ID NO 527
<211> LENGTH: 6
<212> TYPE: PRT
<213> ORGANISM: Artificial sequence
<220> FEATURE:
<223> OTHER INFORMATION: Synthetic peptide

<400> SEQUENCE: 527

Gln Ser Val Arg Ser Trp
1               5

<210> SEQ ID NO 528

<400> SEQUENCE: 528

000

<210> SEQ ID NO 529
<211> LENGTH: 9
<212> TYPE: PRT
<213> ORGANISM: Artificial sequence
<220> FEATURE:
<223> OTHER INFORMATION: Synthetic peptide

<400> SEQUENCE: 529

Gln Gln Tyr Gln Thr Phe Ser Trp Thr
1               5

<210> SEQ ID NO 530
<211> LENGTH: 11
<212> TYPE: PRT
<213> ORGANISM: Artificial sequence
<220> FEATURE:
<223> OTHER INFORMATION: Synthetic peptide

<400> SEQUENCE: 530

Gln Ser Leu Leu Gln Ser Asp Gly Tyr Ser Tyr
1               5                   10

<210> SEQ ID NO 531

<400> SEQUENCE: 531

000

<210> SEQ ID NO 532
<211> LENGTH: 9
<212> TYPE: PRT
<213> ORGANISM: Artificial sequence
<220> FEATURE:
<223> OTHER INFORMATION: Synthetic peptide

<400> SEQUENCE: 532

Met Gln Ala Leu Gln Thr Pro Trp Thr
1               5
```

<210> SEQ ID NO 533
<211> LENGTH: 12
<212> TYPE: PRT
<213> ORGANISM: Artificial sequence
<220> FEATURE:
<223> OTHER INFORMATION: Synthetic peptide

<400> SEQUENCE: 533

Gln Ser Val Leu Phe Ser Ser Asn Asn Lys Asn Tyr
1               5                   10

<210> SEQ ID NO 534

<400> SEQUENCE: 534

000

<210> SEQ ID NO 535
<211> LENGTH: 9
<212> TYPE: PRT
<213> ORGANISM: Artificial sequence
<220> FEATURE:
<223> OTHER INFORMATION: Synthetic peptide

<400> SEQUENCE: 535

Gln Gln Phe Tyr Thr Thr Pro Leu Thr
1               5

<210> SEQ ID NO 536
<211> LENGTH: 8
<212> TYPE: PRT
<213> ORGANISM: Artificial sequence
<220> FEATURE:
<223> OTHER INFORMATION: Synthetic peptide

<400> SEQUENCE: 536

Thr Ser Asn Ile Glu Thr Asn Tyr
1               5

<210> SEQ ID NO 537

<400> SEQUENCE: 537

000

<210> SEQ ID NO 538
<211> LENGTH: 11
<212> TYPE: PRT
<213> ORGANISM: Artificial sequence
<220> FEATURE:
<223> OTHER INFORMATION: Synthetic peptide

<400> SEQUENCE: 538

Ala Ala Trp Asp Asp Ser Leu Lys Ala Pro Val
1               5                   10

<210> SEQ ID NO 539
<211> LENGTH: 9
<212> TYPE: PRT
<213> ORGANISM: Artificial sequence
<220> FEATURE:
<223> OTHER INFORMATION: Synthetic peptide

<400> SEQUENCE: 539

Ser Thr Asn Ile Gly Ala Gly Tyr Asp
1               5

<210> SEQ ID NO 540

<400> SEQUENCE: 540

000

<210> SEQ ID NO 541
<211> LENGTH: 11
<212> TYPE: PRT
<213> ORGANISM: Artificial sequence
<220> FEATURE:
<223> OTHER INFORMATION: Synthetic peptide

<400> SEQUENCE: 541

Gln Ser Tyr Asp Arg Ser Leu Ser Thr Tyr Val
1               5                   10

<210> SEQ ID NO 542
<211> LENGTH: 6
<212> TYPE: PRT
<213> ORGANISM: Artificial sequence
<220> FEATURE:
<223> OTHER INFORMATION: Synthetic peptide

<400> SEQUENCE: 542

Asn Ile Gly Thr Lys Ser
1               5

<210> SEQ ID NO 543

<400> SEQUENCE: 543

000

<210> SEQ ID NO 544
<211> LENGTH: 11
<212> TYPE: PRT
<213> ORGANISM: Artificial sequence
<220> FEATURE:
<223> OTHER INFORMATION: Synthetic peptide

<400> SEQUENCE: 544

Gln Val Trp Asp Ser Tyr Asn Val His Tyr Val
1               5                   10

<210> SEQ ID NO 545
<211> LENGTH: 8
<212> TYPE: PRT
<213> ORGANISM: Artificial sequence
<220> FEATURE:
<223> OTHER INFORMATION: Synthetic peptide

<400> SEQUENCE: 545

Ser Ser Asn Ile Glu Tyr Asn Tyr
1               5

<210> SEQ ID NO 546

<400> SEQUENCE: 546

000

<210> SEQ ID NO 547
<211> LENGTH: 11
<212> TYPE: PRT
<213> ORGANISM: Artificial sequence
<220> FEATURE:

<223> OTHER INFORMATION: Synthetic peptide

<400> SEQUENCE: 547

Ala Ala Trp Asp Asp Ile Leu Ser Gly Val Val
1               5                   10

<210> SEQ ID NO 548
<211> LENGTH: 9
<212> TYPE: PRT
<213> ORGANISM: Artificial sequence
<220> FEATURE:
<223> OTHER INFORMATION: Synthetic peptide

<400> SEQUENCE: 548

Ser Asn Asp Val Gly Gly Tyr Asn Phe
1               5

<210> SEQ ID NO 549

<400> SEQUENCE: 549

000

<210> SEQ ID NO 550
<211> LENGTH: 10
<212> TYPE: PRT
<213> ORGANISM: Artificial sequence
<220> FEATURE:
<223> OTHER INFORMATION: Synthetic peptide

<400> SEQUENCE: 550

Cys Ser Tyr Ala Gly Thr Tyr Thr Trp Val
1               5                   10

<210> SEQ ID NO 551
<211> LENGTH: 7
<212> TYPE: PRT
<213> ORGANISM: Artificial sequence
<220> FEATURE:
<223> OTHER INFORMATION: Synthetic peptide

<400> SEQUENCE: 551

Gln Arg Val Val Asn Asn Tyr
1               5

<210> SEQ ID NO 552

<400> SEQUENCE: 552

000

<210> SEQ ID NO 553
<211> LENGTH: 8
<212> TYPE: PRT
<213> ORGANISM: Artificial sequence
<220> FEATURE:
<223> OTHER INFORMATION: Synthetic peptide

<400> SEQUENCE: 553

Gln Gln Tyr Gly Ser Pro Trp Thr
1               5

<210> SEQ ID NO 554
<211> LENGTH: 6
<212> TYPE: PRT
<213> ORGANISM: Artificial sequence
<220> FEATURE:

-continued

<223> OTHER INFORMATION: Synthetic peptide

<400> SEQUENCE: 554

Gln Ser Ile Ser Lys Trp
1               5

<210> SEQ ID NO 555

<400> SEQUENCE: 555

000

<210> SEQ ID NO 556
<211> LENGTH: 9
<212> TYPE: PRT
<213> ORGANISM: Artificial sequence
<220> FEATURE:
<223> OTHER INFORMATION: Synthetic peptide

<400> SEQUENCE: 556

Gln Gln His Asn Ser Tyr Ser Tyr Thr
1               5

<210> SEQ ID NO 557
<211> LENGTH: 7
<212> TYPE: PRT
<213> ORGANISM: Artificial sequence
<220> FEATURE:
<223> OTHER INFORMATION: Synthetic peptide

<400> SEQUENCE: 557

Gln Ser Val Ile Ser Thr Tyr
1               5

<210> SEQ ID NO 558

<400> SEQUENCE: 558

000

<210> SEQ ID NO 559
<211> LENGTH: 9
<212> TYPE: PRT
<213> ORGANISM: Artificial sequence
<220> FEATURE:
<223> OTHER INFORMATION: Synthetic peptide

<400> SEQUENCE: 559

His Gln Tyr Gly Ser Ser Pro Ala Thr
1               5

<210> SEQ ID NO 560
<211> LENGTH: 6
<212> TYPE: PRT
<213> ORGANISM: Artificial sequence
<220> FEATURE:
<223> OTHER INFORMATION: Synthetic peptide

<400> SEQUENCE: 560

Gln Ser Val Gly Thr Tyr
1               5

<210> SEQ ID NO 561

<400> SEQUENCE: 561

000

<210> SEQ ID NO 562
<211> LENGTH: 11
<212> TYPE: PRT
<213> ORGANISM: Artificial sequence
<220> FEATURE:
<223> OTHER INFORMATION: Synthetic peptide

<400> SEQUENCE: 562

Gln Leu Arg Ile Thr Trp Pro Pro Ile Phe Thr
1               5                   10

<210> SEQ ID NO 563
<211> LENGTH: 9
<212> TYPE: PRT
<213> ORGANISM: Artificial sequence
<220> FEATURE:
<223> OTHER INFORMATION: Synthetic peptide

<400> SEQUENCE: 563

Ser Ser Asp Val Gly Gly Tyr Asn Tyr
1               5

<210> SEQ ID NO 564

<400> SEQUENCE: 564

000

<210> SEQ ID NO 565
<211> LENGTH: 10
<212> TYPE: PRT
<213> ORGANISM: Artificial sequence
<220> FEATURE:
<223> OTHER INFORMATION: Synthetic peptide

<400> SEQUENCE: 565

Ser Ser Tyr Ala Gly Ser Asn Asn Leu Val
1               5                   10

<210> SEQ ID NO 566
<211> LENGTH: 8
<212> TYPE: PRT
<213> ORGANISM: Artificial sequence
<220> FEATURE:
<223> OTHER INFORMATION: Synthetic peptide

<400> SEQUENCE: 566

Thr Ser Ser Ile Gly Ser Asn Ile
1               5

<210> SEQ ID NO 567

<400> SEQUENCE: 567

000

<210> SEQ ID NO 568
<211> LENGTH: 11
<212> TYPE: PRT
<213> ORGANISM: Artificial sequence
<220> FEATURE:
<223> OTHER INFORMATION: Synthetic peptide

<400> SEQUENCE: 568

Ala Ala Trp Asp Asp Ser Leu Asn Gly Trp Val
1               5                   10

```
<210> SEQ ID NO 569
<211> LENGTH: 6
<212> TYPE: PRT
<213> ORGANISM: Artificial sequence
<220> FEATURE:
<223> OTHER INFORMATION: Synthetic peptide

<400> SEQUENCE: 569

Gln Ser Val Gly Ser Thr
1               5

<210> SEQ ID NO 570

<400> SEQUENCE: 570

000

<210> SEQ ID NO 571
<211> LENGTH: 10
<212> TYPE: PRT
<213> ORGANISM: Artificial sequence
<220> FEATURE:
<223> OTHER INFORMATION: Synthetic peptide

<400> SEQUENCE: 571

His Gln Tyr Ile Asn Trp Pro Pro Trp Thr
1               5                   10

<210> SEQ ID NO 572
<211> LENGTH: 9
<212> TYPE: PRT
<213> ORGANISM: Artificial sequence
<220> FEATURE:
<223> OTHER INFORMATION: Synthetic peptide

<400> SEQUENCE: 572

Ser Ser Asp Val Gly Ala Tyr Ser Tyr
1               5

<210> SEQ ID NO 573

<400> SEQUENCE: 573

000

<210> SEQ ID NO 574
<211> LENGTH: 10
<212> TYPE: PRT
<213> ORGANISM: Artificial sequence
<220> FEATURE:
<223> OTHER INFORMATION: Synthetic peptide

<400> SEQUENCE: 574

Cys Ser His Ala Gly Ser His Thr Trp Val
1               5                   10

<210> SEQ ID NO 575
<211> LENGTH: 6
<212> TYPE: PRT
<213> ORGANISM: Artificial sequence
<220> FEATURE:
<223> OTHER INFORMATION: Synthetic peptide

<400> SEQUENCE: 575

Gln Ser Ile Ser Arg Asn
1               5
```

<210> SEQ ID NO 576

<400> SEQUENCE: 576

000

<210> SEQ ID NO 577
<211> LENGTH: 9
<212> TYPE: PRT
<213> ORGANISM: Artificial sequence
<220> FEATURE:
<223> OTHER INFORMATION: Synthetic peptide

<400> SEQUENCE: 577

Gln Gln Tyr Ser Lys Leu Pro Ile Thr
1               5

<210> SEQ ID NO 578
<211> LENGTH: 6
<212> TYPE: PRT
<213> ORGANISM: Artificial sequence
<220> FEATURE:
<223> OTHER INFORMATION: Synthetic peptide

<400> SEQUENCE: 578

Gln Ser Val Arg Ser Tyr
1               5

<210> SEQ ID NO 579

<400> SEQUENCE: 579

000

<210> SEQ ID NO 580
<211> LENGTH: 10
<212> TYPE: PRT
<213> ORGANISM: Artificial sequence
<220> FEATURE:
<223> OTHER INFORMATION: Synthetic peptide

<400> SEQUENCE: 580

Gln Gln Arg Ser Tyr Trp Pro Pro Phe Thr
1               5                   10

<210> SEQ ID NO 581
<211> LENGTH: 6
<212> TYPE: PRT
<213> ORGANISM: Artificial sequence
<220> FEATURE:
<223> OTHER INFORMATION: Synthetic peptide

<400> SEQUENCE: 581

Gln Ser Val Ser Ser Tyr
1               5

<210> SEQ ID NO 582

<400> SEQUENCE: 582

000

<210> SEQ ID NO 583
<211> LENGTH: 10
<212> TYPE: PRT
<213> ORGANISM: Artificial sequence

```
<220> FEATURE:
<223> OTHER INFORMATION: Synthetic peptide

<400> SEQUENCE: 583

Gln Gln Arg Ser Asp Trp Pro Pro Gly Thr
1               5                   10

<210> SEQ ID NO 584
<211> LENGTH: 9
<212> TYPE: PRT
<213> ORGANISM: Artificial sequence
<220> FEATURE:
<223> OTHER INFORMATION: Synthetic peptide

<400> SEQUENCE: 584

Ser Ser Asp Val Gly Gly Tyr Asn Phe
1               5

<210> SEQ ID NO 585

<400> SEQUENCE: 585

000

<210> SEQ ID NO 586
<211> LENGTH: 10
<212> TYPE: PRT
<213> ORGANISM: Artificial sequence
<220> FEATURE:
<223> OTHER INFORMATION: Synthetic peptide

<400> SEQUENCE: 586

Cys Ser Tyr Gly Gly Asn Asn Ser Trp Met
1               5                   10

<210> SEQ ID NO 587
<211> LENGTH: 6
<212> TYPE: PRT
<213> ORGANISM: Artificial sequence
<220> FEATURE:
<223> OTHER INFORMATION: Synthetic peptide

<400> SEQUENCE: 587

Val Leu Ser Asn Gln Tyr
1               5

<210> SEQ ID NO 588

<400> SEQUENCE: 588

000

<210> SEQ ID NO 589
<211> LENGTH: 10
<212> TYPE: PRT
<213> ORGANISM: Artificial sequence
<220> FEATURE:
<223> OTHER INFORMATION: Synthetic peptide

<400> SEQUENCE: 589

Gln Ser Ala Asp Asn Thr Arg Ile Thr Val
1               5                   10

<210> SEQ ID NO 590
<211> LENGTH: 11
<212> TYPE: PRT
<213> ORGANISM: Artificial sequence
```

```
<220> FEATURE:
<223> OTHER INFORMATION: Synthetic peptide

<400> SEQUENCE: 590

Gln Ser Leu Val Tyr Ser Asp Gly Asn Thr Tyr
1               5                   10

<210> SEQ ID NO 591

<400> SEQUENCE: 591

000

<210> SEQ ID NO 592
<211> LENGTH: 9
<212> TYPE: PRT
<213> ORGANISM: Artificial sequence
<220> FEATURE:
<223> OTHER INFORMATION: Synthetic peptide

<400> SEQUENCE: 592

Met Gln Gly Thr His Trp Pro Arg Thr
1               5

<210> SEQ ID NO 593
<211> LENGTH: 8
<212> TYPE: PRT
<213> ORGANISM: Artificial sequence
<220> FEATURE:
<223> OTHER INFORMATION: Synthetic peptide

<400> SEQUENCE: 593

Arg Ser Asn Ile Gly Ser Tyr Thr
1               5

<210> SEQ ID NO 594

<400> SEQUENCE: 594

000

<210> SEQ ID NO 595
<211> LENGTH: 11
<212> TYPE: PRT
<213> ORGANISM: Artificial sequence
<220> FEATURE:
<223> OTHER INFORMATION: Synthetic peptide

<400> SEQUENCE: 595

Ala Ala Trp Asp Asp Ser Leu Asn Gly Val Val
1               5                   10

<210> SEQ ID NO 596
<211> LENGTH: 6
<212> TYPE: PRT
<213> ORGANISM: Artificial sequence
<220> FEATURE:
<223> OTHER INFORMATION: Synthetic peptide

<400> SEQUENCE: 596

Gln Ser Ile Asn Ile Tyr
1               5

<210> SEQ ID NO 597

<400> SEQUENCE: 597
```

000

```
<210> SEQ ID NO 598
<211> LENGTH: 9
<212> TYPE: PRT
<213> ORGANISM: Artificial sequence
<220> FEATURE:
<223> OTHER INFORMATION: Synthetic peptide

<400> SEQUENCE: 598

Gln Gln Ser Tyr Arg Ser Pro Arg Thr
1               5

<210> SEQ ID NO 599
<211> LENGTH: 7
<212> TYPE: PRT
<213> ORGANISM: Artificial sequence
<220> FEATURE:
<223> OTHER INFORMATION: Synthetic peptide

<400> SEQUENCE: 599

Ser Gly His Ser Arg Tyr Ala
1               5

<210> SEQ ID NO 600
<211> LENGTH: 7
<212> TYPE: PRT
<213> ORGANISM: Artificial sequence
<220> FEATURE:
<223> OTHER INFORMATION: Synthetic peptide

<400> SEQUENCE: 600

Ile Asn Ser Asp Gly Arg His
1               5

<210> SEQ ID NO 601
<211> LENGTH: 9
<212> TYPE: PRT
<213> ORGANISM: Artificial sequence
<220> FEATURE:
<223> OTHER INFORMATION: Synthetic peptide

<400> SEQUENCE: 601

Gln Thr Trp Gly Thr Gly Phe Arg Val
1               5

<210> SEQ ID NO 602
<211> LENGTH: 6
<212> TYPE: PRT
<213> ORGANISM: Artificial sequence
<220> FEATURE:
<223> OTHER INFORMATION: Synthetic peptide

<400> SEQUENCE: 602

Gln Ser Val Ser Ser Tyr
1               5

<210> SEQ ID NO 603

<400> SEQUENCE: 603

000

<210> SEQ ID NO 604
<211> LENGTH: 9
<212> TYPE: PRT
<213> ORGANISM: Artificial sequence
```

```
<220> FEATURE:
<223> OTHER INFORMATION: Synthetic peptide

<400> SEQUENCE: 604

Gln Gln Arg Ser Asn Trp Pro Ile Thr
1               5

<210> SEQ ID NO 605
<211> LENGTH: 6
<212> TYPE: PRT
<213> ORGANISM: Artificial sequence
<220> FEATURE:
<223> OTHER INFORMATION: Synthetic peptide

<400> SEQUENCE: 605

Gln Asp Ile Ser Ser Trp
1               5

<210> SEQ ID NO 606

<400> SEQUENCE: 606

000

<210> SEQ ID NO 607
<211> LENGTH: 8
<212> TYPE: PRT
<213> ORGANISM: Artificial sequence
<220> FEATURE:
<223> OTHER INFORMATION: Synthetic peptide

<400> SEQUENCE: 607

Gln Gln Ala Asp Ser Phe Ile Thr
1               5

<210> SEQ ID NO 608
<211> LENGTH: 6
<212> TYPE: PRT
<213> ORGANISM: Artificial sequence
<220> FEATURE:
<223> OTHER INFORMATION: Synthetic peptide

<400> SEQUENCE: 608

Gln Ser Ile Gly Asp Asn
1               5

<210> SEQ ID NO 609

<400> SEQUENCE: 609

000

<210> SEQ ID NO 610
<211> LENGTH: 9
<212> TYPE: PRT
<213> ORGANISM: Artificial sequence
<220> FEATURE:
<223> OTHER INFORMATION: Synthetic peptide

<400> SEQUENCE: 610

Gln Gln Tyr Lys Asn Trp Pro Arg Thr
1               5

<210> SEQ ID NO 611
<211> LENGTH: 7
<212> TYPE: PRT
<213> ORGANISM: Artificial sequence
```

```
<220> FEATURE:
<223> OTHER INFORMATION: Synthetic peptide

<400> SEQUENCE: 611

Gln Ser Val Arg Ser Ser Tyr
1               5

<210> SEQ ID NO 612

<400> SEQUENCE: 612

000

<210> SEQ ID NO 613
<211> LENGTH: 8
<212> TYPE: PRT
<213> ORGANISM: Artificial sequence
<220> FEATURE:
<223> OTHER INFORMATION: Synthetic peptide

<400> SEQUENCE: 613

Gln Gln Tyr Gly Thr Ser Ile Thr
1               5

<210> SEQ ID NO 614
<211> LENGTH: 6
<212> TYPE: PRT
<213> ORGANISM: Artificial sequence
<220> FEATURE:
<223> OTHER INFORMATION: Synthetic peptide

<400> SEQUENCE: 614

Val Leu Ser Lys Gln Tyr
1               5

<210> SEQ ID NO 615

<400> SEQUENCE: 615

000

<210> SEQ ID NO 616
<211> LENGTH: 9
<212> TYPE: PRT
<213> ORGANISM: Artificial sequence
<220> FEATURE:
<223> OTHER INFORMATION: Synthetic peptide

<400> SEQUENCE: 616

Gln Ser Ala Asp Thr Arg Ile Thr Val
1               5

<210> SEQ ID NO 617
<211> LENGTH: 6
<212> TYPE: PRT
<213> ORGANISM: Artificial sequence
<220> FEATURE:
<223> OTHER INFORMATION: Synthetic peptide

<400> SEQUENCE: 617

Val Leu Ser Asn Gln Tyr
1               5

<210> SEQ ID NO 618

<400> SEQUENCE: 618
```

000

<210> SEQ ID NO 619
<211> LENGTH: 9
<212> TYPE: PRT
<213> ORGANISM: Artificial sequence
<220> FEATURE:
<223> OTHER INFORMATION: Synthetic peptide

<400> SEQUENCE: 619

Gln Thr Ala Asp Thr Lys Tyr Thr Val
1               5

<210> SEQ ID NO 620
<211> LENGTH: 6
<212> TYPE: PRT
<213> ORGANISM: Artificial sequence
<220> FEATURE:
<223> OTHER INFORMATION: Synthetic peptide

<400> SEQUENCE: 620

Gln Arg Ile Ser Thr Tyr
1               5

<210> SEQ ID NO 621

<400> SEQUENCE: 621

000

<210> SEQ ID NO 622
<211> LENGTH: 9
<212> TYPE: PRT
<213> ORGANISM: Artificial sequence
<220> FEATURE:
<223> OTHER INFORMATION: Synthetic peptide

<400> SEQUENCE: 622

Gln Gln Ser Tyr Ser Pro Pro Trp Thr
1               5

<210> SEQ ID NO 623
<211> LENGTH: 6
<212> TYPE: PRT
<213> ORGANISM: Artificial sequence
<220> FEATURE:
<223> OTHER INFORMATION: Synthetic peptide

<400> SEQUENCE: 623

Gln Ser Ile Lys Lys Tyr
1               5

<210> SEQ ID NO 624

<400> SEQUENCE: 624

000

<210> SEQ ID NO 625
<211> LENGTH: 9
<212> TYPE: PRT
<213> ORGANISM: Artificial sequence
<220> FEATURE:
<223> OTHER INFORMATION: Synthetic peptide

<400> SEQUENCE: 625

Gln Gln Ser Asp Ser Ala Pro Pro Thr

```
<210> SEQ ID NO 626
<211> LENGTH: 6
<212> TYPE: PRT
<213> ORGANISM: Artificial sequence
<220> FEATURE:
<223> OTHER INFORMATION: Synthetic peptide

<400> SEQUENCE: 626

Gln Ser Ile Arg Asp Tyr
1               5

<210> SEQ ID NO 627

<400> SEQUENCE: 627

000

<210> SEQ ID NO 628
<211> LENGTH: 9
<212> TYPE: PRT
<213> ORGANISM: Artificial sequence
<220> FEATURE:
<223> OTHER INFORMATION: Synthetic peptide

<400> SEQUENCE: 628

Gln Gln Ser Tyr Leu Thr Pro Pro Thr
1               5

<210> SEQ ID NO 629
<211> LENGTH: 6
<212> TYPE: PRT
<213> ORGANISM: Artificial sequence
<220> FEATURE:
<223> OTHER INFORMATION: Synthetic peptide

<400> SEQUENCE: 629

Asn Ile Gly Ile Arg Thr
1               5

<210> SEQ ID NO 630

<400> SEQUENCE: 630

000

<210> SEQ ID NO 631
<211> LENGTH: 11
<212> TYPE: PRT
<213> ORGANISM: Artificial sequence
<220> FEATURE:
<223> OTHER INFORMATION: Synthetic peptide

<400> SEQUENCE: 631

Gln Val Trp Asp Ser Ser Ser Asp His Val Val
1               5                   10

<210> SEQ ID NO 632
<211> LENGTH: 9
<212> TYPE: PRT
<213> ORGANISM: Artificial sequence
<220> FEATURE:
<223> OTHER INFORMATION: Synthetic peptide

<400> SEQUENCE: 632

Ser Ser Asp Val Gly Ala Tyr Asn Tyr
1               5
```

```
1               5

<210> SEQ ID NO 633

<400> SEQUENCE: 633

000

<210> SEQ ID NO 634
<211> LENGTH: 10
<212> TYPE: PRT
<213> ORGANISM: Artificial sequence
<220> FEATURE:
<223> OTHER INFORMATION: Synthetic peptide

<400> SEQUENCE: 634

Ser Ser Tyr Ala Gly Asn Asn Asn Leu Val
1               5                   10

<210> SEQ ID NO 635
<211> LENGTH: 6
<212> TYPE: PRT
<213> ORGANISM: Artificial sequence
<220> FEATURE:
<223> OTHER INFORMATION: Synthetic peptide

<400> SEQUENCE: 635

Asn Ile Glu Arg Lys Ser
1               5

<210> SEQ ID NO 636

<400> SEQUENCE: 636

000

<210> SEQ ID NO 637
<211> LENGTH: 11
<212> TYPE: PRT
<213> ORGANISM: Artificial sequence
<220> FEATURE:
<223> OTHER INFORMATION: Synthetic peptide

<400> SEQUENCE: 637

Gln Val Trp Asp Ser Thr Thr Asp His Gly Val
1               5                   10

<210> SEQ ID NO 638
<211> LENGTH: 6
<212> TYPE: PRT
<213> ORGANISM: Artificial sequence
<220> FEATURE:
<223> OTHER INFORMATION: Synthetic peptide

<400> SEQUENCE: 638

Gln Ser Val Ser Gly Tyr
1               5

<210> SEQ ID NO 639

<400> SEQUENCE: 639

000

<210> SEQ ID NO 640
<211> LENGTH: 8
<212> TYPE: PRT
```

```
<213> ORGANISM: Artificial sequence
<220> FEATURE:
<223> OTHER INFORMATION: Synthetic peptide

<400> SEQUENCE: 640

Gln Gln Arg Ser Asn Gly Leu Thr
1               5

<210> SEQ ID NO 641
<211> LENGTH: 16
<212> TYPE: DNA
<213> ORGANISM: Artificial sequence
<220> FEATURE:
<223> OTHER INFORMATION: Synthetic primer

<400> SEQUENCE: 641
cctccggccc ctgaat                                                   16

<210> SEQ ID NO 642
<211> LENGTH: 20
<212> TYPE: DNA
<213> ORGANISM: Artificial sequence
<220> FEATURE:
<223> OTHER INFORMATION: Synthetic primer

<400> SEQUENCE: 642
ccattgaatc cctgggcctt                                               20

<210> SEQ ID NO 643
<211> LENGTH: 28
<212> TYPE: PRT
<213> ORGANISM: Homo sapiens

<400> SEQUENCE: 643

Ala Arg Asp Arg Pro Ile Met Glu Gly Glu Gly Leu Asp Glu Leu Thr
1               5                   10                  15

Gly Tyr Tyr Val Tyr Gln Tyr Tyr Ala Met Asp Val
            20                  25

<210> SEQ ID NO 644
<211> LENGTH: 11
<212> TYPE: PRT
<213> ORGANISM: Homo sapiens

<400> SEQUENCE: 644

Ala Ala Trp Asp Asp Arg Leu Ser Gly Val Val
1               5                   10

<210> SEQ ID NO 645
<211> LENGTH: 9
<212> TYPE: PRT
<213> ORGANISM: Homo sapiens

<400> SEQUENCE: 645

Gln Gln Tyr Asn Ser Tyr Pro Leu Thr
1               5

<210> SEQ ID NO 646
<211> LENGTH: 10
<212> TYPE: PRT
<213> ORGANISM: Homo sapiens

<400> SEQUENCE: 646

Gln Gln Arg Ser Asn Trp Pro Pro Leu Thr
1               5                   10
```

```
<210> SEQ ID NO 647
<211> LENGTH: 9
<212> TYPE: PRT
<213> ORGANISM: Homo sapiens

<400> SEQUENCE: 647

Gln Gln Tyr Asn Ser Leu Pro Trp Thr
1               5
```